(12) United States Patent
Kohchi et al.

(10) Patent No.: US 9,266,853 B2
(45) Date of Patent: Feb. 23, 2016

(54) ORALLY AVAILABLE VIRIDIOFUNGIN DERIVATIVE POSSESSING ANTI-HCV ACTIVITY

(71) Applicant: Chugai Seiyaku Kabushiki Kaisha, Tokyo (JP)

(72) Inventors: Yasunori Kohchi, Kanagawa (JP); Kimitaka Nakama, Kanagawa (JP); Susumu Komiyama, Kanagawa (JP); Fumio Watanabe, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/421,577

(22) PCT Filed: Aug. 16, 2013

(86) PCT No.: PCT/JP2013/072034
§ 371 (c)(1),
(2) Date: Feb. 13, 2015

(87) PCT Pub. No.: WO2014/027696
PCT Pub. Date: Feb. 20, 2014

(65) Prior Publication Data
US 2015/0210666 A1    Jul. 30, 2015

(30) Foreign Application Priority Data
Aug. 17, 2012 (JP) .................................. 2012-181225

(51) Int. Cl.
| | | |
|---|---|---|
| C07D 293/00 | (2006.01) | |
| C07D 317/00 | (2006.01) | |
| C07D 317/36 | (2006.01) | |
| C07D 293/06 | (2006.01) | |
| C07D 317/34 | (2006.01) | |
| C07D 317/40 | (2006.01) | |
| C07C 235/28 | (2006.01) | |
| A61K 31/192 | (2006.01) | |
| A61K 31/357 | (2006.01) | |
| C07C 235/74 | (2006.01) | |

(52) U.S. Cl.
CPC ............ *C07D 317/36* (2013.01); *A61K 31/192* (2013.01); *A61K 31/357* (2013.01); *C07C 235/28* (2013.01); *C07C 235/74* (2013.01); *C07D 293/06* (2013.01); *C07D 317/34* (2013.01); *C07D 317/40* (2013.01); *C07C 2101/16* (2013.01)

(58) Field of Classification Search
USPC .................................. 548/100; 549/296, 313
See application file for complete search history.

(56) References Cited

U.S. PATENT DOCUMENTS

| | | |
|---|---|---|
| 7,378,446 B2 | 5/2008 | Sudoh et al. |
| 7,776,918 B2 | 8/2010 | Aoki et al. |
| 7,897,783 B2 | 3/2011 | Kato et al. |
| 8,183,005 B1 | 5/2012 | Sudo et al. |
| 2011/0160252 A1 | 6/2011 | Mizokami et al. |

FOREIGN PATENT DOCUMENTS

| | | |
|---|---|---|
| WO | WO 2004/071503 A1 | 8/2004 |
| WO | WO 2005/005372 A1 | 1/2005 |
| WO | WO 2006/016657 A1 | 2/2006 |
| WO | WO 2006/088071 A1 | 8/2006 |
| WO | WO 2009/154248 A1 | 12/2009 |

*Primary Examiner* — Andrew D Kosar
*Assistant Examiner* — Raymond Covington
(74) *Attorney, Agent, or Firm* — Foley & Lardner LLP

(57) ABSTRACT

An object of the present invention is to provide a compound that is useful as an orally available anti-HCV agent. The present invention relates to a compound represented by formula (1) or a pharmaceutically acceptable salt thereof. This compound has an anti-HCV activity and is useful as a medicine.

15 Claims, 2 Drawing Sheets

ORALLY AVAILABLE VIRIDIOFUNGIN DERIVATIVE POSSESSING ANTI-HCV ACTIVITY

CROSS-REFERENCE TO RELATED APPLICATIONS

This application is a National Stage application of PCT/JP2013/072034, filed Aug. 16, 2013, which claims priority from Japanese application JP 2012-181225, filed Aug. 17, 2012.

TECHNICAL FIELD

The present invention relates to a novel orally available viridiofungin derivative having an anti-HCV activity, and to a pharmaceutical composition, in particular a prophylactic or therapeutic agent for hepatitis C virus infection, including the compound as an active ingredient.

BACKGROUND ART

Hepatitis C virus (herein after also referred to as HCV) infection is estimated to afflict about 100 million to 200 million persons around the world, and around 1.5 million to 2.0 million persons in Japan. The infection in about 50% of the infected persons progresses to chronic hepatitis, and 20% of them develop cirrhosis and/or liver cancer thirty years or more after the infection. Hepatitis C is considered to account for about 90% of cases of liver cancer. In Japan, not less than 20,000 patients each year die from liver cancer due to HCV infection.

HCV is a single-stranded RNA virus, classified in the Hepacivirus genus in the Flaviviridae family. The HCV particle is 55 to 65 nm in diameter and composed of a core protein, envelope proteins and RNA. This particle adheres to and enters into human hepatocytes and then uncoats and releases RNA. In the hepatocytes, replicates of mRNA and viral gene RNA are synthesized by RNA-dependent RNA polymerase of the virus itself. Based on information of the mRNA, viral structural proteins, protease, helicase, RNA polymerase, etc. are made, virions are formed, transported through the Golgi apparatus to the cell membrane, and released from hepatocytes, and the virus proliferates.

HCV evades the host immune system by an unknown mechanism as yet. Therefore, even when adults with a mature immune system are infected, persistent infections are established in many cases, and these develop into chronic hepatitis, liver cirrhosis, and liver cancer. It is also known that even when the cancer is removed by surgery, many patients have recurring liver cancer due to the inflammation continuously induced in non-cancerous parts.

Currently, the main effective therapies for HCV clearance are combination therapies of interferon (injection) and ribavirin (oral formulation), but they are considered to be directed toward therapies with combinations of compounds having various modes of virus inhibition in future.

Clinical trials have been conducted on combinations of agents having various mechanisms of action targeting the HCV virus, such as protease inhibitors, nucleic acid.non-nucleic acid polymerase inhibitors that inhibit viral nucleic acid synthesis, and NS5A inhibitors, and reports on clinical results indicating high therapeutic performance are gradually increasing. It is considered, based on these findings, that therapeutic methods using combinations of several agents having different modes of inhibition will be established for treatment of hepatitis C in future, as they have been for treatment of HIV.

In administering several agents to patients with hepatitis C, needs for combinations with orally available agents are considered to be higher than combinations with injections in healthcare settings.

In addition, treatment with orally available agent does not require hospitalization of patients, and allows outpatient treatment, greatly reducing burden on patients. It is also considered that outpatient treatment may greatly contribute to the reduction of medical expenses in comparison with hospitalization treatment.

We previously found that viridiofungin derivatives (PTLs 1 and 2), for example, compounds represented by the following formula:

[Chem. 1]

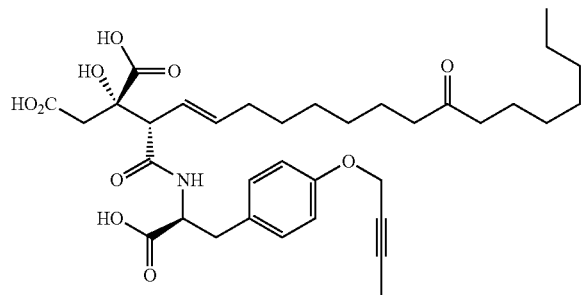

have an inhibitory activity on replication of hepatitis C virus (HCV) and a unique mechanism of action, i.e., serine palmitoyl transferase (SPT) inhibition (PTL3), and they are useful as therapeutic agents for HCV infection. Effective synthetic methods of the compounds and intermediates used for the same are disclosed in PTL4.

CITATION LIST

Patent Literature

PTL1: International Publication No. 2004/071503
PTL2: International Publication No. 2005/005372
PTL3: International Publication No. 2006/016657
PTL4: International Publication No. 2006/088071

SUMMARY OF INVENTION

Technical Problem

The aforementioned compounds were, however, found to have a poor bioavailability of less than 1% when administered to rats orally. Therefore, their dosage form for administration to the living body had to be injection. If they can be administered orally as a tablet, a capsule, or the like, administration will become easier, for example, without requiring hospitalization, and combining with other agents will become easier as well, making it possible to provide more patients with useful agents.

The present invention was made in view of such a situation and an object thereof is to provide a compound that is useful as an orally administrable anti-HCV agent.

Solution to Problem

The present inventors repeated the structural conversion of the aforementioned compounds while maintaining or improving the anti-HCV activity, for the purpose of the development of compounds suitable for oral administration. As a result, the present inventors have found that viridiofungin derivatives represented in formula (1) below or pharmaceutically acceptable salts thereof have superior anti-HCV activities, and useful as medicine, thereby completing the present invention based on the findings.

Accordingly, the present invention relates to a compound represented by formula (1) below or a pharmaceutically acceptable salt thereof:

[Chem. 2]

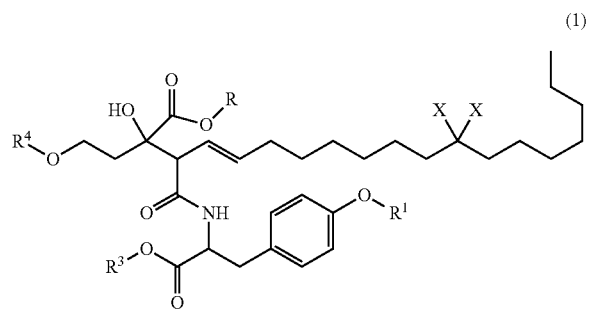

(1)

wherein R is selected from a hydrogen atom and a group represented by formula (2) below:

[Chem. 3]

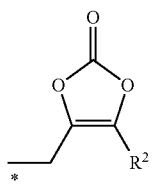

(2)

wherein
$R^1$ is $C_{1-10}$ alkyl;
$R^2$ is selected from a hydrogen atom, $C_{1-6}$ alkyl, and aryl;
$R^3$ is selected from a hydrogen atom and $C_{1-6}$ alkyl;
$R^4$ is $C_{1-6}$ alkyl; and
two Xs are the same or different, and each represent a halogen atom.

The present invention also relates to a pharmaceutical composition, in particular, a prophylactic and/or therapeutic agent for hepatitis C virus infection, including a compound of formula (1) above or a pharmaceutically acceptable salt thereof as an active ingredient.

The present invention also relates to a method for preventing and/or treating hepatitis C virus infection, using a compound of formula (1) above or a pharmaceutically acceptable salt thereof as an active ingredient.

The present invention also relates to use of a compound of formula (1) above or a pharmaceutically acceptable salt thereof for producing a pharmaceutical composition, in particular, a prophylactic and/or therapeutic agent for hepatitis C virus infection.

Advantageous Effects of Invention

A compound represented by formula (1) above or a pharmaceutically acceptable salt thereof (hereinafter, also referred to as "a compound of the present invention") exhibits oral bioavailability sufficient to maintain adequate efficacy concentrations in the liver, a target organ of the anti-HCV agent. In addition, the compound of the present invention has a reduced inhibitory activity on cytochrome P450 (CYP), indicating that the risk of drug interaction is low. Therefore, it can be used as a safe drug that is easier to be used as medicine. As to CYP inhibition, particularly TDI (Time Dependent Inhibition; the phenomenon in which a substrate is metabolized and further increased in its inhibitory activity on CYP) is an important factor that has a major impact on the metabolism of other drugs (Drug metabolism and pharmacokinetics 20 (1), 23-25, 2005 Feb. 28). The compound of the present invention has a low CYP-inhibition-level ratio between a value measured without incubation of the substrate and a value measured after incubation of the substrate, indicating that it is a safe compound with which TDI tends not to occur.

DESCRIPTION OF EMBODIMENTS

Figure 1:
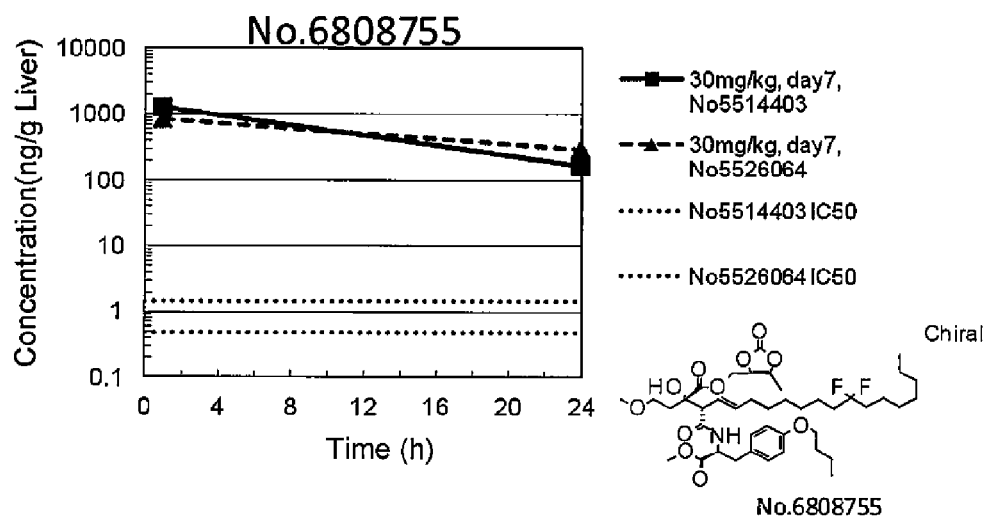
FIG. 1 is a graph showing concentrations of metabolites and IC50 values of anti-replicon activity thereof in the liver after oral administration of the prodrug compound No. 6808755 to rat. In the graph, the solid and dashed lines indicate concentrations of the metabolites No. 5514403 and No. 5526064, respectively. The dotted lines with black and grey dots indicate IC50 values of the metabolites No. 5514403 and No. 5526064, respectively. The chemical structural formula of the prodrug compound No. 6808755 is also illustrated.

Regarding the present invention, "$C_{1-10}$ alkyl" refers to a linear or branched alkyl group having 1 to 10 carbon atoms. Specific examples include methyl, ethyl, n-propyl, i-propyl, n-butyl, sec-butyl, t-butyl, 1-methylpropyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-heptyl, 5-methylhexyl, 1,1-dimethylpentyl, n-octyl, 5-methylheptyl, 2,3-dimethylhexyl, n-nonyl, 7-methyloctyl, 5-ethylheptyl, n-decyl, 8-methylnonyl, 5,5-dimethyloctyl, and 4-ethyl-6-methylheptyl.

"$C_{1-6}$ alkyl" refers to a linear or branched alkyl group having 1 to 6 carbon atoms. Specific examples include those having 1 to 6 carbon atoms among those listed as specific examples of $C_{1-10}$ alkyl.

"Aryl" refers to an aromatic hydrocarbon group having 6 to 10 carbon atoms. Specific examples include phenyl, 1-naphthyl, and 2-naphthyl.

A "halogen atom" refers to a fluorine atom, a chlorine atom, a bromine atom or an iodine atom.

R in the above formula (1) is selected from a hydrogen atom and a group represented by formula (2) below:

[Chem. 4]

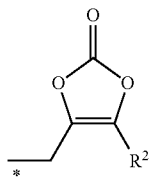

(2)

wherein $R^2$ is as defined above.

A compound wherein R is a hydrogen atom or a pharmaceutically acceptable salt thereof serves as a compound that exhibits a pharmacological activity such as an anti-HCV activity in vivo. The compound can be also used as an intermediate in the synthesis of a compound wherein R is a group represented by formula (2) or a pharmaceutically acceptable salt thereof.

A compound wherein R is a group represented by formula (2) or a pharmaceutically acceptable salt thereof serves as a prodrug that is converted into a compound wherein R is a hydrogen atom or a pharmaceutically acceptable salt thereof in vivo.

$R^1$ in formula (1) is $C_{1-10}$ alkyl, preferably methyl, ethyl, n-propyl, i-propyl, n-butyl, t-butyl, n-pentyl, n-hexyl, n-heptyl, or the like, and more preferably, n-butyl.

$R^2$ in formula (1) is selected from a hydrogen atom, $C_{1-6}$ alkyl, and aryl. $C_{1-6}$ alkyl is preferably methyl, ethyl, n-propyl, i-propyl, n-butyl, or the like, and more preferably, methyl. Aryl is preferably phenyl or 1-naphthyl. $R^2$ is preferably a hydrogen atom, methyl or the like.

$R^3$ in formula (1) is selected from a hydrogen atom and $C_{1-6}$ alkyl. $C_{1-6}$ alkyl is preferably methyl, ethyl, n-propyl, i-propyl, n-butyl, t-butyl, n-pentyl, 1-methylbutyl, 2-methylbutyl, 3-methylbutyl, or the like, and more preferably, methyl. $R^3$ is preferably a hydrogen atom, methyl or the like.

$R^4$ in formula (1) is $C_{1-6}$ alkyl, preferably methyl, ethyl, n-propyl, i-propyl, n-butyl, t-butyl, n-pentyl, 1-methylbutyl, 2-methylbutyl, 3-methylbutyl, or the like, and more preferably, methyl.

Two Xs in formula (1) are the same or different, and each represent a halogen atom, for example, a fluorine, chlorine, bromine, or iodine atom. Preferably, the two Xs are the same, and more preferably, the two Xs are the same and each represent a fluorine atom.

Compounds represented by formula (1) and pharmaceutically acceptable salts thereof can have at least one asymmetric carbon atom, and be present in the form of optically pure enantiomers and racemates.

A preferable example of the compounds represented by formula (1) and pharmaceutically acceptable salts thereof is a compound represented by formula (1') below or a pharmaceutically acceptable salt thereof:

[Chem. 5]

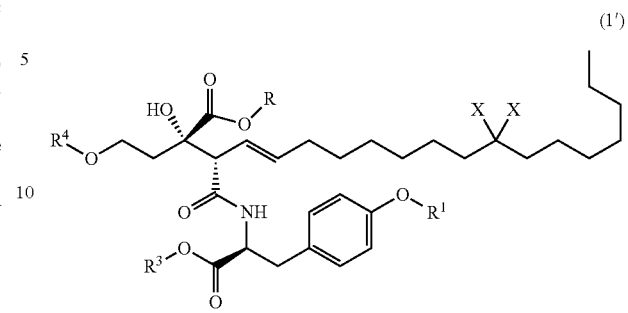

(1')

wherein R, $R^1$, $R^3$, $R^4$, and X are as defined above.

Examples of the compounds represented by formula (1) and pharmaceutically acceptable salts thereof include (5-methyl-2-oxo-[1,3]dioxol-4-yl)methyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate, represented by formula (1a) below, or a pharmaceutically acceptable salt thereof.

[Chem. 6]

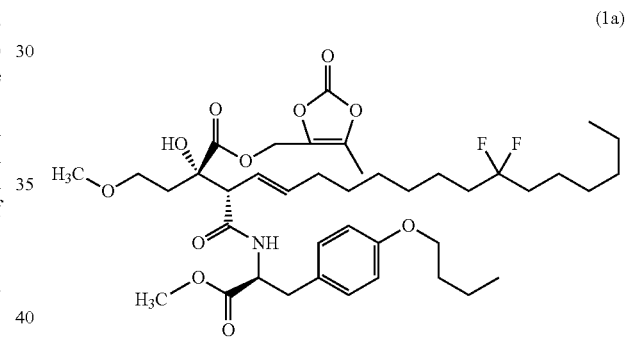

(1a)

Other examples of compounds represented by formula (1) and pharmaceutically acceptable salts thereof include compounds selected from (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoic acid and (E)-(2S,3S)-3-[(S)-2-(4-butoxy-phenyl)-1-carboxy-ethylcarbamoyl]-12,12-difluoro-2-hydroxy-2-(2-methoxy-ethyl)-nonadec-4-enoic acid, represented by formulae (1b) and (1c) below, or pharmaceutically acceptable salts thereof.

[Chem. 7]

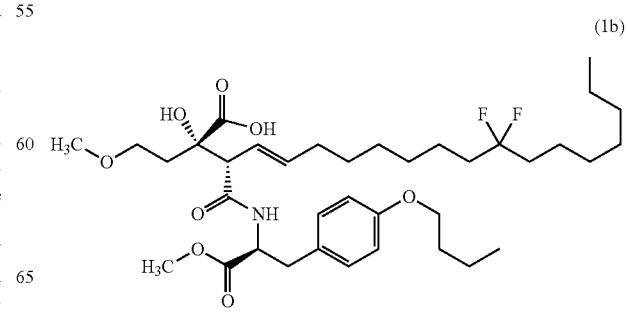

(1b)

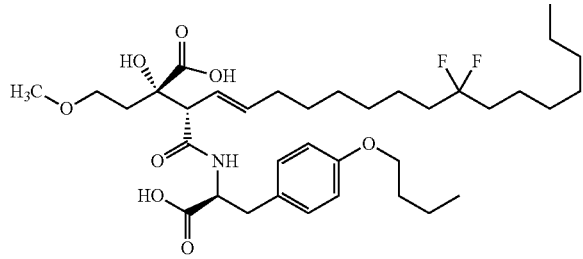

A pharmaceutically acceptable salt of a compound represented by formula (1) is not particularly limited, as long as it is pharmaceutically acceptable, and examples thereof include salts of mineral acids such as hydrochloric acid, sulfuric acid, nitric acid, phosphoric acid and hydrobromic acid; salts of organic acids such as acetic acid, tartaric acid, lactic acid, citric acid, fumaric acid, maleic acid, succinic acid, methanesulfonic acid, ethanesulfonic acid, benzenesulphonic acid, toluenesulfonic acid, naphthalenesulfonic acid, camphorsulfonic acid; and salts of alkali metals and alkaline earth metals such as sodium, potassium and calcium.

A compound according to the present invention can be synthesized, for example, by General Production Process-1.

General Production Process-1

[Chem. 8]

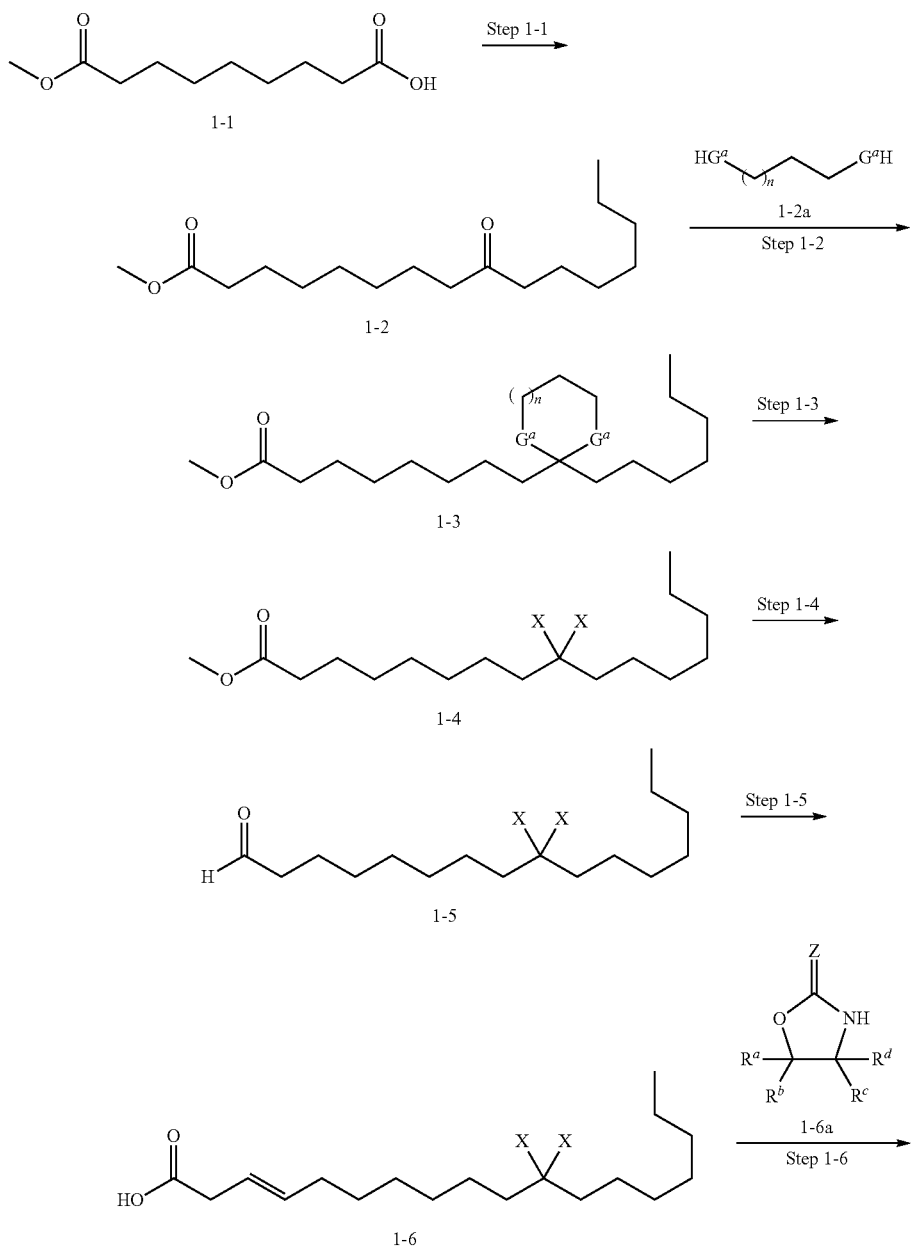

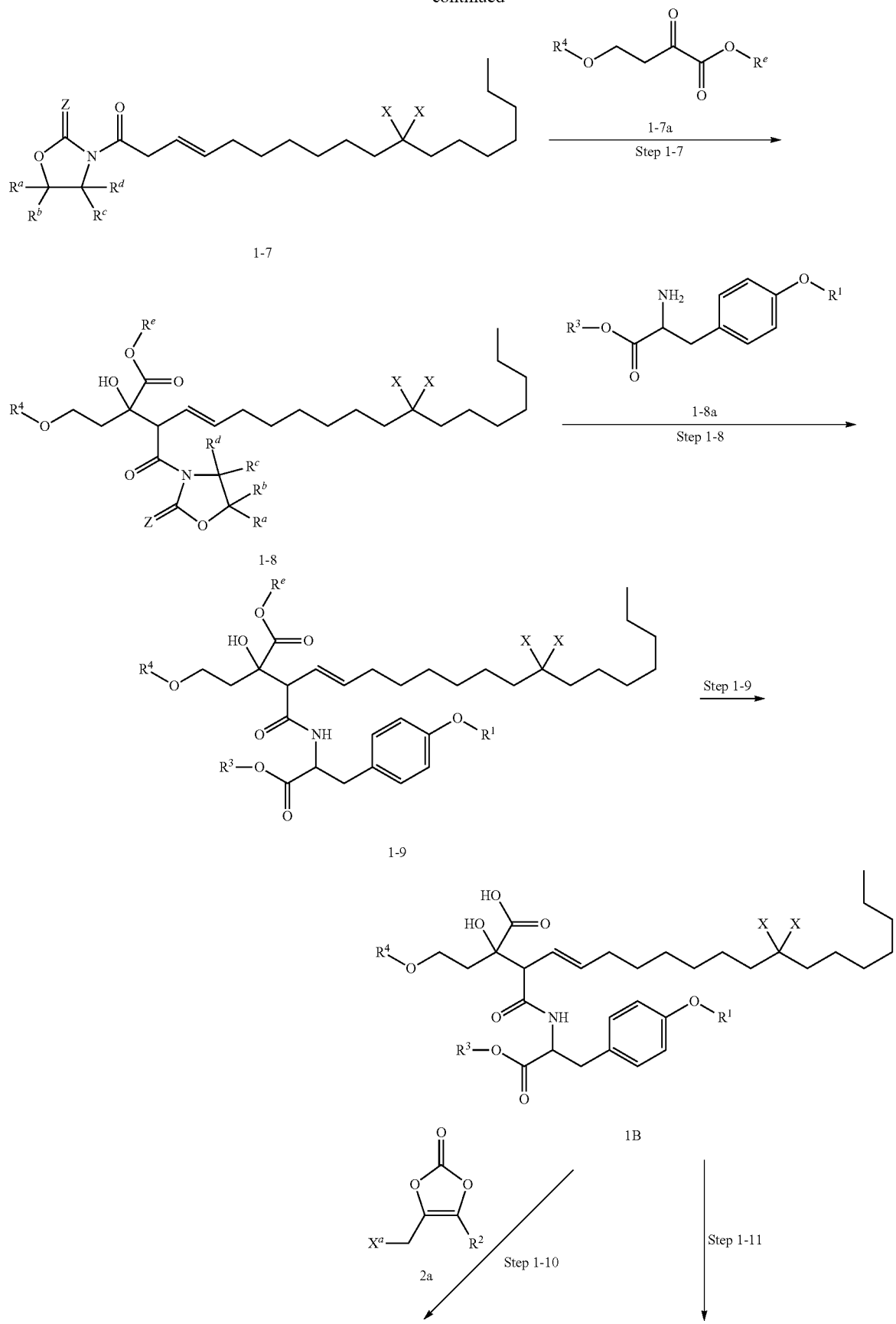

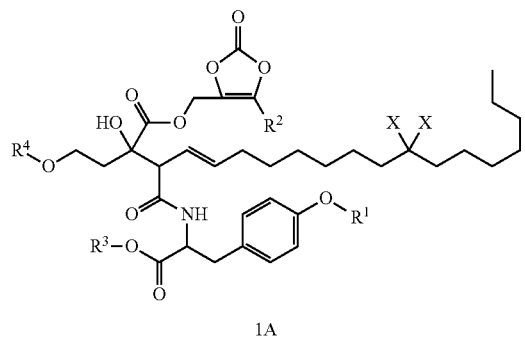

1A

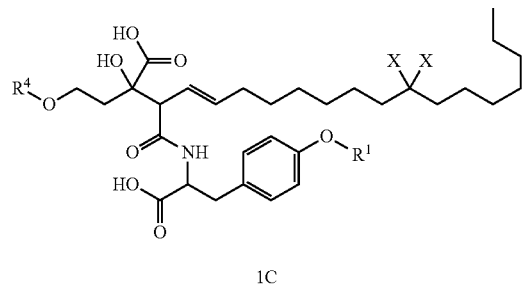

1C

In General Production Process-1 above, $G^a$ is an oxygen atom or a sulfur atom, and preferably a sulfur atom. n is an integer of 0 or 1, and preferably 0. $R^a$, $R^b$, $R^c$, and $R^d$ are the same or different, and each represent a hydrogen atom, optionally substituted aryl, optionally substituted heteroaryl, optionally substituted $C_{1-6}$ alkyl, optionally substituted linear or branched alkenyl or optionally substituted linear or branched alkynyl. $R^e$ is $C_{1-6}$ alkyl, and preferably branched $C_{3-5}$ alkyl. Z is an oxygen atom or a sulfur atom, and preferably a sulfur atom. $X^a$ is a halogen atom, and preferably a chlorine atom or a bromine atom. X, $R^1$, $R^2$, $R^3$, and $R^4$ are as defined above.

Step 1-1

Step 1-1 is constituted of a step (Step 1-1a) of converting carboxy in Compound 1-1 into —COB (B represents a leaving group such as a halogen atom, methoxymethylamino, 1-imidazolyl, or phenylthio) and a step (Step 1-1b) of further converting —COB into —CO n-heptyl.

Step 1-1a

Compound 1-1 is a commercially available compound (for example, Monomethyl Azelate (trade name), manufactured by Tokyo Chemical Industry Co., Ltd.). Carboxy of Compound 1-1 can be converted into —COB by reacting this Compound 1-1 with 1 equivalent to a large excess, preferably 1 to 3 equivalents of a halogenating agent such as a chlorinating agent such as oxalyl dichloride, thionyl chloride or phosphorus oxychloride, or a fluorinating agent such as cyanuric fluoride; an imidazolylating agent such as carbodiimidazole; or amine such as methoxymethylamine and an amidating agent; or with an acid halogenating agent such as pivaloyl chloride or acetyl chloride; or a thiolating agent such as phenylthiol, in the presence of 0.001 to 1 equivalent, preferably 0.005 to 0.1 equivalents of N,N-dimethylformamide, in an inert solvent for the reaction, or with no solvent depending on the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride and chloroform can be used alone or in admixture. In particular, toluene, N,N-dimethylformamide, and methylene chloride are preferable. The reaction is carried out at a temperature between −78 to 100° C., preferably 40 to 80° C. and is completed usually in 30 minutes to 10 hours. As an amidating agent, a condensation agent in Step 1-6 described below can be also used.

Step 1-1b

Compound 1-2 in which —COB has been converted into —CO n-heptyl can be obtained by reacting the compound obtained in Step 1-1a, in which carboxy of Compound 1-1 has been converted into —COB, with 1 to 10 equivalents, preferably 1 to 2 equivalents of a Grignard reagent such as n-heptylmagnesium bromide or n-heptylmagnesium iodide, or n-heptyllithium, in the presence of 0.0001 to 1 equivalent, preferably 0.001 to 0.01 equivalents of a catalyst, as needed, in an inert solvent for the reaction. The inert solvent for the reaction may be any solvent as long as it is inert for the reaction, and solvents such as, but not limited to, ethers such as diethyl ether, tetrahydrofuran and dioxane; benzene, n-hexane, toluene, cyclohexane, N,N-dimethylformamide and dimethyl sulfoxide can be used alone or in admixture. In particular, diethyl ether, tetrahydrofuran, and dioxane are preferable. The reaction is carried out at a temperature between −78 to 100° C., preferably −78 to 0° C., and is completed usually in 20 minutes to 5 hours. As a catalyst, for example, a copper compound, a cadmium compound, an iron compound, a cobalt compound, or a zinc compound is used. In particular, copper chloride and tris(2,4-pentadionato)iron (III) are preferable.

Step 1-2

Compound 1-3 in which carbonyl is protected can be obtained by reacting Compound 1-2 obtained in Step 1-1b with 1 to 10 equivalents, preferably 1 to 2 equivalents of Compound 1-2a, for example, ethylene glycol, propylene glycol, 1,2-ethanedithiol, 1,3-propanedithiol, preferably 1,2-ethanedithiol, in the presence of 0.1 to 5 equivalents, preferably 1 to 2 equivalents of an acid catalyst, in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, methylene chloride, chloroform and acetonitrile can be used alone or in admixture. In particular, benzene, toluene, and methylene chloride are preferable. The reaction is carried out at a temperature between −10 to 90° C., preferably −5 to 25° C., and is usually completed in 1 hour to 20 hours. As an acid catalyst, for example, methanesulfonic acid, toluenesulfonic acid, pyridinium p-toluenesulfonate, dilute hydrochloric acid, dilute sulphuric acid, acetic acid, trifluoroborane-diethyl ether complex, trimethylsilane chloride, aluminum oxide, titanium tetrachloride, copper chloride, adipic acid, selenium oxide, ruthenium chloride, or ion-exchange resin is used. In particular, toluenesulfonic acid, pyridinium p-toluenesulfonate, and a trifluoroborane-diethyl ether complex are preferable.

Step 1-3

Compound 1-4 in which carbonyl of Compound 1-2 has been converted into two halogen atoms can be obtained by reacting Compound 1-3 obtained in Step 1-2 with halogenating agent in an inert solvent for the reaction. The production process will be described for each halogen atom below.

When X is a fluorine atom, 1 to 50 equivalents, preferably 5 to 25 equivalents of a fluorinating agent, for example, a hydrogen fluoride-pyridine complex, N,N-diethyl-1,1,2,3,3,3-hexafluoro-1-propaneamine (Ishikawa's Reagent), N,N-diethylaminosulfur trifluoride (DAST), preferably hydrogen fluoride-pyridine complex is used. In addition, 1 to 10 equivalents, preferably 1 to 2 equivalents of a brominating agent, for example, 1,3-dibromo-5,5-dimethylhydantoin, N-bromosuccinimide (NBS), preferably N-bromosuccinimide may be and is preferably used simultaneously. The inert solvent for the reaction may be any solvent as long as it is inert for the reaction, and solvents such as, but not limited to, ethers such as diethyl ether, tetrahydrofuran, dioxane and ethylene glycol dimethyl ether; benzene, toluene, cyclohexane, 1,2-dichloroethane, ethyl acetate, N,N-dimethylformamide, dimethyl sulfoxide, methylene chloride, chloroform and acetonitrile can be used alone or in admixture. In particular, benzene, toluene, and methylene chloride are preferable. The reaction is carried out at a temperature between −78 to 30° C., preferably −78 to 0° C., and is usually completed in 1 hour to 12 hours.

When X is a chlorine atom, for example, 2 to 5 equivalents, preferably 2 to 4 equivalents of mercury chloride is used in an inert solvent for the reaction. The reaction is carried out at a temperature between −50 to 100° C., preferably 0 to 50° C.

Alternatively, 2 to 5 equivalents, preferably 2 to 4 equivalents of a chlorinating agent, for example, N-chlorosuccinimide or phosphorus pentachloride can be used in the presence of 2 to 10 equivalents, preferably 4 to 5 equivalents of a reaction accelerator in an inert solvent for the reaction. The reaction is carried out at a temperature between 0 to 100° C., preferably 0 to 40° C. As a reaction accelerator, for example, mercury chloride and methyl iodide are used.

In either case, the inert solvent for the reaction may be any solvent as long as it is inert for the reaction, and solvents such as, but not limited to, ethers such as diethyl ether, tetrahydrofuran, dioxane and ethylene glycol dimethyl ether; benzene, toluene, cyclohexane, 1,2-dichloroethane, ethyl acetate, N,N-dimethylformamide, dimethyl sulfoxide, methylene chloride, chloroform and acetonitrile can be used alone or in admixture. In particular, methylene chloride and toluene are preferable. The reaction is usually completed in 1 hour to 12 hours.

When X is a bromine atom, for example, 1 to 50 equivalents, preferably 5 to 20 equivalents of bromine is used. In addition, 1 to 5 equivalents, preferably 1 to 2 equivalents of mercury chloride may be and is preferably used simultaneously. The inert solvent for the reaction may be any solvent as long as it is inert for the reaction, and solvents such as, but not limited to, ethers such as diethyl ether, tetrahydrofuran, dioxane and ethylene glycol dimethyl ether; benzene, toluene, cyclohexane, 1,2-dichloroethane, ethyl acetate, N,N-dimethylformamide, dimethyl sulfoxide, methylene chloride, chloroforth and acetonitrile can be used alone or in admixture. In particular, methylene chloride is preferable. The reaction is carried out at a temperature between −50 to 100° C., preferably 0 to 20° C. and is usually completed in 1 hour to 12 hours.

When X is an iodine atom, for example, 1 to 20 equivalents, preferably 1.5 to 5 equivalents of an iodinating agent is used in the presence of 1 to 10 equivalents, preferably 1 to 2 equivalents of acetyl chloride. The inert solvent for the reaction may be any solvent as long as it is inert for the reaction, and solvents such as, but not limited to, ethers such as diethyl ether, tetrahydrofuran, dioxane and ethylene glycol dimethyl ether; benzene, toluene, cyclohexane, 1,2-dichloroethane, ethyl acetate, N,N-dimethylformamide, dimethyl sulfoxide, methylene chloride, chloroform and acetonitrile can be used alone or in admixture. In particular, acetonitrile is preferable. The reaction is carried out at a temperature between 0 to 100° C., preferably 80 to 90° C. and is usually completed in 1 hour to 12 hours. As an iodinating agent, for example, lithium iodide, sodium iodide or potassium iodide is used, and preferably sodium iodide is used.

Compound 1-4 in which X is an iodine atom can be also synthesized by directly converting carbonyl in Compound 1-2 into two iodine atoms with 1 to 30 equivalents, preferably 1 to 5 equivalents of an iodinating agent in the presence of 1 to 10 equivalents, preferably 1 to 2 equivalents of a base and 1 to 15 equivalents, preferably 2 to 6 equivalents of a hydrazonating agent in an inert solvent for the reaction. As a base, for example, triethylamine, N,N-dimethyl aminopyridine, N,N-diisopropylethylamine and pyridine can be used, and preferably triethylamine is used. As a hydrazonating agent, for example, t-butoxycarbonylhydrazine, monomethylhydrazine, or unsubstituted hydrazine, preferably unsubstituted hydrazine is used. Hydrazine may be anhydride or hydrate, but is preferably hydrate. For iodinating agent, 1,3-diiodo-5,5'-dimethylhydantoin (DIH), N-iodosuccinimide (NIS), or preferably iodine is used. The inert solvent for the reaction may be any solvent as long as it is inert for the reaction, and solvents such as, but not limited to, diethyl ether, tetrahydrofuran, acetonitrile, N,N-dimethylformamide, methanol, ethanol and propanol can be used alone or in admixture. In particular, ethanol is preferable. The reaction is usually completed in 1 hour to 12 hours.

Step 1-4

Compound 1-5 can be obtained by reacting Compound 1-4 obtained in Step 1-3 with 1 to 2 equivalents, preferably 1 to 1.5 equivalents of a reducing agent in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene and cyclohexane can be used alone or in admixture. In particular, diethyl ether, tetrahydrofuran and toluene are preferable. The reaction is carried out at a temperature between −100 to −30° C., preferably −80 to −60° C. and is completed usually in 30 minutes to 4 hours. As a reducing agent, for example, diisobutylaluminum hydride, sodium dihydridobis(2-methoxyethoxy)aluminate, lithium boron tetrahydride, lithium tri-s-butylborohydride, potassium tri-s-butylborohydride, or lithium triethylborohydride is used. In particular, diisobutylaluminum hydride is preferable.

Step 1-5

Compound 1-6 can be obtained by reacting Compound 1-5 obtained in Step 1-4 with 1 to 5 equivalents, preferably 1 to 2.5 equivalents of malonic acid in the presence of 1 to 20 equivalents, preferably 1 to 2.5 equivalents of a base in an inert solvent for the reaction. The inert solvent for the reaction may be any solvent as long as it is inert for the reaction, and solvents such as, but not limited to, ethers such as diethyl ether, tetrahydrofuran and dioxane; benzene, n-hexane, toluene, cyclohexane, 1,2-dichloroethane, ethyl acetate, N,N-dimethylformamide (DMF), dimethyl sulfoxide, methylene chloride and chloroform can be used alone or in admixture. In particular, benzene, toluene, a mixture of benzene and DMF, and a mixture of toluene and DMF are preferable. The reaction is carried out at a temperature between 40 to 150° C., preferably 70 to 110° C. and is usually completed in 1 hour to 30 hours. As a base, for example, triethylamine, N,N-diisopropylethylamine, pyridine, diazabicycloundecene, potassium t-butoxide, or sodium methoxide is used. In particular, triethylamine and N,N-diisopropylethylamine are preferable.

Step 1-6

Compound 1-7 can be obtained by reacting Compound 1-6 obtained in Step 1-5 with 1 to 3 equivalents, preferably 1 to 1.2 equivalents of Compound 1-6a, a chiral building block in the presence of a catalytic quantity to 5 equivalents, preferably 0.01 to 0.5 equivalents of a base and 1 to 10 equivalents, preferably 1 to 1.3 equivalents of a condensation agent in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, N,N -dimethylformamide, dimethyl sulfoxide, methylene chloride and chloroform can be used alone or in admixture. In particular, toluene and methylene chloride are preferable. The reaction is carried out at a temperature between 0 to 50°C., preferably 0 to 30°C. and is completed usually in 30 minutes to 50 hours. As a base, for example, triethylamine, N,N-dimethylaminopyridine, N,N-diisopropylethylamine, or pyridine is used. In particular, triethylamine and N,N -dimethylaminopyridine are preferable. As a condensation agent, for example, dicyclohexylcarbodiimide (DCC), diisopropylcarbodiimide (DIPC), 1-ethyl-3-(3-dimethylaminopropyl)carbodiimide (which may be abbreviated to EDC or WSCI) and hydrochloride thereof (WSC-HCl), benzotriazol-1-yl-tris(dimethylamino)phosphonium hexafluorophosphide salt (BOP), or diphenylphosphoryl azide (DPPA) can be used alone, or in combination with N-hydroxysuccinimide (HONSu), 1-hydroxybenzotriazole (HOBt), 3-hydroxy -4-oxo-3,4-dihydro-1,2,3-benzotriazine (HOObt) or the like. In particular, 1-ethyl-3-(3-dimethylaminopropyl)carbodiimide hydrochloride is preferable. As Compound 1-6a, for example, oxazolidine-2-thione containing (R or S)-4-alkyl or 4,4-dialkyl, 5-alkyl or 5,5-dialkyl or a combination thereof, or oxazolidin-2-one containing (R or S)-4-alkyl or 4,4-dialkyl, 5-alkyl or 5,5-dialkyl or a combination thereof can be used. In particular, (S)-4-isopropyl-5,5-diphenyloxazolidin-2-one- and (S)-4-isopropyl-5,5-diphenyloxazolidine-2-thione are preferable.

Step 1-7

Compound 1-8 can be obtained by reacting Compound 1-7 obtained in Step 1-6 with 1 to 3 equivalents, preferably 1 to 2 equivalents of Compound 1-7a in the presence of 1 to 5 equivalents, preferably 1 to 1.5 equivalents of a base in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, and N,N-dimethylformamide can be used alone or in admixture. In particular, tetrahydrofuran and toluene are preferable. The reaction is carried out at a temperature between −78 to 0° C., preferably −78 to −25° C., and is completed usually in 30 minutes to 10 hours. As a base, for example, lithium hexamethyldisilazide and lithium diisopropylamide are used, and lithium hexamethyldisilazide is preferable. This step progresses in the absence or presence of lithium chloride, but Compound 1-7 obtained in the presence of lithium chloride is highly stereoselective. Therefore, it is preferable to carry out this step in the presence of 1 to 5 equivalents, preferably 2 to 4 equivalents of lithium chloride based on Compound 1-7.

Step 1-8

Compound 1-9 can be obtained by dissolving Compound 1-8 obtained in Step 1-7 and 1 to 5 equivalents, preferably 1 to 2 equivalents of Compound 1-8a in an inert solvent for the reaction, distilling off the solvent, and heating the resulting mixture. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform and acetonitrile can be used alone or in admixture. In particular, methylene chloride is preferable. The heating is carried out at a temperature between 30 to 100° C., preferably 40 to 60° C., and is usually completed in 12 hours to 5 days.

When $R^3$ of Compound 1-8a is a hydrogen atom, —O—$R^3$ can be converted into —O—$R^e$, wherein $R^e$ is preferably t-butyl, to protect carboxy before Step 1-8. Carboxy can be protected using a method described in "Theodora Greene (1999), Protective Groups in Organic Synthesis, Wiley-Interscience". —O—$R^e$ can be converted into —O—$R^3$, for example, by conducting Step 1-9.

Step 1-9

Compound 1B can be obtained by deprotecting Compound 1-9 obtained by

Step 1-8 with a deprotecting agent for the tertiary carboxy. Conditions of this reaction are suitably selected based on the type of the protecting group for the tertiary carboxy, but the following conditions are preferable. Compound 1B can be obtained by reacting Compound 1-8 with 1 to 1000 equivalents, preferably 300 to 700 equivalents of an acid in an inert solvent for the reaction. The inert solvent for the reaction may be any solvent as long as it is inert for the reaction, and solvents such as, but not limited to, ethers such as diethyl ether, tetrahydrofuran and dioxane; benzene, n-toluene, cyclohexane, 1,2-dichloroethane, ethyl acetate, N,N-dimethylformamide, dimethyl sulfoxide, methylene chloride, chloroform, acetonitrile, and water can be used alone or in admixture. In particular, methylene chloride is preferable. The reaction is carried out at a temperature between −20 to 90° C., preferably 0 to 30° C., and is usually completed in 15 minutes to 24 hours. As an acid, for example, trifluoroacetic acid (TFA), trifluoroacetic acid anhydride (TFAA), formic acid, acetic acid, hydrochloric acid, oxalic acid, p-toluenesulfonic acid, trifluoromethanesulfonic acid, or trifluoroborane-diethyl ether complex is used. In particular, trifluoroacetic acid is preferable.

Compound 1B is a pharmacologically active ingredient produced in vivo. when Compound 1A, a prodrug, is administered to a mammal, such as human or rat. At the same time, it can be also used as an intermediate to synthesize Compound 1A as shown in Step 1-10.

Step 1-10

Compound 1A can be obtained by reacting Compound 1B obtained in Step 1-9 with 1 to 5 equivalents, preferably 1 to 3 equivalents of Compound 2a in the presence of 1 to 100 equivalents, preferably 1 to 20 equivalents of a base in an inert solvent for the reaction. The inert solvent for the reaction may be any solvent as long as it is inert for the reaction, and solvents such as, but not limited to, dimethyl sulfoxide, dimethyl acetamide, dimethyl imidazolidinone, N,N-dimethylformamide, N-methylpyrrolidone, acetonitrile, 1,2-dichloroethane, methylene chloride, chloroform and acetonitrile can be used alone or in admixture. In particular, N,N-dimethylformamide is preferable. As a base, for example, lithium hydroxide, sodium hydroxide, potassium hydroxide, calcium hydroxide, barium hydroxide, cesium hydroxide, potassium carbonate, sodium carbonate, sodium bicarbonate, triethylamine, N,N-dimethylaminopyridine, N,N-diisopropylethylamine or pyridine is used. In particular, sodium bicarbonate is preferable. The reaction is carried out at a temperature between 0 to 100° C., preferably 10 to 35° C. and is usually completed in 1 hour to 24 hours. In addition, 1 to 3 equivalents, preferably 1 to 2 equivalents of sodium iodide may be and is preferably used simultaneously to promote the reaction.

Step 1-11

Compound 1C can be obtained by reacting Compound 1B, obtained in Step 1-9, wherein $R^3$ is $C_{1-6}$ alkyl with 1 to 20 equivalents, preferably 4 to 8 equivalents of a base in the presence of water in an inert solvent for the reaction. The inert solvent for the reaction may be any solvent as long as it is inert for the reaction, and solvents such as, but not limited to, ethers such as diethyl ether, tetrahydrofuran and dioxane; N,N-dimethylformamide, dimethyl sulfoxide, acetonitrile and water can be used alone or in admixture. In particular, water-containing acetonitrile is preferable. As a base, for example, triethylamine, N,N-dimethyl aminopyridine, N,N -diisopropylethylamine or pyridine is used. In particular, triethylamine is preferable. The reaction is carried out at a temperature between 0 to 100°C., preferably 30 to 70 °C. and is usually completed in 1 hour to 15 hours. In addition, 10 to 50 equivalents, preferably 15 to 30 equivalents of lithium bromide may be and is preferably used simultaneously to promote a reaction.

Compound 1C is a major metabolite of Compound 1B, and has an anti-HCV activity approximately equivalent to that of Compound 1B. At the same time, it can be used as an intermediate to synthesize Compounds 1A and 1B. For example, Compound 1B wherein $R^3$ is $C_{1-6}$ alkyl can be obtained by subjecting Compound 1C to a usual esterification reaction. In this reaction, Compound 1B wherein $R^3$ is $C_{1-6}$ alkyl can be obtained by protecting the tertiary carboxy of Compound 1C, subsequently esterifying the secondary carboxy, and deprotecting the tertiary carboxy. Examples of the usual esterification reaction include, for example, reactions with TMS diazomethane, dehydration condensation reactions with $C_{1-6}$ alcohol using an acid catalyst or a condensation agent, reactions with $C_{1-6}$ alkyl alcohol in the presence of a base after conversion to carboxylic acid halide, and reactions with halogenated $C_{1-6}$ alkyl or tosylated $C_{1-6}$ alkyl in the presence of a base.

When $R^3$ is $C_{1-6}$ alkyl, Compound 1A wherein $R^3$ is a hydrogen atom can be obtained by subjecting Compound 1A to Step 1-11.

Furthermore, Compound 1A wherein $R^3$ is a hydrogen atom can be obtained by subjecting Compound 1C to Step 1-10. In this reaction, Compound 1A wherein $R^3$ is a hydrogen atom can be obtained by protecting the secondary carboxy in Compound 1C, subsequently reacting the tertiary carboxy with Compound 2a, and deprotecting the secondary carboxy. As reaction conditions for the protection and the deprotection, conditions described in "Theodora Greene (1999), Protective Groups in Organic Synthesis, Wiley-Interscience" can be used.

Compound 1-7a to be used in Step 1-7 can be synthesized, for example, according to General Production Process-2 below.

General Production Process-2

[Chem. 9]

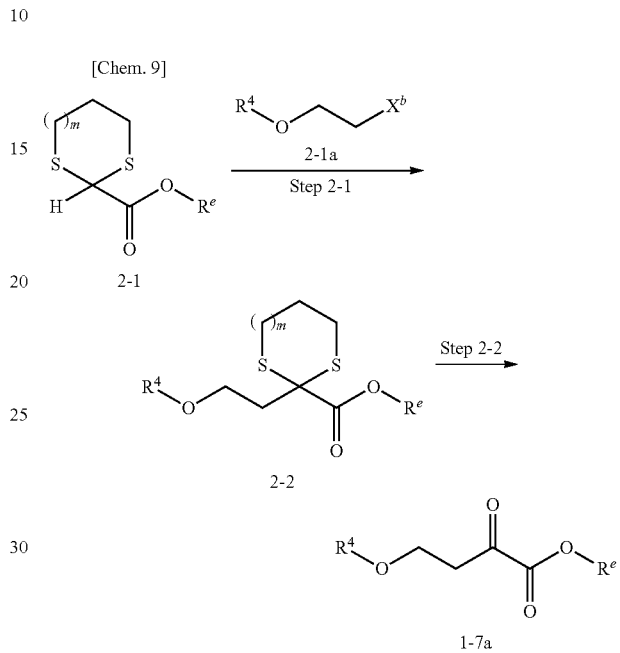

wherein m represents an integer of 0 or 1, preferably 1. $X^b$ represents a halogen atom or a leaving group, preferably a bromine atom. $R^e$ and $R^4$ are as defined above.

Step 2-1

Compound 2-2 can be obtained by reacting Compound 2-1 with 1 to 10 equivalents, preferably 1 to 3 equivalents of Compound 2-1a in the presence of 1 to 5 equivalents, preferably 1 to 2 equivalents of a base in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, n-hexane and cyclohexane can be used alone or in admixture. In particular, diethyl ether, tetrahydrofuran, n-hexane or a mixture thereof is preferably used. The reaction is carried out at a temperature between −100 to 50° C., preferably −80 to 30° C. and is completed usually in 10 minutes to 24 hours. As a base, for example, sodium hydride, potassium hydride, lithium diisopropylamide, n-butyllithium, or t-butyllithium is used. In particular, n-butyllithium is preferable. Compound 2-1a is commercially available. In addition, Compound 2-1 is disclosed as Compound 4-3 in General Production Process-4, for example, Compound 17 in Example 4 in PTL4 (International Publication No. 2006/088071).

Step 2-2

Compound 1-7a can be obtained by reacting Compound 2-2 obtained in Step 2-1 with 1 to 20 equivalents, preferably 1 to 10 equivalents of an oxidizing agent such as iodine, N-bromosuccinimide (NBS), N-chlorosuccinimide (NCS), bistrifluoroacetoxyiodobenzene, sodium chlorite, and ortho-iodoxybenzoic acid or an alkylating agent such as methyl iodide, ethyl iodide and methyl bromide in the presence of water in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, acetone, and acetonitrile can be used alone or in admixture. In particular, acetone and acetonitrile are preferable. The reaction is carried out at a temperature between −60 to 30° C., preferably −30 to 0° C., and is completed usually in 15 minutes to 5 hours. As an oxidizing agent, for example, iodine or N-bromosuccinimide is preferable. As an alkylating agent, methyl iodide is preferable. When N-bromosuccinimide is used for the reaction, 1 to 20 equivalents, preferably 1 to 5 equivalents of lutidine and silver nitrate may be added in the reaction.

Compound 1-8a used in Step 1-8 can be synthesized, for example, according to General Production Process-3 below.

General Production Process-3

[Chem. 10]

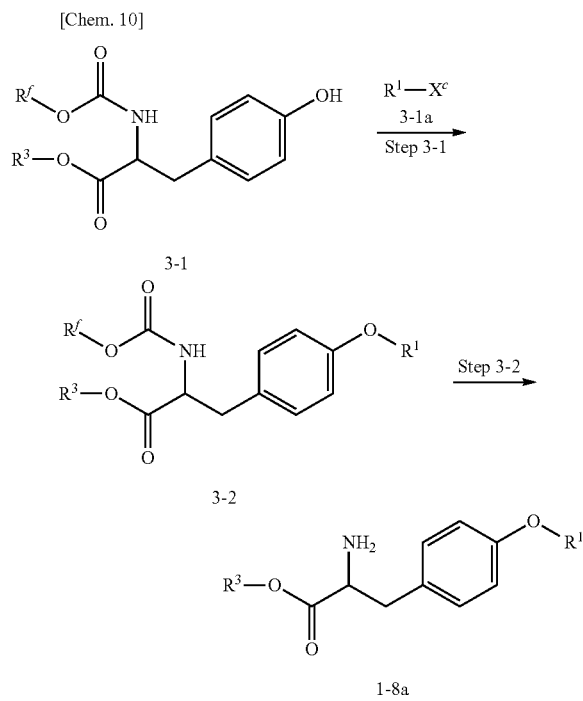

wherein $R^f$ represents $C_{1-6}$ alkyl or aryl $C_{1-6}$ alkyl, preferably t-butyl. $X^c$ represents a halogen atom, preferably an iodine atom. $R^1$ and $R^3$ are as defined above.

Step 3-1

Compound 3-2 can be obtained by reacting Compound 3-1 with 1 to 10 equivalents, preferably 1 to 2 equivalents of Compound 3-1a in the presence of 1 to 10 equivalents, preferably 1 to 1.5 equivalents of a base in an inert solvent for the reaction. The inert solvent for the reaction may be any solvent as long as it is inert for the reaction, and solvents such as, but not limited to, ethers such as tetrahydrofuran and dioxane; N,N-dimethyl acetamide, and N,N-dimethylformamide can be used alone or in admixture. In particular, N,N-dimethylformamide is preferable. The reaction is carried out at a temperature between 0 to 100° C., preferably 20 to 60° C. and is usually completed in 1 hour to 48 hours. As a base, for example, sodium hydride, potassium hydride, lithium diisopropylamide, n-butyllithium, t-butyllithium, sodium carbonate, potassium carbonate, magnesium carbonate, sodium hydrogen carbonate, lithium hydroxide, sodium hydroxide, or potassium hydroxide is used. In particular, potassium carbonate is preferable. Compound 3-1 is commercially available, for example (N-BOC-L-tyrosine, Wako Pure Chemical Industries, Ltd.). Alternatively, Compound 3-1 can be readily synthesized from tyrosine, and can be obtained by protecting amino with a suitable protecting group such as t-butoxycarbonyl and benzyloxycarbonyl. As reaction conditions for this reaction, conditions for protection described in "Theodora Greene (1999), Protective Groups in Organic Synthesis, Wiley-Interscience" are used.

Step 3-2

Compound 1-8a can be obtained by deprotecting amino in Compound 3-2 obtained in Step 3-1 using 1 to 10 equivalents, preferably 1 to 3 equivalents of an acid in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, n-hexane and cyclohexane can be used alone or in admixture. In particular, ethyl acetate and tetrahydrofuran are preferable. The reaction is carried out at a temperature between −100 to 50° C., preferably −80 to 30° C. Examples of the acid include, for example, trifluoroacetic acid and hydrogen chloride. Preferably examples include hydrogen chloride. Conditions for deprotection of amino described in "Theodora Greene (1999), Protective Groups in Organic Synthesis, Wiley-Interscience" can be used.

Compound 2a used in Step 1-10 can be synthesized, for example, according to General Production Process-4. Compound 2a wherein $R^2$ is methyl, and $X^a$ is a chlorine atom or a bromine atom can be commercially available as 4-chloromethyl-5-methyl-1,3-dioxol-2-one (Tokyo Chemical Industry Co., Ltd.) or 4-bromomethyl-5-methyl-1,3-dioxol-2-one (Apollo Scientific Ltd.).

General Production Process-4

[Chem. 11]

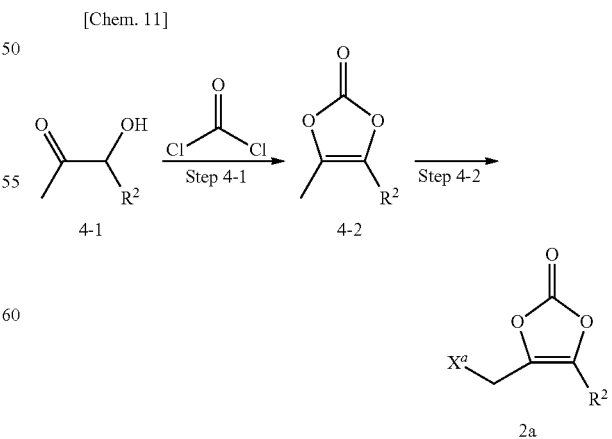

wherein $R^2$ and $X^a$ are as defined above.

Step 4-1

Compound 4-2 can be obtained by reacting Compound 4-1 with 1 to 2 equivalents, preferably 1 to 1.2 equivalents of a phosgene equivalent in the presence of 1 to 2 equivalents, preferably 1 to 1.2 equivalents of a base in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, acetone and acetonitrile can be used alone or in admixture. In particular, methylene chloride is preferable. The reaction is carried out at a temperature between −30 to 150° C., preferably 0 to 40° C. and is usually completed in 1 hour to 24 hours. As a base, for example, triethylamine, N,N-diisopropylethylamine, 1,8-diazabicyclo [5.4.0]-7-undecene, pyridine, dimethylaminopyridine or pyrazine is used. In particular, pyridine is preferable. Examples of the phosgene equivalent include, for example, phosgene and carbonyldiimidazole. Compound 4-1 is commercially available, or can be readily synthesized by a known method.

Step 4-2

Compound 2a can be obtained by reacting Compound 4-2 obtained in Step 4-1 with 1 to 10 equivalents, preferably 1 to 5 equivalents of a halogenating agent in an inert solvent for the reaction. The inert solvent for the reaction may be any solvent as long as it is inert for the reaction, and solvents such as, but not limited to, ethers such as diethyl ether, tetrahydrofuran and dioxane; benzene, toluene, cyclohexane, 1,2-dichloroethane, methylene chloride, chloroform and carbon tetrachloride can be used alone or in admixture. In particular, methylene chloride is preferable. The reaction is carried out at a temperature between −30 to 100° C., preferably −10 to 0° C. and is usually completed in 1 hour to 12 hours. As the halogenating agent, for example, N-chlorosuccinimide, N-bromosuccinimide, or N-iodosuccinimide is used. As needed, 0.05 to 0.1 equivalents of azobisisobutyronitrile, benzoylperoxide, or the like, preferably azobisisobutyronitrile may be used simultaneously as a catalyst.

The compound of the present invention can be used as medicine. In particular, it can be used in the prevention and/or treatment of hepatitis C virus infection, especially hepatitis C because it has a superior anti-HCV activity.

Accordingly, the present invention relates to a pharmaceutical composition, in particular, a prophylactic and/or therapeutic agent for hepatitis C virus infection, including a compound of the present invention as an active ingredient.

As an index to evaluate anti-HCV activity, the IC50 value of anti-replicon activity can be used. The replicon assay is an in vitro RNA reproduction system of hepatitis C virus, and the assay system is used to estimate the proliferation ability of HCV at the cellular level. Because there has been no cell culture system for HCV in vitro, in order to evaluate anti-HCV drugs, a substitute virus assay using another related virus had to be used in the past. In recent years, it has become possible to observe HCV replication in vitro using non-structural regions of HCV, according to Lohmann et al. (V. Lohmann et al., Science: 285, 110-113, 1999), and replicon assay methods have enabled easy evaluation of anti-HCV agents. While the original method involves detecting the number of HCV-RNAs by polymerase chain reaction (PCR), an alternative method involving introduction of a reporter gene into an HCV gene is generally used and utilized for the evaluation as a more effective assay method.

As a reporter gene, for example, a gene into which a luciferase gene derived from a firefly is introduced can be used. Specifically, according to the method of Krieger et al. (N. Krieger et al., J. Virology: 75, 4614-24, 2001), a firefly luciferase gene is introduced, in a form fused with a neomycin-resistant gene, immediately downstream of an internal ribosome entry site (IRES) of the HCV gene. After synthesizing the RNA in vitro, it is introduced into suitable cells by, for example, electroporation to obtain firefly luciferase HCV replicon cells. These cells are seeded in wells of 96-well plates, to which a diluted test substance is added, and cultured for several days. The substrate is then added, and the luminescence is measured with a plate reader. All values are expressed as differences from the background which is measured without cells and IC50 (50% inhibitory concentration) of the test substance can be calculated based on the value when no test substance is added defined as 0% inhibition.

This replicon assay system is considered to faithfully reproduce the replication process of HCV in cells and it is a cell-based assay system useful for the identification of compounds that inhibit the replication of HCV.

As used herein, the term "treatment of hepatitis C virus infection" refers to eliminating HCV or reducing HCV levels, suppressing further propagation of HCV, and reducing HCV infection symptoms by administering a pharmaceutical composition of the present invention to a subject. Examples of a symptom of HCV infection include hepatitis C, liver cirrhosis, liver fibrosis, and liver cancer.

The amount of the compound of the present invention included as an active ingredient in the aforementioned pharmaceutical composition is not particularly limited, and selected widely as appropriate, and, for example, 0.1 to 99.5% by weight, preferably 0.5 to 90% by weight.

The aforementioned pharmaceutical composition may include an ingredient having anti-HCV activity besides a compound of the present invention as an active ingredient.

A compound of the present invention can be formulated as a principal ingredient according to a usual method using known adjuvants that may be used ordinarily in the art of pharmaceutical preparation such as excipients, binders, disintegrators, lubricants, flavoring agents, solubilizing adjuvants, suspending agents, and coating agents. When shaping into the form of tablets, a wide variety of substances conventionally known as carriers in the art can be used, and examples include excipients such as lactose, sucrose, sodium chloride, glucose, urea, starch, calcium carbonate, kaolin, crystalline cellulose, and silicic acid; binders such as water, ethanol, propanol, simple syrup, glucose solution, starch solution, gelatin solution, carboxymethylcellulose, shellac, methylcellulose, potassium phosphate, and polyvinylpyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic monoglyceride, starch, and lactose; disintegration inhibitors such as sucrose, stearin, cacao butter, and hydrogenated oil; absorbefacients such as quaternary ammonium salts and sodium lauryl sulfate; moisturizers such as glycerin and starch; adsorbents such as starch, lactose, kaolin, bentonite, and colloidal silicic acid; and lubricants such as purified talc, stearate, boric acid powder, and polyethylene glycol.

Tablets can be prepared, as necessary, as ordinary coated tablets, such as sugar-coated tablets, gelatin-coated tablets, enteric-coated tablets, and film-coated tablets, or as double layered tablets or multilayered tablets. When shaping into the form of pills, a wide variety of substances conventionally known as carriers in the art can be used, and examples include excipients such as glucose, lactose, cacao butter, starch, hardened vegetable oil, kaolin, and talc; binders such as gum arabic powder, tragacanth powder, gelatin, and ethanol; and disintegrators such as laminaran agar. When shaping into the form of suppositories, a wide variety of substances conventionally known as carriers in this art can be used, and examples include polyethylene glycol, cacao butter, higher alcohols, esters of higher alcohols, gelatin, and semi-synthetic glycerides. When preparing injections, solutions and suspensions are sterilized and are preferably isotonic with blood, and when making these solution, emulsion, and suspension forms, any substances commonly used as diluents in the art can be used, such as water, ethanol, propylene glycol, ethoxylated isostearyl alcohol, polyoxylated isostearyl alcohol, and polyoxyethylene sorbitan fatty acid esters. In these instances, adequate amounts of sodium chloride, glucose, or glycerin can be contained in the pharmaceutical preparations to prepare isotonic solutions, and ordinary solubilizing adjuvants, buffers, analgesic agents, and such may also be added. The pharmaceutical preparations may further contain, as necessary, coloring agents, preservatives, flavors, flavoring agents, and sweeteners, as well as other pharmaceutical agents.

The pharmaceutical composition of the present invention is preferably administered in a dosage unit form. While the pharmaceutical composition of the present invention can be administered orally, the route of administration is not particularly limited, and it can be also administered interstitially (subcutaneously, intramuscularly, intravenously, and such), topically (percutaneously), or transrectally. Naturally, the pharmaceutical compositions are administered in dosage forms suited to these administration methods.

When administering the compounds of the present invention as pharmaceutical agents, the doses of the antiviral agents are preferably adjusted with consideration of the patient's condition such as age and weight, the administration route, and the characteristics and severity of the disease; however, for humans, the daily dose of the active ingredient of the compound of the present invention for adults is usually within the range of 0.1 to 2000 mg. While doses lower than the above range may be sufficient in some cases, doses higher than this range may be required in other cases. When a high dose is used, the daily dosage is preferably administered in several divided doses.

The above-mentioned oral administration can be carried out using solid, powdered, or liquid dosage units, such as powders, powdered drugs, tablets, sugar-coated agents, capsules, drops, sublingual tablets, and other dosage forms.

The above-mentioned interstitial administration can be carried out, for example, using liquid unit dosage forms for subcutaneous, intramuscular, or intravenous injections, such as solutions and suspensions. These are produced by suspending or dissolving a certain amount of a compound of the present invention in a non-toxic liquid carrier suitable for purposes of injection, such as an aqueous or oily medium, and then sterilizing this suspension or solution.

The above-mentioned topical administration (percutaneous administration and such) can be carried out using external preparation forms such as solutions, creams, powders, pastes, gels, and ointments. These are produced by combining a certain amount of a compound of the present invention with one or more of a flavor, coloring agent, filler, surfactant, moisturizer, emollient, gelling agent, carrier, preservative, and stabilizer suited to the aim of the external preparation.

The above-mentioned transrectal administration can be carried out using a suppository or the like, prepared by mixing a certain amount of a compound of the present invention or a pharmaceutically acceptable salt thereof into a low melting point solid composed of, for example, higher esters such as myristyl palmitate, polyethylene glycol, cacao butter, or a mixture thereof.

The above-mentioned administrations can be carried out using liquid unit dosage forms for subcutaneous, intramuscular, or intravenous injections, such as solutions or suspensions. These are produced by suspending or dissolving a certain amount of a compound of the present invention in a non-toxic liquid carrier appropriate to the purpose of the injection, such as an aqueous or oily medium, and then sterilizing this suspension or solution.

EXAMPLES

Hereinafter, aspects of the present invention will be specifically described with reference to Examples (Production Example and Test Examples).

In the following Production Example (Synthesis Example), $^1$H-NMR analysis was carried out with JNM-EX270 (JEOL Ltd.; 270 MHz), JNM-GSX400 (JEOL Ltd.; 400 MHz), 400-MR (Varian; 400 MHz); and $^1$H-NMR data was expressed in ppm (parts per million, $\delta$) and compared with the deuterium lock signal obtained from the sample solvent.

Mass spectrum data was measured with MS Auto Purification System (trade name: FuractionLynx, Waters) and AQA (Finningan). The conditions for HPLC in LCMS measurements were as follows: a gradient system of A:B=10:90 in which Mobile Phase Liquid A: acetonitrile (containing 0.05% trifluoroacetic acid (TFA)), Mobile Phase B: distilled water (containing 0.05% TFA) (the solvents were products from Wako Pure Chemical Industries, Ltd.) at 0 minutes; A:B=95:5 at 3.5 minutes to A:B=10:90 at 4.5 minutes; a flow rate of 4 mL/min; and the column Sunfire C18, 5 µM, φ4.6 mm×50 mm were used.

Analysis was carried out using gradient systems (1) to (4) depending on the physical properties of compounds.

(1) A gradient system of A:B=30:70 at 0 minutes to A:B=98:2 at 5 minutes (2) A gradient system of A:B=40:60 at 0 minutes to A:B=98:2 at 5 minutes (3) A gradient system of A:B=60:40 at 0 minutes to A:B=98:2 at 5 minutes (4) A gradient system of A:B=60:40 at 0 minutes to A:B=98:2 at 10 minutes Conditions of HPLC in purification were as follows.

Detection unit: Otuka Electronics Photal MCPD-3600, Column: Tosoh ODS-80TS (20×250 mm).

Mobile phase: acetonitrile-distilled water (containing 0.05% TFA), Flow rate: 15 mL/min.

Gradient conditions: 0 min. (50% acetonitrile)→0.5 min. (50%)→1 min. (70%)→18 min. (98%)→20 min. (98%) →21 min. (50%)

The expression "purification on Biotage" or "purification with SP1" refers to the automatic purification with a specially adapted cartridge (silica gel) in SP1™ FLASH purification system (PART No. SP1-B2AO, Biotage).

Commercially available reagents were used in the reactions without any pretreatment such as distillation and recrystallization. When a commercially available solvent was used as a reaction solvent, a dehydrated solvent was used.

All chemical reactions were carried out in a nitrogen or argon atmosphere, and at room temperature, unless otherwise indicated. Evaporation of the solvent was done under reduced pressure unless otherwise noted.
Production Example 5
Compounds No. 5514403, No. 5526064, No. 6808755
The title compounds were produced according to the following synthetic scheme.
[Chem. 12]
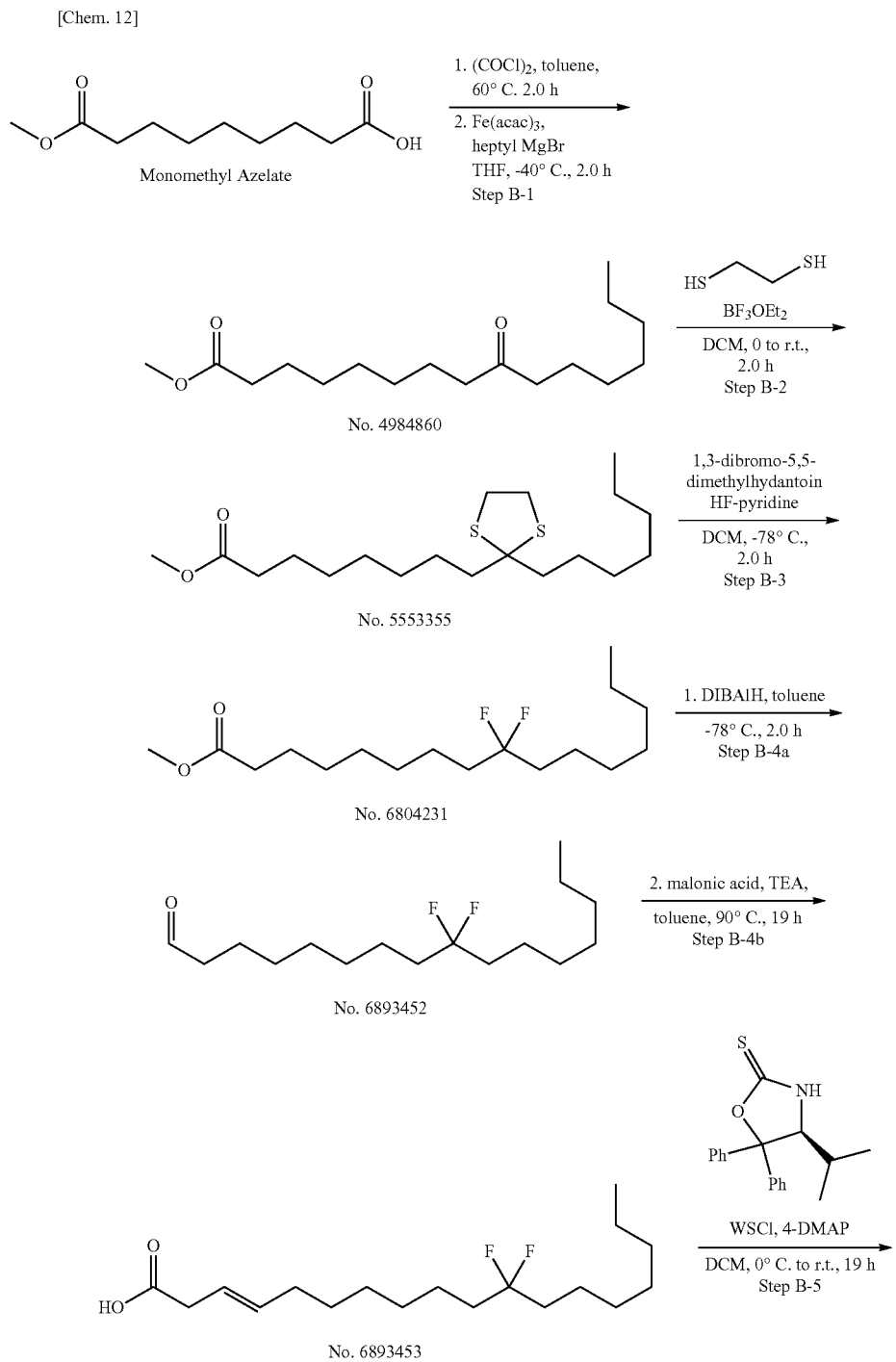

-continued
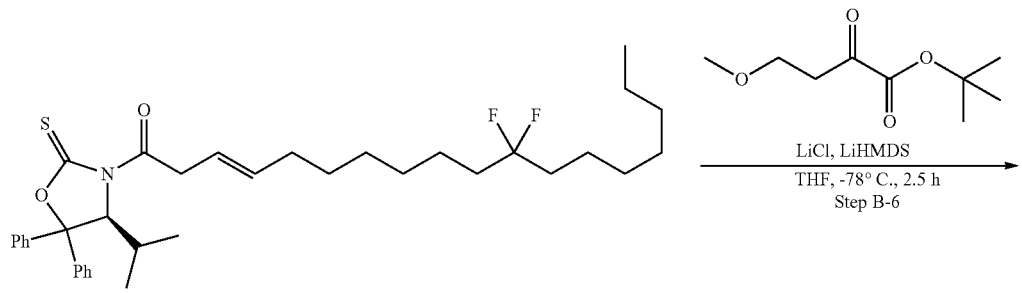
No. 5547308
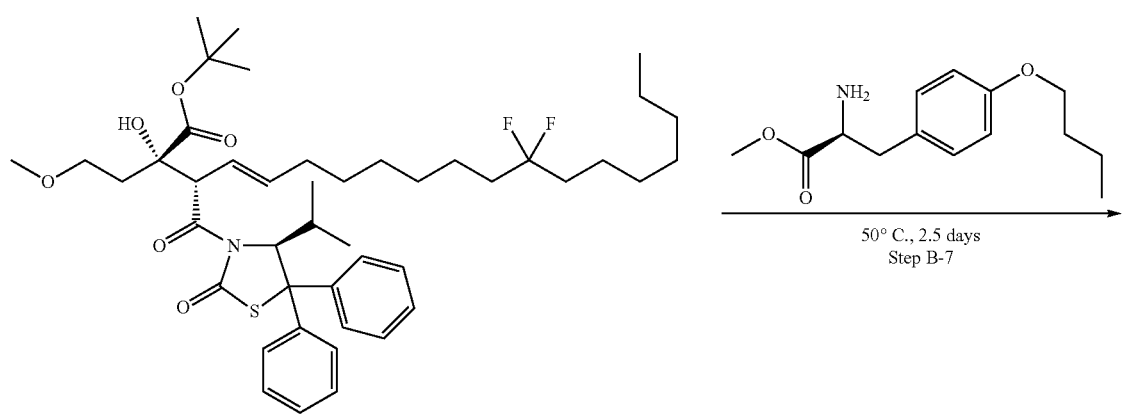
No. 5552816
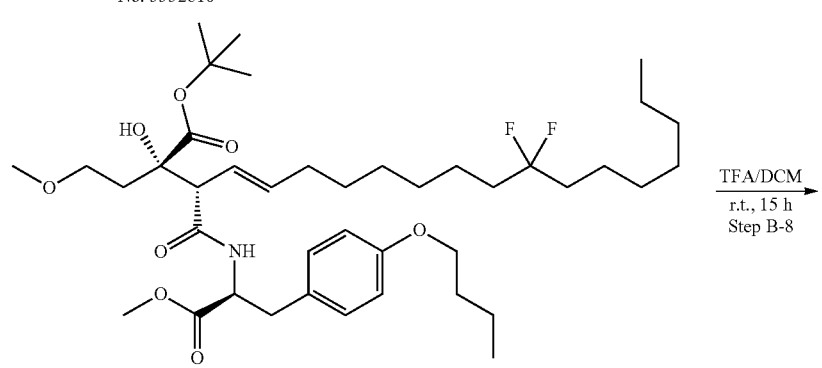
No. 5552820
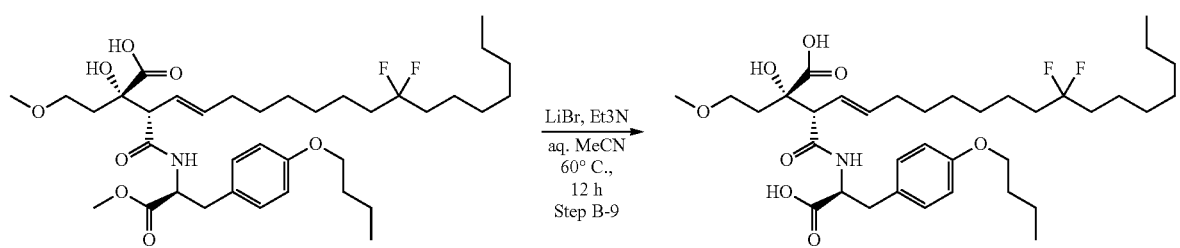
No. 5514403          No. 5526064
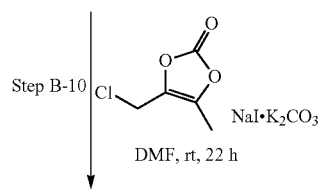

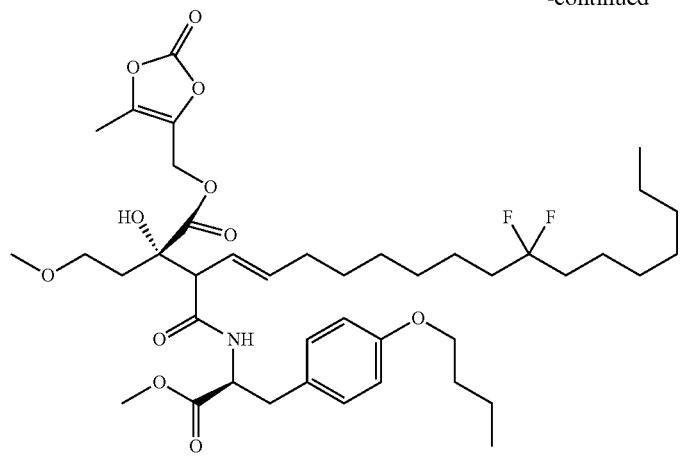

No. 68087855

Step B-1

Under a nitrogen atmosphere, monomethyl azelate (6.70 g, 33.1 mmol), commercially available from Tokyo Chemical Industry Co., Ltd., was dissolved in toluene (60 mL), N,N-dimethylformamide (DMF, 25.6 µL, 0.331 mmol) was added thereto, and the solution was warmed to 60° C. While maintaining the temperature at 60° C., a solution of oxalyl chloride (2.94 mL, 34.8 mmol) in toluene (7.0 mL) was added dropwise over 10 minutes. After completion of the dropwise addition, the mixture was stirred at 60° C. for 2.0 hours. Toluene and oxalyl chloride were distilled off under reduced pressure, and subsequently tetrahydrofuran (THF, 67 mL) was added to distill off the solvent. Under a nitrogen atmosphere, this crude product was dissolved in THF (50 mL), tris(2,4-pentandionato) iron (III) (Fe(acac)$_3$, 0.585 g, 0.166 mmol) was added thereto, and the solution was cooled to −40° C. Subsequently, a dilution of n-heptyl magnesium bromide (1 M solution in THF, 36.4 mL, 36.4 mmol) with THF (30 mL) was added dropwise over 1 hour. After completion of the dropwise addition, the mixture was stirred at −40° C. for 1.5 hours. To the reaction solution was added 0.5 M aqueous hydrochloric acid solution (40 mL) to stop the reaction, and the solution was extracted with ethyl acetate. The aqueous layer was washed with ethyl acetate, and the organic layers were combined, washed sequentially with water, a saturated sodium bicarbonate aqueous solution, and a saturated brine and dried over anhydrous sodium sulfate. After the organic layer was filtered and the solvent was distilled off, the resulting residue was purified with SP1 (SiO2 cartridge, 10% ethyl acetate/n-hexane, Rf=0.2) to obtain methyl 9-oxo-hexadecanoate (No. 4984860; 7.33 g, 78% yield).

Physicochemical Properties of Compound No. 4984860

$^1$H-NMR (CDCl$_3$) δ: 0.88 (3H, t, J=6.8 Hz), 1.21-1.37 (14H, m), 1.50-1.75 (6H, m), 2.30 (2H, t, J=7.6 Hz), 2.40 (4H, t, J=7.6 Hz), 3.63 (3H, s).

ESI (LC/MS positive mode) m/z 285 (M+H); Rt 2.28 min.

Step B-2

Under a nitrogen atmosphere, methyl 9-oxo-hexadecanoate (No. 4984860; 2.39 g, 8.40 mmol) was dissolved in dichloromethane (47 mL), and the solution was cooled to 0° C. While maintaining the temperature at 0° C., 1,2-ethanedithiol (840 µL, 10.1 mmol), and borontrifluoride-ethylether complex (1.24 mL, 10.1 mmol) were sequentially added, and the mixture was stirred at 0° C. for 5 minutes and at room temperature for 2 hours. Water was added to the reaction solution to stop the reaction, and the solution was extracted with dichloromethane. The organic layer was sequentially washed with a saturated sodium bicarbonate aqueous solution and a saturated brine, and dried over anhydrous sodium sulfate. After the organic layer was filtered and the solvent was distilled off, the resulting residue was purified with SP1 (SiO2 cartridge, 5.0% ethyl acetate/n-hexane, Rf=0.5) to obtain methyl 8-(2-heptyl-[1,3]dithiolan-2-yl)-octanoate (No. 5553355; 2.57 g, 85% yield).

Physicochemical Properties of Compound No. 5553355

$^1$H-NMR (CDCl$_3$) δ: 0.88 (3H, t, J=6.6 Hz), 1.25-1.37 (14H, m), 1.39-1.51 (4H, m), 1.58-1.67 (2H, m), 1.87-1.91 (4H, m), 2.30 (2H, t, J=7.7 Hz), 3.26 (4H, s), 3.66 (3H, s).

ESI (LC/MS positive mode) m/z 361 (M+H); Rt 2.85 min.

Step B-3

Under a nitrogen atmosphere, 1,3-dibromo-5,5-dimethylhydantoin (2.04 g, 7.13 mmol) was dissolved in dichloromethane (DCM, 70 mL), and cooled to −78° C. While maintaining the temperature at −78° C., 70% pyridine-hydrogen fluoride complex (4.07 g, 143 mmol) was added, and subsequently a solution (30 mL) of methyl 8-(2-heptyl-[1,3]-dithiolan-2-yl) octanoate (No. 5553355; 2.57 g, 7.13 mmol) in dichloromethane was added dropwise, and the mixture was stirred at −40° C. for 2 hours. Water was added to the reaction solution to stop the reaction, and the solution was extracted with dichloromethane. The organic layer was sequentially washed with a sodium bicarbonate aqueous solution and a saturated brine, and dried over anhydrous sodium sulfate. After the organic layer was filtered and the solvent was distilled off, the resulting residue was purified with SP1 (SiO2 cartridge, 5.0% ethyl acetate/n-hexane, Rf=0.5) to obtain methyl 9,9-difluorohexadecanoate (No. 6804231; 990 mg, 45% yield).

Physicochemical Property of Compound No. 6804231

$^1$H-NMR (CDCl$_3$) δ: 0.82 (3H, t, J=6.6 Hz), 1.18-1.29 (14H, m), 1.33-1.42 (4H, m), 1.52-1.59 (2H, m), 1.65-1.78 (4H, m), 2.23 (2H, t, J=7.7 Hz), 3.60 (3H, s).

Step B-4a

Under a nitrogen atmosphere, methyl 9,9-difluoro-hexadecanoate (No. 6804231; 990 mg, 3.23 mmol) was dissolved in toluene (14 mL), and cooled to –78° C. While maintaining the temperature at –78° C., a dilution of diisobutylaluminum hydride (DIBAlH, 1.5 M solution in toluene, 2.59 mL, 3.88 mmol) with toluene (3.8 mL) was added dropwise, and the mixture was stirred at –78° C. for 2.0 hours. Methanol (0.86 mL) was added to the reaction solution, and the mixture was stirred at –78° C. for 10 minutes to stop the reaction. A saturated Rochelle salt aqueous solution (4.0 mL) and water (12 mL) were further added and the mixture was stirred at 0° C. for 1 hour. After insoluble material was filtered off and washed with dichloromethane, the filtrate was extracted with dichloromethane, the organic layer was washed with water, and dried over anhydrous sodium sulfate. Subsequently, the organic layer was filtered and dichloromethane was distilled off to obtain a crude product of 9,9-difluoro-hexadecanal (No. 6893452).

Step B-4b

The crude product of 9,9-difluoro-hexadecanal (No. 6893452) obtained in step B-4a was placed under nitrogen atmosphere with remaining toluene solvent. After triethylamine (TEA) (811 μL, 5.82 mmol) was added at room temperature, a solution of malonic acid (605 mg, 5.81 mmol) in DMF (0.932 mL) was sequentially added, and the mixture was stirred at 90° C. for 19 hours. After cooling to room temperature, an aqueous solution (8.8 mL) of 30% sodium dihydrogen phosphate was added, and subsequently the mixture was extracted with ethyl acetate (17.6 mL). The organic layer was washed with water. After the aqueous layer was extracted with ethyl acetate again, the combined organic layer was washed again with water and a saturated brine in this order. The organic layer was dried over anhydrous sodium sulfate and filtered, and the solvent was distilled off.

To the resulting residue were added acetonitrile (9.0 mL), n-hexane (9.0 mL), an aqueous solution of 5.0% sodium bicarbonate (9.0 mL), and the mixture was stirred at room temperature for 2 minutes before the partition. The top hexane layer was removed, the remaining acetonitrile and aqueous layers were combined and washed with n-hexane (9.0 mL), and the hexane layer was removed again. Then, 0.5 M aqueous citric acid solution was added to pH 4.0 and subsequently the mixture was extracted with ethyl acetate. The organic layer was sequentially washed with water and a saturated brine, and dried over anhydrous sodium sulfate. After the organic layer was filtered and the solvent was distilled off, 502.7 mg of (E)-11,11-difluoro-octadec-3-enoic acid (No. 6893453) was obtained.

Physicochemical Property of Compound No. 6893453
$^1$H-NMR (CDCl$_3$) δ: 0.89 (3H, t, J=6.6 Hz), 1.23-1.50 (18H, m), 1.73-1.85 (4H, m), 2.04 (2H, q, J=13.2, 6.6 Hz), 3.07 (2H, d, J=5.5 Hz), 5.48-5.63 (2H, m).

Step B-5

Under a nitrogen atmosphere, (E)-11,11-difluoro-octadec-3-enoic acid (No. 6893453; 502.7 mg, 1.58 mmol) obtained in step B-4 and a commercially available reagent (S)-4-isopropyl-5,5-diphenyl-oxazolidine-2-thione (469.5 mg, 1.58 mmol) were dissolved in dichloromethane (7.5 mL), and the solution was cooled to 0° C. While maintaining the temperature at 0° C., N,N-dimethyl-4-aminopyridine (4-DMAP; 19.3 mg, 0.158 mmol) and 1-ethyl-3-(3-dimethylaminopropyl)-carbodiimide hydrochloride (WSCl; 393.4 mg, 2.05 mmol) were sequentially added, and the mixture was stirred at 0° C. for 2 minutes and at room temperature for 19 hours. An aqueous solution (9.0 mL) of 10% sodium dihydrogen phosphate and ethyl acetate were added to the reaction solution before extraction. The organic layer was sequentially washed with water and a saturated brine, and dried over anhydrous sodium sulfate. After the organic layer was filtered and the solvent was distilled off, the resulting residue was purified with SP1 (SiO2 cartridge, 10% ethyl acetate/n-hexane, Rf=0.6) to obtain (E)-11,11-difluoro-1-((S)-4-isopropyl-5,5-diphenyl-2-thioxo-oxazolidin-3-yl)-octadec-3-en-1-one (No. 5547308; 647.9 mg, 3 steps, 34% yield).

Physicochemical Properties of Compound No. 5547308
$^1$H-NMR (CDCl$_3$) δ: 0.78 (3H, d, J=7.1 Hz), 0.85 (3H, d, J=7.1 Hz), 0.88 (3H, t, J=6.6 Hz), 1.22-1.36 (14H, m), 1.38-1.49 (4H, m), 1.72-1.85 (4H, m), 1.92-1.98 (2H, m), 1.99-2.06 (1H, m), 3.84 (1H, dd, J=17.3, 5.5 Hz), 4.00 (1H, dd, J=17.3, 5.5 Hz), 5.42 (1H, dd, J=15.4, 5.5 Hz), 5.49 (1H, dd, J=15.4, 5.5 Hz), 6.59 (1H, d, J=3.8 Hz), 7.25-7.36 (6H, m), 7.40-7.48 (4H, m).
ESI (LC/MS positive mode) m/z 598 (M+H); Rt 3.87 min.

Step B-6

Lithium chloride (21.6 mg, 0.51 mmol) was heat dried with a heat gun under reduced pressure. Under a nitrogen atmosphere, THF (2.03 mL) solution of (E)-11,11-difluoro-1-((S)-4-isopropyl-5,5-diphenyl-2-thioxo-oxazolidin-3-yl)-octadec-3-en-1-one (No. 5547308; 101.4 mg, 0.170 mmol) was added at room temperature. After stirring till the reaction mixture became homogeneous solution, the reaction vessel was cooled to –78° C. in a dry ice/acetone cooling bath. Lithium hexamethyldisilazide (LiHMDS, 1 M solution in THF, 0.220 mL, 0.220 mmol) was added and the mixture was stirred for 1 hour. To the reaction mixture was added a solution of tert-butyl 4-methoxy-2-oxo-butyrate (47.9 mg, 0.254 mmol) in THF (1.32 mL) with dripping rates adjusted so as to keep inner temperature of the reaction solution under –60° C., and the mixture was further stirred for 1.5 hours. To the reaction mixture was added acetic acid (26.6 μL, 0.465 mmol), and the cooling bath was removed. A saturated aqueous solution (0.49 mL) of ammonium chloride, water (0.49 mL), and ethyl acetate (5.3 mL) were added, and the mixture was warmed to room temperature. After ethyl acetate extraction, the aqueous layer was washed with ethyl acetate, followed by drying over anhydrous sodium sulfate. After the organic layer was filtered and the solvent was distilled off, the resulting residue was purified with SP1 (SiO2 cartridge, 17% ethyl acetate/n-hexane, Rf=0.25) to obtain tert-butyl (E)-(2S,3S)-12,12-difluoro-2-hydroxy-3-((S)-4-isopropyl-2-oxo-5,5-diphenyl-thiazolidine-3-carbonyl)-2-(2-methoxy-ethyl)-nonadec-4-enoate (No. 5552816; 81.2 mg, 61% yield).

Physicochemical Properties of Compound No. 5552816
$^1$H-NMR (CDCl$_3$) δ: 0.73 (3H, d, J=6.6 Hz), 0.80 (3H, d, J=6.6 Hz), 0.88 (3H, t, J=6.6 Hz), 1.11 (1H, dt, J=14.3, 4.9 Hz), 1.24-1.45 (18H, m), 1.47 (9H, s), 1.70-1.83 (5H, m), 1.97-2.05 (3H, m), 3.08-3.14 (4H, m), 3.20-3.26 (1H, m), 3.50 (1H, s), 5.57 (1H, dd, J=15.4, 9.3 Hz), 5.67 (1H, d, J=3.8 Hz), 5.88-5.95 (1H, m), 6.14 (1H, d, J=9.3 Hz), 7.25-7.29 (2H, m), 7.34 (4H, t, J=7.7 Hz), 7.42-7.46 (2H, m), 7.48-7.51 (2H, m).
ESI (LC/MS positive mode) m/z 786 (M+H); Rt 3.95 min.

Step B-7 tert-Butyl (E)-(2S,3S)-12,12-difluoro-2-hydroxy-3-((S)-4-isopropyl-2-oxo-5,5-diphenyl-thiazolidine-3-carbonyl)-2-

(2-methoxy-ethyl)-nonadec-4-enoate (No. 5552816; 17.0 mg, 0.0216 mmol) and methyl (S)-2-amino-3-(4-butoxy-phenyl)-propionate (8.2 mg, 0.0324 mmol) were dissolved in dichloromethane and the solvent was distilled off. The resulting mixture was stirred at 50° C. for 2.5 days, cooled to room temperature, and subsequently the residue was purified by preparative TLC (33% ethyl acetate/n-hexane, Rf=0.6) to obtain tert-butyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 5552820; 13.9 mg, 87% yield).

Physicochemical Property of Compound No. 5552820
ESI (LC/MS positive mode) m/z 740 (M+H); Rt 2.93 min.

Step B-8 tert-Butyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 5552820; 13.9 mg, 0.0188 mmol) was dissolved in dichloromethane (2.1 mL), and trifluoroacetic acid (TFA, 0.7 mL) was added to the solution. The mixture was stirred at room temperature for 16 hours, and the solvent was distilled off. To the residue was added dichloromethane, and the solvent was again distilled off. This operation was repeated twice. Subsequently, HPLC purification (water with 0.05% TFA-acetonitrile with 0.05% TFA) was performed to obtain (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoic acid (No. 5514403; 5.6 mg, 44% yield, white powder).

Physicochemical Properties of Compound No. 5514403
$^1$H-NMR (CD$_3$OD) δ: 0.90 (3H, t, J=7.1 Hz), 0.98 (3H, t, J=7.1 Hz), 1.22-1.54 (20H, m), 1.67-1.85 (7H, m), 1.92-2.10 (3H, m), 2.88 (1H, dd, J=14.3, 9.3 Hz), 3.11 (1H, dd, J=14.3, 4.9 Hz), 3.22 (1H, d, J=8.2 Hz), 3.24 (3H, s), 3.38-3.44 (2H, m), 3.70 (3H, s), 3.92 (2H, t, J=6.6 Hz), 4.61-4.67 (1H, m), 5.45-5.59 (2H, m), 6.79 (2H, d, J=8.8 Hz), 7.07 (2H, d, J=8.8 Hz), 8.22 (0.7H, d, J=7.7 Hz, the integral value was observed as 0.7H due to H-D exchange)
ESI (LC/MS positive mode) m/z 684 (M+H); Rt 2.48 min.

Step B-9

(E)-(2S,3S)-3-[(S)-2-(4-butoxy-phenyl)-1-carboxy-ethylcarbamoyl]-12,12-difluoro-2-hydroxy-2-(2-methoxy-ethyl)-nonadec-4-enoic acid (No. 5526064)

(E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoic acid (No. 5514403, 100 mg, 0.142 mmol) was dissolved in acetonitrile (1.0 mL), and subsequently water (0.005 mL, 0.278 mmol), triethylamine (0.118 mL, 0.847 mmol) and anhydrous lithium bromide (244 mg, 2.81 mmol) were sequentially added at room temperature. The mixture was stirred at 50° C. for 11.5 hours. After cooling the reaction solution to room temperature, a preparative HPLC was performed to obtain 51.1 mg of the title compound (0.07629 mmol, 54% yield).

Physicochemical Properties of Compound No. 5526064
$^1$H-NMR (CD$_3$OD) δ: 0.91 (3H, t, J=7.2 Hz), 0.98 (3H, t, J=7.2 Hz), 1.20-1.57 (20H, m), 1.64-1.87 (7H, m), 1.90-2.01 (2H, m), 2.06 (1H, dt, J=13.7, 7.7 Hz), 2.89 (1H, dd, J=14.3, 9.4 Hz), 3.16 (1H, dd, J=14.3, 4.9 Hz), 3.21 (1H, d, J=8.8 Hz), 3.23 (3H, s), 3.36-3.47 (2H, m), 3.93 (2H, t, J=6.5 Hz), 4.63 (1H, dd, J=9.4, 4.9 Hz), 5.48 (1H, dd, J=15.4, 8.8 Hz), 5.56 (1H, dd, J=15.4, 6.1 Hz), 6.79 (2H, d, J=8.8 Hz), 7.10 (2H, d, J=8.8 Hz).
ESI (LC/MS positive mode) m/z 670 (M+H); Rt 2.33 min.

Step B-10

(5-methyl-2-oxo-[1,3]dioxol-4-yl)methyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 6808755)

To the mixture of (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoic acid (No. 5514403, 50 mg, 0.0731 mmol), sodium iodide (16.4 mg, 0.110 mmol), sodium bicarbonate (7.4 mg, 0.877 mmol) and the DMF (1 mL) was added commercially available 4-chloromethyl-5-methyl-1,3-dioxol-2-one (15.9 μL, 0.145 mmol) at room temperature, and the mixture was stirred as it was for 22 hours. After confirming the consumption of the starting materials by LCMS, the reaction solution was filtered through a syringe filter, and purified as it was by preparative HPLC. The purified fraction was freeze-dried to obtain the title compound (48 mg, 83% yield) as yellow oil.

Physicochemical properties of Compound No. 6808755
$^1$H-NMR (CD$_3$OD) δ: 0.90 (3H, t, J=6.8 Hz), 0.98 (3H, t, J=9.5 Hz), 1.25-1.36 (14H, m), 1.39-1.55 (6H, m), 1.63 (1H, td, J=9.3, 4.7 Hz), 1.70-1.85 (6H, m), 1.90-1.97 (2H, m), 2.05-2.13 (1H, m), 2.16 (3H, s), 2.86 (1H, dd, J=13.9, 9.5 Hz), 3.11 (1H, dd, J=13.9, 5.1 Hz), 3.18 (3H, s), 3.22 (1H, d, J=8.8 Hz), 3.32-3.37 (1H, m), 3.45 (1H, td, J=9.7, 4.4 Hz), 3.70 (3H, s), 3.92 (2H, t, J=6.4 Hz), 4.60-4.66 (1H, m), 4.83 (1H, d, J=13.7 Hz), 4.95 (1H, d, J=13.7 Hz), 5.42-5.57 (2H, m), 6.79 (2H, d, J=8.4 Hz), 7.06 (2H, d, J=8.4 Hz), 8.24 (1H, d, J=7.9 Hz).
ESI (LC/MS positive mode) m/z 796 (M+H); Rt 1.22 min.

tert-Butyl 4-methoxy-2-oxo-butyrate

The title compound was produced according to the following synthetic scheme.

[Chem. 13]

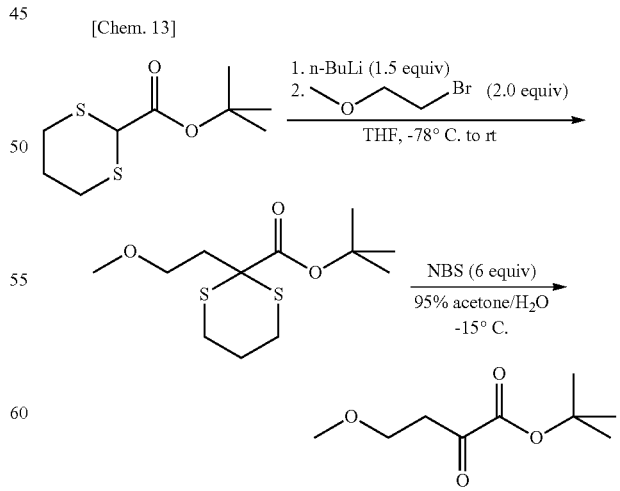

The starting material tert-butyl[1,3]dithiane-2-carboxylate is disclosed, as compound 17 in Example 4 in PTL4 (International Publication No. 2006/088071).

A solution of tert-butyl[1,3]dithiane-2-carboxylate (2 g, 9.08 mmol) in THF (16 mL) was cooled to −78° C., and a solution of n-butyllithium (1.58 M in Hexane, 8.62 mL, 13.6 mmol) was added. After stirring for 1 hour, 2-bromoethyl methyl ether (1.70 mL, 18.1 mmol) was added. After stirring at −78° C. for 15 minutes, the cooling bath was removed, and, while allowing the temperature to gradually return to room temperature, the solution was stirred at room temperature for 16 hours. After confirming the consumption of the starting materials by LCMS, a saturated aqueous solution of ammonium chloride was added, and the mixture was extracted with ethyl acetate. The organic layer was sequentially washed with water and a saturated brine, and subsequently dried over anhydrous sodium sulfate. The organic layer was filtered, and the solvent was distilled off. The resulting residue was purified with SP1 (SiO2 cartridge) to obtain tert-butyl 2-(2-methoxy-ethyl)-[1,3]dithiane-2-carboxylate (1.75 g, 69% yield).

Physicochemical property of tert-butyl 2-(2-methoxy-ethyl)-[1,3]dithiane-2-carboxylate ESI (LC/MS positive mode) m/z 279 (M+H); Rt 2.72 min.

To a solution of tert-butyl 2-(2-methoxy-ethyl)-[1,3]dithiane-2-carboxylate (1.14 g, 4.09 mmol) in acetone (23 mL) was then added water (1.14 mL), and subsequently the solution was cooled to −15° C., to which N-bromosuccinimide (NBS, 4.37 g, 24.6 mmol) was gradually added. After stirring for 30 minutes and confirming the consumption of the starting materials by TLC, to the solution was added a solution of sodium bicarbonate (1.71 g, 20.35 mmol) in water (9.0 mL), and subsequently, an aqueous solution (8 mL) of 5% sodium thiosulfate. After extraction with dichloromethane, the organic layer was washed with water, and dried over anhydrous sodium sulfate. The organic layer was filtered and the solvent was distilled off. The resulting residue was purified with SP1 (SiO2 cartridge, 10% ethyl acetate/n-hexane, Rf=0.4) to obtain tert-butyl 4-methoxy-2-oxo-butyrate (550 mg, 72% yield).

Physicochemical property of tert-butyl 4-methoxy-2-oxo-butyrate $^1$H-NMR (CDCl$_3$) δ: 1.54 (9H, s), 3.04 (2H, t, J=6.0 Hz), 3.34 (3H, s), 3.70 (2H, t, J=6.2 Hz).

Methyl (S)-2-amino-3-(4-butoxy-phenyl)-propionate and hydrochloride thereof

The title compound was produced according to the following synthetic scheme.

[Chem. 14]

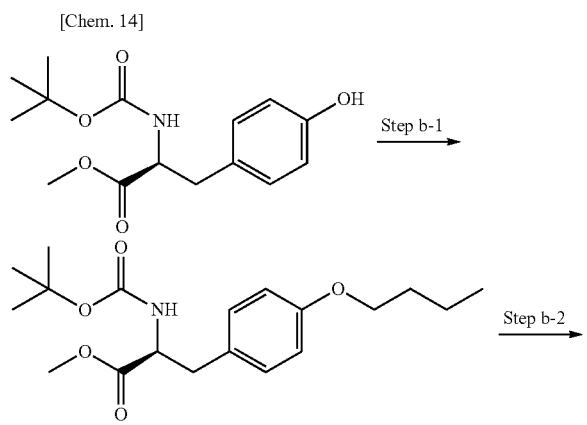

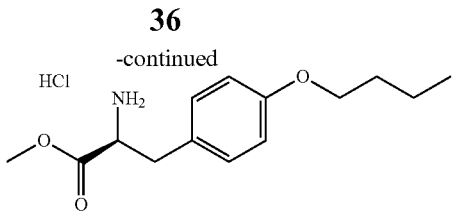

Step b-1

Commercially available (S)-methyl 2-((tert-butoxycarbonyl)amino)-3-(4-hydroxyphenyl)propanoate (12 g, 40.63 mmol, 1 eq.) was dissolved in dehydrated DMF (30 mL), and potassium carbonate (6.177 g, 44.695 mmol, 1.1 eq.) and 1-iodobutane (5.55 mL, 48.756 mmol, 1.2 eq.) were added to the solution, which was stirred at 40° C. for a whole day and night and cooled to room temperature. The mixture was diluted with ethyl acetate, washed 3 times with water, and then with a saturated aqueous solution of ammonium chloride, and dried over anhydrous sodium sulfate. The organic layer was filtered and the solvent was distilled off. The residue was purified by aminosilica gel column chromatography (by elution with dichloromethane) to obtain the desired compound, (S)-methyl 2-((tert-butoxycarbonyl)amino)-3-(4-butoxyphenyl)propanoate as a white solid (11.842 g, 83% yield).

Physicochemical properties of (S)-methyl 2-((tert-butoxycarbonyl)amino)-3-(4-butoxyphenyl)propanoate $^1$H-NMR (CDCl$_3$) δ: 0.97 (3H, t, J=7.2 Hz), 1.42 (9H, s), 1.44-1.53 (2H, m), 1.70-1.79 (2H, m), 2.94-3.08 (2H, m), 3.71 (3H, s), 3.92 (2H, t, J=6.8 Hz), 4.48-4.57 (1H, m), 4.94 (1H, broad d, J=8.8 Hz), 6.81 (2H, d, J=7.2 Hz), 7.01 (2H, d, J=7.2 Hz).

ESI (LC/MS positive mode) m/z 352 (M+H); Rt 4.15 min.

Step b-2a (S)-Methyl 2-((tert-butoxycarbonyl)amino)-3-(4-butoxyphenyl)propanoate (5.1 g, 14.5 mmol) was dissolved in ethyl acetate (20 mL), 4 M hydrogen chloride (a solution in ethyl acetate, 6.75 mL) was added to the solution, which was stirred for a whole day and night at room temperature. The resulting white deposits were collected by filtration, washed with ethyl acetate, and subsequently dried to obtain the desired compound, (S)-methyl 2-amino-3-(4-butoxyphenyl) propanoate hydrochloride as a white solid (3.4195 g, 82% yield).

Physicochemical properties of (S)-methyl 2-amino 3-(4-butoxyphenyl)propanoate hydrochloride $^1$H-NMR (DMSO-d$_6$) δ: 0.93 (3H, t, J=7.6 Hz), 1.43 (2H, dt, J=15.0, 7.3 Hz), 1.65-1.72 (2H, m), 2.97-3.14 (2H, m), 3.69 (3H, s), 3.94 (2H, t, J=6.4 Hz), 4.23 (1H, t, J=6.4 Hz), 6.88 (2H, d, J=8.5 Hz), 7.12 (2H, d, J=8.5 Hz), 8.47 (3H, broad s).

ESI (LC/MS positive mode) m/z 252 (M+H); Rt 2.42 min.

Step b-2b

In the case where (S)-methyl 2-amino-3-(4-butoxyphenyl)propanoate hydrochloride was used in the condensation reaction in step B-7, it was used after desalination. A general method is as follows. (S)-methyl 2-amino-3-(4-butoxyphenyl) propanoate hydrochloride required for the reaction was first weighed, and then dissolved in ethyl acetate. The solution was washed with a saturated aqueous solution of sodium bicarbonate, the organic layer was dried over anhydrous sodium sulfate and filtered, and the solvent was then distilled off before use.

Comparative Examples

Control Prodrugs

The title compound was produced according to the following synthetic scheme.

[Chem. 15]

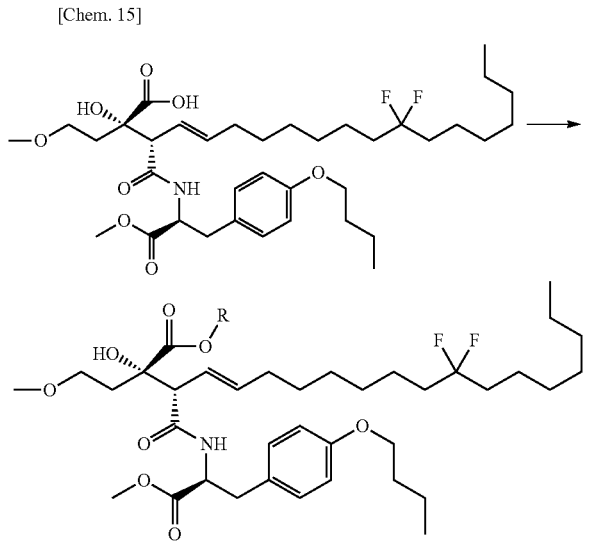

When R=CH$_3$COCH$_2$—:
Methoxycarbonylmethyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 6811559)

Under a nitrogen atmosphere, Compound No. 5514403 (3.95 g, 5.78 mmol) was dissolved in DMF (60 mL), and sodium bicarbonate (582 mg, 6.93 mmol), sodium iodide (1.30 g, 8.67 mmol), and methyl bromoacetate (1.09 mL, 11.5 mmol) were sequentially added to the solution, which was stirred at room temperature for 16 hours. After further stirring at 50° C. for 40 minutes, water was added to the reaction mixture to stop the reaction, followed by extraction with ethyl acetate. The aqueous layer was washed with ethyl acetate, and the combined organic layer was washed with water and dried over anhydrous sodium sulfate. After the organic layer was filtered and the solvent was distilled off, the resulting residue was purified with SP1 (SiO2 cartridge, 50% ethyl acetate/n-hexane, Rf=0.6) to obtain methoxycarbonylmethyl (E)-(2S, 3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 6811559; 4.20 g, 96% yield).

Physicochemical Properties of Compound No. 6811559

$^1$H-NMR (CDCl$_3$) δ: 0.88 (3H, t, J=6.9 Hz), 0.97 (3H, t, J=7.4 Hz), 1.22-1.37 (14H, m), 1.38-1.53 (6H, m), 1.72-1.84 (7H, m), 1.98-2.09 (3H, m), 3.00 (1H, dd, J=14.0, 6.9 Hz), 3.09 (1H, dd, J=13.7, 5.5 Hz), 3.24 (1H, d, J=8.2 Hz), 3.28 (3H, s), 3.48-3.57 (2H, m), 3.71 (3H, s), 3.76 (3H, s), 3.92 (2H, t, J=6.6 Hz), 4.63 (2H, dd, J=20.1, 15.7 Hz), 4.79-4.84 (2H, m), 5.57-5.70 (2H, m), 6.77-6.82 (3H, m), 7.02 (2H, d, J=8.2 Hz).

ESI (LC/MS positive mode) m/z 756 (M+H); Rt 2.62 min.

When R=—CH$_3$: Methyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate (No. 6809532)

Compound No. 5514403 (50 mg, 0.073 mmol) was dissolved in methanol (0.4 mL) and benzene (1.2 mL), and trimethylsilyl diazomethane (TMSCHN$_2$) (244 μL, 0.146 mmol) was added at room temperature. After confirming the consumption of the starting materials by LCMS, the solvent was distilled off, and the residue was purified by preparative HPLC. The obtained fraction was freeze-dried to obtain the title compound (38 mg, 75% yield, white powder).

Physicochemical Properties of Compound No. 6809532

$^1$H-NMR (CD$_3$OD) δ: 0.90 (3H, t, J=7.1 Hz), 0.98 (3H, t, J=7.5 Hz), 1.24-1.38 (14H, m), 1.39-1.55 (6H, m), 1.61 (1H, td, J=9.5, 4.6 Hz), 1.70-1.85 (6H, m), 1.93-2.00 (2H, m), 2.02-2.09 (1H, m), 2.87 (1H, dd, J=14.1, 9.3 Hz), 3.11 (1H, dd, J=14.3, 5.1 Hz), 3.19-3.22 (4H, m), 3.32-3.36 (1H, m), 3.39-3.44 (1H, m), 3.65 (3H, s), 3.70 (3H, s), 3.93 (2H, t, J=6.4 Hz), 4.63 (1H, dd, J=9.3, 4.9 Hz), 5.42-5.58 (2H, m), 6.79 (2H, d, J=8.8 Hz), 7.07 (2H, d, J=8.8 Hz).

ESI (LC/MS positive mode) m/z 698 (M+H); Rt 1.25 min.

Test Example 1

Replicon Assay and Cytotoxicity Test

Test Method

According to the method of Krieger et al. (N. Krieger et al., J. Virology: 75, 4614-24, 2001), a firefly luciferase gene was introduced, in a form fused with a neomycin-resistant gene, immediately downstream of an internal ribosome entry site (TRES) of the HCV gene. After synthesizing the RNA in vitro, it was introduced into Huh7 cells by electroporation and the cells were isolated as G418-resistant clones.

The firefly luciferase HCV replicon cells (Huh3-1) were suspended in Dulbecco's MEM (Gibco cat. No. 10,569-010) containing 5% fetal bovine serum (Hyclone cat. No. SH30071.03), seeded at 4500 cells/90 μL/well in 96-well plates, and cultured overnight in 5% CO$_2$ at 37° C. After 20 hours, 10 μL per well of compounds prepared at a concentration 10 times the final concentration were added, and they were further cultured for 3 days.

Two series of assay plates, one series of white plates and another series of clear plates, were prepared and used for the assay.

After culturing, the white plates were used for the replicon assay with Steady-Glo Luciferase Assay System (Promega cat. No. E2520). More specifically, 100 μL per well of the reagent was added, it was mixed 3-4 times by pipetting and allowed to stand for 5 minutes, and subsequently the luminescence was measured with a plate reader (EnVision™ 2103 Multilabel Reader). All values were expressed as differences from the background which was measured with neither cells nor drug and IC$_{50}$ (50% inhibitory concentration) values of drugs were calculated based on the value when no drug was added defined as 0% inhibition.

Clear plates were used for a cytotoxicity test (WST-8). Cytotoxicity was measured using Cell counting kit-8 (Dojindo cat. No. CK04). More specifically, 100 μL of Cell counting kit-8 diluted 10-fold from the stock solution with PBS (SIGMA cat. No. D8537) was added to each well in the aforementioned clear plates from which medium was removed and the plates were incubated at 37° C. for 30 to 60 minutes. Absorbance was measured at a wavelength of 460 nm and a control wavelength of 590 nm by a plate reader (EnVision™ 2103 Multilabel Reader). All values were expressed as differences from the background which was measured with neither cells nor drug and IC$_{50}$ (50% inhibitory concentration) values of drugs were calculated based on the value when no drug was added defined as 0% inhibition.

The assay results are shown in Table 1.

immediate hydrolysis of the prodrug moiety in No. 6808755 in the body and conversion of No. 6808755 into the active compound No. 5514403, and further metabolism of No. 5514403 into the active metabolite No. 5526064, so, No. 5514403 and No. 5526064 were exposed at high levels in liver

TABLE 1

Result of Replicon Assay and Cytotoxicity Test

| Compound No. | Chemical Structure | Anti-replicon Activity (μM) | Cytotoxicity WST8 (μM) | Ratio |
|---|---|---|---|---|
| No. 5514403 | 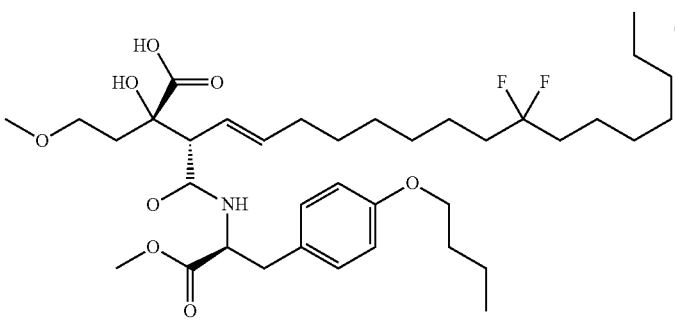 Chiral | 0.00060 | >1 | >1672 |
| No. 5526064 | 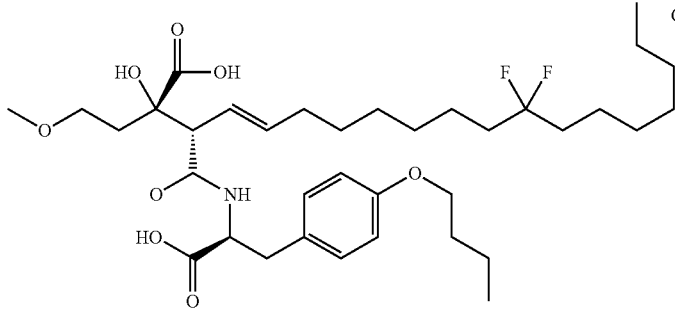 Chiral | 0.00215 | >1 | >465 |

Test Example 2

Rat PK Test

The test was carried out according to the following protocol.
Animal: Wistar rat (male, 7 weeks old),
Route of administration: p.o.
Dose frequency: once a day
Dosing period: 7 days
Dose: 30 mg/kg (per dose)
Dosing solution: 0.01% formic acid/10% DMSO/10% Cremophor EL solution
Composition: administered dissolved in the dosing solution
Volume: 10 mL/kg
Sampling site: liver (frozen in dry ice)
Sampling point: 1 and 24 h (7 days after dosing)
(Method of Analysis)

Using LC-MS/MS (API 4000), standard curves for standard compounds were prepared, and the concentrations of the active metabolites No. 5514403 and No. 5526064 at the data points were calculated. The results of the rat PK tests are shown in FIGS. 1 to 3.

Figure 4:
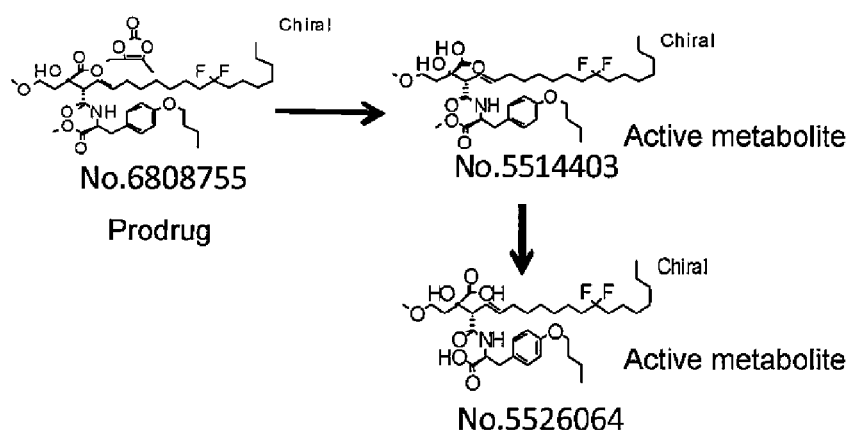
FIG. 4 illustrates a metabolic pathway of the prodrug compound No. 6808755.

Oral administration of 3 prodrug compounds No. 6808755, No. 6809532, and No. 6811559 to rat was found to result in (FIG. 1). The metabolic pathway of the prodrug compound No. 6808755 is shown in FIG. 4.

Because the active compound No. 5514403 and its active metabolite No. 5526064 were found to remain at 100 ng/g or more even 24 hours after dosing, No. 6808755 is considered to have a good oral absorbability and be a prodrug compound that is well converted into an active compound in the body.

Figure 2:
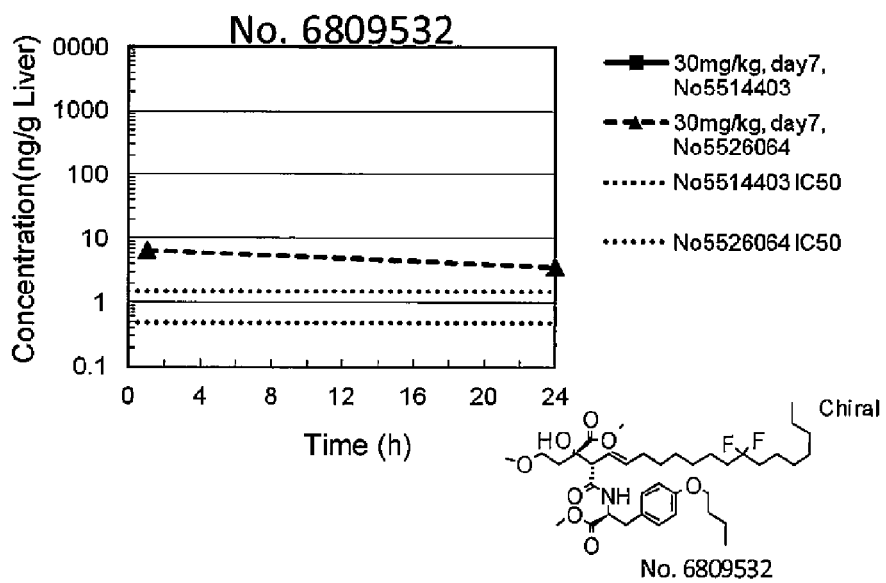
FIG. 2 is a graph showing concentrations of metabolites and IC50 values of anti-replicon activity thereof in the liver after oral administration of the prodrug compound No. 6809532 to rat. In the graph, the solid and dashed lines indicate concentrations of the metabolites No. 5514403 and No. 5526064, respectively. The dotted lines with black and grey dots indicate IC50 values of the metabolites No. 5514403 and No. 5526064, respectively. The chemical structural formula of the prodrug compound No. 6809532 is also illustrated.
Figure 3:
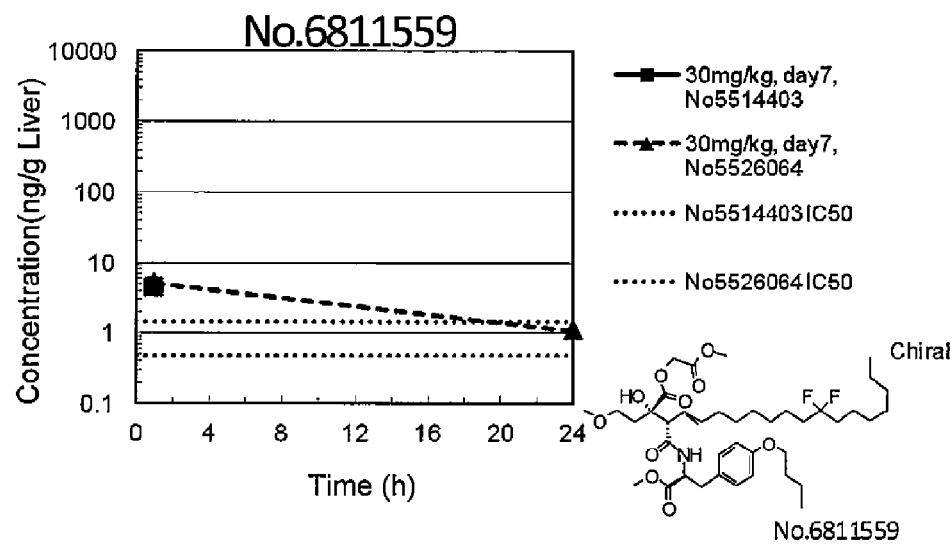
FIG. 3 is a graph showing concentrations of metabolites and IC50 levels of anti-replicon activity thereof in the liver after oral administration of the prodrug compound No. 6811559 to rat. In the graph, the solid and dashed lines indicate concentrations of the metabolites No. 5514403 and No. 5526064, respectively. The dotted lines with black and grey dots indicate IC50 values of the metabolites No. 5514403 and No. 5526064, respectively. The chemical structural formula of the prodrug compound No. 6811559 is also illustrated.

However, as to the prodrugs No. 6809532 and No. 6811559, the presence of the active compound No. 5514403 was hardly detected in the liver, and only the active metabolite No. 5526064 was detected at 10 ng/g or less 24 hours after dosing (FIGS. 2 and 3).

These results indicate that No. 6808755 leads to significantly higher exposure of the liver to the active drugs in comparison with No. 6809532 and No. 6811559, and is a prodrug of No. 5514403 that is expected to have a sufficient anti-HCV effect when orally administered.

The dotted lines in the graphs in FIGS. 1 to 3 indicate IC50 values of antireplicon activity of the active compound No. 5514403 and its active metabolite No. 5526064. In the figures, the unit of IC50 has been converted from μM to ng/g assuming that the liver has a specific gravity corresponding to the expression 1 g=1 mL. Accordingly, 0.0006 μM of IC50 of No. 5514403 in Table 1 corresponds to 0.48 ng/g in FIGS. 1 to 3, and 0.00215 μM of IC50 of No. 5526064 in Table 1 corresponds to 1.44 ng/g in FIGS. 1 to 3.

Test Example 3

Inhibition Experiment of CYP3A4, CYP2C9

Tests were carried out according to the following experiment method.

<Assay Conditions>

TABLE 2

| CYP Species | CYP3A4 | CYP2C9 |
|---|---|---|
| Substrate | Midazolam | Dicrofenac |
| Substrate Concentration | 0.5 µmol/L | 0.2 µmol/L |
| Substrate Solvent | 50% Methanol | 50% Methanol |
| Incubation Time | 5 min. | 5 min. |
| Preincubation Time | 30 min. | 30 min. |
| Test Substance Concentration | 50, 16.7, 5.56, 1.85, 0.617 µmol/L (n = 2) | |
| Test Substance Solvent | DMSO | DMSO |

<Incubation Mixture>
100 mM phosphate buffer (pH 7.4)
0.1 mg/mL of pooled human liver microsomes (male and female mixture, a pool of 50 donors)
<NADPH Aqueous Solution>
10 mM NADPH (final concentration 1 mM NADPH)
<Measurement of Metabolite>

After incubation, the concentrations of the produced metabolites were measured using LC-MS/MS (API4000 or 5500QTRAP). Warfarin was used as internal standard (IS). The concentration was calculated using a standard curve created using a metabolite standard solution.

<Assay Procedure>
(1) Without Preincubation

To a 96 deep well plate was added 2.5 µL, of the test substance solution (×200 concentration), 442.5 µL of Incubation Mixture, and 5 µL of the substrate solution, and the solution was mixed and warmed to 37° C. for 5 minutes. To this incubation solution 50 µL of 10 mM NADPH was added to start the reaction, and incubated at 37° C. for 5 minutes. After the incubation, 100 µL of the Incubation Mixture was removed, added to 150 µL of isopropanol containing IS and mixed. This mixture was transferred onto a multi-screen filter, centrifuged at 500×g at 4° C. for 10 minutes. The filtrate was used for LC-MS/MS analysis.

(2) With Preincubation

To a 96 deep well plate was added 2.5 µL of the test substance solution (×200 concentration), and 442.5 µL of Incubation Mixture, and the solution was mixed and warmed to 37° C. for 5 minutes. To this incubation solution 50 µL of 10 mM NADPH was added and preincubated at 37° C. for 30 minutes. After the preincubation, 5 µL of the substrate solution was added and the solution was mixed and further incubated at 37° C. for 5 minutes for the reaction. After the reaction, 100 µL of the Incubation Mixture was removed, added to 150 µL of isopropanol containing IS and mixed. This mixture was transferred onto a multi-screen filter, centrifuged at 500×g at 4° C. for 10 minutes. The filtrate was used for LC-MS/MS analysis.

<Calculation of IC50>

Based on the metabolite production of the DMSO control group defined as 100, percent inhibitions of the metabolite production in the test substance group were determined, and inhibition curves were plotted at 5 concentrations. The test substance concentration showing 50% inhibition (IC50) was determined from the fitting curve of the inhibition curve.

Time dependent inhibition (TDI) was calculated as a ratio of dividing IC50 of the sample without preincubation treatment by the IC50 value measured after the preincubation treatment.

TABLE 3

Result of CYP Inhibition (CYP3A4, CYP2C9)

| Compound No. | Chemical Structure | | CYP3A4 (IC50 µM) untreated | CYP3A4 (IC50 µM) Preincubation | Time Dependent (TDI) (untreated/ Preincubation) | CYP2C9 (IC50 µM) untreated | CYP2C9 (IC50 µM) Preincubation | TDI Ratio |
|---|---|---|---|---|---|---|---|---|
| No. 5514403 | 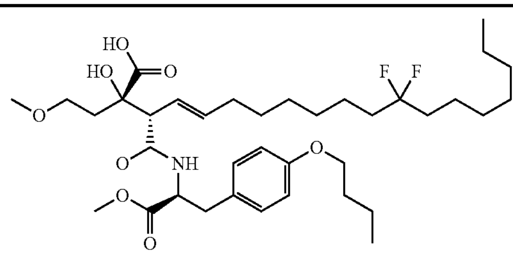 | Chiral | 23.8 | 11.9 | 1.98 | 7.7 | 19.64 | 0.39 |
| No. 5526064 | 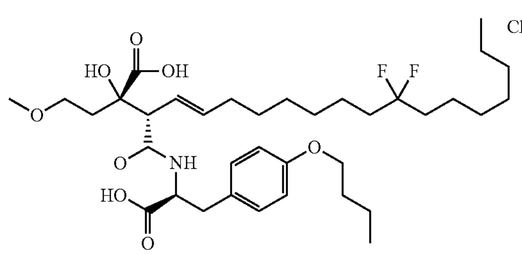 | Chiral | 16.23 | 11.84 | 1.37 | 12.53 | 24.40 | 0.51 |

The result of CYP inhibition is shown in Table 3. Drug interactions of these compounds are considered to be not significant because of the large IC50 values of CYP inhibition and the low ratios of time dependent inhibition (TDI).

Reference Example 1

NA808-Prodrug

The title compound was produced according to the following general synthetic scheme.

[Chem. 16]

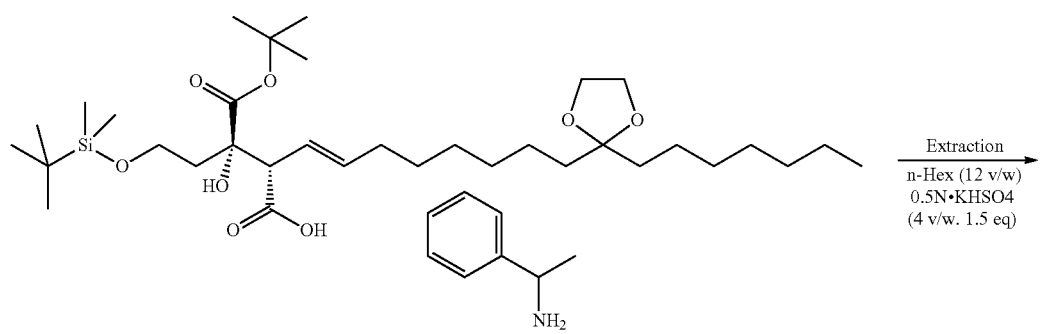

No. 4976198
Compound A'

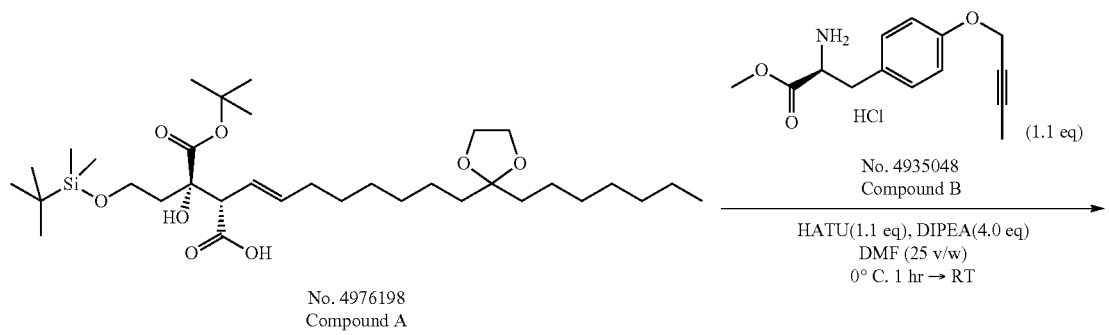

No. 4976198
Compound A

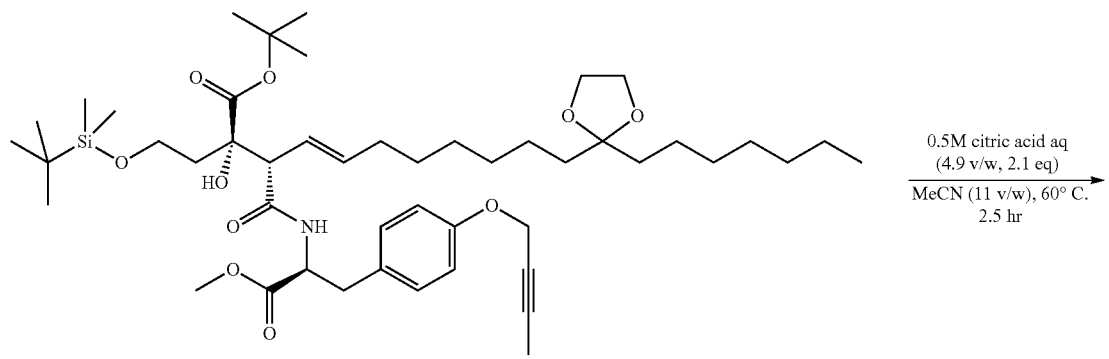

No. 5327507
Compound c

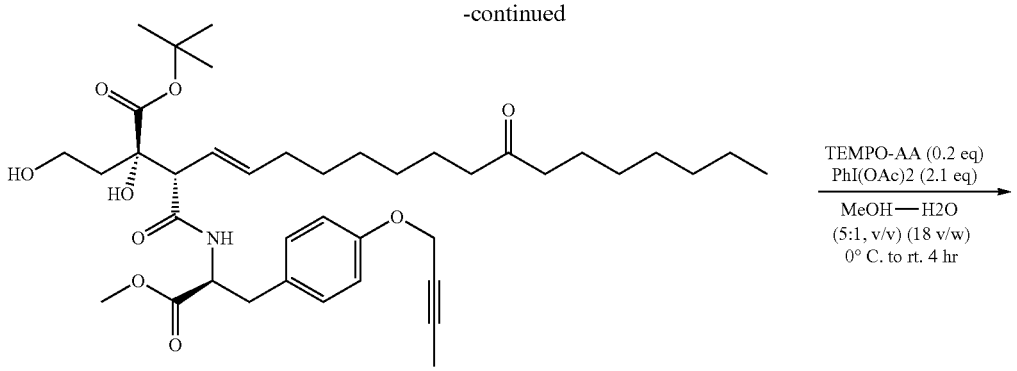

No. 5217614
Compound D

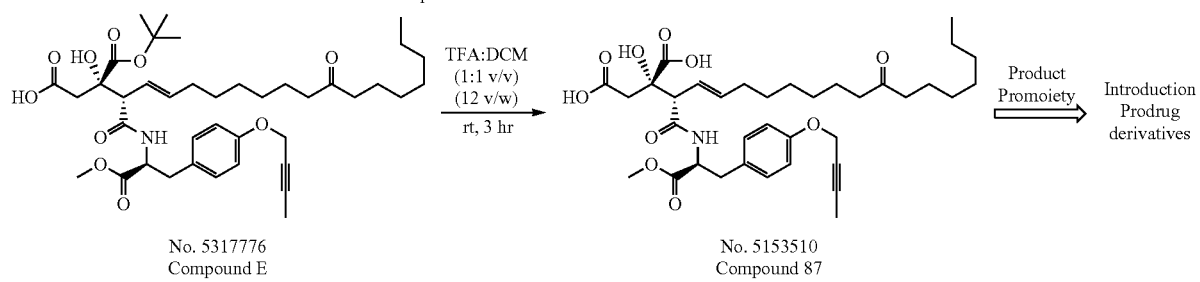

No. 5317776
Compound E

No. 5153510
Compound 87

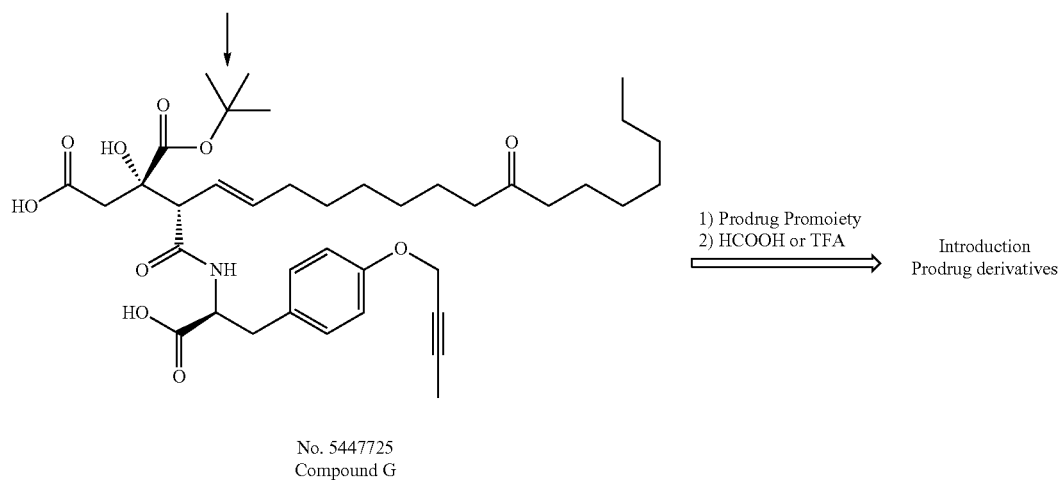

No. 5447725
Compound G

No. 4976198 (Compound A') was synthesized according to a method described in WO2006/08807. No. 4935048 (Compound B) was synthesized according to a synthetic method in Production Example 2 described in WO2007/000994. No. 4630808 (Compound 93) was synthesized according to the method described in WO2006/08807.

No. 4976198 (Compound A)

1-tert-Butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate To (S)-1-phenyl-ethylamine salt (1:1) of Compound A' 1-tert-butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (35.0 g, 46.7 mmol) were added n-hexane (420 mL) and an aqueous solution of 0.5 M potassium hydrogen sulfate (140 mL, 70.0 mmol), and subsequently, the solution was vigorously stirred for 30 minutes. The solution was transferred into a separatory funnel and then the hexane layer was separated. The aqueous layer was extracted with n-hexane (210 mL) twice. The hexane layer was washed with a saturated aqueous solution (210 mL) of sodium chloride, and then dried over anhydrous sodium sulfate. After filtration, n-hexane was distilled off under reduced pressure to obtain 29.5 g of (46.9 mmol, quant.) of No. 4976198 (Compound A).

$^{1}$H-NMR (CDCl$_3$) δ: 0.07 (3H, s), 0.08 (3H, s), 0.88 (3H, t, J=7.0 Hz), 0.90 (9H, s), 1.17-1.70 (22H, m), 1.47 (9H, s), 1.90-2.13 (4H, m), 3.39 (1H, d, J=9.2 Hz), 3.78 (2H, t, J=5.9 Hz), 3.93 (4H, s), 5.53 (1H, dd, J=15.2, 9.2 Hz), 5.74 (1H, dt, J=15.2, 6.5 Hz)

ESI (LC/MS positive mode) m/z 573 (M+H); Rt 4.63 min.

No. 5327507 (Compound C)

tert-Butyl (E)-(2S,3S)-2-[2-(tert-butyl-dimethyl-silanyloxy)-ethyl]-3-[(S)-2-(4-but-2-ynyloxy-phenyl)-1-methoxycarbonyl-ethylcarbamoyl]-11-(2-heptyl-[1,3]dioxolan-2-yl)-2-hydroxy-undec-4-enoate No. 4976198 (Compound A; 29.4 g, 46.7 mmol) was dissolved in N,N-dimethylformamide (700 mL), and then the solution was cooled to 0° C. in an ice bath. No. 4935048 Compound B (14.6 g, 51.3 mmol), N,N-diisopropylethylamine (32.5 mL, 186 mmol), and O-(7-azabenzotriazol-1-yl)-N,N,N',N'-tetramethyluronium hexafluophosphate (HATU; 19.5 g, 51.3 mmol) were added in this order, before stirring at room temperature for 2 hours. After quenching with a mixture of a cooled aqueous solution (160 mL) of 0.5 M potassium hydrogen sulfate and water (960 mL), the resulting solution was extracted with 20% ethyl acetate/n-hexane (470 mL). The aqueous layer was further extracted with 20% ethyl acetate/n-hexane (235 mL) 3 times. After combining the organic layers, it was washed with a mixture of a saturated aqueous solution (36 mL) of sodium chloride and water (180 mL). The organic layer was separated, and the aqueous layer was extracted with 20% ethyl acetate/n-hexane (100 mL). The organic layers were combined and then dried over anhydrous sodium sulfate. After filtration, n-hexane was distilled off under reduced pressure to obtain 42.5 g (49.5 mmol, quant.) of No. 5327507 (Compound C) tert-butyl (E)-(2S, 3S)-2-[2-(tert-butyl-dimethyl-silanyloxy)-ethyl]-3-[(S)-2-(4-but-2-ynyloxy-phenyl)-1-methoxycarbonyl-ethylcarbamoyl]-11-(2-heptyl-[1,3]dioxolan-2-yl)-2-hydroxy-undec-4-enoate.

$^1$H-NMR (CDCl$_3$) δ: 0.06 (3H, s), 0.07 (3H, s), 0.89 (3H, t, J=6.7 Hz), 0.91 (9H, s), 1.20-1.73 (22H, m), 1.45 (9H, s), 1.79-2.10 (4H, m), 1.87 (3H, d, J=2.4 Hz), 3.00-3.13 (2H, m), 3.18 (1H, d, J=9.4 Hz), 3.60-3.75 (2H, m), 3.69 (3H, s), 3.93 (4H, s), 4.38 (1H, s), 4.62 (2H, q, J=2.4 Hz), 4.84 (1H, dd, J=13.9, 6.9 Hz), 5.50 (1H, dd, J=15.3, 9.4 Hz), 5.67 (1H, dt, J=15.3, 6.7 Hz), 6.87 (2H, d, J=8.6 Hz), 7.09 (2H, d, J=8.6 Hz)

ESI (LC/MS positive mode) m/z 858 (M+H); Rt 4.80 min.

No. 5217614 (Compound D)

tert-Butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate No. 5327507 Compound C (50.8 g, 59.2 mmol) was dissolved in acetonitrile (560 mL), and then an aqueous solution of 0.5 M citric acid (249 mL, 125 mmol) was added to the solution, which was stirred at 60° C. for 2.5 hours. After confirming that inner temperature had returned to room temperature, a mixture of a saturated aqueous solution of sodium chloride (51 mL) and water (813 mL) was added. The solution was extracted with 20% ethyl acetate/n-hexane (457 mL) 3 times. The organic layers were combined, then washed twice with a saturated aqueous solution (230 mL) of sodium chloride, dried over anhydrous sodium sulfate, and filtered. The solvent was then distilled off under reduced pressure and the residue was purified on Biotage (silica gel, n-hexane/acetone) to obtain 23.6 g (33.7 mmol, 57% yield) of No. 5217614 (Compound D).

$^1$H-NMR (CDCl$_3$) δ: 0.90 (3H, t, J=6.9 Hz), 1.18-1.61 (14H, m), 1.45 (9H, s), 1.66-1.79 (1H, m), 1.82 (3H, t, J=2.3 Hz), 1.90-2.08 (3H, m), 2.44 (4H, t, J=7.4 Hz), 2.91 (1H, dd, J=14.1, 9.0 Hz), 3.11 (1H, dd, J=14.1, 5.1 Hz), 3.20 (1H, d, J=8.9 Hz), 3.47-3.68 (2H, m), 3.70 (3H, s), 4.61 (2H, q, J=2.3 Hz), 4.64 (1H, dd, J=9.0, 5.1 Hz), 5.47 (1H, dd, J=15.3, 8.9 Hz), 5.59 (1H, dt, J=15.3, 6.2 Hz), 6.85 (2H, d, J=8.8 Hz), 7.10 (2H, d, J=8.8 Hz)

ESI (LC/MS positive mode) m/z 700 (M+H); Rt 2.25 min.

No. 5317766 (Compound E)

1-tert-Butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate No. 5217614 Compound D (19.1 g, 27.3 mmol) was dissolved in acetonitrile (287 mL), and then water (58 mL) was added to the solution, which was cooled to 0° C. in an ice bath. 4-acetamide-2,2,6,6-tetramethylpiperidine 1-oxyl (1.17 g, 5.49 mmol), and (diacetoxy)iodobenzene (18.5 g, 57.4 mmol) were added in this order, and then the ice bath was removed. After stirring at room temperature for 5 hours, a mixture of 0.5 M aqueous citric acid (146 mL) and water (581 mL) was added and extracted with ethyl acetate (720 mL) twice. The organic layers were combined, washed 4 times with an aqueous solution (600 mL) of 10% sodium thiosulfate and finally with a saturated aqueous solution (600 mL) of sodium chloride, then dried over anhydrous sodium sulfate and filtered. The solvent was distilled off under reduced pressure and the resulting residue was purified on Biotage (diol, n-hexane/acetone) to obtain 18.8 g (26.3 mmol, 96% yield) of No. 5317766 (Compound E).

$^1$H-NMR (CDCl$_3$) δ: 0.90 (3H, t, J=6.9 Hz), 1.18-1.65 (18H, m), 1.44 (9H, s), 1.82 (3H, t, J=2.3 Hz), 1.92-2.07 (2H, m), 2.44 (4H, t, J=7.4 Hz), 2.50 (1H, d, J=6.0 Hz), 2.81 (1H, t, J=6.0 Hz), 2.92 (1H, dd, J=14.0, 8.9 Hz), 3.11 (1H, dd, J=14.0, 5.1 Hz), 3.16 (1H, d, J=8.6 Hz), 3.72 (3H, s), 4.60 (2H, q, J=2.3 Hz), 4.63 (1H, dd, J=8.9, 5.1 Hz), 5.43-5.65 (2H, m), 6.85 (2H, d, J=8.7 Hz), 7.10 (2H, d, J=8.7 Hz)

ESI (LC/MS positive mode) m/z 714 (M+H); Rt 2.27 min.

No. 5153510 (Compound 87)

(S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinic acid A mixture {56.9 g, the amount of No. 5217614 (Compound D) to be contained is 39.6 g (55.5 mmol) in calculation} of No. 5217614 (Compound D) and iodobenzene at a molar ratio of 2/2 was dissolved in dichloromethane (341 mL), and then trifluoroacetic acid (341 mL) was added, at room temperature, to the solution, which was stirred for 3 hours, and then concentrated under reduced pressure. The resulting residue was purified on Biotage (diol, n-hexane/acetone) to obtain 32.6 g of the title compound (49.6 mmol, yield 89%).

$^1$H-NMR (CD$_3$OD) δ: 0.90 (3H, t, J=7.0 Hz), 1.20-1.42 (14H, m), 1.47-1.62 (4H, m), 1.82 (3H, t, J=2.3 Hz), 1.92-2.04 (2H, m), 2.44 (4H, t, J=7.4 Hz), 2.57 (1H, d, J=16.2 Hz), 2.90 (1H, d, J=16.2 Hz), 2.91 (1H, dd, J=14.1, 9.0 Hz), 3.12 (1H, dd, J=14.1, 5.1 Hz), 3.20 (1H, d, J=8.4 Hz), 3.73 (3H, s), 4.59 (2H, q, J=2.3 Hz), 4.63 (1H, dd, J=9.0, 5.1 Hz), 5.44-5.62 (2H, m), 6.85 (2H, d, J=8.6 Hz), 7.11 (2H, d, J=8.6 Hz)

ESI (LC/MS positive mode) m/z 658 (M+H); Rt 2.70 min.

No. 5214357 (Compound T) was produced according to the following synthetic scheme.

[Chem. 17]
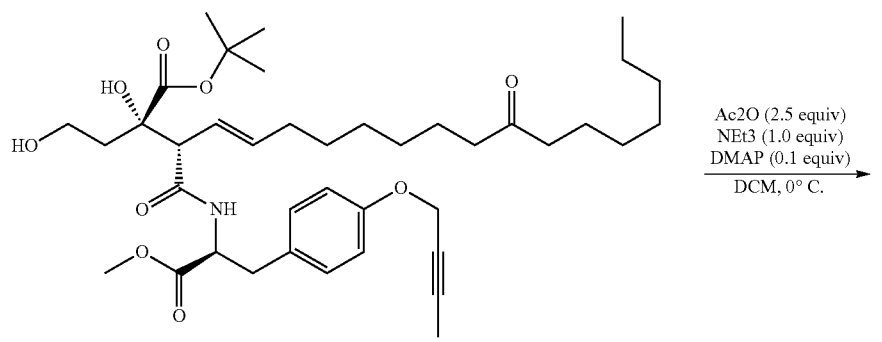
No. 5217614
Compound D
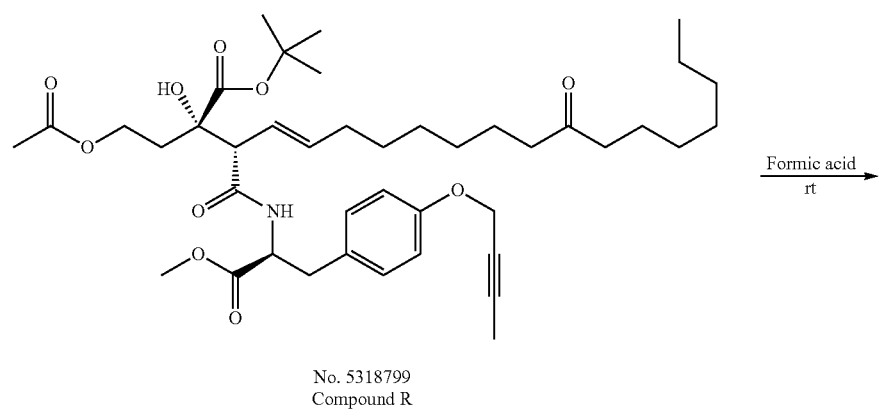
No. 5318799
Compound R
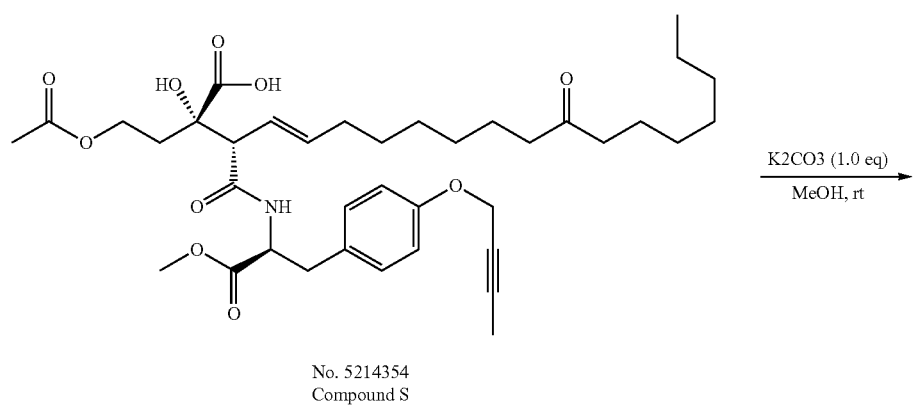
No. 5214354
Compound S
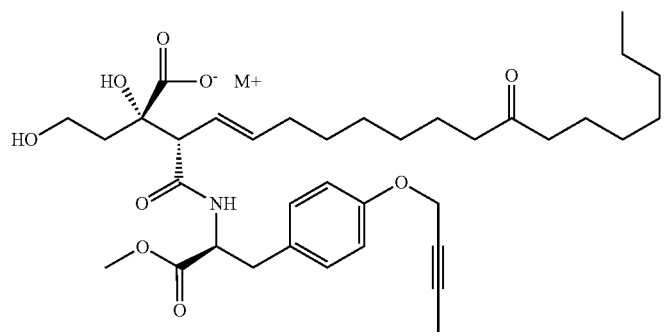
(M = Na or K)
No. 5214357
Compound T

Step 1: Synthesis of No. 5318799 (Compound R)

tert-Butyl (E)-(2S,3S)-2-(2-acetoxy-ethyl)-3-[(S)-2-(4-but-2-ynyloxy-phenyl)-1-methoxycarbonyl-ethylcarbamoyl]-2-hydroxy-12-oxo-nonadec-4-enoate No. 5217614 Compound D (13.7 g, 19.6 mmol) was dissolved in dichloromethane (274 mL), and then acetic anhydride (4.64 mL, 49.1 mmol), triethylamine (2.74 mL, 19.7 mmol) and dimethylaminopyridine (240 mg, 1.96 mmol) were added, at 0° C., to the solution, which was stirred for 1.5 hours and quenched with water (195 mL), and then partitioned into two layers. The aqueous layer was extracted with dichloromethane (195 mL). The dichloromethane layers were combined, washed with a saturated aqueous solution (140 mL) of sodium chloride, dried over anhydrous sodium sulfate, and filtered. The solvent was distilled off under reduced pressure, and the residue was purified on Biotage (silica gel, n-hexane/ethyl acetate) to obtain 11.0 g (14.8 mmol, 76% yield) of No. 5318799 (Compound R).

$^1$H-NMR (CD$_3$OD) δ: 0.88 (3H, t, J=7.0 Hz), 1.20-1.38 (14H, m), 1.45 (9H, s), 1.46-1.58 (4H, m), 1.68-1.78 (1H, m), 1.80 (3H, t, J=2.3 Hz), 1.92-2.08 (3H, m), 1.98 (3H, s), 2.42 (4H, t, J=7.4 Hz), 2.88 (1H, dd, J=14.1, 9.4 Hz), 3.12 (1H, dd, J=14.1, 4.9 Hz), 3.19 (1H, d, J=9.2 Hz), 3.70 (3H, s), 3.92-4.12 (2H, m), 4.60 (2H, q, J=2.3 Hz), 4.64 (1H, dd, J=9.4, 4.9 Hz), 5.45-5.52 (1H, m), 5.59 (1H, dt, J=15.3, 6.4 Hz), 6.84 (2H, d, J=8.5 Hz), 7.09 (2H, d, J=8.5 Hz)

ESI (LC/MS positive mode) m/z 742 (M+H); Rt 3.33 min.

Step 2: Synthesis of No. 5214354 (Compound S)

(E)-(2S,3S)-2-(2-acetoxy-ethyl)-3-[(S)-2-(4-but-2-ynyloxy-phenyl)-1-methoxycarbonyl-ethylcarbamoyl]-2-hydroxy-12-oxo-nonadec-4-enoic acid No. 5318799 (Compound R; 11.4 g, 15.4 mmol) was dissolved in formic acid (229 mL), and then the solution was stirred at room temperature for 3 hours. The reaction solution was concentrated under reduced pressure, and then dissolved in ethyl acetate (250 mL). After washing twice with a 6:1 mixture (250 mL) of an aqueous solution of 1% sodium bicarbonate and a saturated aqueous solution of sodium chloride, the solution was washed with a 6:1 mixture (220 mL) of an aqueous solution of 10% ammonium chloride and a saturated aqueous solution of sodium chloride, and finally with a saturated aqueous solution of sodium chloride (100 mL), dried over anhydrous sodium sulfate, and filtered. The solvent was distilled off under reduced pressure. The residue was purified on Biotage (silica gel, dichloromethane/methanol) to obtain 10.5 g (15.3 mmol, 99% yield) of No. 5214354 (Compound S).

$^1$H-NMR (CD$_3$OD) δ: 0.88 (3H, t, J=7.0 Hz), 1.19-1.38 (14H, m), 1.40-1.58 (4H, m), 1.60-1.71 (1H, m), 1.76-1.84 (3H, m), 1.90-2.03 (2H, m), 1.95 (3H, s), 2.07-2.20 (1H, m), 2.42 (4H, t, J=7.2 Hz), 2.88 (1H, dd, J=14.1, 9.2 Hz), 3.12 (1H, dd, J=14.1, 4.9 Hz), 3.19 (1H, d, J=8.8 Hz), 3.70 (3H, s), 4.00-4.10 (2H, m), 4.60 (2H, br.q, J=2.2 Hz), 4.65 (1H, dd, J=9.2, 4.9 Hz), 5.47 (1H, dd, J=15.3, 8.8 Hz), 5.56 (1H, dt, J=15.3, 6.5 Hz), 6.84 (2H, d, J=8.6 Hz), 7.09 (2H, d, J=8.6 Hz)

ESI (LC/MS positive mode) m/z 686 (M+H); Rt 4.68 min.

Step 3: Synthesis of No. 5214357 (Compound T)

(E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoic acid potassium salt or sodium salt or a mixture of Na salt and K salt No. 5214354 (Compound S; 13.6 g, 19.8 mmol) was dissolved in methanol (721 mL), and potassium carbonate (2.69 g, 19.5 mmol) was added, at room temperature, to the solution, which was stirred for 23 hours. Subsequently, water (544 mL) and a saturated aqueous solution of sodium chloride (272 mL) were added to the solution, and the mixture was extracted with ethyl acetate (1,088 mL). The aqueous layer was extracted with ethyl acetate (544 mL) twice. The organic layers were combined, then washed twice with a saturated aqueous solution of sodium chloride (326 mL), dried over anhydrous sodium sulfate, and filtered. The solvent was distilled off under reduced pressure. To the resulting residue was added methanol (100 mL) and the mixture was concentrated under reduced pressure. This operation of "adding methanol and then concentrating under reduced pressure" was further repeated twice and the residue was solidified. Methanol (68 mL) was added and then the mixture was stirred at room temperature for 1.5 hours. Insoluble material was filtered, and the insoluble (powder) was washed twice with methanol (14 mL). The resulting powder was dried using a vacuum pump to obtain 10.6 g (15.5 mmol, 78% yield) of No. 5214357 (Compound T).

$^1$H-NMR (CD$_3$OD) δ: 0.90 (3H, t, J=7.0 Hz), 1.19-1.36 (14H, m), 1.45-1.58 (4H, m), 1.70-1.80 (1H, m), 1.82 (3H, t, J=2.3 Hz), 1.87-2.03 (2H, m), 2.36-2.46 (4H, m), 2.95 (1H, dd, J=14.1, 8.4 Hz), 3.07 (1H, dd, J=14.1, 6.3 Hz), 3.23 (1H, d, J=7.8 Hz), 3.43-3.54 (1H, m), 3.57-3.68 (1H, m), 3.69 (3H, s), 4.60 (2H, q, J=2.3 Hz), 4.64 (1H, dd, J=8.4, 6.3 Hz), 5.43 (1H, dd, J=15.3, 7.8 Hz), 5.51 (1H, dt, J=15.3, 6.5 Hz), 6.86 (2H, d, J=8.8 Hz), 7.13 (2H, d, J=8.8 Hz)

ESI (LC/MS positive mode) m/z 644 (M+H); Rt 2.68 min.

No. 5447725 (Compound G)

1-tert-Butyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate No. 5317776 (Compound E) (4.06 g, 5.69 mmol) was dissolved in methanol (200 mL) and water (20 mL), and then lithium hydroxide monohydrate (955 mg, 22.78 mmol) and triethylamine (97.9 μL, 0.703 mmol) were added at room temperature and stirred at 50° C. for 2 hours. After completing the reaction, the solution was neutralized with 1 M hydrochloric acid, and extracted with ethyl acetate. The organic layer was washed with water and a saturated brine, and dried over anhydrous sodium sulfate. After the organic layer was filtered and the solvent was distilled off, it was purified by diol silica gel column chromatography (n-hexane:acetone=2:1, Rf=0.4) to obtain 2.78 g (70% yield) of the desired compound.

$^1$H-NMR (CDCl$_3$) δ: 0.88 (3H, t, J=6.6 Hz), 1.12-1.36 (14H, m), 1.42 (9H, s), 1.45-1.60 (4H, m), 1.85 (3H, s), 1.90-2.05 (2H, m), 2.33-2.44 (4H, m), 2.48 (1H, d, J=15.9 Hz), 2.79 (1H, d, J=15.9 Hz), 3.00 (1H, dd, J=13.7, 8.2 Hz), 3.15-3.23 (3H, m), 3.24-3.73 (2H, br.s), 4.56-4.62 (2H, m), 4.76-4.83 (1H, m), 5.44 (1H, dd, J=14.8, 9.3 Hz), 5.61-5.67 (1H, m), 6.68 (2H, d, J=6.0 Hz), 6.95 (1H, d, J=7.1 Hz), 7.14 (2H, d, J=6.6 Hz).

ESI (LC/MS positive mode) m/z 700 (M+H); Rt 2.72 min.

Compound 4 (No. 5426448)

4-(1-Acetoxy-ethyl) S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate $^1$H-NMR (CD$_3$OD) δ: 0.90 (3H, t, J=9.2 Hz), 1.20-1.38 (14H, m), 1.43 (1.5H, d, J=5.4 Hz), 1.44 (1.5H, d, J=5.4 Hz), 1.44-1.58 (4H, m), 1.81 (3H, t, J=2.4 Hz), 1.97-2.01 (2H, m), 2.03 (3H, s), 2.43 (4H, t, J=7.4 Hz), 2.61 (0.5H, d, J=15.8 Hz), 2.65 (0.5H, d, J=15.8 Hz), 2.87-2.99 (2H, m), 3.08-3.16 (1H,

[Chem. 18]

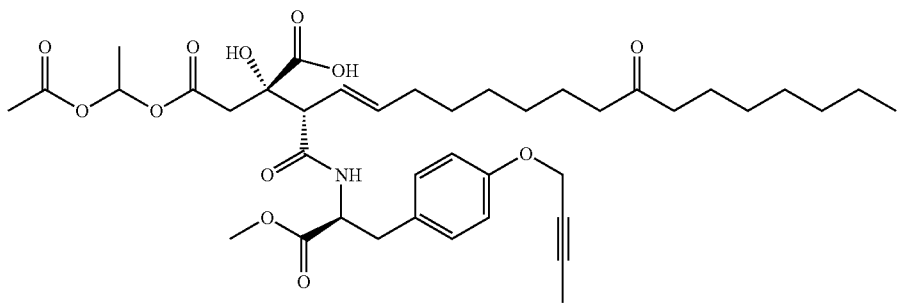

No. 5317776 (compound E; 3.19 g, 4.47 mmol) was dissolved in dichloromethane (31.4 mL), and then 1-bromoethyl acetate (3.29 g, 19.7 mmol), N,N-diisopropylethylamine (2.37 mL, 13.6 mmol), and sodium iodide (675 mg, 4.50 mmol) were added at room temperature. The mixture was stirred for 6 hours, then quenched with water (20 mL), and then extracted with dichloromethane (30 mL). The dichloromethane layer was washed with a saturated aqueous solution of sodium chloride (30 mL), then dried over anhydrous sodium sulfate, and filtered. The solvent was distilled off under reduced pressure. The residue was purified on Biotage (silica gel, n-hexane/ethyl acetate) to obtain 2.88 g (3.60 mmol, 81% yield, ESI (LC/MS positive mode) m/z 800 (M+H); Rt 2.40 min.) of 1-tert-butyl 4-(1-acetoxy-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate.

The obtained compound (27.5 mg, 0.0344 mmol) was dissolved in formic acid (1.0 mL, 26.5 mmol), and the solution was then stirred at room temperature for 16 hours. After the concentration under reduced pressure, the residue was purified by preparative HPLC to obtain 16.7 mg (0.0224 mmol, yield 65%) of Compound 4 (No. 5426448) as a diastereomeric mixture.

No. 5317776 (Compound E) was synthesized according to the method described in WO2003/014126.

m), 3.20 (0.5H, d, J=8.8 Hz), 3.22 (0.5H, d, J=8.8 Hz), 3.72 (3H, s), 4.59-4.68 (3H, m), 5.45-5.62 (2H, m), 6.77-6.83 (1H, m), 6.83-6.88 (2H, m), 7.08-7.12 (2H, m).

ESI (LC/MS positive mode) m/z 744 (M+H); Rt 3.08 min.

Compound 17 (No. 5401485)

4-Dimethylcarbamoylmethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 19]

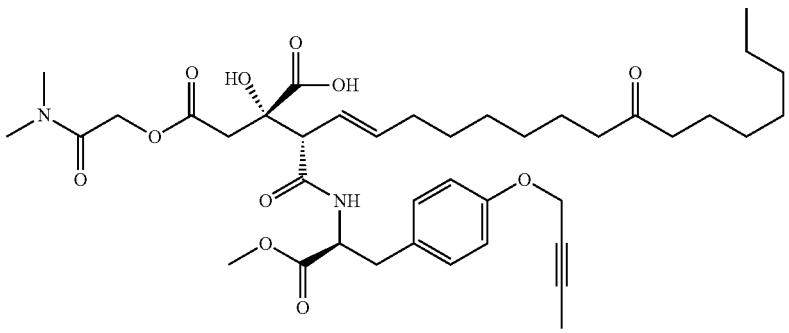

No. 5317776 (compound E; 48.8 mg, 0.0684 mmol) was dissolved in N,N-dimethylformamide (0.64 mL), and then N,N-diisopropylethylamine (14.7 μL, 0.0844 mmol) and commercially available 2-chloro-N,N-dimethylacetamide (7.2 μL, 0.0699 mmol) were added at room temperature. The mixture was stirred for 24 hours, and then extracted with ethyl acetate (30 mL) and water (20 mL). The organic layer was dried over anhydrous sodium sulfate. After filtration, the filtrate was concentrated under reduced pressure. The residue was purified by preparative HPLC to obtain 28.0 mg (0.0350 mmol, yield 51%, ESI (LC/MS positive mode) m/z 799 (M+H); Rt 3.08 min.) of 4-dimethylcarbamoylmethyl 1-tertbutyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate.

The obtained compound (21.2 mg, 0.0265 mmol) was dissolved in formic acid (1.0 mL), and then the solution was stirred at room temperature for 24 hours. After the concentration under reduced pressure, the residue was purified by preparative HPLC to obtain 13.7 mg (0.0184 mmol, yield 70%) of Compound 17.

Used was a 2-chloro-N,N-dimethyl acetamide reagent commercially available from Aldrich (cat. No. 24350, 25 mL).

$^1$H-NMR (CD$_3$OD) δ: 0.88 (3H, t, J=6.8 Hz), 1.20-1.35 (14H, m), 1.42-1.57 (4H, m), 1.80 (3H, t, J=2.3 Hz), 1.91-2.03 (2H, m), 2.42 (4H, t, J=7.4 Hz), 2.73 (1H, d, J=15.1 Hz), 2.85-2.95 (1H, m), 2.93 (3H, s), 2.99 (3H, s), 3.06 (1H, d, J=15.1 Hz), 3.10 (1H, dd, J=14.6, 4.7 Hz), 3.24 (1H, d, J=8.4 Hz), 3.70 (3H, s), 4.59 (2H, q, J=2.3 Hz), 4.60-4.67 (1H, m), 4.72 (1H, d, J=14.9 Hz), 4.86 (1H, d, J=14.9 Hz), 5.45-5.62 (2H, m), 6.83 (2H, d, J=8.6 Hz), 7.09 (2H, d, J=8.6 Hz). ESI (LC/MS positive mode) m/z 743 (M+H); Rt 2.81 min.

Compound 18 (No. 5422038)

4-(5-Methyl-2-oxo-[1,3]dioxol-4-ylmethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate reaction solution was concentrated under reduced pressure, and then purified by preparative HPLC to obtain 37.8 mg (0.0458 mmol, yield 61%, ESI (LC/MS positive mode) m/z 826 (M+H); Rt 3.49 min.) of 4-(5-methyl-2-oxo-[1,3]dioxol-4-ylmethyl) 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate.

The obtained compound (32.8 mg, 0.0397 mmol) was dissolved in formic acid (1.0 mL, 26.5 mmol), and then the solution was stirred at room temperature for 14 hours. After the concentration under reduced pressure, the residue was purified by preparative HPLC to obtain 23.3 mg (0.0303 mmol, 76% yield) of Compound 18. Used was a 4-chloromethyl-5-methyl 1,3-dioxole reagent commercially available from Aldrich (cat. No. 80841-78-7).

$^1$H-NMR (CD$_3$OD) δ: 0.88 (3H, t, J=7.0 Hz), 1.17-1.38 (14H, m), 1.46-1.58 (4H, m), 1.80 (3H, t, J=2.3 Hz), 1.90-2.05 (2H, m), 2.14 (3H, s), 2.42 (4H, t, J=7.2 Hz), 2.62 (1H, d, J=15.7 Hz), 2.90 (1H, dd, J=14.1, 9.0 Hz), 2.94 (1H, d, J=15.7 Hz), 3.11 (1H, dd, J=14.1, 5.1 Hz), 3.20 (1H, d, J=8.6 Hz), 3.70 (3H, s), 4.59 (2H, q, J=2.3 Hz), 4.64 (1H, dd, J=9.0, 5.1 Hz), 4.86 (2H, d, J=14.5 Hz), 4.91 (2H, d, J=14.5 Hz), 5.43-5.60 (2H, m), 6.83 (2H, d, J=8.6 Hz), 7.08 (2H, d, J=8.6 Hz).

ESI (LC/MS positive mode) m/z 770 (M+H); Rt 2.51 min.

[Chem. 20]

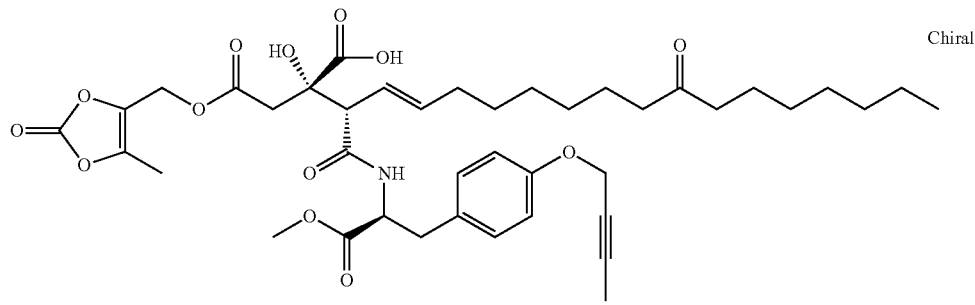

No. 5317776 (Compound E; 53.3 mg, 0.0747 mmol) was dissolved in N,N-dimethylformamide (0.64 mL), and then N,N-diisopropylethylamine (14 µL, 0.0804 mmol), 4-chloromethyl-5-methyl 1,3-dioxole (14 mg, 0.0943 mmol), and sodium iodide (10 mg, 0.0667 mmol) were added at room temperature. After the mixture was stirred for 39 hours, the Compound 19 (No. 5422039)

4-(2-Morpholin-4-yl-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 21]

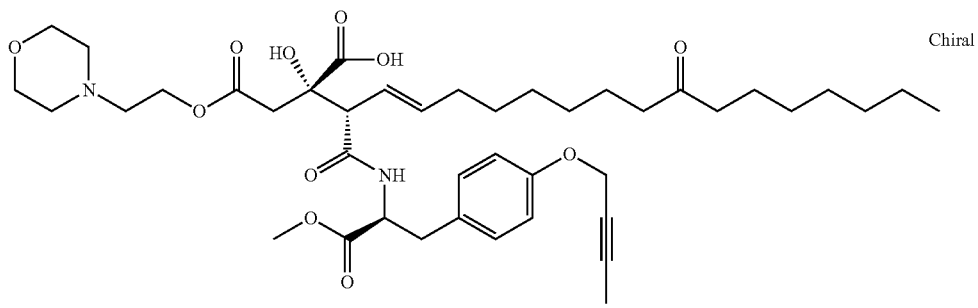

No. 5317776 (Compound E; 49.4 mg, 0.0692 mmol) was dissolved in N,N-dimethylformamide (0.64 mL), and then N,N-diisopropylethylamine (27 µL, 0.155 mmol), N-(2-chloroethyl)morpholine hydrochloride (13 mg, 0.0699 mmol), and sodium iodide (10 mg, 0.0701 mmol) were added at room temperature. After the mixture was stirred for 22 hours, the outer temperature was increased to 50° C., and the mixture was stirred for 20 hours. Without further processing, the reaction solution was purified by preparative HPLC to obtain 22.8 mg (0.0276 mmol, 40% yield, ESI (LC/MS positive mode) m/z 828 (M+H); Rt 3.22 min.) of 4-(2-morpholin-4-ylethyl) 1-tert-butyl (S)-2-{(E)-(S)-1-[(S)-2-(4-but-2-yloxy-phenyl)-1-methoxycarbonyl-ethylcarbamoyl]-10-oxo-heptadec-2-enyl}-2-hydroxy-succinate.

The obtained compound (15.0 mg, 0.0181 mmol) was dissolved in formic acid (1.0 mL, 26.5 mmol), and then the solution was stirred at room temperature for 24 hours. After the concentration under reduced pressure, the residue was purified by preparative HPLC to obtain 10.3 mg (0.0134 mmol, yield 74%) of Compound 19.

$^1$H-NMR (CD$_3$OD) δ: 0.88 (3H, t, J=7.0 Hz), 1.20-1.36 (14H, m), 1.46-1.58 (4H, m), 1.80 (3H, t, J=2.4 Hz), 1.90-2.05 (2H, m), 2.42 (4H, t, J=7.2 Hz), 2.73 (1H, d, J=14.9 Hz), 2.88 (1H, dd, J=14.1, 9.0 Hz), 3.08 (1H, d, J=14.9 Hz), 3.13 (1H, dd, J=14.1, 5.1 Hz), 3.25-3.50 (6H, m), 3.34 (1H, d, J=9.0 Hz), 3.71 (3H, s), 3.85-4.07 (4H, m), 4.24-4.34 (1H, m), 4.60 (2H, q, J=2.4 Hz), 4.61-4.69 (2H, m), 5.44 (1H, dd, J=15.4, 9.0 Hz), 5.57 (1H, dt, J=15.4, 6.7 Hz), 6.84 (2H, d, J=8.8 Hz), 7.09 (2H, d, J=8.8 Hz).

ESI (LC/MS positive mode) m/z 771 (M+H); Rt 2.91 min.

Compound 20 (No. 5422041)

4-(2-Dimethylamino-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate No. 5317776 (Compound E; 135 mg, 0.189 mmol) was dissolved in N,N-dimethylformamide (1.35 mL), and then N,N-diisopropylethylamine (370 µL, 2.12 mmol), 2-dimethylaminoethyl hydrochloride (275 mg, 1.91 mmol) and sodium iodide (285 mg, 1.90 mmol) were added at room temperature. The mixture was stirred at 50° C. for 4 hours. Without further processing, the reaction solution was purified by preparative HPLC to obtain 11.8 mg (0.0153 mmol, yield 8%, ESI (LC/MS positive mode) m/z 786 (M+H); Rt 2.25 min.) of 4-(2-dimethylamino-ethyl) 1-tert-butyl (S)-2-{(E)-(S)-1-[(S)-2-(4-but-2-yloxy-phenyl)-1-methoxycarbonyl-ethylcarbamoyl]-10-oxo-heptadec-2-enyl}-2-hydroxy-succinate.

The obtained compound (11.8 mg, 0.0150 mmol) was dissolved in formic acid (0.64 mL, 17.0 mmol), and then the solution was stirred at room temperature for 17 hours. After the concentration under reduced pressure, the residue was purified by preparative HPLC to obtain 6.7 mg (0.00919 mmol, yield 64%) of Compound 20.

Used was a 2-dimethylaminoethyl hydrochloride reagent commercially available from Tokyo Chemical Industry Co., Ltd. (cat. No. C0106).

$^1$H-NMR (CD$_3$OD) δ: 0.88 (3H, t, J=7.0 Hz), 1.21-1.36 (14H, m), 1.47-1.60 (4H, m), 1.80 (3H, t, J=2.4 Hz), 2.73 (1H, d, J=15.1 Hz), 2.88 (1H, dd, J=14.1, 9.0 Hz), 3.06 (1H, d, J=15.1 Hz), 3.12 (1H, dd, J=14.1, 5.1 Hz), 3.31 (1H, d, J=9.0 Hz), 3.36-3.42 (2H, m), 3.72 (3H, s), 4.25-4.34 (1H, m), 4.54-4.67 (2H, m), 4.59 (2H, q, J=2.4 Hz), 5.44 (1H, dd, J=15.5, 9.0 Hz), 5.56 (1H, dt, J=15.5, 6.7 Hz), 6.84 (2H, d, J=8.6 Hz), 7.08 (2H, d, J=8.6 Hz).

ESI (LC/MS positive mode) m/z 729 (M+H); Rt 1.96 min.

[Chem. 22]

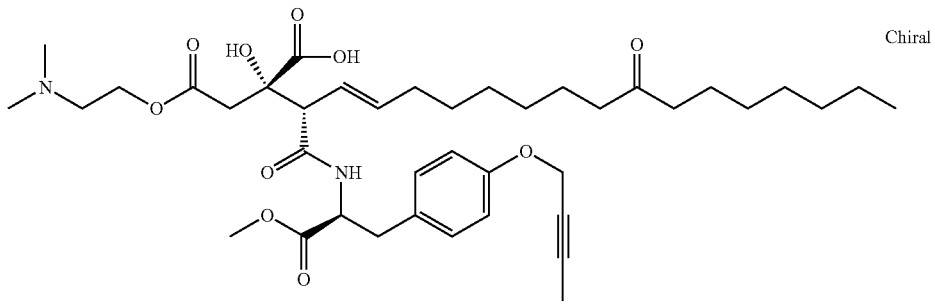

Compound 21 (No. 5426450)

4-(2-Oxo-2-piperidin-1-yl-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 23]

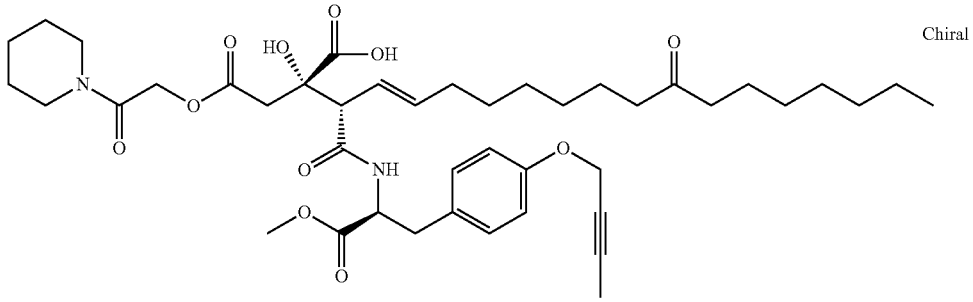

No. 5317776 (Compound E; 53.5 mg, 0.0749 mmol) was dissolved in N,N-dimethylformamide (1.0 mL), and then N,N-diisopropylethylamine (17.2 μL, 0.0988 mmol), 2-chloro-1-piperidin-1-yl-ethanone (14.5 mg, 0.0897 mmol), and sodium iodide (11.6 mg, 0.0774 mmol) were added at room temperature. The mixture was stirred for 39 hours, and then extracted with ethyl acetate (60 mL) and water (40 mL). The organic layer was dried over anhydrous sodium sulfate. After filtration, the solvent was distilled off under reduced pressure. The residue was purified on Biotage (silica gel, n-hexane/ethyl acetate) to obtain 44.5 mg (0.0530 mmol, yield 71%, ESI (LC/MS positive mode) m/z 840 (M+H); Rt 3.59 min.) of 4-(2-oxo-2-piperidin-1-yl-ethyl) 1-tert-butyl (S)-2-{(E)-(S)-1-[(S)-2-(4-but-2-yloxy-phenyl)-1-methoxycarbonyl-ethylcarbamoyl]-10-oxo-heptadec-2-enyl}-2-hydroxy-succinate.

The obtained compound (38.9 mg, 0.0470 mmol) was dissolved in formic acid (1.0 mL, 26.5 mmol), and then the solution was stirred at room temperature for 16 hours. After the concentration under reduced pressure, the residue was purified by preparative HPLC to obtain 27.1 mg (0.0346 mmol, yield 74%) of Compound 21.

Used was a 2-chloro-1-piperidin-1-yl-ethanone reagent commercially available from CHESS GmbH (cat. No. 2106-050).

$^1$H-NMR (CD$_3$OD) δ: 0.88 (3H, t, J=7.2 Hz), 1.20-1.38 (14H, m), 1.45-1.70 (10H, m), 1.80 (3H, t, J=2.3 Hz), 1.92-2.04 (2H, m), 2.42 (4H, t, J=2.3 Hz), 2.73 (1H, d, J=15.8 Hz), 2.92 (1H, dd, J=14.1, 8.8 Hz), 3.05 (1H, d, J=15.8 Hz), 3.10 (1H, dd, J=14.1, 4.9 Hz), 3.25 (1H, d, J=8.4 Hz), 3.32-3.40 (2H, m), 3.48-3.54 (2H, m), 3.70 (3H, s), 4.59 (2H, q, J=2.3 Hz), 4.63 (1H, dd, J=8.8, 4.9 Hz), 4.72 (1H, d, J=14.7 Hz), 4.86 (1H, d, J=14.7 Hz), 5.46-5.62 (2H, m), 6.83 (2H, d, J=8.6 Hz), 7.09 (2H, d, J=8.6 Hz).

ESI (LC/MS positive mode) m/z 783 (M+H); Rt 3.06 min.

Compound 22 (No. 5444514)

4-[1-(2,2-Dimethyl-propionyloxy)-ethyl](S)-2-((E)-(S)-1-{(S)-2-(4-but-2-ynyloxy-phenyl)-1-[1-(2,2-dimethyl-propionyloxy)-ethoxycarbonyl]-ethylcarbamoyl}-10-oxo-heptadec-2-enyl)-2-hydroxy-succinate

[Chem. 24]

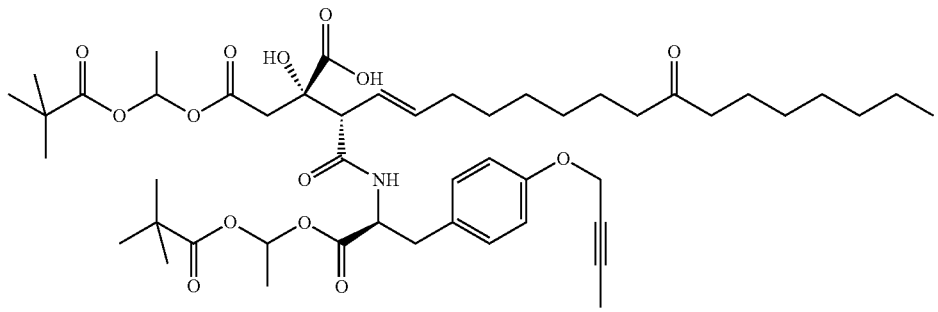

No. 5447725 (compound G; 64.3 mg, 0.0919 mmol) was dissolved in dichloromethane (3.0 mL), and then 4-iodo-2,2-dimethyl-pentan-3-one (177 mg, 0.737 mmol) and N,N,N',N'-tetramethyl1,8-naphthalenediamine (189 mg, 0.882 mmol) were added at room temperature. The mixture was stirred for 24 hours, and then extracted with ethyl acetate (30 mL) and water (20 mL). The organic layer was washed with a saturated aqueous solution of sodium chloride (10 mL), then dried over anhydrous sodium sulfate, and filtered. The solvent was distilled off under reduced pressure. The residue was purified on Biotage (silica gel, n-hexane/ethyl acetate) to obtain 65.4 mg (0.0684 mmol, yield 74%, ESI (LC/MS positive mode) m/z 956 (M+H); Rt 4.60 min.) of 4-[1-(2,2-dimethyl-propionyloxy)-ethyl]1-tert-butyl (S)-2-((E)-(S)-1-{(S)-2-(4-but-2-ynyloxy-phenyl)-1-[1-(2,2-dimethyl-propionyloxy)-ethoxycarbonyl]-ethylcarbamoyl}-10-oxo-heptadec-2-enyl)-2-hydroxy-succinate as a diastereomeric mixture.

The obtained compound (53.5 mg, 0.0559 mmol) was dissolved in formic acid (2.0 mL, 53.0 mmol), and then the solution was stirred at room temperature for 27 hours. After the concentration under reduced pressure, the residue was purified by preparative HPLC to obtain 32.8 mg (0.0364 mmol, yield 65%) of Compound 22 as a diastereomeric mixture.

Synthesis of 1-iodo-ethyl 2,2-dimethyl-propionate (Reference; Journal of antibiotics (1986) 39 (9), 1329-42)

[Chem. 25]

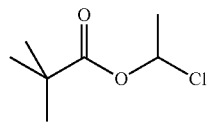

Pivaloyl chloride (1.05 mL, 8.71 mmol) was dissolved in dichloromethane (19 mL), and then the solution was cooled at −18° C. Zinc chloride (18.1 mg, 0.133 mmol) was added, and then a solution of acetaldehyde (750 mg, 17.0 mmol) in dichloromethane (3.0 mL) was added dropwise. After completion of the dropwise addition, the mixture was stirred at an outer temperature from −10 to −18° C. for 2 hours. The mixture was quenched with water (10 mL), and then separated into layers to obtain a dichloromethane layer, which was dried over anhydrous sodium sulfate, and filtered. The solvent was distilled off under reduced pressure.

The resulting residue (1.08 g) was dissolved in acetonitrile (4.5 mL), and then sodium iodide (2.93 g, 19.5 mmol) was added at room temperature. The mixture was stirred for 20 hours, then quenched with water (30 mL), and extracted with dichloromethane (40 mL). The dichloromethane layer was dried over anhydrous sodium sulfate, and filtered. The solvent was distilled off under reduced pressure to obtain 486 mg (2.02 mmol, yield 23%) of 1-iodo-ethyl 2,2-dimethyl-propionate.

$^{1}$H-NMR (CD$_{3}$OD) δ: 0.88 (3H, t, J=6.8 Hz), 1.10-1.62 (42H, m), 1.84 (3H, t, J 2.2 Hz), 1.87-2.10 (2H, m), 2.25-2.75 (6H, m), 2.85-3.27 (3H, m), 4.60 (2H, br.s), 4.62-4.82 (1H, m), 5.40-5.63 (2H, m), 6.70-6.90 (4H, m), 6.95-7.08 (2H, m).

ESI (LC/MS positive mode) m/z 900 (M+H); Rt 3.90 min.

No. 5724856 (Compound RR) and No. 5724858 (Compound SS) were prepared according to the following synthetic scheme.

[Chem. 26]

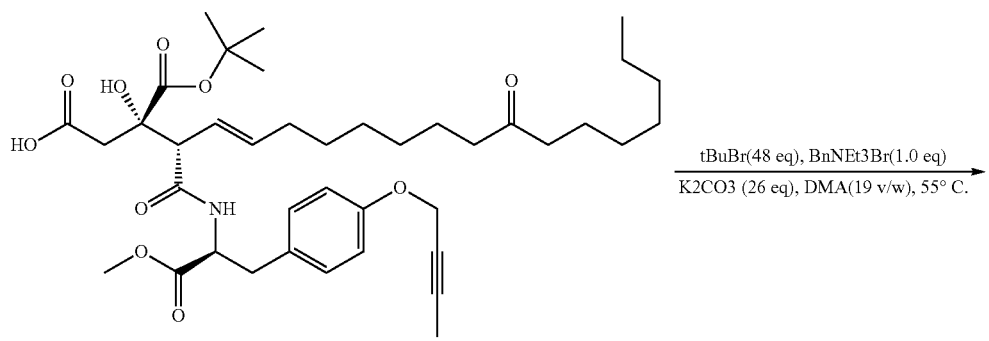

No. 5317776
Compound E

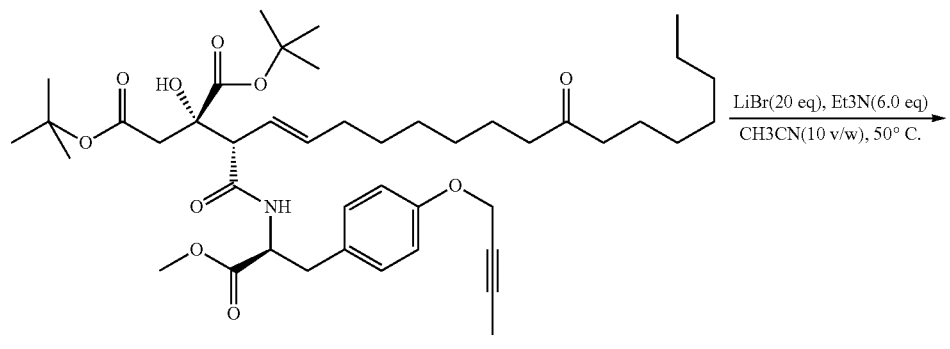

No. 5724856
Compound RR

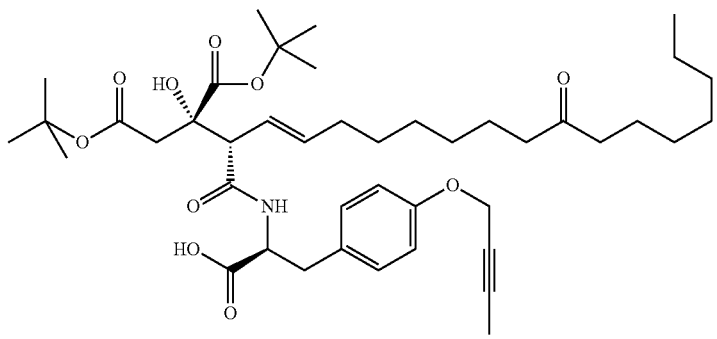

No. 5724858
Compound SS

Synthesis of No. 5724856 (Compound RR)

Di-tert-butyl (S)-2-{(E)-(S)-1-[(S)-2-(4-but-2-yny-loxy-phenyl)-1-methoxycarbonyl-ethylcarbamoyl]-10-oxo-heptadec-2-enyl}-2-hydroxy-succinate No. 5317776 (compound E; 300 mg, 0.420 mmol) was dissolved in N,N-dimethylacetamide (5.7 mL), and then 2-bromo-2-methyl-propane (2.27 mL, 20.2 mmol), benzyl-triethylammonium bromide (115 mg, 0.422 mmol), and potassium carbonate (1.51 g, 10.9 mmol) were added at room temperature. The reaction solution was stirred at 55° C. for 4 hours, and then cooled to room temperature. After cooled water (77 mL) was added, the reaction solution was extracted twice with ethyl acetate (77 mL). The organic layer was washed with water (77 mL) and a saturated aqueous solution of sodium chloride (77 mL) in this order, and then dried over anhydrous sodium sulfate, and filtered. The solvent was distilled off under reduced pressure. The residue was purified on Biotage (silica gel, n-hexane/ethyl acetate) to obtain 261 mg (0.339 mmol, yield 81%) of No. 5724856 (Compound RR).

$^1$H-NMR (CD$_3$OD) δ: 0.88 (3H, t, J=6.6 Hz), 1.18-1.60 (18H, m), 1.44 (9H, s), 1.45 (9H, s), 1.82 (3H, t, J=2.3 Hz), 1.91-2.08 (2H, m), 2.44 (4H, t, J=7.4 Hz), 2.50 (1H, d, J=16.2 Hz), 2.77 (1H, d, J=16.2 Hz), 2.92 (1H, dd, J=14.1, 8.9 Hz), 3.11 (1H, dd, J=14.1, 4.9 Hz), 3.13 (1H, d, J=8.6 Hz), 3.72 (3H, s), 4.56-4.68 (3H, m), 5.40-5.65 (2H, m), 6.84 (2H, d, J=8.7 Hz), 7.10 (2H, d, J=8.7 Hz).

ESI (LC/MS positive mode) m/z 771 (M+H); Rt 2.60 min.

Synthesis of No. 5724858 (Compound SS)

Di-tert-butyl (S)-2-{(E)-(S)-1-[(S)-2-(4-but-2-yny-loxy-phenyl)-1-carboxy-ethylcarbamoyl]-10-oxo-heptadec-2-enyl}-2-hydroxy-succinate No. 5724856 (Compound RR; 250 mg, 0.325 mmol) was dissolved in acetonitrile (2.5 mL), and then triethylamine (0.272 mL, 1.95 mmol) and lithium bromide (564 mg, 6.49 mmol) were added at room temperature. The reaction solution was stirred at 55° C. for 20 hours, then cooled to room temperature, and quenched by the addition of 1 M hydrochloric acid (20 mL), followed by extraction with ethyl acetate (30 mL). The organic layer was washed twice with water (20 mL) and then twice with a saturated aqueous solution of sodium chloride (20 mL), and dried over anhydrous sodium sulfate, then filtered, and concentrated under reduced pressure. The residue was purified on Biotage (diol, n-hexane/acetone) to obtain 147 mg (0.194 mmol, yield 60%) of No. 5724858 (Compound SS).

$^1$H-NMR (CD$_3$OD) δ: 0.90 (3H, t, J=6.6 Hz), 1.17-1.63 (18H, m), 1.43 (9H, s), 1.44 (9H, s), 1.82 (3H, t, J=2.3 Hz), 1.91-2.03 (2H, m), 2.44 (4H, t, J=7.3 Hz), 2.50 (1H, d, J=16.2 Hz), 2.76 (1H, d, J=16.2 Hz), 2.92 (1H, dd, J=14.1, 8.9 Hz), 3.08-3.21 (2H, m), 4.55-4.68 (3H, m), 5.40-5.65 (2H, m), 6.84 (2H, d, J=8.8 Hz), 7.13 (2H, d, J=8.8 Hz).

ESI (LC/MS positive mode) m/z 757 (M+H); Rt 2.47 min.

Compound 23 (No. 5479585) and Compound 24 (No. 5479590) were prepared according to the following synthetic scheme.

[Chem. 27]

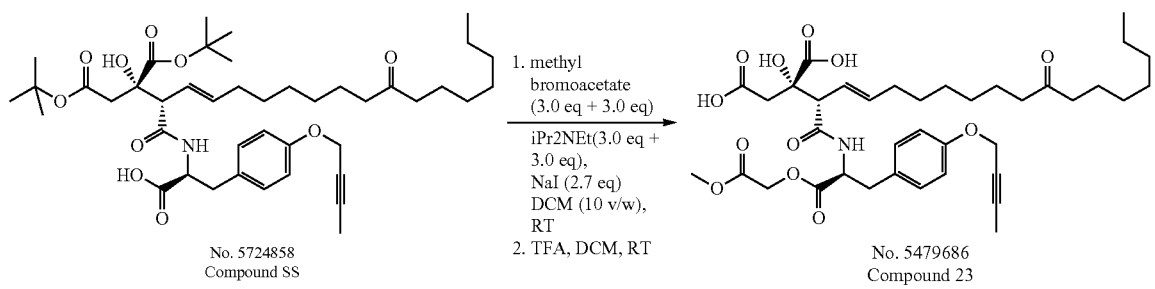

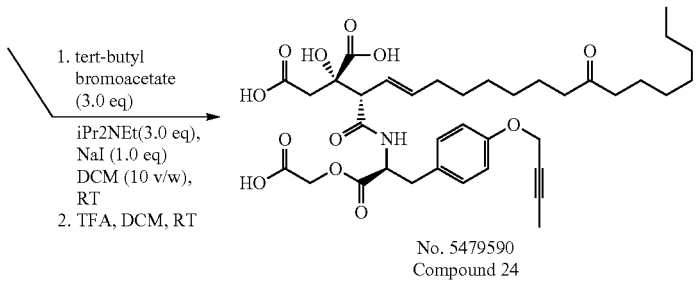

No. 5479590
Compound 24

Compound 23 (No. 5479585)

(S)-2-{(E)-(S)-1-[(S)-2-(4-But-2-ynyloxy-phenyl)-1-methoxycarbonylmethoxycarbonyl ethylcarbamoyl]-10-oxo-heptadec-2-enyl}-2-hydroxy-succinic acid No. 5724858 (Compound SS; 43.4 mg, 0.0574 mmol) was dissolved in dichloromethane (0.43 mL), and then methyl bromoacetate (0.0165 mL, 0.174 mmol), N,N-diisopropylethylamine (0.030 mL, 0.172 mmol), and sodium iodide (23.5 mg, 0.157 mmol) were added at room temperature. After the mixture was stirred for 21 hours, methyl bromoacetate (0.0165 mL, 0.174 mmol) was added. After the mixture was stirred for 3 hours, N,N-diisopropylethylamine (0.030 mL, 0.172 mmol) was added. After the mixture was stirred for 2.5 hours, the outer temperature was warmed up to 40° C. and then kept it for 3.5 hours. The mixture was extracted with ethyl acetate (30 mL) and water (20 mL), and then the organic layer was dried over anhydrous sodium sulfate. After filtration, the filtrate was concentrated under reduced pressure. The residue was purified on Biotage (silica gel, n-hexane/ethyl acetate) to obtain 43.7 mg (0.0528 mmol, yield 92%, ESI (LC/MS positive mode) m/z 829 (M+H); Rt 2.55 min.) of di-tert-butyl (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate.

The obtained compound (37.4 mg, 0.0452 mmol) was dissolved in dichloromethane (1.0 mL), and then trifluoroacetic acid (0.5 mL, 6.78 mmol) was added at room temperature. The mixture was stirred for 4.5 hours, and then concentrated under reduced pressure. The residue was purified by preparative HPLC to obtain 25.4 mg (0.0355 mmol, yield 79%) of Compound 23. Used was a methyl bromoacetate reagent commercially available from Wako Pure Chemical Industries, Ltd. (cat. No. 135-14472).

$^1$H-NMR (CD$_3$OD) δ: 0.90 (3H, t, J=6.9 Hz), 1.15-1.43 (14H, m), 1.44-1.65 (4H, m), 1.82 (3H, t, J=2.3 Hz), 1.90-2.10 (2H, m), 2.44 (4H, t, J=7.4 Hz), 2.54 (1H, d, J=15.7 Hz), 2.88 (1H, d, J=15.7 Hz), 2.94 (1H, dd, J=14.1, 9.7 Hz), 3.19 (1H, d, J=8.4 Hz), 3.23 (1H, dd, J=14.1, 4.7 Hz), 3.76 (3H, s), 4.60 (2H, q, J=2.3 Hz), 4.68 (1H, d, 16.0 Hz), 4.75 (1H, dd, J=9.7, 4.7 Hz), 4.78 (1H, d, 16.0 Hz), 5.43-5.62 (2H, m), 6.85 (2H, d, J=8.7 Hz), 7.15 (2H, d, J=8.7 Hz).

ESI (LC/MS positive mode) m/z 716 (M+H); Rt 2.02 min.

Compound 24 (No. 5479590)

(S)-2-{(E)-(S)-1-[(S)-2-(4-But-2-ynyloxy-phenyl)-1-carboxymethoxycarbonyl-ethylcarbamoyl]-10-oxo-heptadec-2-enyl}-2-hydroxy-succinic acid Used was a tert-butyl bromoacetate reagent commercially available from Wako Pure Chemical Industries, Ltd. (cat. No. 028-06972).

No. 5724858 (Compound SS; 53.2 mg, 0.0704 mmol) was dissolved in dichloromethane (0.53 mL), and then tert-butyl bromoacetate (0.027 mL, 0.214 mmol), diisopropylethylamine (0.037 mL, 0.212 mmol), and sodium iodide (32 mg, 0.214 mmol) were added at room temperature. The outer temperature was warmed up to 40° C. and then kept it for 20 hours. The mixture was extracted with ethyl acetate (30 mL) and water (20 mL), and then the organic layer was dried over anhydrous sodium sulfate. After filtration, the filtrate was concentrated under reduced pressure. The residue was purified on Biotage (silica gel, n-hexane/ethyl acetate) to obtain 54.6 mg (0.0628 mmol, yield 89%, ESI (LC/MS positive mode) m/z 871 (M+H); Rt 2.75 min.) of di-tert-butyl (S)-2-{(E)-(S)-1-[(S)-1-tert-butoxycarbonylmethoxycarbonyl-2-(4-but-2-ynyloxy-phenyl)-ethylcarbamoyl]-10-oxo-heptadec-2-enyl}-2-hydroxy-succinate.

The obtained compound (46.5 mg, 0.0534 mmol) was dissolved in dichloromethane (1.0 mL), and then trifluoroacetic acid (0.5 mL, 6.78 mmol) was added at room temperature. The mixture was stirred for 5 hours, and then concentrated under reduced pressure. The residue was purified by preparative HPLC to obtain 30.7 mg (0.0437 mmol, yield 82%) of Compound 24.

$^1$H-NMR (CD$_3$OD) δ: 0.90 (3H, t, J=6.9 Hz), 1.12-1.42 (14H, m), 1.42-1.63 (4H, m), 1.82 (3H, t, J=2.3 Hz), 1.89-2.06 (2H, m), 2.44 (4H, t, J=7.5 Hz), 2.54 (1H, d, J=16.2 Hz), 2.88 (1H, d, J=16.2 Hz), 2.94 (1H, dd, =14.2, 9.7 Hz), 3.19 (1H, d, J=8.1 Hz), 3.20 (1H, dd, J=9.6, 4.6 Hz), 4.60 (2H, q, J=2.3 Hz), 4.65 (1H, d, 16.0 Hz), 4.74 (1H, d, 16.0 Hz), 4.76 (1H, dd, J=9.7, 4.6 Hz), 5.42-5.61 (2H, m), 6.84 (2H, d, J=8.7 Hz), 7.15 (2H, d, J=8.7 Hz).

ESI (LC/MS positive mode) m/z 702 (M+H); Rt 1.87 min.

Compound 25 (No. 5485784) was produced according to the following synthetic scheme.

[Chem. 28]
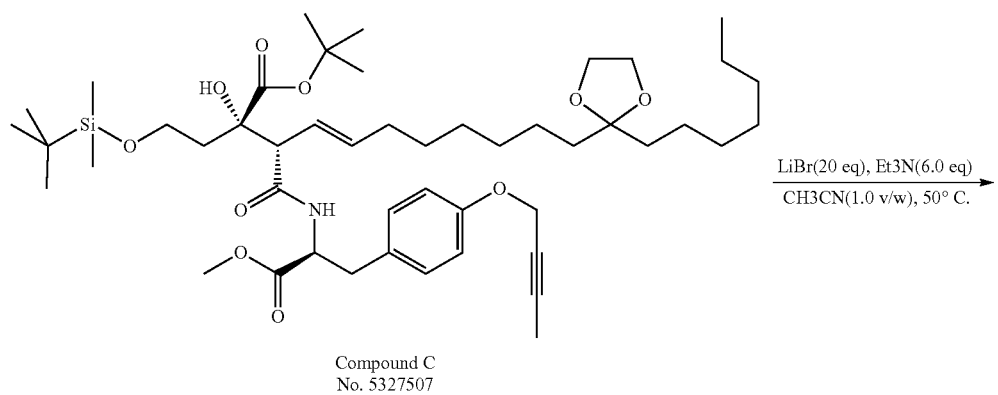
Compound C
No. 5327507
LiBr(20 eq), Et3N(6.0 eq) / CH3CN(1.0 v/w), 50° C.
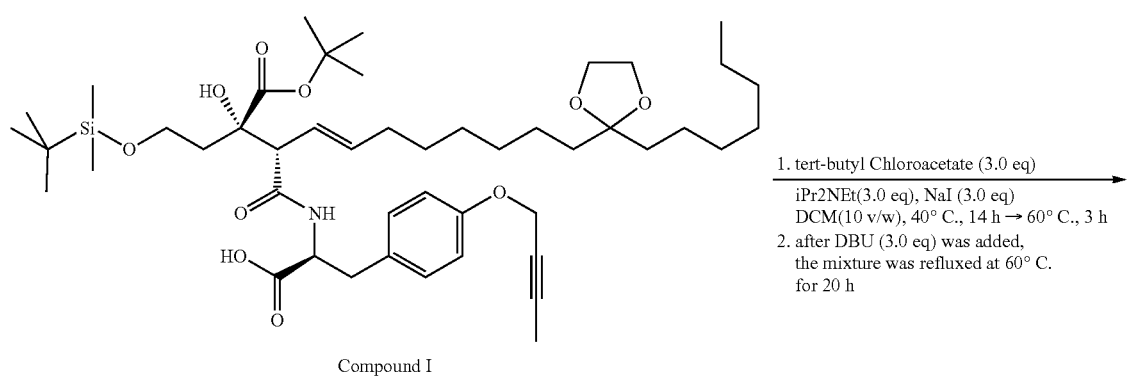
Compound I
1. tert-butyl Chloroacetate (3.0 eq)
iPr2NEt(3.0 eq), NaI (3.0 eq)
DCM(10 v/w), 40° C., 14 h → 60° C., 3 h
2. after DBU (3.0 eq) was added,
the mixture was refluxed at 60° C.
for 20 h
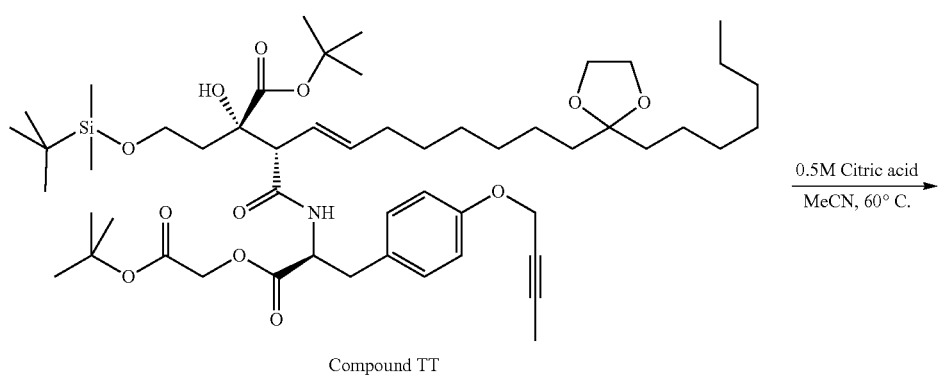
Compound TT
0.5M Citric acid / MeCN, 60° C.
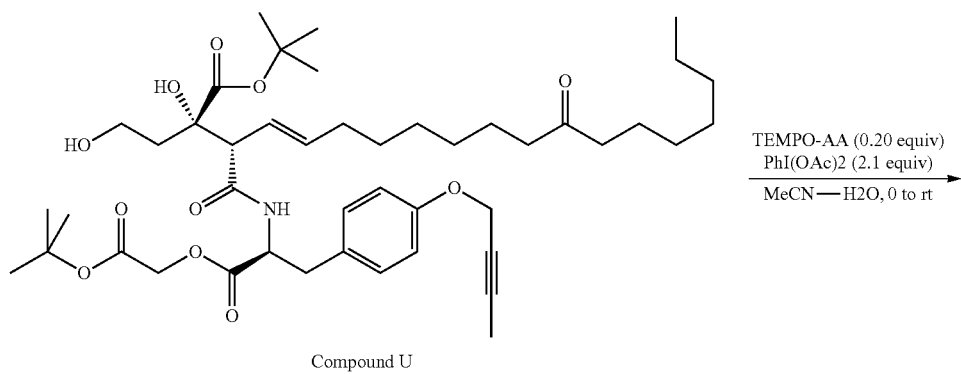
Compound U
TEMPO-AA (0.20 equiv)
PhI(OAc)2 (2.1 equiv) / MeCN—H2O, 0 to rt

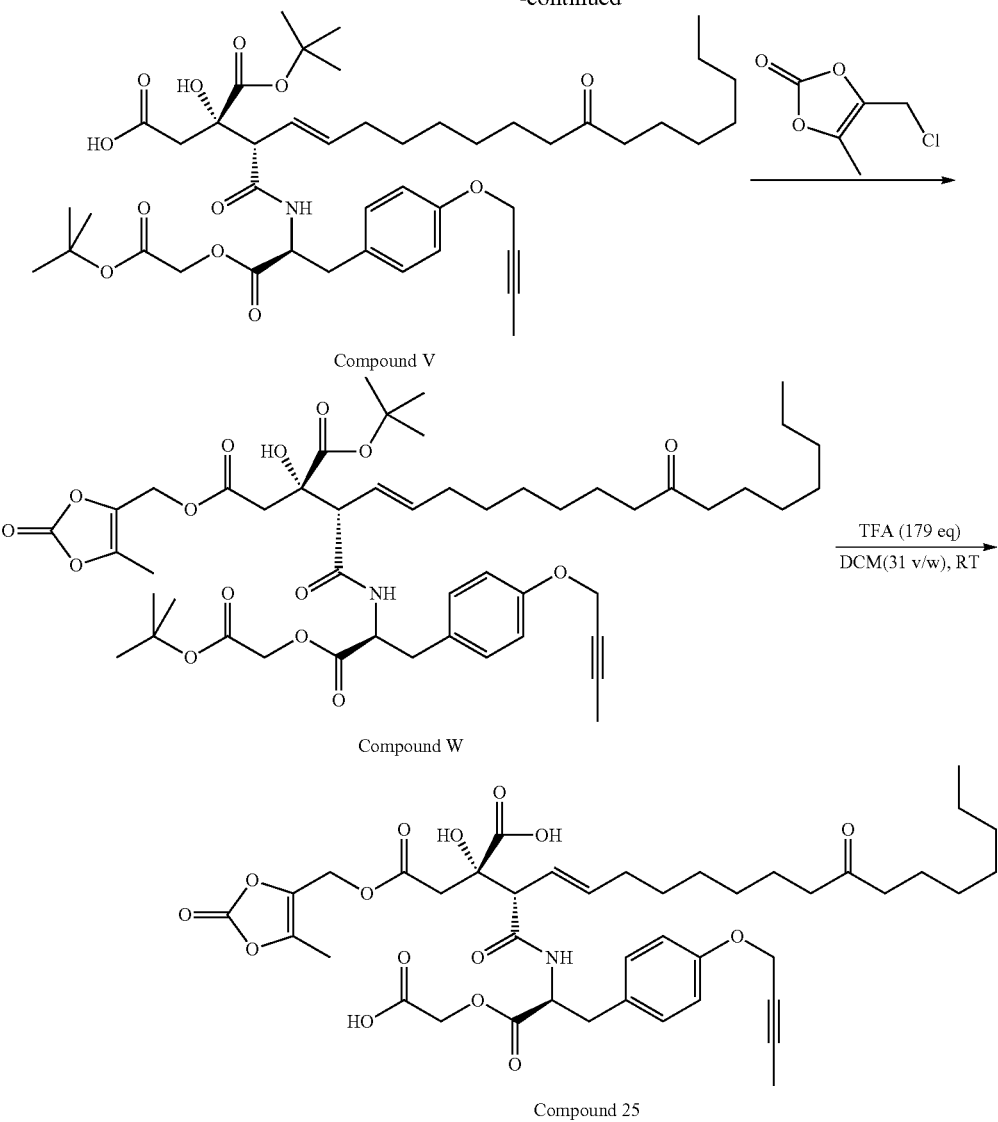

Compound V

Compound W

Compound 25

Synthesis of Compound U

No. 5327507 (Compound C; 1.09 g, 1.27 mmol) was dissolved in acetonitrile (10.9 mL), and then water (0.109 mL), triethylamine (1.06 mL, 7.61 mmol), and lithium bromide (2.91 g, 33.5 mmol) were added at room temperature. The reaction solution was stirred at 50° C. for 3.5 hours, then cooled to room temperature, quenched by the addition of 1 M hydrochloric acid (30 mL), and then extracted with ethyl acetate (100 mL). The organic layer was washed twice with water (100 mL) and then with a saturated aqueous solution of sodium chloride (100 mL). The organic layer was dried over anhydrous sodium sulfate, filtered, and concentrated under reduced pressure to obtain 1.08 g (purity 71%, ESI (LC/MS positive mode) m/z 845 (M+H); Rt 3.32 min.) of Compound I, tert-butyl (E)-(2S,3S)-2-[2-(tert-butyl-dimethyl-silanyloxy)-ethyl]-3-[(S)-2-(4-but-2-ynyloxy-phenyl)-1-carboxyethylcarbamoyl]-11-(2-heptyl-[1,3]dioxolan-2-yl)-2-hydroxy-undec-4-enoate as a crude product.

The obtained Compound I (1.07 g) was dissolved in dichloromethane (10.7 mL), and then tert-butyl chloroacetate (0.547 mL, 3.81 mmol), N,N-diisopropylethylamine (0.665 mL, 3.82 mmol), and sodium iodide (573 mg, 3.82 mmol) were added at room temperature. The mixture was stirred at an outer temperature of 40° C. for 13.5 hours, and then stirred under reflux for 3 hours. The reaction solution was cooled to room temperature, 1,8-diazabicyclo[5.4.0]undec-7-ene (0.57 mL, 3.81 mmol) was added thereto, and then the mixture was stirred under reflux for 20 hours. The reaction solution was cooled to room temperature, and then extracted with ethyl acetate (30 mL) and water (20 mL). The organic layer was dried over anhydrous sodium sulfate, and filtered. The solvent was distilled off under reduced pressure to obtain 1.36 g (purity 41%, ESI (LC/MS positive mode) m/z 959 (M+H); Rt 4.45 min.) of Compound TT, tert-butyl (E)-(2S,3S)-3-[(S)-1-tert-butoxycarbonylmethoxycarbonyl-2-(4-but-2-ynyloxyphenyl)-ethylcarbamoyl]-2-[2-(tert-butyl-dimethyl-silanyloxy)-ethyl]-11-(2-heptyl-[1,3]dioxolan-2-yl)-2-hydroxyundec-4-enoate as a crude product.

The obtained Compound TT (1.35 g) was dissolved in acetonitrile (13.3 mL), and then an aqueous solution of 0.5 M citric acid (5.3 mL, 2.65 mmol) was added to the solution, which was then stirred at 60° C. for 4 hours. The reaction solution was cooled to room temperature, a mixture of a saturated aqueous solution of sodium chloride (2.0 mL) and water (20 mL) were added. The mixture was extracted twice with 20% ethyl acetate/n-hexane (33 mL). The organic layers were combined, then washed with a saturated aqueous solution of sodium chloride (20 mL), dried over anhydrous sodium sulfate, and filtered. The solvent was then distilled off under reduced pressure. The residue was purified on Biotage (silica gel, n-hexane/acetone) to obtain 321 mg (0.401 mmol, 32% (3 steps yield), purity 96%) of Compound U, tert-butyl (E)-(2S,3S)-3-[(S)-1-tert-butoxycarbonylmethoxycarbonyl-2-(4-but-2-ynyloxy-phenyl)-ethylcarbamoyl]-2-hydroxy-2-(2-hydroxy-ethyl)-12-oxo-nonadec-4-enoate.

$^1$H-NMR (CD$_3$OD) δ: 0.90 (3H, t, J=6.4 Hz), 1.16-1.62 (18H, m), 1.44 (9H, s), 1.48 (9H, s), 1.62-1.75 (1H, m), 1.82 (3H, t, J=2.3 Hz), 1.87-2.09 (3H, m), 2.44 (4H, t, J=7.3 Hz), 2.93 (1H, dd, J=14.1, 9.9 Hz), 3.20 (1H, d, J=8.7 Hz), 3.24 (1H, dd, J=14.1, 4.4 Hz), 3.45-3.68 (2H, m), 4.53 (1H, d, J=15.7 Hz), 4.61 (2H, q, J=2.3 Hz), 4.63 (1H, d, 15.7 Hz), 4.74 (1H, d, 9.9, 4.4 Hz), 5.39-5.70 (2H, m), 6.85 (2H, d, J=8.7 Hz), 7.15 (2H, m).

ESI (LC/MS positive mode) m/z 801 (M+H); Rt 2.40 min.

Used was a tert-butyl chloroacetate reagent commercially available from Wako Pure Chemical Industries, Ltd. (cat. No. 322-58322).

Synthesis of Compound W

Compound U (315 mg, 0.394 mmol) was dissolved in acetonitrile (5.0 mL), and then water (1.0 mL) was added, and the mixture was cooled to 0° C. in an ice bath.

To the mixture were added 4-acetamide-2,2,6,6-tetramethylpiperidine 1-oxyl (16.8 mg, 0.0788 mmol) and diacetoxyiodobenzene (267 mg, 0.829 mmol) in this order, and then the ice bath was removed. The mixture was stirred at room temperature for 6.5 hours, and then a mixture of an aqueous solution of 0.5 M citric acid (3.0 mL) and water (10 mL) was added. The mixture was extracted twice with ethyl acetate (20 mL). The organic layers were combined, and washed four times with an aqueous solution (20 mL) of 10% sodium thiosulfate, finally with a saturated aqueous solution of sodium chloride (20 mL), then dried over anhydrous sodium sulfate, and filtered. The solvent was distilled off under reduced pressure to obtain 471 mg (purity 43%, ESI (LC/MS positive mode) m/z 815 (M+H); Rt 2.37 min.) of Compound V, 1-tert-butyl (S)-2-{(E)-(S)-1-[(S)-1-tert-butoxycarbonyl-methoxycarbonyl-2-(4-but-2-ynyloxy-phenyl)-ethylcarbamoyl]-10-oxo-heptadec-2-enyl}-2-hydroxy-succinate as a crude product.

The obtained Compound V was dissolved in dichloromethane (4.7 mL), and then 4-chloromethyl-5-methyl-[1,3]dioxol-2-one (176 mg, 1.185 mmol), N,N-diisopropylethylamine (0.206 mL, 1.18 mmol), and sodium iodide (177 mg, 1.18 mmol) were added at room temperature. The outer temperature was warmed up to 40° C., and the mixture was stirred for 5 hours, warmed at an outer temperature of 35° C. for 14 hours, and then extracted with ethyl acetate (70 mL) and water (20 mL). The organic layer was washed with a saturated aqueous solution of sodium chloride (30 mL), and then dried over anhydrous sodium sulfate. After filtration, the solvent was distilled off under reduced pressure. The residue was purified on Biotage (silica gel, n-hexane/ethyl acetate) to obtain 322 mg (0.348 mmol, 88% (yield over 2 steps)) of Compound W, 4-(5-methyl-2-oxo-[1,3]dioxol-4-ylmethyl) 1-tert-butyl (S)-2-{(E)-(S)-1-[(S)-1-tert-butoxycarbonyl-methoxycarbonyl-2-(4-but-2-ynyloxy-phenyl)-ethylcarbamoyl]-10-oxo-heptadec-2-enyl}-2-hydroxy-succinate.

$^1$H-NMR (CD$_3$OD) δ: 0.90 (3H, t, J=6.9 Hz), 1.16-1.63 (18H, m), 1.43 (9H, s), 1.48 (9H, s), 1.82 (3H, t, J=2.3 Hz), 1.87-2.08 (2H, m), 2.16 (3H, s), 2.44 (4H, t, J=7.3 Hz), 2.55 (1H, d, J=15.8 Hz), 2.85 (1H, d, J=15.8 Hz), 2.92 (1H, dd, J=14.3, 10.2 Hz), 3.17 (1H, d, J=8.4 Hz), 3.26 (1H, dd, J=14.3, 4.4 Hz), 4.59 (1H, d, 15.7 Hz), 4.61 (2H, q, J=2.3 Hz), 4.63 (1H, d, 15.7 Hz), 4.75 (1H, dd, J=10.2, 4.5 Hz), 4.86 (1H, d, J=14.2 Hz), 4.94 (1H, d, J=14.2 Hz), 5.39-5.65 (2H, m), 6.84 (2H, d, J=8.8 Hz), 7.15 (2H, d, J=8.8 Hz).

ESI (LC/MS positive mode) m/z 927 (M+H); Rt 2.43 min.

Compound 25 (No. 5485784)

Compound W (315 mg, 0.340 mmol) was dissolved in dichloromethane (3.0 mL), and then trifluoroacetic acid (3.0 mL, 40.7 mmol) was added at room temperature. The mixture was stirred for 2.5 hours, and then concentrated under reduced pressure.

The residue was purified by preparative HPLC to obtain 147 mg (0.181 mmol, yield 53%) of Compound 25 (No. 5485784), 4-(5-methyl-2-oxo-[1,3]dioxol-4-ylmethyl) (S)-2-{(E)-(S)-1-[(S)-2-(4-but-2-yloxy-phenyl)-1-methoxycarbonyl-ethylcarbamoyl]-10-oxo-heptadec-2-enyl}-2-hydroxy-succinate.

$^1$H-NMR (CD$_3$OD) δ: 0.88 (3H, t, J=7.1 Hz), 1.19-1.39 (14H, m), 1.45-1.58 (4H, m), 1.80 (3H, t, J=2.2 Hz), 1.90-1.99 (2H, m), 2.14 (3H, s), 2.42 (4H, t, J=7.5 Hz), 2.60 (1H, d, J=15.9 Hz), 2.91 (1H, d, J=15.9 Hz), 2.92 (1H, dd, J=14.6, 10.2 Hz), 3.20 (1H, d, J=8.4 Hz), 3.24 (1H, dd, J=14.6, 4.9 Hz), 4.59 (2H, q, J=2.2 Hz), 4.63 (1H, d, 15.9 Hz), 4.71 (1H, d, 15.9 Hz), 4.73-4.80 (1H, m), 4.86 (1H, d, J=14.5 Hz), 4.90 (1H, d, J=14.5 Hz), 5.41-5.57 (2H, m), 6.82 (2H, d, J=8.8 Hz), 7.13 (2H, d, J=8.8 Hz).

ESI (LC/MS positive mode) m/z 815 (M+H); Rt 2.03 min.

Compound 101 (No. 5488899)

(S)-2-{(E)-(S)-1-[(S)-2-(4-But-2-ynyloxy-phenyl)-1-methoxycarbonyl-ethylcarbamoyl]-10-methoxy-heptadec-2-enyl}-2-hydroxy-succinic acid Compound 101 was produced according to the following synthetic scheme.

[Chem. 29]
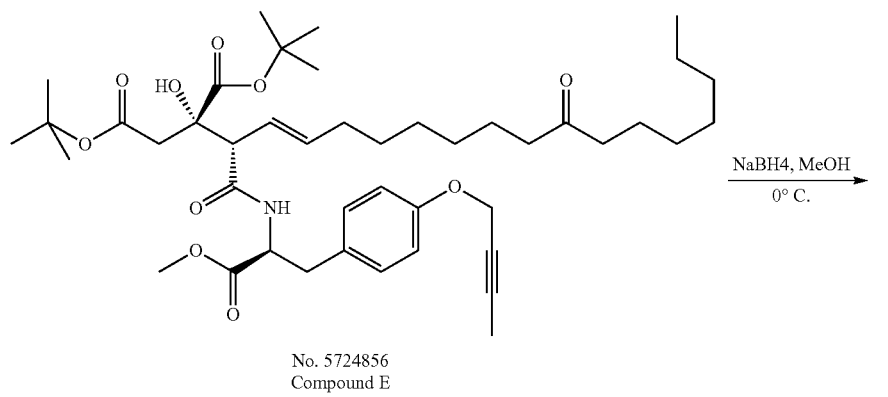
No. 5724856
Compound E
NaBH4, MeOH
0° C.
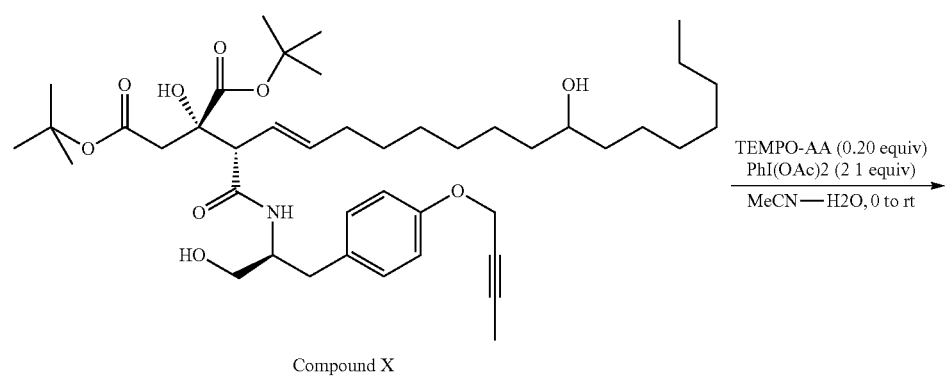
Compound X
TEMPO-AA (0.20 equiv)
PhI(OAc)2 (2.1 equiv)
MeCN—H2O, 0 to rt
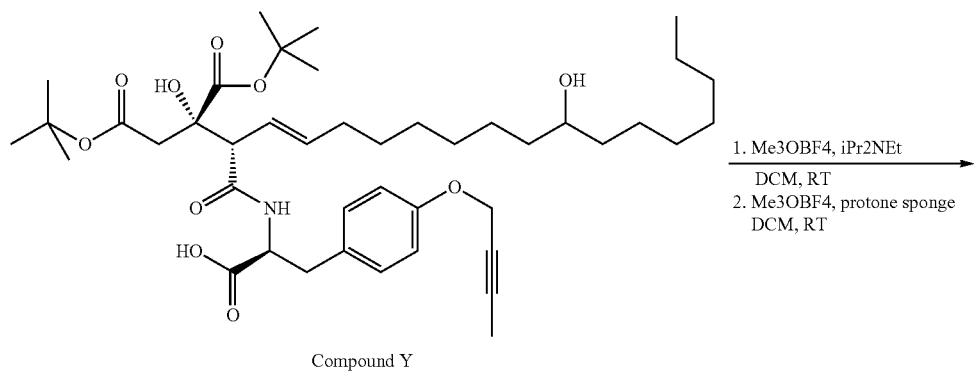
Compound Y
1. Me3OBF4, iPr2NEt
DCM, RT
2. Me3OBF4, protone sponge
DCM, RT
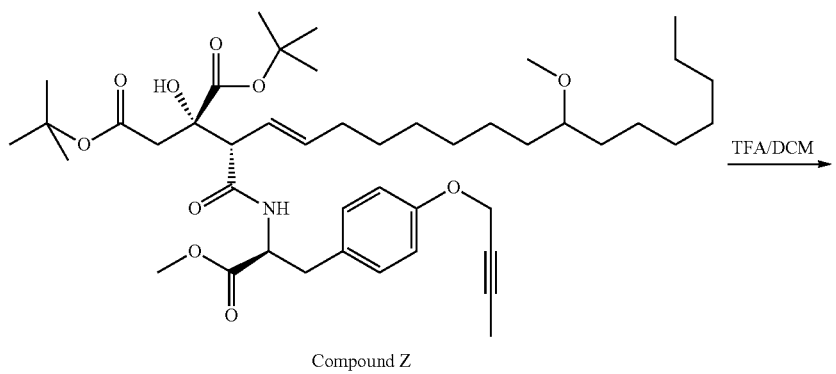
Compound Z
TFA/DCM

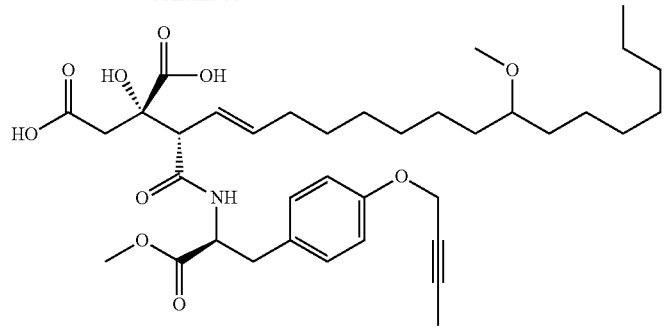

NO. 5488898
Compound 101

Compound Y

Di-tert-butyl (S)-2-{(E)-(S)-1-[(S)-2-(4-but-2-yny-loxy-phenyl)-1-carboxy-ethylcarbamoyl]-10-hydroxy-heptadec-2-enyl}-2-hydroxy-succinate No. 5724856-Compound E (1.41 g, 1.83 mmol) was dissolved in methanol (38 mL), then sodium borohydride (693 mg, 18.3 mmol) was added at 0° C., and the mixture was stirred for 1.5 hours. The mixture was quenched by adding an aqueous solution of 0.5 M citric acid (100 mL), and then extracted with ethyl acetate (100 mL). The organic layer was washed with a saturated aqueous solution of sodium chloride (50 mL), then dried over anhydrous sodium sulfate, and filtered. The solvent was distilled off under reduced pressure to obtain 1.36 g (1.83 mmol, quant., purity 90%, ESI (LC/MS positive mode) m/z 745 (M+H); Rt 2.45 min.) of Compound X, di-tert-butyl (S)-2-{(E)-(S)-1-[(S)-2-(4-but-2-ynyloxy-phenyl)-1-hydroxymethyl-ethylcarbamoyl]-10-hydroxy-heptadec-2-enyl}-2-hydroxy-succinate as a crude product.

The obtained Compound X (1.36 g) was dissolved by adding acetonitrile (21 mL) and water (4.2 mL), and the solution was then cooled to 0° C. in an ice bath. To the solution were added 4-acetamide-2,2,6,6-tetramethylpiperidine 1-oxyl (78 mg, 0.366 mmol) and diacetoxyiodobenzene (1.25 g, 3.88 mmol) in this order, and then the ice bath was removed. The mixture was stirred at room temperature for 18 hours, then a mixture of an aqueous solution of 0.5 M citric acid (20 mL) and water (80 mL) was added, and the resulting mixture was extracted twice with ethyl acetate (80 mL). The organic layers were combined, and washed four times with an aqueous solution (60 mL) of 10% sodium thiosulfate, and finally with a saturated aqueous solution of sodium chloride (60 mL), then dried over anhydrous sodium sulfate, and filtered. The solvent was distilled off under reduced pressure. The resulting residue was purified on Biotage (diol, n-hexane/ethyl acetate) to obtain 673 mg (0.8879 mmol, 48% (yield over 2 steps)) of Compound Y.

$^1$H-NMR (CD$_3$OD) δ: 0.90 (3H, t, J=6.4 Hz), 1.20-1.60 (22H, m), 1.44 (9H, s), 1.45 (9H, s), 1.82 (3H, t, J=2.3 Hz), 1.91-2.04 (2H, m), 2.44 (1H, t, J=7.4 Hz), 2.50 (1H, d, J=6.2 Hz), 2.76 (1H, d, J=6.2 Hz), 2.93 (1H, dd, J=14.0, 6.1 Hz), 3.08-3.22 (2H, m), 3-44-3.55 (1H, m), 4.53-4.68 (3H, m), 5.41-5.67 (2H, m), 6.85 (2H, d, J=8.7 Hz), 7.13 (2H, d, J=8.7 Hz)

ESI (LC/MS positive mode) m/z 759 (M+H); Rt 2.43 min.

Compound Z

Di-tert-butyl (S)-2-{(E)-(S)-1-[(S)-2-(4-but-2-yny-loxy-phenyl)-1-methoxycarbonyl-ethylcarbamoyl]-10-methoxy-heptadec-2-enyl}-2-hydroxy-succinate Compound Y (82.0 mg, 0.108 mmol) was dissolved in dichloromethane (2.5 mL), then trimethyloxonium tetrafluoroborate (216 mg, 1.46 mmol) and N,N-diisopropylethylamine (0.248 mL, 1.42 mmol) were added at room temperature. The mixture was stirred for 8 hours, quenched with water (20 mL), and then extracted twice with ethyl acetate (50 mL). The organic layer was concentrated under reduced pressure and the residue (80.3 mg) was then dissolved in dichloromethane (2.5 mL) again. To the solution were added 1,8-bis(dimethylamino)naphthalene (219 mg, 1.02 mmol) and trimethyloxonium tetrafluoroborate (150 mg, 1.01 mmol) at room temperature. The mixture was stirred for 1 hour, quenched with methanol (2.0 mL), and then concentrated under reduced pressure. Methanol (2.0 mL) and ethyl acetate (5.0 mL) were added and the mixture was then filtered to remove insoluble material. The insoluble material was washed with ethyl acetate (5 mL). The filtrate was concentrated under reduced pressure. The resulting residue was purified by preparative HPLC to obtain 30.2 mg (0.0384 mmol, yield 36%) of Compound Z.

$^1$H-NMR (CD$_3$OD) δ: 0.90 (3H, t, J=6.9 Hz), 1.23-1.53 (22H, m), 1.44 (9H, s), 1.45 (9H, s), 1.82 (3H, t, J=2.3 Hz), 1.92-2.06 (2H, m), 2.50 (1H, d, J=16.3 Hz), 2.78 (1H, d, J=16.3 Hz), 2.92 (1H, dd, J=14.0, 9.2 Hz), 3.06-3.22 (2H, m), 3.13 (1H, d, J=7.7 Hz), 3.31 (3H, s, overlapped with the peak of CD$_3$OD), 3.72 (3H, s), 4.58-4.68 (3H, m), 5.40-5.65 (2H, m), 6.85 (2H, d, J=8.7 Hz), 7.10 (2H, d, J=8.7 Hz)

ESI (LC/MS positive mode) m/z 787 (M+H); Rt 3.07 min.

Compound 101 (No. 5488899)

(S)-2-{(E)-(S)-1-[(S)-2-(4-But-2-yloxy-phenyl)-1-methoxycarbonyl-ethylcarbamoyl]-10-methoxy-heptadec-2-enyl}-2-hydroxy-succinic acid Compound Z (28.0 mg, 0.0356 mmol) was dissolved in dichloromethane (0.5 mL), and then trifluoroacetic acid (0.5 mL, 0.678 mmol) was added at room temperature. The mixture was stirred for 3 hours, and then concentrated under reduced pressure. The resulting residue was purified by preparative HPLC to obtain 19.3 mg (0.0286 mmol, yield 80%) of Compound 101.

$^{1}$H-NMR (CD$_{3}$OD) δ: 0.90 (3H, t, J=6.9 Hz), 1.20-1.56 (22H, m), 1.82 (3H, t, J=2.3 Hz), 1.91-2.08 (2H, m), 2.56 (1H, d, J=16.2 Hz), 2.90 (1H, d, J=16.2 Hz), 2.92 (1H, dd, J=14.2, 9.1 Hz), 3.07-3.24 (3H, m), 3.31 (3H, s, overlapped with the peak of CD$_{3}$OD), 3.72 (3H, s), 4.60 (2H, q, J=2.3 Hz), 4.64 (1H, dd, J=9.1, 5.1 Hz), 5.44-5.64 (2H, m), 6.85 (2H, d, J=8.7 Hz), 7.10 (2H, d, J=8.7 Hz)

ESI (LC/MS positive mode) m/z 675 (M+H); Rt 3.40 min.

Compound 3 (No. 5315851)

1-(1-Acetoxy-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 30]

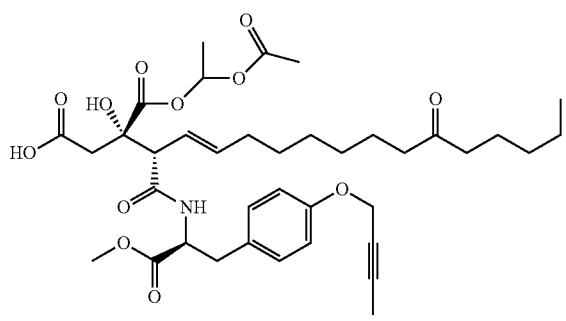

To a mixture of No. 5153510: Compound 87 (25 mg, 0.038 mmol), NaHCO$_{3}$ (4.8 mg, 0.114 mmol), and THF (1.3 mL) was added 1-bromo-ethyl acetate (39.9 μL, 0.342 mmol) and the mixture was stirred at room temperature. After confirming the consumption of No. 5153510: Compound 87 by LCMS, water was added and the mixture was extracted with ethyl acetate. The organic layer was washed with a saturated brine and dried over anhydrous sodium sulfate, and then the filtrate was concentrated under reduced pressure. The resulting residue was purified by preparative HPLC, and then extracted with ethyl acetate. The organic layer was washed with 1% NaHCO$_{3}$, a saturated brine, a saturated aqueous solution of ammonium chloride, and a saturated brine, and then dried over anhydrous sodium sulfate. The filtrate was concentrated under reduced pressure to obtain No. 5315851: Compound 3 as a diastereomeric mixture (11 mg, yield 39%, colorless oil).

$^{1}$H-NMR (CD$_{3}$OD, diastereomeric mixture) δ: 0.86 (3H, t, J=6.9 Hz), 1.20-1.36 (14H, m), 1.39-1.43 (3H, m), 1.46-1.56 (4H, m), 1.78 (3H, t, J=2.3 Hz), 1.91-2.04 (0H, m), 2.40 (4H, t, J=7.3 Hz), 2.44-2.61 (1H, m), 2.78-2.91 (2H, m), 3.06-3.20 (2H, m), 3.68 (1H, s), 3.69 (2H, s), 4.57-4.62 (3H, m), 5.41-5.55 (2H, m), 6.75-6.85 (3H, m), 7.05-7.09 (2H, m)

ESI (LC/MS positive mode) m/z 745 (M+H); Rt 3.00 min.

Compound 2 (No. 5169356)

1-(5-Methyl-2-oxo-[1,3]dioxol-4-ylmethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 31]

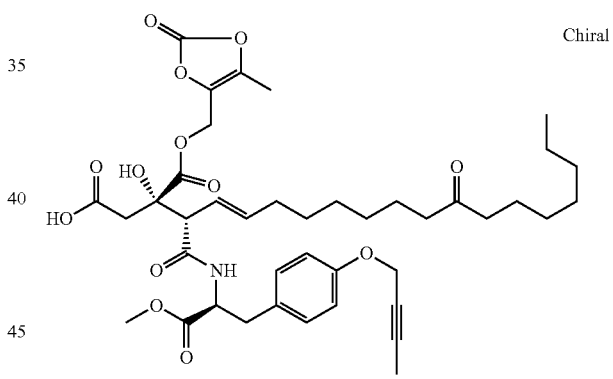

Synthetic method 1 of Compound 2 (No. 5169356)

To a mixture of No. 5153510: Compound 87 (300 mg, 0.456 mmol), NaHCO$_{3}$ (42 mg, 0.500 mmol), and DMF (1.3 mL) was added 4-bromomethyl-5-methyl-[1,3]dioxol-2-one (103.5 μL, 0.912 mmol) and the mixture was stirred at room temperature. After confirming the consumption of No. 5153510: Compound 87 by LCMS, a saturated aqueous solution of ammonium chloride was added, and the mixture was extracted with ethyl acetate. The organic layer was washed with a saturated brine and dried over anhydrous sodium sulfate, and then the filtrate was concentrated under reduced pressure. The resulting residue was purified by diol column chromatography to obtain No. 5169356, Compound 2 (203 mg, yield 58%, colorless oil).

Synthetic Method 2 of Compound 2 (No. 5169356)

[Chem. 32]

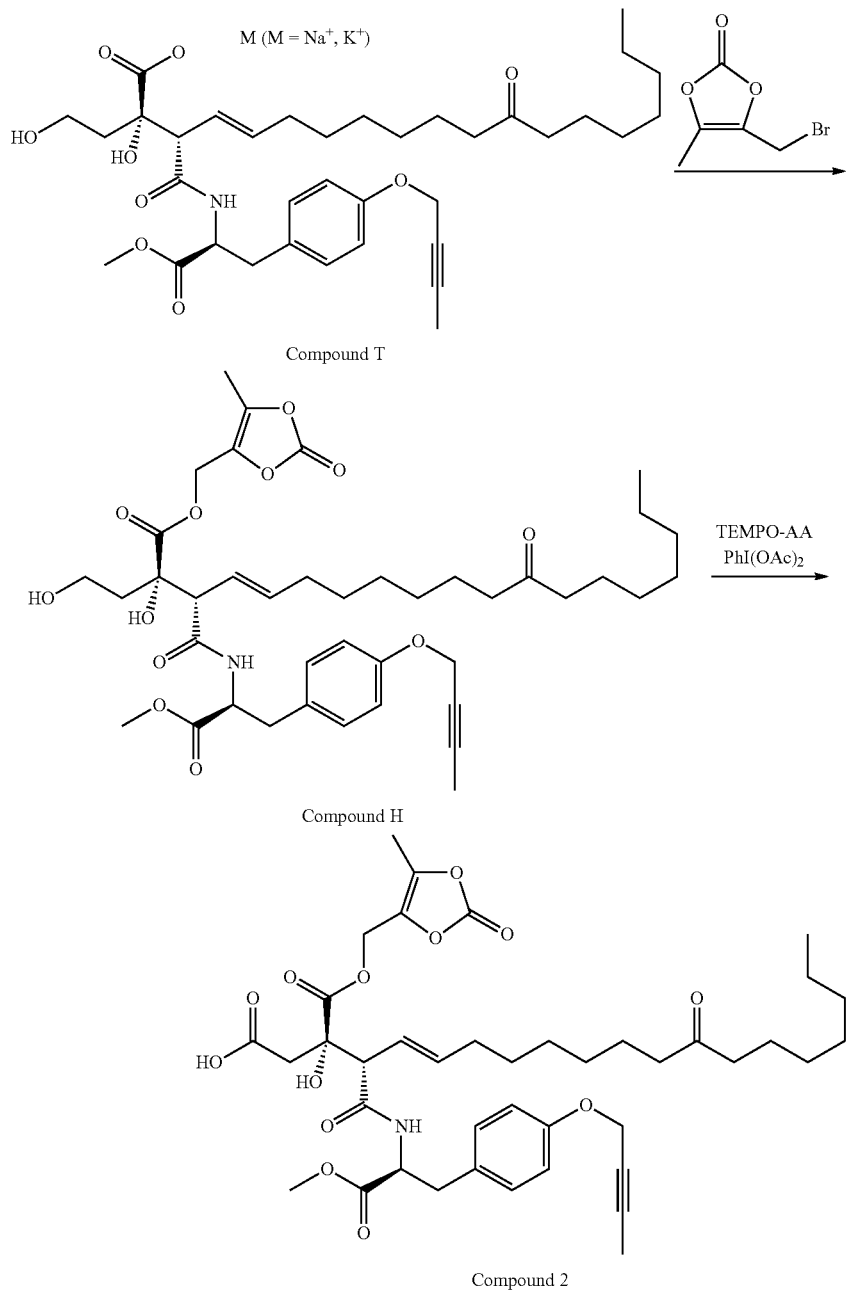

To a mixture of No. 5214357: Compound T (5.0 g, 7.33 mmol), NaI (1.65 g, 10.99 mmol), and DMF was added 4-chloromethyl-5-methyl-[1,3]dioxol-2-one (1.59 mL, 14.66 mmol) and the mixture was stirred at 40° C. for 1 hour. After confirming the consumption of the starting materials, a saturated aqueous solution of ammonium chloride was added, and the mixture was extracted with ethyl acetate. The organic layer was washed with a saturated brine and dried over anhydrous sodium sulfate, and then the filtrate was concentrated under reduced pressure. The resulting residue was purified by diol column chromatography to obtain No. 5725513: Compound H (5.36 g, yield 97%, colorless oil, ESI (LC/MS posi- tive mode) m/z 756 (M+H); Rt 1.09 min). To a mixture of the obtained No. 5725513, Compound H (5.31 g, 7.02 mmol), acetonitrile (106 mL), and distilled water (5.3 mL) were added 4-acetamide-TEMPO (TEMPO-AA; 449 mg, 2.10 mmol) and iodobenzene diacetate (9.05 g, 28.1 mmol) and the mixture was stirred at room temperature. After confirming the consumption of the starting materials by LCMS, an aqueous solution of 0.5 M citric acid was added, and the mixture was extracted with ethyl acetate. The organic layer was washed with an aqueous solution of 5% sodium thiosulfate and a saturated brine and dried over anhydrous sodium sulfate, and then the filtrate was concentrated under reduced pressure. The resulting residue was purified by diol column chromatography to obtain Compound 2 (4.40 g, 82% yield, yellow oil).

4-Bromomethyl-5-methyl-[1,3]dioxol-2-one was obtained from Ochem Incorporation (cat. No., 715B226) and used. 4-Chloromethyl-5-methyl-[1,3]dioxol-2-one (cat. No., 3B3-011353) was obtained from 3B Scientific Corporation, and used.

$^1$H-NMR (CD$_3$OD) δ: 0.89 (3H, t, J=7.1 Hz), 1.25-1.34 (14H, m), 1.53 (4H, td, J=14.0, 6.5 Hz), 1.82 (3H, t, J=2.4 Hz), 1.94-1.98 (2H, m), 2.16 (3H, s), 2.44 (4H, td, J=7.4, 1.1 Hz), 2.59 (1H, d, J=16.2 Hz), 2.87-2.94 (2H, m), 3.11 (1H, dd, J=13.9, 4.9 Hz), 3.20 (1H, d, J=8.6 Hz), 3.72 (3H, s), 4.59-4.65 (3H, m), 4.95 (3H, dd, J=22.9, 13.9 Hz), 5.48-5.52 (2H, m), 6.84 (2H, d, J=9.0 Hz), 7.08 (2H, d, J=8.6 Hz), 8.26 (1H, d, J=7.6 Hz).

ESI (LC/MS positive mode) m/z 771 (M+H); Rt 2.75 min.

Compound 36 (No. 5045280)

4-Methyl S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 33]

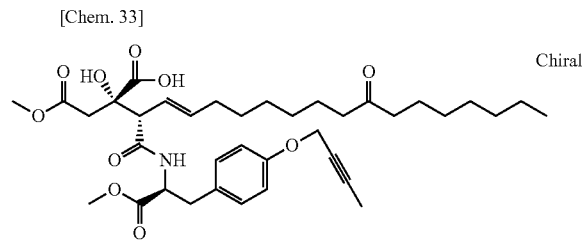

To a mixture of No. 4630808: Compound 93 (200 mg, 0.277 mmol) and methanol (30 mL) was added concentrated hydrochloric acid (265 μL, 2.54 mmol) and the mixture was stirred at room temperature. After confirming the consumption of No. 4630808, Compound 93 by LCMS, water was added and the mixture was extracted with ethyl acetate. The organic layer was washed with a saturated brine and dried over anhydrous sodium sulfate, and then the filtrate was concentrated under reduced pressure. The resulting residue was purified by preparative HPLC. The resulting fraction was freeze-dried to obtain Compound 36 (80 mg, 43% yield, white powder).

$^1$H-NMR (CDCl$_3$) δ: 0.88 (3H, t, J=6.8 Hz), 1.10-1.41 (14H, m), 1.53-1.54 (4H, m), 1.86 (3H, t, J=2.2 Hz), 1.94-2.12 (2H, m), 2.35-2.50 (4H, m), 2.63 (1H, d, J=16.2 Hz), 2.95 (1H, d, J=16.2 Hz), 2.98-3.15 (2H, m), 3.23 (1H, d, J=9.2 Hz), 3.69 (3H, s), 3.71 (3H, s), 4.61 (2H, q, J=2.2 Hz), 4.75-4.85 (1H, m), 5.51 (1H, dd, J=15.3, 9.2 Hz), 5.59-5.73 (1H, m), 6.71 (1H, d, J=8.1 Hz), 6.85 (2H, d, J=8.6 Hz), 7.02 (2H, d, J=8.6 Hz).

ESI (LC/MS positive mode) m/z 672 (M+H); Rt 3.13 min.

Compound 51: No. 5112408

(S)-2-{(E)-(S)-1-[(S)-2-(4-But-2-ynyloxy-phenyl)-1-phenoxycarbonyloxymethoxy-carbonyl-ethylcarbamoyl]-10-oxo-heptadec-2-enyl}-2-hydroxy-succinic acid

[Chem. 34]

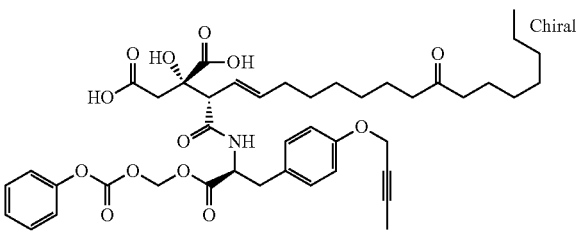

A mixture of No. 4630808: Compound 93 (20 mg, 0.0311 mmol), N,N,N',N'-tetramethyl-naphthalene-1,8-diamine (13.3 mg, 0.0622 mmol), and acetonitrile (2.0 mL) was cooled to 0° C., TMSCl (8 μL, 0.0622 mmol) was added and the mixture was stirred at room temperature for 1 hour. N,N,N',N'-Tetramethyl-naphthalene-1,8-diamine (14.7 mg, 0.0686 mmol) and phenyl iodomethyl carbonate (11.3 μL, 0.0686 mmol) were added to the reaction mixture. The reaction mixture was stirred for 24 hours, then purified, without further processing, by preparative HPLC. The obtained fraction was freeze-dried to obtain Compound 51: No. 5112408 (15 mg, 61% yield, white powder).

Phenyl iodomethyl carbonate was synthesized by a method similar to that of isopropyl iodomethyl esters.

$^1$H-NMR (CD$_3$OD) δ: 0.89 (3H, t, J=6.8 Hz), 1.26-1.28 (16H, m), 1.51-1.54 (4H, m), 1.81 (3H, t, J=2.4 Hz), 1.97 (2H, q, J=6.8 Hz), 2.40-2.44 (4H, m), 2.57 (1H, d, J=16.1 Hz), 2.89 (1H, d, J=16.1 Hz), 3.00 (1H, dd, J=14.2, 8.8 Hz), 3.15-3.22 (2H, m), 4.59 (2H, q, J=2.3 Hz), 4.74 (2H, dd, J=8.8, 5.4 Hz), 5.48-5.60 (2H, m), 5.86 (1H, d, J=5.9 Hz), 5.92 (1H, d, J=5.9 Hz), 6.86 (2H, d, J=8.8 Hz), 7.14 (2H, d, J=8.8 Hz), 7.22 (2H, dd, J=8.8, 1.0 Hz), 7.28 (1H, t, J=7.6 Hz), 7.42 (2H, dd, J=10.7, 5.4 Hz).

ESI (LC/MS positive mode) m/z 795 (M±H); Rt 2.53 min.

Compound 38: No. 5081962

4-Propyl (S)-2-{(E)-(S)-1-[(S)-2-(4-but-2-ynyloxy-phenyl)-1-propoxycarbonyl-ethylcarbamoyl]-10-oxo-heptadec-2-enyl}-2-hydroxy-succinate

[Chem. 35]

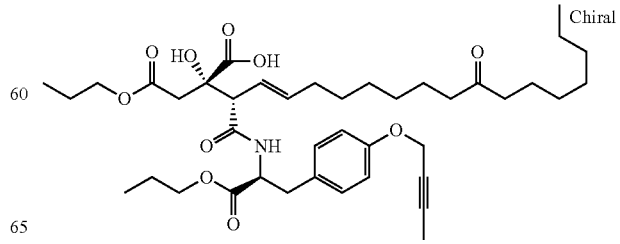

Compound 38 was obtained by a method similar to that of No. 5045280: Compound 36 except that a commercially available reagent of n-propanol was used instead of methanol.

$^1$H-NMR (CDCl$_3$) δ: 0.88-0.92 (9H, m), 1.27 (14H, dd, J=29.1, 18.3 Hz), 1.54-1.69 (8H, m), 1.86 (3H, t, J=2.2 Hz), 1.93-2.09 (2H, m), 2.41-2.47 (4H, m), 2.66 (1H, d, J=16.1 Hz), 2.96 (1H, d, J=16.1 Hz), 3.07 (2H, ddd, J=24.7, 14.2, 6.1 Hz), 3.22 (1H, d, J=9.3 Hz), 4.01-4.13 (4H, m), 4.61 (2H, q, J=2.3 Hz), 4.79-4.82 (1H, m), 5.48-5.70 (3H, m), 6.66 (1H, d, J=7.8 Hz), 6.85 (2H, d, J=8.8 Hz), 7.02 (2H, d, J=8.3 Hz).

ESI (LC/MS positive mode) m/z 728 (M+H); Rt 3.40 min.

Compound 41: No. 5081965

4-Butyl (S)-2-{(E)-(S)-1-[(S)-1-butoxycarbonyl-2-(4-but-2-ynyloxy-phenyl)-ethylcarbamoyl]-10-oxo-heptadec-2-enyl}-2-hydroxy-succinate

[Chem. 36]

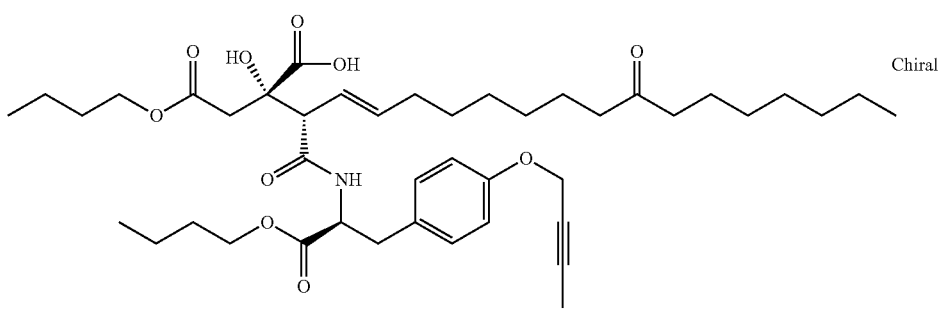

Compound 41 was obtained by a method similar to that of No. 5045280: Compound 36 except that a commercially available reagent of n-butanol was used instead of methanol.

ESI (LC/MS positive mode) m/z 757 (M+H); Rt 3.64 min.

Compound 42: No. 5081966

4-Pentyl (S)-2-{(E)-(S)-1-[(S)-2-(4-but-2-ynyloxy-phenyl)-1-pentyloxycarbonyl-ethylcarbamoyl]-10-oxo-heptadec-2-enyl}-2-hydroxy-succinate

[Chem. 37]

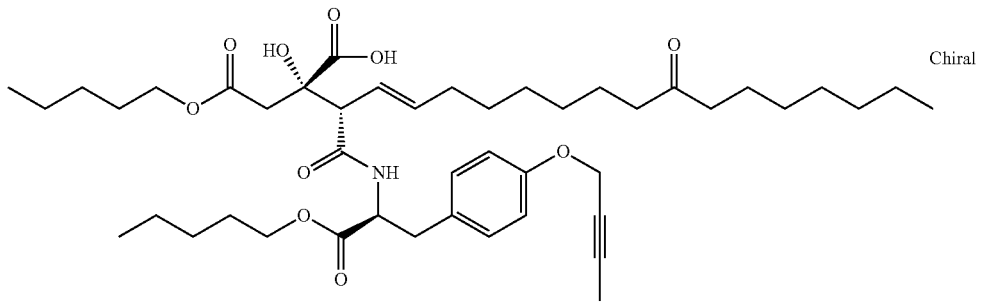

Compound 42 was obtained by a method similar to that of No. 5045280: Compound 36 except that a commercially available reagent of n-pentanol was used instead of methanol.

ESI (LC/MS positive mode) m/z 785 (M+H); Rt 3.87 min.

85

Compound 44: No. 5094972

1-(2,2-Dimethyl-propionyloxymethyl) (S)-2-((E)-(S)-1-{(S)-2-(4-but-2-ynyloxy-phenyl)-1-[1-(2,2-dimethyl-propionyloxy-methoxycarbonyl)-ethylcarbamoyl}-10-oxo-heptadec-2-enyl)-2-hydroxy-succinate

[Chem. 38]

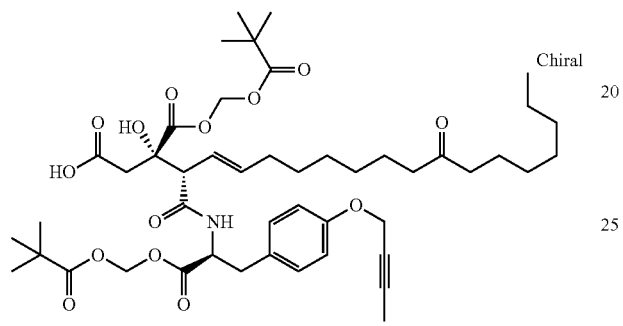

A mixture of No. 4630808: Compound 93 (100 mg, 0.155 mmol), iodomethyl 2,2-dimethyl-propionate (51.5 micro L, 0.326 mmol) and acetonitrile (10 mL) was cooled to 0° C., and N,N,N',N'-tetramethyl-naphthalene-1,8-diamine (66.4 mg, 0.310 mmol) was added. The mixture was stirred at 0° C. for 10 minutes, and then warmed to room temperature and stirred for 24 hours. The solvent was distilled off under reduced pressure. The residue was purified by preparative HPLC, and freeze-dried to obtain Compound 44 (27 mg, 20% yield, colorless oil).

Used was a iodomethyl 2,2-dimethyl-propionate reagent commercially available from Waterstone Technology (cat. No: 22459).

86

$^1$H-NMR (CD$_3$OD) δ: 0.90 (3H, t, J=6.8 Hz), 1.18-1.20 (18H, m), 1.28-1.34 (14H, m), 1.54 (4H, t, J=6.8 Hz), 1.82 (3H, t, J=2.2 Hz), 1.98 (2H, q, J=6.3 Hz), 2.44 (4H, td, J=7.2, 1.6 Hz), 2.56 (1H, d, J=16.6 Hz), 2.84-2.94 (2H, m), 3.12 (1H, dd, J=14.2, 4.9 Hz), 3.19 (1H, d, J=8.3 Hz), 4.61 (2H, q, J=2.3 Hz), 4.64-4.68 (1H, m), 5.52 (2H, tt, J=21.0, 7.1 Hz), 5.73 (3H, tt, J=10.0, 3.4 Hz), 5.83 (1H, dd, J=5.4, 2.9 Hz), 6.85 (2H, d, J=8.3 Hz), 7.11 (2H, d, J=8.3 Hz).

ESI (LC/MS positive mode) m/z 873 (M+H); Rt 3.68 min.

Compound 46: No. 5108595

Diisopropoxycarbonyloxymethyl (S)-2-{(E)-(S)-1-[(S)-2-(4-but-2-ynyloxy-phenyl)-1-isopropoxycarbonyloxymethoxy-carbonyl-ethylcarbamoyl]-10-oxo-heptadec-2-enyl}-2-hydroxy-succinate

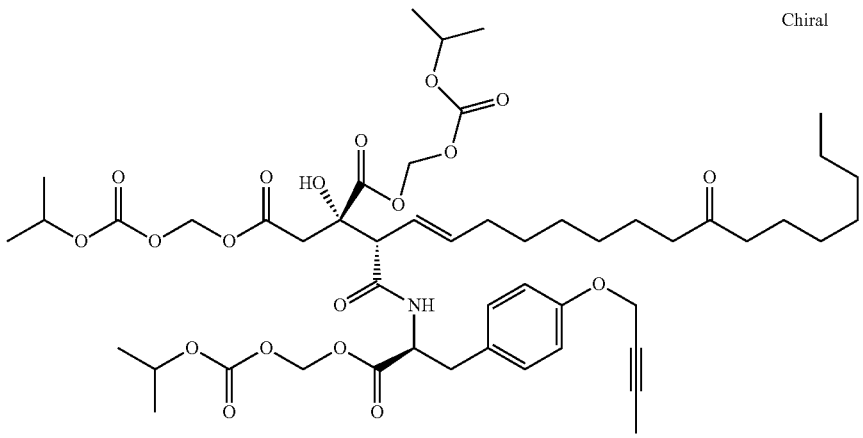

To a mixture of No. 4630808: Compound 93 (30 mg, 0.0466 mmol), N,N,N',N'-tetramethyl-naphthalene-1,8-diamine (49.9 mg, 0.233 mmol) and DMF (2 mL) was added isopropyl iodomethyl carbonate (71.5 μL, 0.466 mmol), and the mixture was stirred at room temperature for 18 hours, and then the reaction mixture was purified by preparative HPLC. The triester peak fraction was collected, and then freeze-dried to obtain Compound 46 (17.8 mg, 39% yield, colorless oil).

Isopropyl iodomethyl carbonate was synthesized according to the description in Tetrahedron Letters, 48 (1), 109-112, 2006.

ESI (LC/MS positive mode) m/z 993 (M+H); Rt 3.77 min.

Compound 47: No. 5112404

(S)-2-{(E)-(S)-1-[(S)-1-Acetoxymethoxycarbonyl-2-(4-but-2-ynyloxy-phenyl)-ethylcarbamoyl]-10-oxo-heptadec-2-enyl}-2-hydroxy-succinic acid

[Chem. 40]

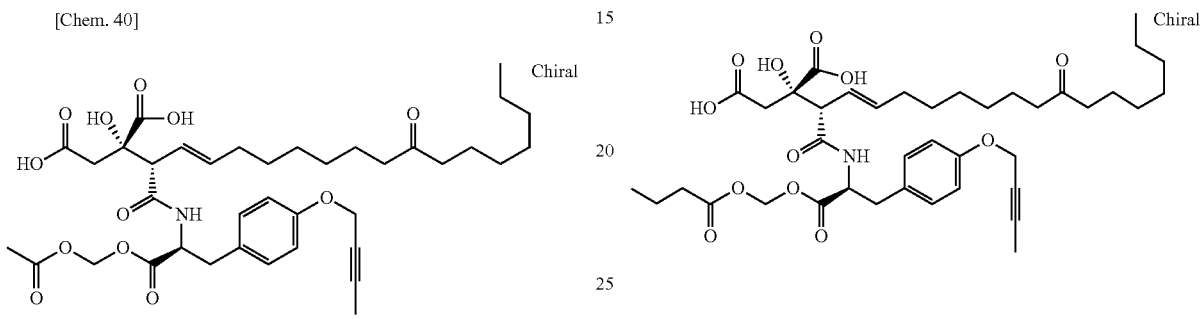

Compound 47 was obtained by a synthetic method similar to that of Compound 51 except that bromomethyl acetate was used instead of phenyl iodomethyl carbonate.

Used was a bromomethyl acetate reagent commercially available reagent from Aldrich (cat. No: 303208).

$^1$H-NMR (CD$_3$OD) δ: 0.90 (3H, t, J=7.1 Hz), 1.22-1.36 (14H, m), 1.54-1.55 (4H, m), 1.82 (3H, t, J=2.4 Hz), 1.96-1.98 (2H, m), 2.08 (3H, s), 2.44 (4H, t, J=7.3 Hz), 2.57 (1H, d, J=16.1 Hz), 2.86 (1H, d, J=15.6 Hz), 2.94 (1H, dd, J=14.2, 8.8 Hz), 3.11-3.15 (1H, m), 3.22 (1H, d, J=7.3 Hz), 4.61 (2H, q, J=2.3 Hz), 4.68 (1H, dd, J=9.0, 5.1 Hz), 5.46-5.57 (2H, m), 5.73 (1H, d, J=5.9 Hz), 5.80 (1H, d, J=5.9 Hz), 6.85 (2H, d, J=8.3 Hz), 7.12 (2H, d, J=8.8 Hz).

ESI (LC/MS positive mode) m/z 716 (M+H); Rt 1.89 min.

Compound 48: No. 5112405

(S)-2-{(E)-(S)-1-[(S)-2-(4-But-2-ynyloxy-phenyl)-1-butyryloxymethoxycarbonyl-ethylcarbamoyl]-10-oxo-heptadec-2-enyl}-2-hydroxy-succinic acid

[Chem. 41]

Compound 48 was obtained by a synthetic method similar to that of Compound 51 except that iodomethyl butyrate was used instead of phenyl iodomethyl carbonate.

Iodomethyl butyrate was synthesized by a method according to Synthesis, (2), 272-278; 2008.

$^1$H-NMR (CD$_3$OD) δ: 0.90 (3H, t, J=6.8 Hz), 0.96 (3H, t, J=7.3 Hz), 1.25-1.33 (14H, m), 1.51-1.55 (3H, m), 1.63-1.67 (2H, m), 1.82 (3H, t, J=2.2 Hz), 1.92-1.95 (2H, m), 2.35 (2H, t, J=7.3 Hz), 2.43 (4H, t, J=7.3 Hz), 2.57 (1H, d, J=17.1 Hz), 2.83-2.96 (3H, m), 3.11-3.15 (1H, m), 4.61 (2H, dd, J=8.5, 6.1 Hz), 4.67-4.69 (1H, m), 5.45-5.58 (2H, m), 5.75 (1H, d, J=5.4 Hz), 5.83 (1H, d, J=5.9 Hz), 6.85 (2H, d, J=8.3 Hz), 7.12 (2H, d, J=8.8 Hz).

ESI (LC/MS positive mode) m/z 744 (M+H); Rt 2.43 min.

Compound 49: No. 5112406

(S)-2-{(E)-(S)-1-[(S)-2-(4-But-2-ynyloxy-phenyl)-1-propoxycarbonyloxymethoxycarbonyl-ethylcarbamoyl]-10-oxo-heptadec-2-enyl}-2-hydroxy-succinic acid

[Chem. 42]

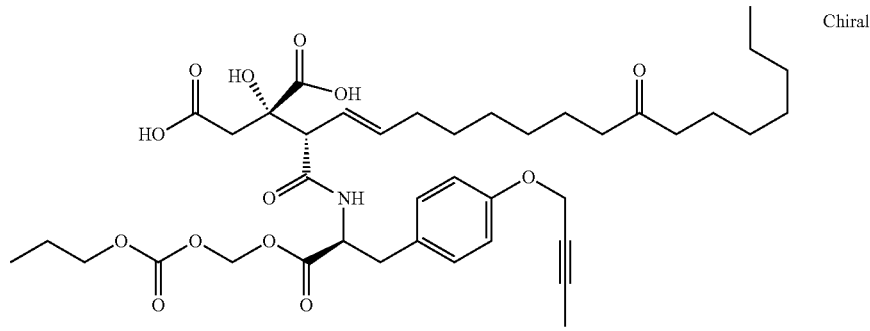

Compound 49 was obtained by a synthetic method similar to that of No. 5112408: Compound 51 except that propyl iodomethyl carbonate was used instead of phenyl iodomethyl carbonate.

Propyl iodomethyl carbonate was synthesized by a method similar to that used to synthesize isopropyl iodomethyl esters.

¹H-NMR (CD₃OD) δ: 0.89 (3H, t, J=7.1 Hz), 0.97 (3H, t, J=7.6 Hz), 1.26-1.33 (14H, m), 1.48-1.57 (4H, m), 1.71 (2H, td, J=14.0, 7.2 Hz), 1.82 (3H, t, J=2.4 Hz), 1.98 (2H, q, J=6.7 Hz), 2.43 (4H, t, J=7.3 Hz), 2.56 (1H, d, J=16.6 Hz), 2.88-2.95 (2H, m), 3.14 (1H, dd, J=13.9, 5.1 Hz), 3.22 (1H, d, J=7.3 Hz), 4.14 (2H, t, J=6.6 Hz), 4.61 (2H, q, J=2.1 Hz), 4.70 (1H, dd, J=8.8, 5.4 Hz), 5.46-5.58 (2H, m), 5.75 (1H, d, J=5.9 Hz), 5.82 (1H, d, J=5.9 Hz), 6.85 (2H, d, J=8.8 Hz), 7.12 (2H, d, J=8.3 Hz).

ESI (LC/MS positive mode) m/z 760 (M+H); Rt 2.41 min.

Compound 50: No. 5112407

(S)-2-{(E)-(S)-1-[(S)-2-(4-But-2-ynyloxy-phenyl)-1-isopropoxycarbonyloxymethoxy-carbonyl-ethylcarbamoyl]-10-oxo-heptadec-2-enyl}-2-hydroxy-succinic acid

[Chem. 43]

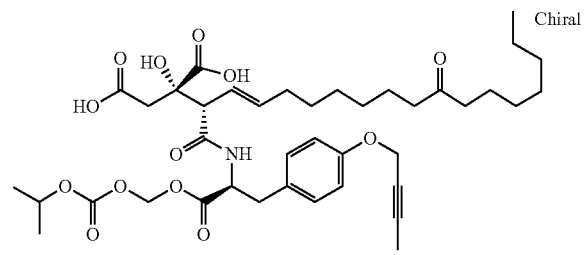

Compound 50 was obtained by a synthetic method similar to that of No. 5112408: Compound 51 except that isopropyl iodomethyl carbonate was used instead of phenyl iodomethyl carbonate.

¹H-NMR (CD₃OD) a: 0.89 (3H, t, J=7.1 Hz), 1.20-1.36 (20H, m), 1.48-1.57 (4H, m), 1.82 (3H, t, J=2.2 Hz), 1.95-2.00 (2H, m), 2.43 (4H, t, J=7.3 Hz), 2.56 (1H, d, J=15.6 Hz), 2.86 (1H, d, J=16.6 Hz), 2.95 (1H, dd, J=14.2, 8.8 Hz), 3.14 (1H, dd, J=13.9, 4.6 Hz), 4.61 (2H, q, J=2.3 Hz), 4.71 (1H, dd, J=8.5, 5.1 Hz), 5.51 (2H, t, =23.9 Hz), 5.74 (1H, d, J=5.9 Hz), 5.81 (1H, d, J=5.9 Hz), 6.85 (2H, d, J=8.3 Hz), 7.12 (2H, d, J=8.3 Hz).

ESI (LC/MS positive mode) m/z 760 (M+H); Rt 2.40 min.

Compound 52: No. 5131795

(S)-2-{(E)-(S)-1-[(S)-1-Benzoyloxymethoxycarbonyl-2-(4-but-2-ynyloxy-phenyl)-ethylcarbamoyl]-10-oxo-heptadec-2-enyl}-2-hydroxy-succinic acid

[Chem. 44]

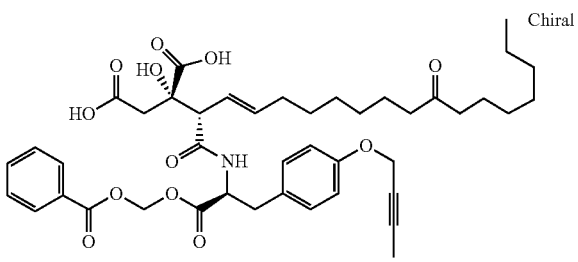

Compound 52 was obtained by a synthetic method similar to that of No. 5112408: Compound 51 except that phenyl iodomethyl carbonate was used instead of phenyl iodomethyl carbonate.

Iodomethyl benzoate was synthesized according to the description in Journal of the American Chemical Society, 123 (33), 8139-8140; 2001.

¹H-NMR (CD₃OD) δ: 0.89 (3H, t, J=7.1 Hz), 1.28 (14H, dt, J=29.1, 14.4 Hz), 1.47-1.56 (4H, m), 1.80 (3H, t, J=2.2 Hz), 1.97 (2H, q, J=7.0 Hz), 2.42 (4H, t, J=7.3 Hz), 2.57 (1H, d, J=16.1 Hz), 2.88 (1H, d, J=16.1 Hz), 2.99 (1H, dd, J=13.9, 9.0 Hz), 3.16-3.23 (2H, m), 4.58 (2H, q, J=2.3 Hz), 4.74 (1H, dd, J=9.0, 5.1 Hz), 5.54 (2H, ddd, J=28.3, 15.4, 7.1 Hz), 5.86 (1H, d, J=5.9 Hz), 5.92 (1H, d, J=5.9 Hz), 6.85 (2H, d, J=8.3 Hz), 7.14 (2H, d, J=8.3 Hz), 7.21-7.23 (2H, m), 7.28 (1H, dd, J=12.0, 4.2 Hz), 7.42 (2H, td, J=8.1, 3.6 Hz).

ESI (LC/MS positive mode) m/z 779 (M+H); Rt 2.52 min.

Compound 59: No. 5165194

4-Methoxycarbonylmethyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 45]

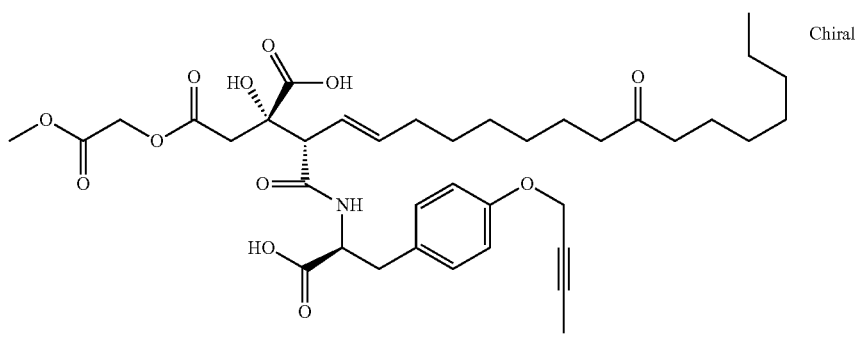

Compound 59 was obtained by a synthetic method similar to that of Compound 53: No. 5135025 except that methyl glycolate was used instead of phenol, and formic acid was used instead of trifluoroacetic acid/water/dichloromethane (4/1/5, v/v, 4 mL).

$^1$H-NMR (CD$_3$OD) δ: 0.89 (3H, t, J=7.1 Hz), 1.29 (14H, s), 1.53 (4H, s), 1.82 (3H, t, J=2.4 Hz), 1.98 (2H, q, J=6.7 Hz), 2.43 (4H, t, J=7.3 Hz), 2.71 (1H, d, J=16.1 Hz), 2.96 (2H, dt, J=26.2, 9.6 Hz), 3.15-3.25 (2H, m), 3.73 (3H, s), 4.58-4.76 (5H, m), 5.55 (2H, tt, J=20.8, 6.9 Hz), 6.85 (2H, d, J=8.3 Hz), 7.13 (2H, d, J=8.8 Hz).

ESI (LC/MS positive mode) m/z 717 (M+H); Rt 1.13 min.

Used was methyl glycolate commercially available from Wako Pure Chemical Industries (cat. No: 320-20412).

Compound 53: No. 5135025

4-Phenyl (S)-2-{(E)-(S)-1-[(S)-2-(4-but-2-ynyloxy-phenyl)-1-carboxy-ethylcarbamoyl]-10-oxo-hepta-dec-2-enyl}-2-hydroxy-succinate anhydrous sodium sulfate. The filtrate was concentrated under reduced pressure. To the resulting residue was added a mixture of trifluoroacetic acid/water/dichloromethane (4/1/5, v/v, 4 mL) and the mixture was stirred at room temperature. After confirming the consumption of the starting materials by LCMS, the organic solvent was distilled off under reduced pressure. The resulting residue was purified by preparative HPLC, and then freeze-dried to obtain Compound 53 (9.8 mg, 51% yield, amorphous).

$^1$H-NMR (CD$_3$CN) δ: 0.88 (3H, t, J=6.8 Hz), 1.28-1.31 (14H, m), 1.46-1.53 (4H, m), 1.82 (3H, t, J=2.4 Hz), 2.39 (4H, td, J=7.3, 2.9 Hz), 2.85 (1H, d, J=15.6 Hz), 2.93 (1H, dd, J=14.4, 8.5 Hz), 3.12-3.19 (2H, m), 3.29 (1H, d, J=9.3 Hz), 4.62-4.67 (3H, m), 5.44 (1H, dd, J=15.1, 9.3 Hz), 5.61 (1H, dd, J=14.4, 7.6 Hz), 6.86 (2H, d, J=8.8 Hz), 7.08 (2H, d, J=7.3 Hz), 7.13 (2H, d, J=8.8 Hz), 7.27 (1H, t, J=7.6 Hz), 7.41 (2H, t, J=7.8 Hz).

ESI (LC/MS positive mode) m/z 721 (M+H); Rt 1.67 min.

[Chem. 46]

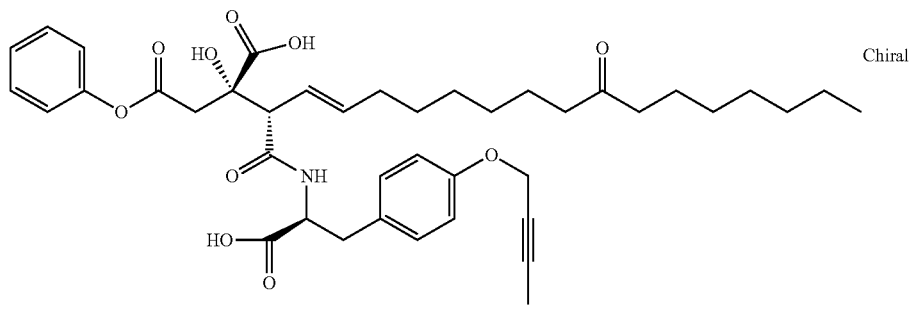

To a mixture of No. 5317776: Compound E (20 mg, 0.0265 mmol), phenol (45 mg, 0.478 mmol), and DMF (2.0 mL) were added N,N-diisopropylethylamine (20.9 μL, 0.119 mmol) and HATU (11.1 mg, 0.0292 mmol), and the mixture was stirred at room temperature. After confirming the consumption of the starting materials by LCMS, an aqueous solution of 0.5 M KHSO$_4$ and a saturated brine were added, and the mixture was extracted with ethyl acetate. The organic layer was washed with a saturated brine, and then dried over Compound 59: No. 5165194

4-Methoxycarbonylmethyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 47]

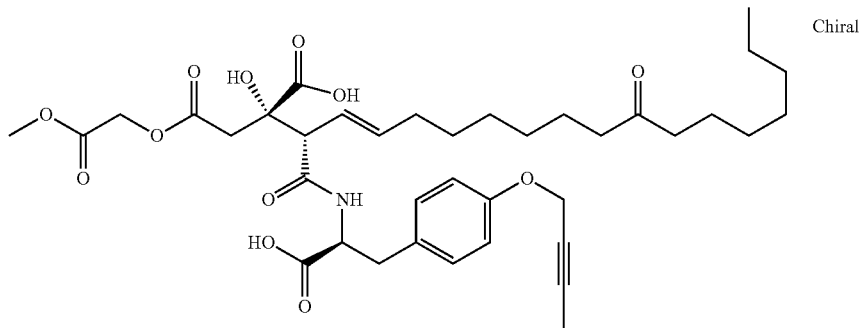

Compound 59 was obtained by a synthetic method similar to that of Compound 53: No. 5135025 except that methyl glycolate was used instead of phenol, and formic acid was used instead of trifluoroacetic acid/water/dichloromethane (4/1/5, v/v, 4 mL).

Used was a methyl glycolate reagent commercially available from Wako Pure Chemical Industries (cat. No: 320-20412).

$^1$H-NMR (CD$_3$OD) δ: 0.89 (3H, t, J=7.1 Hz), 1.29 (14H, s), L53 (4H, s), 1.82 (3H, t, J=2.4 Hz), 1.98 (2H, q, J=6.7 Hz), 2.43 (4H, t, J=7.3 Hz), 2.71 (1H, d, J=16.1 Hz), 2.96 (2H, dt, J=26.2, 9.6 Hz), 3.15-3.25 (2H, m), 3.73 (3H, s), 4.58-4.76 (5H, m), 5.55 (2H, tt, J=20.8, 6.9 Hz), 6.85 (2H, d, J=8.3 Hz), 7.13 (2H, d, J=8.8 Hz).

ESI (LC/MS positive mode) m/z 717 (M+H); Rt 1.13 min.

water was added and the mixture was extracted with ethyl acetate. The organic layer was washed with a saturated brine and dried over anhydrous sodium sulfate, and then the filtrate was concentrated under reduced pressure. The resulting residue was purified by preparative HPLC and freeze-dried to obtain Compound 39 (8 mg, 4% yield, white powder).

$^1$H-NMR (CD$_3$OD) δ: 0.89-0.93 (6H, m), 1.28-1.30 (15H, m), 1.49-1.53 (5H, m), 1.65 (2H, td, J=14.0, 7.2 Hz), 1.82 (3H, t, J=2.2 Hz), 1.97-1.99 (2H, m), 2.44 (4H, t, J=7.3 Hz), 2.56 (1H, d, J=16.1 Hz), 2.86-2.96 (2H, m), 3.10-3.15 (1H, m), 3.19 (1H, d, J=8.3 Hz), 4.07 (2H, t, J=6.6 Hz), 4.61-4.64 (3H, m), 5.53-5.55 (2H, m), 6.85 (2H, d, J=8.8 Hz), 7.11 (2H, d, J=8.8 Hz), 8.20 (1H, d, J=8.8 Hz).

ESI (LC/MS positive mode) m/z 687 (M+H); Rt 2.96 min.

Compound number 60: No. 5322968

[(7S,10S,11S)-7-(4-But-2-ynyloxy-benzyl)-11-hydroxy-2,6,9,12-tetraoxo-10-((E)-9-oxo-hexadec-1-enyl)-4,7,8,9,10,11,12,14-octahydro-6H-1,3,5,13-tetraoxa-8-aza-cyclopentacyclotridecen-11-yl]-acetic acid

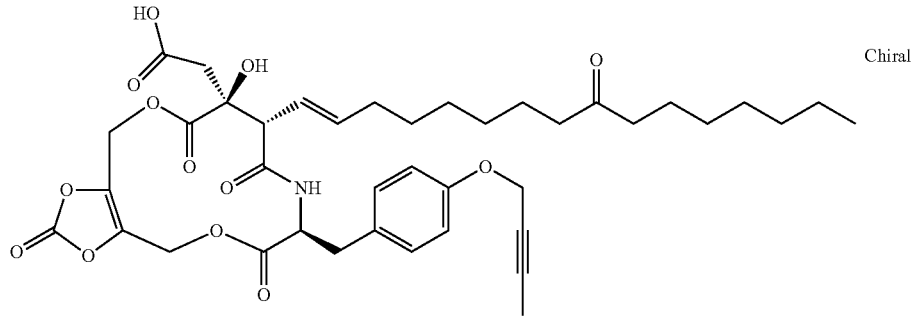

[Chem. 49]

Compound 39: No. 5081963

(S)-2-{(E)-(S)-1-[(S)-2-(4-But-2-ynyloxy-phenyl)-1-propoxycarbonyl-ethylcarbamoyl]-10-oxo-heptadec-2-enyl}-2-hydroxy-succinic acid

[Chem. 48]

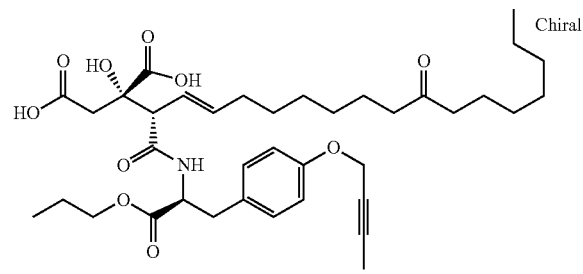

To a mixture of No. 4630808: Compound 93 (200 mg, 0.277 mmol), n-propanol (7.5 mL), and dichloromethane (7.5 mL) was added concentrated hydrochloric acid (1.15 mL) and the mixture was stirred at room temperature. After confirming the consumption of No. 4630808: Compound 93 by LCMS, To a mixture of No. 4630808: Compound 93 (50 mg, 0.0702 mmol) and DMF (2.0 mL) was added 4,5-bis-bromomethyl-[1,3]dioxol-2-one and the mixture was stirred at room temperature. After confirming the consumption of the starting materials by LCMS, the product was purified by direct preparative HPLC and freeze-dried to obtain Compound number 60 (2.0 mg, 4% yield).

4,5-Bis-bromomethyl-[1,3]dioxol-2-one (CAS No. 62458-19-9) was synthesized according to the method described in WO 2005/097760.

$^1$H-NMR (CD$_3$OD) δ: 0.89 (3H, t, J=6.9 Hz), 1.27-1.30 (21H, m), 1.53-1.55 (4H, m), 1.82 (3H, t, J=2.2 Hz), 1.97-1.98 (2H, m), 2.44 (4H, t, J=7.3 Hz), 2.58 (1H, d, J=17.0 Hz), 2.87 (1H, dd, J=14.2, 10.1 Hz), 3.08 (1H, dd, J=13.7, 6.3 Hz), 3.18 (1H, d, J=7.6 Hz), 3.42 (1H, d, J=17.0 Hz), 4.53-4.56 (1H, m), 4.60-4.61 (2H, m), 4.91 (2H, d, J=3.1 Hz), 5.05 (2H, dd, J=43.0, 14.3 Hz), 5.37-5.43 (2H, m), 6.85 (2H, d, J=8.6 Hz), 7.12 (2H, d, J=8.6 Hz), 8.54 (1H, d, J=7.6 Hz).

ESI (LC/MS positive mode) m/z 755 (M+H); Rt 2.82 min.

Compound 61: No. 5334171

4-(2-Methoxy-ethyl) (S)-2-{(E)-(S)-1-[(S)-2-(4-but-2-ynyloxy-phenyl)-1-(2-methoxy-ethoxycarbonyl)-ethylcarbamoyl]-10-oxo-heptadec-2-enyl}-2-hydroxy-succinate

[Chem. 50]

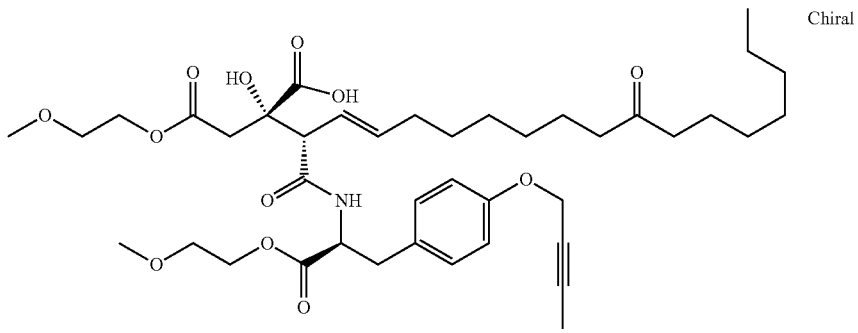

Compound 61 was obtained by the synthesis similar to that of No. 5045280: Compound 36 except that a commercially available reagent of 2-methoxyethanol was used instead of methanol.

$^1$H-NMR (CD$_3$OD) δ: 0.90 (3H, t, J=6.9 Hz), 1.30-1.32 (25H, m), 1.52-1.55 (4H, m), 1.82 (3H, t, J=2.2 Hz), 1.95-1.98 (2H, m), 2.43 (4H, t, J=7.3 Hz), 2.66 (1H, d, J=15.7 Hz), 2.93-2.96 (2H, m), 3.13-3.22 (2H, m), 3.35 (3H, s), 3.36 (3H, s), 3.59-3.60 (4H, m), 4.19-4.31 (4H, m), 4.61 (2H, q, J=2.3 Hz), 4.69 (1H, dd, J=8.6, 5.3 Hz), 5.52-5.54 (2H, m), 6.85 (2H, d, J=8.8 Hz), 7.12 (2H, d, J=8.8 Hz).

ESI (LC/MS positive mode) m/z 761 (M+H); Rt 2.87 min.

Compound 69: No. 5454351

4-Isopropyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 51]

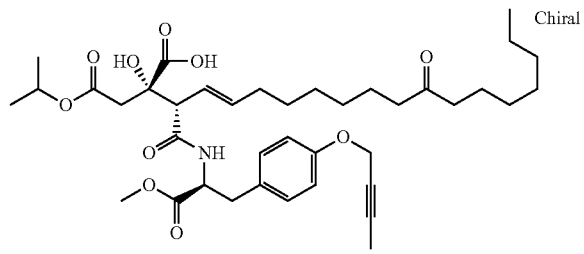

To a mixture of No. 5317776: Compound E (50 mg, 0.070 mmol), HATU (39.9 mg, 0.105 mmol), and DMAP (34.2 mg, 0.280 mmol) were added DMF (2.0 mL) and 2-propanol (21.4 μL, 0.280 mmol) and the mixture was stirred at room temperature for 17 hours. Water (20 mL) was added to the reaction mixture, which was followed by extraction with ethyl acetate (15 mL×3). The resulting organic layer was washed with a saturated brine (10 mL), dried over anhydrous sodium sulfate, and filtered. The organic solvent was distilled off under reduced pressure. The obtained composition was purified by silica gel column chromatography to obtain 4-isopropyl 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate (19 mg, 36% yield, ESI (LC/MS positive mode) m/z 756 (M+H); Rt 3.02 min). To the purified compound was added formic acid (1.9 mL) and the mixture was stirred at room temperature. Formic acid was distilled off under reduced pressure. The residue was purified by preparative HPLC and then freeze-dried to obtain Compound 69 (9 mg, 48% yield).

$^1$H-NMR (CD$_3$OD) δ: 0.89 (3H, t, J=6.8 Hz), 1.25-1.34 (22H, m), 1.50-1.56 (4H, m), 1.81 (3H, t, J=2.4 Hz), 1.98 (2H, q, J=6.3 Hz), 2.44 (4H, t, J=7.3 Hz), 2.57 (1H, d, J=15.4 Hz), 2.87-2.95 (2H, m), 3.12 (1H, dd, J=13.9, 5.1 Hz), 3.21 (1H, d, J=8.4 Hz), 3.72 (3H, s), 4.61-4.65 (3H, m), 4.91-4.98 (1H, m), 5.50-5.55 (1H, m), 6.85 (2H, d, J=8.4 Hz), 7.10 (2H, d, J=8.4 Hz), 8.27 (1H, d, J=7.9 Hz).

ESI (LC/MS positive mode) m/z 700 (M+H); Rt 2.00 min.

Compound 70: No. 5455808

1-(5-Methyl-2-oxo-[1,3]dioxol-4-ylmethyl) 4-methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 52]

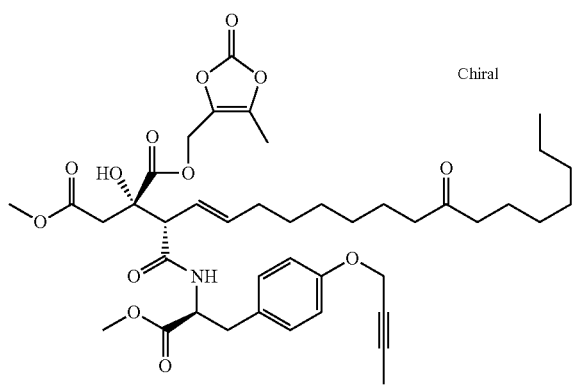

To a mixture of No. 5045280: Compound 36 (22 mg, 0.0327 mmol) and THF (1 mL) were added 4-chloromethyl-5-methyl-1,3-dioxol-2-one (7.1 mg, 0.0655 mmol), tetrabutyl ammonium iodide (1.2 mg, 0.0033 mmol), and N,N-diisopropylethylamine (11.4 µL, 0.0655 mmol) and the mixture was stirred at room temperature. After confirming the consumption of the starting materials by LCMS, the product was purified by preparative HPLC. Water was added to the purified fraction, which was followed by extraction with ethyl acetate. The organic layer was washed with a saturated brine and then dried over anhydrous sodium sulfate. The filtrate was concentrated under reduced pressure to obtain Compound 70 (13 mg, 51% yield).

$^1$H-NMR (CD$_3$OD) δ: 0.89 (3H, t, J=7.1 Hz), 1.27-1.30 (16H, m), 1.50-1.57 (4H, m), 1.82 (3H, t, J=2.2 Hz), 1.95-1.97 (2H, m), 2.17 (3H, s), 2.44 (4H, t, J=7.5 Hz), 2.60 (1H, d, J=15.9 Hz), 2.86-2.95 (2H, m), 3.12 (1H, dd, J=13.9, 5.1 Hz), 3.20 (1H, d, J=8.4 Hz), 3.62 (3H, s), 3.72 (3H, s), 4.62-4.64 (3H, m), 4.96 (2H, s), 5.47-5.53 (2H, m), 6.84 (2H, d, J=8.8 Hz), 7.08 (2H, d, J=8.4 Hz), 8.25 (1H, d, J=7.9 Hz).

ESI (LC/MS positive mode) m/z 784 (M+H); Rt 2.98 min.

Compound 71: No. 5456195

4-Methyl 1-(1-acetoxy-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 53]

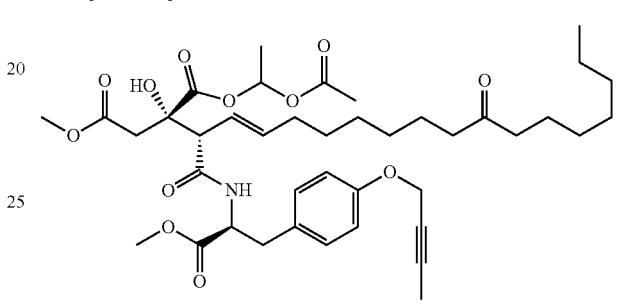

To a mixture of No. 5045280: Compound 36 (24 mg, 0.0357 mmol) and dichloromethane were added 1-bromo-ethyl acetate (12.5 mg, 0.107 mmol), N,N-diisopropylethylamine (18.7 µL, 0.107 m mL), and TBAI (6.6 mg, 0.0179 mmol) and the mixture was stirred at room temperature. After confirming the consumption of the starting materials by LCMS, the organic solvent was distilled off under reduced pressure, and the residue was purified by preparative HPLC. Water was added to the purified fraction, which was followed by extraction with ethyl acetate, washing with a saturated brine, and drying over anhydrous sodium sulfate. The solvent was distilled off under reduced pressure to obtain Compound 71 (18.5 mg, 68% yield).

$^1$H-NMR (CD$_3$OD) δ: 0.90 (3H, t, J=7.1 Hz), 1.22-1.37 (15H, m), 1.46 (2H, t, J=6.0 Hz), 1.54 (4H, t, J=7.1 Hz), 1.80-1.82 (3H, m), 2.04 (3H, d, J=7.5 Hz), 2.44 (4H, t, J=7.3 Hz), 2.58 (1H, dt, J=16.2, 2.6 Hz), 2.89 (2H, tt, J=11.0, 4.0 Hz), 3.10-3.26 (3H, m), 3.65 (3H, d, J=1.3 Hz), 3.73 (3H, d, J=3.5 Hz), 4.60-4.67 (3H, m), 5.42-5.57 (2H, m), 6.83-6.85 (3H, m), 7.09 (2H, dd, J=8.5, 1.4 Hz), 8.21-8.23 (1H, m), diastereomeric mixture, ESI (LC/MS positive mode) m/z 758 (M+H); Rt 2.28 min.

Compound 65: No. 5426831

4-Pyridin-4-ylmethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 54]

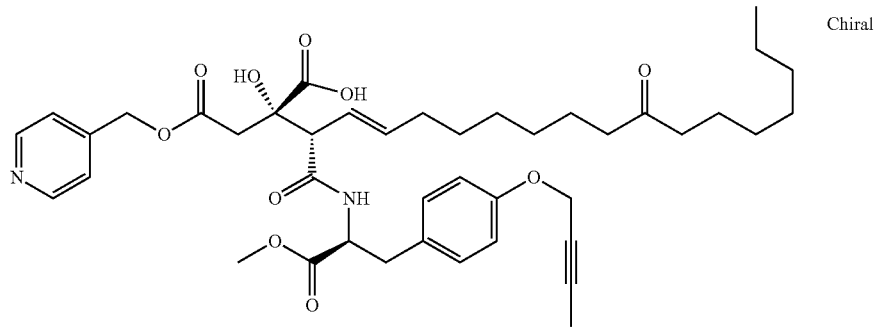

Compound 65 was synthesized by a synthetic method similar to that of No. 5454351 (Compound 69) except that 4-pyridinecarbinol was used instead of isopropanol.

$^1$H-NMR (CD$_3$OD) δ: 0.89 (3H, t, J=6.8 Hz), 1.28-1.30 (14H, m), 1.49-1.57 (4H, m), 1.81 (3H, t, J=2.3 Hz), 1.99-2.00 (2H, m), 2.44 (4H, t, J=7.3 Hz), 2.79 (1H, d, J=15.3 Hz), 2.92 (1H, dd, J=14.1, 9.4 Hz), 3.12-3.16 (2H, m), 3.28 (1H, s), 3.73 (3H, s), 4.59 (2H, q, J=2.2 Hz), 4.67 (1H, dt, J=13.6, 4.5 Hz), 5.41 (2H, d, J=2.3 Hz), 5.54 (2H, ddd, J=31.1, 14.6, 8.4 Hz), 6.84 (2H, d, J=8.6 Hz), 7.11 (2H, d, J=8.6 Hz), 7.96 (2H, d, J=6.1 Hz), 8.37 (1H, d, J=9.0 Hz), 8.76 (2H, d, J=5.5 Hz).

ESI (LC/MS positive mode) m/z 749 (M+H); Rt 1.92 min.

Compound 66: No. 5426834

4-Pyridin-2-ylmethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 55]

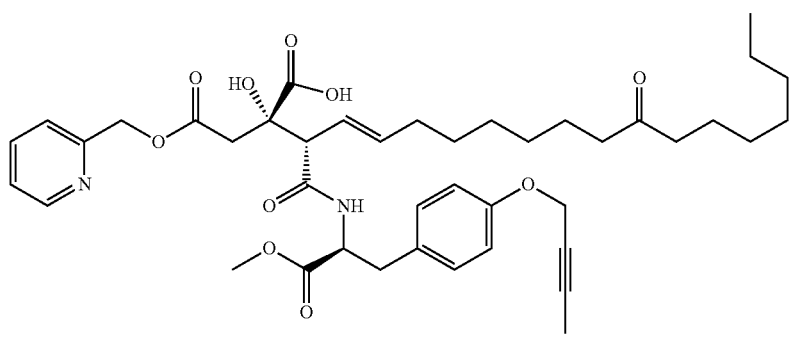

Compound 66 was synthesized by a synthetic method similar to that of No. 5454351: Compound 69 except that 2-(hydroxymethyl)pyridine was used instead of isopropanol.

$^1$H-NMR (CD$_3$OD) δ: 0.89 (3H, t, J=6.9 Hz), 1.22-1.31 (14H, m), 1.49-1.57 (4H, m), 1.81 (4H, t, J=2.3 Hz), 1.98 (3H, dd, J=13.2, 7.9 Hz), 2.43 (4H, t, J=7.4 Hz), 2.76 (1H, d, J=15.7 Hz), 2.92 (1H, dd, J=14.1, 9.2 Hz), 3.06-3.15 (2H, m), 3.27 (1H, d, J=8.6 Hz), 3.71 (3H, s), 4.58 (3H, q, J=2.3 Hz), 4.66 (1H, dd, J=9.0, 5.1 Hz), 5.28 (2H, dd, J=17.2, 14.1 Hz), 5.54 (2H, tt, J=19.8, 6.6 Hz), 6.83 (2H, dt, J=9.3, 2.5 Hz), 7.10 (2H, dt, J=9.2, 2.5 Hz), 7.54 (1H, dd, J=7.0, 5.9 Hz), 7.67 (1H, d, J=7.8 Hz), 8.06 (1H, td, J=7.8, 1.7 Hz), 8.59 (1H, d, J=5.3 Hz).

ESI (LC/MS positive mode) m/z 749 (M+H); Rt 2.10 min.

Compound 62: No. 5398707

[(8S,11S,12S)-8-(4-But-2-ynyloxy-benzyl)-12-hydroxy-7,10,13-trioxo-11-((E)-9-oxo-hexadec-1-enyl)-5,8,9,10,11,12,13,15-octahydro-7H-6,14-dioxa-9-aza-benzocyclotridecen-12-yl]-acetic acid

[Chem. 56]

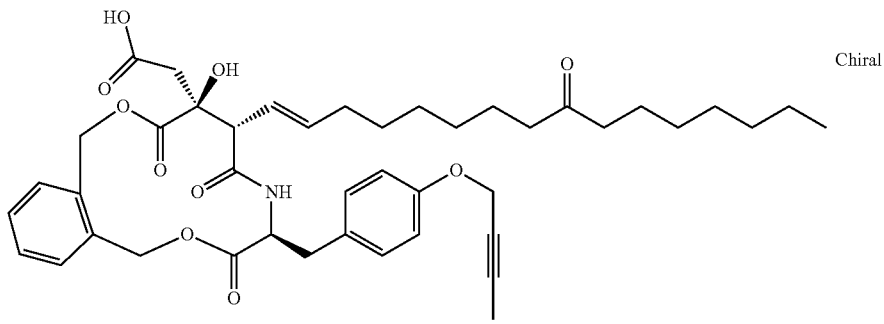

To a mixture of Compound 93: No. 4630808 (50 mg, 0.0702 mmol) and DMF was added xylenedibromide (20.4 mg, 0.0772 mmol) and the mixture was stirred at room temperature. After confirming the consumption of the starting materials by LCMS, a saturated aqueous solution of ammonium chloride was added, and the mixture was extracted with ethyl acetate. The organic layer was then dried over anhydrous sodium sulfate, and then the filtrate was concentrated under reduced pressure. The residue was purified by preparative HPLC. The corresponding fraction was freeze-dried to obtain Compound 62 (8.4 mg, 16% yield).

Used was a xylene dibromide reagent commercially available from Wako Pure Chemical Industries (cat No: 042-15672).

$^1$H-NMR (CD$_3$OD) δ: 0.89 (3H, t, J=7.0 Hz), 1.26-1.34 (14H, m), 1.51-1.57 (4H, m), 1.81 (3H, t, J=2.3 Hz), 1.91-1.93 (2H, m), 2.42-2.46 (4H, m), 2.52 (1H, d, J=17.2 Hz), 2.81 (1H, dd, J=14.1, 10.8 Hz), 3.12 (2H, dt, J=9.5, 4.4 Hz), 4.54-4.59 (3H, m), 5.08 (2H, dd, J=16.6, 11.2 Hz), 5.23-5.28 (3H, m), 5.39 (1H, dd, J=15.5, 7.6 Hz), 6.81 (2H, dt, J=9.3, 2.5 Hz), 7.09 (2H, dt, J=9.3, 2.5 Hz), 7.33-7.42 (4H, m).

ESI (LC/MS positive mode) m/z 747 (M+H); Rt 2.72 min.

Compound 64: No. 5426610

(7S,10S,11S)-7-(4-But-2-ynyloxy-benzyl)-11-hydroxy-2,6,9,13-tetraoxo-10-((E)-9-oxo-hexadec-1-enyl)-4,6,7,8,9,10,11,12,13,15-decahydro-1,3,5,14-tetraoxa-8-aza-cyclopentacyclotetradecene-11-carboxylic acid

[Chem. 57]

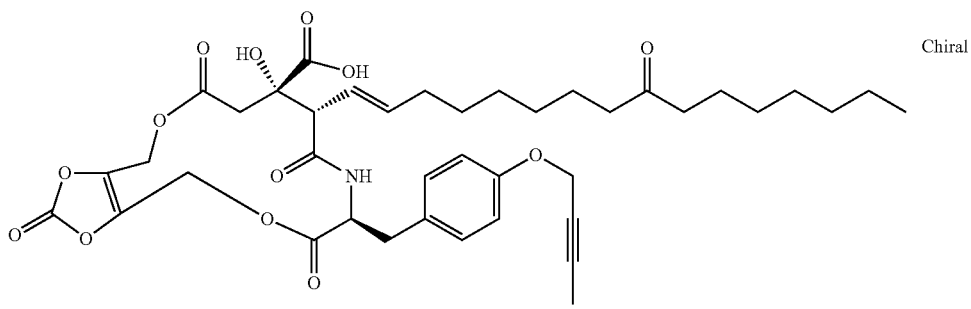

To a mixture of Compound G (No. 5447725; 84.3 mg, 0.128 mmol ) and DMF (8.4 mL) were added 4,5-bis-bromomethyl-[1,3]dioxol-2-one (37.8 mg, 0.141 mmol) and N,N -diisopropylethylamine (22.3 μL, 0.128 mmol) and the mixture was stirred at room temperature. After confirming the consumption of the starting materials by LCMS, the product was purified by preparative HPLC. Water was added to the purified fraction, which was followed by extraction with ethyl acetate. The resulting organic layer was washed with a saturated brine and then dried over anhydrous sodium sulfate. The filtrate was concentrated under reduced pressure to obtain tert-butyl (7S,10S,11S)-7-(4-but-2-ynyloxy-benzyl)-11-hydroxy-2,6,9,13-tetraoxo-10-((E)-9-oxo-hexadec-1-enyl)-4,6,7,8,9,10,11,12,13,15-decahydro-1,3,5,14-tetraoxa-8-aza-cyclopentacyclotetradecene-11-carboxylate (16.3 mg, 16% yield). To the obtained tert-butyl (7S ,10S ,11S)-7-(4-but-2-ynyloxy-benzyl)-11-hydroxy-2,6,9,13-tetraoxo-10-((E)-9- oxo-hexadec-1-enyl)-4.6,7,8,9,10,11,12,13,15-decahydro-1,3,5,14-tetraoxa-8-aza-cyclopentacyclotetradecene-11-carboxylate (16.3 mg, 0.0201 mmol) was added formic acid (8.2 mL) and the mixture was stirred at room temperature. After confirming the consumption of the starting materials by LCMS, dichloromethane was added and the organic solvent was distilled off under reduced pressure. The resulting residue was purified by preparative HPLC. Water was added to the purified fraction, which was followed by extraction with ethyl acetate. The obtained organic layer was washed with a saturated brine, and then dried over anhydrous sodium sulfate. The filtrate was concentrated under reduced pressure to obtain Compound 64 (15 mg, 99% yield).

$^1$H-NMR (CD$_3$OD) δ: 0.89 (3H, t, J=6.8 Hz), 1.28 (14H, d, J=4.7 Hz), 1.54 (4H, q, J=7.0 Hz), 1.82 (3H, t, J=2.2 Hz), 1.92 (2H, s), 2.44 (4H, td, J=7.4, 2.2 Hz), 2.88 (3H, td, J=15.2, 5.9 Hz), 3.10 (1H, dd, J=14.1, 5.7 Hz), 3.50 (1H, d, J=8.8 Hz), 4.61 (2H, q, J=2.2 Hz), 4.68-4.73 (1H, m), 4.97 (2H, dd, J=18.7, 10.5 Hz), 5.05 (2H, dd, J=14.2, 10.7 Hz), 5.37 (1H, dd, J=15.4, 8.9 Hz), 5.47-5.54 (1H, m), 6.84 (2H, d, J=8.4 Hz), 7.10 (2H, d, J=8.4 Hz), 8.58 (1H, d, J=8.8 Hz).

ESI (LC/MS positive mode) m/z 755 (M+H); Rt 2.63 min.

Compound 63: No. 5426387

4-(4-Acetoxy-benzyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate To a mixture of No. 5317776: Compound E (50 mg, 0.070 mmol) and DMF (2.5 mL) were added 4-bromomethyl-phenyl acetate (24.1 mg, 0.105 mmol) and N,N-diisopropylethylamine (19.5 μL, 0.112 mmol). After 3 hours, 4-bromomethyl-phenyl acetate (24.1 mg, 0.105 mmol) and N,N-diisopropylethylamine (19.5 μL, 0.112 mmol) were added again. After confirming the consumption of the starting materials by LCMS, a saturated aqueous solution of ammonium chloride was added and the mixture was extracted with ethyl acetate. The resulting organic layer was washed with a saturated brine and dried over anhydrous sodium sulfate. The filtrate was concentrated under reduced pressure. The resulting residue was purified with SP1 to obtain 1-tert-butyl 4-(4-acetoxy-benzyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate (54 mg, 89% yield).

To the obtained 1-tert-butyl 4-(4-acetoxy-benzyl) (S)-2-{(E)-(S)-1-[(S)-2-(4-but-2-ynyloxy-phenyl)-1-methoxycarbonyl-ethylcarbamoyl]10-oxo-heptadec-2-enyl}-2-hydroxy-succinate was added formic acid (2.5 mL) and the mixture was stirred at room temperature. After confirming the consumption of the starting materials by LCMS, dichloromethane was added and the solvent was distilled off under reduced pressure. The residue was purified by preparative HPLC. Water was added to the purified fraction, which was followed by extraction with ethyl acetate. The resulting organic layer was washed with a saturated brine and then dried over anhydrous sodium sulfate. The filtrate was concentrated under reduced pressure to obtain Compound 63 (48 mg, 95% yield).

Used was a 4-bromomethyl-phenyl acetate reagent commercially available from Advanced Technology & Industrial Co., Ltd (cat No: 4232725).

$^1$H-NMR (CD$_3$OD) δ: 0.89 (3H, t, J=6.9 Hz), 1.27-1.29 (14H, m), 1.53-1.54 (4H, m), 1.81 (3H, t, J=2.3 Hz), 1.98 (2H, dd, J=15.4, 7.9 Hz), 2.26 (3H, s), 2.43 (4H, t, J=7.3 Hz), 2.66 (1H, d, J=15.8 Hz), 2.90-2.97 (2H, m), 3.10-3.14 (1H, m), 3.21 (1H, d, J=8.2 Hz), 3.70 (3H, s), 4.58 (2H, q, J=2.3 Hz), 4.62-4.67 (1H, m), 5.11 (2H, s), 5.53 (2H, ddd, J=27.9, 15.4, 7.1 Hz), 6.81-6.84 (2H, m), 7.06-7.10 (4H, m), 7.38-7.41 (2H, m), 8.26 (1H, d, J=8.0 Hz).

ESI (LC/MS positive mode) m/z 807 (M+H); Rt 2.92 min.

[Chem. 58]

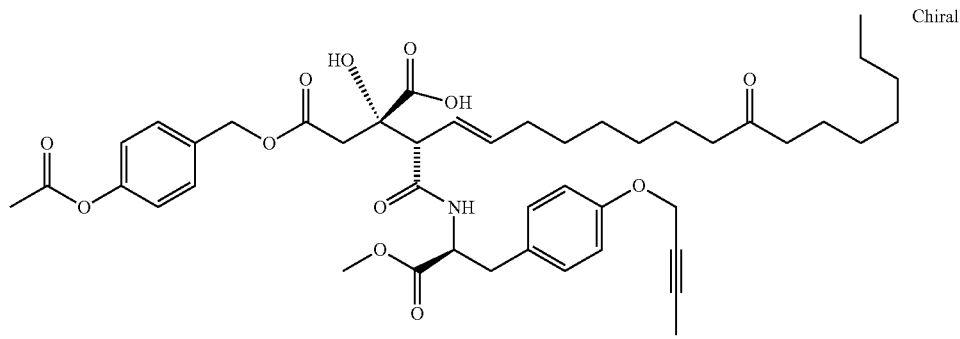

Compound 67: No. 5446900

4-(2-Methoxycarbonyl-allyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 59]

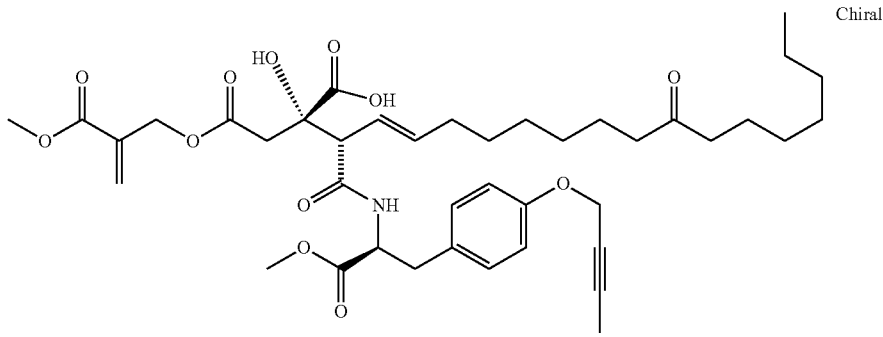

Compound 67 was obtained by the synthesis similar to that of No. 5426387, Compound 63 except that methyl 2-bromomethyl-acrylate was used instead of 4-bromomethyl-phenyl acetate.

Used was a methyl 2-bromomethyl-acrylate reagent commercially available from Aldrich (cat No: 302546).

$^1$H-NMR (CD$_3$OD) δ: 0.90 (3H, t, J=6.7 Hz), 1.28-1.33 (15H, m), 1.52-1.54 (4H, m), 1.81 (3H, t, J=2.3 Hz), 1.98 (2H, dd, J=13.5, 7.0 Hz), 2.43 (4H, t, J=7.5 Hz), 2.66 (1H, d, J=15.5 Hz), 2.91-2.98 (2H, m), 3.13 (1H, dd, J=14.2, 5.0 Hz), 3.22 (1H, d, J=7.8 Hz), 3.72 (3H, s), 3.76 (3H, s), 4.60 (2H, q, J=2.4 Hz), 4.65 (1H, dt, J=13.7, 4.6 Hz), 4.79 (2H, td, J=2.6, 1.4 Hz), 5.51-5.56 (2H, m), 5.91 (1H, q, J=1.4 Hz), 6.32 (1H, q, J=1.0 Hz), 6.84 (2H, d, J=9.4 Hz), 7.10 (2H, d, J=9.0 Hz), 8.25 (0H, d, J=7.4 Hz).

ESI (LC/MS positive mode) m/z 757 (M+H); Rt 2.80 min.

Compound 37: No. 5071258

4-(5-Amino-pentyl) (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate To a mixture of 1-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate (1.0 g, 1.322 mmol) and DMF (14 mL) were added tert-butyl (5-iodo-pentyl)-carbamate (1.66 g, 5.30 mmol) and NaHCO$_3$ (1.11 g, 13.2 mmol) and the mixture was stirred at room temperature. After confirming the consumption of the starting materials by LCMS, the mixture was extracted with ethyl acetate. The resulting organic layer was washed with a saturated brine and then dried over anhydrous sodium sulfate. The filtrate was concentrated under reduced pressure. A mixture (4/5/1, 20 mL) of trifluoroacetic acid/dichloromethane/water was added to the resulting residue, which was followed by stirring at room temperature. After confirming the consumption of the starting materials by LCMS, the organic solvent was distilled off under reduced pressure. The residue was purified by preparative HPLC. The purified fraction was freeze-dried to obtain the title compound (537 mg, 55% yield).

The starting material 1-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate was synthesized according to the method (Compound No. 29) described in WO2006/088071.

[Chem. 60]

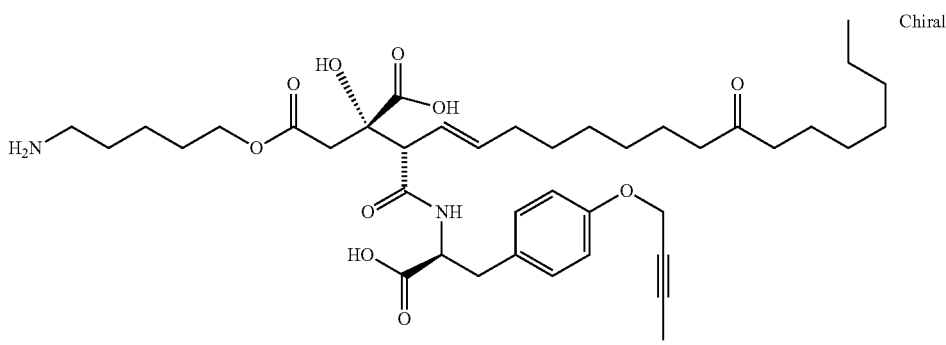

tert-Butyl (5-iodo-pentyl)-carbamate was synthesized by a method similar to that of tert-butyl (5-iodo-butyl)-carbamate described in Journal of Organic Chemistry, 71 (10), 3942-3951, 2006.

$^1$H-NMR (CD$_3$OD) δ 0.89 (3H, t, J=7.1 Hz), 1.21-1.36 (15H, m), 1.51-1.54 (6H, m), 1.64-1.68 (4H, m), 1.82 (3H, t, J=2.4 Hz), 1.94-1.96 (2H, m), 2.43 (4H, td, J=7.3, 2.4 Hz), 2.50 (1H, d, J=14.6 Hz), 2.89-2.95 (4H, m), 3.14-3.18 (2H, m), 4.06 (1H, dd, J=11.0, 5.1 Hz), 4.14 (1H, dd, J=11.5, 5.6 Hz), 4.58-4.62 (3H, m), 5.52 (2H, ddd, J=25.6, 15.4, 6.6 Hz), 6.83 (2H, d, J=8.8 Hz), 7.15 (2H, d, J=8.8 Hz).

ESI (LC/MS positive mode) m/z 729 (M+H); Rt 1.87 min.

Compound 40: No. 5081964

4-Propyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 61]

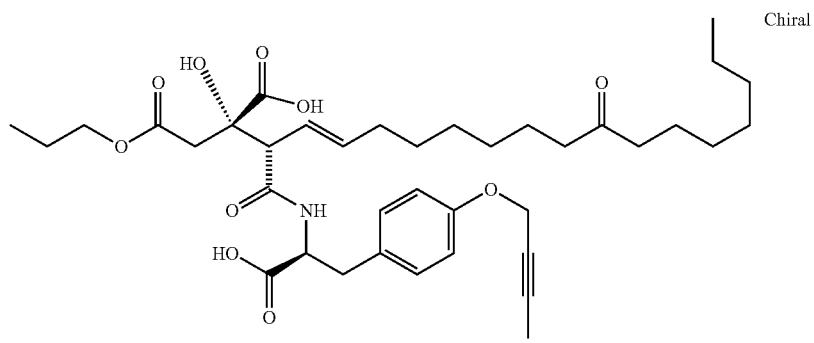

The title compound was obtained by a method similar to that of No. 5045280: Compound 36 except that n-propanol was used instead of methanol.

$^1$H-NMR (CD$_3$OD) δ: 0.89-0.93 (6H, m), 1.28-1.30 (1H, m), 1.52-1.54 (4H, m), 1.62-1.64 (2H, m), 1.81 (3H, t, J=2.3 Hz), 1.96-1.97 (2H, m), 2.43 (4H, t, J=7.1 Hz), 2.60 (1H, d, J=15.6 Hz), 2.90-2.93 (2H, m), 3.16-3.21 (2H, m), 4.01 (2H, t, J=5.7 Hz), 4.59-4.60 (3H, m), 5.52 (2H, dq, J=31.9, 7.8 Hz), 6.83 (2H, d, J=8.7 Hz), 7.12 (2H, d, J=8.2 Hz).

ESI (LC/MS positive mode) m/z 686 (M+H); Rt 2.85 min.

Compound 43: No. 5088599

(S)-2-{(E)-(S)-1-[(S)-2-(4-But-2-ynyloxy-phenyl)-1-(2,2-dimethyl-propionyloxy-methoxycarbonyl)-ethylcarbamoyl]-10-oxo-heptadec-2-enyl}-2-hydroxy-succinic acid

[Chem. 62]

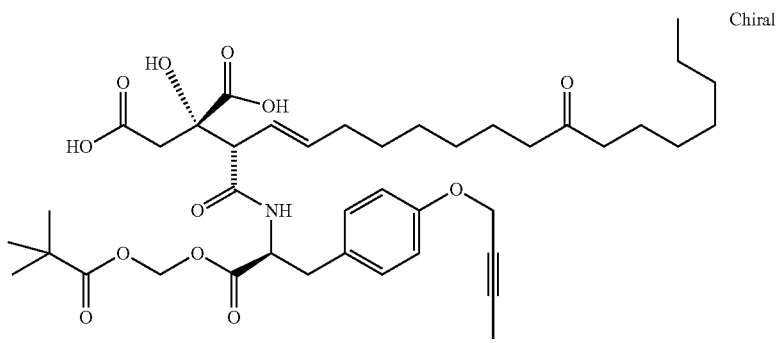

The title compound was obtained by a synthetic method similar to that of No. 5112408: Compound 51 except that iodomethyl 2,2-dimethyl-propionate was used instead of phenyl iodomethyl carbonate.

$^1$H-NMR (CD$_3$OD) δ: 0.90 (3H, t, J=6.8 Hz), 1.21 (9H, s), 1.27-1.33 (15H, m), 1.50-1.57 (4H, m), 1.82 (3H, t, J=2.4 Hz), 1.96-1.99 (2H, m), 2.44 (4H, t, J=7.3 Hz), 2.54 (1H, d, J=16.6 Hz), 2.90 (2H, dt, J=22.9, 8.3 Hz), 3.14-3.17 (2H, m), 4.61 (2H, q, J=2.3 Hz), 4.67 (1H, dd, J=9.3, 4.9 Hz), 5.52 (2H, td, J=17.3, 11.1 Hz), 5.76 (1H, d, J=5.4 Hz), 5.83 (1H, d, J=5.4 Hz), 6.85 (2H, d, J=8.8 Hz), 7.12 (2H, d, J=8.8 Hz).

ESI (LC/MS positive mode) m/z 758 (M+H); Rt 3.10 min.

Compound 45: No. 5107442

Diacetoxymethyl (S)-2-{(E)-(S)-1-[(S)-1-acetoxytnethoxycarbonyl-2-(4-but-2-ynyloxy-phenyl)-ethylcarbamoyl]-10-oxo-heptadec-2-enyl}-2-hydroxy-succinate

[Chem. 63]

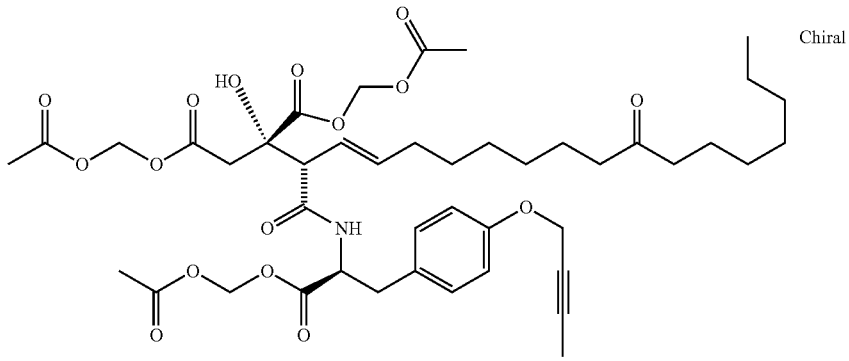

Compound 45 was obtained by a synthetic method similar to that of Compound 46 except that bromomethyl acetate was used instead of an iodomethyl ester isopropyl ester.

$^1$H-NMR (CD$_3$OD) δ: 0.88-0.93 (3H, m), 1.27-1.36 (15H, m), 1.49-1.59 (4H, m), 1.82 (3H, dd, J=10.7, 8.8 Hz), 1.97-

2.01 (2H, m), 2.07-2.12 (9H, m), 2.44 (4H, td, J=7.3, 1.8 Hz), 2.65 (1H, d, J=16.1 Hz), 2.90 (1H, d, J=13.7 Hz), 2.97 (1H, d, J=16.1 Hz), 3.12 (1H, d, J=9.3 Hz), 3.21 (1H, d, J=9.3 Hz), 4.62-4.66 (3H, m), 5.47-5.54 (2H, m), 5.66-5.80 (6H, m), 6.85 (2H, d, J=8.8 Hz), 7.10 (2H, d, J=8.8 Hz).

ESI (LC/MS positive mode) m/z 861 (M+H); Rt 2.91 min.

Compound 68: No. 5452085

Diacetoxymethyl (S)-2-{(E)-(S)-1-[(S)-1-acetoxymethoxycarbonyl-2-(4-but-2-ynyloxy-phenyl)-ethylcarbamoyl]-10-oxo-heptadec-2-enyl}-2-hydroxy-succinate

[Chem. 64]

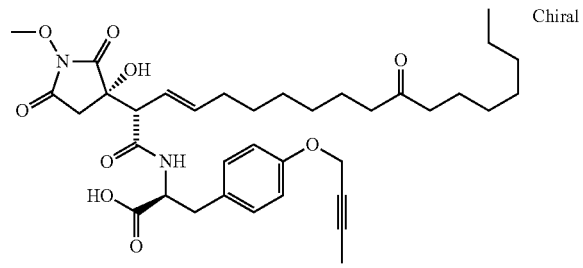

Compound 68 was obtained by a synthetic method similar to that of Compound 53: No. 5135025 except that O-methylhydroxylamine hydrochloride was used instead of phenol.

$^1$H-NMR (CD$_3$OD) δ: 0.90 (3H, t, J=6.6 Hz), 1.27-1.33 (14H, m), 1.55 (4H, td, J=14.2, 7.4 Hz), 1.82 (3H, s), 1.99-2.03 (2H, m), 2.30 (1H, d, J=17.6 Hz), 2.45 (4H, t, J=7.3 Hz), 2.83-2.91 (3H, m), 3.14 (1H, dd, J=13.9, 4.6 Hz), 3.62 (1H, d, J=7.9 Hz), 3.84 (3H, s), 4.57 (1H, dd, J=9.0, 4.6 Hz), 4.63 (2H, d, J=1.8 Hz), 5.30 (1H, dd, J=15.4, 7.9 Hz), 5.48 (1H, dt, J=15.6, 6.7 Hz), 6.86 (2H, d, J=7.9 Hz), 7.10 (2H, d, J=8.4 Hz).

ESI (LC/MS positive mode) m/z 656 (M+H); Rt 2.47 min.

Compound 100: No. 5456198

4-(1-Acetoxy-ethyl) (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate

[Chem. 65]

1-tert-Butyl (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate (18 mg, 0.0233 mmol) was dissolved in dichloromethane (1.8 mL), and bromoethyl acetate (8.2 μL, 0.0700 mmol), N,N-diisopropylethylamine (12.2 μL, 0.0700 mmol), and sodium iodide (10.5 mg, 0.0700 mol) were added. The mixture was stirred at 40° C. for 19 hours and cooled to room temperature, and a saturated aqueous solution of ammonium chloride (15 mL) was then added. After ethyl acetate extraction, the organic layer was dried over anhydrous sodium sulfate. The solvent was then distilled off to obtain 19 mg of crude 1-tert-butyl 4-(1-acetoxy-ethyl) (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate. The obtained crude product was used in the next reaction without further purification (ESI (LC/MS positive mode) m/z 858 (M+H); Rt 2.82 min.).

To 1-tert-butyl 4-(1-acetoxy-ethyl) (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate (18 mg, 0.021 mol) was added formic acid (1.8 mL) at room temperature, and the mixture was stirred for 1 hour without further processing. After confirming the completion of the reaction by LCMS, 10 mL of dichloromethane was added and the organic solvent and formic acid were distilled off under reduced pressure. The residue was separated by preparative-HPLC and the fraction was extracted with ethyl acetate. The organic layer was washed with a saturated brine and then dried over anhydrous sodium sulfate. The filtrate was concentrated under reduced pressure to obtain 10.5 mg (62% yield) of Compound 100 as a diastereomeric mixture, $^1$H-NMR (CD$_3$OD) δ: 0.89 (3H, t, J=6.8 Hz), 1.23-1.33 (14H, m), 1.43 (3H, t, J=6.0 Hz), 1.52-1.55 (4H, m), 1.82 (3H, t, J=2.2 Hz), 1.96 (2H, q, J=6.5 Hz), 2.03 (3H, d, J=0.9 Hz), 2.44 (4H, t, J=7.3 Hz), 2.61 (1H, t, J=16.3 Hz), 2.88-2.98 (2H, m), 3.18-3.23 (2H, m), 3.76 (3H, s), 4.61 (2H, td, J=3.1, 2.2 Hz), 4.67-4.79 (3H, m), 5.47-5.54 (2H, m), 6.78 (1H, q, J=5.4 Hz), 6.86 (2H, d, J=7.5 Hz), 7.15 (2H, dd, J=8.6, 2.0 Hz), diastereomeric mixture ESI (LC/MS positive mode) m/z 803 (M+H); Rt 1.83 min.

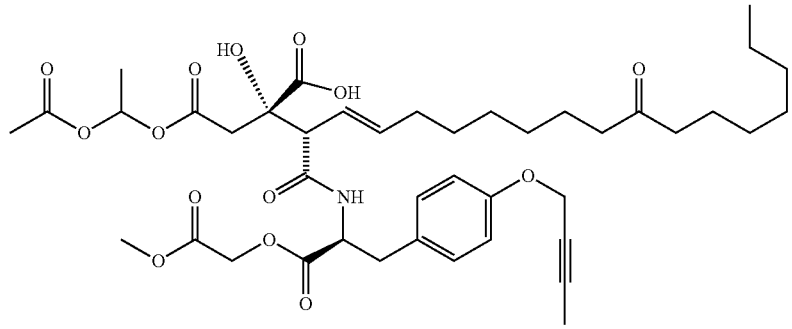

113

Compound 72: No. 5321601

(S)-2-{(E)-(S)-1-[(S)-2-(4-But-2-ynyloxy-phenyl)-1-methoxycarbonyl-ethylcarbamoyl]-10-hydroxy-heptadec-2-enyl}-2-hydroxy-succinic acid

[Chem. 66]

114

Compound 89: No. 4957200

(S)-2-{(E)-(S)-1-[(S)-2-(4-But-2-ynyloxy-phenyl)-1-carboxy-ethylcarbamoyl]-10-hydroxy-heptadec-2-enyl}-2-hydroxy-succinic acid

[Chem. 67]

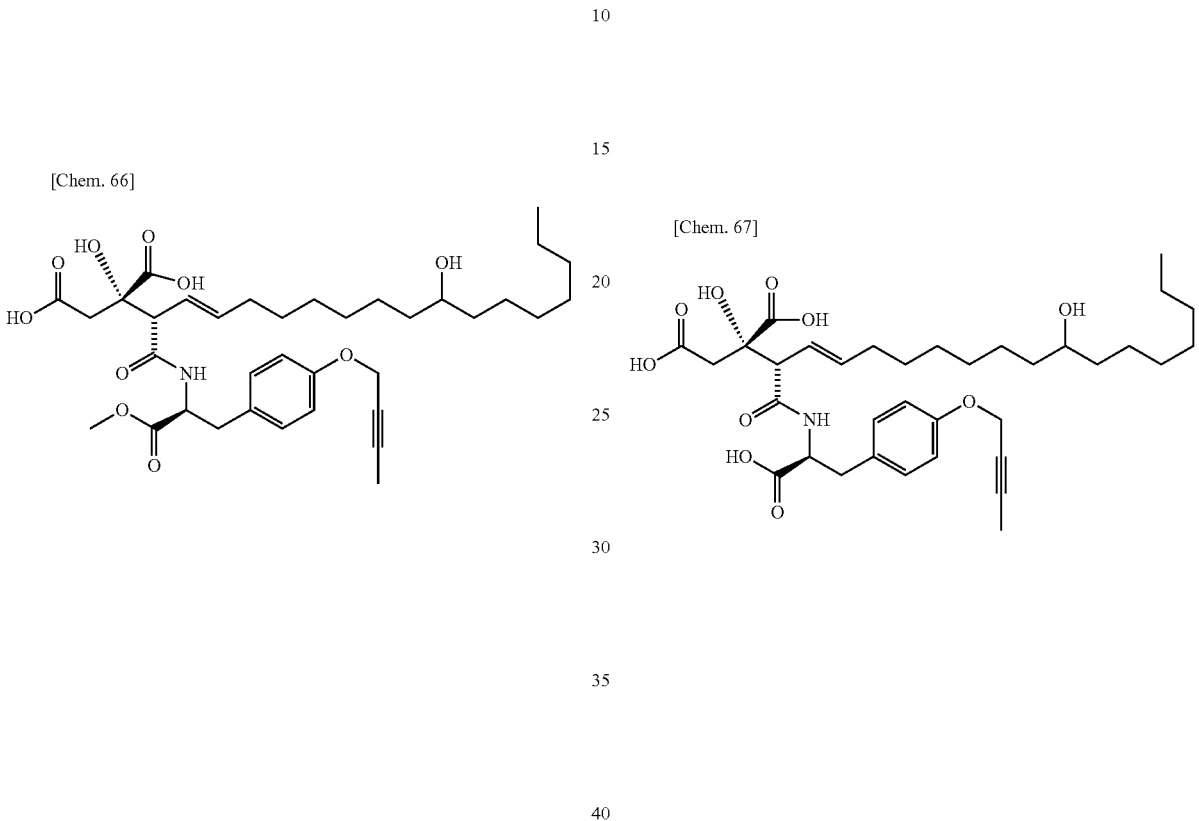

No. 5153510 (Compound 87) (20 mg, 0.0304 mmol) was dissolved in methanol, and NaBH$_4$ (8.4 mg, 0.222 mmol) was added at room temperature. After confirming the consumption of the starting materials by LCMS, a saturated aqueous solution of ammonium chloride was added, and the mixture was extracted with ethyl acetate. The organic layer was then washed with a saturated brine and dried over anhydrous sodium sulfate. The filtrate was concentrated under reduced pressure. The residue was purified by preparative HPLC. To the resulting fraction was added a saturated brine, and the mixture was extracted with ethyl acetate. The organic layer was washed with a saturated brine and then dried over anhydrous sodium sulfate. The filtrate was concentrated under reduced pressure to obtain Compound 72 as a diastereomeric mixture (8.1 mg, 40% yield).

$^1$H-NMR (CD$_3$OD, diastereomeric mixture) δ: 0.91 (3H, dd, J=13.3, 6.5 Hz), 1.27-1.40 1.82 (22H, m), (3H, t, J=2.3 Hz), 1.96-2.01 2.58 (2H, m), (1H, d, J=16.2 Hz), 2.88-2.95 3.10-3.15 3.21 (2H, m), (1H, m), (1H, d, J=8.6 Hz), 3.47-3.52 3.72 4.60-4.68 5.54 (1H, m), (3H, s), (3H, m), (2H, ft, J=19.6, 6.5 Hz), 6.84-6.87 7.09-7.12 8.29 (2H, m), (2H, m), (1H, d, J=7.8 Hz).

ESI (LC/MS positive mode) m/z 661 (M+H); Rt 2.50 min.

No. 4630808 (Compound 93; 210 mg, 0.326 mmol) was dissolved in ethanol and NaBH$_4$ (49.4 mg, 1.30 mmol) was added on an ice bath. After confirming the consumption of the starting materials by LCMS, 0.2 M hydrochloric acid was added, the mixture was extracted with ethyl acetate, and the organic layer was then washed with a saturated brine and dried over anhydrous sodium sulfate. The filtrate was then concentrated under reduced pressure. The resulting residue was purified with a dial column to obtain Compound 89 as a diastereomeric mixture (86 mg, 41% yield).

$^1$H-NMR (CD$_3$OD) δ: 0.90 (3H, t, J=6.8 Hz), 1.25-1.46 (22H, m), 1.82 (3H, t, J=2.4 Hz), 1.97-1.98 (2H, m), 2.57 (1H, d, J=15.9 Hz), 2.88 (1H, d, J=15.9 Hz), 2.94 (1H, t, J=7.1 Hz), 3.17 (2H, dt, J=13.7, 5.6 Hz), 3.50 (1H, dd, J=14.6, 7.5 Hz), 4.60 (2H, q, J=2.4 Hz), 4.62-4.67 (1H, m), 5.54 (2H, ddd, J=30.4, 15.2, 7.3 Hz), 6.85 (2H, dt, J=9.3, 2.5 Hz), 7.13 (2H, dt, J=9.3, 2.4 Hz).

ESI (LC/MS positive mode) m/z 646 (M+H); Rt 2.87 min.

Compound 90: No. 5083661

4-{2-[2-(2-Ethoxy-ethoxy)-ethoxy]-ethyl}(S)-2-[(E)-(S)-1-((S)-2-(4-but-2-ynyloxy-phenyl)-1-{2-[2-(2-ethoxy-ethoxy)-ethoxy]-ethoxycarbonyl}-ethylcarbamoyl)-10-oxo-heptadec-2-enyl]-2-hydroxy-succinate

[Chem. 68]

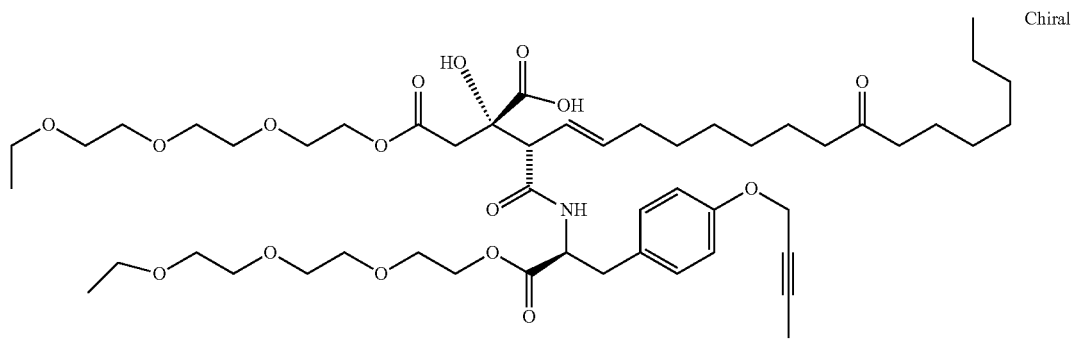

Compound 90 was obtained by the synthesis in a method similar to that of No. 5045280: Compound 36 except that triethylene glycol monoethyl ether was used instead of methanol.

ESI (LC/MS positive mode) m/z 965 (M+H); Rt 3.08 min.

Compound 91: No. 5083662

4-[2-(2-Methoxy-ethoxy)-ethyl](S)-2-((E)-(S)-1-{(S)-2-(4-but-2-ynyloxy-phenyl)-1-[2-(2-methoxy-ethoxy)-ethoxycarbonyl]-ethylcarbamoyl}-10-oxo-heptadec-2-enyl)-2-hydroxy-succinate

[Chem. 69]

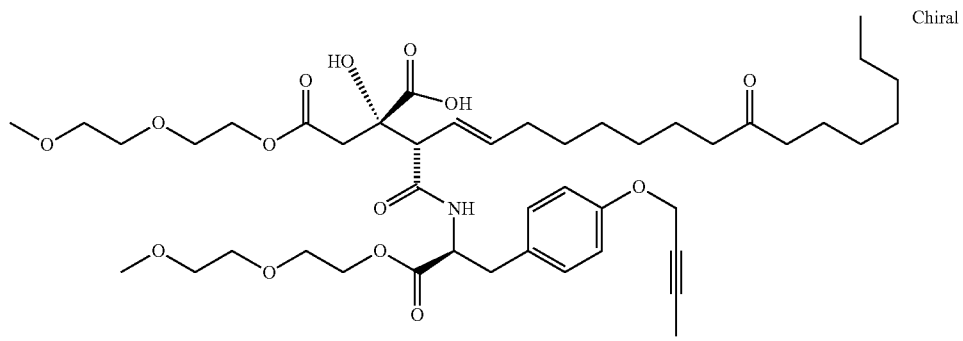

Compound 91 was obtained by the synthesis similar to that of No. 5045280: Compound 36 except that a commercially available reagent of diethyleneglycol monomethyl ether was used instead of methanol.

ESI (LC/MS positive mode) m/z 849 (M+H); Rt 2.88 min.

Compound 92: No. 5062718

4-Ethyl (S)-2-{(E)-(S)-1-[(S)-2-(4-but-2-ynyloxy-phenyl)-1-ethoxycarbonyl-ethylcarbamoyl]-10-oxo-heptadec-2-enyl}-2-hydroxy-succinate

[Chem. 70]

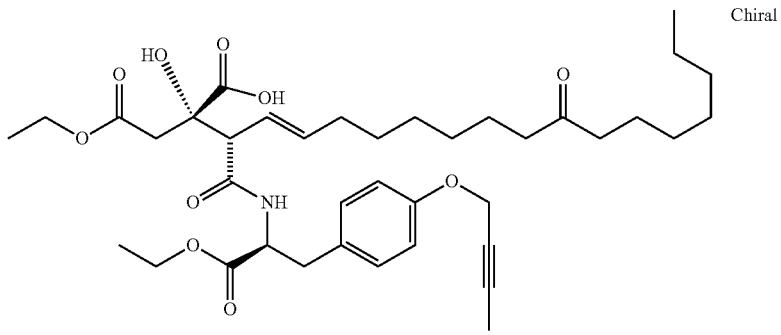

Compound 92 was obtained by a method similar to that of No. 5045280, Compound 36 except that ethanol was used instead of methanol.

$^1$H-NMR (CDCl$_3$) δ: 0.88 (3H, t, J=7.1 Hz), 1.08-1.43 (20H, m), 1.54-1.60 (4H, m), 1.86 (3H, t, J=2.2 Hz), 1.96-2.06 (2H, m), 2.39-2.49 (4H, m), 2.65 (1H, d, J=15.6 Hz), 2.94 (1H, d, J=16.1 Hz), 3.07 (2H, ddd, J=24.6, 13.9, 5.9 Hz), 3.22 (1H, d, J=9.8 Hz), 4.12-4.22 (4H, m), 4.61 (2H, td, J=5.5, 3.6 Hz), 4.79 (1H, q, J=6.7 Hz), 5.51 (1H, dd, J=15.1, 9.3 Hz), 5.63-5.67 (2H, m), 6.65 (1H, d, J=7.8 Hz), 6.85 (2H, d, J=8.3 Hz), 7.02 (2H, d, J=8.3 Hz).

ESI (LC/MS positive mode) m/z 700 (M+H); Rt 6.20 min.

Compound 5: No. 5444292

4-(1-Acetoxy-ethyl) (S)-2-{(E)-(S)-1-[(S)-1-(1-acetoxy-ethoxycarbonyl)-2-(4-but-2-ynyloxy-phenyl)-ethylcarbamoyl]-10-oxo-heptadec-2-enyl}-2-hydroxy-succinate

[Chem. 71]

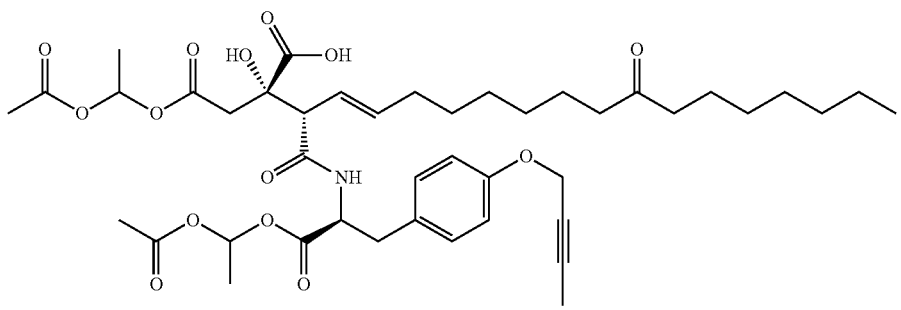

Under a nitrogen atmosphere, No. 5447725 (Compound G; 2.50 g, 3.572 mmol) was dissolved in dichloromethane (100 mL), and then acetoxyethyl bromide (2.38 g, 14.25 mmol) and N,N-diisopropylethylamine (2.49 mL, 14.29 mmol) were added at room temperature. The mixture was stirred under reflux for 19 hours. After completing the reaction, the mixture was extracted with dichloromethane. The organic layer was washed with water and a saturated brine and dried over anhydrous sodium sulfate. After filtration and distilling off the solvent, the residue was purified by silica gel column chromatography (n-hexane:ethyl acetate=2:1, Rf=0.45)) to obtain 2.33 g (75%) of the triester form.

Under a nitrogen atmosphere, formic acid (2.04 mL) was then added to this triester form (203.6 mg, 0.233 mmol), and the mixture was stirred at room temperature for 3 hours. After completing the reaction, dichloromethane (16 mL) was added. The solvent was distilled off in a rotary evaporator. The residue was then purified by dial silica gel column chromatography (n-hexane:ethyl acetate=2:1, Rf=0.2) to obtain 157.2 mg (83% yield) of Compound 5 as a diastereomeric mixture.

$^1$H-NMR (CDCl$_3$, mixture of four diastereomers) δ: 0.88 (3H, t, J=6.9 Hz), 1.12-1.38 (14H, m), 1.38-1.65 (10H, m), 1.86 (3H, t, J=2.2 Hz), 2.01-2.13 (8H, m), 2.41 (3H, t, J=7.1 Hz), 2.41-2.54 (1H, m), 2.66-2.75 (1H, m), 2.92-3.12 (3H, m), 3.18-3.24 (1H, m), 4.59-4.64 (2H, m), 4.77-4.83 (1H, m), 5.22-5.44 (1H, br.d), 5.44-5.53 (1H, m), 5.56-5.69 (1H, m), 6.56-6.69 (1H, m), 6.79-6.90 (4H, m), 6.99-7.10 (2H, m).

ESI (LC/MS positive mode) m/z 816 (M+H); Rt 3.36 min.

Compound 73: No. 5428381

4-Diethylcarbamoylmethyl (S)-2-{(E)-(S)-1-[(S)-2-(4-but-2-ynyloxy-phenyl)-1-diethylcarbamoyl-methoxycarbonyl-ethylcarbamoyl]-10-oxo-heptadec-2-enyl}-2-hydroxy-succinate

[Chem. 72]

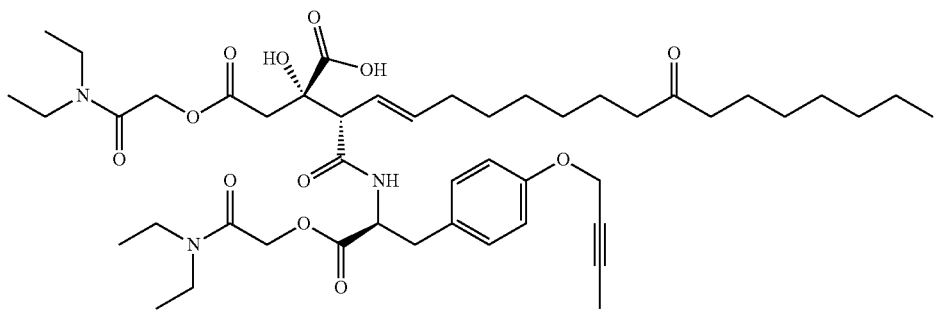

Under a nitrogen atmosphere, N,N-diethyl-2-hydroxy-acetamide (42 mg, 0.320 mmol) was dissolved in dichloromethane (1.5 mL) and the mixture was cooled to 0° C. Triphenylphosphine (125.9 mg, 0.480 mmol) and N-bromosuccinimide (85.4 mg, 0.480 mmol) were added in order and the mixture was stirred at room temperature for 3.5 hours. The mixture was warmed to room temperature and 2-bromo-N,N-diethylacetamide was prepared in situ. To the mixture, solution of No. 5447725 (Compound G; 56 mg, 0.080 mmol) in dichloromethane (1.0 mL) was added dropwise under a nitrogen atmosphere. N,N-Diisopropylethylamine (69.7 µL, 0.40 mmol) was then added at room temperature, and the mixture was stirred under feflux for 14 hours. After completing the reaction, the mixture was extracted with dichloromethane. The organic layer was washed with water and a saturated brine and dried over anhydrous sodium sulfate. After the organic layer was filtered and the solvent was distilled off, the residue was then purified by HPLC (water with 0.05% TFA-acetonitrile with 0.05% TFA) to obtain 31.2 mg (42% yield) of the triester form.

Under a nitrogen atmosphere, formic acid (0.4 mL) was then added to this triester form (31.2 mg, 0.034 mmol), and the mixture was stirred at room temperature for 14 hours. After completing the reaction, dichloromethane (12 mL) was added and the solvent was distilled off in a rotary evaporator. The residue was then purified by HPLC (water with 0.05% TFA-acetonitrile with 0.05% TFA) to obtain 16.0 mg (55% yield) of the target compound.

$^1$H-NMR (CDCl$_3$) δ: 0.88 (3H, t, J=6.7 Hz), 1.13 (3H, t, J=7.3 Hz), 1.14 (3H, t, J=7.3 Hz), 1.17-1.37 (20H, m), 1.47-1.68 (4H, m), 1.86 (3H, t, J=1.8 Hz), 1.90-2.08 (2H, m), 2.39 (4H, t, J=7.3 Hz), 2.73 (1H, d, J=15.2 Hz), 3.02-3.08 (1H, m), 3.10 (1H, d, J=15.2 Hz), 3.21-3.29 (5H, m), 3.34-3.45 (4H, m), 3.51 (1H, d, J=8.5 Hz), 4.53-4.74 (4H, m), 4.76-4.96 (3H, m), 5.43-5.66 (2H, m), 5.72-6.38 (1H, br.d), 6.84 (2H, d, J=8.5 Hz), 7.17 (2H, d, J=8.5 Hz), 7.73 (1H, d, J=7.9 Hz).

ESI (LC/MS positive mode) m/z 871 (M+H); Rt 3.20

Synthesis of 1-bromo-ethyl isobutyrate

[Chem. 73]

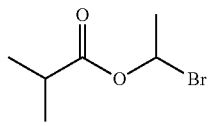

Zinc(II) chloride (136 mg, 0.998 mmol) was cooled to −20° C. and isobutyryl bromide (1.51 g, 10.00 mmol) and acetaldehyde (613 µL, 11.00 mmol) were added sequentially. The mixture was stirred at −20° C. for 2.5 hours. After completing the reaction, dichloromethane and water were added. The mixture was extracted, dried over anhydrous sodium sulfate, and filtered. The solvent was distilled off to obtain 1.89 g of the target compound as a crude product.

$^1$H-NMR (CDCl$_3$) δ: 1.20 (3H, d, J=2.3 Hz), 1.21 (3H, d, J=2.3 Hz), 2.00 (3H, d, J=5.9 Hz), 2.52-2.64 (1H, m), 6.69-6.75 (1H, m).

No. 5444294 (Compound 74)

4-(1-Isobutyryloxy-ethyl) (S)-2-{(E)-(S)-1-[(S)-2-(4-but-2-ynyloxy-phenyl)-1-(1-isobutyryloxy-ethoxy-carbonyl)-ethylcarbamoyl]-10-oxo-heptadec-2-enyl}-2-hydroxy-succinate

[Chem. 74]

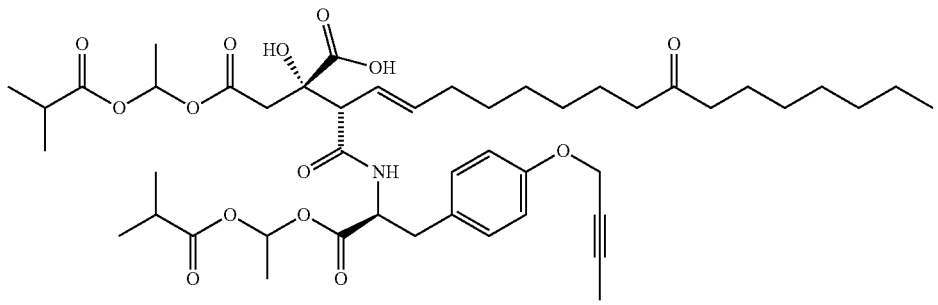

Under a nitrogen atmosphere, No. 5447725 (Compound G; 67 mg, 0.096 mmol) was dissolved in DMF (1.5 mL) and 1-bromo-ethyl isobutyrate (133 µL) and N,N-diisopropyl-ethylamine (83 µL) were then added at room temperature. The mixture was stirred at 60° C. for 19 hours. After completing the reaction, the mixture was extracted with ethyl acetate. The organic layer was washed with water and a saturated brine, dried over anhydrous sodium sulfate, and filtered. The solvent was distilled off. The residue was then purified by silica gel column chromatography (n-hexane:ethyl acetate=2:1, Rf=0.25) to obtain 67 mg (75% yield) of the triester form.

Under a nitrogen atmosphere, formic acid (1.0 mL) was then added to this triester form (67 mg, 0.072 mmol), and the mixture was stirred at room temperature for 14 hours. After completing the reaction, dichloromethane (16 mL) was added and the solvent was distilled off in a rotary evaporator. The residue was then purified by HPLC (water with 0.05% TFA-acetonitrile with 0.05% TFA) to obtain 38.1 mg (42% yield) of Compounds 74 as a diastereomeric mixture.

$^1$H-NMR (CDCl$_3$, mixture of four diastereomers) δ: 0.84 (3H, t, J=6.7 Hz), 1.11-1.19 (12H, m), 1.19-1.35 (14H, m), 1.37-1.63 (10H, m), 1.85 (3H, s), 1.91-2.06 (2H, m), 2.30-2.45 (4H, t, J=7.3 Hz), 2.47-2.58 (2H, m), 2.64-2.75 (1H, m), 2.89-3.12 (3H, m), 3.19-3.33 (1H, m), 4.55-4.65 (2.5H, m), 4.71-4.79 (0.5H, m), 5.45-5.66 (2H, m), 6.05-6.71 (2H, br.d), 6.72-6.79 (0.5H, br.d), 6.79-6.90 (4H, m), 6.99-7.08 (2H, m), 7.08-7.16 (0.5H, br.d).

ESI (LC/MS positive mode) m/z 873 (M+H); Rt 2.35 min.

Compound 84: No. 5426239

4-(5-Methyl-2-oxo-[1,3]dioxol-4-ylmethyl) (S)-2-ynyloxy-phenyl)-1-(5-methyl-2-oxo-[1,3]dioxol-4-ylmethoxycarbonyl)-ethylcarbamoyl]-10-oxo-heptadec-2-enyl}-2-hydroxy-succinate

[Chem. 75]

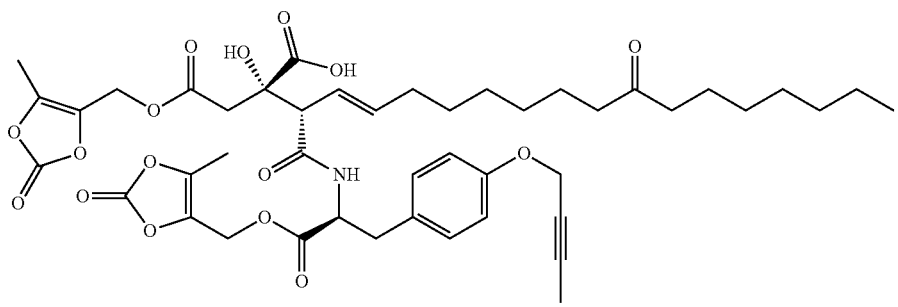

Compound 84 was obtained by a synthetic method similar to that of No. 5444294 (Compound 74) except that 4-chloromethyl-5-methyl-[1,3]dioxol-2-one was used instead of 1-bromo-ethyl isobutyrate, and 2 equivalents of sodium iodide was added as an additive.

¹H-NMR (CDCl₃) δ: 0.88 (3H, t, J=6.9 Hz), 1.11-1.41 (14H, m), 1.46-1.66 (4H, m), 1.87 (3H, t, J=2.3 Hz), 1.93-2.08 (2H, m), 2.14 (3H, s), 2.15 (3H, s), 2.36-2.54 (4H, m), 2.72 (1H, d, J=16.2 Hz), 2.87-3.13 (3H, m), 3.26 (1H, d, J=9.1 Hz), 4.56-4.66 (2H, m), 4.72-4.96 (5H, m), 5.45-5.71 (2H, m), 6.75 (1H, d, J=7.7 Hz), 6.85 (2H, d, J=8.6 Hz), 7.00 (2H, d, J=8.6 Hz).

ESI (LC/MS positive mode) m/z 868 (M+H); Rt 3.22 min.

Compound 83: No. 5426238

4-Dimethylcarbamoylmethyl (S)-2-{(E)-(S)-1-[(S)-2-(4-but-2-ynyloxy-phenyl)-1-dimethylcarbamoyl-methoxy-carbonyl-ethylcarbamoyl]-10-oxo-heptadec-2-enyl}-2-hydroxy-succinate

[Chem. 76]

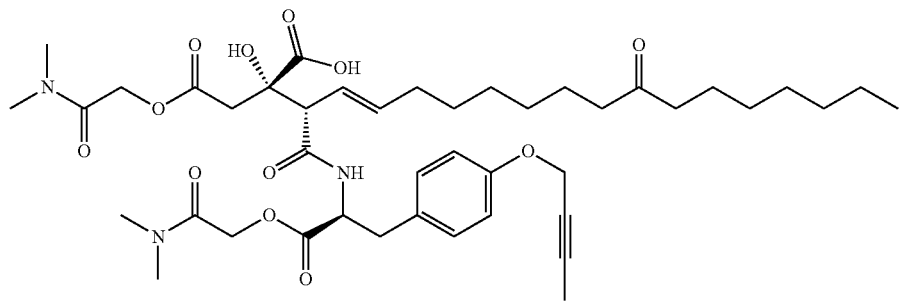

The title compound was obtained by a synthetic method similar to that of No. 5444294 (Compound 74) except that 2-chloro-N,N-dimethyl-acetamide was used instead of 1-bromo-ethyl isobutyrate.

ESI (LC/MS positive mode) m/z 815 (M+H); Rt 2.85 min.

Compound 6: No. 5444293

4-(1-Isobutyryloxy-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate Synthetic method of Compound 6: No. 5444293

Under a nitrogen atmosphere, No. 5317776 (Compound E; 53.3 mg, 0.075 mmol) was dissolved in DMF (1.5 mL) and 1-bromo-ethyl isobutyrate (113 μL) and N,N-diisopropyl-ethylamine (65 μL) were then added at room temperature. The mixture was stirred at 60° C. for 24 hours. After completing the reaction, the mixture was extracted with ethyl acetate. The organic layer was washed with water and a saturated brine, dried over anhydrous sodium sulfate, and filtered. The solvent was distilled off. The residue was then purified by silica gel column chromatography (n-hexane:acetone=4:1, Rf=0.3) to obtain 53.9 mg (87%) of the triester form.

Under a nitrogen atmosphere, formic acid (1.0 mL) was then added to this triester form (53.9 mg, 0.065 mmol), and the mixture was stirred at room temperature for 14 hours. After completing the reaction, dichloromethane (16 mL) was added, and the solvent was distilled off in a rotary evaporator. The residue was then purified by HPLC (water with 0.05% TFA-acetonitrile with 0.05% TFA) to obtain 32.9 mg (65%) of Compound 6 as a diastereomeric mixture.

¹H-NMR (CDCl₃, diastereomeric mixture) δ: 0.87 (3H, t, J=6.7 Hz), 1.12 (6H, d, J=6.7 Hz), 1.19-1.36 (14H, m), 1.39-1.46 (3H, m), 1.49-1.62 (4H, m), 1.85 (3H, s), 1.95-2.05 (2H, m), 2.35-2.44 (4H, m), 2.45-2.58 (1H, m), 2.7 (1H, d, J=16.5 Hz), 2.90-3.10 (3H, m), 3.24-3.34 (1H, m), 3.71 (3H, s), 4.57-4.62 (2H, m), 4.71-4.76 (1H, m), 5.50-5.67 (2H, m), 6.75-6.90 (4H, m), 6.98 (2H, d, J=7.3 Hz), 7.22-7.72 (2H, br.d).

ESI (LC/MS positive mode) m/z 772 (M+H); Rt 2.23 min.

[Chem. 77]

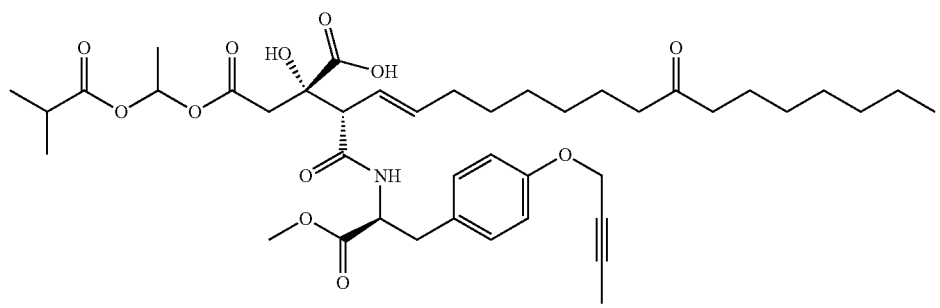

3-[(1-Chloro-ethoxycarbonyl)-methyl-amino]-propyl acetate

[Chem. 78]

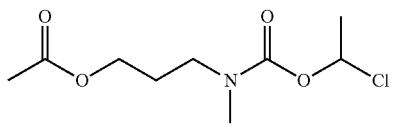

Under a nitrogen atmosphere, 3-methylamino-propan-1-ol (343.4 mg, 3.85 mmol) was dissolved in dichloromethane (5.0 mL), and triethylamine (588.2 μL, 4.24 mmol) was added. The mixture was cooled to 0° C. While maintaining the reaction temperature at 0° C., 1-chloroethyl chloroformate (415.7 μL, 3.85 mmol) was then added and the mixture was stirred for 1 hour. While maintaining the reaction temperature at 0° C., acetic anhydride (400 μL, 4.24 mmol) and pyridine (314.4 μL, 3.85 mmol) were then added, and the mixture was stirred at room temperature for 15 hours. After completing the reaction, the mixture was extracted with dichloromethane. The organic layer was washed with 1.0 M hydrochloric acid, water, and a saturated brine, dried over anhydrous sodium sulfate, and filtered. The solvent was distilled off. The residue was then purified by silica gel column chromatography (n-hexane:ethyl acetate=2:1, Rf=0.6) to obtain 479.5 mg (52% yield) of 3-[(1-chloro-ethoxycarbonyl)-methyl-amino]-propyl acetate.

$^1$H-NMR (CDCl$_3$, observed as rotermer mixture) δ: 1.80 (1.5H, d, J=7.1 Hz), 1.82 (1.5H, d, J=2.6 Hz), 1.84-1.96 (2H, m), 2.06 (1.5H, s), 2.07 (1.5H, s), 2.94 (1.5H, s), 2.96 (1.5H, s), 3.32-3.49 (2H, m), 4.08-4.11 (2H, m), 6.54-6.63 (1H, m).

ESI (LC/MS positive mode) m/z 238 (M+H); Rt 1.70 min.

1-Chloro-ethyl pyrrolidine-1-carboxylate

[Chem. 79]

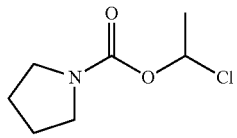

Under a nitrogen atmosphere, pyrrolidine (363.9 μL, 4.4 mmol) and triethylamine (555.2 μL, 4.00 mmol) were dissolved in dichloromethane (5.0 mL), and the mixture was cooled to 0° C. While maintaining the reaction temperature at 0° C., 1-chloroethyl chloroformate (431.6 μL, 4.00 mmol) was added, and the mixture was stirred at 0° C. for 10 minutes and at room temperature for 20 minutes. After completing the reaction, the mixture was extracted with dichloromethane. The organic layer was washed with 1 M hydrochloric acid, a saturated aqueous solution of sodium bicarbonate, and a saturated brine, dried over anhydrous sodium sulfate, and filtered. The solvent was distilled off. The residue was then purified by silica gel column chromatography (dichloromethane, Rf=0.35) to obtain 424.2 mg (60% yield) of 1-chloro-ethyl pyrrolidine-1-carboxylate.

$^1$H-NMR (CDCl$_3$) δ: 1.81 (3H, d, J=5.8 Hz), 1.84-1.95 (4H, m), 3.31-3.51 (4H, m), 6.61 (1H, q, J=5.8 Hz).

ESI (LC/MS positive mode) m/z 178 (M+H); Rt 1.77 min.

1-Chloro-ethyl dimethyl-carbamate

[Chem. 80]

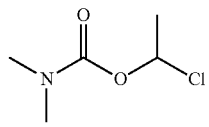

The title compound 1-chloro-ethyl dimethyl-carbamate was obtained by the synthetic method of 1-chloro-ethyl pyrrolidine-1-carboxylate except that N,N-dimethylamine hydrochloride was used instead of pyrrolidine.

$^1$H-NMR (CDCl$_3$) δ: 1.82 (3H, d, J=5.8 Hz), 2.95 (3H, s), 2.96 (3H, s), 6.58 (1H, q, J=5.8 Hz).

ESI (LC/MS positive mode) m/z 152 (M+H); Rt 1.43 min.

Ethyl [(1-chloro-ethoxycarbonyl)-methyl-amino]-acetate

[Chem. 81]

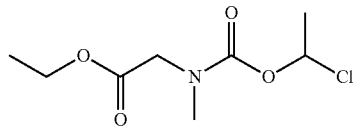

The title compound was obtained by the synthetic method of 1-chloro-ethyl pyrrolidine-1-carboxylate except that ethyl sarcosine hydrochloride was used instead of pyrrolidine.

ESI (LC/MS positive mode) m/z 224 (M+H); Rt 1.77 min.

No. 5454360 (Compound 77)

4-{1-[(3-Acetoxy-propyl)-methyl-carbamoyloxy]-ethyl}(S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 82]

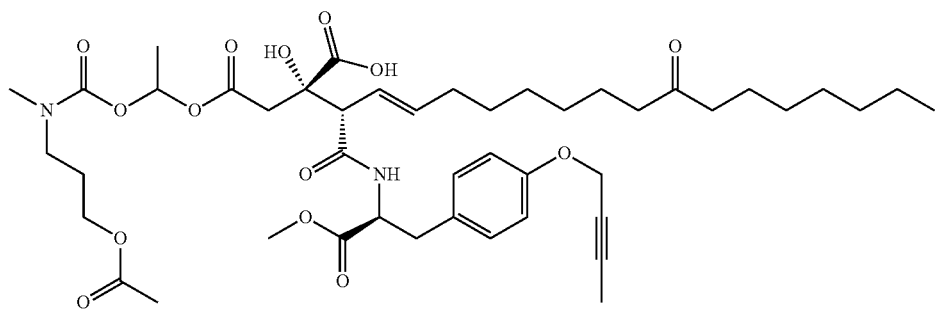

Under a nitrogen atmosphere, No. 5317776: Compound E (71.6 mg, 0.100 mmol) was dissolved in DMF (2.5 mL), and 3-[(1-chloro-ethoxycarbonyl)-methyl-amino]-propyl acetate (143 mg, 0.602 mmol), sodium iodide (90.2 mg, 0.602 mmol), and N,N-diisopropylethylamine (139.8 μL, 0.803 mmol) were then added at room temperature. The mixture was stirred at 80° C. for 20 hours. After completing the reaction, the mixture was extracted with ethyl acetate. The organic layer was washed with water and a saturated brine, dried over anhydrous sodium sulfate, and filtered. The solvent was distilled off. The residue was then purified by silica gel column chromatography (n-hexane:acetone=3:1, Rf=0.15) to obtain 32.9 mg (36% yield) of the triester form.

Under a nitrogen atmosphere, formic acid (0.75 mL) was then added to this triester form (32.9 mg, 0.036 mmol), and the mixture was stirred at room temperature for 16 hours. After completing the reaction, dichloromethane (16 mL) was added, and the solvent was distilled off in a rotary evaporator. The residue was then purified by HPLC (water with 0.05% TFA-acetonitrile with 0.05% TFA) to obtain 16.7 mg (57%) of Compound 77 as a diastereomeric mixture.

$^1$H-NMR (CDCl$_3$, 1:1 diastereomeric mixture) δ: 0.87 (1.5H, t, J=7.1 Hz), 0.88 (1.5H, t, J=7.1 Hz), 1.15-1.39 (14H, m), 1.41-1.51 (3H, m), 1.51-1.62 (4H, m), 1.80-1.92 (5H, m), 1.95-2.10 (5H, m), 2.34-2.43 (3H, m), 2.63-2.72 (1H, m), 2.86-3.10 (6H, m), 3.21-3.32 (2H, m), 3.35-3.49 (1H, m), 3.72 (3H, s), 4.01-4.20 (2H, m), 4.57-4.63 (2H, m), 4.76-4.81 (1H, m), 5.51 (1H, dd, J=15.4, 9.3 Hz), 5.61-5.68 (1H, m), 5.72-6.54 (2H, br.d), 6.70-6.81 (1H, m), 6.81-6.89 (3H, m), 6.99-7.03 (2H, m).

ESI (LC/MS positive mode) m/z 859 (M+H); Rt 3.32 min.

Compound 78: No. 5454361

4-[1-(Pyrrolidine-1-carbonyloxy)-ethyl](S)-2-{(E)-(S)-1-[(S)-2-(4-but-2-ynyloxy-phenyl)-1-methoxy-carbonyl-ethylcarbamoyl]-10-oxo-heptadec-2-enyl}-2-hydroxy-succinate

[Chem. 83]

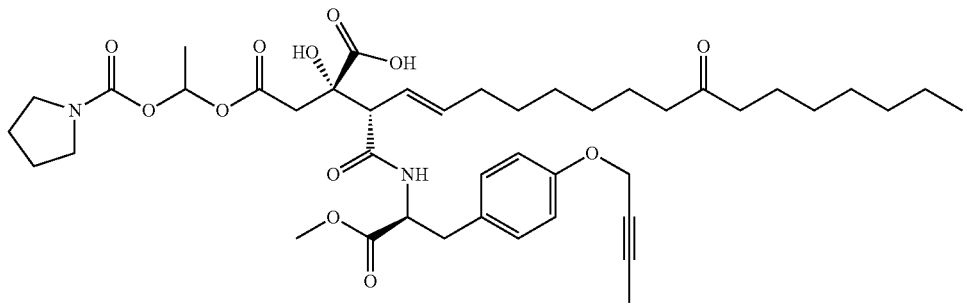

Compound 78 was obtained as a diastereomeric mixture by the synthetic method of No. 5454360 (Compound 77) except that 1-chloro-ethyl pyrrolidine-1-carboxylate was used instead of 3-[(1-chloro-ethoxycarbonyl)-methyl-amino]-propyl acetate.

$^1$H-NMR (CDCl$_3$ diastereomeric mixture) δ: 0.85-0.92 (3H, m), 1.16-1.38 (14H, m), 1.45-1.50 (3H, m), 1.51-1.61 (4H, m), 1.78-1.93 (7H, m), 1.94-2.08 (2H, m), 2.37-2.41 (4H, m), 2.64-2.73 (1H, m), 2.94-3.11 (3H, m), 3.25-3.36 (5H, m), 3.72 (3H, s), 4.56-4.64 (2H, m), 4.72-4.82 (1H, m), 4.92-5.35 (2H, brd), 5.46-5.69 (2H, m), 6.75-6.91 (3H, m), 6.96-7.05 (2H, m).

ESI (LC/MS positive mode) m/z 799 (M+H); Rt 3.37 min.

Compound 79: No. 5454362

4-(1-Dimethylcarbamoyloxy-ethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 84]

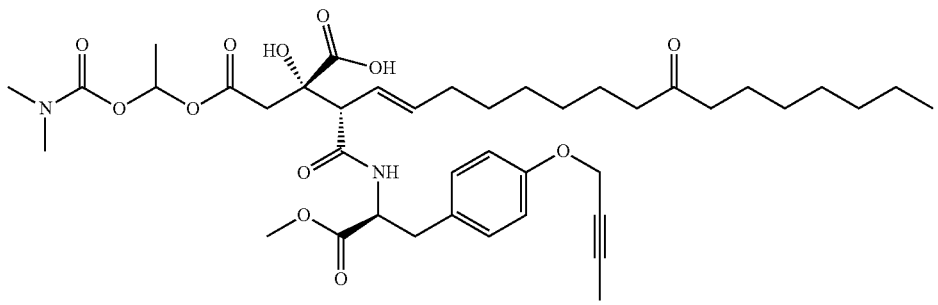

The title compound was obtained by the synthetic method of No. 5454360 (Compound 77) except that 1-chloro-ethyl dimethyl-carbamate was used instead of 3-[(1-chloro-ethoxycarbonyl)-methyl-amino]-propyl acetate.

$^1$H-NMR (CDCl$_3$, diastereomeric mixture) δ: 0.88 (3H, t, J=6.9 Hz), 1.15-1.40 (14H, m), 1.45-1.65 (7H, m), 1.86 (3H, t, J=2.3 Hz), 1.95-2.10 (2H, m), 2.36-2.50 (4H, m), 2.68 (1H, dd, J=15.7, 10.9 Hz), 2.86-3.15 (9H, m), 3.27 (1H, dd, J=11.4, 9.1 Hz), 3.73 (1.5H, s), 3.74 (1.5H, s), 4.60-4.62 (2H, m), 4.77-5.00 (3H, br.d), 5.47-5.71 (2H, m), 6.73-6.88 (4H, m), 7.00-7.03 (2H, m).

ESI (LC/MS positive mode) m/z 773 (M+H); Rt 3.28 min.

Compound 80: No. 5456178

4-[1-(Ethoxycarbonylmethyl-methyl-carbamoyloxy)-ethyl](S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 85]

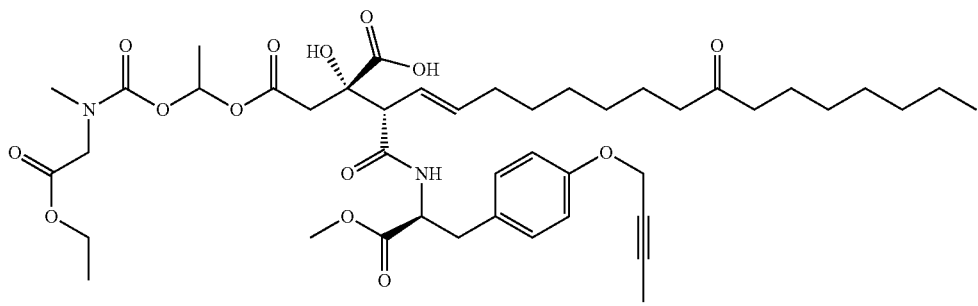

Compound 80 was obtained by the synthetic method of No. 5454360 (Compound 77) except that ethyl [(1-chloro-ethoxycarbonyl)-methyl-amino]-acetate was used instead of 3-[(1-chloro-ethoxycarbonyl)-methyl-amino]-propyl acetate.

$^1$H-NMR (CDCl$_3$, diastereomeric mixture) δ: 0.88 (3H, t, J=6.6 Hz), 1.12-1.37 (14H, m), 1.44-1.62 (7H, m), 1.86 (3H, t, J=2.2 Hz), 1.94-2.09 (2H, m), 2.33-2.71 (6H, m), 2.93-3.28 (9H, m), 3.73 (3H, s), 3.92-4.10 (2H, m), 4.17-4.25 (2H, m), 4.59-4.63 (2H, m), 4.77-4.82 (1H, m), 5.49-5.57 (1H, m), 5.62-5.69 (1H, m), 6.70-6.88 (4H, m), 6.98-7.05 (2H, m).

ESI (LC/MS positive mode) m/z 845 (M+H); Rt 3.37 min.

Compound 81: No. 5456179 (diastereomeric mixture)

4-(1-Dimethylcarbamoyloxy-ethyl) (S)-2-{(E)-(S)-1-[(S)-2-(4-but-2-ynyloxy-phenyl)-1-(1-dimethylcarbamoyloxy-ethoxycarbonyl)-ethylcarbamoyl]-10-oxo-heptadec-2-enyl}-2-hydroxy-succinate

[Chem. 86]

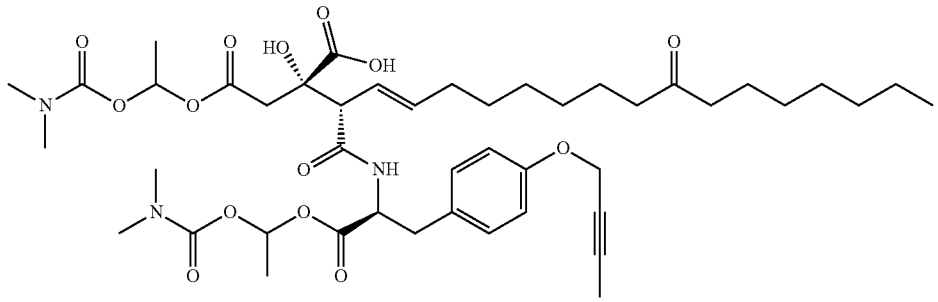

Compound 81 was obtained in a way similar to the synthetic method of No. 5444294 (Compound 74) except that 1-chloro-ethyl dimethyl-carbamate was used instead of 1-bromo-ethyl isobutyrate and 8 equivalents of sodium iodide was added as an additive.

(CDCl$_3$, four diastereomeric mixture) δ: 0.86-0.91 (3H, m), 1.15-1.40 (14H, m), 1.45-1.65 (10H, m), 1.86 (3H, m), 1.92-2.06 (2H, m), 2.32-2.45 (4H, m), 2.60-2.72 (1H, m), 2.85-2.95 (15H, m), 3.12-3.33 (1H, m), 4.54-4.81 (3H, m), 5.45-5.66 (2H, m), 6.73-6.93 (4H, m), 7.00-7.14 (2H, m).

ESI (LC/MS positive mode) m/z 874 (M+H); Rt 3.37 min.

Compound 82: No. 5479738

4-(5-Methyl-2-oxo-[1,3]dioxol-4-ylmethyl) (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 87]

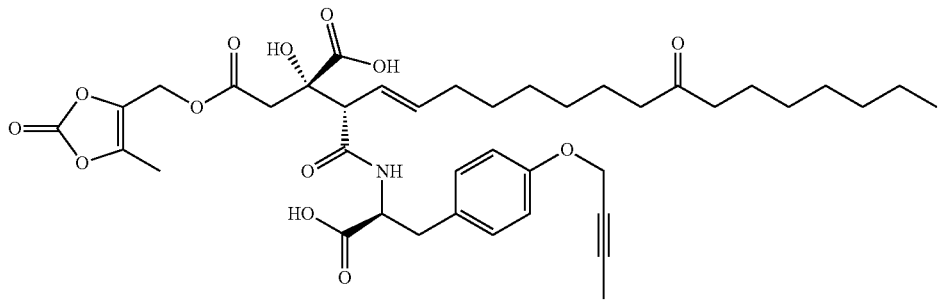

Under a nitrogen atmosphere, (Compound 29 described in WO2006/08807) (71.8 mg, 0.095 mmol) was dissolved in dichloromethane (2.1 mL), and 4-chloromethyl-5-methyl-[1,3]dioxol-2-one (17.1 mg, 0.014 mmol), sodium iodide (17.1 mg, 0.014 mmol), and N,N-diisopropylethylamine (33.1 μL, 0.19 mmol) were then added at room temperature. The mixture was stirred under reflux for 15 hours. After completing the reaction, the mixture was extracted with dichloromethane. The organic layer was washed with water and a saturated brine, dried over anhydrous sodium sulfate, and filtered. The solvent was distilled off. The residue was then purified by silica gel column chromatography (n-hexane: ethyl acetate=2:1, Rf=0.4) to obtain 74.5 mg (90% yield) of the triester form.

Under a nitrogen atmosphere, a solution (3.0 mL) of trifluoroacetic acid-dichloromethane (1:3) was then added to this triester form (74.5 mg, 0.086 mmol), and the mixture was stirred at room temperature for 2 hours. After completing the reaction, the solvent was distilled off under reduced pressure. Further dichloromethane (10 mL) was added and the solvent was distilled off. This operation was repeated twice and the product was then purified by HPLC (water with 0.05% TFA-acetonitrile with 0.05% TFA) to obtain 42 mg (65% yield) of Compound 82.

$^1$H-NMR (CD$_3$OD) δ: 0.89 (3H, t, J=6.6 Hz), 1.23-1.36 (16H, m), 1.48-1.58 (4H, m), 1.81 (3H, t, J=2.2 Hz), 1.94-2.01 (2H, m), 2.15 (3H, s), 2.44 (4H, t, J=7.1 Hz), 2.63 (1H, d, J=15.9 Hz), 2.88-2.95 (2H, m), 3.15-3.23 (2H, m), 4.59-4.65 (3H, m), 5.45-5.59 (2H, m), 6.81-6.85 (2H, m), 7.11 (2H, d, J=8.2 Hz).

ESI (LC/MS positive mode) m/z 756 (M+H); Rt 2.48 min.

Compound 75: No. 5444295

4-(4-Methoxy-phenyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 88]

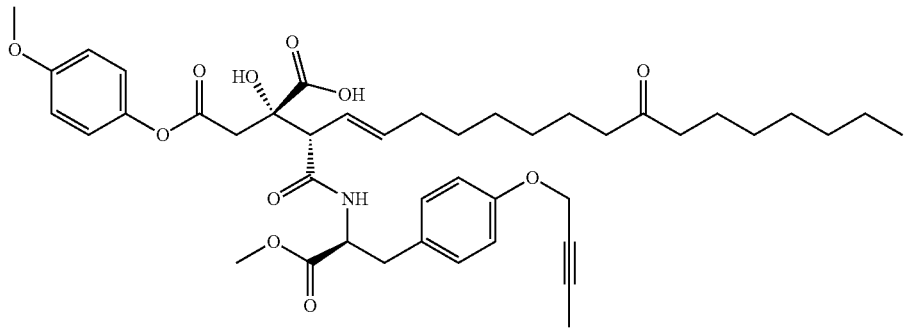

Under a nitrogen atmosphere, No. 5317776: Compound E (78.8 mg, 0.110 mmol) was dissolved in dichloromethane (3.1 mL) and the mixture was cooled to −20° C. WSC hydrochloride (33.7 mg, 0.177 mmol), 4-methoxyphenol (37.0 mg, 0.298 mmol), and dimethylaminopyridine (6.7 mg, 0.055 mmol) were then added at −20° C. The mixture was warmed to room temperature and stirred for 17 hours. After completing the reaction, the mixture was extracted with ethyl acetate. The organic layer was washed with water and a saturated brine, dried over anhydrous sodium sulfate, and filtered. The solvent was distilled off. The residue was then purified by silica gel column chromatography (n-hexane:ethyl acetate=2:1, Rf=0.4) to obtain 84.9 mg (94%) of the triester form.

Under a nitrogen atmosphere, formic acid (1.0 mL) was then added to this triester form (84.9 mg, 0.104 mmol) and the mixture was stirred at room temperature for 16 hours. After completing the reaction, toluene (16 mL) was added and the solvent was distilled off in a rotary evaporator. The residue was then purified by HPLC (water with 0.05% TFA-acetonitrile with 0.05% TFA) to obtain 64.8 mg (82% yield) of (No. 5444295) Compound 75.

$^1$H-NMR (CDCl$_3$) δ: 0.87 (3H, t, J=6.7 Hz), 1.15-1.42 (15H, m), 1.49-1.63 (4H, m), 1.82-1.83 (3H, m), 1.96-2.09 (2H, m), 2.35-2.51 (4H, m), 2.88 (1H, d, J=15.9 Hz), 2.99-3.12 (2H, m), 3.16 (1H, d, J=15.9 Hz), 3.33 (1H, d, J=9.8 Hz), 3.73 (3H, s), 3.77 (3H, s), 4.55-4.61 (2H, m), 4.80 (1H, q, J=12.8, 6.1 Hz), 5.31 (1H, br.d), 5.54 (1H, dd, J=15.3, 9.8 Hz), 5.64-5.71 (1H, m), 6.76 (1H, d, J=7.9 Hz), 6.85 (4H, d, J=7.9 Hz), 6.99-7.02 (4H, m).

ESI (LC/MS positive mode) m/z 764 (M+H); Rt 2.18 min.

Compound 76: No. 5452082 (diastereomeric mixture):

4-(1-Isobutyryloxy-ethyl) (S)-2-{(E)-(S)-1-[(S)-2-(4-but-2-ynyloxy-phenyl)-1-diethylcarbamoylmethoxycarbonyl-ethylcarbamoyl]-10-oxo-heptadec-2-enyl}-2-hydroxy-succinate

[Chem. 89]

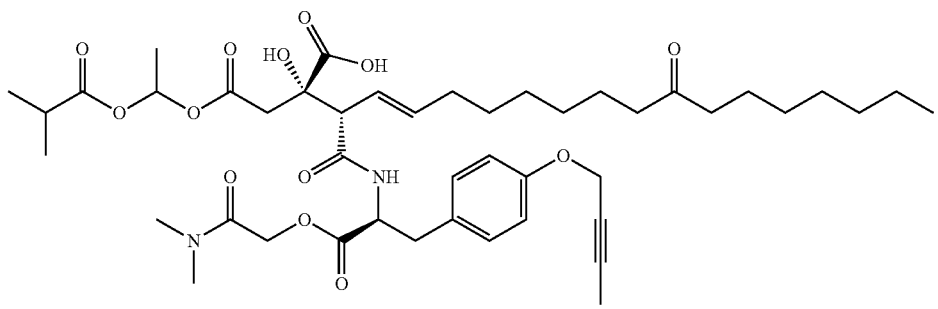

Compound 76 was obtained by a method similar to the synthesis of No. 5444293: Compound 6 except that No. 5459788: Compound Q was used instead of No. 5447725: Compound G.

$^1$H-NMR (CDCl$_3$, diastereomeric mixture) δ: 0.88 (3H, t, J=6.6 Hz), 1.13 (6H, d, J=6.0 Hz), 1.18-1.35 (14H, m), 1.44 (3H, t, J=4.9 Hz), 1.50-1.62 (4H, m), 1.83-1.89 (3H, m), 1.92-2.05 (2H, m), 2.31-2.45 (4H, m), 2.42-2.57 (1H, m), 2.66 (1H, dd, J=16.2, 7.1 Hz), 2.96 (6H, s), 2.98-3.07 (2H, m), 3.13-3.24 (2H, m), 4.57-4.64 (2H, m), 4.72-4.87 (3H, m), 5.48-5.63 (2H, m), 6.79-6.83 (1H, m), 6.85 (2H, d, J=8.8 Hz), 6.90-7.01 (1H, br.d), 7.09 (1H, d, J=8.2 Hz), 7.10 (1H, d, J=8.2 Hz).

ESI (LC/MS positive mode) m/z 843 (M+H); Rt 3.32 min.

Compound 102 and Compound 103 were produced according to the following synthetic scheme.

[Chem. 90]

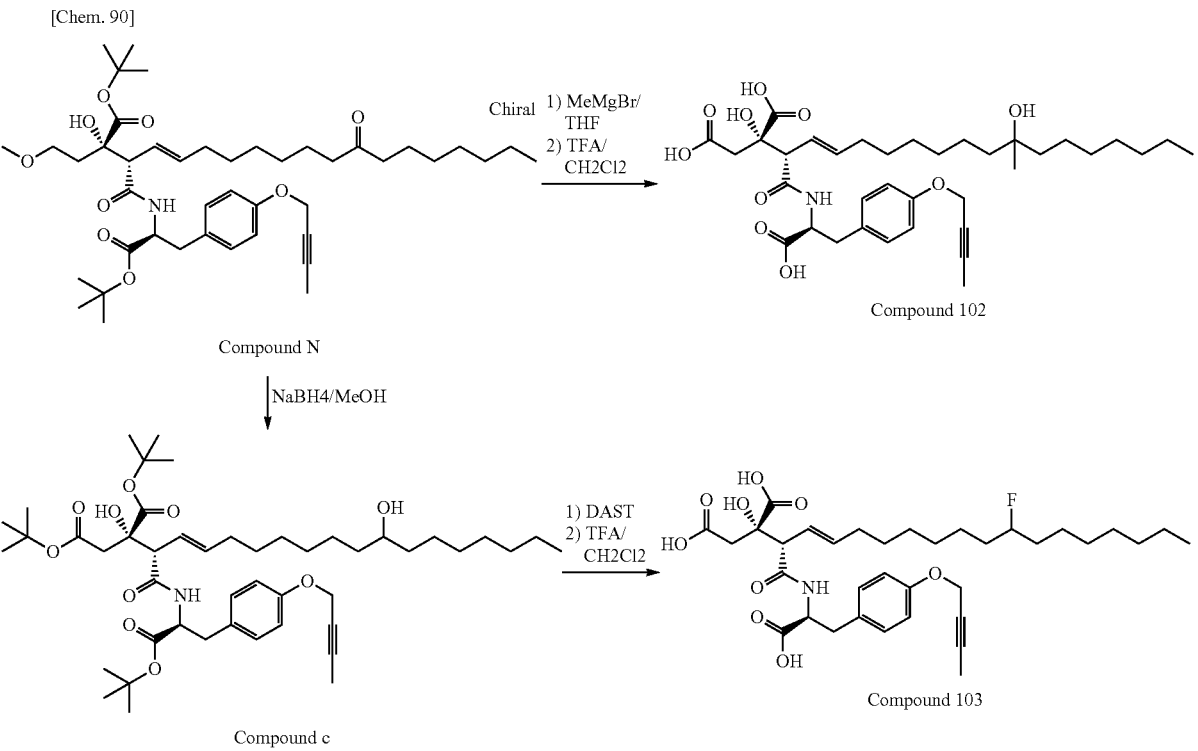

Compound 102: No. 5506095

(S)-2-{(E)-(S)-1-[(S)-2-(4-But-2-ynyloxy-phenyl)-1-carboxy-ethylcarbamoyl]-10-hydroxy-10-methyl-heptadec-2-enyl}-2-hydroxy-succinic acid Under a nitrogen atmosphere, di-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate (42.6 mg, 0.053 mmol) was dissolved in THF (1.28 mL), and the mixture was cooled to 0° C. A solution of methyl magnesium bromide in diethyl ether (3.0 M, 52.5 µL, 0.157 mmol) was then added dropwise, and the mixture was stirred at 0° C. for 1 hour and at room temperature for 2 hours. After completing the reaction, a saturated aqueous solution of ammonium chloride was added, and the mixture was extracted with ethyl acetate. The organic layer was washed with water and a saturated brine, dried over anhydrous sodium sulfate, and filtered. The solvent was distilled off. The residue was then purified by silica gel column chromatography (n-hexane:ethyl acetate=2:1, Rf=0.5) to obtain 23.9 mg (55% yield) of the tertiary alcohol form.

Under a nitrogen atmosphere, a solution (4.0 mL) of trifluoroacetic acid-dichloromethane (1:3) was added to this tertiary alcohol form (23.9 mg, 0.029 mmol), and the mixture was stirred at room temperature for 15 hours. After completing the reaction, the solvent was distilled off in a rotary evaporator. Further dichloromethane (10 mL) was added and the solvent was distilled off. This operation was repeated twice, and methanol (2.0 mL) and an aqueous solution of 28% ammonium (20 µL) were then added to the residue. The mixture was stirred at room temperature for 1.5 hours. After completing the reaction, the solvent was distilled off under reduced pressure. The residue was then purified by HPLC (water with 0.05% TFA-acetonitrile with 0.05% TFA) to obtain 10 mg (53% yield) of Compound 102 as a diastereomeric mixture.

Compound N, di-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate was prepared according to the method described in WO20041071503 (Compound n).

$^1$H-NMR (DMSO-$d_6$, diastereomeric mixture) δ: 0.88 (3H, t, J=6.6 Hz), 0.98 (3H, s), 1.12-1.35 (18H, m), 1.82 (3H, t, J=2.2 Hz), 1.84-1.94 (2H, m), 2.43 (1H, d, J=15.9 Hz), 2.50-2.56 (5H, m), 2.62 (1H, d, J=15.9 Hz), 2.88 (1H, dd, J=13.7, 7.7 Hz), 2.94-2.99 (1H, m), 3.16 (1H, d, J=7.7 Hz), 3.82-3.98 (1H, br.s), 4.35-4.40 (1H, m), 4.65-4.69 (2H, m), 5.30-5.45 (2H, m), 6.83 (2H, d, J=8.2 Hz), 7.13 (2H, d, J=8.8 Hz), 7.80-7.95 (1H, br.d).

ESI (LC/MS positive mode) m/z 660 (M+H); Rt 2.82 min.

Compound 103: No. 5507191

(S)-2-{(E)-(S)-1-[(S)-2-(4-But-2-ynyloxy-phenyl)-1-carboxy-ethylcarbamoyl]-10-fluoro-heptadec-2-enyl}-2-hydroxy-succinic acid Under a nitrogen atmosphere, Compound N, di-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate (90 mg, 0.111 mmol) was dissolved in methanol (1.8 mL), and sodium tetrahydroborate (5.0 mg, 0.132 mmol) was then added at room temperature. The mixture was stirred for 1.0 hours. The progress of the reaction was stopped by adding water. The mixture was then extracted with ethyl acetate. The organic layer was washed with water and a saturated brine, dried over anhydrous sodium sulfate, and filtered. The solvent was distilled off. The residue was then purified by silica gel column chromatography (n-hexane: ethyl acetate=2:1, Rf=0.6) to obtain 86.9 mg (96%) of Compound c, a secondary alcohol derivative (ESI (LC/MS positive mode) m/z 815 (M+H); Rt 2.70 min.).

Under a nitrogen atmosphere, this Compound c (86.9 mg, 0.107 mmol) was then dissolved in dichloromethane (4.3 mL), and the solution was cooled to −78° C. Bis(2-methoxyethyl)aminosulfur trifluoride (39.3 μL, 0.213 mmol) was added and the mixture was stirred at −78° C. for 3 hours. The progress of the reaction was stopped by adding water, and the mixture was then extracted with dichloromethane. The organic layer was washed with water and a saturated brine, dried over anhydrous sodium sulfate, and filtered. The solvent was distilled off. The residue was then purified by silica gel column chromatography (n-hexane:ethyl acetate=4:1, Rf=0.45) to obtain 64.4 mg (purity 64%) of the monofluoro form.

A solution (4.0 mL) of trifluoroacetic acid-dichloromethane (1:3) was added to this monofluoro form (64.4 mg), and the mixture was stirred at room temperature for 6 hours. After completing the reaction, the solvent was distilled off under reduced pressure. Further dichloromethane (10 mL) was added and the solvent was distilled off. This operation was repeated twice and the residue was then purified by HPLC (water with 0.05% TFA-acetonitrile with 0.05% TFA) to obtain 26.4 mg (38%, yield over 2 steps) of Compounds 103.

$^1$H-NMR (DMSO-$d_6$, diastereomeric mixture) δ: 0.86 (3H, m), 1.14-1.41 (18H, m), 1.42-1.58 (4H, m), 1.79-1.83 (3H, m), 1.84-1.93 (2H, m), 2.42-2.57 (1H, m), 2.67-2.83 (2H, m), 2.95-3.00 m), 3.12-3.21 (1H, m), 4.33-4.42 (1.5H, m), 4.47-4.55 (0.5H, m), 4.61-4.69 (2H, m), 5.03-5.23 (1H, br.d), 5.35-5.45 (2H, m), 6.80 (2H, d, J=6.6 Hz), 7.11 (2H, d, J=6.6 Hz), 8.17-8.33 (1H, br.d), 12.4-12.9 (1H, br.d). ESI (LC/MS positive mode) m/z 648 (M+H); Rt 2.12 min.

Compound 7: No. 5323942

1-(1-Acetoxy-ethyl) (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 91]

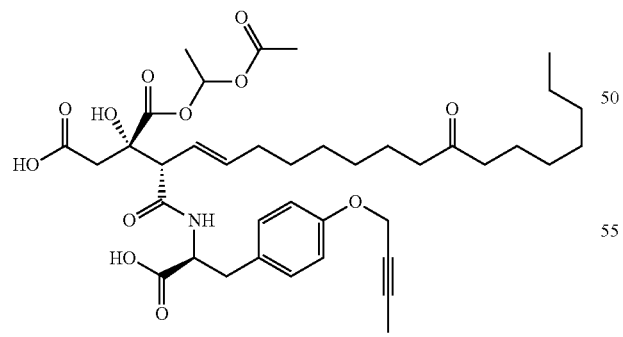

$^1$H-NMR (CD$_3$OD, diastereomeric mixture) δ: 0.89 (3H, t, J=7.2 Hz), 1.27-1.32 (14H, m), 1.40-1.45 (3H, m), 1.50-1.56 (4H, m), 1.76-1.81 (3H, m), 1.95-2.03 (5H, m), 2.44 (4H, t, J=7.2 Hz), 2.53-2.58 (1H, m), 2.83-2.93 (2H, m), 3.13-3.21 (2H, m), 4.58-4.63 (3H, m), 5.46-5.56 (2H, m), 6.81-6.86 (3H, m), 7.08-7.12 (2H, m).
ESI (LC/MS positive mode) m/z 731 (M+H); Rt 2.72 min.

Compound 8: No. 5323943

(S)-2-{(E)-(S)-1-[(S)-1-Acetoxy-ethoxycarbonyl-2-(4-but-2-ynyloxy-phenyl)-ethylcarbamoyl]-10-oxo-heptadec-2-enyl}-2-hydroxy-succinic acid

[Chem. 92]

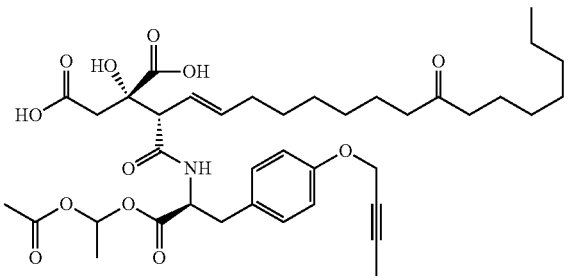

$^1$H-NMR (CD$_3$OD; diastereomeric mixture) δ: 0.88 (3H, t, J=7.6 Hz), 1.28-1.32 (14H, m), 1.39-1.53 (7H, m), 1.74-1.76 (0.5H, m), 1.79-1.81 (2.5H, m), 1.96-2.04 (5H, m), 2.43 (4H, t, J=7.2 Hz), 2.53-2.58 (1H, m), 2.84-2.94 (2H, m), 3.09-3.19 (1H, m), 3.28-3.46 (1H, m), 4.58-4.63 (3H, m), 5.48-5.56 (2H, m), 6.81-6.86 (3H, m), 7.10-7.12 (2H, m).
ESI (LC/MS positive mode) m/z 731 (M+H); Rt 2.67 and 2.77 min.

To a mixture of Compound 93: No. 4630808 (50 mg, 0.078 mmol), NaHCO$_3$ (7.8 mg), and dichloromethane (0.77 mL) was added 1-bromo-ethyl acetate (15.5 mg) and the mixture was stirred at room temperature. After being stirred for 6 hours, 1-bromo-ethyl acetate (15.5 mg) was added, and 9 hours later, 1-bromo-ethyl acetate ester (31 mg) was added. At 25 hours after initiation of the reaction, a saturated aqueous solution of ammonium chloride (5 mL) was added, and the mixture was extracted with ethyl acetate. The organic layer was washed with a saturated brine, dried over anhydrous sodium sulfate, and then the filtrate was concentrated under reduced pressure. The resulting residue was purified by preparative HPLC and then freeze-dried to obtain a diastereomeric mixture of Compound 7 (8.9 mg, 16% yield, white powder) and a diastereomeric mixture of Compound 8 (4.5 mg, 8% yield, white powder).

The reaction reagent 1-bromo-ethyl acetate was prepared according to the description in WO2003/014126.

Compound 9: No. 5328644

Diallyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 93]

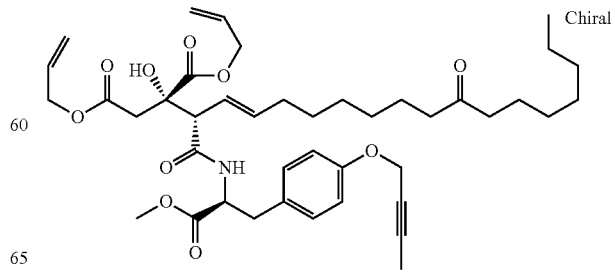

To a mixture of No. 5153510: Compound 87 (299 mg, 0.304 mmol), triethylamine (424 μL, 3.04 mmol), and DMF (2 mL) was added allyl bromide (257 μL, 3.04 mmol) commercially available from Wako Pure Chemical Industries, Ltd. (cat. No. 018-01386) and the mixture was stirred at room temperature. After being stirred for 18 hours, ethyl acetate (20 mL) was added to the reaction solution. The organic layer was washed with water, a saturated aqueous solution of ammonium chloride, and a saturated brine, and dried over anhydrous sodium sulfate. The filtrate was then concentrated under reduced pressure. The resulting residue was purified by silica gel column chromatography (n-hexane/acetic acid ester) to obtain Compound 9 (77 mg, 27% yield, clear and colorless solid).

$^1$H-NMR (CDCl$_3$) δ(PPM) 0.86 (3H, t, J=8 Hz), 1.22-1.28 (14H, m), 1.50-1.56 (4H, m), 1.84-1.85 (3H, m), 1.94-2.00 (2H, m), 2.34-2.38 (4H, m), 2.65 (1H, d, J=16 Hz), 2.90 (1H, d, J=16 Hz), 2.97-3.02 (1H, m), 3.07-3.12 (1H, m), 3.17 (1H, d, J=12 Hz), 3.70 (3H, s), 4.42 (1H, s), 4.57-4.62 (6H, m), 4.77-4.80 (1H, m), 5.21-5.25 (2H, m), 5.28-5.34 (2H, m), 5.44-5.52 (1H, m), 5.57-5.65 (1H, m), 5.80-5.94 (2H, m), 6.78 (1H, d, J=8), 7.84 (2H, d, J=8 Hz), 7.03 (2H, d, J=8 Hz)

ESI (LC/MS positive mode) m/z 739 (M+H); Rt 3.43 min.

Compound 10: No. 5336306

1-(2,2-Dimethyl-propionyloxymethyl) (S)-2-{(E)-(S)-1-[(S)-2-(4-but-2-ynyloxy-phenyl)-1-methoxy-carbonyl-ethylcarbamoyl]-10-oxo-heptadec-2-enyl}-2-hydroxy-succinate

[Chem. 94]

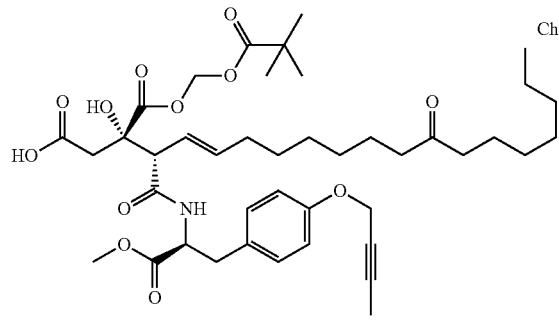

$^1$H-NMR (CD$_3$OD) δ(PPM) 0.88 (3H, t, J=8 Hz), 1.18 (9H, s), 1.22-1.28 (14H, m), 1.50-1.56 (4H, m), 1.79-1.81 (3H, m), 1.94-2.02 (2H, m), 2.40-2.46 (4H, m), 2.57 (1H, d, J=16 Hz), 2.86-2.91 (2H, m), 3.08-3.12 (1H, m), 3.18 (1H, d, J=12 Hz), 3.71 (3H, s), 4.58-4.64 (3H, m), 5.42-5.58 (2H, m), 5.70-5.76 (2H, m), 6.83 (2H, d, J=8), 7.07 (2H, d, J=8 Hz), 8.24 (1H, d, J=8 Hz)

ESI (LC/MS positive mode) m/z 772 (M+H); Rt 2.68 min.

Compound 11: No. 5336308

Bis-(2,2-dimethyl-propionyloxymethyl) (S)-2-{(E)-(S)-1-[(S)-2-(4-but-2-ynyloxy-phenyl)-1-methoxy-carbonyl-ethylcarbamoyl]-10-oxo-heptadec-2-enyl}-2-hydroxy-succinate

[Chem. 95]

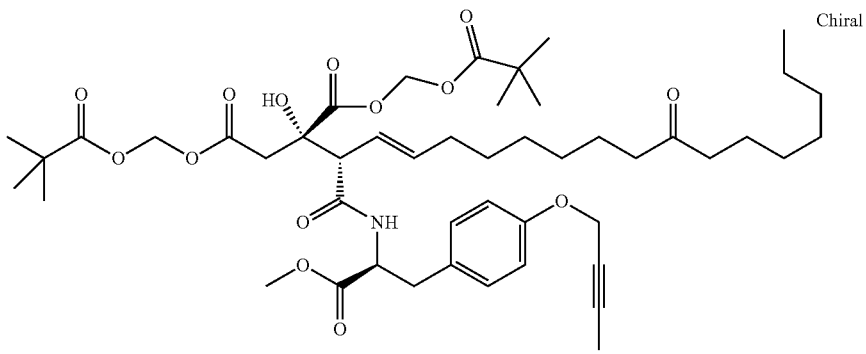

$^1$H-NMR (CD$_3$OD) δ(PPM) 0.88 (3H, t, J=8 Hz), 1.18-1.23 (18H, m), 1.27-1.36 (14H, m), 1.50-1.56 (4H, m), 1.79-1.81 (3H, m), 1.95-2.00 (2H, m), 2.40-2.44 (4H, m), 2.65 (1H, d, J=16 Hz), 2.84-2.90 (1H, m), 2.95 (1H, d, J=16 Hz), 3.08-3.12 (1H, m), 3.20 (1H, d, J=8 Hz), 3.70 (3H, s), 4.58-4.62 (3H, m), 5.43-5.58 (2H, m), 5.68-5.72 (3H, m), 5.77 (1H, d, J=4 Hz), 6.83 (2H, d, J=8), 7.07 (2H, d, J=8 Hz), 8.24 (1H, d, J=8 Hz) ESI (LC/MS positive mode) m/z 772 (M+H); Rt 3.13 min.

To a mixture of No. 5153510: Compound 87 (35 mg, 0.053 mmol), NaI (71.8 mg, 0.479 mmol), and acetone (0.88 mL) were added N,N-diisopropylethylamine (16.7 μL, 0.096 mmol) and chloromethyl 2,2-dimethyl-propionate (69.4 μL, 0.479 mmol) commercially available from Aldrich (cat. No. 141186-25G) and the mixture were stirred at room temperature. After being stirred for 23 hours, a saturated aqueous solution of ammonium chloride (5 mL) was added, and the mixture was extracted with ethyl acetate. The organic layer was washed with a saturated brine, dried over anhydrous sodium sulfate, and the filtrate was then concentrated under reduced pressure. The resulting residue was purified by preparative HPLC. Water was then added to the separated fraction and the fraction was extracted with ethyl acetate. The organic layer was washed with a saturated brine, and then dried over anhydrous sodium sulfate. The filtrate was concentrated under reduced pressure to obtain the title compounds: Compound 10 (16 mg, 39%, clear and colorless solid) and Compound 11 (17.8 mg, 38% yield, clear and colorless solid).

Compound 12: No. 5336310

Dibenzoyloxymethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 96]

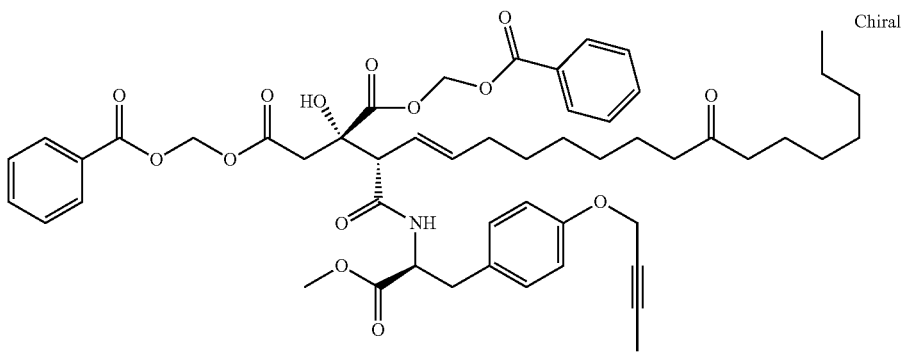

$^1$H-NMR (CD$_3$OD) δ(PPM) 0.87 (3H, t, J=8 Hz), 1.20-1.30 (14H, m), 1.44-1.53 (4H, m), 1.77-1.78 (3H, m), 1.98 (1H, d, J=8 Hz), 2.37-2.43 (4H, m), 2.71 (1H, d, J=16 Hz), 2.84-2.90 (1H, m), 3.02-3.10 (2H, m), 3.21 (1H, d, J=8 Hz), 3.68 (3H, s), 4.55-4.62 (3H, m), 5.40-5.46 (2H, m), 5.86 (1H, d, J=8 Hz), 5.91 (1H, d, J=8 Hz), 5.93 (1H, d, J=8 Hz), 6.03 (1H, d, J=8 Hz), 6.83 (2H, d, J=8 Hz), 7.03 (2H, d, J=8 Hz), 7.45-7.49 (4H, m), 7.60-7.64 (2H, m), 7.99-8.19 (4H, m)

ESI (LC/MS positive mode) m/z 926 (M+H); Rt 3.01 min.

Compound 13: No. 5337462

1-Benzoyloxymethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 97]

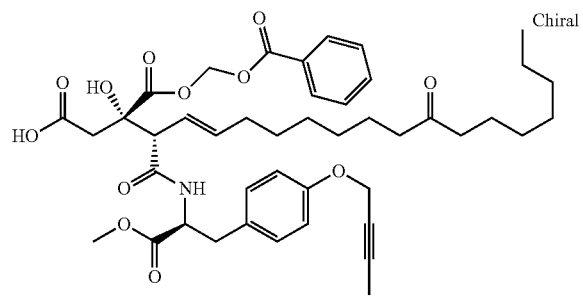

$^1$H-NMR (CD$_3$OD) δ(PPM) 0.88 (3H, t, J=8 Hz), 1.24-1.30 (14H, m), 1.45-1.56 (4H, m), 1.78-1.81 (3H, m), 2.38-2.44 (4H, m), 2.60 (1H, d, J=16 Hz), 2.84-2.89 (1H, m), 2.94 (1H, d, J=16 Hz), 3.06-3.10 (1H, m), 3.19 (1H, d, J=8 Hz), 3.70 (3H, s), 4.56-4.62 (3H, m), 5.40-5.44 (2H, m), 5.94 (1H, d, J=8 Hz), 6.03 (1H, d, J=8 Hz), 6.81 (2H, d, J=8 Hz), 7.05 (2H, d, J=8 Hz), 7.47-7.1 (2H, m), 7.62-7.65 (1H, m), 8.03-8.05 (2H, m)

ESI (LC/MS positive mode) m/z 793 (M+H); Rt 2.98 min.

To a mixture of No. 5153510: Compound 87 (35 mg, 0.053 mmol), NaI (71.8 mg, 0.479 mmol), and acetone (0.88 mL) were added N,N-diisopropylethylamine (16.7 μL, 0.096 mmol) and chloromethyl benzoate (81.3 mg, 0.479 mmol) commercially available from Wako Pure Chemical Industries, Ltd. (cat. No. 323-73,671) and the mixture was stirred at room temperature. The title compounds, Compound 12 (21 mg, 43% yield, clear and colorless solid) and Compound 13 (12 mg, 29%, clear and colorless solid) were obtained by methods similar to those used in the purification of No. 5336306: Compound 10 and No. 5336308: Compound 11.

Compound 14: No. 5452519

4-(1,3-Dioxo-1,3-dihydro-isoindole-2-ylmethyl) (S)-2-{(E)-(S)-1-[(S)-2-(4-but-2-ynyloxy-phenyl)-1-(1,3-dioxo-1,3-dihydro-isoindole-2-ylmethoxycarbonyl)-ethylcarbamoyl]-10-oxo-heptadec-2-enyl}-2-hydroxy-succinate

[Chem. 98]

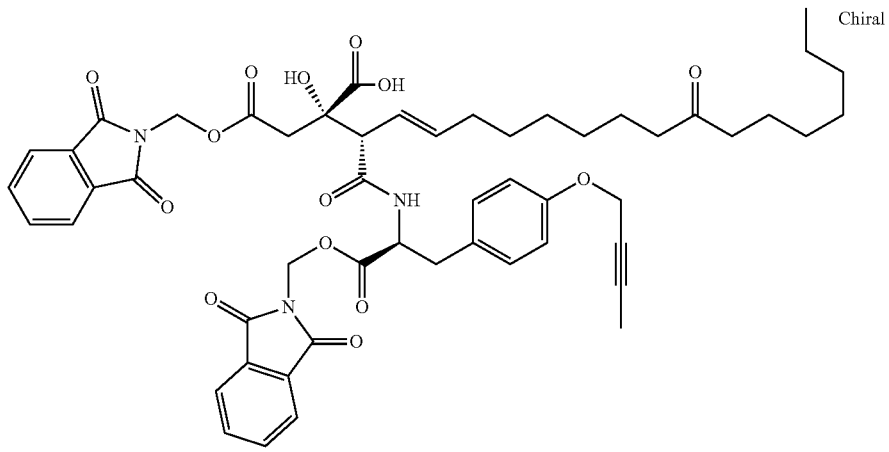

To a mixture of No. 5447725 (Compound G; 40 mg, 0.07 mmol), DBU (26 µL, 0.171 mmol), and dichloromethane (0.57 mL) was added 2-bromomethyl-isoindole-1,3-dione (41 mg, 0.171 mmol) commercially available from Aldrich (cat. No. 252611-5G). After the mixture was stirred at room temperature for 17 hours, further 2-bromomethyl-isoindole-1,3-dione (41 mg, 0.171 mmol) and DBU (9 µL, 0.057 mmol) were added. After further 2 hours, the reaction solution was concentrated under reduced pressure. The residue was purified by silica gel column chromatography to obtain 4-(1,3-dioxo-1,3-dihydro-isoindole-2-ylmethyl) 1-butyl (S)-2-{(E)-(S)-1-[(S)-2-(4-but-2-ynyloxy-phenyl)-1-(1,3-dioxo-1,3-dihydro-isoindole-2-ylmethoxycarbonyl)-ethylcarbamoyl]-10-oxo-heptadec-2-enyl}-2-hydroxy-succinate (51 mg, 89%; ESI (LC/MS positive mode) m/z 1018 (M+H); Rt 3.40 min.).

The obtained compound was stirred in formic acid at room temperature and, 16 hours later, formic acid was distilled off under reduced pressure. The resulting residue was purified by a diol column (n-hexane/ethyl acetate) to obtain the title compound, Compound 14 (26 mg, 55% yield).

$^1$H-NMR (CD$_3$OD) δ(PPM) 0.87 (3H, t, J=8 Hz), 1.22-1.28 (14H, m), 1.48-1.52 (4H, m), 1.70-1.78 (3H, m), 1.88-1.92 (2H, m), 2.38-2.44 (4H, m), 2.59 (1H, d, J=16 Hz), 2.85-2.94 (2H, m), 3.01-3.06 (1H, m), 3.17 (1H, d, J=12 Hz), 4.42-4.45 (2H, m), 4.61-4.65 (1H, m), 5.40-5.53 (2H, m), 5.61-5.74 (4H, m), 6.69 (2H, d, J=8 Hz), 7.02 (2H, d, J=8 Hz), 7.80-7.92 (8H, m)

ESI (LC/MS positive mode) m/z 962 (M+H); Rt 2.87 min.

Compound 15: No. 5454592

4-(1,3-Dioxo-1,3-dihydro-isoindole-2-ylmethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 99]

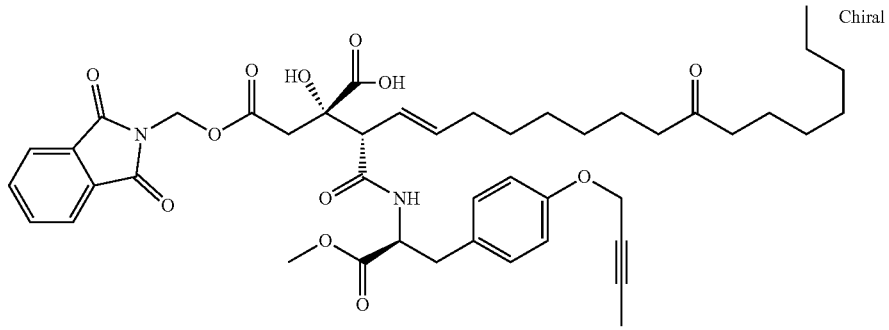

To a mixture of No. 5317776 (Compound E; 60 mg, 0.08 mmol), DBU (19 µL, 0.126 mmol) and dichloromethane (0.84 mL) was added 2-bromomethyl-isoindole-1,3-dione (30 mg, 0.126 mmol) commercially available from Aldrich (cat. No. 252611). After the mixture was stirred at room temperature for 6 hours, further 2-bromomethyl-isoindole-1, 3-dione (10 mg, 0.04 mmol) and DBU (6.3 µL, 0.04 mmol) were added. Then, 4-(1,3-dioxo-1,3-dihydro-isoindole-2-yl-methyl) 1-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate (56 mg, 76%) was obtained (ESI (LC/MS positive mode) m/z 873 (M+H); Rt 3.38 min.).

The obtained compound (56 mg, 0.064 mmol) was stirred in formic acid (128 µL) at room temperature and, 41 hours later, formic acid was distilled off under reduced pressure. The resulting residue was purified by preparative HPLC and then freeze-dried to obtain the title compound (37 mg, 70% yield, clear and colorless solid).

$^1$H-NMR (CD$_3$OD) δ(PPM) 0.88 (3H, t, J=8 Hz), 1.23-1.28 (14H, m), 1.49-1.53 (4H, m), 1.70-1.78 (3H, m), 1.92-1.96 (2H, m), 2.38-2.43 (4H, m), 2.60 (1H, d, J=16 Hz), 2.87-2.93 (2H, m), 3.07-3.10 (1H, m), 3.18 (1H, d, J=8 Hz), 3.67 (3H, s), 4.51-4.52 (2H, m), 4.60-4.62 (1H, m), 5.43-5.57 (2H, m), 5.65 (1H, d, J=8 Hz), 5.71 (1H, d, J=8 Hz), 6.81 (2H, d, J=8 Hz), 7.06 (2H, d, J=8 Hz), 7.85-7.91 (4H, m)

ESI (LC/MS positive mode) m/z 817 (M+H); Rt 2.83 min.

Compound 16: No. 5454862

4-Methoxycarbonylmethyl (S)-2-{(E)-(S)-1-[(S)-2-(4-but-2-ynyloxy-phenyl)-1-methoxycarbonyl-methoxycarbonyl-ethylcarbamoyl]-10-oxo-heptadec-2-enyl}-2-hydroxy-succinate

[Chem. 100]

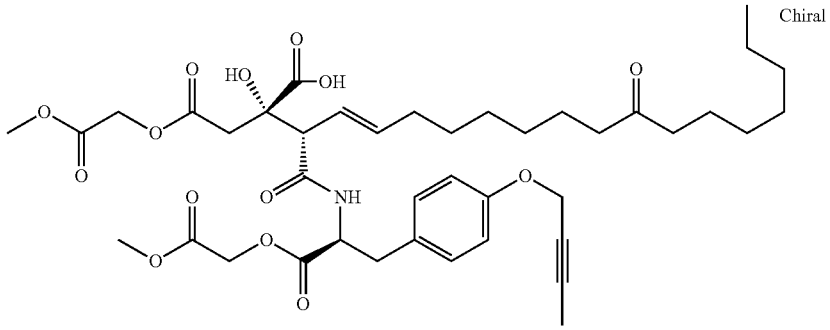

The compound was synthesized in a way similar to the synthesis of No. 5452519: Compound 14 except that methyl 2-bromoacetate commercially available from Wako Pure Chemical Industries, Ltd. (cat. No. 131-14475) was used instead of 2-bromomethyl-isoindole-1,3-dione.

$^1$H-NMR (CD$_3$OD) δ(PPM) 0.88 (3H, t, J=8 Hz), 1.22-1.32 (15H, m), 1.50-1.56 (4H, m), 1.79-1.81 (3H, m), 1.94-1.97 (2H, m), 2.38-2.40 (4H, m), 2.68 (1H, d, J=16 Hz), 2.94-3.01 (2H, m), 3.21-3.23 (2H, m), 3.72 (3H, s), 3.75 (3H, s), 4.59-4.8 (6H, m), 5.48-5.53 (2H, m), 6.84 (2H, d, J=8 Hz), 7.15 (2H, d, J=8 Hz)

ESI (LC/MS positive mode) m/z 788 (M+H); Rt 1.68 min.

Compound 1: No. 5456339

4-(5-Methyl-2-oxo-[1,3]dioxol-4-ylmethyl) (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate

[Chem. 101]

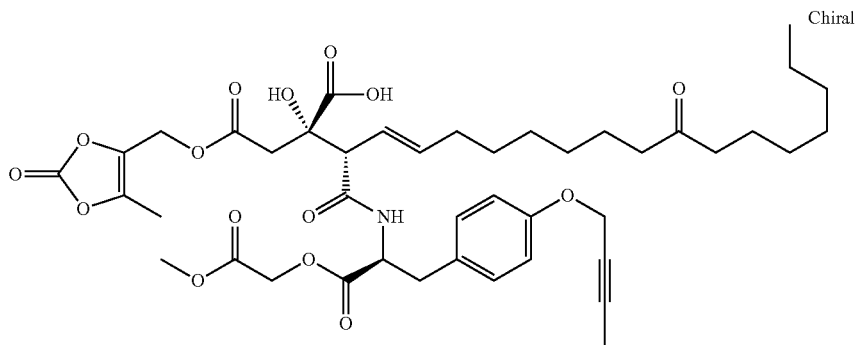

Synthesis of No. 5456339: Compound 1 (No. 1)

[Chem. 102]

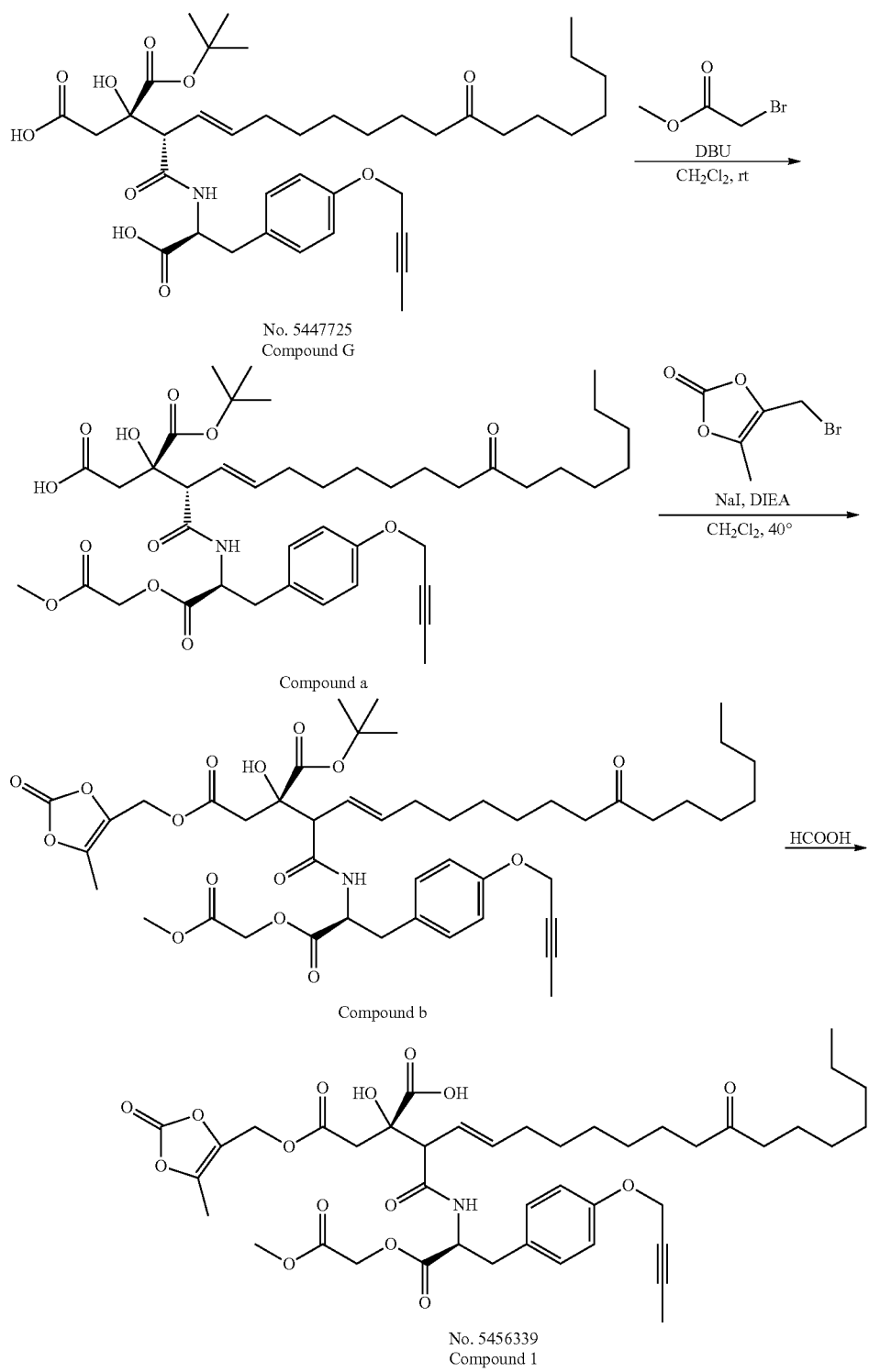

To a mixture of No. 5447725 (Compound G; 175 mg, 0.25 mmol), DBU (37 µL, 0.25 mmol) and dichloromethane (2.5 mL) was added methyl 2-bromoacetate (26 µL, 0.250 mmol). After the mixture was stirred at room temperature for 1 hour, further methyl 2-bromoacetate (13 µL, 0.125 mmol) commercially available from Wako Pure Chemical Industries, Ltd. (cat. No. 131-14475) and DBU (18µL, 0.125 mmol) were added. After the mixture was stirred at room temperature for further 2 hours, the reaction solution was stirred at 40° C. for 4 hours. The solution was purified by preparative HPLC, and then freeze-dried to obtain Compound a, 1-tert-butyl (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate (10 mg, 5% yield; ESI (LC/MS positive mode) ink 772 (M+H); Rt 2.22 min.).

To a mixture of the obtained Compound a (10 mg, 0.013 mmol), NaI (5.8 mg, 0.039 mmol), N,N-diisopropylethylamine (6.8 µL, 0.039 mmol) and dichloromethane (1.0 mL) was added 4-chloromethyl-5-methyl-[1,3]dioxol-2-one (5.8 mg, 0.039 mmol), and the mixture was stirred at 40° C. overnight. The reaction solution was then concentrated, and purified by preparative TLC (n-hexane-ethyl acetate) to obtain Compound b, 4-(5-methyl-2-oxo-[1,3]dioxol-4-ylmethyl) 1-butyl (S)-2-{(E)-(S)-1-[(S)-2-(4-but-2-ynyloxy-phenyl)-1-methoxycarbonylmethoxycarbonyl-ethylcarbamoyl]-10-oxo-heptadec-2-enyl}-2-hydroxy-succinate (ESI (LC/MS positive mode) m/z 884 (M+H); Rt 3.63 min.).

Compound b was then stirred in formic acid at room temperature for 24 hours, and the reaction solution was concentrated. The resulting residue was purified by preparative HPLC and then freeze-dried. The resulting residue was purified by preparative TLC (n-hexane/acetone) to obtain No. 5456339: Compound 1 (2.4 mg, colorless oil).

$^1$H-NMR (CDCl$_3$) δ(PPM) 0.88 (3H, t, J=6.48 Hz), 1.24-1.30 (14H, m), 1.45-1.58 (4H, m), 1.86-1.87 (3H, m), 1.91-2.09 (2H, m), 2.16 (3H, s), 2.39-2.44 (4H, m), 2.66 (1H, d, J=12.7 Hz), 2.95 (1H, d, J=12.7 Hz), 3.02-3.10 (1H, m), 3.19-3.27 (2H, m), 3.79 (3H, s), 4.59-4.93 (7H, m), 5.41-5.65 (3H, m), 6.64 (1H, d, J=8.1 Hz), 6.88 (2H, d, J=8.64 Hz), 7.10 (2H, d, J=8.64 Hz)

ESI (LC/MS positive mode) m/z 828 (M+H); Rt 2.11 min.

Synthesis of No. 5456339: Compound 1 (No. 2)

[Chem. 103]

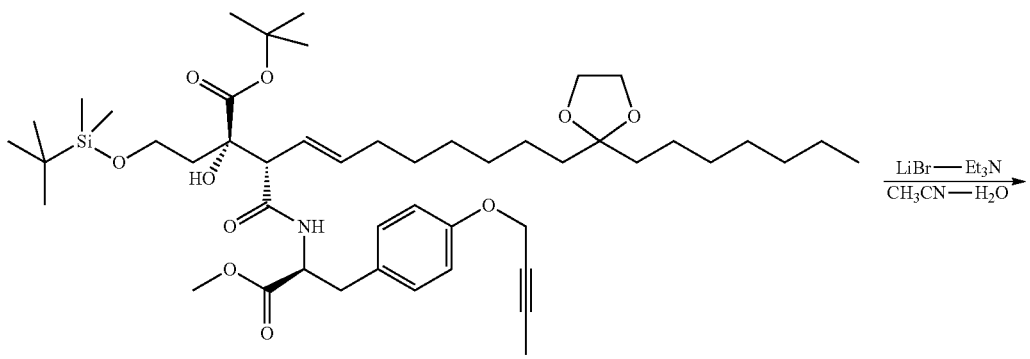

No. 5327507
Compound C

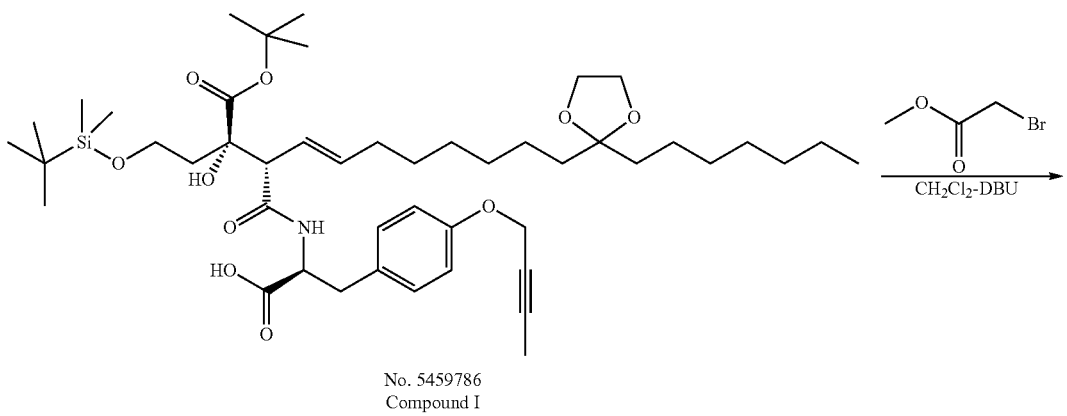

No. 5459786
Compound I

-continued
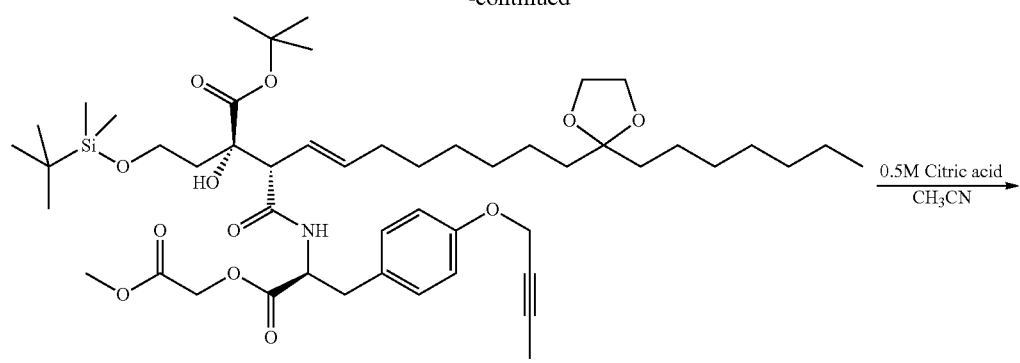
No. 5725525
Compound J
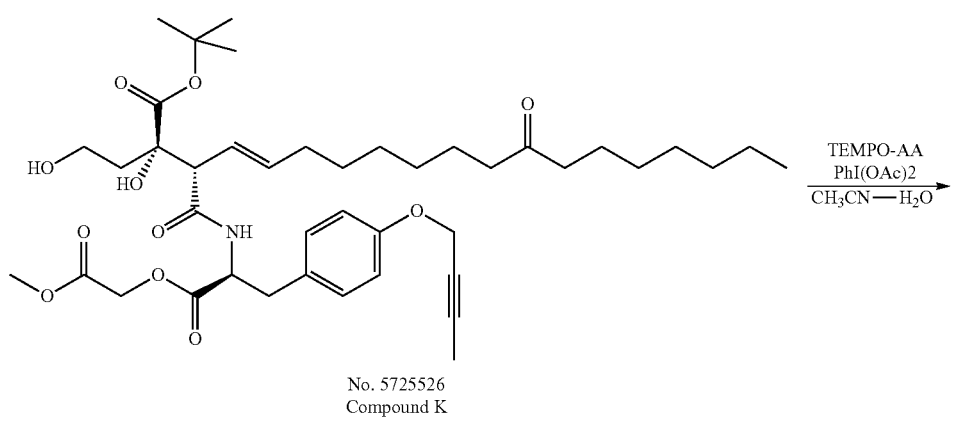
No. 5725526
Compound K
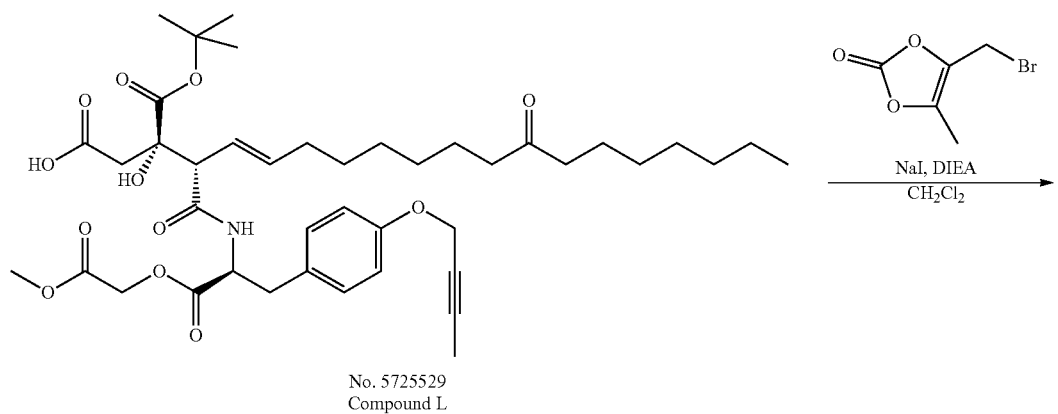
No. 5725529
Compound L
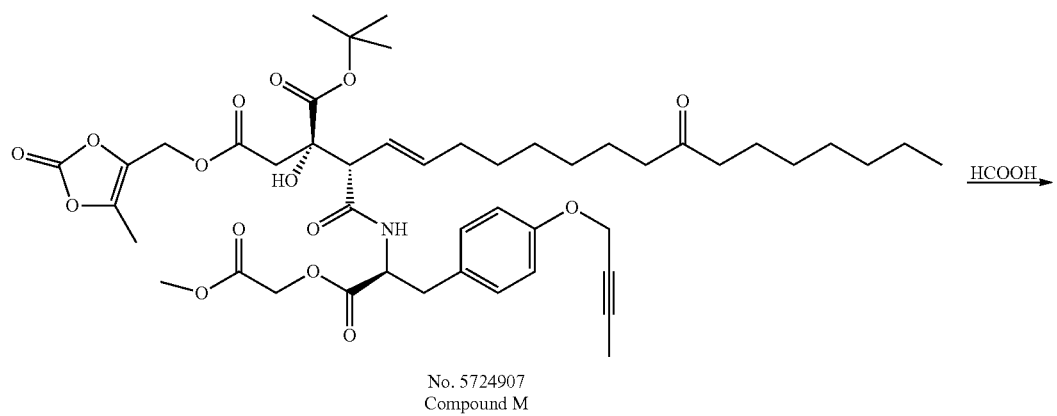
No. 5724907
Compound M -continued

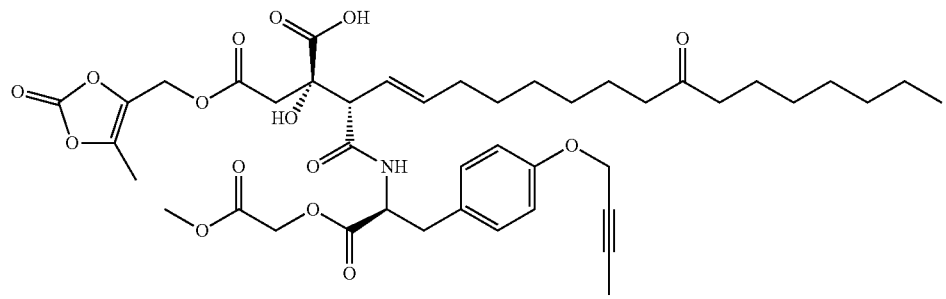

No. 5456339
Compound 1

No. 5327507: Compound C was prepared by the method described in WO2006/088071 (Compound 35)

To a mixture of No. 5327507: Compound C (4.74 g, 5.52 mmol), acetonitrile (23 mL) and distilled water (460 μL) were added triethylamine (2.3 mL, 16.6 mmol) and lithium bromide (4.80 g, 55.2 mmol), and the mixture was stirred at 50° C. After confirming the consumption of the starting materials by LCMS, the mixture was cooled to room temperature and an aqueous solution of 0.5 M citric acid was added. The mixture was extracted with ethyl acetate. The organic layer was washed with a saturated brine, and dried over anhydrous sodium sulfate. The filtrate was then concentrated under reduced pressure to obtain No. 5459786: Compound I (4.64 g, 99% yield, ESI (LC/MS positive mode) m/z 845 (M+H); Rt 3.88 min.).

To a mixture of the obtained No. 5459786: Compound I (4.59 g, 5.43 mmol) and dichloromethane (45 mL) were added methyl bromoacetate (1,026 μL, 10.86 mmol) and DBU (1,625 μL, 10.86 mmol) and the mixture was stirred at room temperature.

After confirming the consumption of the starting materials by LCMS, a saturated aqueous solution of ammonium chloride was added and the mixture was extracted with dichloromethane. The organic layer was dried over anhydrous sodium sulfate and then filtered through a layer of a small amount of SiO₂. The filtrate was concentrated under reduced pressure to obtain No. 5725525: Compound J (5.02 g, yield 99% or more, ESI (LC/MS positive mode) ink 917 (M+H); Rt 3.30 min.).

The obtained No. 5725525: Compound J (4.96 g, 5.87 mmol), acetonitrile (50 mL) and 0.5 M aqueous solution of citric acid (23.4 mL) were mixed, and the mixture was stirred at 60° C. After confirming the consumption of the starting materials by LCMS, water was added, and the mixture was extracted with ethyl acetate. The organic layer was washed with a saturated brine, and dried over anhydrous sodium sulfate. The filtrate was then concentrated under reduced pressure to obtain No. 5725526: Compound K (3.0 g, 67% yield, ESI (LC/MS positive mode) m/z 758 (M+H); Rt 3.05 min.).

To a mixture of obtained No. 5725526: Compound K (2.10 g, 2.77 mmol), acetonitrile (10.5 mL), and distilled water (1.05 mL) were added TEMPO-AA (236 mg, 1.10 mmol) and iodobenzene diacetate (2.68 g, 8.31 mmol). The mixture was stirred at room temperature. After confirming the consumption of the starting materials by LCMS, an aqueous solution of 0.5 M citric acid was added, and the mixture was extracted with ethyl acetate. The organic layer was washed with an aqueous solution of 5% sodium thiosulfate and a saturated brine, and dried over anhydrous sodium sulfate. The filtrate was then concentrated under reduced pressure. The resulting residue was purified by diol column chromatography to obtain No. 5725529: Compound L (1.87 g, 87% yield, ESI (LC/MS positive mode) m/z 772 (M+H); Rt 2.95 min.).

To a mixture of the obtained No. 5725529: Compound L (1.87 g, 2.42 mmol), dichloromethane (37.4 mL), sodium iodide (1.09 g, 7.27 mmol), and 4-chloromethyl-5-methyl-[1,3]dioxol-2-one (788 μL, 7.27 mmol) was added N,N-diisopropylethylamine (1.26 mL, 7.27 mmol) and the mixture was stirred at 45° C. After confirming the consumption of the starting materials by LCMS, dichloromethane was added. The mixture was washed with a saturated aqueous solution of ammonium chloride. The resulting organic layer was dried over anhydrous sodium sulfate. The filtrate was then concentrated under reduced pressure. The resulting residue was purified by column chromatography to obtain No. 5724907: Compound M (1.61 g, 75% yield, (ESI (LC/MS positive mode) m/z 885 (M+H); Rt 3.28 min.).

To the obtained No. 5724907: Compound M (1.60 g, 1.81 mmol) was added formic acid (16 mL) and the mixture was stirred at room temperature. After confirming the consumption of the starting materials by LCMS, formic acid was distilled off under reduced pressure. The resulting residue was purified by diol column chromatography to obtain No. 5456339: Compound 1, 4-(5-methyl-2-oxo-[1,3]dioxol-4-ylmethyl) (S)-2-{(E)-(S)-1-[(S)-2-(4-but-2-ynyloxy-phenyl)-1-methoxycarbonyl-methoxycarbonyl-ethylcarbamoyl]-10-oxo-heptadec-2-enyl}-2-hydroxy-succinate (1.14 g, 76% yield, ESI (LC/MS positive mode) m/z 828 (M+H); Rt 2.73 min.).

155

Compound 85: No. 5098223

Bis-(5-methyl-2-oxo-[1,3]dioxol-4-ylmethyl) (S)-2-{(E)-(S)-1-[(S)-2-(4-but-2-ynyloxy-phenyl)-1-(5-methyl-2-oxo-[1,3]dioxol-4-ylmethoxycarbonyl)-ethylcarbamoyl]-10-oxo-heptadec-2-enyl}-2-hydroxy-succinate

[Chem. 104]

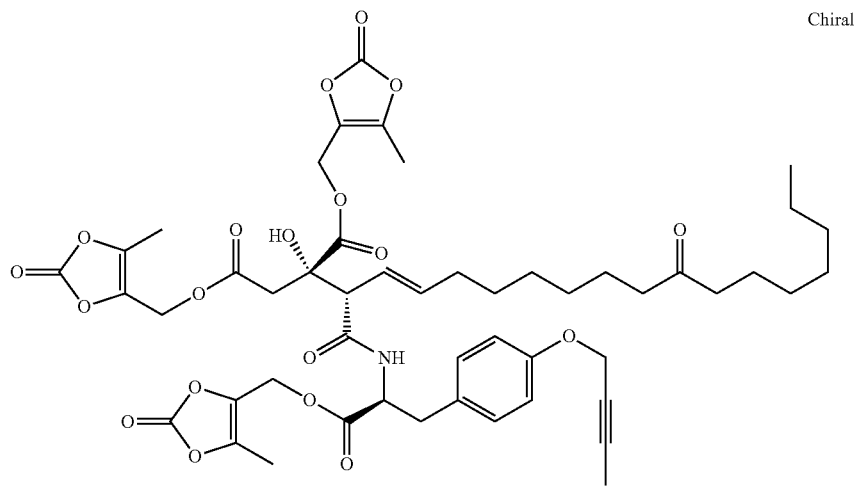

No. 4630808: Compound 93 (50 mg) was dissolved in DMF (2 mL) and, at room temperature, NaHCO₃ (14 mg) and 4-bromomethyl-5-methyl-[1,3]dioxol-2-one (32 mg) were added and the mixture was stirred. After being stirred for 17 hours, the reaction solution was extracted with ethyl acetate. The organic layer was washed with water and a saturated brine in this order, and dried over anhydrous sodium sulfate. The solvent was then distilled off under reduced pressure. The obtained partially purified product was purified by preparative TLC (developing solvent: 10% methanol/dichloromethane) to obtain 7 mg of Compound 85.

The starting material, No. 4630808: Compound 93 was synthesized according to methods described in WO2004/071503, WO2006/088071, and WO2007/000994.

$^1$H-NMR (CDCl$_3$) δ: 0.90 (3H, t, J=6.3 Hz), 1.20-1.36 (14H, m), 1.51-1.55 (4H, m), 1.82 (3H, t, J=2.3 Hz), 1.95-2.10 (2H, m), 2.10-2.21 (9H, m), 2.43 (4H, m), 2.95-3.20 (2H, m), 3.30 (4H, m), 4.60-4.62 (2H, m), 4.89 (6H, s), 4.96 (2H, m), 5.47-5.55 (2H, m), 6.85 (2H, m), 7.07 (2H, m)

ESI (LC/MS positive mode) m/z 981 (M+H); Rt 3.38 min.

156

Compound 86: No. 5098224

1-(5-Methyl-2-oxo-[1,3]dioxol-4-ylmethyl) (S)-2-{(E)-(S)-1-[(S)-2-(4-but-2-ynyloxy-phenyl)-1-(5-methyl-2-oxo-[1,3]dioxol-4-ylmethoxycarbonyl)-ethylcarbamoyl]-10-oxo-heptadec-2-enyl}-2-hydroxy-succinate

[Chem. 105]

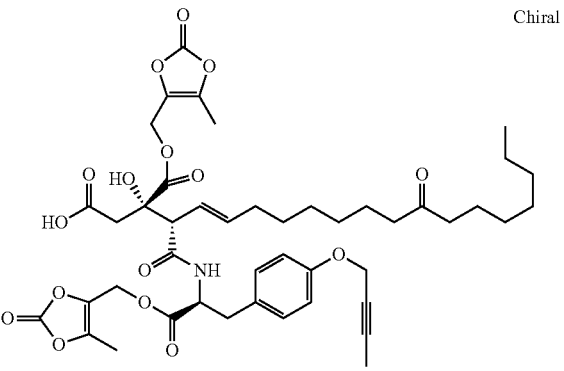

Compound 86: No. 5098224 was isolated and purified in an amount of 3.2 mg as a byproduct by preparative TLC in the synthesis of Compound 93 (No. 4630808).

$^1$H-NMR (CD$_3$CN) δ: 0.87 (3H, t, J=6.4 Hz), 1.25 (14H, m), 1.47 (4H, m), 1.82 (3H, t, J=2.3 Hz), 2.10-2.14 (6H, m), 2.36 (4H, m), 2.51-3.07 (6H, m), 4.26 (1H, s), 4.54-4.62 (4H, m), 4.81-4.94 (4H, m), 5.35-5.77 (2H, m), 6.83 (2H, m), 7.05 (2H, m)

ESI (LC/MS positive mode) m/z 868 (M+H); Rt 3.20 min.

Compound 88: No. 5169040

Bis-(5-methyl-2-oxo-[1,3]dioxol-4-ylmethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 106]

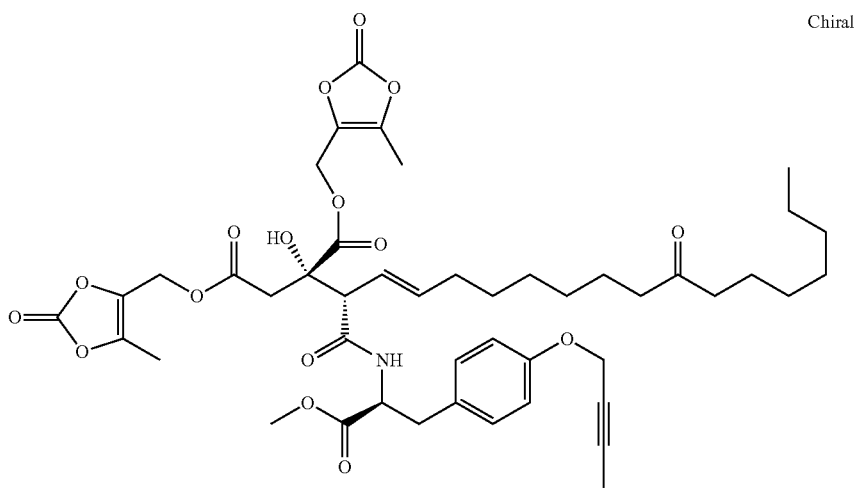

Compound 88 was synthesized by a method similar to the synthesis of compound 85, in which No. 5153510: Compound 87 was dissolved in DMF, and 4-bromomethyl-5-methyl-[1,3]dioxol-2-one was used as an alkylating agent.

$^1$H-NMR (CDCl$_3$) δ: 0.88 (3H, t, J=6.9 Hz), 1.27-1.31 (14H, m) 1.51-1.55 (4H, m), 1.86 (3H, t, J=2.3 Hz), 2.00 (2H, q, J=7.0 Hz), 2.16 (3H, S), 2.18 (3H, s), 2.39 (4H, m), 2.67 (1H, d, J=16 Hz), 2.90 (1H, d, J=16 Hz), 3.01 (1H, dd, J=14.0, 6.6 Hz), 3.09 (1H, dd, J=14.0, 5.5 Hz), 3.13 (1H, d, J=9.6 Hz), 3.74 (3H, s), 4.58 (1H, s), 4.61 (2H, m), 4.95-4.77 (5H, m), 5.52 (1H, dd, J=15.0, 9.6 Hz), 5.63 (1H, dd, J=15.0, 6.6 Hz), 6.45 (1H, d, J=7.8 Hz), 6.85 (2H, m), 7.00 (2H, m)

ESI (LC/MS positive mode) m/z 883 (M+H); Rt 3.42 min.

Synthesis of Compound 96: No. 5153164 and Compound 97: No. 5153165

[Chem. 107]

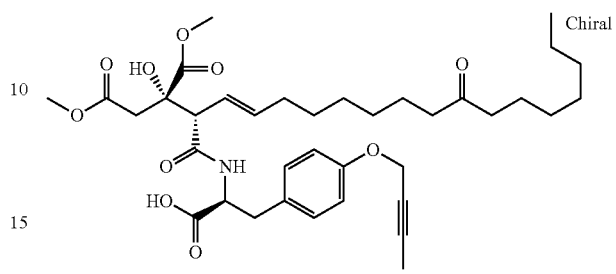

Dimethyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate Compound 93: No. H4630808 (100 mg) was dissolved in DMF (5.0 mL), iodomethane (49 mg) was added in the presence of sodium bicarbonate (28 mg), and the mixture was reacted at room temperature for 16 hours.

The reaction mixture was extracted with ethyl acetate. After washing with water and a saturated brine in this order, the organic layer was dried with anhydrous magnesium sulfate. The solvent was distilled off under reduced pressure. The crude products were isolated by preparative HPLC to obtain Compound 96 and Compound 97. The physicochemical properties of the obtained compounds are as follows.

Compound 96: No. 5153164

¹H-NMR (CD₃CN) δ: 0.88 (3H, t, J=7.0 Hz), 1.19-1.35 (14H, m), 1.44-1.53 (4H, m), 1.82 (3H, t, J=2.3 Hz), 1.95-2.00 (2H, m), 2.05 (1H, m), 2.38 (4H, t, J=7.4 Hz), 2.59 (1H, d, J=15.5 Hz), 2.81 (1H, d=15.5 Hz), 2.91 (2H, m), 3.10 (1H, dd, J=13.8, 4.7 Hz), 3.15 (1H, d, J=9.4 Hz), 3.60 (3H, s), 3.65 (3H, s), 4.55 (2H, m), 4.63 (2H, m), 5.42 (1H, m), 5.54 (1H, m), 6.84 (2H, d, J=8.7 Hz), 7.10 (1H, br.s), 7.12 (2H, d, J=8.3 Hz)

ESI (LC/MS positive mode) m/z 672 (M+H); Rt 3.13 min.

Compound 97: No. 5153165

[Chem. 108]

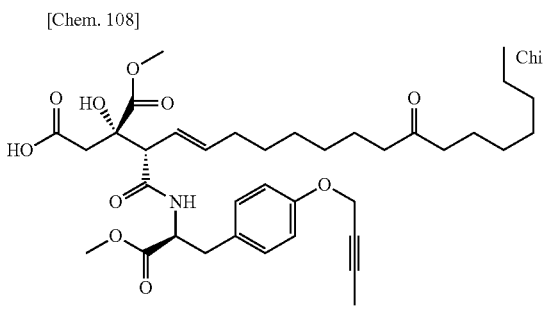

1-Methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate ¹H-NMR (CD₃CN) δ: 0.88 (3H, t, J=7.2 Hz), 1.20-1.33 (14H, m), 1.45-1.53 (4H, m), 1.82 (3H, t, J=2.3 Hz), 1.95-2.00 (2H, m), 2.05 (1H, m), 2.38 (4H, t, J=7.4 Hz), 2.58 (1H, d, J=16.2 Hz), 2.85 (1H, d=16.2 Hz), 2.91 (1H, dd, J=14.0, 8.3 Hz), 3.06 (1H, dd, J=14.2, 5.1 Hz), 3.15 (1H, d, J=9.4 Hz), 3.64 (3H, s), 3.68 (3H, s), 4.58 (2H, m), 4.63 (2H, m), 5.42 (1H, m), 5.55 (1H, m), 6.81 (2H, d, J=8.2 Hz), 7.06 (1H, d, J=8.7 Hz), ESI(LC/MS positive mode) m/z 672 (M+H); Rt 2.90 min.

Compound 98: No. 5153888

[Chem. 109]

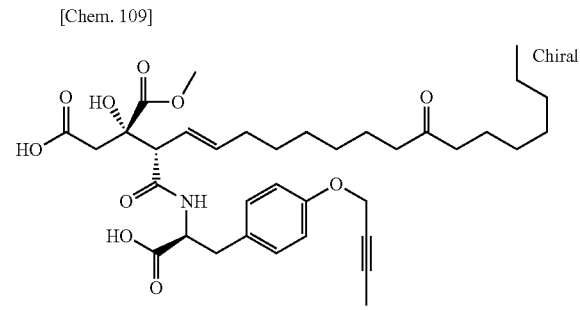

1-Methyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate Step 1

Synthesis of (S)-2-amino-3-(4-but-2-ynyloxy-phenyl)-propionic acid

[Chem. 110]

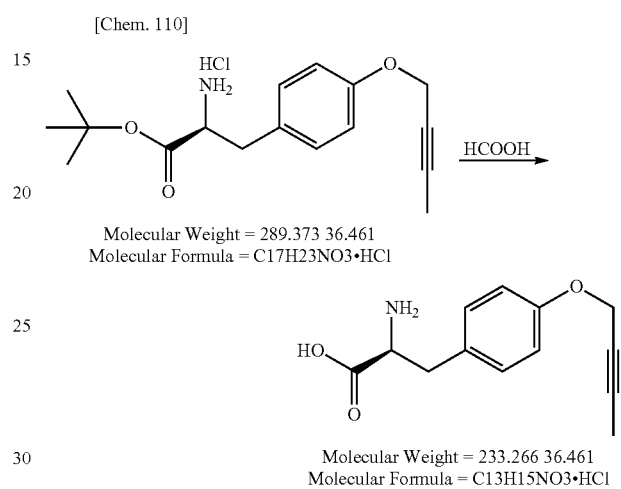

Formic acid (5 mL), and anisole (20 μL) were added to tert-butyl (S)-2-amino-3-(4-but-2-ynyloxy-phenyl)-propionate HCl salt (200 mg) and the mixture was stirred at room temperature for 18 hours. Completion of the reaction was confirmed by detecting the target product by LCMS (LCMS m/z 234 (M+1), Rt 0.83 min.). The reaction solution was concentrated under reduced pressure to obtain (S)-2-amino-3-(4-but-2-ynyloxy-phenyl)-propionic acid (186 mg).

The starting material, tert-butyl (S)-2-amino-3-(4-but-2-ynyloxy-phenyl)-propionate HCl salt was synthesized according to the method described in WO 2005/005372.

Step 2

Synthesis of (S)-2-tert-butoxycarbonylamino-3-(4-but-2-ynyloxy-phenyl)-propionic acid

[Chem. 11]

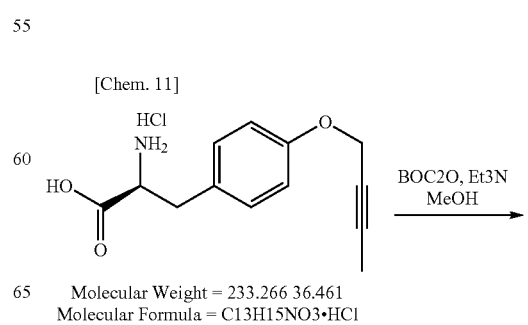

Molecular Weight = 233.266 36.461
Molecular Formula = C13H15NO3•HCl

-continued

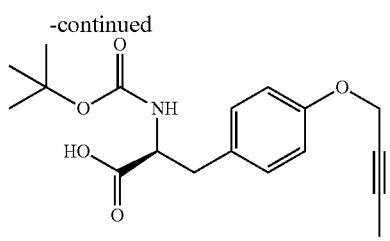

Molecular Weight = 333.382
Molecular Formula = C18H23NO5

(S)-2-Amino-3-(4-but-2-ynyloxy-phenyl)-propionic acid, hydrochloride (186 mg) was suspended in methanol (20 mL), and Et₃N (221 µL) was added. After 5 minutes, di-tert-butyl dicarbonate (331 mg) was added. After 5 minutes of stirring, the reaction solution was concentrated under reduced pressure, dissolved in ethyl acetate and washed with diluted hydrochloric acid and water in this order. The organic layer was dried over anhydrous sodium sulfate. The solvent was distilled off under reduced pressure to obtain (S)-2-tert-butoxycarbonylamino-3-(4-but-2-ynyloxy-phenyl)-propionic acid (369 mg, LCMS m/z 334 (M+1), Rt 2.02 min.).

Step 3

Synthesis of 2-oxo-2-phenyl-ethyl (S)-2-tert-butoxycarbonylamino-3-(4-but-2-ynyloxy-phenyl)-propionate

[Chem. 112]

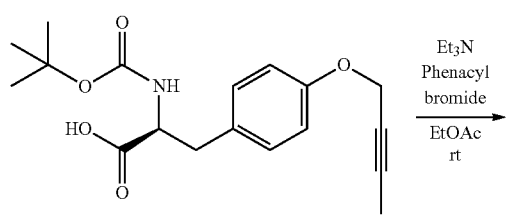

Molecular Weight = 333.382
Molecular Formula = C18H23NO5

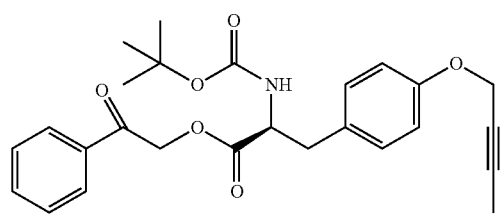

Molecular Weight = 451.516
Molecular Formula = C26H29NO6

(S)-2-tert-Butoxycarbonylamino-3-(4-but-2-ynyloxy-phenyl)-propionic acid (380 mg) was dissolved in ethyl acetate (5.0 mL). A commercially available reagent of 2-bromoacetophenone (164 mg) and Et₃N (115.7 µL) were added and the mixture was stirred at room temperature for 2 days. To the reaction solution was added ethyl acetate and the mixture was washed with water and a saturated brine in this order. The organic layer was dried over anhydrous sodium sulfate. The solvent was distilled off under reduced pressure. The product was purified by recrystallization in 15% ethyl acetate/n-hexane to obtain 2-oxo-2-phenyl-ethyl (S)-2-tert-butoxycarbonylamino-3-(4-but-2-ynyloxy-phenyl)-propionate (277 mg, yield 89% over 2 steps) as colorless crystal (LCMS m/z 452 (M+1) Rt 232 min.).

Step 4

Synthesis of 2-oxo-2-phenyl-ethyl (S)-2-amino-3-(4-but-2-ynyloxy-phenyl)-propionate trifluoroacetate

[Chem. 113]

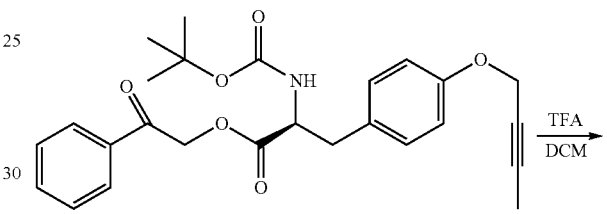

Molecular Weight = 451.516
Molecular Formula = C26H29NO6

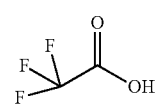

Molecular Weight = 351.400 114.022
Molecular Formula = C21H21NO4•C2HF3O2

2-Oxo-2-phenyl-ethyl (S)-2-tert-butoxycarbonylamino-3-(4-but-2-ynyloxy-phenyl)-propionate (275 mg) was dissolved in methylene chloride (5.0 mL), and trifluoroacetic acid (1.0 mL) was added. The mixture was reacted with stirring for 30 minutes. After completing the reaction, the solvent was distilled off under reduced pressure. An appropriate amount (ca. 5 mL) of toluene was added and the mixture was concentrated in vacuo three times (azeotropic distillation) to obtain 290 mg of the target compound (LCMS m/z 352 (M+1) Rt 1.38 min.).

Step 4

Synthesis of tert-butyl (E)-(2S,3S)-2-[2-(tert-butyl-dimethyl-silanyloxy)-ethyl]-3-[(S)-2-(4-but-2-yny-loxy-phenyl)-1-(2-oxo-2-phenyl-ethoxycarbonyl)-ethylcarbamoyl]-11-(2-heptyl-[1,3]dioxolan-2-yl)-2-hydroxy-undec-4-enoate

[Chem. 114]

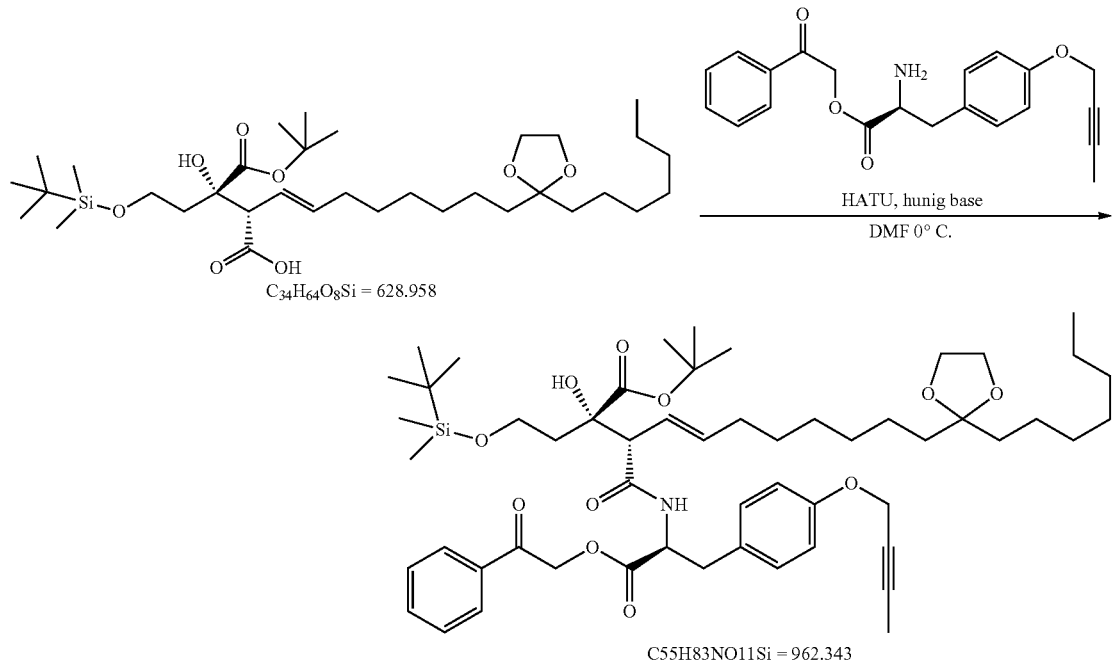

1-tert-Butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (compound A; 300 mg) was dissolved in DMF (5.0 mL) cooled to 5° C., and HATU (185 mg), 2-oxo-2-phenyl-ethyl (S)-2-amino-3-(4-but-2-ynyloxy-phenyl)-propionate, trifluoroacetate (244 mg), and N,N-diisopropylethylamine (322 µL) were added. The mixture was stirred at room temperature for 2.5 hours. Ethyl acetate/n-hexane mixture (1:1) was added to the reaction solution, which was washed with an aqueous solution of 0.5 M KHSO$_4$. The organic layer was dried over anhydrous sodium sulfate. The solvent was then distilled off under reduced pressure. The crude product was purified by silica gel chromatography (elution solvent: 15% ethyl acetate/n-hexane) to obtain 344 mg of the title compound (LCMS m/z 963 (M+1) Rt 3.7 min.).

Step 5

[Chem. 115]

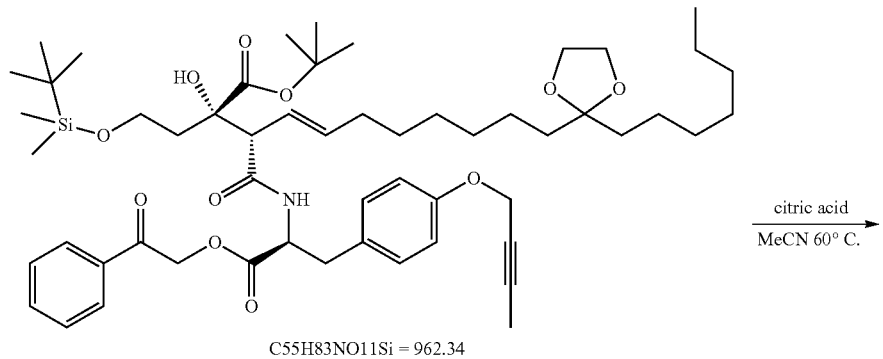

-continued

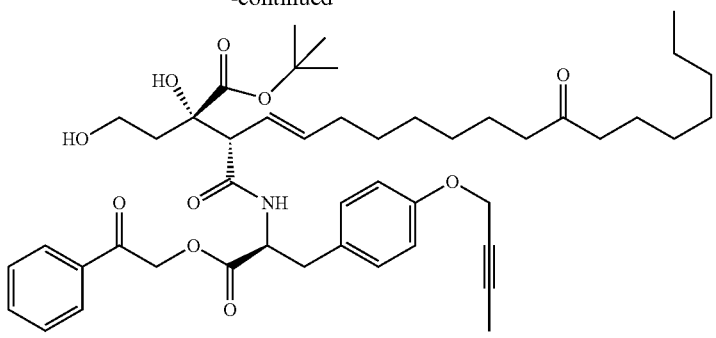

C47H65NO10 = 804.03

Synthesis of 1-tert-butyl (E)-(2S,3S)-3-[(S)-2-(4-but-2-ynyloxy-phenyl)-1-(2-oxo-2-phenyl-ethoxycarbonyl)-ethylcarbamoyl]-2-hydroxy-2-(2-hydroxy-ethyl)-12-oxo-nonadec-4-enoate tert-Butyl (E)-(2S,3S)-3-[(S)-2-(4-but-2-ynyloxy-phenyl)-1-(2-oxo-2-phenyl-ethoxycarbonyl)-ethylcarbamoyl]-2-hydroxy-2-(2-hydroxy-ethyl)-12-oxo-nonadec-4-enoate (116 mg) was dissolved in acetonitrile (5.0 mL), and an aqueous solution of 0.5 M citric acid was added. The mixture was warmed to 60° C. and stirred for 1 hour. After completing the reaction, ethyl acetate was added to the residue, concentrated under reduced pressure, which was washed with water and a saturated brine in this order. The organic layer was dried over anhydrous sodium sulfate and the solvent was distilled off under reduced pressure. The crude product was purified by silica gel chromatography (elution solvent: 30%-60% ethyl acetate/n-hexane) to obtain the title compound (82 mg, LCMS m/z805 (M+1) Rt 3.73 min.).

Step 6

Synthesis of 1-tert-butyl (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate

[Chem. 116]

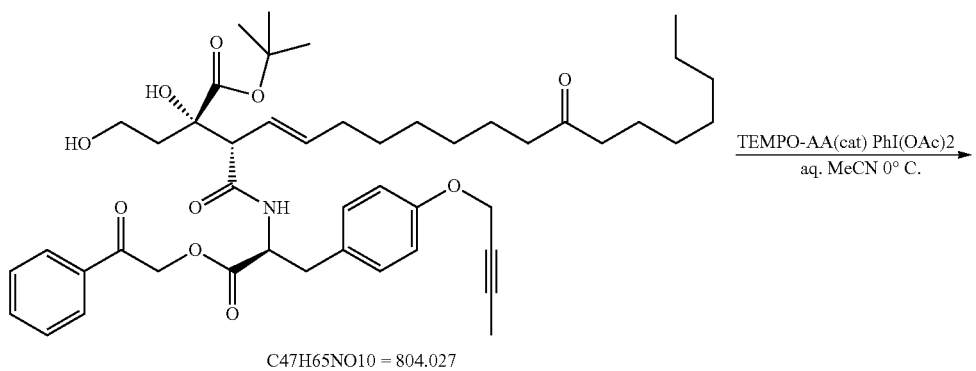

C47H65NO10 = 804.027

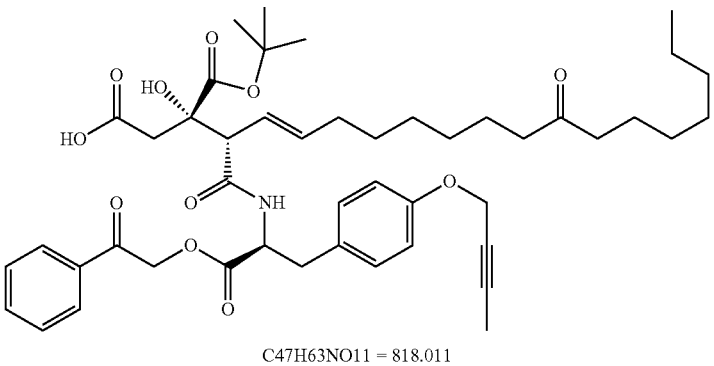

C47H63NO11 = 818.011 tert-Butyl (E)-(2S,3S)-3-[(S)-2-(4-but-2-ynyloxy-phenyl)-1-(2-oxo-2-phenyl-ethoxycarbonyl)-ethylcarbamoyl]-2-hydroxy-2-(2-hydroxy-ethyl)-12-oxo-nonadec-4-enoate (82 mg) was dissolved in acetonitrile (5 mL), and water (0.5 mL) was added. The mixture was stirred well. TEMPO-AA (2.0 mg) commercially available from Wako Pure Chemical Industries, Ltd. and diacetoxyiodobenzene (100 mg) commercially available from Wako Pure Chemical Industries, Ltd. were added and the mixture was stirred at room temperature for 18 hours. After completing the reaction, the mixture was extracted with ethyl acetate. The extract was washed with water, an aqueous solution of sodium thiosulfate, and a saturated brine sequentially.

The organic layer was dried over anhydrous sodium sulfate. The solvent was distilled off under reduced pressure to obtain the title compound (88.3 mg, LCMS m/z 819 (M+1) Rt 3.53 min.).

Step 7

Synthesis of 4-(2-oxo-2-phenyl-ethyl) 1-tert-butyl (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate

[Chem. 117]

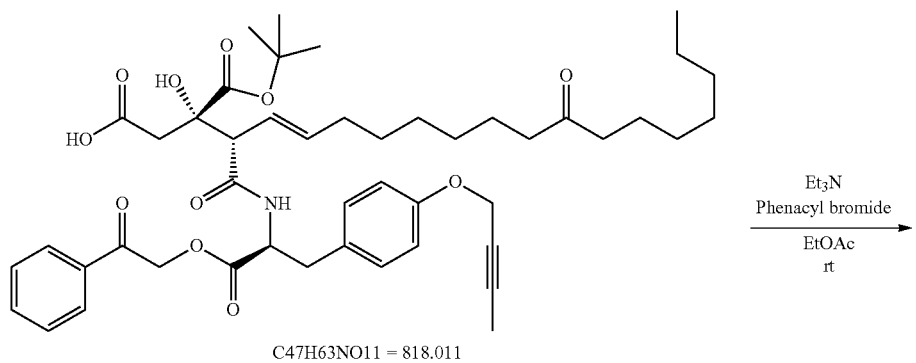

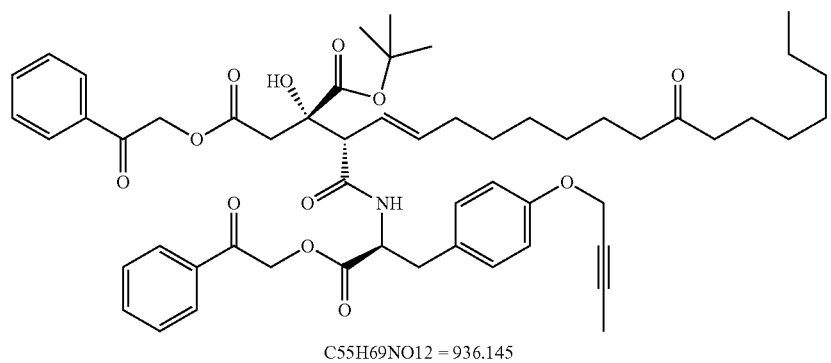

1-tert-Butyl (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate (88.3 mg) was dissolved in ethyl acetate (5 mL), and a commercially available reagent of 2-bromoacetophenone (32 mg) and $Et_3N$ (24 μL) were added. The mixture was stirred at room temperature for 18 hours. To the reaction solution was added ethyl acetate and the mixture was washed with water and a saturated brine in this order. The organic layer was dried over anhydrous sodium sulfate. The solvent was distilled off under reduced pressure. The product was purified by silica gel chromatography (Megabondelute was used, elution solvent 20%-40% ethyl acetate/n-hexane) to obtain 56.6 mg (56%) of the title compound (LCMS m/z 937 (M+1) Rt 3.80 min.).

Step 8

Synthesis of 4-(2-oxo-2-phenyl-ethyl) (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate

[Chem. 118]

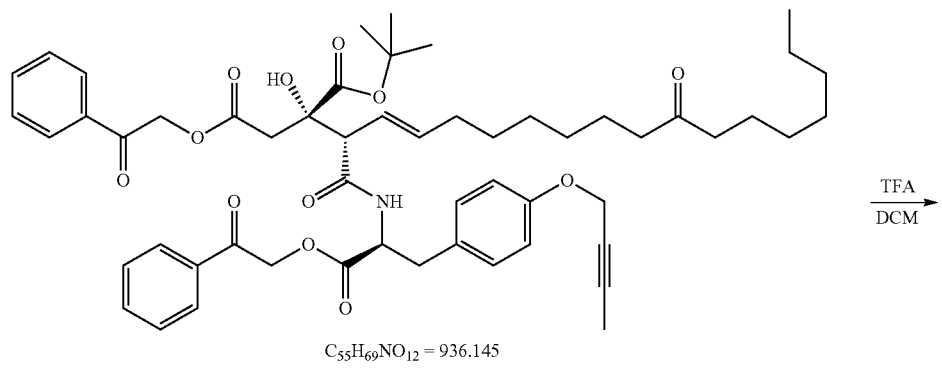

4-(2-Oxo-2-phenyl-ethyl) 1-tert-butyl (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate (56.5 mg) was dissolved in methylene chloride (5 mL), and trifluoroacetic acid (0.2 mL) was added. The mixture was stirred at room temperature for 17 hours. After completing the reaction, the solvent was distilled off under reduced pressure to obtain the title compound (59 mg, quant., LCMS m/z 881 (M+1) Rt 3.43 min.).

Step 9

Synthesis of 1-methyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 119]

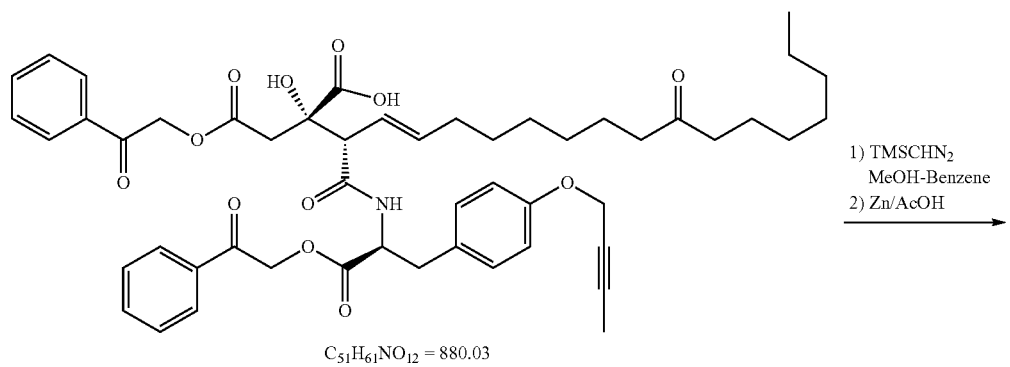

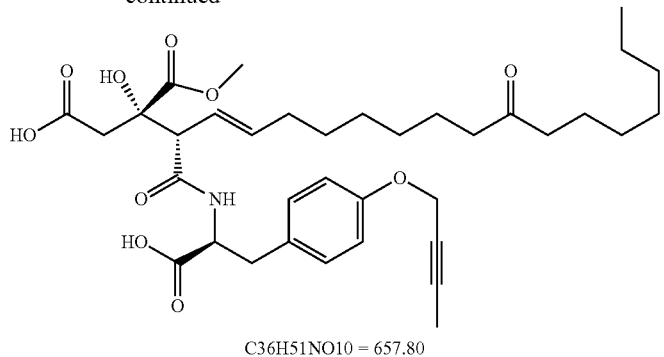

C36H51NO10 = 657.80

4-(2-Oxo-2-phenyl-ethyl) (S)-2-{(E)-(S)-1-[(S)-2-(4-but-2-ynyloxy-phenyl)-1-(2-oxo-2-phenyl-ethoxycarbonyl)-ethylcarbamoyl]-10-oxo-heptadec-2-enyl}-2-hydroxy-succinate (106 mg) was dissolved in methanol (2 mL) and benzene (6 mL) and, at room temperature, a solution of a commercially available reagent of TMS diazomethane in n-hexane (255 μL) was added and stirred for 30 minutes. After completing the reaction, the solvent was distilled off under reduced pressure to obtain the methyl ester form (LCMS m/z 894 (M+1) Rt 3.62 min.). This compound was then dissolved in acetic acid (4.0 mL), and zinc dust (125 mg) was added at room temperature and stirred it for 16 hours. After completing the reaction, the mixture was filtered through a membrane filter. The filtrate was concentrated under reduced pressure. The crude product was purified by preparative TLC (Merck & Co., cat. No. 05715; developing solvent 2% methanol/dichloromethane) to obtain Compound 98 (23 mg).

$^1$H-NMR (CD$_3$OD) δ: 0.89 (3H, t, J=6.6 Hz), 1.21-1.46 (14H, m), 1.46-1.62 (4H, m), 1.81 (3H, t, J=2.1 Hz), 2.03 (2H, m), 2.23 (1H, m), 2.44 (4H, t, J=7.3 Hz), 2.54 (1H, m), 2.80 (1H, d=16.2 Hz), 2.91 (1H, dd, J=14.3, 7.3 Hz), 3.13 (1H, m), 3.68 (3H, s), 4.49 (1H, m), 4.60 (2H, m), 5.54 (2H, m), 6.85 (2H, d, J=8.7 Hz), 7.02 (1H, d, J=7.6 Hz), 7.08 (2H, d, J=8.3 Hz)

ESI (LC/MS positive mode) m/z 658 (M+H); Rt 3.13 min.

Compound 99: No. 5131548

4-Methyl (S)-2-{(E)-(S)-1-[(S)-2-(4-but-2-ynyloxy-phenyl)-1-carboxy-ethylcarbamoyl]-10-oxo-heptadec-2-enyl}-2-hydroxy-succinate

[Chem. 120]

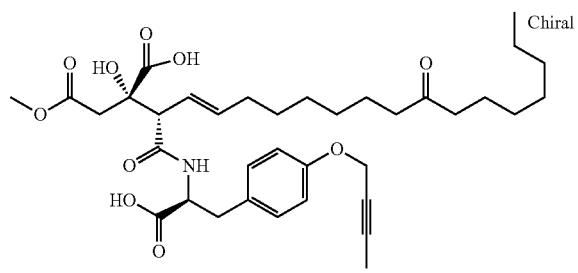

1-tert-Butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate (314 mg, 0.416 mmol) was dissolved in methanol (2.0 mL) and benzene (6.0 mL). The solution was treated at room temperature with a commercially available reagent of TMS-diazomethane (840 μL, 0.5 mmol) for 1 hour. The solvent was distilled off under reduced pressure. The residue was then purified by silica gel chromatography (elution solvent, 30% ethyl acetate/n-hexane) to obtain 315 mg of the triester form as colorless oil (LCMS m/z 792 (M+Na)). This triester form (11 mg) was then reacted with formic acid (1.0 mL) for 1 hour to deprotect the t-butyl group. After the reaction, the solvent was distilled off under reduced pressure to obtain 10 mg (quant.) of the target compound as colorless oil.

The starting material, 1-tert-butyl (S)-2-{(E)-(S)-1-[(S)-1-tert-butoxycarbonyl-2-(4-but-2-ynyloxy-phenyl)-ethylcarbamoyl]-10-oxo-heptadec-2-enyl}-2-hydroxy-succinate was synthesized according to the synthesis of (Compound 29) described in WO2006/088071.

$^1$H-NMR (CD$_3$OD) δ: 0.89 (3H, t, J=6.7 Hz), 1.19-1.40 (14H, m), 1.46-1.62 (4H, m), 1.82 (3H, t, J=2.2 Hz), 1.98 (2H, m), 2.44 (4H, t, J=7.3 Hz), 2.60 (1H, d, J=15.3 Hz), 2.91 (1H, d=16.0 Hz), 2.93 (1H, dd, J=9.2, 5.1 Hz), 3.15 (1H, d, J=4.6 Hz), 3.21 (2H, m), 3.64 (3H, s), 4.54-4.68 (3H, m), 5.53 (2H, m), 6.84 (2H, d, J=8.6 Hz), 7.13 (1H, d, J=8.6 Hz), 8.17 (1H, br. d, J=8.6 Hz)

ESI (LC/MS positive mode) m/z 658 (M+H); Rt 2.92 min.

Compound 26: No. 5324791

Methyl [(S)-3-(4-but-2-ynyloxy-phenyl)-2-[(E)-(S)-2-((S)-7-hydroxy-2,6,9-trioxo-4,6,7,8,9,11-hexahydro-1,3,5,10-tetraoxa-cyclopentacyclodecene-7-yl)-11-oxo-octadec-3-enoylamino]-propionate

[Chem. 121]

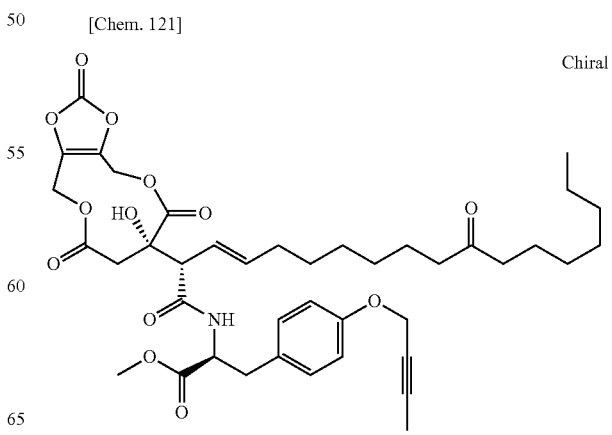

Compound 26 was obtained as colorless oil by a synthetic method similar to that of No. 542661: Compound 64 except that No. 5153510: Compound 87 was used as a substrate and 4,5-bis-bromomethyl-[1,3]dioxol-2-one was used as an alkylating agent.

4,5-Bis-bromomethyl-[1,3]dioxol-2-one (CAS No. 62458-19-9) was synthesized according to the method described in WO 2005/097760.

δ: $^1$H-NMR (CDCl$_3$) δ: 0.88 (3H, t, J=6.8 Hz), 1.19-1.35 (14H, m), 1.53-1.54 (4H, m), 1.87 (3H, t, J=2.1 Hz), 2.03 (2H, dd, J=6.5 Hz, 6.5 Hz), 2.38 (4H, t, J=7.3 Hz), 2.64 (1H, d, J=12.8 Hz), 2.87 (1H, d, J=12.8 Hz), 2.00-3.11 (2H, m), 3.31 (1H, d, J=8.5 Hz), 3.75 (3H, s), 4.60-4.64 (2H, m), 4.75-4.81 (1H, m), 4.92-5.02 (2H, m), 5.11 (1H, s), 5.20 (1H, d, J=15.2 Hz), 5.31 (1H, d, J=15.2 Hz), 5.63-5.77 (2H, m), 6.46 (1H, d, J=7.9 Hz), 6.87 (2H, d, J=8.5 Hz), 6.99 (2H, d, J=8.5 Hz).

ESI (LC/MS positive mode) m/z 768 (M+H); Rt 2.80 min.

Synthesis of No. 5346849: Compound 28 and No. 5346851: Compound 29

No. 5346849: Compound 28 and No. 5346851: Compound 29 were obtained as colorless oil by a synthetic method similar to that of No. 5169356: Compound 2, except that commercially available reagent of benzyl chloromethyl ether was used as an alkylating agent, the reaction was carried out using No. 5153510: Compound 87 as a substrate and regioisomers were separated and purified on a reverse phase column. Supelco, Discovery HS F5 was used as a preparative column.

No. 5346849: Compound 28

1-Benzoyloxymethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 122]

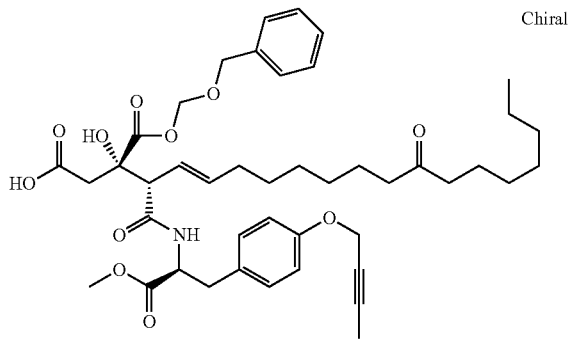

$^1$H-NMR (CDCl$_3$) δ: 0.87 (3H, t, J=6.7 Hz), 1.18-1.34 (14H, m), 1.47-1.60 (4H, m), 1.86 (3H, t, J=2.4 Hz), 1.94-2.01 (2H, m), 2.33-2.40 (4H, m), 2.64 (1H, d, J=15.9 Hz), 2.88 (1H, d, J=15.9 Hz), 3.00 (1H, dd, J=14.0, 6.7 Hz), 3.09 (1H, dd, J=14.0, 5.2 Hz), 3.21 (1H, d, J=9.8 Hz), 3.72 (3H, s), 4.60 (2H, q, J=2.2 Hz), 4.69 (2H, s), 4.77-4.83 (1H, m), 5.37-5.43 (2H, m), 5.53 (1H, dd, J=15.3, 9.8 Hz), 5.63-5.71 (1H, m), 6.68 (1H, d, J=7.9 Hz), 6.86 (2H, d, J=8.5 Hz), 7.04 (2H, d, J=8.5 Hz), 7.28-7.38 (5H, m).

ESI (LC/MS positive mode) ink 778 (M+H); Rt 3.03 min.

No. 5346851: Compound 29

4-Benzoyloxymethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 123]

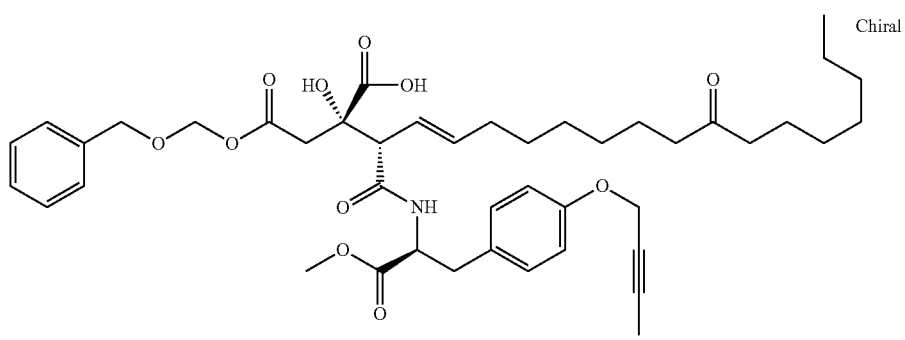

$^1$H-NMR (CDCl$_3$) δ: 0.88 (3H, t, J=6.9 Hz), 1.17-1.42 (14H, m), 1.50-1.63 (4H, m), 1.85 (3H, t, J=2.4 Hz), 1.94-2.13 (2H, m), 2.34-2.53 (4H, m), 2.71 (1H, d, J=15.9 Hz), 2.96-3.14 (3H, m), 3.24 (1H, d, J=9.2 Hz), 3.75 (3H, s), 4.60 (2H, q, J=2.4 Hz), 4.68 (2H, s), 4.79-4.85 (1H, m), 5.33-5.38 (2H, m), 5.52 (1H, dd, J=15.3, 9.8 Hz), 5.59 (1H, br.s), 5.63-5.71 (1H, m), 6.62 (1H, d, J=7.9 Hz), 6.86 (2H, d, J=8.2 Hz), 7.01 (2H, d, J=8.2 Hz), 7.28-7.38 (5H, m).

ESI (LC/MS positive mode) m/z 778 (M+H); Rt 3.03 min.

No. 5455130: Compound 32

Bis(2-oxo-propyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate

[Chem. 124]

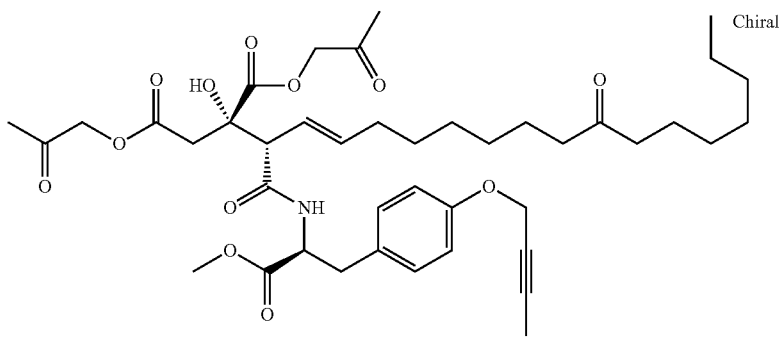

Compound 32 was obtained as colorless oil by a synthetic method similar to that of No. 5336308: Compound 11, except that a commercially available reagent of bromoacetone was used as an alkylating agent.

$^1$H-NMR (CDCl$_3$) δ: 0.88 (3H, t, J=6.9 Hz), 1.21-1.35 (14H, m), 1.49-1.59 (4H, m), 1.86 (3H, t, J=2.2 Hz), 1.99-2.05 (2H, m), 2.16 (6H, s), 2.38 (4H, t, J=7.4 Hz), 2.74 (1H, d, J=16.5 Hz), 2.97-3.14 (3H, m), 3.35 (1H, d, J=8.8 Hz), 3.72 (3H, s), 4.59-4.83 (7H, m), 4.99 (1H, br. s), 5.61 (1H, dd, J=15.4, 6.6 Hz), 5.70 (1H, dt, J=15.4, 6.6 Hz), 6.76 (1H, d, J=7.7 Hz), 6.85 (2H, d, J=8.2 Hz), 7.05 (2H, d, J=8.2 Hz).

ESI (LC/MS positive mode) m/z 770 (M+H); Rt 2.61 min.

No. 5455131: Compound 33

[Chem. 125]

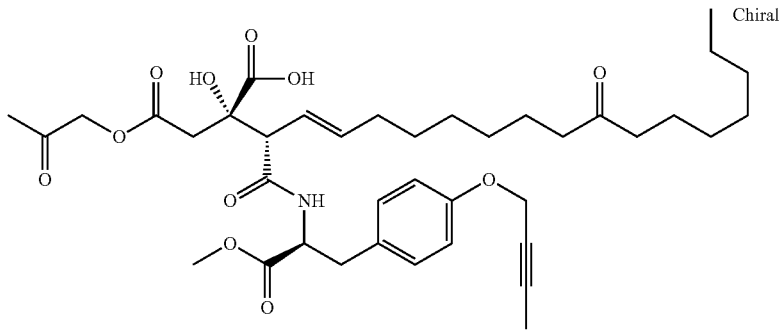

4-(2-Oxo-propyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate Compound 33 was obtained as white solid by a synthetic method similar to that of No. 5444293: Compound 6 except that a commercially available reagent of bromoacetone was used as an alkylating agent.

$^1$H-NMR (CDCl$_3$) δ: 0.88 (3H, t, J=6.9 Hz), 1.17-1.39 (14H, m), 1.50-1.63 (4H, m), 1.86 (3H, t, J=2.2 Hz), 1.93-2.11 (2H, m), 2.16 (3H, s), 2.36-2.51 (4H, m), 2.78 (1H, d, J=15.4 Hz), 2.98-3.14 (3H, m), 3.34 (1H, d, J=9.3 Hz), 3.74 (3H, s), 4.59-4.76 (4H, m), 4.80 (1H, dd, J=14.0, 6.3 Hz), 5.52 (1H, dd, J=15.4, 9.3 Hz), 5.62-5.71 (1H, m), 6.86 (2H, d, J=8.2 Hz), 6.88 (1H, d, J=7.7 Hz), 7.03 (2H, d, J=8.2 Hz).

ESI (LC/MS positive mode) m/z 714 (M+H); Rt 2.34 min.

No. 5456267: Compound 35

[Chem. 126]

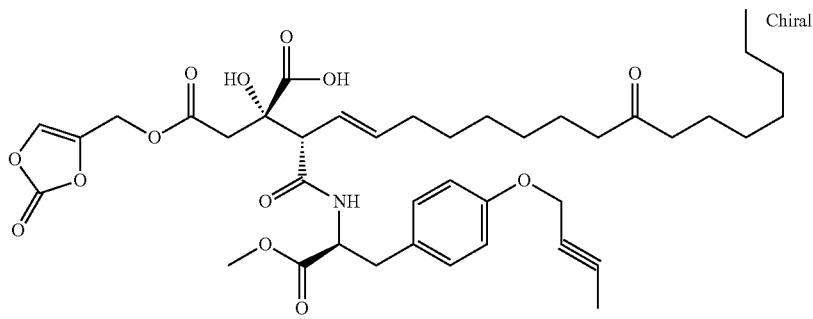

4-(2-Oxo-[1,3]dioxol-4-ylmethyl) (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate Compound 35 was obtained as white solid by a synthetic method similar to that of Compound 6: No. 5444293, except that 4-(bromomethyl)-1,3-dioxol-2-one was used as an alkylating agent.

4-(Bromomethyl)-1,3-dioxol-2-one was synthesized according to the method described in Heterocycles 28 (1) p 93 (1989).

$^1$H-NMR (CDCl$_3$) δ: 0.87 (3H, t, J=6.6 Hz), 1.15-1.42 (14H, m), 1.50-1.65 (4H, m), 1.86 (3H, t, J=2.2 Hz), 1.92-2.14 (2H, m), 2.35-2.54 (4H, m), 2.70 (1H, d, J=15.9 Hz), 2.94-3.14 (3H, m), 3.23 (1H, d, J=9.3 Hz), 3.75 (3H, s), 4.59-4.62 (2H, m), 4.77-4.93 (3H, m), 5.49 (1H, dd, J=14.8, 9.3 Hz), 5.61 (1H, m), 6.68 (1H, d, J=7.7 Hz), 6.85 (2H, d, J=8.8 Hz), 7.00 (2H, d, J=8.8 Hz), 7.13 (1H, s).

ESI (LC/MS positive mode) m/z 756 (M+H); Rt 2.39 min.

Compound 34: No. 5456254

Bis(2-oxo-propyl) (S)-2-{(E)-(S)-1-[(S)-2-(4-but-2-ynyloxy-phenyl)-1-(2-oxo-propoxycarbonyl)-ethylcarbamoyl]-10-oxo-heptadec-2-enyl}-2-hydroxy-succinate

[Chem. 127]

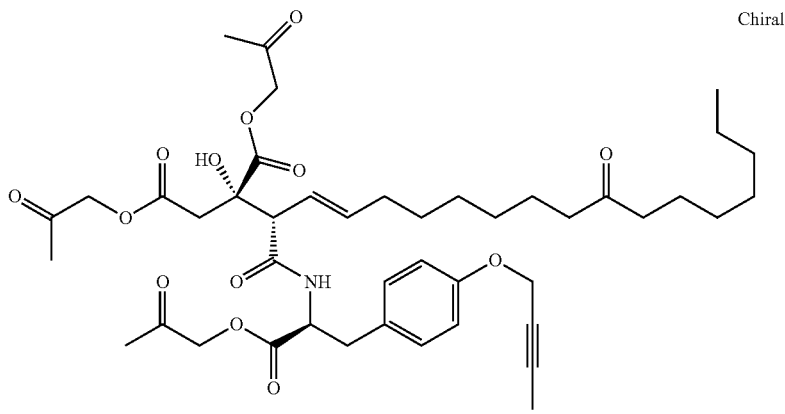

The tri-sodium salt of Compound 93 (No. 4630808) (30 mg, 0.04 mmol) was dissolved in N,N-dimethylformamide (2.5 mL), and bromoacetone (12 μL, 0.14 mmol) was added. The mixture was stirred at room temperature for 18 hours. The reaction solution was diluted in ethyl acetate, and washed three times with water. The separated organic layer was then dried over anhydrous sodium sulfate and filtered.

The filtrate was concentrated, and the residue was purified by silica gel thin layer chromatography (dichloromethane:methanol=15:1) to obtain Compound 34 as white solid at a yield of 73%.

$^1$H-NMR (CDCl$_3$) δ: 0.88 (3H, t, J=6.9 Hz), 1.21-1.34 (14H, m), 1.49-1.59 (4H, m), 1.86 (3H, t, J=2.5 Hz), 1.99 (2H, q, J=6.8 Hz), 2.15 (3H, s), 2.16 (3H, s), 2.16 (3H, s), 2.38 (4H, t, J=7.4 Hz), 2.67 (1H, d, J=16.5 Hz), 3.00-3.09 (2H, m), 3.24 (1H, dd, J=14.3, 5.5 Hz), 3.33 (1H, d, J=8.8 Hz), 4.58-4.80 (8H, m), 4.83-4.90 (1H, m), 4.91 (1H, s), 5.57 (1H, dd, J=15.4, 9.3 Hz), 5.63-5.72 (1H, m), 6.83 (1H, d, J=7.7 Hz), 6.86 (2H, d, J=8.8 Hz), 7.14 (2H, d, J=8.8 Hz).

ESI (LC/MS positive mode) m/z 812 (M+H); Rt 2.50 min.

mL), and trimethylsilyldiazomethane (2 M solution in n-hexane, 1.0 mL) was added to this solution at room temperature, which was stirred overnight. The progress of the reaction was stopped by adding acetic acid. The reaction solution was concentrated in a rotary evaporator. The residue was purified by silica gel column chromatography (n-hexane/dichloromethane/ethyl acetate=10:1:2) to obtain 101 mg of Compound 94 as white solid.

$^1$H-NMR (CDCl$_3$) δ: 0.87 (3H, t, J=6.6 Hz), 1.19-1.35 (14H, m), 1.50-1.59 (4H, m), 1.86 (3H, t, J=2.3 Hz), 1.94-2.05 (2H, m), 2.38 (4H, t, J=7.4 Hz), 2.59 (1H, d, J=16.2 Hz), 2.85 (1H, d, J=16.2 Hz), 2.95-3.18 (3H, m), 3.68 (3H, s), 3.72 (3H, s), 3.76 (3H, s), 4.45 (1H, s), 4.61 (2H, q, J=2.3 Hz), 4.80 (1H, dd, J=12.8, 7.2 Hz), 5.44-5.69 (2H, m), 6.76 (1H, d, J=7.9 Hz), 6.85 (2H, d, J=8.6 Hz), 7.05 (2H, d, J=8.6 Hz).

ESI (LC/MS positive mode) m/z 686 (M+H); Rt 3.17 min.

Compound 94: No. 5005088

Compound 30: No. 5443976

[Chem. 128]

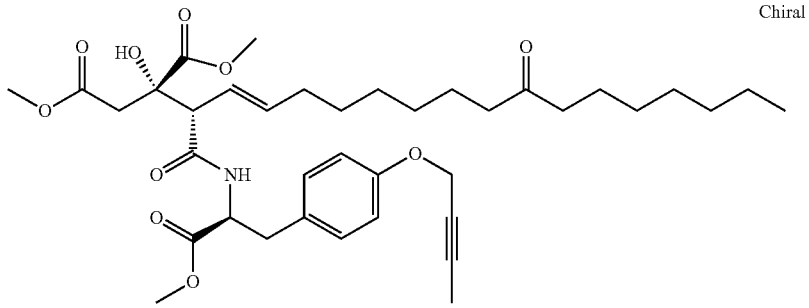

Dimethyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate Compound 93 (No. 4630808; 123 mg, 0.19 mmol) was dissolved in dichloromethane (1.0 mL) and methanol (1.0

[Chem. 129]

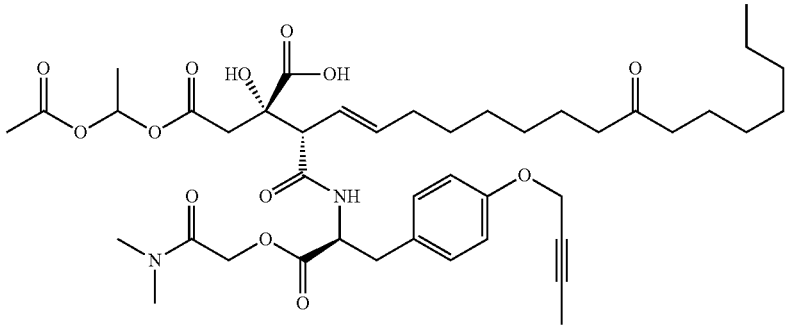

4-(1-Acetoxy-ethyl) (S)-2-{(E)-(S)-1-[(S)-2-(4-but-2-ynyloxy-phenyl)-1-diethylcarbamoylmethoxycarbonyl-ethylcarbamoyl]-10-oxo-heptadec-2-enyl}-2-hydroxy-succinate A diastereomeric mixture of Compound 30 was obtained as white solid by a synthetic method similar to the synthetic method (No. 2) of Compound 1 (No. 5456339) except that, in Step 5 of the synthetic method, No. 5459788 Compound Q was used as the starting material, and 1-bromoethyl acetate was used as an alkylating agent.

$^1$H-NMR (CDCl$_3$, diastereomeric mixture) δ: 0.88 (3H, t, J=6.7 Hz), 1.18-1.38 (14H, m), 1.44-1.49 (3H, m), 1.51-1.62 (4H, m), 1.87 (3H, t, J=2.4 Hz), 1.92-2.08 (5H, m), 2.34-2.50 (4H, m), 2.64-2.71 (1H, m), 2.96-3.25 (10H, m), 4.59-4.95 (5H, m), 5.50 (1H, dd, J=15.3, 8.5 Hz), 5.56-5.65 (1H, m), 6.52-6.63 (1H, m), 6.80-6.89 (3H, m), 7.07-7.12 (2H, m).
ESI (LC/MS positive mode) m/z 871 (M+H); Rt 3.23 min.

Synthetic Scheme of Compound 31

[Chem. 130]

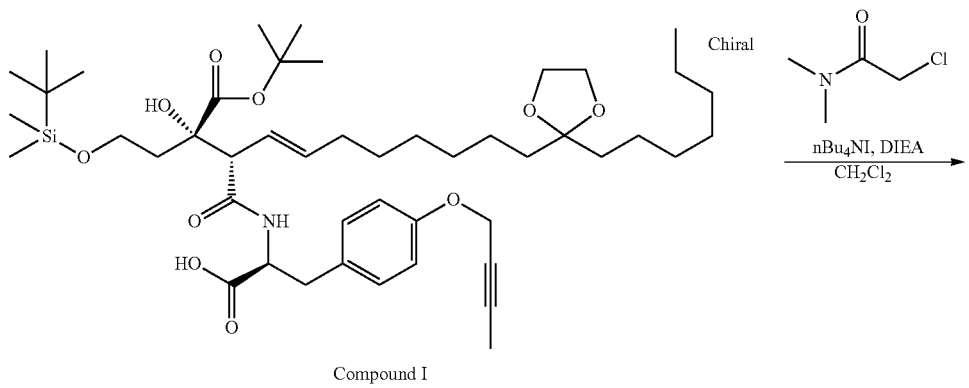

Compound I

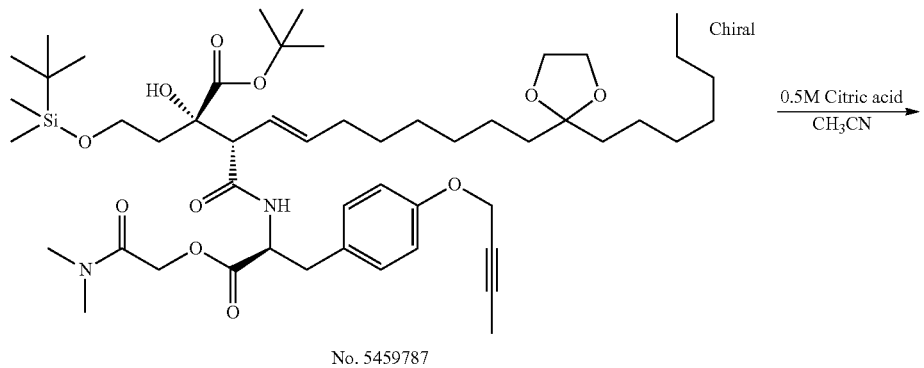

No. 5459787
Compound O

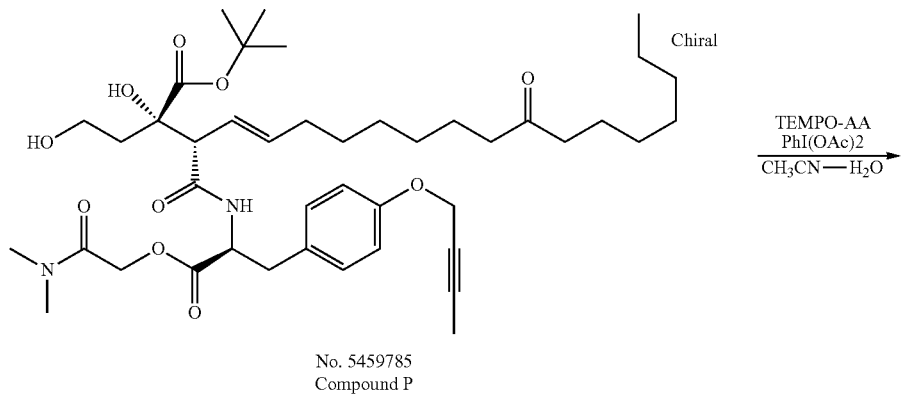

No. 5459785
Compound P

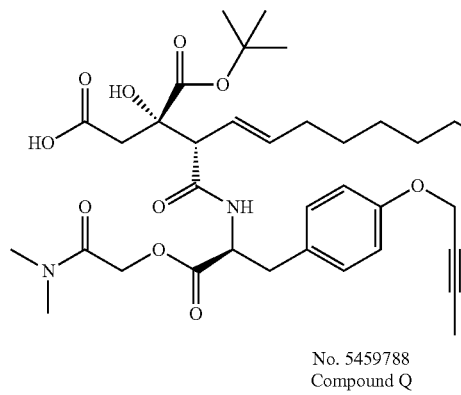

No. 5459788
Compound Q

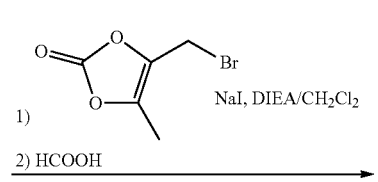

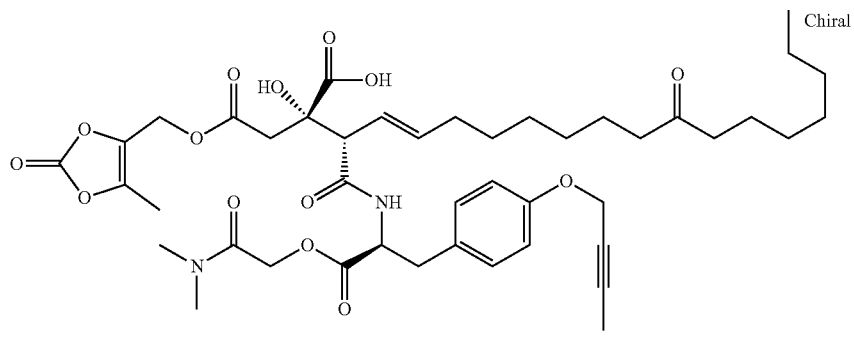

Compound 31

Compound 31: No. 5444030

4-(5-Methyl-2-oxo-[1,3]dioxol-4-ylmethyl) (S)-2-{(E)-(S)-1-[(S)-2-(4-but-2-ynyloxy-phenyl)-1-diethylcarbamoylmethoxycarbonyl-ethylcarbamoyl]-10-oxo-heptadec-2-enyl}-2-hydroxy-succinate No. 5459786: Compound I (11.21 g, 13.279 mmol) was dissolved in dichloromethane (33 mL), and 2-chloro-N,N-dimethylacetamide (1.5 mL, 14.6 mmol), tetrabutylammonium iodide (980 mg, 2.66 mmol), N,N-diisopropylethylamine (2.5 mL) were added in order. The reaction mixture was stirred at 50° C. for 12 hours, cooled to room temperature, then diluted in ethyl acetate (100 mL), and washed with a saturated aqueous solution of ammonium chloride (100 mL). The separated organic layer was dried over anhydrous sodium sulfate and filtered. The filtrate was concentrated under reduced pressure to obtain No. 5459787: Compound O (12.4 g, yield 99% or more, ESI (LC/MS positive mode) m/z 930 (M+H); Rt 4.59 min.).

Obtained No. 5459787: Compound O was converted into Compound P: No. 5459785 (ESI (LC/MS positive mode) m/z 771 (M+H); Rt 2.47 min.) under reaction conditions similar to those in Step 3 of the synthetic method described in Synthetic method (No. 2) of Compound 1 (No. 5456339).

Obtained Compound P: No. 5459785 was then converted into Compound Q: No. 5459788 (ESI (LC/MS positive mode) m/z 785 (M+H); Rt 2.51 min.) by oxidization in reaction conditions similar to those in Step 4 of the synthetic method described in Synthetic method (No. 2) of Compound 1 (No. 5456339).

Compound 31 was obtained as white solid by alkylating and deprotecting the obtained Compound Q: No. 5459788 under conditions similar to those in Steps 5 and 6 of the synthetic method described in Synthetic method (No. 2) of Compound 1 (No. 5456339).

$^1$H-NMR (CDCl$_3$) δ: 0.88 (3H, t, J=6.7 Hz), 1.16-1.38 (14H, m), 1.50-1.61 (4H, m), 1.86 (3H, t, J=2.4 Hz), 1.92-2.07 (2H, m), 2.14 (3H, s), 2.32-2.49 (4H, m), 2.68 (1H, d, J=16.5 Hz), 2.99 (6H, s), 2.99-3.14 (5H, m), 4.60 (2H, q, J=2.2 Hz), 4.69-4.94 (5H, m), 5.48 (1H, dd, J=15.2, 9.1 Hz), 5.60 (1H, dt, J=15.2, 6.6 Hz), 6.71 (1H, d, J=8.5 Hz), 6.85 (2H, d, J=8.5 Hz), 7.09 (2H, d, J=8.5 Hz).

ESI (LC/MS positive mode) m/z 841 (M+H); Rt 2.09 min.

Reference Example 2
Compound No. 5444958 was produced according to the following synthetic scheme.
[Chem. 131]
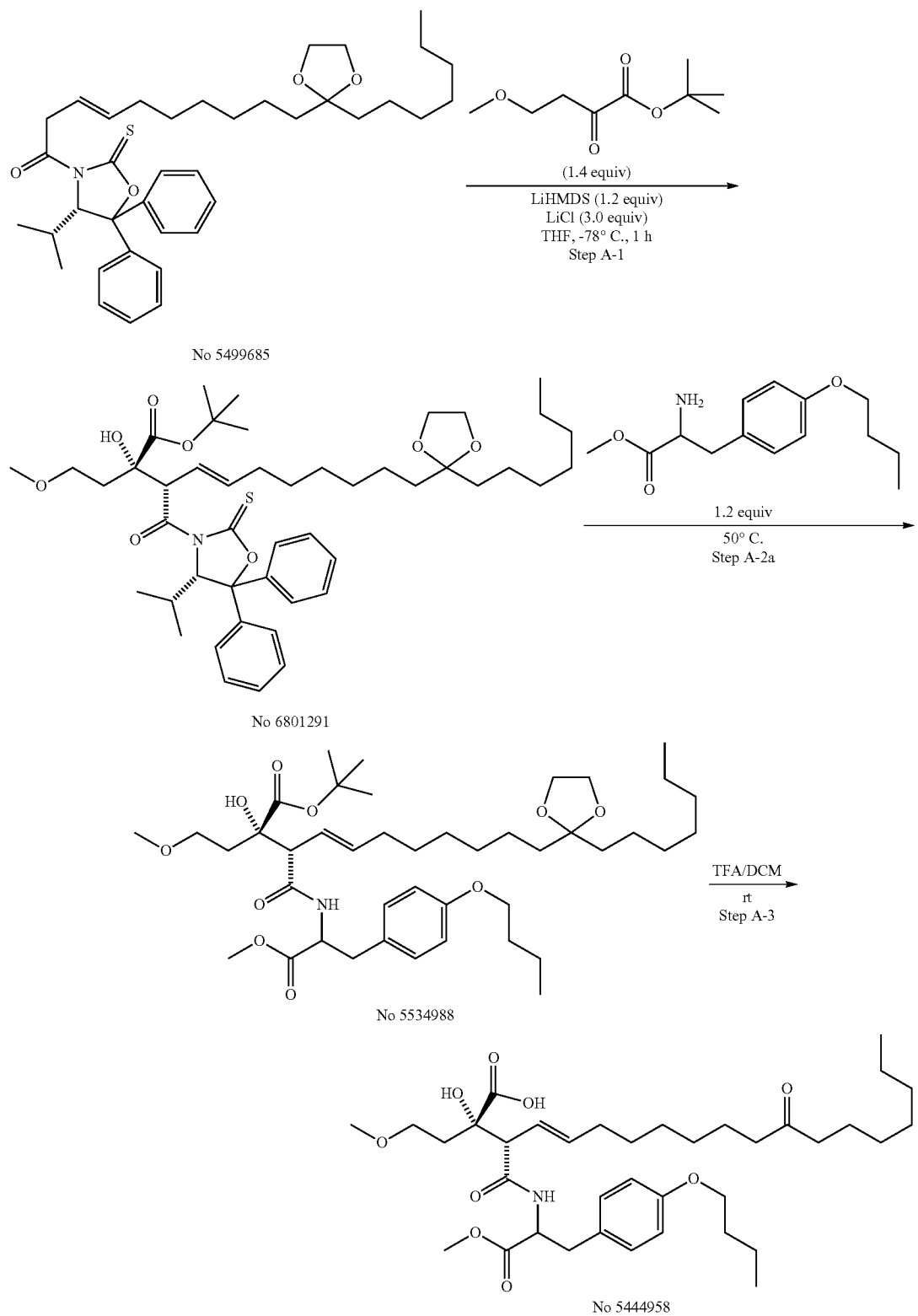

Alternative method: Step A-2b

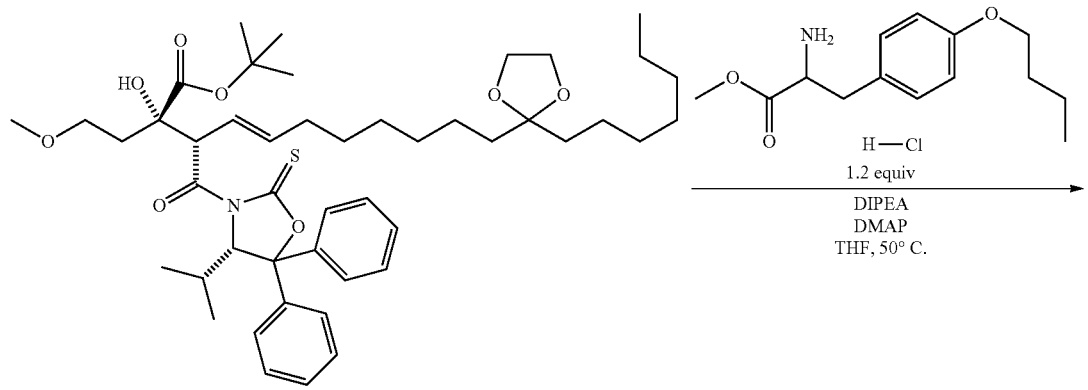

No 6801291

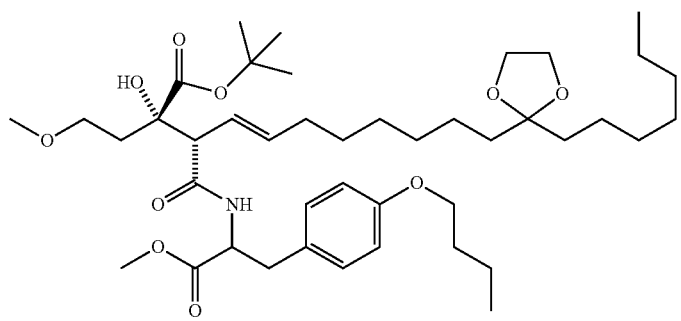

No 5534988

Step A-1

Lithium chloride (5.12 g, 121 mmol) was heat dried with a heat gun under reduced pressure. Under a nitrogen atmosphere, a mixture of No. 5499685 (E)-10-(2-heptyl-[1,3]dioxolan-2-yl)-1-((S)-4-isopropyl-5,5-diphenyl-2-thioxo-oxazolidin-3-yl)-dec-3-en-1-one (25.0 g, 40.3 mmol) and THF (80 mL) was added at room temperature. Further THF (145 mL) was then added to the reaction vessel. The mixture was stirred until it became homogeneous and then cooled to −78° C. Lithium hexamethyldisilazide (1 M solution in THF, 7.74 mL, 7.74 mmol) was added, and the mixture was stirred for 2 h. To the reaction mixture was added dropwise a mixture of tert-butyl 4-methoxy-2-oxo-butyrate (10.6 g, 56.5 mmol) and THF (25 mL) and the mixture was stirred for further 1 hour. To the reaction mixture was added acetic acid (4.61 mL, 80.6 mmol) and the cooling bus was removed. Water was added and the mixture was extracted with ethyl acetate. The organic layer was then washed with water, an aqueous solution of 1% $NaHCO_3$, water, and a saturated brine in this order, and dried over anhydrous sodium sulfate. The solvent was then distilled off under reduced pressure. The resulting residue was purified with SP1 ($SiO_2$ cartridge, 20% ethyl acetate/n-hexane, Rf=0.3) to obtain No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate (25.9 g, 80% yield).

$^1$H-NMR ($CDCl_3$) δ: 0.74 (3H, d, J=6.6 Hz), 0.79 (3H, d, J=7.1 Hz), 0.86-0.89 (3H, m), 1.11 (1H, td, J=9.6, 4.6 Hz), 1.21-1.37 (18H, m), 1.47 (9H, s), 1.54-1.60 (5H, m), 1.72-1.79 (1H, m), 2.01 (2H, dd, J=12.3, 5.7 Hz), 3.08-3.14 (4H, m), 3.24 (1H, td, J=9.0, 5.6 Hz), 3.50 (1H, s), 3.91 (4H, s), 5.57 (1H, dd, J=15.4, 9.3 Hz), 5.68 (1H, d, J=4.0 Hz), 5.89-5.96 (1H, m), 6.15 (1H, d, J=9.3 Hz), 7.27-7.30 (2H, m), 7.34 (4H, t, J=7.7 Hz), 7.45 (2H, t, J=4.2 Hz), 7.50 (2H, d, J=10.1 Hz).

ESI (LC/MS positive mode) m/z 809 (M+H); Rt 1.20 min.

Step A-2a

No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate (26.96 g, 35.84 mmol) and methyl (S)-2-amino-3-(4-butoxy-phenyl)-propionate were dissolved in dichloromethane, and the solvent was distilled off under reduced pressure. The resulting mixture was reacted at 50° C. for 2 days. After confirming the consumption of the starting materials by LCMS, n-hexane was added, and white powder was filtered. The solvent was distilled off under reduced pressure. The residue was purified with SP1 ($SiO_2$ cartridge, 20% ethyl acetate/n-hexane, Rf=0.5) to obtain No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate (21.5 g, 79% yield).

Alternative Method Step A-2b

To No. 6801291 tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate (716 mg, 0.952 mmol) and methyl (S)-2-amino-3-(4-butoxy-phenyl)-propionate hydrochloride (328 mg, 1.14 mmol) was added THF (1.4 mL). N,N-Diisopropylethylamine (829 μL, 4.76 mmol) and DMAP (23.2 mg, 0.190 mmol) were added to the reaction mixture, which was reacted at 50° C. with stirring for 1 day. After confirming by LCMS that 95% or more of the starting compound had been converted, ethyl acetate and an aqueous solution of 1 M HCl were added, and the mixture was extracted with ethyl acetate. The organic layer was washed with an aqueous solution (pH 8.3) of 2% $NaHCO_3$, a saturated brine, a saturated aqueous solution of ammonium chloride, and a saturated brine in this order, and dried over anhydrous sodium sulfate. The solvent was then distilled out of the filtrate under reduced pressure. The resulting residue was purified with SP1 ($SiO_2$ cartridge, 20% ethyl acetate/dichloromethane, Rf=0.5) to obtain No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate (559 mg, 77% yield).

$^1$H-NMR ($CDCl_3$) δ: 0.88 (3H, t, J=7.1 Hz), 0.97 (3H, t, J=7.5 Hz), 1.21-1.37 (18H, m), 1.42 (9H, s), 1.49 (2H, dd, J=15.0, 7.5 Hz), 1.55-1.61 (6H, m), 1.75 (2H, dt, J=15.7, 6.1 Hz), 1.95-2.02 (2H, m), 2.97 (1H, dd, J=14.1, 7.5 Hz), 3.08-3.15 (2H, m), 3.21 (3H, s), 3.28 (1H, dt, J=12.3, 3.7 Hz), 3.36 (1H, td, J=9.0, 4.9 Hz), 3.70 (3H, s), 3.88-3.96 (6H, m), 4.81 (1H, td, J=7.9, 5.3 Hz), 5.45 (1H, dd, J=15.2, 9.5 Hz), 5.66 (1H, dt, J=15.4, 6.6 Hz), 6.78 (2H, d, J=8.8 Hz), 7.05 (3H, d, J=9.3 Hz).

ESI (LC/MS positive mode) m/z 763 (M+H); Rt 0.83 min.

Step A-3

No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate (21.5 g, 28.2 mmol) was dissolved in dichloromethane (215 mL), and trifluoroacetic acid (215 mL) was added. The mixture was stirred at room temperature for 2 hours. After confirming the consumption of the starting materials by LCMS, the solvent was distilled off under reduced pressure. Ethyl acetate was added to the residue, which was washed with water, an aqueous solution of 2% $NaHCO_3$ (to about pH 7.3), water, a saturated aqueous solution of ammonium chloride, and a saturated brine, and dried over anhydrous sodium sulfate. The solvent was then distilled off under reduced pressure. The residue was purified with SP1 (Diol cartridge, 50% ethyl acetate/n-hexane, Rf=0.4) to obtain No. 5444958, (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoic acid (11.1 g, 61% yield, white powder).

$^1$H-NMR ($CD_3OD$) δ: 0.89 (3H, t, J=6.8 Hz), 0.98 (3H, t, J=7.5 Hz), 1.30 (14H, dd, J=21.8, 9.5 Hz), 1.45-1.57 (6H, m), 1.65-1.78 (3H, m), 1.96 (2H, dd, J=13.0, 6.0 Hz), 2.02-2.09 (1H, m), 2.43 (4H, td, J=7.4, 1.6 Hz), 2.89 (1H, dd, J=14.1, 9.3 Hz), 3.09-3.13 (1H, m), 3.22 (1H, d, J=8.4 Hz), 3.24 (3H, s), 3.41 (2H, ft, J=10.1, 2.6 Hz), 3.70 (3H, s), 3.93 (2H, t, J=6.4 Hz), 4.64 (1H, dd, J=9.3, 5.3 Hz), 5.45-5.60 (2H, m), 6.79 (2H, d, J=8.4 Hz), 7.08 (2H, d, J=8.8 Hz).

ESI (LC/MS positive mode) m/z 662 (M+H); Rt 0.67 min.

Alternative Method: Step A-4

[Chem. 132]

Step A-4

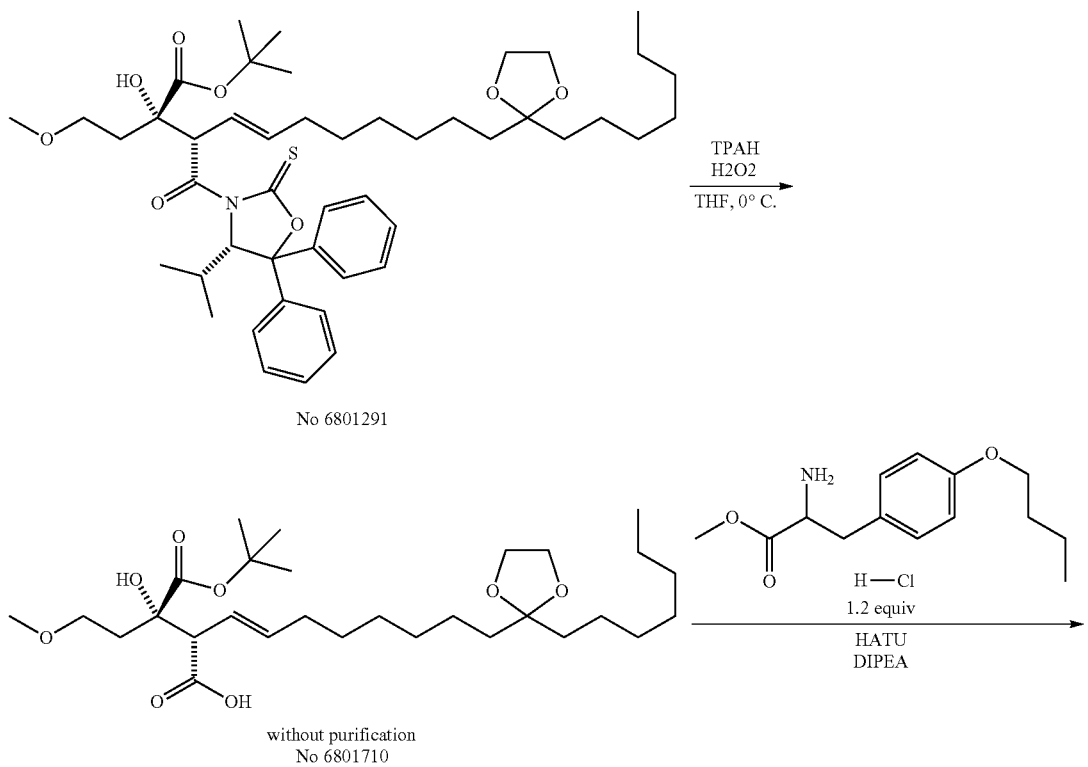

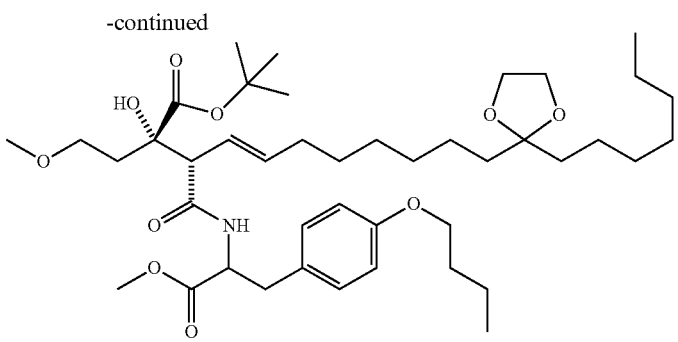

No 5534988

No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate (25.03 g, 31.0 mmol) was dissolved in THF (500 mL), and the mixture was cooled to 4° C. To the mixture were added an aqueous solution of 35% hydrogen peroxide (6.02 mL, 61.9 mmol) and tetrapropylammonium hydroxide (40% aqueous solution, 31.5 mL, 61.9 mmol). After the mixture was stirred for 1 hour, the consumption of the starting materials was confirmed by LCMS. An aqueous solution of 20% sodium thiosulfate was then added and the mixture was stirred well. Ethyl acetate and an aqueous solution of 5% citric acid (about pH 5.3) were added, and the mixture was extracted with ethyl acetate. The organic layer was washed with water and a saturated brine, and then dried over anhydrous magnesium sulfate. The solvent was distilled out of the filtrate under reduced pressure. n-Hexane was added to the resulting residue and the mixture was stirred for 30 minutes. The resulting white solid was filtered out. The solvent was distilled out of the filtrate under reduced pressure to obtain No. 6801710, 1-tert-butyl (2S,3S)-3-[(E)-8-(2-heptyl-[1,3]dioxolan-2-yl)-oct-1-enyl]-2-hydroxy-2-(2-methoxy-ethyl)-succinate (yield 99% or more, incl. chiral AUX and other impurities, 21.07 g, ESI (LC/MS positive mode) m/z 529 (M+H); Rt 0.67 min.). Obtained No. 6801710, 1-tert-butyl (2S,3S)-3-[(E)-8-(2-heptyl-[1,3]dioxolan-2-yl)-oct-1-enyl]-2-hydroxy-2-(2-methoxy-ethyl)-succinate was used in the next reaction without purification.

To No. 6801710, 1-tert-butyl (2S,3S)-3-[(E)-8-(2-heptyl-[1,3]dioxolan-2-yl)-oct-1-enyl]-2-hydroxy-2-(2-methoxy-ethyl)-succinate (21.07 g, 31.9 mmol as the content was 80%) was added DMF (217 mL), and the mixture was cooled to 4° C. To the reaction solution were added methyl (S)-2-amino-3-(4-butoxy-phenyl)-propionate hydrochloride (11.3 g, 39.4 mmol), 1-[bis(dimethylamino)methyliumyl]-1H-1,2,3-triazolo[4,5-B]pyridine-3-oxide hexafluorophosphate (18.7 g, 49.3 mmol), and N,N-diisopropylethylamine (28.6 mL, 164 mmol), and the mixture was stirred for 30 minutes. The consumption of the starting materials was then confirmed by LCMS. An aqueous solution of 0.5 M KHSO$_4$ was added, and the mixture was extracted with ethyl acetate. The organic layer was washed with an aqueous solution of 0.5 M KHSO$_4$ and a saturated brine, and dried over anhydrous sodium sulfate. The solvent was distilled off under reduced pressure. The residue was purified with SP1 (SiO$_2$ cartridge, 20% ethyl acetate/n-hexane, Rf=0.2) to obtain No. 5534988, tert-butyl (E)-(2S,3S)-3-[(S)-2-(4-butoxy-phenyl)-1-methoxycarbonyl-ethylcarbamoyl]-11-(2-hept yl-[1,3]dioxolan-2-yl)-2-hydroxy-2-(2-methoxy-ethyl)-undec-4-enoate (12.0 g, 51% yield, white solid).

Synthetic Method of #39, No. 5444958, Alternative Method

Synthesis of (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoic acid Step 1

Synthesis of (2S,3S,E)-tert-butyl 3-((S)-3-(4-butoxyphenyl)-1-methoxy-1-oxopropan-2-ylcarbamoyl)-2-hydroxy-2-(2-methoxy-ethyl)-12-oxo-nonadec-4-enoate

[Chem. 133]

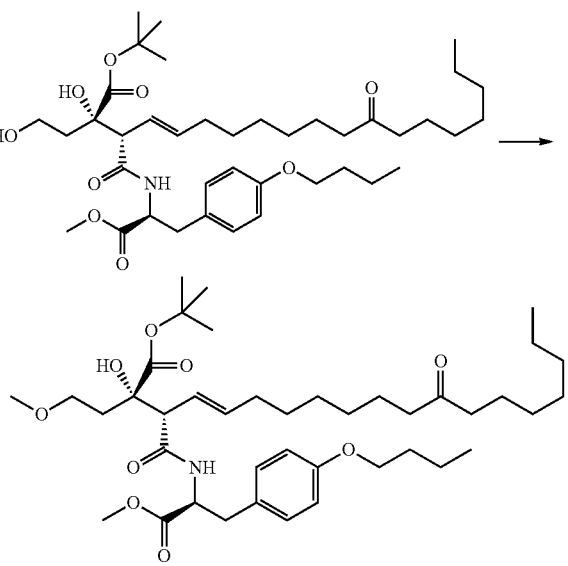

(2S,3S,E)-tert-Butyl 3-((S)-3-(4-butoxyphenyl)-1-methoxy-1-oxopropan-2-ylcarbamoyl)-2-hydroxy-2-(2-hydroxy-ethyl)-12-oxo-nonadec-4-enoate (90 mg, 0.128 mmol), obtained in Step 2 of the synthesis of #37, was dissolved in dichloromethane and the mixture was cooled to 0° C. 2,6-Dimethylpyridine (16 μL, 0.14 mmol) and trimethyloxonium tetrafluoroborate (42.5 mg, 0.287 mmol) were added. The mixture was stirred at 0° C. overnight. The progress of the reaction was then stopped by adding a saturated aqueous solution of ammonium chloride. The mixture was extracted with ethyl acetate. The separated organic layer was dried over anhydrous sodium sulfate, filtered, and concentrated. The resulting residue was purified by silica gel thin layer chromatography (n-hexane:ethyl acetate=3:2) to obtain the target compound at a yield of 65% as light yellow oil.

ESI (LC/MS positive mode) m/z 718 (M+H); Rt 4.31 min.

Step 2 #39, No. 5444958

Synthesis of (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoic acid

[Chem. 134]

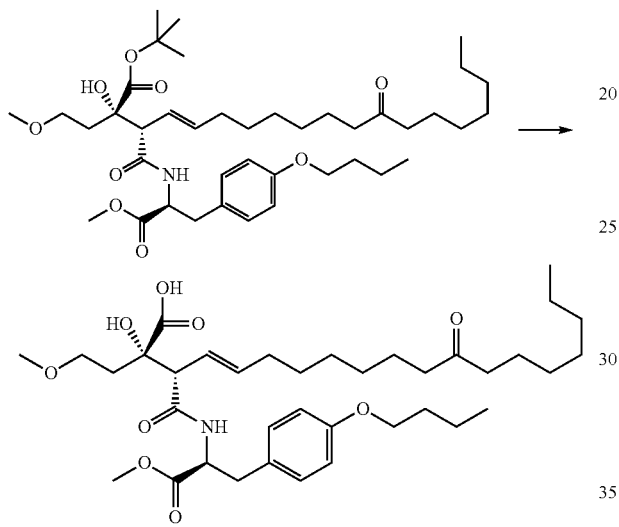

(2S,3S,E)-tert-Butyl 3-((S)-3-(4-butoxyphenyl)-1-methoxy-1-oxopropan-2-ylcarbamoyl)-2-hydroxy-2-(2-methoxy-ethyl)-12-oxo-nonadec-4-enoate (14.4 mg), obtained in Step 1, was dissolved in formic acid (1.0 mL) and the mixture was stirred for a whole day and night at room temperature. The reaction solution was then concentrated. The residue was dissolved in ethyl acetate and concentrated again. The resulting residue was purified by diol thin layer chromatography (dichloromethane:methanol=40:1) to obtain the target compound as white solid at a yield of 78%.

$^1$H-NMR (CDCl$_3$) δ: 0.88 (3H, t, J=6.7 Hz), 0.97 (3H, t, J=7.3 Hz), 1.13-1.37 (14H, m), 1.43-1.61 (6H, m), 1.71-1.84 (3H, m), 1.93-2.17 (3H, m), 2.35-2.48 (4H, m), 3.02 (1H, dd, J=14.0, 6.1 Hz), 3.08 (1H, dd, J=14.0, 5.5 Hz), 3.17 (1H, d, J=9.1 Hz), 3.29 (3H, s), 3.42-3.57 (2H, m), 3.73 (3H, s), 3.92 (2H, t, J=6.4 Hz), 4.77-4.83 (1H, m), 5.50-5.68 (2H, m), 6.62 (1H, d, J=7.9 Hz), 6.78 (2H, d, J=8.5 Hz), 6.98 (2H, d, J=8.5 Hz).

ESI (LC/MS positive mode) m/z 662 (M+H); Rt 3.11 min.

37, No. 5444031

Synthesis of (S)-2-{(E)-(S)-1-[(S)-2-(4-butoxy-phenyl)-1-methoxycarbonyl-ethylcarbamoyl]-10-oxo-heptadec-2-enyl}-2-hydroxy-succinic acid Step 1

[Chem. 135]

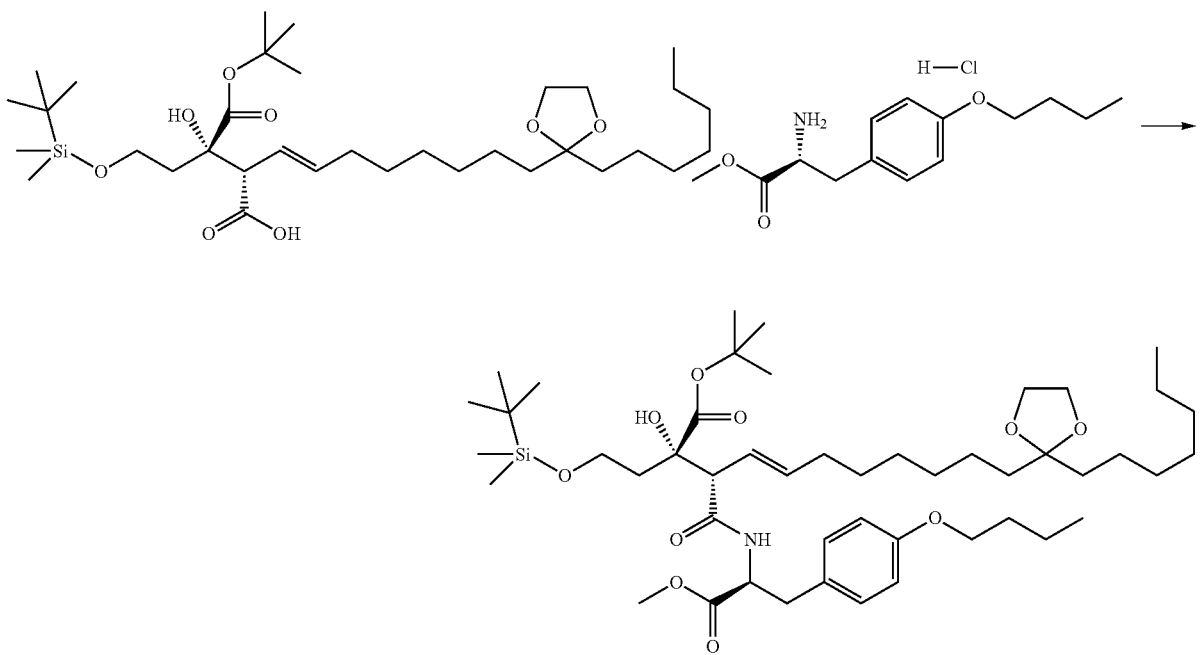

Synthesis of (2S,3S,E)-tert-butyl 3-((S)-3-(4-butoxyphenyl)-1-methoxy-1-oxopropan-2-ylcarbamoyl)-2-(2-(tert-butyldimethylsilyloxy)ethyl)-11-(2-heptyl-1,3-dioxolan-2-yl)-2-hydroxyundec-4-enoate (S,E)-2-((S)-1-tert-Butoxy-4-(tert-butyldimethylsilyloxy)-2-hydroxy-1-oxobutan-2-yl)-10-(2-heptyl-1,3-dioxolan-2-yl)dec-3-enoic acid (5.464 g, 8.69 mmol) and (S)-methyl 2-amino-3-(4-butoxyphenyl) propanoate hydrochloride (2.5 g, 8.687 mmol) were dissolved in N,N-dimethylformamide (60 mL), and 1H-benzo[d][1,2,3]triazol-1-ol hydrate (4 g, 26 mmol), WSC hydrochloride (5 g, 26 mmol), and N-ethyl-N-isopropylpropane-2-amine (9 mL) were added in order. The reaction mixture was stirred at room temperature overnight, diluted in water (200 mL), and extracted with ethyl acetate (250 mL). The separated organic layer was washed three times with a diluted aqueous solution of ammonium chloride (200 mL), washed with a saturated aqueous solution of sodium bicarbonate, then dried over anhydrous sodium sulfate, filtered, and then concentrated. The resulting residue was used in the next step.

ESI (LC/MS positive mode) m/z 862 (M+H); Rt 5.73 min.

Step 2

Synthesis of (2S,3S,E)-tert-butyl 3-((S)-3-(4-butoxyphenyl)-1-methoxy-1-oxopropan-2-ylcarbamoyl)-2-hydroxy-2-(2-hydroxyethyl)-12-oxo-nonadec-4-enoate

[Chem. 136]

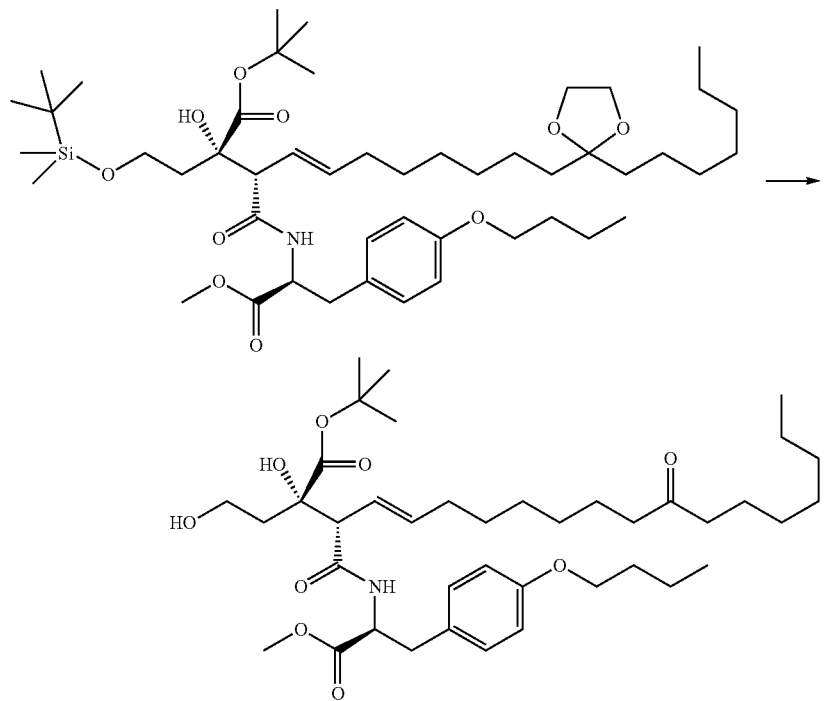

Partially purified (2S,3S,E)-tert-butyl 3-((S)-3-(4-butoxyphenyl)-1-methoxy-1-oxopropan-2-ylcarbamoyl)-2-(2-(tert-butyldimethylsilyloxy)ethyl)-11-(2-heptyl-1,3-dioxolan-2-yl)-2-hydroxyundec-4-enoate, obtained in Step 1, was dissolved in acetonitrile (90 mL) and an aqueous solution of 0.5 M citric acid (44 mL) was added. The mixture was stirred at 80° C. for 4 hours. The flask was cooled to room temperature. The reaction mixture was then diluted in water, and extracted with ethyl acetate. The separated organic layer was further washed with water and a saturated brine in order, dried over anhydrous sodium sulfate, and filtered. The filtrate was concentrated and the resulting residue was purified by silica gel column chromatography (n-hexane/ethyl acetate) to obtain the target compound (2.543 g) as white amorphous.

ESI (LC/MS positive mode) m/z 704 (M+H); Rt 3.43 min.

Step 3

Synthesis of (3S,4S,E)-3-(tert-butoxycarbonyl)-4-((S)-3-(4-butoxyphenyl)-1-methoxy-1-oxopropan-2-ylcarbamoyl)-3-hydroxy-13-oxoicos-5-enoic acid

[Chem. 137]

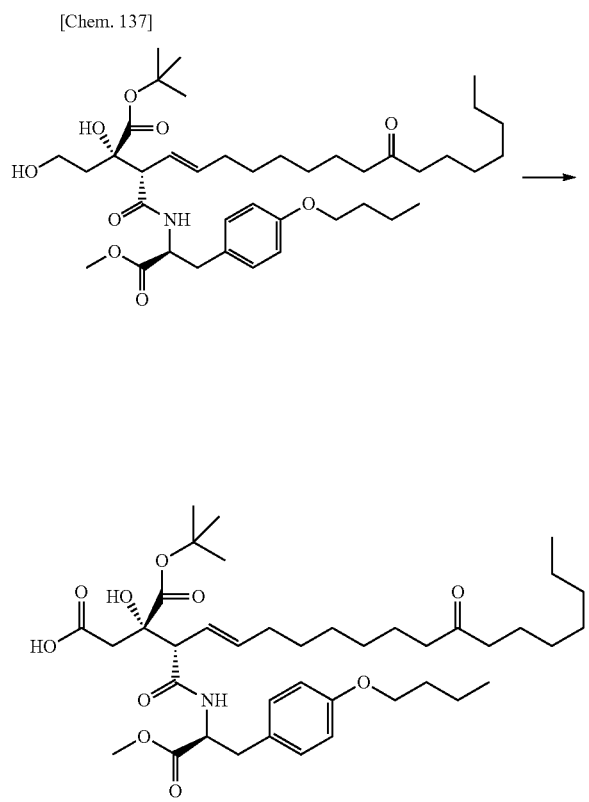

(2S,3S,E)-tert-Butyl 3-((S)-3-(4-butoxyphenyl)-1-methoxy-1-oxopropan-2-ylcarbamoyl)-2-hydroxy-2-(2-hydroxyethyl)-12-oxo-nonadec-4-enoate (237 mg, 0.34 mmol), obtained in Step 2, was dissolved in acetonitrile (3.6 mL) and water (0.7 mL). To this solution were added 2,2,6,6-tetramethyl-4-acetamidepiperidine-1-oxyl (14 mg, 0.0673 mmol) and iodobenzene diacetate (217 mg, 0.673 mmol), and the mixture was stirred at room temperature overnight. The reaction solution was concentrated, then diluted in ethyl acetate, and washed with an aqueous solution of citric acid and an aqueous solution of sodium sulfite in order. The organic layer was washed with water and a saturated brine in order, and dried over anhydrous sodium sulfate. The filtrate was concentrated and the resulting residue was purified by diol column chromatography (dichloromethane/methanol) to obtain the target compound quantitatively as colorless oil.

ESI (LC/MS positive mode) m/z 718 (M+H); Rt 3.50 min.

Step 4, Synthesis of #37, No. 5444031

(S)-2-{(E)-(S)-1-[(S)-2-(4-butoxy-phenyl)-1-methoxycarbonyl-ethylcarbamoyl]-10-oxo-heptadec-2-enyl}-2-hydroxy-succinic acid

[Chem. 138]

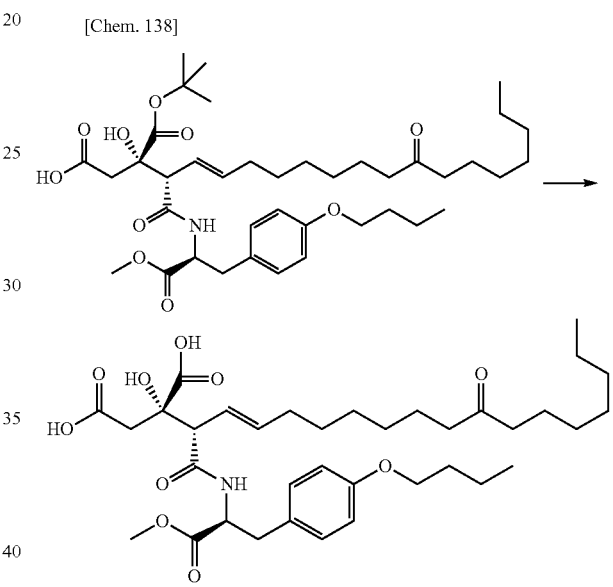

(3S,4S,E)-3-(tert-Butoxycarbonyl)-4-((S)-3-(4-butoxyphenyl)-1-methoxy-1-oxopropan-2-ylcarbamoyl)-3-hydroxy-13-oxoicos-5-enoic acid (25 mg, 0.035 mmol), obtained in Step 3, was dissolved in formic acid (1.0 mL) and the mixture was stirred at room temperature overnight. The reaction solution was concentrated, dissolved in ethyl acetate, and again concentrated. The resulting residue was purified by diol thin layer chromatography (dichloromethane:methanol=50:1) to obtain the target compound as white solid at a yield of 60%.

$^1$H-NMR (CDCl$_3$) δ: 0.87 (3H, t, J=7.0 Hz), 0.97 (3H, t, J=7.3 Hz), 1.15-1.38 (14H, m), 1.42-1.61 (6H, m), 1.70-1.79 (2H, m), 1.93-2.09 (2H, m), 2.35-2.48 (4H, m), 2.68 (1H, d, J=16.5 Hz), 2.94-3.10 (3H, m), 3.26 (1H, d, J=9.2 Hz), 3.73 (3H, s), 3.91 (2H, t, J=6.7 Hz), 4.76-4.84 (1H, m), 5.51 (1H, dd, J=15.3, 9.2 Hz), 5.63-5.72 (1H, m), 6.78 (2H, d, J=8.5 Hz), 6.91 (1H, d, J=7.9 Hz), 7.00 (2H, d, J=8.5 Hz).

ESI (LC/MS positive mode) m/z 662 (M+H); Rt 2.61 min.

199

38, No. 5444034

Synthesis of (E)-(2S,3S)-3-[(S)-2-(4-butoxy-phenyl)-1-methoxycarbonyl-ethylcarbamoyl]-2-carbamoylmethyl-2-hydroxy-12-oxo-nonadec-4-enoic acid

Step 1

Synthesis of (2S,3S,E)-tert-butyl 2-(2-amino-2-oxoethyl)-3-((S)-3-(4-butoxyphenyl)-1-methoxy-1-oxopropan-2-ylcarbamoyl)-2-hydroxy-12-oxo-nonadec-4-enoate

[Chem. 139]

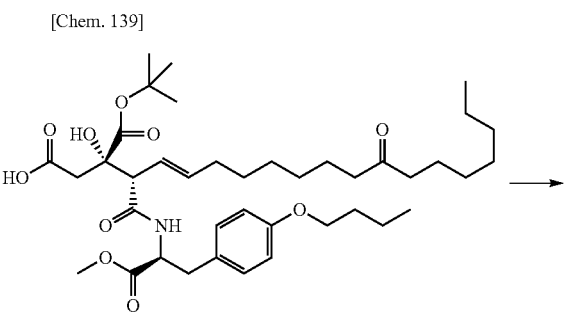

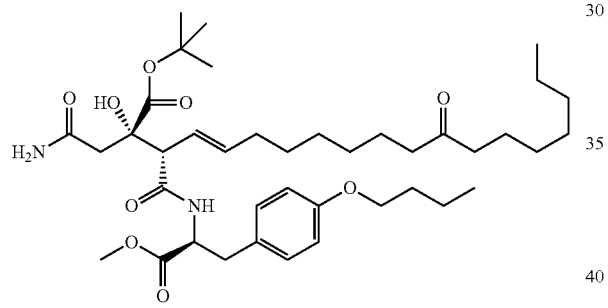

(3S,4S,E)-3-(tert-butoxycarbonyl)-4-((S)-3-(4-butoxyphenyl)-1-methoxy-1-oxopropan-2-ylcarbamoyl)-3-hydroxy-13-oxoicos-5-enoic acid (30 mg, 0.042 mmol), obtained in Step 3 of the synthesis of #37, No. 5444031, and ammonium chloride (7 mg, 0.125 mmol) were suspended in N,N-dimethylformamide (60 mL), and 1H-benzo[d][1,2,3]triazol-1-ol hydrate (19 mg), WSC hydrochloride (24 mg), and N-ethyl-N-isopropylpropane-2-amine (21 µL) were added in order. The mixture was stirred at room temperature overnight. The reaction mixture was diluted with water, and extracted with ethyl acetate. The separated organic layer was washed three times with a diluted aqueous solution of ammonium chloride, and with a saturated aqueous solution of sodium bicarbonate, then dried over anhydrous sodium sulfate, filtered, and then concentrated under reduced pressure. The resulting residue was used in the next step.

ESI (LC/MS positive mode) m/z 717 (M+H); Rt 3.33 min.

200

Step 2

Synthesis of (E)-(2S,3S)-3-[(S)-2-(4-butoxy-phenyl)-1-methoxycarbonyl-ethylcarbamoyl]-2-carbamoylmethyl-2-hydroxy-12-oxo-nonadec-4-enoic acid

[Chem. 140]

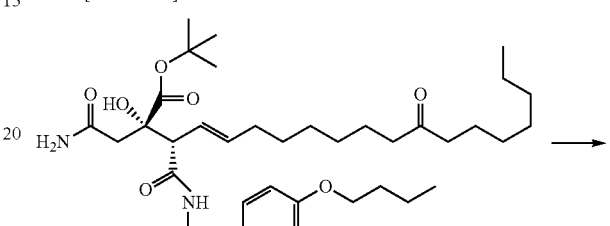

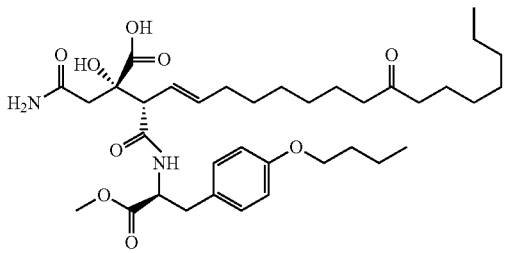

A crude product (27.4 mg) of (2S,3S,E)-tert-butyl 2-(2-amino-2-oxoethyl)-3-((S)-3-(4-butoxyphenyl)-1-methoxy-1-oxopropan-2-ylcarbamoyl)-2-hydroxy-12-oxo-nonadec-4-enoic acid, obtained in Step 1, was dissolved in formic acid (2.0 mL) and the mixture was stirred for a whole day and night. The reaction mixture was concentrated. The resulting residue was purified by diol thin layer chromatography (dichloromethane:methanol=30:1) to obtain the target compound as white solid at a yield of 74%.

$^1$H-NMR (CDCl$_3$) δ: 0.87 (3H, t, J=6.7 Hz), 0.97 (3H, t, J=7.3 Hz), 1.17-1.35 (14H, m), 1.42-1.60 (6H, m), 1.70-1.79 (2H, m), 1.93-2.06 (2H, m), 2.34-2.53 (5H, m), 2.81 (1H, dd, J=15.6 Hz), 3.00 (1H, dd, J=14.0, 7.9 Hz), 3.12 (1H, dd, J=14.0, 5.5 Hz), 3.24 (1H, d, J=9.2 Hz), 3.73 (3H, s), 3.91 (2H, t, J=6.4 Hz), 4.77 (1H, q, J=6.7 Hz), 5.48 (1H, dd, J=15.3, 9.2 Hz), 5.61-5.71 (1H, m), 5.99 (1H, br.s), 6.32 (1H, br.s), 6.80 (2H, d, J=7.9 Hz), 6.90 (1H, d, J=7.3 Hz), 7.04 (2H, d, J=7.9 Hz).

ESI (LC/MS positive mode) m/z 661 (M+H); Rt 2.41 min.

#40, No. 5454381

Synthesis of (E)-(2S,3S)-3-[(S)-2-(4-butoxy-phenyl)-1-carboxy-ethylcarbamoyl]-2-hydroxy-2-(2-methoxy-ethyl)-12-oxo-nonadec-4-enoic acid

Step 1 Synthesis of (S)-2-((S,E)-2-((S)-1-tert-butoxy-2-hydroxy-4-methoxy-1-oxobutan-2-yl)-11-oxooctadec-3-eneamide)-3-(4-butoxyphenyl)propanoic acid

[Chem. 141]

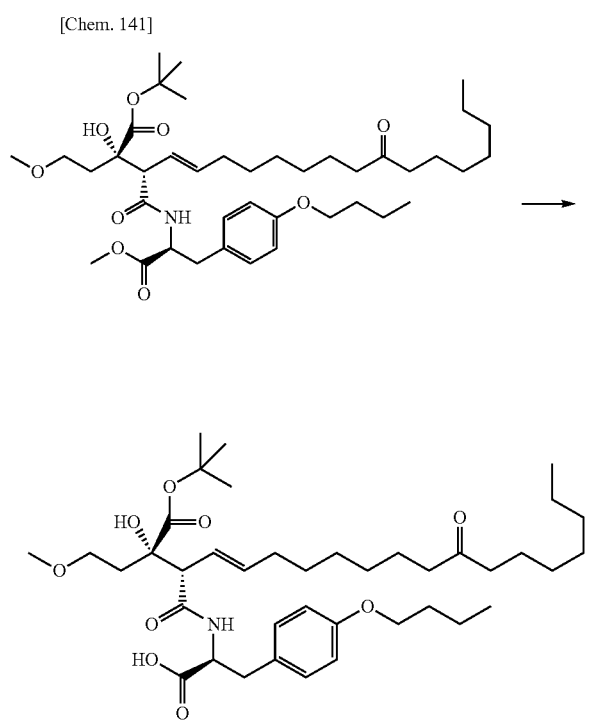

(2S,3S,E)-tert-Butyl 3-((S)-3-(4-butoxyphenyl)-1-methoxy-1-oxopropan-2-ylcarbamoyl)-2-hydroxy-2-(2-methoxy-ethyl)-12-oxo-nonadec-4-enoate (59.8 mg, 0.083 mmol), obtained in Step 1 of the synthesis of #39, No. 5444958, was dissolved in acetonitrile (2.0 mL) and water (20 μL), and to the solution were added triethylamine (35 μL, 0.25 mmol) and lithium bromide (72 mg, 0.83 mmol). The mixture was stirred at room temperature for 3 days, diluted in ethyl acetate, and washed with an aqueous solution of 0.5% citric acid. The separated organic layer was washed twice with water, dried over anhydrous sodium sulfate, filtered, and concentrated. The resulting residue was purified by diol thin layer chromatography (dichloromethane:methanol=30:1) to obtain the target compound as colorless oil at a yield of 71%.

ESI (LC/MS positive mode) m/z 704 (M+H); Rt 3.77 min.

Step 2 #40, No. 5454381

Synthesis of (E)-(2S,3S)-3-[(S)-2-(4-butoxy-phenyl)-1-carboxy-ethylcarbamoyl]-2-hydroxy-2-(2-methoxy-ethyl)-12-oxo-nonadec-4-enoic acid

[Chem. 142]

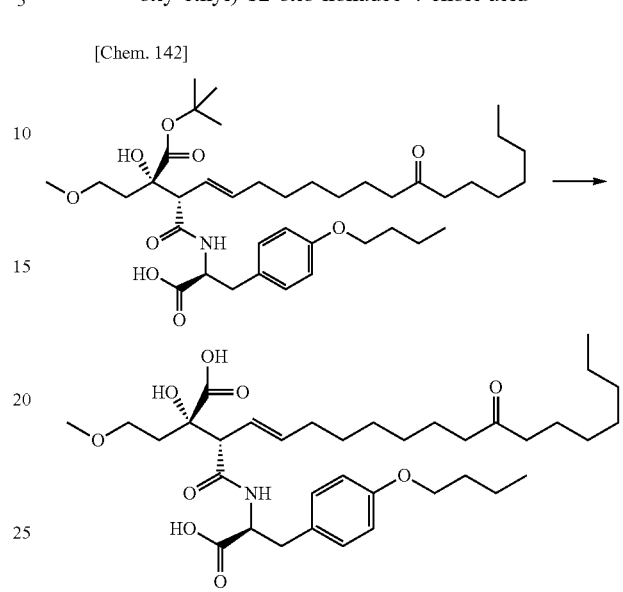

(S)-2-((S,E)-2-((S)-1-tert-Butoxy-2-hydroxy-4-methoxy-1-oxobutan-2-yl)-11-oxooctadec-3-eneamide)-3-(4-butoxyphenyl)propanoic acid (20 mg, 0.028 mmol), obtained in Step 1, was dissolved in formic acid (1.0 mL). The mixture was stirred at room temperature overnight and concentrated. The residue was diluted in ethyl acetate, and then concentrated again. This residue was purified by diol thin layer chromatography (dichloromethane:methanol=30:1) to obtain the target compound as white solid at a yield of 90%.

$^1$H-NMR (CDCl$_3$) δ: 0.88 (3H, t, J=6.9 Hz), 0.97 (3H, t, J=7.4 Hz), 1.13-1.36 (14H, m), 1.43-1.60 (6H, m), 1.70-1.79 (3H, m), 1.96-2.13 (3H, m), 2.37-2.49 (4H, m), 3.03 (1H, dd, J=14.3, 7.1 Hz), 3.16 (1H, dd, J=14.3, 5.5 Hz), 3.21 (1H, d, J=9.3 Hz), 3.30 (3H, s), 3.39-3.55 (2H, m), 3.92 (2H, t, J=6.3 Hz), 4.71-4.80 (1H, m), 5.51 (1H, dd, J=15.1, 9.1 Hz), 5.57-5.67 (1H, m), 6.80 (2H, d, J=8.2 Hz), 6.85 (1H, d, J=7.9 Hz), 7.08 (2H, d, J=8.2 Hz).

ESI (LC/MS positive mode) m/z 648 (M+H); Rt 2.48 min.

#41, No. 5454382

Synthesis of (E)-(2S,3S)-3-[(S)-2-(4-butoxy-phenyl)-1-carboxy-ethylcarbamoyl]-2-carbamoylmethyl-2-hydroxy-12-oxo-nonadec-4-enoic acid

Step 1

Synthesis of (S)-2-((S,E)-2-((S)-4-amino-1-tert-butoxy-2-hydroxy-1,4-dioxobutan-2-yl)-11-oxooctadec-3-eneamide)-3-(4-butoxyphenyl)propanoic acid

[Chem. 143]

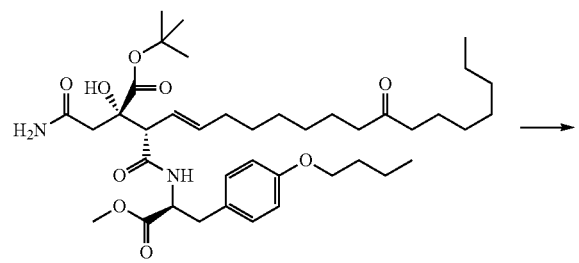

203

-continued

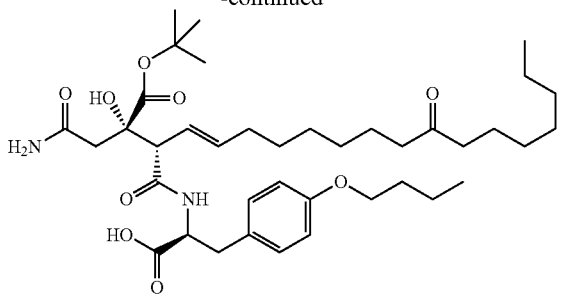

(2S,3S,E)-tert-Butyl 2-(2-amino-2-oxoethyl)-3-((S)-3-(4-butoxyphenyl)-1-methoxy-1-oxopropan-2-ylcarbamoyl)-2-hydroxy-12-oxo-nonadec-4-enoic acid (161 mg, 0.22 mmol) obtained in Step 4 of the synthesis of #38, No. 5444034, (E)-(2S,3S)-3-[(S)-2-(4-butoxy-phenyl)-1-methoxycarbonyl-ethylcarbamoyl]-2-carbamoylmethyl-2-hydroxy-12-oxo-nonadec-4-enoic acid was dissolved in acetonitrile (2 mL) and water (40 µL) was added. To the mixture were added triethylamine (0.674 mmol, 94 µL) and lithium bromide (195 mg, 2.25 mmol), and the mixture was stirred at room temperature for 5 days. The reaction solution was diluted in ethyl acetate, and washed with an aqueous solution of 0.5% citric acid. The separated organic layer was washed twice with water and then with a saturated brine, and dried over anhydrous sodium sulfate. The filtrate was concentrated to obtain the target compound as white solid.

ESI (LC/MS positive mode) m/z 703 (M+H); Rt 2.80 min.

Step 2

Synthesis of 41, No. 5454382 (E)-(2S,3S)-3-[(S)-2-(4-butoxy-phenyl)-1-carboxy-ethylcarbamoyl]-2-carbamoylmethyl-2-hydroxy-12-oxo-nonadec-4-enoic acid

[Chem. 144]

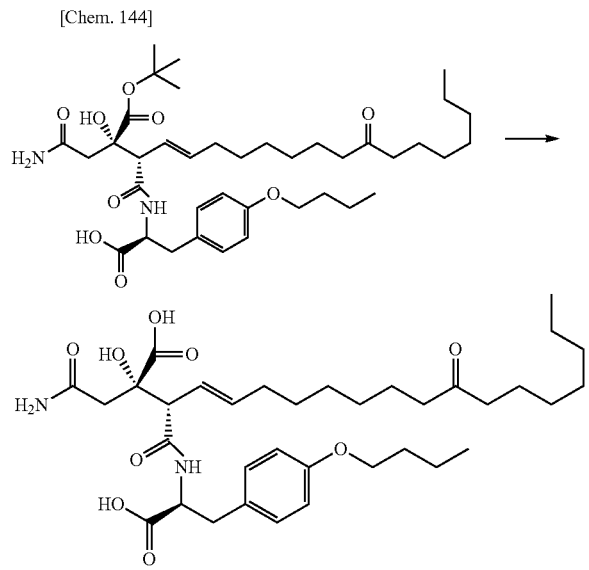

(S)-2-((S,E)-2-((S)-4-Amino-1-tert-butoxy-2-hydroxy-1,4-dioxobutan-2-yl)-11-oxooctadec-3-eneamide)-3-(4-butoxyphenyl)propanoic acid (20 mg), obtained in Step 1, was dissolved in formic acid (1.0 mL), and the mixture was stirred at room temperature overnight. The reaction mixture was concentrated. The residue was dissolved in ethyl acetate and concentrated. The resulting residue was purified by diol thin layer chromatography (dichloromethane:methanol=9:1) to obtain the target compound as white solid at a yield of 57%.

¹H-NMR (DMSO-d₆) δ: 0.85 (3H, t, J=6.9 Hz), 0.92 (3H, t, J=7.4 Hz), 1.13-1.30 (14H, m), 1.37-1.47 (6H, m), 1.62-1.71 (2H, m), 1.84-1.91 (2H, m), 2.30 (1H, d, J=14.8 Hz), 2.33-2.39 (4H, m), 2.57 (1H, d, J=14.8 Hz), 2.81 (1H, dd, J=13.7, 8.8 Hz), 2.97 (1H, dd, J=13.5, 4.7 Hz), 3.13-3.18 (2H, m), 3.89 (2H, t, J=6.3 Hz), 4.34-4.42 (1H, m), 5.35-5.45 (2H, m), 6.76 (2H, d, J=8.8 Hz), 7.0 (1H, s), 7.08 (2H, d, J=8.8 Hz), 7.33 (1H, s), 8.08 (1H, d, J=7.7 Hz).

ESI (LC/MS positive mode) m/z 647 (M+H); Rt 1.88 min.

99. No. 5518587

(E)-(2R,3S)-3-[(S)-2-(4-Butoxy-phenyl)-1-methoxycarbonyl-ethylcarbamoyl]-2-hydroxy-2-methoxymethyl-12-oxo-nonadec-4-enoic acid

[Chem. 145]

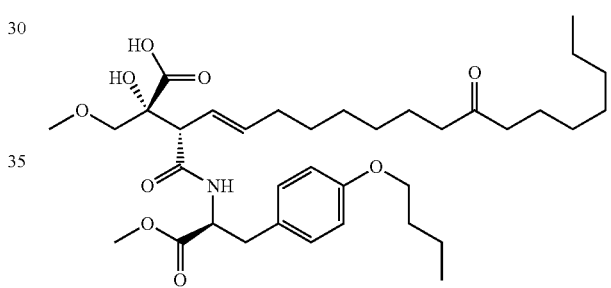

tert-Butyl (E)-(2R,3S)-11-(2-heptyl-[1,3]dioxolan-2-yl)-2-hydroxy-3-((S)-4-isopropyl-2-oxo-5,5-diphenyl-thiazolidine-3-carbonyl)-2-methoxymethyl-undec-4-enoate (ESI (LC/MS positive mode) m/z 794 (M+H); Rt 3.87 min.) was synthesized by using tert-butyl 3-methoxy-2-oxo-propionate instead of tert-butyl 4-methoxy-2-oxo-butyrate in Step A-1. Under the conditions of the following Step A-2a, tert-butyl (E)-(2R,3S)-3-[(S)-2-(4-butoxy-phenyl)-1-methoxycarbonyl-ethylcarbamoyl]-11-(2-heptyl-[1,3]dioxolan-2-yl)-2-hydroxy-2-methoxymethyl-undec-4-enoate (ESI (LC/MS positive mode) m/z 748 (M+H); Rt 2.87 min.) with an amino acid introduced was synthesized. Under conditions similar to those of Step A-3, (E)-(2R,3S)-3-[(S)-2-(4-butoxy-phenyl)-1-methoxycarbonyl-ethylcarbamoyl]-2-hydroxy-2-methoxymethyl-12-oxo-nonadec-4-enoic acid (No. 5518587) was synthesized.

¹H-NMR (CD₃OD) δ: 0.90 (3H, t, J=6.6 Hz), 0.98 (3H, t, J=6.6 Hz), 1.23-1.37 (14H, m), 1.44-1.57 (6H, m), 1.69-1.76 (2H, m), 1.97 (2H, q, J=6.4 Hz), 2.43 (4H, t, J=7.4 Hz), 2.90 (1H, dd, J=14.3, 9.3 Hz), 3.10 (1H, m), 3.25-3.28 (5H, m), 3.57 (1H, d, J=9.3 Hz), 3.70 (3H, s), 3.92 (2H, t, J=6.3 Hz), 4.63 (1H, dd, J=8.8, 4.9 Hz), 5.44-5.60 (2H, m), 6.80 (2H, d, J=8.2 Hz), 7.08 (2H, d, J=8.2 Hz).

ESI (LC/MS positive mode) m/z 648 (M+H); Rt 3.47 min.

102. No. 5518590

(E)-(2R,3S)-3-[(S)-2-(4-Butoxy-phenyl)-1-methyl-carbamoyl-ethylcarbamoyl]-2-hydroxy-2-methoxymethyl-12-oxo-nonadec-4-enoic acid

[Chem. 146]

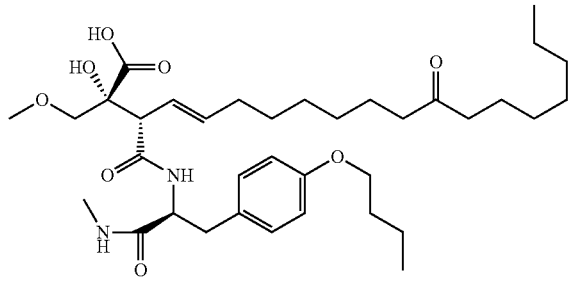

tert-Butyl (E)-(2R,3S)-11-(2-heptyl-[1,3]dioxolan-2-yl)-2-hydroxy-3-((S)-4-isopropyl-2-oxo-5,5-diphenyl-thiazolidine-3-carbonyl)-2-methoxymethyl-undec-4-enoate (ESI (LC/MS positive mode) m/z 794 (M+H); Rt 3.87 min.) was synthesized by using tert-butyl 3-methoxy-2-oxo-propionate instead of tert-butyl 4-methoxy-2-oxo-butyrate in Step A-1.

tert-Butyl (E)-(2R,3S)-3-[(S)-2-(4-butoxy-phenyl)-1-methylcarbamoyl-ethylcarbamoyl]-11-(2-heptyl-[1,3]dioxolan-2-yl)-2-hydroxy-2-methoxymethyl-undec-4-enoate (ESI (LC/MS positive mode) m/z 747 (M+H); Rt 2.67 min.) with an amino acid introduced was synthesized by using (S)-2-amino-3-(4-butoxy-phenyl)-N-methyl-propionamide instead of methyl (S)-2-amino-3-(4-butoxy-phenyl)-propionate in the following Step A-2a.

Furthermore, (E)-(2R,3S)-3-[(S)-2-(4-butoxy-phenyl)-1-methylcarbamoyl-ethylcarbamoyl]-2-hydroxy-2-methoxymethyl-12-oxo-nonadec-4-enoic acid (No. 5518590) was synthesized under conditions similar to those of Step A-3.

$^1$H-NMR (CD$_3$OD) δ: 0.89 (3H, t, J=6.9 Hz), 0.96 (3H, t, J=7.1 Hz), 1.22-1.36 (14H, m), 1.44-1.56 (6H, m), 1.69-1.76 (2H, m), 1.94-1.97 (2H, m), 2.42 (4H, t, J=7.1 Hz), 2.70 (3H, s), 2.79 (1H, dd, J=13.7, 9.3 Hz), 3.06 (1H, dd, J=13.7, 5.5 Hz), 3.24-3.27 (1H, m), 3.29 (3H, s), 3.32 (1H, m), 3.56 (1H, d, J=9.9 Hz), 3.91 (2H, t, J=6.6 Hz), 4.49 (1H, dd, J=9.1, 5.2 Hz), 5.48-5.58 (2H, m), 6.79 (2H, d, J=8.8 Hz), 7.09 (2H, d, J=8.8 Hz).

ESI (LC/MS positive mode) m/z 647 (M+H); Rt 3.20 min.

105. No. 5518596

(E)-(2R,3S)-3-[(S)-2-(4-Butoxy-phenyl)-1-carbamoyl-ethylcarbamoyl]-2-hydroxy-2-methoxymethyl-12-oxo-nonadec-4-enoic acid

[Chem. 147]

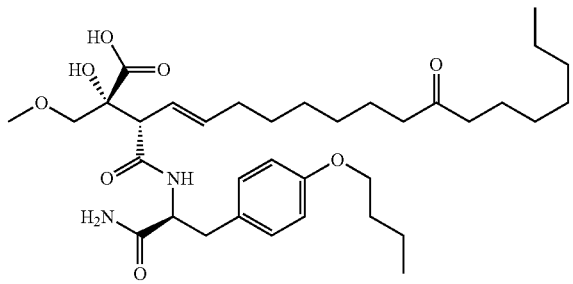

tert-Butyl (E)-(2R,3S)-11-(2-heptyl-[1,3]dioxolan-2-yl)-2-hydroxy-3-((S)-4-isopropyl-2-oxo-5,5-diphenyl-thiazolidine-3-carbonyl)-2-methoxymethyl-undec-4-enoate was synthesized (ESI (LC/MS positive mode) m/z 794 (M+H); Rt 3.87 min.) by using tert-butyl 3-methoxy-2-oxo-propionate instead of tert-butyl 4-methoxy-2-oxo-butyrate in Step A-1.

tert-Butyl (E)-(2R,3S)-3-[(S)-2-(4-butoxy-phenyl)-1-carbamoyl-ethylcarbamoyl]-11-(2-heptyl-[1,3]dioxolan-2-yl)-2-hydroxy-2-methoxymethyl-undec-4-enoate (ESI (LC/MS positive mode) m/z 733 (M+H); Rt 2.57 min.) with an amino acid introduced was synthesized by using (S)-2-amino-3-(4-butoxy-phenyl)-propionamide instead of methyl (S)-2-amino-3-(4-butoxy-phenyl)-propionate in the following Step A-2a. Furthermore, (E)-(2R,3S)-3-[(S)-2-(4-butoxy-phenyl)-1-carbamoyl-ethylcarbamoyl]-2-hydroxy-2-methoxymethyl-12-oxo-nonadec-4-enoic acid (No. 5518596) was synthesized under conditions similar to those of Step A-3.

$^1$H-NMR (CD$_3$OD) δ: 0.89 (3H, t, J=6.9 Hz), 0.97 (3H, t, J=7.1 Hz), 1.23-1.36 (15H, m), 1.44-1.57 (6H, m), 1.69-1.76 (2H, m), 1.93-1.98 (2H, m), 2.43 (4H, t, J=7.4 Hz), 2.80 (1H, dd, J=14.0, 9.6 Hz), 3.09-3.14 (1H, m), 3.23-3.26 (1H, m), 3.27 (3H, s), 3.53 (1H, d, J=9.9 Hz), 3.92 (2H, t, J=6.3 Hz), 4.55 (1H, dd, J=9.9, 4.9 Hz), 5.47-5.56 (2H, m), 6.77-6.81 (2H, m), 7.12 (2H, d, J=8.8 Hz).

ESI (LC/MS positive mode) m/z 633 (M+H); Rt 3.12 min.

161. No. 5529363

(E)-(2S,3S)-3-[(S)-1-Carboxy-2-(2'-fluoro-biphenyl-4-yl)-ethylcarbamoyl]-2-hydroxy-12-oxo-2-propyl-nonadec-4-enoic acid

[Chem. 148]

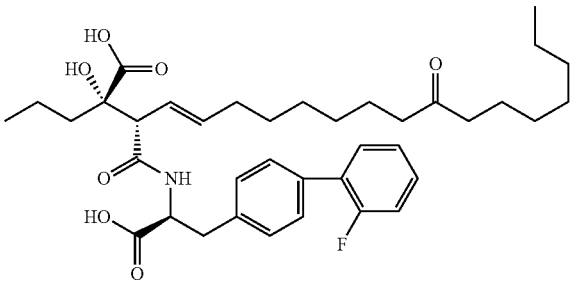

(E)-(2S,3S)-3-[(S)-1-Carboxy-2-(2'-fluoro-biphenyl-4-yl)-ethylcarbamoyl]-2-hydroxy-12-oxo-2-propyl-nonadec-4-enoic acid (No. 5529363) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using tert-butyl (E)-(2S,3S)-3-[(S)-1-carboxy-2-(2'-fluoro-biphenyl-4-yl)-ethylcarbamoyl]-2-hydroxy-12-oxo-2-propyl-nonadec-4-enoate (No. 5523860) as the starting material.

$^1$H-NMR (DMDO-d$_6$) δ: 0.73 (3H, t, J=7.1 Hz), 0.85 (3H, t, J=7.1 Hz), 0.98-1.04 (1H, m), 1.14-1.46 (21H, m), 1.52-1.63 (1H, m), 1.80-1.86 (2H, m), 2.27-2.38 (4H, m), 2.93 (1H, dd, J=13.7, 9.3 Hz), 3.08-3.16 (2H, m), 4.42-4.47 (1H, m), 5.32-5.43 (2H, m), 7.25-7.33 (4H, m), 7.36-7.43 (3H, m), 7.46-7.50 (1H, m), 8.06 (1H, d, J=6.6 Hz).

ESI (LC/MS positive mode) m/z 654 (M+H); Rt 2.18 min.

162. No. 5529364

(E)-(2S,3S)-3-{(S)-1-Carboxy-2-[4-(3-fluoro-propoxy)-phenyl]-ethylcarbamoyl}-2-hydroxy-12-oxo-2-propyl-nonadec-4-enoic acid

[Chem. 149]

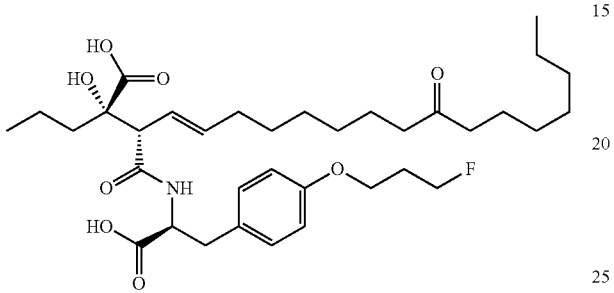

(E)-(2S,3S)-3-{(S)-1-Carboxy-2-[4-(3-fluoro-propoxy)-phenyl]-ethylcarbamoyl}-2-hydroxy-12-oxo-2-propyl-nonadec-4-enoic acid (No. 5529364) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using tert-butyl (E)-(2S,3S)-3-[(S)-1-carboxy-2-[4-(3-fluoro-propoxy)-phenyl]-ethylcarbamoyl]-2-hydroxy-12-oxo-2-propyl-nonadec-4-enoate (No. 5523861) as the starting material.

$^1$H-NMR (DMSO-d$_6$) δ: 0.77 (3H, t, J=7.1 Hz), 0.85 (3H, t, J=7.1 Hz), 0.97-1.04 (1H, m), 1.18-1.47 (21H, m), 1.50-1.59 (1H, m), 1.82-1.92 (2H, m), 2.01-2.14 (2H, m), 2.36 (4H, dt, J=7.4, 2.7 Hz), 2.80 (1H, dd, J=13.7, 9.3 Hz), 2.98 (1H, dd, J=14.0, 4.7 Hz), 3.13-3.15 (1H, m), 4.00 (2H, t, J=6.3 Hz), 4.33-4.39 (1H, m), 4.52 (1H, t, J=6.0 Hz), 4.64 (1H, t, J=6.0 Hz), 5.36-5.42 (2H, m), 6.80 (2H, d, J=8.8 Hz), 7.11 (2H, d, J=8.8 Hz), 8.08 (1H, d, J=7.7 Hz).

ESI (LC/MS positive mode) m/z 636 (M+H); Rt 2.03 min.

190. No. 6800893

(E)-(2S,3S)-3-[(S)-1-Carboxy-2-(2'-fluoro-biphenyl-4-yl)-ethylcarbamoyl]-2-hydroxy-2-(2-methoxy-ethyl)-12-oxo-nonadec-4-enoic acid

[Chem. 150]

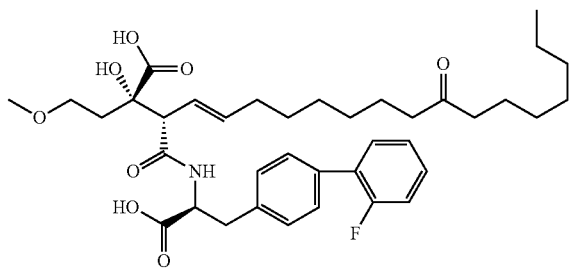

(E)-(2S,3S)-3-[(S)-1-Carboxy-2-(2'-fluoro-biphenyl-4-yl)-ethylcarbamoyl]-2-hydroxy-2-(2-methoxy-ethyl)-12-oxo-nonadec-4-enoic acid (No. 6800893) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using tert-butyl (E)-(2S,3S)-3-[(S)-1-carboxy-2-(2'-fluoro-biphenyl-4-yl)-ethylcarbamoyl]-2-hydroxy-2-(2-methoxy-ethyl)-12-oxo-nonadec-4-enoate (No. 5535539) as a starting material.

$^1$H-NMR (CD$_3$OD) δ: 0.89 (3H, t, J=7.1 Hz), 1.11-1.34 (15H, m), 1.41-1.57 (4H, m), 1.69-1.78 (1H, m), 1.89-1.96 (2H, m), 2.02-2.12 (1H, m), 2.34-2.44 (4H, m), 3.03 (1H, d, J=14.0, 9.4 Hz), 3.20 (3H, s), 3.24 (1H, d, J=8.2 Hz), 3.36-3.45 (2H, m), 4.74 (1H, dd, J=9.2, 4.6 Hz), 5.44-5.62 (2H, m), 7.13-7.37 (5H, m), 7.43-7.49 (3H, m).

ESI (LC/MS positive mode) m/z 670 (M+H); Rt 3.08 min.

188. No. 6800894

(E)-(2S,3S)-3-{(S)-1-Carboxy-2-[4-(3-fluoro-propoxy)-phenyl]-ethylcarbamoyl}-2-hydroxy-2-(2-methoxy-ethyl)-12-oxo-nonadec-4-enoic acid

[Chem. 151]

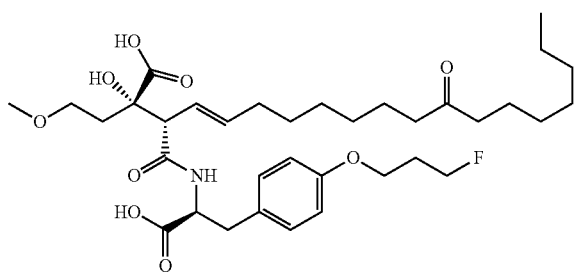

(E)-(2S,3S)-3-{(S)-1-Carboxy-2-[4-(3-fluoro-propoxy)-phenyl]-ethylcarbamoyl}-2-hydroxy-2-(2-methoxy-ethyl)-12-oxo-nonadec-4-enoic acid (No. 6800894) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using tert-butyl (E)-(2S,3S)-3-{(S)-1-carboxy-2-[4-(3-fluoro-propoxy)-phenyl]-ethylcarbamoyl}-2-hydroxy-2-(2-methoxy-ethyl)-12-oxo-nonadec-4-enoate (No. 5542552) as a starting material.

$^1$H-NMR (CD$_3$OD) δ: 0.92 (3H, t, J=6.6 Hz), 1.12-1.36 (15H, m), 1.45-1.49 (4H, m), 1.65-1.74 (1H, m), 1.92-2.21

(4H, m), 2.43 (4H, dt, J=7.3, 1.9 Hz), 2.90 (1H, dd, J=14.1, 9.1 Hz), 3.13-3.25 (5H, m), 3.36-3.44 (2H, m), 4.05 (2H, t, J=6.2 Hz), 4.51 (1H, t, J=5.9 Hz), 4.61-4.71 (2H, m), 5.43-5.62 (2H, m), 6.82 (2H, d, J=8.8 Hz), 7.12 (2H, d, J=8.8 Hz).
ESI (LC/MS positive mode) m/z 652 (M+H); Rt 2.83 min.

Synthesis of No. 5534088

Under a nitrogen atmosphere, methanol (2.0 mL) was added to (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoic acid (No. 5444958; 20.0 mg, 0.0302 mmol) and the mixture was cooled to 0° C. While maintaining the temperature at 0° C., sodium borohydride (1.14 mg, 0.0302 mmol) was added and the mixture was stirred for 30 minutes. The reaction was quenched by adding water, and the mixture was extracted with ethyl acetate. The organic layer was washed with water and a saturated brine, dried over anhydrous sodium sulfate, and filtered. The solvent was distilled off under reduced pressure. The residue was purified by HPLC (water with 0.05% TFA-acetonitrile with 0.05% TFA) to obtain (E)-(2S,3S)-3-[(S)-2-(4-butoxy-phenyl)-1-methoxycarbonyl-ethylcarbamoyl]-2,12-dihydroxy-2-(2-methoxy-ethyl)-nonadec-4-enoic acid (No. 5534088; 11.9 mg, 59% yield).

186. No. 5534088

(E)-(2S,3S)-3-[(S)-2-(4-Butoxy-phenyl)-1-methoxycarbonyl-ethylcarbamoyl]-2,12-dihydroxy-2-(2-methoxy-ethyl)-nonadec-4-enoic acid

[Chem. 152]

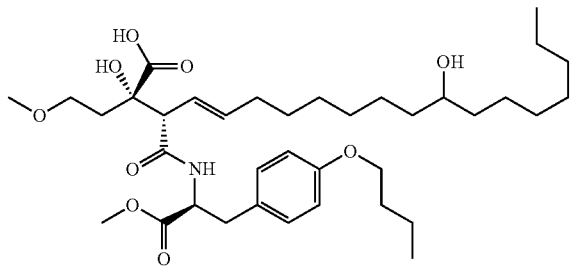

¹H-NMR (DMSO-d₆) δ: 0.85 (3H, t, J=7.1 Hz), 0.92 (3H, t, J=7.1 Hz), 1.16-1.46 (27H, m), 1.60-1.70 (3H, m), 1.83-1.94 (3H, m), 2.81 (1H, dd, J=13.7, 9.3 Hz), 2.95 (1H, dd, J=13.7, 4.9 Hz), 3.12-3.18 (4H, m), 3.20-3.26 (2H, m), 3.60 (3H, s), 3.90 (2H, t, J=6.6 Hz), 4.40-4.45 (1H, m), 5.33-5.41 (2H, m), 6.77 (2H, d, J=8.2 Hz), 7.07 (2H, d, J=8.2 Hz), 8.18-8.26 (1H, br.s).
ESI (LC/MS positive mode) m/z 664 (M+H); Rt 2.28 min.

187. No. 5534089

(E)-(2S,3S)-3-[(S)-2-(4-Butoxy-phenyl)-1-carboxy-ethylcarbamoyl]-2,12-dihydroxy-2-(2-methoxy-ethyl)-nonadec-4-enoic acid

[Chem. 153]

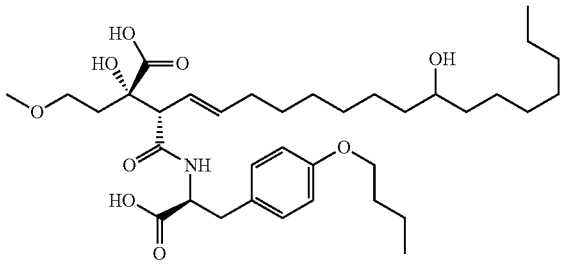

(E)-(2S,3S)-3-[(S)-2-(4-Butoxy-phenyl)-1-carboxy-ethylcarbamoyl]-2,12-dihydroxy-2-(2-methoxy-ethyl)-nonadec-4-enoic acid (No. 5534089) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-butoxy-phenyl)-1-methoxycarbonyl-ethylcarbamoyl]-2,12-dihydroxy-2-(2-methoxy-ethyl)-nonadec-4-enoic acid (No. 5534088) as a starting material.
¹H-NMR (DMSO-d₆) δ: 0.85 (3H, t, J=7.1 Hz), 0.92 (3H, t, J=7.1 Hz), 1.14-1.46 (27H, m), 1.62-1.70 (3H, m), 1.82-1.97 (3H, m), 2.78 (1H, dd, J=14.0, 9.1 Hz), 2.97 (1H, dd, J=14.0, 4.7 Hz), 3.13-3.16 (4H, m), 3.18-3.25 (2H, m), 3.89 (2H, t, J=6.6 Hz), 4.33-4.41 (1H, m), 5.33-5.42 (2H, m), 6.76 (2H, d, J=8.8 Hz), 7.08 (2H, d, J=8.8 Hz), 8.16-8.13 (1H, br.s).
ESI (LC/MS positive mode) m/z 650 (M+H); Rt 2.08 min.
(Step B Addition)
Compound No. 5513213 was produced according to the following synthetic scheme.

[Chem. 154]

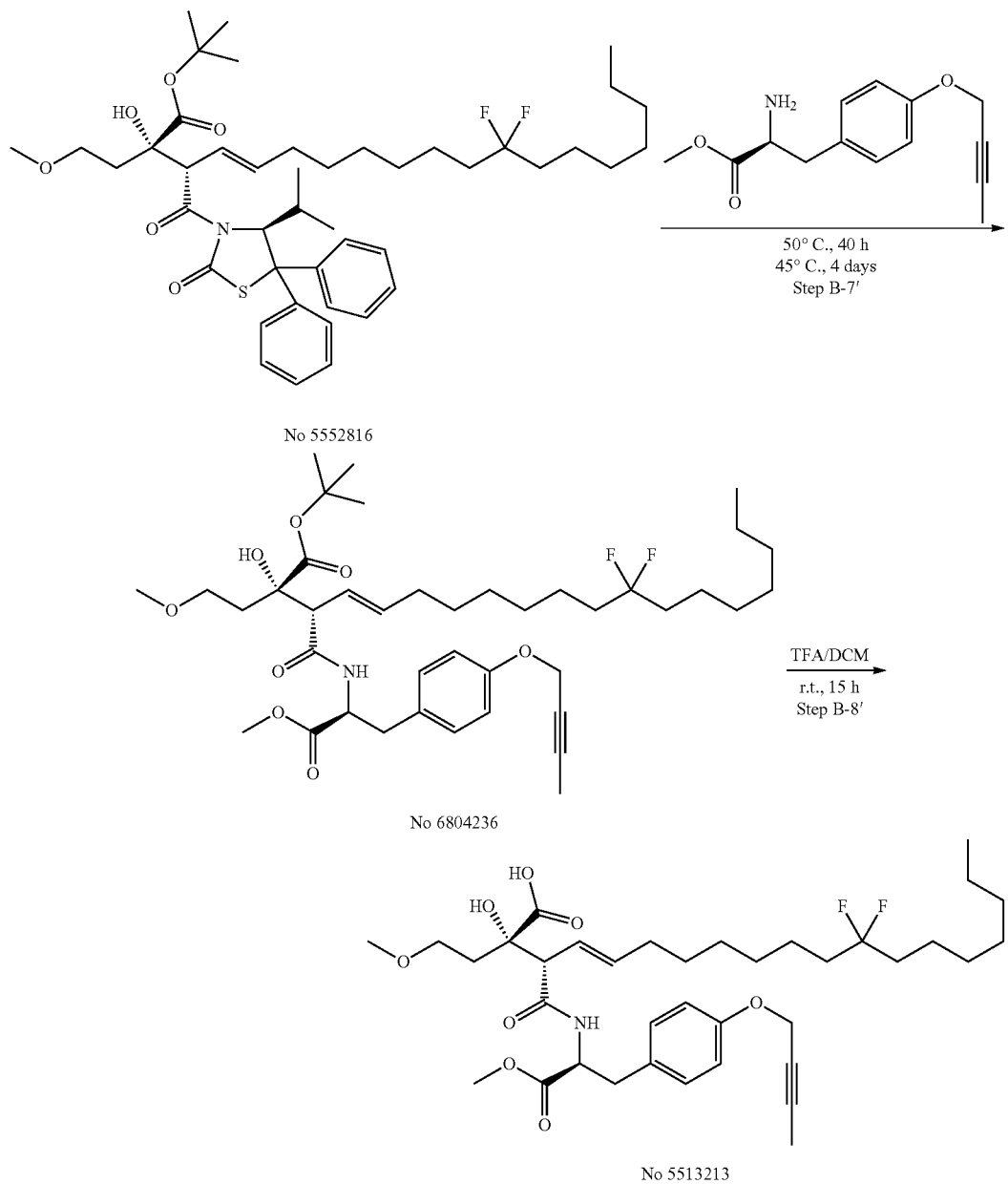

Step B-7' tert-Butyl (E)-(2S,3S)-12,12-difluoro-2-hydroxy-3-((S)-4-isopropyl-2-oxo-5,5-diphenyl-thiazolidine-3-carbonyl)-2-(2-methoxy-ethyl)-nonadec-4-enoate (No. 5552816; 38.8 mg, 0.0494 mmol) synthesized in Steps B1 to B6 and methyl (S)-2-amino-3-(4-but-2-ynyloxy-phenyl)-propionate (18.3 mg, 0.074 mmol) were dissolved in dichloromethane, and the solvent was distilled off under reduced pressure. The obtained mixture was stirred at 45° C. for 4 days, cooled to room temperature, and then extracted by adding ethyl acetate and water. The organic layer was washed with a saturated brine, dried over anhydrous sodium sulfate, and then filtered. The solvent was distilled out of the filtrate under reduced pressure and the residue was purified with SP1 (SiO$_2$ cartridge, 25% ethyl acetate/n-hexane, Rf=0.1) to obtain tert-butyl (E)-(2S, 3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate (No. 6804236; 28.9 mg, 80% yield).

$^1$H-NMR (CDCl$_3$) δ: 0.88 (3H, t, J=6.6 Hz), 1.20-1.37 (14H, m), 1.38-1.50 (13H, m), 1.56 (1H, dt, J=14.3, 4.9 Hz), 1.72-1.86 (7H, m), 1.94-2.03 (3H, m), 2.97 (1H, dd, J=14.3, 7.7 Hz), 3.09-3.15 (2H, m), 3.21 (3H, s), 3.26-3.39 (2H, m), 3.70 (3H, s), 4.15 (1H, s), 4.61 (2H, s), 4.77-4.84 (1H, m), 5.45 (1H, dd, J=15.4, 9.3 Hz), 5.66 (1H, dt, J=15.4, 6.6 Hz), 6.85 (2H, d, J=8.2 Hz), 7.07-7.10 (3H, m).

ESI (LC/MS positive mode) m/z 736 (M+H); Rt 2.58 min.

Step B-8' tert-Butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate (No. 6804236; 28.9 mg, 0.0393 mmol) was dissolved in dichloromethane (3.0 mL), and trifluoroacetic acid (1.0 mL) was added. The mixture was stirred at room temperature for 15 hours. The solvent was distilled off under reduced pressure. To the residue was added dichloromethane, and the solvent was again distilled off under reduced pressure. This operation was repeated twice and the residue was then purified by HPLC (water with 0.05% TFA-acetonitrile with 0.05% TFA) to obtain (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoic acid (No. 5513213; 20.1 mg, 75% yield, white powder).

$^1$H-NMR (CD$_3$OD) δ: 0.90 (3H, t, J=7.1 Hz), 1.23-1.38 (14H, m), 1.38-1.49 (4H, m), 1.66-1.85 (8H, m), 1.93-2.09 (3H, m), 2.90 (1H, dd, J=14.3, 9.3 Hz), 3.08-3.16 (1H, m), 3.22-3.24 (4H, m), 3.37-3.44 (2H, m), 3.70 (3H, s), 4.60-4.68 (3H, m), 5.45-5.60 (2H, m), 6.84 (2H, d, J=8.8 Hz), 7.10 (2H, d, J=8.8 Hz).

ESI (LC/MS positive mode) m/z 681 (M+H); Rt 2.30 min.

No. 5444958 (50 mg, 0.0733 mmol) was dissolved in methanol (0.4 mL) and benzene (1.2 mL), and trimethylsilyl diazomethane (244 μL, 0.146 mmol) was added at room temperature. After confirming the consumption of the starting materials by LCMS, the solvent was distilled off under reduced pressure. The residue was purified by preparative HPLC. The obtained fraction was freeze-dried to obtain the title compound (48 mg, 97% yield, white powder).

$^1$H-NMR (CD$_3$OD) δ: 0.89 (3H, t, J=6.8 Hz), 0.98 (3H, t, J=7.3 Hz), 1.23-1.37 (14H, m), 1.44-1.65 (7H, m), 1.69-1.78 (2H, m), 1.92-2.00 (2H, m), 2.01-2.10 (1H, m), 2.43 (4H, t, J=7.3 Hz), 2.87 (1H, dd, J=13.9, 9.5 Hz), 3.11 (1H, dd, J=13.9, 5.1 Hz), 3.18-3.22 (3H, m), 3.32-3.36 (1H, m), 3.39-3.43 (1H, m), 3.65 (3H, s), 3.70 (3H, s), 3.93 (2H, t, J=6.4 Hz), 4.63 (1H, dd, J=9.5, 5.1 Hz), 5.42-5.58 (2H, m), 6.79 (2H, d, J=8.8 Hz), 7.07 (2H, d, J=8.4 Hz).

ESI (LC/MS positive mode) m/z 676 (M+H); Rt 1.16 min.

No. 6809530

Synthesis of methyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate

[Chem. 155]

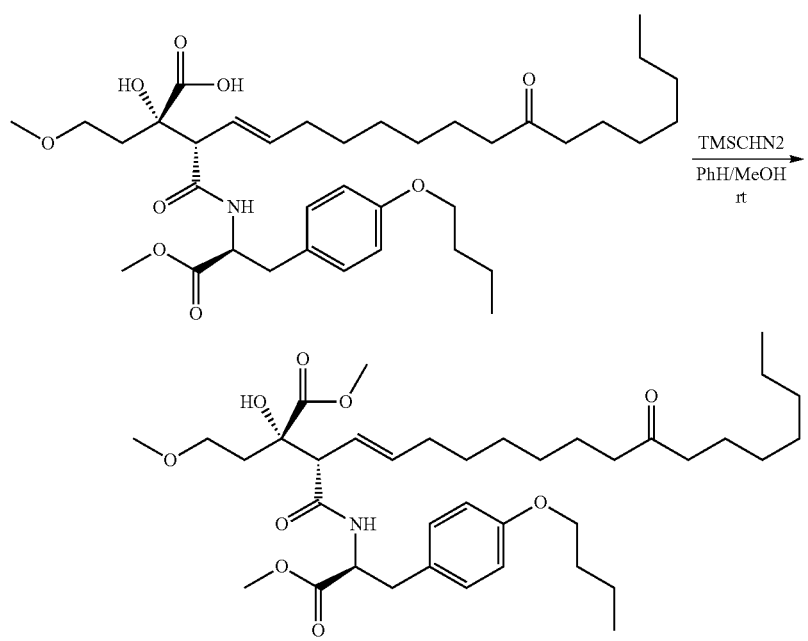

No. 6809532

Synthesis of methyl (E)-(2S,3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate

[Chem. 156]

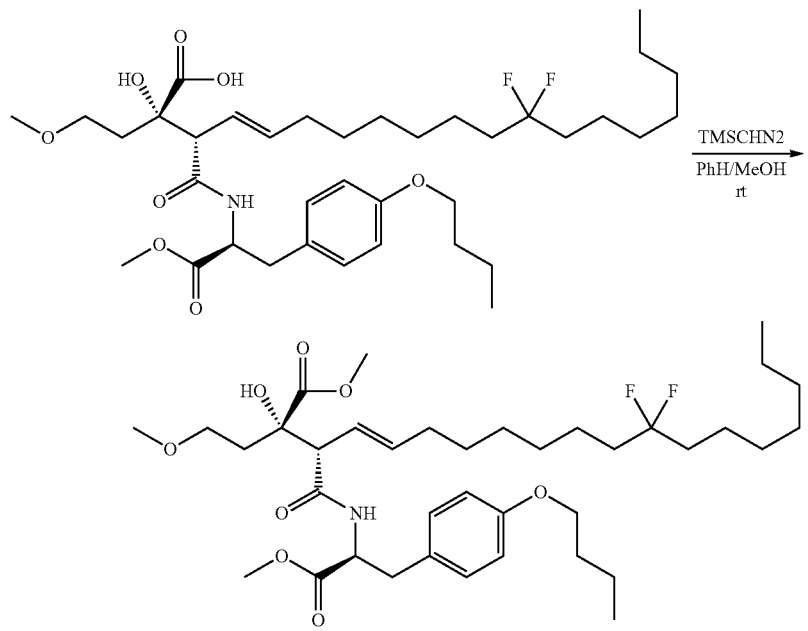

The title compound was obtained by the synthesis in the method similar to that of No. 6809530 except that No. 5514403 was used instead of No. 5444958.

¹H-NMR (CD₃OD) δ: 0.90 (3H, t, J=7.1 Hz), 0.98 (3H, t, J=7.5 Hz), 1.24-1.38 (14H, m), 1.39-1.55 (6H, m), 1.61 (1H, td, J=9.5, 4.6 Hz), 1.70-1.85 (6H, m), 1.93-2.00 (2H, m), 2.02-2.09 (1H, m), 2.87 (1H, dd, J=14.1, 9.3 Hz), 3.11 (1H, dd, J=14.3, 5.1 Hz), 3.19-3.22 (4H, m), 3.32-3.36 (1H, m), 3.39-3.44 (1H, m), 3.65 (3H, s), 3.70 (3H, s), 3.93 (2H, t, J=6.4 Hz), 4.63 (1H, dd, J=9.3, 4.9 Hz), 5.42-5.58 (2H, m), 6.79 (2H, d, J=8.8 Hz), 7.07 (2H, d, J=8.8 Hz).

ESI (LC/MS positive mode) m/z 698 (M+H); Rt 1.25 min.

No. 6810070

Synthesis of methoxycarbonylmethyl (E)-(2S,3S)-3-[(S)-2-(4-butoxy-phenyl)-1-methoxycarbonyl-ethyl-carbamoyl]-2-hydroxy-2-(2-methoxy-ethyl)-12-oxo-nonadec-4-enoate

[Chem. 157]

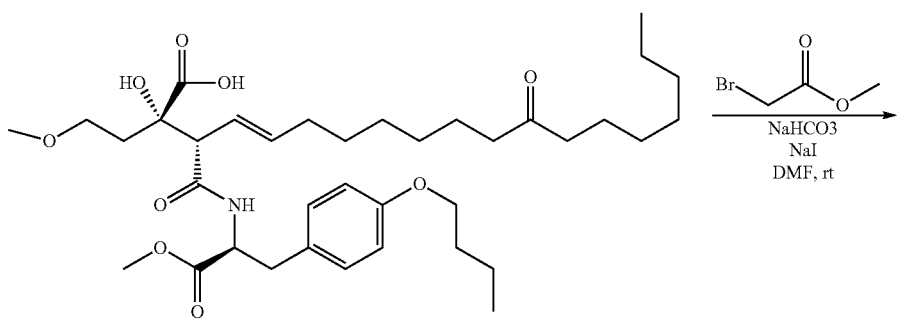

Molecular Weight = 661.87
Exact Mass = 661
Molecular Formula = C37H59NO9

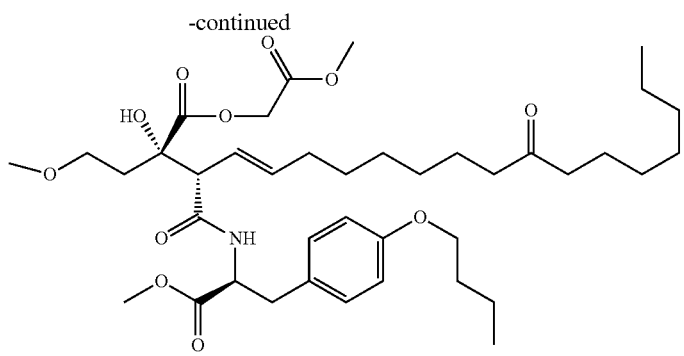

Molecular Weight = 733.93
Exact Mass = 733
Molecular Formula = C40H63NO11

The title compound was obtained by the synthesis in the method similar to that of No. 6808754 except that a commercially available reagent of methyl bromoacetate was used instead of 4-chloromethyl-5-methyl-1,3-dioxol-2-one.

$^1$H-NMR (CD$_3$OD) δ: 0.89 (3H, t, J=6.8 Hz), 0.98 (3H, t, J=7.5 Hz), 1.22-1.37 (14H, m), 1.45-1.59 (6H, m), 1.74 (3H, dt, J=20.9, 6.6 Hz), 1.93-2.01 (2H, m), 2.06-2.13 (1H, m), 2.43 (4H, t, J=7.5 Hz), 2.88 (2H, dd, J=13.7, 9.3 Hz), 3.11 (2H, dd, J=14.3, 5.1 Hz), 3.24 (3H, s), 3.28 (1H, d, J=10.0 Hz), 3.48 (2H, ddd, J=24.7, 10.8, 6.8 Hz), 3.71 (3H, s), 3.75 (3H, s), 3.93 (2H, t, J=6.4 Hz), 4.58-4.69 (4H, m), 5.47-5.62 (2H, m), 6.79 (2H, d, J=8.8 Hz), 7.07 (2H, d, J=8.8 Hz).

ESI (LC/MS positive mode) m/z 734 (M+H); Rt 1.15 min.

No. 6810892

Synthesis of carboxymethyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate

[Chem. 158]

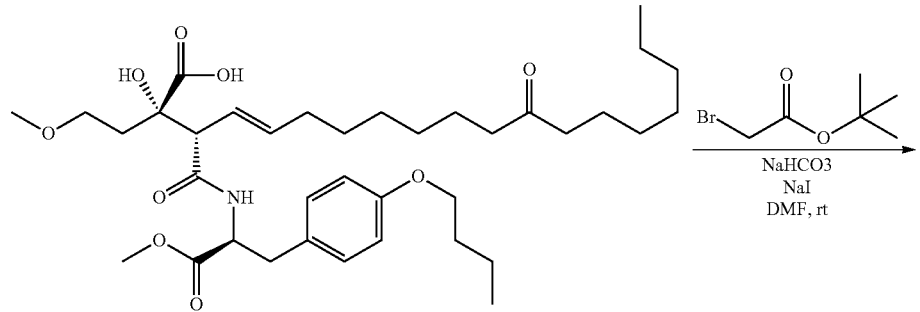

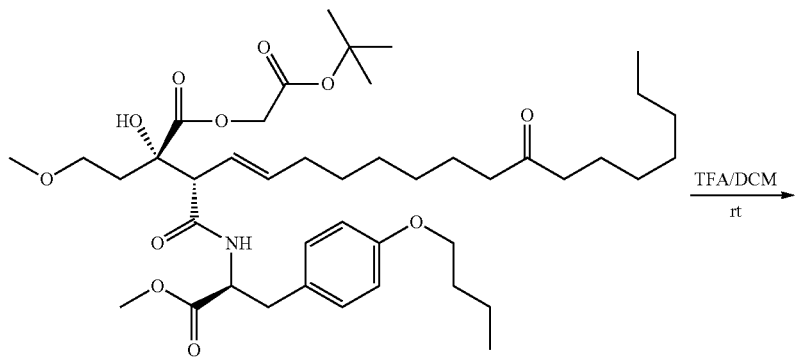

-continued

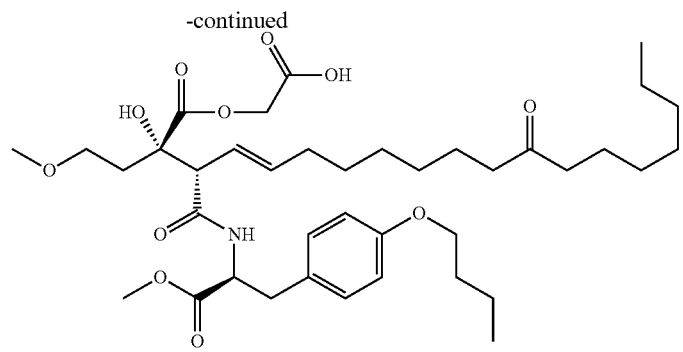

An intermediate, tert-butoxycarbonylmethyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate (ESI (LC/MS positive mode) m/z 777 (M+H); Rt 1.25 min.) was obtained by the synthesis in the method similar to that of No. 6808754, except that commercially available tert-butyl bromoacetate was used instead of 4-chloromethyl-5-methyl-1,3-dioxol-2-one. The obtained intermediate was used in the next synthesis without purification. Dichloromethane (1.0 mL) and trifluoroacetic acid (1.0 mL) were added to the obtained intermediate (48 mg, 0.0618 mmol), and the mixture was stirred at room temperature. After confirming the consumption of the starting materials by LCMS, the solvent was distilled off under reduced pressure. The residue was purified by preparative HPLC. The obtained fraction was freeze-dried to obtain the title compound (44 mg, 98% yield, white powder).

$^1$H-NMR (CD$_3$OD) δ: 0.89 (3H, t, J=7.1 Hz), 0.98 (3H, t, J=7.3 Hz), 1.22-1.36 (14H, m), 1.45-1.57 (6H, m), 1.68-1.79 (3H, m), 1.93-2.01 (2H, m), 2.09-2.16 (2H, m), 2.43 (4H, t, J=7.5 Hz), 2.89 (2H, dd, J=14.1, 9.3 Hz), 3.10 (2H, dd, J=13.9, 5.1 Hz), 3.24 (3H, s), 3.30-3.31 (1H, m), 3.42-3.56 (3H, m), 3.71 (3H, s), 3.93 (2H, t, J=6.4 Hz), 4.53-4.57 (2H, m), 4.63-4.68 (1H, m), 5.47-5.62 (2H, m), 6.79 (2H, d, J=8.4 Hz), 7.07 (2H, d, J=8.8 Hz).

ESI (LC/MS positive mode) m/z 720 (M+H); Rt 1.05 min.

85. No. 5501824

(E)-(2S,3S)-3-[(S)-2-(4-But-2-ynyloxy-phenyl)-1-methoxycarbonyl-ethylcarbamoyl]-12,12-difluoro-2-hydroxy-2-propyl-nonadec-4-enoic acid

[Chem. 159]

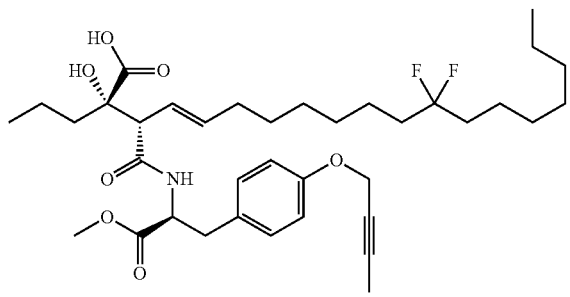

tert-Butyl (E)-(2S,3S)-12,12-difluoro-2-hydroxy-3-((S)-4-isopropyl-2-oxo-5,5-diphenyl-thiazolidine-3-carbonyl)-2-propyl-nonadec-4-enoate was synthesized (ESI (LC/MS positive mode) m/z 770 (M+H); Rt 5.12 min.) except that tert-butyl 2-oxo-pentanoate was used instead of tert-butyl 4-methoxy-2-oxo-butyrate in Step B-6. tert-Butyl (E)-(2S,3S)-3-[(S)-2-(4-but-2-ynyloxy-phenyl)-1-methoxycarbonyl-ethylcarbamoyl]-12,12-difluoro-2-hydroxy-2-propyl-nonadec-4-enoate (ESI (LC/MS positive mode) m/z 720 (M+H); Rt 2.78 min.) was synthesized using the conditions at 150° C. for 1.5 hours instead of those in Step B-7'. (E)-(2S,3S)-3-[(S)-2-(4-But-2-ynyloxy-phenyl)-1-methoxycarbonyl-ethylcarbamoyl]-12,12-difluoro-2-hydroxy-2-propyl-nonadec-4-enoic acid (No. 5501824) was synthesized under conditions similar to those in Step B-8'.

$^1$H-NMR (CD$_3$COCD$_3$) δ: 0.71 (3H, t, J=7.1 Hz), 0.75 (3H, t, J=7.1 Hz), 1.16-1.25 (16H, m), 1.29-1.42 (6H, m), 1.56-1.78 (8H, m), 1.83-1.88 (2H, m), 2.82 (1H, dd, J=14.0, 7.7 Hz), 2.95 (1H, dd, J=14.0, 5.5 Hz), 3.25 (1H, d, J=7.7 Hz), 3.55 (3H, s), 4.52-4.56 (3H, m), 5.40-5.52 (2H, m), 6.74 (2H, d, J=8.8 Hz), 7.02 (2H, d, J=8.8 Hz), 7.72 (1H, d, J=7.7 Hz).

ESI (LC/MS positive mode) m/z 664 (M+H); Rt 3.03 min.

Synthesis of No. 5501825

At room temperature, (E)-(2S,3S)-3-[(S)-2-(4-but-2-ynyloxy-phenyl)-1-methoxycarbonyl-ethylcarbamoyl]-12,12-difluoro-2-hydroxy-2-propyl-nonadec-4-enoic acid (No. 5501824; 27.5 mg, 0.041 mmol) was dissolved in acetonitrile (0.55 mL) and water (22 μL), and triethylamine (34.6 μL, 0.249 mmol) and lithium bromide (72.0 mg, 0.829 mmol) were added in order. The mixture was stirred at 50° C. for 2.0 hours, and cooled to room temperature. The progress of the reaction was then stopped by adding an aqueous solution of 0.5 M citric acid. Ethyl acetate was added, and the mixture was extracted. The organic layer was washed with water, dried over anhydrous sodium sulfate, and filtered. The solvent was distilled off. The residue was then purified by preparative HPLC (water with 0.05% TFA-acetonitrile with 0.05% TFA) to obtain (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825; 22.4 mg, 84% yield, white powder).

86. No. 5501825

(E)-(2S,3S)-3-[(S)-2-(4-But-2-ynyloxy-phenyl)-1-carboxy-ethylcarbamoyl]-12,12-difluoro-2-hydroxy-2-propyl-nonadec-4-enoic acid

[Chem. 160]

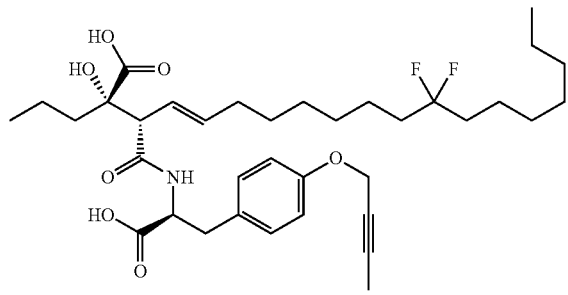

$^1$H-NMR (CD$_3$COCD$_3$) δ: 0.71 (3H, t, J=7.1 Hz), 0.75 (3H, t, J=7.1 Hz), 0.96-1.06 (1H, m), 1.16-1.23 (14H, m), 1.29-1.46 (6H, m), 1.56-1.78 (8H, m), 1.82-1.89 (2H, m), 2.83 (1H, dd, J=14.0, 8.2 Hz), 3.01 (1H, dd, J=14.0, 4.7 Hz), 3.23 (1H, d, J=8.2 Hz), 4.51-4.53 (3H, m), 5.41-5.53 (2H, m), 6.73 (2H, d, J=8.8 Hz), 7.05 (2H, d, J=8.8 Hz), 7.68 (1H, d, J=7.1 Hz).

ESI (LC/MS positive mode) m/z 650 (M+H); Rt 2.88 min.

94. No. 5514404

(E)-(2S,3S)-3-[(S)-2-(4-Butoxy-phenyl)-1-methylcarbamoyl-ethylcarbamoyl]-12,12-difluoro-2-hydroxy-2-(2-methoxy-ethyl)-nonadec-4-enoic acid

[Chem. 161]

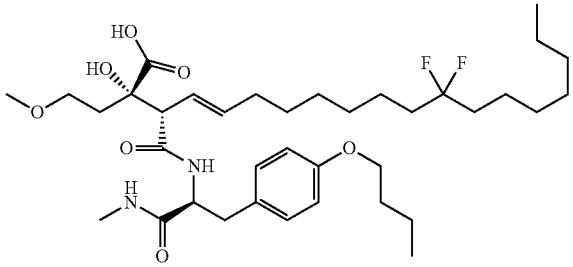

tert-Butyl (E)-(2S,3S)-3-[(S)-2-(4-butoxy-phenyl)-1-methylcarbamoyl-ethylcarbamoyl]-12,12-difluoro-2-hydroxy-2-(2-methoxy-ethyl)-nonadec-4-enoate (PSI (LC/MS positive mode) ink 739 (M+H); Rt 2.72 min.) was synthesized using (S)-2-amino-3-(4-butoxy-phenyl)-N-methyl-propionamide and the conditions at 50° C. for 2.5 days instead of methyl (S)-2-amino-3-(4-butoxy-phenyl)-propionate and the conditions in Step B-7'. (E)-(2S,3S)-3-[(S)-2-(4-Butoxy-phenyl)-1-methylcarbamoyl-ethylcarbamoyl]-12,12-difluoro-2-hydroxy-2-(2-methoxy-ethyl)-nonadec-4-enoic acid (No. 5514404) was synthesized under conditions similar to those in the following Step B-8'.

$^1$H-NMR (CD$_3$OD) δ: 0.90 (3H, t, J=6.6 Hz), 0.97 (3H, t, J=7.1 Hz), 1.24-1.54 (22H, m), 1.60-1.85 (7H, m), 1.94-2.08 (3H, m), 2.70 (3H, s), 2.79 (1H, dd, J=14.3, 9.3 Hz), 3.03 (1H, dd, J=14.3, 5.5 Hz), 3.19 (1H, d, J=8.2 Hz), 3.24 (3H, s), 3.36-3.46 (2H, m), 3.92 (2H, t, J=6.3 Hz), 4.49-4.54 (1H, m), 5.48-5.58 (2H, m), 6.78 (2H, d, J=8.8 Hz), 7.09 (2H, d, J=8.8 Hz).

ESI (LC/MS positive mode) m/z 683 (M+H); Rt 2.35 min.

97. No. 5518585

(E)-(2R,3S)-3-[(S)-2-(4-Butoxy-phenyl)-1-methoxycarbonyl-ethylcarbamoyl]-12,12-difluoro-2-hydroxy-2-methoxymethyl-nonadec-4-enoic acid

[Chem. 162]

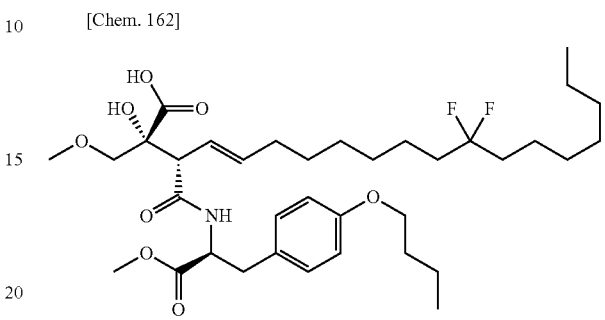

tert-Butyl (E)-(2R,3S)-12,12-difluoro-2-hydroxy-3-((S)-4-isopropyl-2-oxo-5,5-diphenyl-thiazolidine-3-carbonyl)-2-methoxymethyl-nonadec-4-enoate was synthesized (ESI (LC/MS positive mode) m/z 772 (M+H); Rt 3.75 min.) except that tert-butyl 3-methoxy-2-oxo-propionate was used instead of tert-butyl 4-methoxy-2-oxo-butyrate in Step B-6. tert-Butyl (E)-(2R,3S)-3-[(S)-2-(4-butoxy-phenyl)-1-methoxycarbonyl-ethylcarbamoyl]-12,12-difluoro-2-hydroxy-2-methoxymethyl-nonadec-4-enoic acid (ESI (LC/MS positive mode) m/z 726 (M+H); Rt 2.85 min.) was synthesized by carrying out Step B-7' in a similar way. Furthermore, (E)-(2R,3S)-3-[(S)-2-(4-butoxy-phenyl)-1-methoxycarbonyl-ethylcarbamoyl]-12,12-difluoro-2-hydroxy-2-methoxymethyl-nonadec-4-enoic acid (No. 5518585) was synthesized under conditions similar to those in Step B-8'.

$^1$H-NMR (CD$_3$OD) δ: 0.90 (3H, t, J=7.1 Hz), 0.98 (3H, t, J=7.1 Hz), 1.26-1.55 (22H, m), 1.69-1.85 (6H, m), 1.96-2.00 (2H, m), 2.90 (1H, dd, J=14.3, 9.3 Hz), 3.10 (1H, dd, J=14.3, 5.5 Hz), 3.25-3.27 (1H, m), 3.28 (3H, s), 3.57 (1H, d, J=9.9 Hz), 3.71 (3H, s), 3.92 (2H, t, J=6.6 Hz), 4.63 (1H, dd, J=8.8, 4.9 Hz), 5.48-5.61 (2H, m), 6.80 (2H, d, J=8.8 Hz), 7.09 (2H, d, J=8.8 Hz).

ESI (LC/MS positive mode) m/z 670 (M+H); Rt 3.75 min.

100. No. 5518588

(E)-(2R,3S)-3-[(S)-2-(4-Butoxy-phenyl)-1-methylcarbamoyl-ethylcarbamoyl]-12,12-difluoro-2-hydroxy-2-methoxymethyl-nonadec-4-enoic acid

[Chem. 163]

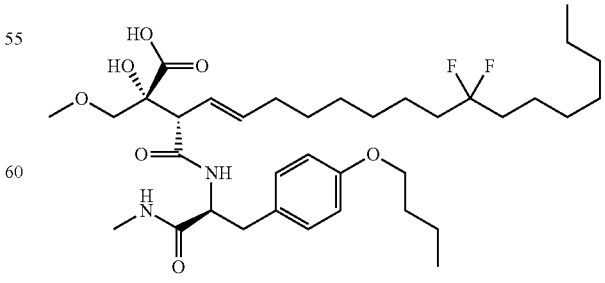

tert-Butyl (E)-(2R,3S)-12,12-difluoro-2-hydroxy-3-((S)-4-isopropyl-2-oxo-5,5-diphenyl-thiazolidine-3-carbonyl)-2- methoxymethyl-nonadec-4-enoate was synthesized (ESI (LC/MS positive mode) m/z 772 (M+H); Rt 3.75 min.) using tert-butyl 3-methoxy-2-oxo-propionate instead of tert-butyl 4-methoxy-2-oxo-butyrate in Step B-6. tert-Butyl (E)-(2R,3S)-3-[(S)-2-(4-butoxy-phenyl)-1-methylcarbamoyl-ethylcarbamoyl]-12,12-difluoro-2-hydroxy-2-methoxymethyl-nonadec-4-enoate (ESI (LC/MS positive mode) m/z 725 (M+H); Rt 2.65 min.) was synthesized using (S)-2-amino-3-(4-butoxy-phenyl)-N-methyl-propionamide and conditions at 50° C. for 2.0 days, instead of methyl (S)-2-amino-3-(4-butoxy-phenyl)-propionate and the conditions in the following Step B-7'. Furthermore, (E)-(2R,3S)-3-[(S)-2-(4-butoxy-phenyl)-1-methylcarbamoyl-ethylcarbamoyl]-12,12-difluoro-2-hydroxy-2-methoxymethyl-nonadec-4-enoic acid (No. 5518588) was synthesized under conditions similar to those in Step B-8'.

¹H-NMR (CD₃OD) δ: 0.90 (3H, t, J=7.1 Hz), 0.97 (3H, t, J=7.1 Hz), 1.25-1.53 (22H, m), 1.69-1.85 (6H, m), 1.94-2.02 (2H, m), 2.71 (3H, s), 2.78 (1H, dd, J=14.3, 9.3 Hz), 3.07 (1H, dd, J=13.7, 5.5 Hz), 3.24-3.26 (1H, m), 3.28 (3H, s), 3.56 (1H, d, J=9.9 Hz), 3.92 (2H, t, J=6.6 Hz), 4.47-4.52 (1H, m), 5.48-5.58 (2H, m), 6.79 (2H, d, J=8.8 Hz), 7.10 (2H, d, J=8.8 Hz).

ESI (LC/MS positive mode) m/z 669 (M+H); Rt 3.55 min.

103. No. 5518594

(E)-(2R,3S)-3-[(S)-2-(4-butoxy-phenyl)-1-carbamoyl-ethylcarbamoyl]-12,12-difluoro-2-hydroxy-2-methoxymethyl-nonadec-4-enoic acid

[Chem. 164]

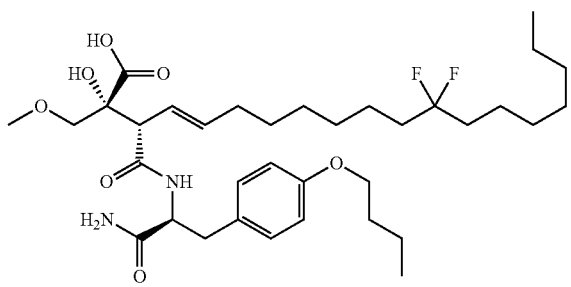

tert-Butyl (E)-(2R,3S)-12,12-difluoro-2-hydroxy-3-((S)-4-isopropyl-2-oxo-5,5-diphenyl-thiazolidine-3-carbonyl)-2-methoxymethyl-nonadec-4-enoate was synthesized (EST (LC/MS positive mode) m/z 772 (M+H); Rt 3.75 min.) by using tert-butyl 3-methoxy-2-oxo-propionate, instead of tert-butyl 4-methoxy-2-oxo-butyrate in Step B-6. tert-Butyl (E)-(2R,3S)-3-[(S)-2-(4-butoxy-phenyl)-1-carbamoyl-ethylcarbamoyl]-12,12-difluoro-2-hydroxy-2-methoxymethyl-nonadec-4-enoate (ESI (LC/MS positive mode) m/z 711 (M+H); Rt 2.58 min.) was synthesized by using (S)-2-amino-3-(4-butoxy-phenyl)-propionamide and conditions at 50° C. for 2.0 days, instead of methyl (S)-2-amino-3-(4-butoxy-phenyl)-propionate and the conditions in the following Step B-7'. Furthermore, (E)-(2R,3S)-3-[(S)-2-(4-butoxy-phenyl)-1-carbamoyl-ethylcarbamoyl]-12,12-difluoro-2-hydroxy-2-methoxymethyl-nonadec-4-enoic acid (No. 5518594) was synthesized under conditions similar to those in Step B-8'.

¹H-NMR (CD₃OD) δ: 0.90 (3H, t, J=6.6 Hz), 0.98 (3H, t, J=6.6 Hz), 1.24-1.53 (22H, m), 1.69-1.85 (6H, m), 1.93-2.00 (2H, m), 2.80 (1H, dd, J=13.7, 9.9 Hz), 3.12 (1H, dd, J=14.3, 4.9 Hz), 3.24-3.26 (1H, m), 3.28 (3H, s), 3.54 (1H, d, J=9.9 Hz), 3.92 (2H, t, J=6.6 Hz), 4.55 (1H, q, J=4.9 Hz), 5.47-5.56 (2H, m), 6.79 (2H, d, J=8.2 Hz), 7.12 (2H, d, J=8.2 Hz).

ESI (LC/MS positive mode) m/z 655 (M+H); Rt 3.47 min.

189. No. 6800895

(E)-(2S,3S)-3-{(S)-1-Carboxy-2-[4-(3-fluoro-propoxy)-phenyl]-ethylcarbamoyl}-12,12-difluoro-2-hydroxy-2-(2-methoxy-ethyl)-nonadec-4-enoic acid

[Chem. 165]

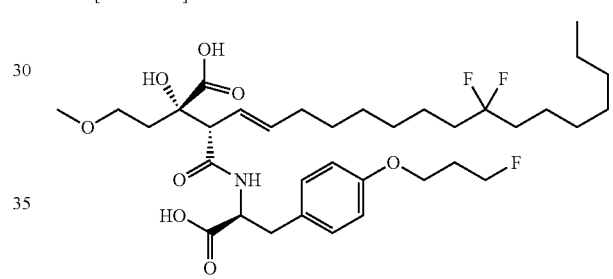

(E)-(2S,3S)-3-{(S)-1-Carboxy-2-[4-(3-fluoro-propoxy)-phenyl]-ethylcarbamoyl}-12,12-difluoro-2-hydroxy-2-(2-methoxy-ethyl)-nonadec-4-enoic acid (No. 6800895) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-12,12-difluoro-3-{(S)-2-[4-(3-fluoro-propoxy)-phenyl]-1-methoxycarbonyl-ethylcarbamoyl}-2-hydroxy-2-(2-methoxy-ethyl)-nonadec-4-enoic acid (No. 5550736) as a starting material.

¹H-NMR (CD₃OD) δ: 0.90 (3H, t, J=6.6 Hz), 1.24-1.48 (19H, m), 1.67-1.85 (5H, m), 1.95-1.99 (2H, m), 2.02-2.18 (3H, m), 2.90 (1H, dd, J=13.7, 9.3 Hz), 3.14-3.21 (1H, m), 3.23 (3H, s), 3.36-3.44 (2H, m), 4.05 (2H, t, J=6.0 Hz), 4.54 (1H, t, J=6.0 Hz), 4.61-4.67 (2H, m), 5.45-5.60 (2H, m), 6.82 (2H, d, J=8.2 Hz), 7.12 (2H, d, J=8.2 Hz).

ESI (LC/MS positive mode) m/z 674 (M+H); Rt 3.20 min.

Compound No. 5513214 was produced according to the following synthetic scheme.

[Chem. 166]

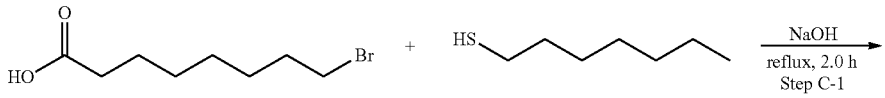

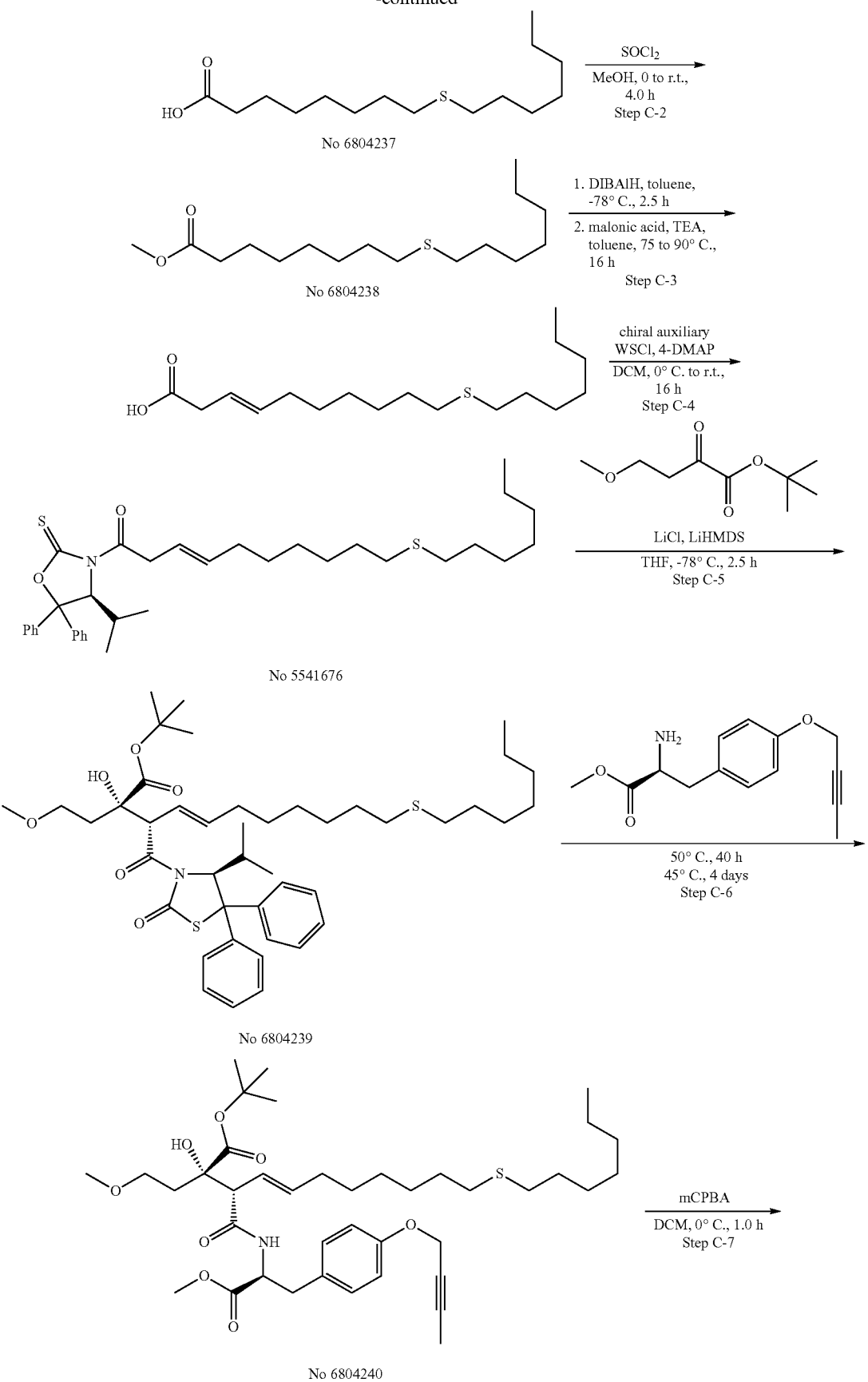

-continued

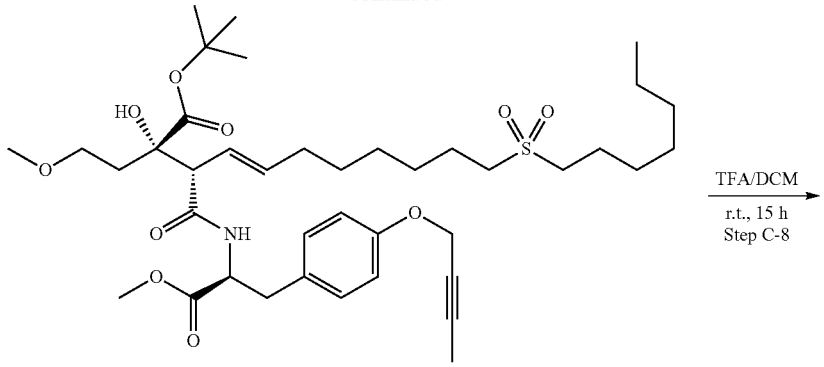

No 6804464

TFA/DCM
r.t., 15 h
Step C-8

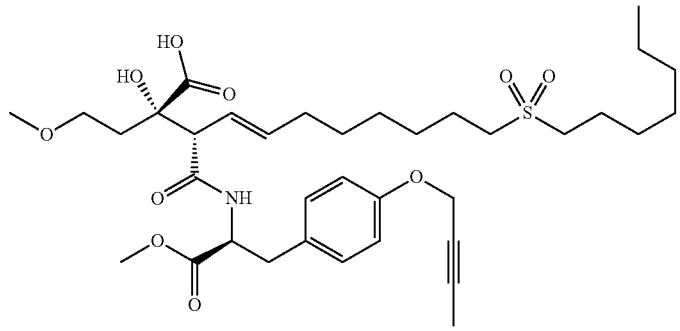

No 5513214

Step C-1

At room temperature, a commercially available reagent of 8-bromo-octanoic acid (97% content, 1.74 g, 7.56 mmol) was dissolved in an aqueous solution (15 mL) of 18% sodium hydroxide, and a commercially available reagent of heptane-1-thiol (1.0 g, 7.56 mmol) was added dropwise. The mixture was then warmed to 100° C., and stirred for 2.0 hours while maintaining the temperature at 100° C. The mixture was cooled to room temperature, and then neutralized to pH 6.0 with concentrated hydrochloric acid. After filtration, solid was washed with dichloromethane, and the filtrate was extracted. The aqueous layer was then washed with ethyl acetate. To the organic layer was added 150 mL of ethyl acetate and the organic layer was washed with water, dried over anhydrous sodium sulfate, and filtered. After the solvent was distilled off, the filtrate was dried under reduced pressure to obtain 8-heptylsulfanyl-octanoic acid (No. 6804237; 2.04 g, 98% yield).

$^1$H-NMR (CDCl$_3$) δ: 0.88 (3H, t, J=6.6 Hz), 1.18-1.45 (14H, m), 1.54-1.65 (6H, m), 2.35 (2H, t, J=7.1 Hz), 2.49 (4H, t, J=7.1 Hz).

ESI (LC/MS positive mode) m/z 275 (M+H); Rt 2.25 min.

Step C-2

Under a nitrogen atmosphere, 8-heptylsulfanyl-octanoic acid (No. 6804237; 2.04 g, 7.43 mmol) was dissolved in methanol (20.4 mL), and the mixture was cooled to 0° C. While maintaining the temperature at 0° C., thionyl chloride (589.5 μL, 8.18 mmol) was added. The mixture was stirred at 0° C. for 5.0 minutes and at room temperature for 4.0 hours. The solvent was distilled off under reduced pressure. Methanol was then added to the residue, and the solvent was again distilled off under reduced pressure. This operation was repeated twice. To the residue was added dichloromethane. The organic layer was washed with water and a saturated brine in order, dried over anhydrous sodium sulfate, and filtered. The solvent was distilled off. The resulting residue was then purified with SP1 (SiO$_2$ cartridge, 10% ethyl acetate/n-hexane, Rf=0.5) to obtain methyl 8-heptylsulfanyl-octanoate (No. 6804238; 2.29 g, quant.).

$^1$H-NMR (CDCl$_3$) δ: 0.88 (3H, t, J=6.6 Hz), 1.22-1.43 (14H, m), 1.53-1.74 (6H, m), 2.30 (2H, t, J=7.7 Hz), 2.49 (4H, t, J=7.1 Hz), 3.66 (3H, s).

ESI (LC/MS positive mode) m/z 289 (M+H); Rt 2.55 min.

Step C-3

Under a nitrogen atmosphere, methyl 8-heptylsulfanyl-octanoate (No. 6804238; 872.5 mg, 3.02 mmol) was dissolved in toluene (13 mL), and the mixture was cooled to −78° C. While maintaining the temperature at −78° C., a diluted solution of diisobutylaluminum hydride (1.5 M solution in toluene, 2.22 mL, 3.33 mmol) in toluene (2.0 mL) was added dropwise. The mixture was stirred at −78° C. for 2.0 hours. After monitoring the reaction by LCMS, further diisobutylaluminum hydride (1.5 M solution in toluene, 0.22 mL, 0.33 mmol) was added to this reaction solution, which was stirred at −78° C. for 30 minutes. Methanol (0.80 mL) was added to the reaction solution, and the mixture was stirred at −78° C. for 10 minutes to stop the reaction. A saturated Rochelle salt aqueous solution (2.5 mL) and water (7.5 mL) were further added and the mixture was stirred at 0° C. for 1.0 hour. Insoluble material was filtered off, and washed with dichloromethane. The filtrate was then extracted with dichloromethane. The organic layer was washed with water, and dried over anhydrous sodium sulfate, and then filtered.

Dichloromethane was distilled off under reduced pressure to obtain 8-heptylsulfanyl-octanal (ESI (LC/MS positive mode) m/z 259 (M+H); Rt 2.43 min.) as the target compound. While the toluene solvent still remained, the atmosphere was changed to a nitrogen atmosphere, and triethylamine (759 μL, 5.44 mmol) and a solution of malonic acid (566 mg, 5.44 mmol) in DMF (0.872 mL) were added in order at 75° C. The mixture was stirred at 90° C. for 16 hours. After cooling to room temperature, an aqueous solution (10.9 mL) of 30% sodium dihydrogen phosphate and ethyl acetate (21.8 mL) were added to extract the mixture. The organic layer was washed with water, and the aqueous layer was washed with ethyl acetate. The combined organic layer was then washed again with water and a saturated brine, dried over anhydrous sodium sulfate and then filtered. The solvent was distilled off. To the resulting residue were added acetonitrile (10 mL), n-hexane (10 mL), and an aqueous solution (10 mL) of 5.0% sodium bicarbonate. The mixture was stirred at room temperature for 2.0 minutes. The hexane layer was removed by extraction. The remaining acetonitrile and aqueous sodium bicarbonate layers were washed with n-hexane, and the hexane layer was removed again. An aqueous solution of 0.5 M citric acid was then added to pH 4.0, and the mixture was back-extracted with ethyl acetate. This ethyl acetate layer was washed with water and a saturated brine in order, dried over anhydrous sodium sulfate, and filtered. The solvent was distilled off to obtain 601.6 mg of (E)-10-heptylsulfanyl-dec-3-enoic acid (ESI (LC/MS positive mode) m/z 301 (M+H); Rt 2.35 min.).

Step C-4

Under a nitrogen atmosphere, (E)-10-heptylsulfanyl-dec-3-enoic acid (601.6 mg, 2.00 mmol), obtained in Step C-3, and (S)-4-isopropyl-5,5-diphenyl-oxazolidine-2-thione (595.4 mg, 2.00 mmol) were dissolved in dichloromethane (9.0 mL). The mixture was cooled to 0° C. While maintaining the temperature at 0° C., N,N-dimethyl-4-aminopyridine (24.4 mg, 0.20 mmol) and WSCl (498.9 mg, 2.60 mmol) were added in order. The mixture was stirred at 0° C. for 2.0 minutes and at room temperature for 16 hours. To the reaction solution were added an aqueous solution (12 mL) of 10% sodium dihydrogen phosphate and ethyl acetate and the mixture was extracted. The organic layer was washed with water and a saturated brine in order, dried over anhydrous sodium sulfate, and filtered. The solvent was distilled off. The resulting residue was then purified with SP1 (SiO$_2$ cartridge, 10% ethyl acetate/n-hexane, Rf=0.6) to obtain (E)-10-heptylsulfanyl-1-((S)-4-isopropyl-5,5-diphenyl-2-thioxo-oxazolidin-3-yl)-dec-3-en-1-one (No. 5541676; 911.6 mg, 3 steps, 52% yield).

$^1$H-NMR (CDCl$_3$) δ: 0.79 (3H, d, J=7.1 Hz), 0.84-0.90 (6H, m), 1.21-1.39 (14H, m), 1.53-1.61 (4H, m), 1.93-2.06 (3H, m), 2.47-2.51 (4H, m), 3.85 (1H, dd, J=16.7, 4.4 Hz), 3.99 (1H, dd, J=16.5, 4.4 Hz), 5.40-5.52 (2H, m), 5.59 (1H, d, J=3.8 Hz), 7.25-7.36 (6H, m), 7.42-7.47 (4H, m).

ESI (LC/MS positive mode) m/z 580 (M+H); Rt 4.32 min.

Step C-5

Lithium chloride (23.0 mg, 0.542 mmol) was heat dried with a heat gun under reduced pressure. Under a nitrogen atmosphere, a solution of (E)-10-heptylsulfanyl-1-((S)-4-isopropyl-5,5-diphenyl-2-thioxo-oxazolidin-3-yl)-dec-3-en-1-one (No. 5541676; 104.7 mg, 0.181 mmol) in THF (2.1 mL) was added at room temperature. The mixture was stirred until it became homogeneous and then cooled to −78° C. Lithium hexamethyldisilazide (1 M solution in THF, 0.235 mL, 0.235 mmol) was added and the mixture was stirred for 1 hour. To this reaction mixture was added dropwise a solution of tert-butyl 4-methoxy-2-oxo-butyrate (51.0 mg, 0.271 mmol) in THF (1.36 mL). The mixture was stirred for further 1.5 hours. To the reaction mixture was added acetic acid (28 μL, 0.495 mmol), and the cooling bath was removed. A saturated aqueous solution (0.52 mL) of ammonium chloride, water (0.52 mL), and ethyl acetate (5.6 mL) were added. The mixture was warmed to room temperature, and extracted with ethyl acetate. The aqueous layer was then washed with ethyl acetate, dried over anhydrous sodium sulfate, and filtered. The solvent was distilled off. The resulting residue was then purified with SP1 (SiO$_2$ cartridge, 17% ethyl acetate/n-hexane, Rf=0.30) to obtain tert-butyl (E)-(2S,3S)-11-heptylsulfanyl-2-hydroxy-3-((S)-4-isopropyl-2-oxo-5,5-diphenyl-thiazolidine-3-carbonyl)-2-(2-methoxy-ethyl)-undec-4-enoate (No. 6804239; 130.2 mg, 94% yield).

$^1$H-NMR (CDCl$_3$) δ: 0.74 (3H, d, J=6.6 Hz), 0.80 (3H, d, J=6.6 Hz), 0.88 (3H, t, J=7.1 Hz), 1.11 (1H, dt, J=13.7, 4.9 Hz), 1.21-1.38 (14H, m), 1.47 (9H, s), 1.56-1.60 (4H, m), 1.71-1.78 (1H, m), 1.97-2.05 (3H, m), 2.45-2.50 (4H, m), 3.08-3.13 (4H, m), 3.20-3.26 (1H, m), 3.50 (1H, s), 5.59 (1H, dd, J=15.4, 9.3 Hz), 5.67 (1H, d, J=3.8 Hz), 5.91 (1H, dt, J=15.4, 6.6 Hz), 6.14 (1H, d, J=9.3 Hz), 7.25-7.29 (2H, m), 7.34 (4H, t, J=7.7 Hz), 7.43-7.59 (2H, m), 7.49-7.51 (2H, m).

ESI (LC/MS positive mode) m/z 768 (M+H); Rt 4.52 min.

Step C-6 tert-Butyl (E)-(2S,3S)-11-heptylsulfanyl-2-hydroxy-3-((S)-4-isopropyl-2-oxo-5,5-diphenyl-thiazolidine-3-carbonyl)-2-(2-methoxy-ethyl)-undec-4-enoate (No. 6804239; 68.3 mg, 0.0889 mmol) and methyl (S)-2-amino-3-(4-but-2-ynyloxy-phenyl)-propionate (33.0 mg, 0.133 mmol) were dissolved in dichloromethane. The solvent was distilled off under reduced pressure. The resulting mixture was stirred at 50° C. for 5 days, cooled to room temperature, and then extracted by adding ethyl acetate and water. The organic layer was washed with a saturated brine, dried over anhydrous sodium sulfate, and then filtered. The solvent was distilled out of the filtrate under reduced pressure. The residue was purified with SP1 (SiO2 cartridge, 25% ethyl acetate/n-hexane, Rf=0.1) to obtain tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate (No. 6804240; 50.9 mg, 80% yield)

$^1$H-NMR (CDCl$_3$) δ: 0.88 (3H, m), 1.22-1.50 (23H, m), 1.53-1.58 (5H, m), 1.86 (3H, s), 1.95-1.99 (3H, m), 2.47-2.50 (4H, m), 2.97 (1H, dd, J=13.7, 7.7 Hz), 3.09-3.15 (2H, m), 3.21 (3H, s), 3.26-3.39 (2H, m), 3.70 (3H, s), 4.15 (1H, s), 4.61 (2H, s), 4.79-4.84 (1H, m), 5.45 (1H, dd, J=15.4, 9.3 Hz), 5.62-5.69 (1H, m), 6.85 (2H, d, J=8.2 Hz), 7.06-7.09 (3H, m).

ESI (LC/MS positive mode) m/z 718 (M+H); Rt 2.67 min.

Step C-7 tert-Butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate (No. 6804240; 50.9 mg, 0.0709 mmol) was dissolved in dichloromethane (3.4 mL), and the mixture was cooled to 0° C. mCPBA (72% content, 34.0 mg, 0.142 mmol) was added, and the mixture was stirred at 0° C. for 30 minutes. After completing the reaction, the progress of the reaction was stopped by adding an aqueous solution of 10% sodium thiosulfate, and the mixture was extracted with dichloromethane. The organic layer was washed with a saturated aqueous solution of sodium bicarbonate, water, and a saturated brine, dried over anhydrous sodium sulfate, and filtered. The solvent was distilled off under reduced pressure to obtain 56.1 mg of tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate (No. 6804464; ESI (LC/MS positive mode) m/z 750 (M+H); Rt 2.15 min.).

Step C-8 tert-Butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate (No. 6804464; 56.1 mg, 0.0748 mmol) was dissolved in dichloromethane (3.0 mL), and trifluoroacetic acid (1.0 mL) was added. The mixture was stirred at room temperature for 15 hours. The solvent was distilled off under reduced pressure. To the residue was added dichloromethane, and the solvent was again distilled off under reduced pressure. This operation was repeated twice. The residue was then purified by HPLC (water with 0.05% TFA-acetonitrile with 0.05% TFA) to obtain (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoic acid (No. 5513214; 36.2 mg, 74% yield, white powder).

$^1$H-NMR (CD$_3$OD) δ: 0.91 (3H, t, J=7.1 Hz), 1.23-1.47 (14H, m), 1.66-1.82 (8H, m), 1.97-2.09 (3H, m), 2.90 (1H, dd, J=13.7, 9.3 Hz), 3.03-3.07 (4H, m), 3.10-3.15 (1H, m), 3.22 (1H, d, J=8.2 Hz), 3.24 (3H, s), 3.37-3.44 (2H, m), 3.71 (3H, s), 4.61-4.68 (3H, m), 5.45-5.59 (2H, m), 6.85 (2H, d, J=8.8 Hz), 7.10 (2H, d, J=8.2 Hz).

ESI (LC/MS positive mode) m/z 694 (M+H); Rt 1.87 min.

83. No. 5500525

(E)-(2S,3S)-3-[(S)-2-(4-But-2-ynyloxy-phenyl)-1-methoxycarbonyl-ethylcarbamoyl]-11-(heptane-1-sulfonyl)-2-hydroxy-2-propyl-undec-4-enoic acid

[Chem. 167]

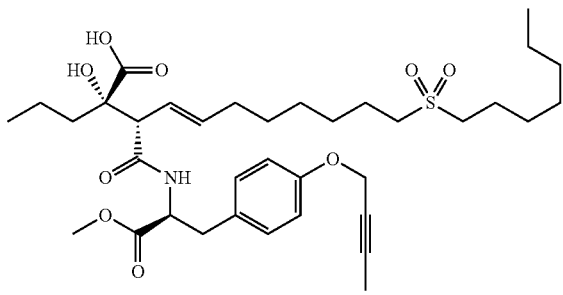

tert-Butyl (E)-(2S,3S)-11-heptylsulfanyl-2-hydroxy-3-((S)-4-isopropyl-2-oxo-5,5-diphenyl-thiazolidine-3-carbonyl)-2-propyl-nonadec-4-enoate was synthesized (ESI (LC/MS positive mode) m/z 753 (M+H); Rt 5.97 min.) by using tert-butyl 2-oxo-pentanoate instead of tert-butyl 4-methoxy-2-oxo-butyrate in Step C-5. Subsequently, tert-butyl (E)-(2S, 3S)-3-[(S)-2-(4-but-2-ynyloxy-phenyl)-1-methoxycarbonyl-ethylcarbamoyl]-11-heptylsulfanyl-2-hydroxy-2-propyl-undec-4-enoate (ESI (LC/MS positive mode) m/z 702 (M+H); Rt 2.90 min.) was synthesized using conditions at 50° C., for 2.0 days instead of the conditions in Step C-6. tert-Butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-propyl-undec-4-enoate was first synthesized (ESI (LC/MS positive mode) m/z 734 (M+H); Rt 2.30 min.) under conditions similar to those in Step C-7. (E)-(2S,3S)-3-[(S)-2-(4-But-2-ynyloxy-phenyl)-1-methoxycarbonyl-ethylcarbamoyl]-11-(heptane-1-sulfonyl)-2-hydroxy-2-propyl-undec-4-enoic acid (No. 5500525) was then synthesized by the reaction under conditions similar to those in Step C-8.

$^1$H-NMR (CD$_3$COCD$_3$) δ: 0.73 (3H, t, J=7.1 Hz), 0.76 (3H, t, J=7.1 Hz), 1.11-1.46 (18H, m), 1.55-1.68 (5H, m), 1.70 (3H, t, J=2.2 Hz), 1.80-1.90 (2H, m), 2.44 (1H, s), 2.83 (1H, dd, J=11.0, 8.2 Hz), 2.87-2.91 (4H, m), 2.97 (1H, dd, J=9.6, 5.5 Hz), 3.20 (1H, d, J=8.2 Hz), 3.56 (3H, s), 4.53-4.58 (3H, m), 5.38-5.49 (2H, m), 6.75 (2H, d, J=8.8 Hz), 7.02 (2H, d, J=8.8 Hz), 7.59 (1H, d, J=7.7 Hz).

ESI (LC/MS positive mode) m/z 678 (M+H); Rt 2.05 min.

84. No. 5501823

(E)-(2S,3S)-3-[(S)-2-(4-But-2-ynyloxy-phenyl)-1-carboxy-ethylcarbamoyl]-11-(heptane-1-sulfonyl)-2-hydroxy-2-propyl-undec-4-enoic acid

[Chem. 168]

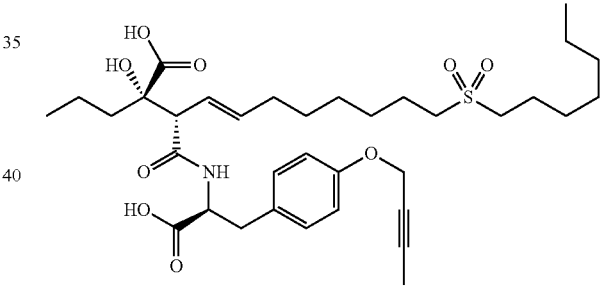

(E)-(2S,3S)-3-[(S)-2-(4-But-2-ynyloxy-phenyl)-1-carboxy-ethylcarbamoyl]-11-(heptane-1-sulfonyl)-2-hydroxy-2-propyl-undec-4-enoic acid (No. 5501823) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-propyl-undec-4-enoic acid (No. 5500525) as a starting material.

$^1$H-NMR (DMSO-d$_6$) δ: 0.79 (3H, t, J=7.1 Hz), 0.86 (3H, t, J=7.1 Hz), 0.97-1.09 (1H, m), 1.25-1.43 (16H, m), 1.53-1.69 (5H, m), 1.82 (3H, s), 1.85-1.96 (2H, m), 2.81 (1H, dd, J=13.7, 9.3 Hz), 2.97-3.05 (5H, m), 3.19 (1H, d, J=6.0 Hz), 4.35-4.40 (1H, m), 4.66 (2H, s), 4.99 (1H, br.s), 5.34-5.47 (2H, m), 6.82 (2H, d, J=7.7 Hz), 7.12 (2H, d, J=7.7 Hz), 8.18 (1H, d, J=7.7 Hz), 12.6 (2H, br.s).

ESI (LC/MS positive mode) m/z 664 (M+H); Rt 2.02 min.

95. No. 5514406

(E)-(2S,3S)-3-[(S)-2-(4-Butoxy-phenyl)-1-methoxy-carbonyl-ethylcarbamoyl]-11-(heptane-1-sulfonyl)-2-hydroxy-2-(2-methoxy-ethyl)-undec-4-enoic acid

[Chem. 169]

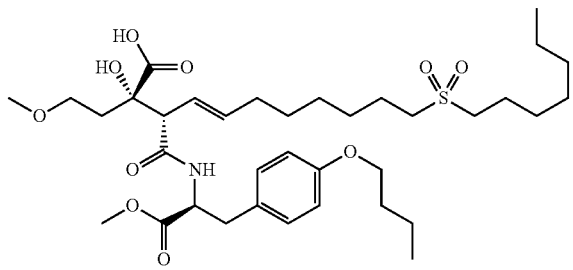

tert-Butyl (E)-(2S,3S)-3-[(S)-2-(4-butoxy-phenyl)-1-methoxycarbonyl-ethylcarbamoyl]-11-heptylsulfanyl-2-hydroxy-2-(2-methoxy-ethyl)-undec-4-enoate (ESI (LC/MS positive mode) m/z 722 (M+H); Rt 3.13 min.) was synthesized by using methyl (S)-2-amino-3-(4-butoxy-phenyl)-propionate and conditions at 50° C., for 2.5 days instead of methyl (S)-2-amino-3-(4-but-2-ynyloxy-phenyl)-propionate and the conditions in Step C-6. Then, tert-butyl (E)-(2S,3S)-3-[(S)-2-(4-butoxy-phenyl)-1-methoxycarbonyl-ethylcarbamoyl]-11-(heptane-1-sulfonyl)-2-hydroxy-2-(2-methoxy-ethyl)-undec-4-enoate was first synthesized (ESI (LC/MS positive mode) m/z 754 (M+H); Rt 2.32 min) under conditions similar to those in Step C-7. Subsequently, (E)-(2S,3S)-3-[(S)-2-(4-butoxy-phenyl)-1-methoxycarbonyl-ethylcarbamoyl]-11-(heptane-1-sulfonyl)-2-hydroxy-2-(2-methoxy-ethyl)-undec-4-enoic acid (No. 5514406) was synthesized by the reaction under conditions similar to those in Step C-8.

¹H-NMR (CD₃OD) δ: 0.91 (3H, t, J=7.1 Hz), 0.98 (3H, t, J=7.1 Hz), 1.23-1.54 (17H, m), 1.66-1.82 (7H, m), 1.92-2.09 (3H, m), 2.89 (1H, dd, J=14.3, 9.3 Hz), 3.02-3.06 (4H, m), 3.11 (1H, dd, J=13.7, 4.9 Hz), 3.24 (3H, s), 3.36-3.46 (2H, m), 3.70 (3H, s), 3.93 (2H, t, J=6.6 Hz), 4.62-4.69 (1H, m), 5.45-5.61 (2H, m), 6.79 (2H, d, J=8.8 Hz), 7.08 (2H, d, J=8.8 Hz).

ESI (LC/MS positive mode) m/z 698 (M+H); Rt 2.05 min.

96. No. 5514408

(E)-(2S,3S)-3-[(S)-2-(4-Butoxy-phenyl)-1-methyl-carbamoyl-ethylcarbamoyl]-11-(heptane-1-sulfonyl)-2-hydroxy-2-(2-methoxy-ethyl)-undec-4-enoic acid

[Chem. 170]

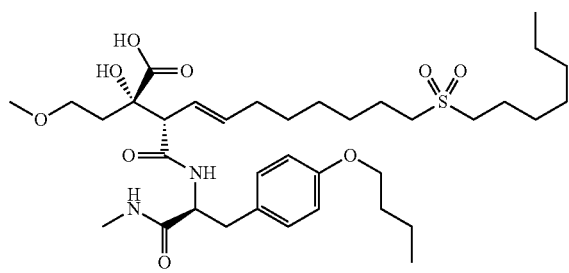

tert-Butyl (E)-(2S,3S)-3-[(S)-2-(4-butoxy-phenyl)-1-methylcarbamoyl-ethylcarbamoyl]-11-heptylsulfanyl-2-hydroxy-2-(2-methoxy-ethyl)-undec-4-enoate (ESI (LC/MS positive mode) m/z 721 (M+H); Rt 2.85 min.) was synthesized by using (S)-2-amino-3-(4-butoxy-phenyl)-N-methyl-propionamide and conditions at 50° C., for 2.5 days instead of methyl (S)-2-amino-3-(4-but-2-ynyloxy-phenyl)-propionate and the conditions in Step C-6. Then, tert-butyl (E)-(2S,3S)-3-[(S)-2-(4-butoxy-phenyl)-1-methylcarbamoyl-ethylcarbamoyl]-11-(heptane-1-sulfonyl)-2-hydroxy-2-(2-methoxy-ethyl)-undec-4-enoate was first synthesized (ESI (LC/MS positive mode) m/z 753 (M+H); Rt 2.17 min.) under conditions similar to those in Step C-7. Subsequently, (E)-(2S,3S)-3-[(S)-2-(4-butoxy-phenyl)-1-methylcarbamoyl-ethylcarbamoyl]-11-(heptane-1-sulfonyl)-2-hydroxy-2-(2-methoxy-ethyl)-undec-4-enoic acid (No. 5514408) was synthesized by the reaction under conditions similar to those in Step C-8.

¹H-NMR (CD₃OD) δ: 0.91 (3H, t, J=7.1 Hz), 0.98 (3H, t, J=7.1 Hz), 1.26-1.54 (17H, m), 1.59-1.66 (1H, m), 1.70-1.82 (6H, m), 1.94-2.07 (3H, m), 2.69 (3H, s), 2.79 (1H, dd, J=13.7, 9.3 Hz), 3.00-3.06 (5H, m), 3.19-3.21 (1H, m), 3.24 (3H, s), 3.34-3.46 (2H, m), 3.92 (2H, t, J=6.6 Hz), 4.48-4.54 (1H, m), 5.48-5.56 (2H, m), 6.79 (2H, d, J=8.8 Hz), 7.10 (2H, d, J=8.8 Hz).

ESI (LC/MS positive mode) m/z 697 (M+H); Rt 1.85 min.

98. No. 5518586

(E)-(2R,3S)-3-[(S)-2-(4-Butoxy-phenyl)-1-methoxy-carbonyl-ethylcarbamoyl]-11-(heptane-1-sulfonyl)-2-hydroxy-2-methoxymethyl-undec-4-enoic acid

[Chem. 171]

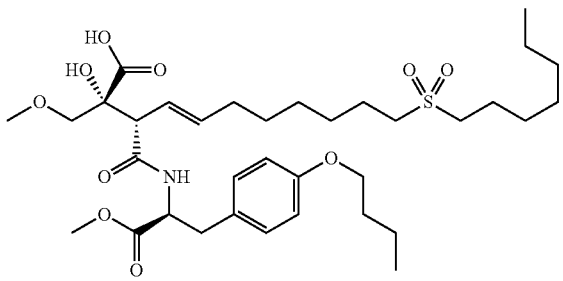

tert-Butyl (E)-(2R,3S)-11-heptylsulfanyl-2-hydroxy-3-((S)-4-isopropyl-2-oxo-5,5-diphenyl-thiazolidine-3-carbonyl)-2-methoxymethyl-undec-4-enoate was synthesized (ESI (LC/MS positive mode) m/z 754 (M+H); Rt 4.15 min.) by using tert-butyl 3-methoxy-2-oxo-propionate instead of tert-butyl 4-methoxy-2-oxo-butyrate in Step C-5. Subsequently, tert-butyl (E)-(2R,3S)-3-[(S)-2-(4-butoxy-phenyl)-1-methoxycarbonyl-ethylcarbamoyl]-11-heptylsulfanyl-2-hydroxy-2-methoxymethyl-tmdec-4-enoate (ESI (LC/MS positive mode) m/z 708 (M+H); Rt 3.00 min.) was synthesized by using methyl (S)-2-amino-3-(4-butoxy-phenyl)-propionate and conditions at 50° C., for 2.0 days instead of methyl (S)-2-amino-3-(4-but-2-ynyloxy-phenyl)-propionate and the conditions in Step C-6. Then, tert-butyl (E)-(2R,3S)-3-[(S)-2-(4-butoxy-phenyl)-1-methoxycarbonyl-ethylcarbamoyl]-11-(heptane-1-sulfonyl)-2-hydroxy-2-methoxymethyl-undec-4-enoate was first synthesized (ESI (LC/MS positive mode) m/z 740 (M+H); Rt 2.27 min.) under conditions similar to those in Step C-7. Subsequently, (E)-(2R,3S)-3-[(S)-2-(4-butoxy-phenyl)-1-methoxycarbonyl-ethylcarbamoyl]-11-(heptane-1-sulfonyl)-2-hydroxy-2- methoxymethyl-undec-4-enoic acid (No. 5518586) was synthesized by the reaction under conditions similar to those in Step C-8.

$^1$H-NMR (CD$_3$OD) δ: 0.91 (3H, t, J=7.1 Hz), 0.98 (3H, t, J=7.1 Hz), 1.28-1.53 (17H, m), 1.69-1.82 (6H, m), 1.95-2.09 (2H, m), 2.90 (1H, dd, J=14.3, 9.3 Hz), 3.02-3.06 (4H, m), 3.10 (1H, dd, J=14.3, 4.9 Hz), 3.24-3.26 (1H, m), 3.28 (3H, s), 3.57 (1H, d, J=9.3 Hz), 3.71 (3H, s), 3.93 (2H, t, J=6.6 Hz), 4.63 (1H, dd, J=9.3, 4.9 Hz), 5.43-5.60 (2H, m), 6.81 (2H, d, J=8.8 Hz), 7.09 (2H, d, J=8.8 Hz).

ESI (LC/MS positive mode) m/z 684 (M+H); Rt 3.00 min.

101. No. 5518589

(E)-(2R,3S)-3-[(S)-2-(4-Butoxy-phenyl)-1-methyl-carbamoyl-ethylcarbamoyl]-11-(heptane-1-sulfonyl)-2-hydroxy-2-methoxymethyl-undec-4-enoic acid

[Chem. 172]

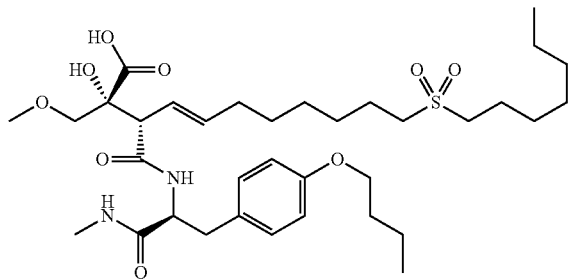

tert-Butyl (E)-(2R,3S)-11-heptylsulfanyl-2-hydroxy-3-((S)-4-isopropyl-2-oxo-5,5-diphenyl-thiazolidine-3-carbonyl)-2-methoxymethyl-undec-4-enoate was synthesized (ESI (LC/MS positive mode) m/z 754 (M+H); Rt 4.15 min.) by using tert-butyl 3-methoxy-2-oxo-propionate instead of tert-butyl 4-methoxy-2-oxo-butyrate in Step C-5. Subsequently, tert-butyl (E)-(2R,3S)-3-[(S)-2-(4-butoxy-phenyl)-1-methylcarbamoyl-ethylcarbamoyl]-11-heptylsulfanyl-2-hydroxy-2-methoxymethyl-undec-4-enoate (ESI (LC/MS positive mode) m/z 707 (M+H); Rt 2.82 min.) was synthesized by using (S)-2-amino-3-(4-butoxy-phenyl)-N-methyl-propionamide and conditions at 50° C., for 2.0 days instead of methyl (S)-2-amino-3-(4-but-2-ynyloxy-phenyl)-propionate and the conditions in Step C-6.

Then, tert-butyl (E)-(2R,3S)-3-[(S)-2-(4-butoxy-phenyl)-1-methylcarbamoyl-ethylcarbamoyl]-11-(heptane-1-sulfonyl)-2-hydroxy-2-methoxymethyl-undec-4-enoate was first synthesized (ESI (LC/MS positive mode) m/z 739 (M+H); Rt 2.12 min.) under conditions similar to those in Step C-7. Subsequently, (E)-(2R,3S)-3-[(S)-2-(4-butoxy-phenyl)-1-methylcarbamoyl-ethylcarbamoyl]-11-(heptane-1-sulfonyl)-2-hydroxy-2-methoxymethyl-undec-4-enoic acid (No. 5518589) was synthesized by the reaction under conditions similar to those in Step C-8.

$^1$H-NMR (CD$_3$OD) δ: 0.91 (3H, t, J=7.1 Hz), 0.98 (3H, t, J=7.1 Hz), 1.27-1.53 (17H, m), 1.69-1.82 (6H, m), 1.96-2.03 (2H, m), 2.70 (3H, s), 2.79 (1H, dd, J=13.7, 9.3 Hz), 3.02-3.09 (5H, m), 3.25-3.27 (1H, m), 3.29 (3H, s), 3.56 (1H, d, J=9.3 Hz), 3.92 (2H, t, J=6.6 Hz), 4.49 (1H, dd, J=9.3, 5.5 Hz), 5.48-5.59 (2H, m), 6.79 (2H, d, J=8.8 Hz), 7.10 (2H, d, J=8.8 Hz).

ESI (LC/MS positive mode) m/z 683 (M+H); Rt 2.70 min.

104. No. 5518595

(E)-(2R,3S)-3-[(S)-2-(4-Butoxy-phenyl)-1-carbamoyl-ethylcarbamoyl]-11-(heptane-1-sulfonyl)-2-hydroxy-2-methoxymethyl-undec-4-enoic acid

[Chem. 173]

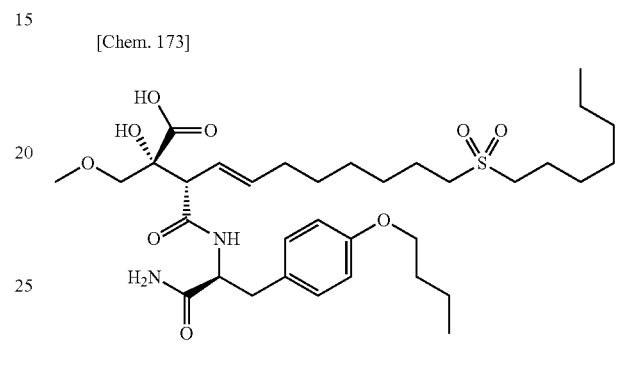

tert-Butyl (E)-(2R,3S)-11-heptylsulfanyl-2-hydroxy-3-((S)-4-isopropyl-2-oxo-5,5-diphenyl-thiazolidine-3-carbonyl)-2-methoxymethyl-undec-4-enoate was synthesized (ESI (LC/MS positive mode) m/z 754 (M+H); Rt 4.15 min.) by using tert-butyl 3-methoxy-2-oxo-propionate instead of tert-butyl 4-methoxy-2-oxo-butyrate in Step C-5. Subsequently, tert-butyl (E)-(2R,3S)-3-[(S)-2-(4-butoxy-phenyl)-1-carbamoyl-ethylcarbamoyl]-11-heptylsulfanyl-2-hydroxy-2-methoxymethyl-undec-4-enoate (ESI (LC/MS positive mode) m/z 693 (M+H); Rt 2.72 min.) was synthesized by using (S)-2-amino-3-(4-butoxy-phenyl)-propionamide and conditions at 50° C., for 2.0 days instead of methyl (S)-2-amino-3-(4-but-2-ynyloxy-phenyl)-propionate and the conditions in Step C-6. Then, tert-butyl (E)-(2R,3S)-3-[(S)-2-(4-butoxy-phenyl)-1-carbamoyl-ethylcarbamoyl]-11-(heptane-1-sulfonyl)-2-hydroxy-2-methoxymethyl-undec-4-enoate was first synthesized (ESI (LC/MS positive mode) m/z 725 (M+H); Rt 2.10 min.) under conditions similar to those in Step C-7. Subsequently, (E)-(2R,3S)-3-[(S)-2-(4-butoxy-phenyl)-1-carbamoyl-ethylcarbamoyl]-11-(heptane-1-sulfonyl)-2-hydroxy-2-methoxymethyl-undec-4-enoic acid (No. 5518595) was synthesized by the reaction under conditions similar to those in Step C-8.

$^1$H-NMR (CD$_3$OD) δ: 0.91 (3H, t, J=7.1 Hz), 0.97 (3H, t, J=7.1 Hz), 1.28-1.53 (17H, m), 1.69-1.82 (6H, m), 1.95-2.02 (2H, m), 2.80 (1H, dd, J=14.3, 9.9 Hz), 3.02-3.14 (5H, m), 3.23-3.26 (1H, m), 3.27 (3H, s), 3.53 (1H, d, J=9.9 Hz), 3.92 (2H, t, J=6.6 Hz), 4.55 (1H, dd, J=9.9, 4.9 Hz), 5.48-5.57 (2H, m), 6.85 (2H, d, J=8.8 Hz), 7.13 (2H, d, J=8.8 Hz).

ESI (LC/MS positive mode) m/z 669 (M+H); Rt 2.63 min.

106. No. 5520941

(E)-(2S,3S)-3-[(S)-2-(4-Butoxy-phenyl)-1-carboxy-ethylcarbamoyl]-11-(heptane-1-sulfonyl)-2-hydroxy-2-(2-methoxy-ethyl)-undec-4-enoic acid

[Chem. 174]

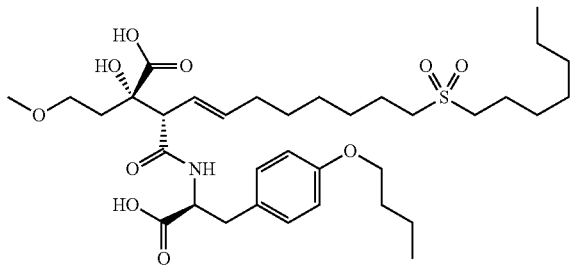

(E)-(2S,3S)-3-[(S)-2-(4-Butoxy-phenyl)-1-carboxy-ethylcarbamoyl]-11-(heptane-1-sulfonyl)-2-hydroxy-2-(2-methoxy-ethyl)-undec-4-enoic acid (No. 5520941) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-butoxy-phenyl)-1-methoxycarbonyl-ethylcarbamoyl]-11-(heptane-1-sulfonyl)-2-hydroxy-2-(2-methoxy-ethyl)-undec-4-enoic acid (No. 5514406) as a starting material.

$^1$H-NMR (DMSO-$d_6$) δ: 0.87 (3H, t, J=7.1 Hz), 0.92 (3H, t, J=7.1 Hz), 1.17-1.46 (17H, m), 1.59-1.70 (7H, m), 1.83-1.99 (3H, m), 2.78 (1H, dd, J=14.3, 9.3 Hz), 2.95-3.05 (5H, m), 3.14 (3H, s), 3.16-3.18 (1H, m), 3.21-3.27 (2H, m), 3.90 (2H, t, J=6.6 Hz), 4.33-4.39 (1H, m), 5.34-5.43 (2H, m), 6.77 (2H, d, J=8.2 Hz), 7.08 (2H, d, J=8.2 Hz), 8.19 (1H, d, J=7.7 Hz).

ESI (LC/MS positive mode) m/z 684 (M+H); Rt 1.85 min.

107. No. 5522097

(E)-(2S,3S)-3-[(S)-2-(4-Butoxy-phenyl)-1-carboxy-ethylcarbamoyl]-11-(heptane-1-sulfonyl)-2-hydroxy-2-propyl-undec-4-enoic acid

[Chem. 175]

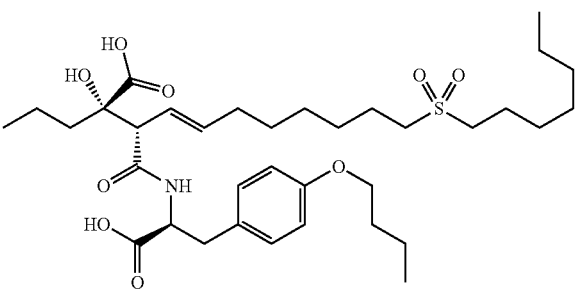

(E)-(2S,3S)-3-[(S)-2-(4-Butoxy-phenyl)-1-carboxy-ethylcarbamoyl]-11-(heptane-1-sulfonyl)-2-hydroxy-2-propyl-undec-4-enoic acid (No. 5522097) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-butoxy-phenyl)-1-methoxycarbonyl-ethylcarbamoyl]-11-(heptane-1-sulfonyl)-2-hydroxy-2-propyl-undec-4-enoic acid (No. 5515491) as a starting material.

$^1$H-NMR (DMSO-$d_6$) δ: 0.78 (3H, J=7.1 Hz), 0.86 (3H, t, J=6.6 Hz), 0.92 (3H, t, J=7.1 Hz), 0.97-1.06 (1H, m), 1.17-1.46 (19H, m), 1.51-1.57 (1H, m), 1.59-1.70 (6H, m), 1.82-1.98 (2H, m), 2.79 (1H, dd, J=13.7, 9.3 Hz), 2.96-3.05 (5H, m), 3.14-3.19 (1H, m), 3.89 (2H, t, J=6.6 Hz), 4.33-4.39 (1H, m), 5.35-5.45 (2H, m), 6.77 (2H, d, J=8.8 Hz), 7.18 (2H, d, J=8.2 Hz), 8.14 (1H, d, J=7.7 Hz).

ESI (LC/MS positive mode) m/z 668 (M+H); Rt 1.95 min.

159. No. 5527300

(E)-(2S,3S)-3-[(S)-2-(4-Butoxy-phenyl)-1-carboxy-ethylcarbamoyl]-2-(2-fluoro-ethyl)-11-(heptane-1-sulfonyl)-2-hydroxy-undec-4-enoic acid

[Chem. 176]

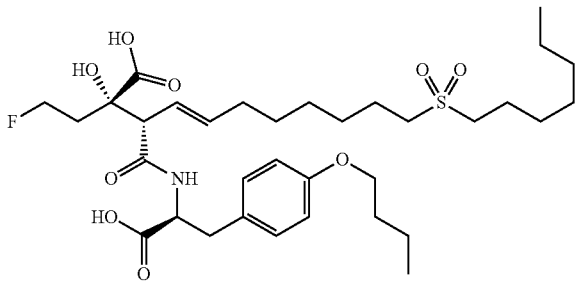

(E)-(2S,3S)-3-[(S)-2-(4-Butoxy-phenyl)-1-carboxy-ethylcarbamoyl]-11-(heptane-1-sulfonyl)-2-hydroxy-2-propyl-undec-4-enoic acid (No. 5527300) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825), using (E)-(2S,3S)-3-[(S)-2-(4-butoxy-phenyl)-1-methoxycarbonyl-ethylcarbamoyl]-2-(2-fluoro-ethyl)-11-(heptane-1-sulfonyl)-2-hydroxy-2-undec-4-enoic acid (No. 5514421) as a starting material.

$^1$H-NMR (DMSO-$d_5$) δ: 0.86 (3H, t, J=7.1 Hz), 0.92 (3H, t, J=7.1 Hz), 1.16-1.46 (18H, m), 1.55-1.70 (5H, m), 1.84-1.94 (2H, m), 2.06-2.20 (1H, m), 2.77-2.83 (1H, m), 2.98-3.05 (5H, m), 3.16-3.22 (1H, m), 3.54 (1H, m), 3.89 (2H, t, J=6.6 Hz), 4.31-4.41 (2H, m), 4.45-4.52 (1H, m), 5.35-5.45 (2H, m), 6.77 (2H, d, J=8.2 Hz), 7.08 (2H, d, J=8.2 Hz), 8.15 (1H, br.s).

ESI (LC/MS positive mode) m/z 672 (M+H); Rt 2.85 min.

164. No. 5540578

(E)-(2S,3S)-3-[(S)-2-(2'-Fluoro-biphenyl-4-yl)-1-methoxycarbonyl-ethylcarbamoyl]-11-(heptane-1-sulfonyl)-2-hydroxy-2-(2-methoxy-ethyl)-undec-4-enoic acid

[Chem. 177]

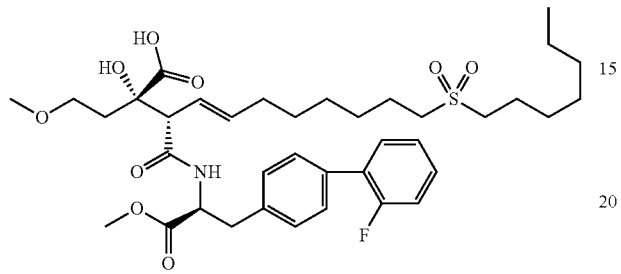

tert-Butyl (E)-(2S,3S)-3-[(S)-2-(2'-fluoro-biphenyl-4-yl)-1-methoxycarbonyl-ethylcarbamoyl]-11-heptylsulfanyl-2-hydroxy-2-(2-methoxy-ethyl)-undec-4-enoate (ESI (LC/MS positive mode) m/z 744 (M+H); Rt 3.77 min.) was synthesized by using methyl (S)-2-amino-3-(2'-fluoro-biphenyl-4-yl)-propionate and conditions at 50° C., for 1.5 days instead of methyl (S)-2-amino-3-(4-but-2-ynyloxy-phenyl)-propionate and the conditions in Step C-6. Then, tert-butyl (E)-(2S, 3S)-3-[(S)-2-(2'-fluoro-biphenyl-4-yl)-1-methoxycarbonyl-ethylcarbamoyl]-11-(heptane-1-sulfonyl)-2-hydroxy-2-(2-methoxy-ethyl)-undec-4-enoate was first synthesized (ESI (LC/MS positive mode) m/z 776 (M+H); Rt 2.23 min.) under conditions similar to those in Step C-7. Subsequently, (E)-(2S,3S)-3-[(S)-2-(2'-fluoro-biphenyl-4-yl)-1-methoxycarbonyl-ethylcarbamoyl]-11-(heptane-1-sulfonyl)-2-hydroxy-2-(2-methoxy-ethyl)-undec-4-enoic acid (No. 5540578) was synthesized by the reaction under conditions similar to those in Step C-8.

$^1$H-NMR (CD$_3$OD) δ: 0.91 (3H, t, J=7.1 Hz), 1.21-1.47 (15H, m), 1.68-1.81 (5H, m), 1.92-1.97 (2H, m), 2.03-2.10 (1H, m), 2.97-3.05 (5H, m), 3.20 (3H, s), 3.22-3.24 (2H, m), 3.37-3.45 (2H, m), 3.74 (3H, s), 4.75 (1H, dd, J=9.3, 4.9 Hz), 5.45-5.59 (2H, m), 7.14-7.37 (5H, m), 7.44-7.48 (3H, m).
ESI (LC/MS positive mode) m/z 720 (M+H); Rt 2.97 min.

174. No. 5541301

(E)-(2S,3S)-3-[(S)-1-Carboxy-2-(2'-fluoro-biphenyl-4-yl)-ethylcarbamoyl]-11-(heptane-1-sulfonyl)-2-hydroxy-2-(2-methoxy-ethyl)-undec-4-enoic acid

[Chem. 178]

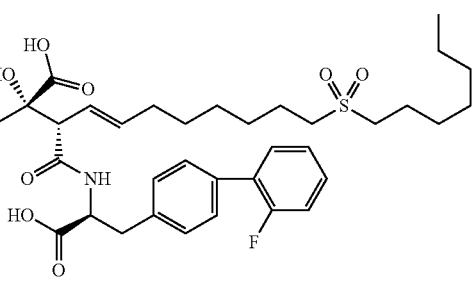

(E)-(2S,3S)-3-[(S)-1-Carboxy-2-(2'-fluoro-biphenyl-4-yl)-ethylcarbamoyl]-11-(heptane-1-sulfonyl)-2-hydroxy-2-(2-methoxy-ethyl)-undec-4-enoic acid (No. 5541301) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825), using (E)-(2S,3S)-3-[(S)-2-(2'-fluoro-biphenyl-4-yl)-1-methoxycarbonyl-ethylcarbamoyl]-11-(heptane-1-sulfonyl)-2-hydroxy-2-(2-methoxy-ethyl)-undec-4-enoic acid (No. 5540578) as a starting material.

$^1$H-NMR (DMSO-d$_6$) δ: 0.86 (3H, t, J=7.1 Hz), 1.12-1.40 (15H, m), 1.54-1.72 (5H, m), 1.81-2.01 (3H, m), 2.89-3.05 (5H, m), 3.08-3.16 (4H, m), 3.19-3.21 (1H, m), 3.24-3.28 (1H, m), 3.29-3.36 (1H, m), 4.45-4.51 (1H, m), 5.36-5.45 (2H, m), 7.27-7.32 (4H, m), 7.35-7.44 (3H, m), 7.47-7.52 (1H, m), 8.30 (1H, d, J=8.2 Hz).
ESI (LC/MS positive mode) m/z 706 (M+H); Rt 2.68 min.

Synthetic Method of No. 5506861 and No. 5506864

[Chem. 179]

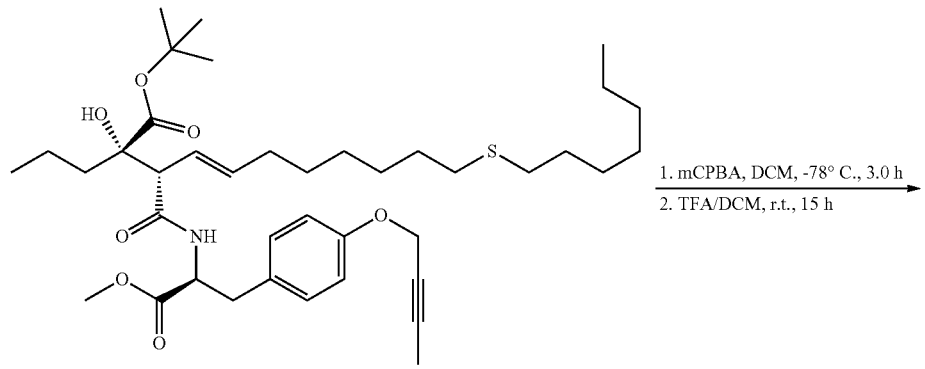

1. mCPBA, DCM, -78° C., 3.0 h
2. TFA/DCM, r.t., 15 h

-continued

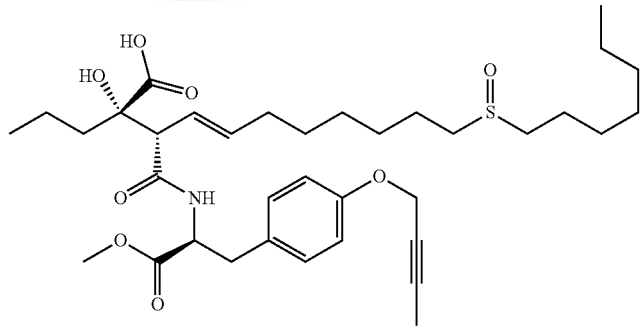

tert-Butyl (E)-(2S,3S)-11-heptylsulfanyl-2-hydroxy-3-((S)-4-isopropyl-2-oxo-5,5-diphenyl-thiazolidine-3-carbonyl)-2-propyl-undec-4-enoate (ESI (LC/MS positive mode) m/z 753 (M+H); Rt 5.97 min.) was synthesized by using tert-butyl 2-oxo-pentanoate instead of tert-butyl 4-methoxy-2-oxo-butyrate in Step C-5. This tert-butyl (E)-(2S,3S)-11-heptylsulfanyl-2-hydroxy-3-((S)-4-isopropyl-2-oxo-5,5-diphenyl-thiazolidine-3-carbonyl)-2-propyl-undec-4-enoate (126.6 mg, 0.180 mmol) was dissolved in dichloromethane (7.6 mL), and the mixture was cooled to −78° C. mCPBA (72% content, 22.4 mg, 0.0935 mmol) was added, and the mixture was stirred at −78° C. for 30 minutes. The reaction was monitored by LCMS, and mCPBA (72% content, 6.7 mg, 0.0280 mmol) was added again. The mixture was stirred at −78° C. for 1.5 hours. The reaction was monitored again by LCMS. Further mCPBA (72% content, 4.5 mg, 0.0188 mmol) was then added, and the mixture was stirred at −78° C. for 1 hour. After completing the reaction, the progress of the reaction was stopped by adding an aqueous solution of 10% sodium thiosulfate and the mixture was extracted with dichloromethane. The organic layer was washed with a saturated aqueous solution of sodium bicarbonate, water, and a saturated brine, dried over anhydrous sodium sulfate, and filtered. The solvent was distilled off. The resulting residue was then purified with SP1 (SiO$_2$ cartridge, 50% ethyl acetate/n-hexane, Rf=0.1) to obtain 89.5 mg (69% yield) of tert-butyl (E)-(2S,3S)-3-[(S)-2-(4-but-2-ynyloxy-phenyl)-1-methoxycarbonyl-ethylcarbamoyl]-11-(heptane-1-sulfinyl)-2-hydroxy-2-propyl-undec-4-enoate (PSI (LC/MS positive mode) m/z 718 (M+H); Rt 2.17 min.).

Furthermore, this tert-butyl (E)-(2S,3S)-3-[(S)-2-(4-but-2-ynyloxy-phenyl)-1-methoxycarbonyl-ethylcarbamoyl]-11-(heptane-1-sulfinyl)-2-hydroxy-2-propyl-undec-4-enoate (89.5 mg, 0.125 mmol) was dissolved in dichloromethane (8.0 mL), and trifluoroacetic acid (3.2 mL) was added. The mixture was stirred at room temperature for 15 hours. The solvent was distilled off under reduced pressure. To the residue was added dichloromethane, and the solvent was again distilled off under reduced pressure. This operation was repeated twice. The residue was then purified by HPLC (water with 0.05% TFA-acetonitrile with 0.05% TFA) to obtain 33.9 mg (41% yield) and 33.2 mg (40% yield), respectively, of diastereomers No. 5506861 and No. 5506864 of (E)-(2S, 3S)-3-[(S)-2-(4-but-2-ynyloxy-phenyl)-1-methoxycarbonyl-ethylcarbamoyl]-11-(heptane-1-sulfinyl)-2-hydroxy-2-propyl-undec-4-enoic acid.

89. No. 5506861

(E)-(2S,3S)-3-[(S)-2-(4-But-2-ynyloxy-phenyl)-1-methoxycarbonyl-ethylcarbamoyl]-11-(heptane-1-sulfinyl)-2-hydroxy-2-propyl-undec-4-enoic acid

[Chem. 180]

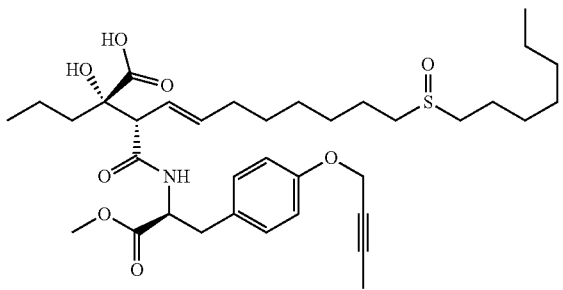

$^1$H-NMR (DMSO-d$_6$) δ: 0.77-0.89 (6H, m), 0.95-1.00 (1H, m), 1.18-1.46 (18H, m), 1.51-1.69 (5H, m), 1.82 (3H, t, J=2.3 Hz), 1.85-1.96 (2H, m), 2.55-2.78 (4H, m), 2.82-3.01 (1H, m), 3.17 (1H, m), 3.61 (3H, s), 4.38-4.46 (1H, m), 4.65-4.68 (2H, m), 5.40-5.49 (2H, m), 6.83 (2H, d, J=8.7 Hz), 7.11 (2H, d, J=8.7 Hz), 8.32 (1H, d, J=7.7 Hz).

ESI (LC/MS positive mode) m/z 662 (M+H); Rt 1.88 min.

90. No. 5506864

(E)-(2S,3S)-3-[(S)-2-(4-But-2-ynyloxy-phenyl)-1-methoxycarbonyl-ethylcarbamoyl]-11-(heptane-1-sulfinyl)-2-hydroxy-2-propyl-undec-4-enoic acid

[Chem. 181]

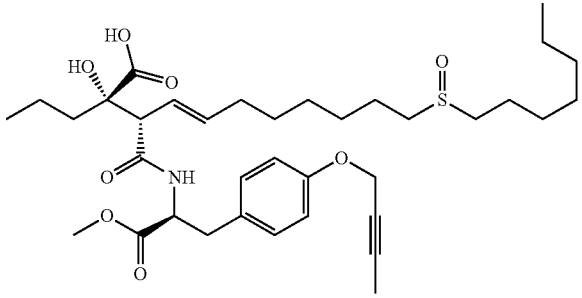

$^1$H-NMR (DMSO-d$_6$) δ: 0.77-0.89 (6H, m), 0.95-1.00 (1H, m), 1.18-1.46 (18H, m), 1.51-1.69 (5H, m), 1.82 (3H, t, J=2.3 Hz), 1.85-1.96 (2H, m), 2.55-2.78 (4H, m), 2.82-3.01 (1H, m), 3.17 (1H, m), 3.61 (3H, s), 4.38-4.46 (1H, m), 4.65-4.68 (2H, m), 5.40-5.49 (2H, m), 6.83 (2H, d, J=8.7 Hz), 7.11 (2H, d, J=8.7 Hz), 8.32 (1H, d, J=7.7 Hz).

ESI (LC/MS positive mode) m/z 662 (M+H); Rt 1.90 min.

Compound No. 6804240 was produced according to the following synthetic scheme.

[Chem. 182]

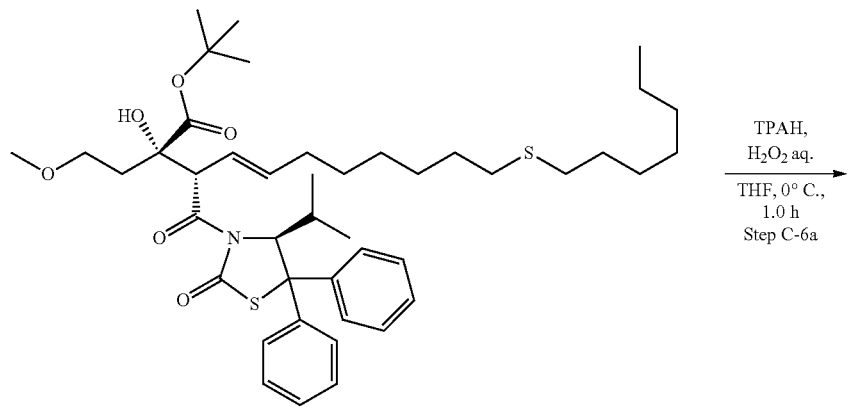

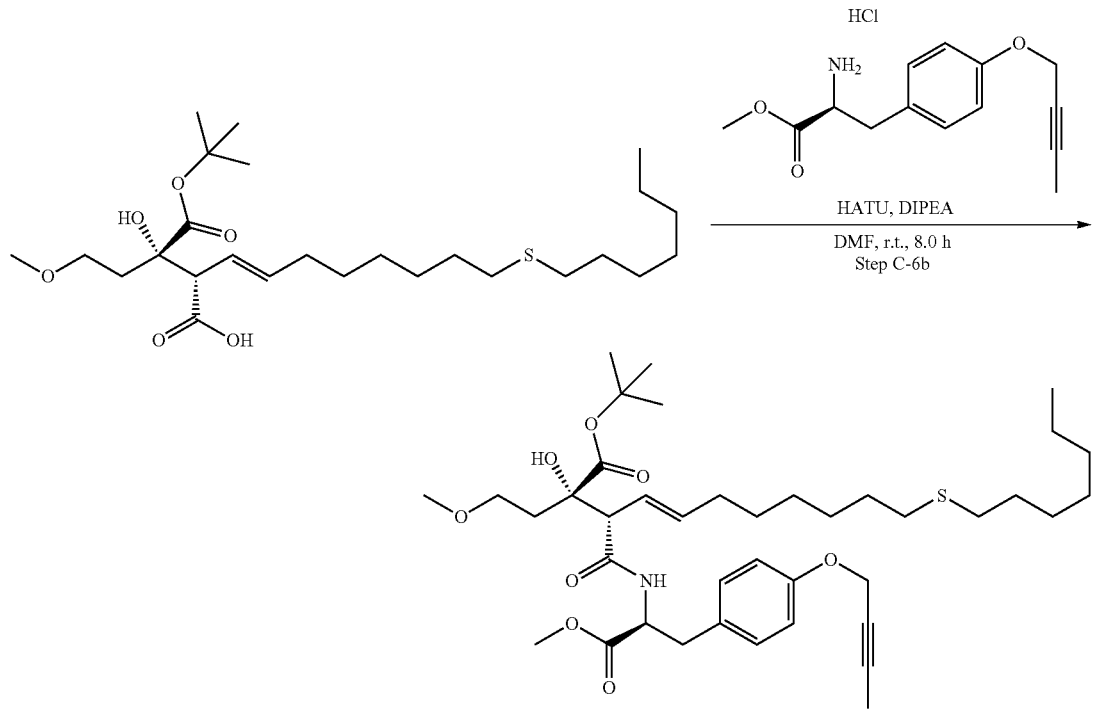

were added. The mixture was stirred for 1 hour, and an aqueous solution (2.72 mL) of 10% sodium thiosulfate was then added and the mixture was stirred for 5 minutes. The mixture was neutralized with an aqueous solution (2.2 mL) of 5% citric acid, and then extracted with ethyl acetate (30 mL). The organic layer was washed with water, dried over anhydrous sodium sulfate, and then filtered. The solvent was distilled out of the filtrate under reduced pressure. To the resulting residue were added acetonitrile (3.3 mL), n-hexane (20 mL), and an aqueous solution (6.61 mL) of 5.0% sodium bicarbonate. The mixture was stirred at room temperature for 2.0 minutes, and left to stand to separate into layers. To the separated hexane layer was added water-acetonitrile (3:1, 12 mL) and the mixture was extracted again. The separated lower layers were combined. To this solution was added an aqueous solution of 5% citric acid to pH 4.0. This solution was back-extracted Step C-6a tert-Butyl (E)-(2S,3S)-11-heptylsulfanyl-2-hydroxy-3-((S)-4-isopropyl-2-oxo-5,5-diphenyl-thiazolidine-3-carbonyl)-2-(2-methoxy-ethyl)-undec-4-enoate (No. 6804239; 330.7 mg, 0.431 mmol) was dissolved in THF (6.61 mL), and the mixture was cooled to 0° C. While maintaining the temperature at 0° C., an aqueous solution of 35% hydrogen peroxide (84 µL, 0.861 mmol) and tetrapropylammonium hydroxide (40% aqueous solution, 0.438 mL, 0.861 mmol)

with n-hexane (20 mL). The separated hexane layer was washed with 12 mL of water: acetonitrile (3:1), dried over anhydrous sodium sulfate, and filtered. After the solvent was distilled off, the same backward extraction was repeated another time to obtain 227.2 mg of 1-tert-butyl (2S,3S)-3-((E)-8-heptylsulfanyl-oct-1-enyl)-2-hydroxy-2-(2-methoxy-ethyl)-succinate (ESI (LC/MS positive mode) m/z 433 (M+H); Rt 2.51 min.).

Step C-6b

Under a nitrogen atmosphere, at room temperature, to 1-tert-butyl (2S,3S)-3-((E)-8-heptylsulfanyl-oct-1-enyl)-2-hydroxy-2-(2-methoxy-ethyl)-succinate (210.0 mg, 0.430 mmol) obtained in Step C-6b in DMF (4.2 mL), were added methyl (S)-2-amino-3-(4-but-2-ynyloxy-phenyl)-propionate hydrochloride (148.4 mg, 0.516 mmol), 1-[bis(dimethylamino)methyliumyl]-1H-1,2,3-triazolo[4,5-B]pyridine-3-oxide hexafluorophosphate (179.1 mg, 0.473 mmol), and N,N-diisopropylethylamine (299.0 μL, 1.72 mmol) in order. After stirring for 8 hours, the progress of the reaction was stopped by adding water. The mixture was extracted with ethyl acetate. The aqueous layer was extracted with ethyl acetate. The combined organic layer was then washed with water and a saturated brine, dried over anhydrous sodium sulfate, and then filtered. The solvent was distilled out of the filtrate under reduced pressure. The resulting residue was purified with SP1 (SiO$_2$ cartridge, 20% ethyl acetate/n-hexane, Rf=0.35) to obtain tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate (No. 6804240; 249.3 mg, 2 steps, 80% yield).

Compound No. 5500523 was produced according to the following synthetic scheme.

[Chem. 183]

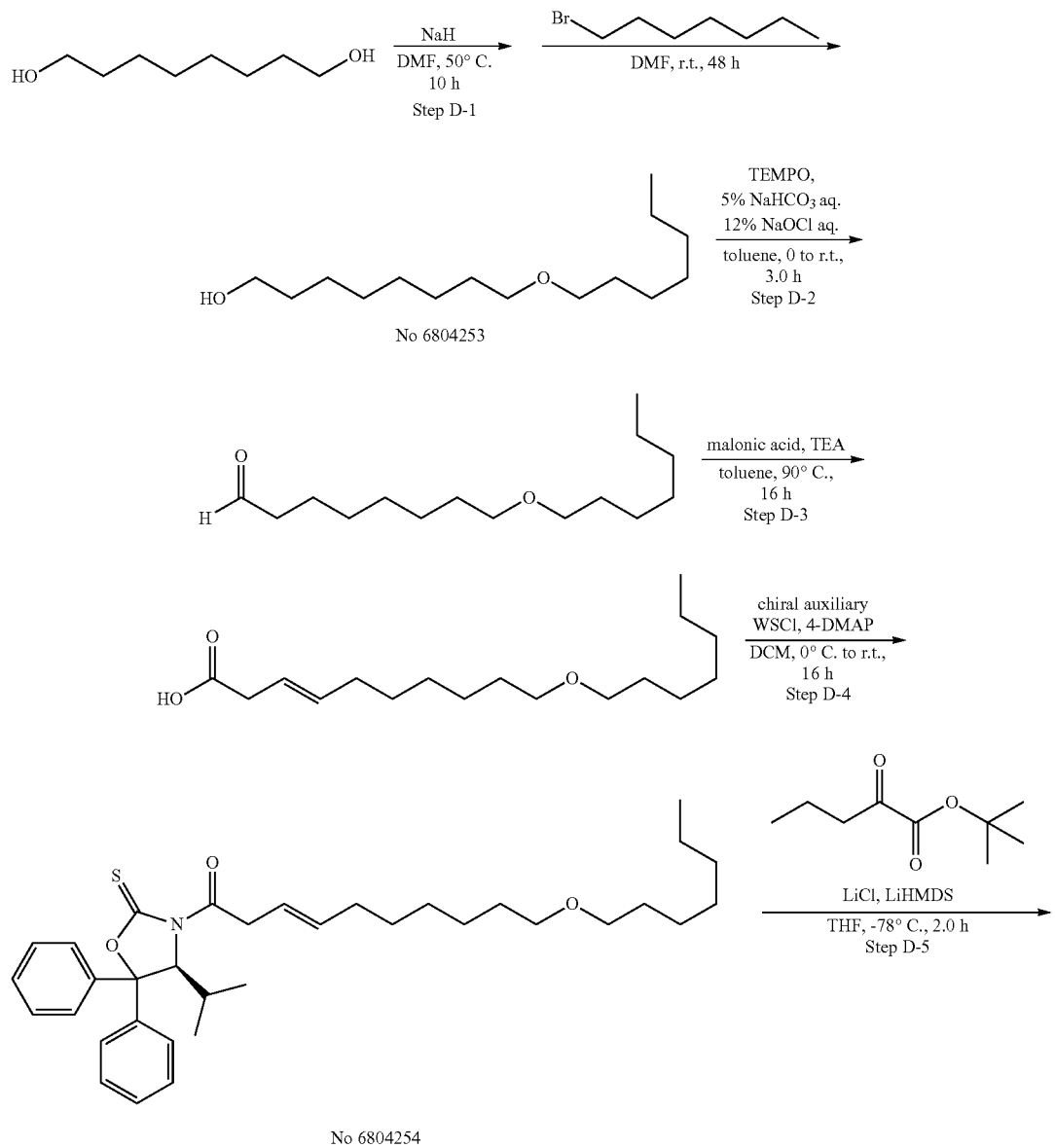

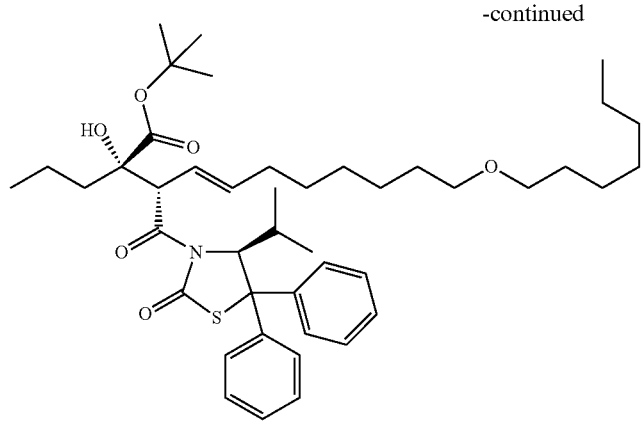

No 6804255

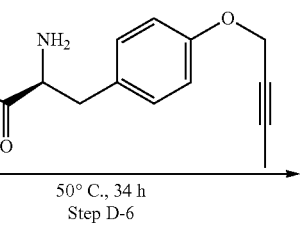

50° C., 34 h
Step D-6

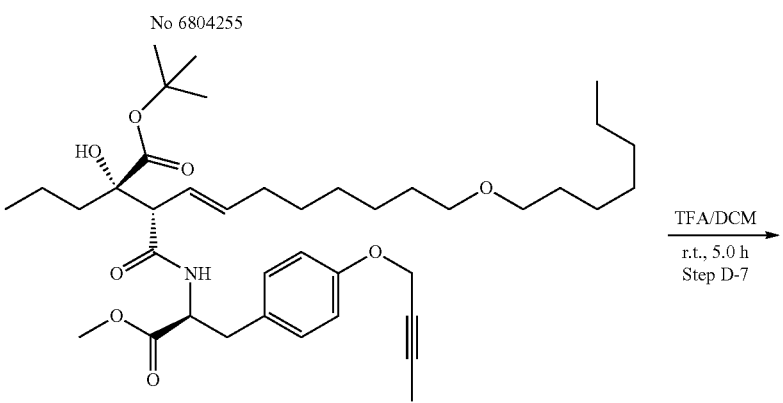

No 6804256

TFA/DCM
r.t., 5.0 h
Step D-7

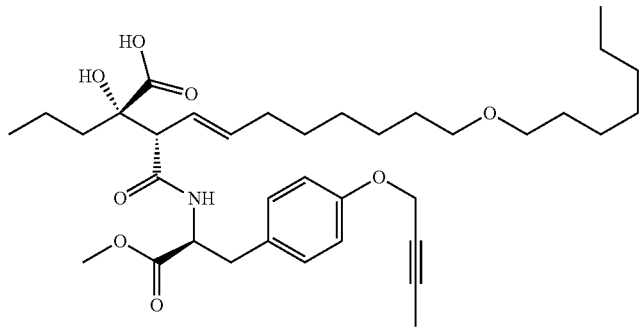

No 5500523

Step D-1

At room temperature, a commercially available reagent of octane-1,8-diol (351.2 mg, 2.40 mmol) was dissolved in DMF (3.0 mL), and sodium hydride (60 wt %, 105.7 mg, 2.64 mmol) was added. The mixture was then warmed to 50° C., stirred for 10 hours while maintaining the temperature at 50° C., and cooled to room temperature. 1-Bromo-heptane (430.2 mg, 2.40 mmol) in DMF (1.5 mL) was then added, and the mixture was stirred at room temperature for 48 hours. The progress of reaction was stopped by adding water. Ethyl acetate was added, and the mixture was extracted. The organic layer was washed with water and a saturated brine, dried over anhydrous sodium sulfate, and filtered. The solvent was distilled off. The resulting residue was then purified with SP1 (SiO$_2$ cartridge, 50% ethyl acetate/n-hexane, Rf=0.8) to obtain 8-heptyloxy-octan-1-ol (No. 6804253; 193.8 mg, 33% yield).

$^1$H-NMR (CDCl$_3$) δ: 0.88 (3H, t, J=6.6 Hz), 1.25-1.40 (16H, m), 1.53-1.60 (6H, m), 3.39 (4H, t, J=6.6 Hz), 3.63 (2H, t, J=6.6 Hz).

ESI (LC/MS positive mode) m/z 245 (M+H); Rt 2.18 min.

Step D-2

8-Heptyloxy-octan-1-ol (No. 6804253; 193.8 mg, 0.793 mmol) was dissolved in toluene (1.36 mL), and 2,2,6,6-tetramethylpiperidine-1-oxyl (TEMPO; 1.2 mg, 0.00768 mmol) and an aqueous solution (1.33 mL) of 5% sodium bicarbonate were added in order. The mixture was cooled to 0° C. While maintaining the temperature at 0° C., an aqueous solution (492 μL) of 12% sodium chloride was added. The mixture was stirred at 0° C. for 2.0 minutes and at room temperature for 2.0 hours. TEMPO (2.4 mg, 0.0154 mmol) and an aqueous solution (49.2 µL) of 12% sodium chloride were added further. The mixture was stirred at room temperature for 1 hour. Ethyl acetate and water were added, and the mixture was extracted. The organic layer was washed with water and a saturated brine, dried over anhydrous sodium sulfate, and filtered. The solvent was distilled off. The resulting residue was then purified with SP1 ($SiO_2$ cartridge, 50% ethyl acetate/n-hexane, Rf=0.3) to obtain the target compound, 8-heptyloxy-octanal (ESI (LC/MS positive mode) m/z 243 (M+H); Rt 2.35 min.; 178.0 mg, 93% yield).

Step D-3

Under a nitrogen atmosphere, 8-heptyloxy-octanal (178.0 mg, 0.734 mmol) obtained in Step D-2 was dissolved in toluene (3.56 mL), and triethylamine (184 µL, 1.32 mmol) and a solution of malonic acid (137.6 mg, 1.32 mmol) in DMF (0.178 mL) were added in order at 75° C. The mixture was stirred at 90° C. for 16 hours. After cooling to room temperature, an aqueous solution (2.6 mL) of 30% sodium dihydrogen phosphate and ethyl acetate (5.2 mL) were added, and the mixture was stirred at room temperature for 5 minutes. After extraction, the organic layer was washed with water. The aqueous layer was washed with ethyl acetate. The combined organic layer was then washed again with water and a saturated brine, dried over anhydrous sodium sulfate, and then filtered. The solvent was distilled off to obtain 209.7 mg (quant.) of (E)-10-heptyloxy-dec-3-enoic acid (ESI (LC/MS positive mode) m/z 285 (M+H); Rt 2.23 min.)

Step D-4

Under a nitrogen atmosphere, (E)-10-heptyloxy-dec-3-enoic acid obtained in Step C-3 (209.7 mg, 0.698 mmol) and a commercially available reagent of (S)-4-isopropyl-5,5-diphenyl-oxazolidine-2-thione (207.5 mg, 0.698 mmol) were dissolved in dichloromethane (3.13 mL), and the mixture was cooled to 0° C. While maintaining the temperature at 0° C., N,N-dimethyl-4-aminopyridine (8.5 mg, 0.0698 mmol) and WSCl (173.9 mg, 0.907 mmol) were added in order. The mixture was stirred at 0° C. for 2.0 minutes and at room temperature for 16 hours. To the reaction solution was added an aqueous solution (4.2 mL) of 10% sodium dihydrogen phosphate and the mixture was extracted with ethyl acetate. The organic layer was washed with water and a saturated brine in order, dried over anhydrous sodium sulfate, and filtered. The solvent was distilled off. The resulting residue was then purified with SP1 ($SiO_2$ cartridge, 10% ethyl acetate/n-hexane, Rf=0.6) to obtain (E)-10-heptyloxy-1-((S)-4-isopropyl-5,5-diphenyl-2-thioxo-oxazolidin-3-yl)-dec-3-en-1-one (No. 6804254; 336.2 mg, 3 steps, 75% yield).

$^1$H-NMR ($CDCl_3$) δ: 0.78 (3H, d, J=7.1 Hz), 0.84-0.89 (6H, m), 1.24-1.36 (14H, m), 1.51-1.58 (4H, m), 1.93-2.06 (3H, m), 3.38 (4H, dt, J=6.6, 1.6 Hz), 3.84 (1H, dd, J=17.0, 5.5 Hz), 3.99 (1H, dd, J=17.0, 5.5 Hz), 5.39-5.52 (2H, m), 5.59 (1H, d, J=3.8 Hz), 7.25-7.35 (6H, m), 7.41-7.47 (4H, m).

ESI (LC/MS positive mode) m/z 564 (M+H); Rt 3.87 min.

Step D-5

Lithium chloride (22.4 mg, 0.529 mmol) was heat dried with a heat gun under reduced pressure and, under a nitrogen atmosphere, a solution of (E)-10-heptyloxy-1-((S)-4-isopropyl-5,5-diphenyl-2-thioxo-oxazolidin-3-yl)-dec-3-en-1-one (No. 6804254; 99.5 mg, 0.177 mmol) in THF (1.3 mL) was added at room temperature. The mixture was stirred until it became homogeneous and then cooled to −78° C. Lithium hexamethyldisilazide (1 M THF solution, 0.235 mL, 0.235 mmol) was added and the mixture was stirred for 1.5 hours.

To this reaction mixture was added dropwise a solution of tert-butyl 2-oxo-pentanoate (33.4 mg, 0.194 mmol) in THF (1.00 mL). The mixture was stirred for further 1.5 hours. To the reaction mixture was added acetic acid (26.8 µL, 0.469 mmol), and the cooling bath was removed. A saturated aqueous solution (0.72 mL) of ammonium chloride, water (0.72 mL), and ethyl acetate (5.3 mL) were added, and the mixture was warmed to room temperature. After ethyl acetate extraction, the aqueous layer was extracted with ethyl acetate again. The extracted organic layers were combined, dried over anhydrous sodium sulfate, and filtered. The solvent was distilled off. The resulting residue was then purified with SP1 ($SiO_2$ cartridge, 17% ethyl acetate/n-hexane, Rf=0.50) to obtain tert-butyl (E)-(2S,3S)-11-heptyloxy-2-hydroxy-3-((S)-4-isopropyl-2-oxo-5,5-diphenyl-thiazolidine-3-carbonyl)-2-propyl-undec-4-enoate (No. 6804255; 76.8 mg, 59% yield).

$^1$H-NMR ($CDCl_3$) δ: 0.65 (3H, t, J=6.6 Hz), 0.73 (3H, d, J=6.0 Hz), 0.79 (3H, d, J=6.0 Hz), 0.87 (3H, t, J=7.1 Hz), 0.99-1.05 (1H, m), 1.24-1.38 (14H, m), 1.48 (9H, s), 1.51-1.56 (8H, m), 1.95-2.04 (3H, m), 3.34-3.39 (4H, m), 5.56 (1H, dd, J=14.8, 9.9 Hz), 5.70 (1H, d, J=3.8 Hz), 5.93 (1H, dt, J=15.4, 6.6 Hz), 6.16 (1H, d, J=9.3 Hz), 7.25-7.29 (2H, m), 7.33 (4H, t, J=7.7 Hz), 7.43 (2H, d, J=7.7 Hz), 7.48 (2H, d, J=8.2 Hz).

ESI (LC/MS positive mode) m/z 737 (M+H); Rt 5.42 min.

Step D-6 tert-Butyl (E)-(2S,3S)-11-heptyloxy-2-hydroxy-3-((S)-4-isopropyl-2-oxo-5,5-diphenyl-thiazolidine-3-carbonyl)-2-propyl-undec-4-enoate (No. 6804255; 75.1 mg, 0.102 mmol) and methyl (S)-2-amino-3-(4-but-2-ynyloxy-phenyl)-propionate (27.8 mg, 0.112 mmol) were dissolved in dichloromethane. The solvent was distilled off under reduced pressure. The resulting mixture was stirred at 50° C. for 34 hours, cooled to room temperature, and then extracted by adding ethyl acetate and water. The organic layer was washed with water and a saturated brine, dried over anhydrous sodium sulfate, and then filtered. The solvent was distilled out of the filtrate under reduced pressure. The residue was purified by preparative HPLC (water with 0.05% TFA-acetonitrile with 0.05% TFA) to obtain tert-butyl (E)-(2S,3S)-3-[(S)-2-(4-but-2-ynyloxy-phenyl)-1-methoxycarbonyl-ethylcarbamoyl]-11-heptyloxy-2-hydroxy-2-propyl-under-4-enoate (No. 6804256; 65.6 mg, 94% yield).

$^1$H-NMR ($CDCl_3$) δ: 0.80-0.90 (6H, m), 1.25-1.36 (18H, m), 1.45 (9H, s), 1.51-1.59 (4H, m), 1.85 (3H, t, J=2.2 Hz), 1.97-2.02 (2H, m), 2.95-3.02 (1H, m), 3.06-3.18 (2H, m), 3.35-3.40 (4H, m), 3.70 (3H, s), 4.10 (1H, br.s), 4.59-4.61 (2H, m), 4.73-4.79 (1H, m), 5.44-5.52 (1H, m), 5.60-5.69 (1H, m), 6.83-6.88 (2H, m), 7.06-7.14 (3H, m).

ESI (LC/MS positive mode) m/z 686 (M+H); Rt 2.75 min.

Step D-7 tert-Butyl (E)-(2S,3S)-3-[(S)-2-(4-but-2-ynyloxy-phenyl)-1-methoxycarbonyl-ethylcarbamoyl]-11-heptyloxy-2-hydroxy-2-propyl-undec-4-enoate (No. 6804256; 65.6 mg, 0.0956 mmol) was dissolved in dichloromethane (3.0 mL), and trifluoroacetic acid (1.0 mL) was added. The mixture was stirred at room temperature for 5.0 hours. The solvent was distilled off under reduced pressure. To the residue was added dichloromethane, and the solvent was again distilled off under reduced pressure. This operation was repeated twice. The residue was then purified by HPLC (water with 0.05% TFA-acetonitrile with 0.05% TFA) to obtain (E)-(2S,3S)-3-[(S)-2-(4-but-2-ynyloxy-phenyl)-1-methoxycarbonyl-ethylcarbamoyl]-11-heptyloxy-2-hydroxy-2-propyl-undec-4-enoic acid (No. 5500523; 19.3 mg, 32% yield).

$^1$H-NMR ($CD_3COCD_3$) δ: 0.71-0.77 (6H, m), 0.96-1.07 (1H, m), 1.13-1.24 (16H, m), 1.33-1.45 (6H, m), 1.53-1.62 (1H, m), 1.69 (3H, t, J=2.2 Hz), 1.83-1.89 (2H, m), 2.83 (1H, dd, J=14.0, 8.0 Hz), 2.96 (1H, dd, J=14.0, 5.2 Hz), 3.18 (1H, d, J=8.2 Hz), 3.23 (4H, t, J=6.6 Hz), 3.55 (3H, s), 4.49-4.57

(3H, m), 5.38-5.50 (2H, m), 6.74 (2H, d, J=8.2 Hz), 7.01 (2H, d, J=8.2 Hz), 7.55 (1H, d, J=7.7 Hz).

ESI (LC/MS positive mode) m/z 630 (M+H); Rt 2.35 min.

No. 5500524

(E)-(2S,3S)-3-[(S)-2-(4-But-2-ynyloxy-phenyl)-1-carboxy-ethylcarbamoyl]-11-heptyloxy-2-hydroxy-2-propyl-undec-4-enoic acid

[Chem. 184]

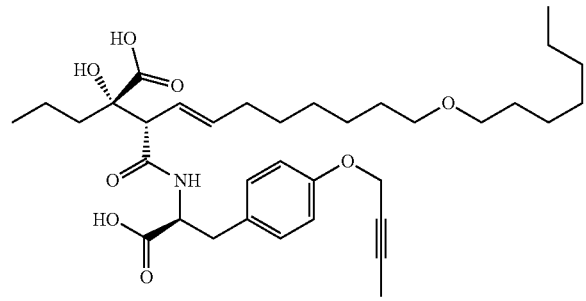

(E)-(2S,3S)-3-[(S)-2-(4-But-2-ynyloxy-phenyl)-1-carboxy-ethylcarbamoyl]-11-heptyloxy-2-hydroxy-2-propyl-undec-4-enoic acid (No. 5500524) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-but-2-ynyloxy-phenyl)-1-methoxycarbonyl-ethylcarbamoyl]-11-heptyloxy-2-hydroxy-2-propyl-undec-4-enoic acid (No. 5500523) as a starting material.

$^1$H-NMR (DMSO-$d_6$) δ: 0.77 (3H, t, J=6.6 Hz), 0.85 (3H, t, J=6.6 Hz), 0.96-1.09 (1H, m), 1.23-1.34 (18H, m), 1.40-1.50 (4H, m), 1.82 (3H, s), 1.84-1.92 (2H, m), 2.81 (1H, dd, J=13.7, 8.8 Hz), 2.98 (1H, dd, J=13.7, 4.4 Hz), 3.14 (1H, d, J=6.6 Hz), 3.19-3.44 (6H, m), 4.33-4.38 (1H, m), 4.62-4.65 (2H, m), 5.36-5.45 (2H, m), 6.81 (2H, d, J=8.8 Hz), 7.11 (2H, d, J=8.2 Hz), 8.04 (1H, br.s).

ESI (LC/MS positive mode) m/z 616 (M+H); Rt 2.23 min.

Compound No. 5502842 was produced according to the following synthetic scheme.

[Chem. 185]

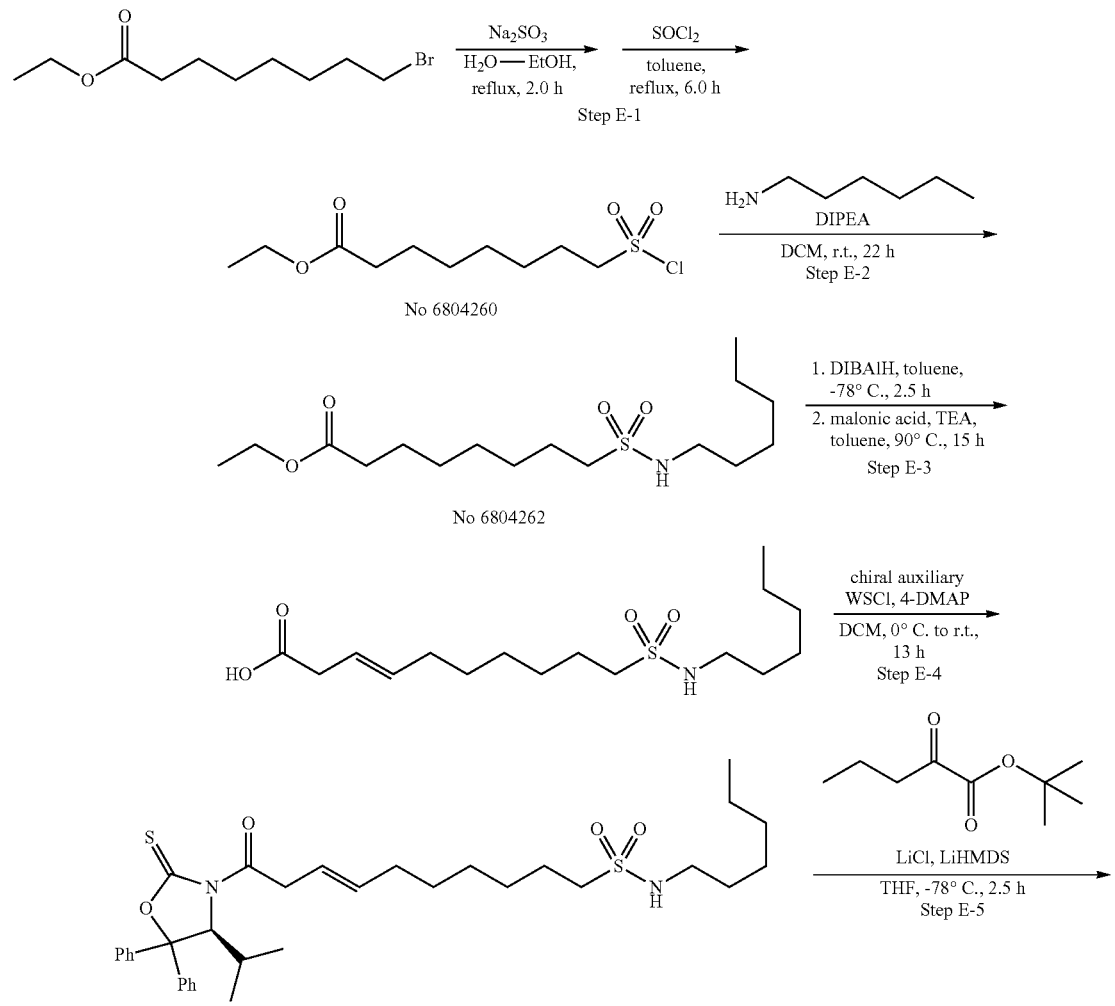

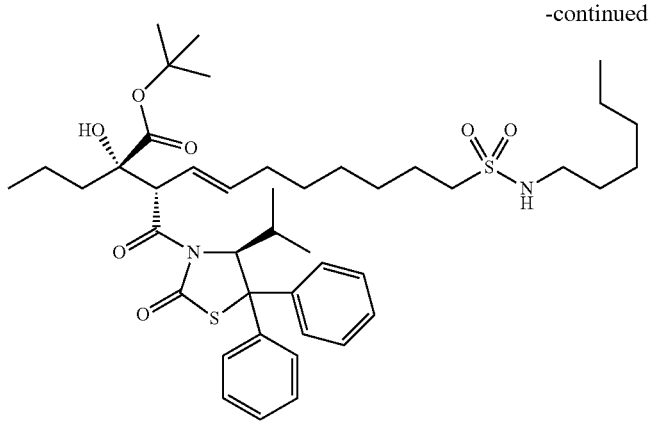

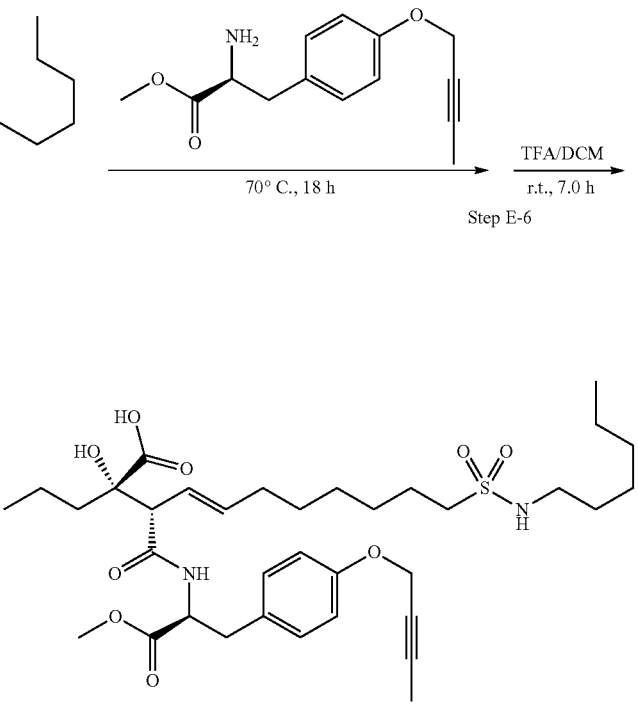

No 5502842

Step E-1

At room temperature, ethyl 8-bromo-octanoate (753.5 mg, 3.00 mmol) was dissolved in ethanol (1.88 mL), and a solution of sodium sulfite (718.4 mg, 5.70 mmol) in water (2.64 mL) was added. The mixture was then stirred under reflux for 2 hours, and cooled to room temperature. The solvent was then distilled off under reduced pressure. To the residue was added ethanol, and the solvent was again distilled off under reduced pressure. The residue was dried in an oil bath at 60° C. under reduced pressure, and toluene (11.3 mL) and DMF (10 μL) were then added at room temperature. Thionyl chloride (2.16 mL, 30.0 mmol) was added dropwise. The mixture was then stirred under reflux for 6 hours and cooled to room temperature. The progress of the reaction was then stopped by adding water. Ethyl acetate was added, and the mixture was extracted. The organic layer was washed with water and a saturated brine, dried over anhydrous sodium sulfate, and filtered. The solvent was distilled off. The resulting residue was then purified with SP1 (SiO$_2$ cartridge, 10% ethyl acetate/n-hexane, Rf=0.2) to obtain ethyl 8-chlorosulfonyl-octanoate (No. 6804260; 692.3 mg, 85% yield).

$^1$H-NMR (CDCl$_3$) δ: 1.26 (3H, t, J=7.1 Hz), 1.31-1.43 (4H, m), 1.47-1.54 (2H, m), 1.60-1.67 (2H, m), 2.00-2.08 (2H, m), 2.30 (2H, t, J=7.1 Hz), 3.64-3.68 (2H, m), 4.12 (2H, q, J=7.1 Hz).

Step E-2

Ethyl 8-chlorosulfonyl-octanoate (No. 6804260; 692.3 mg, 2.56 mmol) was dissolved in dichloromethane (4.0 mL), and a solution of hexylamine (310.5 mg, 3.07 mmol) in dichloromethane (3.0 mL) and N,N-diisopropylethylamine (668 μL, 3.84 mmol) were added in order. The mixture was stirred at room temperature for 22 hours. After completing the reaction, the mixture was neutralized by adding 1 M hydrochloric acid, and extracted with dichloromethane. The organic layer was washed with water and a saturated brine, dried over anhydrous sodium sulfate, and filtered. The solvent was distilled off. The resulting residue was then purified with SP1 (SiO$_2$ cartridge, 25% ethyl acetate/n-hexane, Rf=0.5) to obtain ethyl 8-hexylsulfamoyl-octanoate (No. 6804262; 818.3 mg, 95% yield).

$^1$H-NMR (CDCl$_3$) δ: 0.89 (3H, t, J=7.1 Hz), 1.25 (3H, t, J=7.1 Hz), 1.28-1.46 (12H, m), 1.52-1.66 (4H, m), 1.75-1.83 (2H, m), 2.29 (2H, t, J=7.1 Hz), 2.97-3.01 (2H, m), 3.09 (2H, dd, J=13.7, 7.1 Hz), 4.12 (2H, q, J=7.1 Hz), 4.18 (1H, br.s).

ESI (LC/MS positive mode) m/z 336 (M+H); Rt 1.88 min.

Step E-3

Under a nitrogen atmosphere, ethyl 8-hexylsulfamoyl-octanoate (No. 6804262; 818.3 mg, 2.44 mmol) was dissolved in toluene (11 mL), and the mixture was cooled to −78° C. While maintaining the temperature at −78° C., a diluted solution of diisobutylaluminum hydride (1.5 M solution in toluene, 1.95 mL, 2.93 mmol) in toluene (2.9 mL) was added dropwise over 25 minutes, and the mixture was stirred at −78° C. for 1.5 hours. The reaction was monitored by LCMS. To this reaction solution was, then, further added a diluted solution of diisobutylaluminum hydride (1.5 M solution in toluene, 0.81 mL, 1.22 mmol) in toluene (0.9 mL) was added dropwise over 10 minutes, and the mixture was stirred at −78° C. for 1 hour. Methanol (0.65 mL) was added to the reaction solution, which was stirred at −78° C. for 10 minutes to stop the reaction. A saturated aqueous solution (3.0 mL) of Rochelle salt and water (9.0 mL) were further added and the mixture was stirred at 0° C. for 1 hour. Insoluble material was filtered off and washed with dichloromethane. The filtrate was then extracted with dichloromethane. The organic layer was washed with water, and dried over anhydrous sodium sulfate, and then filtered. Dichloromethane was distilled off to obtain the target 8-oxo-octane-1-sulfonic acid hexyl amide (ESI (LC/MS positive mode) m/z 292 (M+H); Rt 1.68 min.).

While the toluene solvent still remained, the atmosphere was changed to a nitrogen atmosphere, triethylamine (612 µL, 4.39 mmol) and a solution of malonic acid (456.8 mg, 4.39 mmol) in DMF (0.730 mL) were added in order at room temperature, and the mixture was stirred at 90° C. for 15 hours. After cooling to room temperature, an aqueous solution (8.8 mL) of 30% sodium dihydrogen phosphate and ethyl acetate (17.6 mL) were added and the mixture was extracted. The organic layer was washed with water, and the aqueous layer was washed with ethyl acetate. The combined organic layer was then washed again with water and a saturated brine, dried over anhydrous sodium sulfate, and then filtered. The solvent was distilled off. The resulting residue was purified with SP1 (Diol cartridge, dichloromethane, Rf=0.35) to obtain the target compound, (E)-10-hexylsulfamoyl-dec-3-enoic acid (ESI (LC/MS positive mode) m/z 334 (M+H); Rt 1.67 min.; 232.2 mg, 2 steps, 29% yield).

Step E-4

Under a nitrogen atmosphere, (E)-10-hexylsulfamoyl-dec-3-enoic acid (100 mg, 0.30 mmol) obtained in Step C-3 and (S)-4-isopropyl-5,5-diphenyl-oxazolidine-2-thione (89.2 mg, 0.30 mmol) were dissolved in dichloromethane (3.5 mL), and the mixture was cooled to 0° C. While maintaining the temperature at 0° C., N,N-dimethyl-4-aminopyridine (3.7 mg, 0.03 mmol) and 1-ethyl-3-(3-dimethylaminopropyl)carbodiimide hydrochloride (74.7 mg, 0.39 mmol) were added in order, and the mixture was stirred at 0° C. for 2 minutes and at room temperature for 13 hours. To the reaction solution was added an aqueous solution (4.2 mL) of 10% sodium dihydrogen phosphate and ethyl acetate and the mixture was extracted. The organic layer was washed with water and a saturated brine in order, dried over anhydrous sodium sulfate, and filtered. The solvent was distilled off. The resulting residue was then purified with SP1 (SiO$_2$ cartridge, 20% ethyl acetate/n-hexane, Rf=0.25) to obtain the target compound, (E)-104(S)-4-isopropyl-5,5-diphenyl-2-thioxo-oxazolidin-3-yl)-10-oxo-dec-7-ene-1-sulfonic acid hexylamide (ESI (LC/MS positive mode) m/z 613 (M+H); Rt 2.60 min.; 65% purity, 96.8 mg, 53% yield).

Step E-5

Lithium chloride (17.6 mg, 0.416 mmol) was heat dried with a heat gun under reduced pressure and, under a nitrogen atmosphere, a solution of (E)-10-((S)-4-isopropyl-5,5-diphenyl-2-thioxo-oxazolidin-3-yl)-10-oxo-dec-7-ene-1-sulfonic acid hexylamide (42.5 mg, 0.0693 mmol), obtained in Step E-4, in THF (1.5 mL) was added at room temperature. The mixture was stirred until it became homogeneous and then cooled to −78° C. Lithium hexamethyldisilazide (1 M solution in THF, 0.208 mL, 0.208 mmol) was added and the mixture was stirred for 1 hour. To this reaction mixture was added dropwise a solution of tert-butyl 2-oxo-pentanoate (47.8 mg, 0.277 mmol) in THF (1.5 mL). The mixture was stirred for further 1.5 hours. To the reaction mixture was added acetic acid (26.8 µL, 0.987 mmol), and the cooling bath was removed. A saturated aqueous solution (1.5 mL) of ammonium chloride, water (1.5 mL), and ethyl acetate (11.4 mL) were added, and the mixture was warmed to room temperature. After ethyl acetate extraction, the aqueous layer was washed with ethyl acetate, dried over anhydrous sodium sulfate, and filtered. The solvent was distilled off. The resulting residue was then purified with SP1 (SiO$_2$ cartridge, 33% ethyl acetate/n-hexane, Rf=0.70) to obtain the target compound, tert-butyl (E)-(2S,3S)-11-hexylsulfamoyl-2-hydroxy-3-((S)-4-isopropyl-2-oxo-5,5-diphenyl-thiazolidine-3-carbonyl)-2-propyl-undec-4-enoate (ESI (LC/MS positive mode) m/z 785 (M+H); Rt 3.45 min.; 50.3 mg, 92% yield).

Step E-6 tert-Butyl (E)-(2S,3S)-11-hexylsulfamoyl-2-hydroxy-3-((S)-4-isopropyl-2-oxo-5,5-diphenyl-thiazolidine-3-carbonyl)-2-propyl-undec-4-enoate (56.8 mg, 0.0723 mmol) obtained in Step E-5 and methyl (S)-2-amino-3-(4-but-2-ynyloxy-phenyl)-propionate (26.8 mg, 0.108 mmol) were dissolved in dichloromethane. The solvent was distilled off under reduced pressure. The obtained mixture was stirred at 70° C. for 18 hours, cooled to room temperature, and then extracted by adding ethyl acetate and water. The organic layer was washed with water and a saturated brine, dried over anhydrous sodium sulfate, and then filtered. The solvent was distilled out of the filtrate under reduced pressure. The residue was then purified by HPLC (water with 0.05% TFA-acetonitrile with 0.05% TFA) to obtain 34.5 mg (65% yield) of the target compound, tert-butyl (E)-(2S,3S)-3-[(S)-2-(4-but-2-ynyloxy-phenyl)-1-methoxycarbonyl-ethylcarbamoyl]-11-hexylsulfamoyl-2-hydroxy-2-propyl-undec-4-enoate (ESI (LC/MS positive mode) m/z 735 (M+H); Rt 2.68 min.).

This tert-butyl (E)-(2S,3S)-3-[(S)-2-(4-but-2-ynyloxy-phenyl)-1-methoxycarbonyl-ethylcarbamoyl]-11-hexylsulfamoyl-2-hydroxy-2-propyl-undec-4-enoate (34.5 mg, 0.0469 mmol) was dissolved in dichloromethane (3.0 mL), and trifluoroacetic acid (1.0 mL) was added.

The mixture was stirred at room temperature for 7 hours. The solvent was distilled off under reduced pressure. To the residue was added dichloromethane, and the solvent was again distilled off under reduced pressure. This operation was repeated twice.

The residue was then purified by HPLC (water with 0.05% TFA-acetonitrile with 0.05% TFA) to obtain (E)-(2S,3S)-3-[(S)-2-(4-but-2-ynyloxy-phenyl)-1-methoxycarbonyl-ethylcarbamoyl]-11-hexylsulfamoyl-2-hydroxy-2-propyl-undec-4-enoic acid (No. 5502842; 17.2 mg, 54% yield).

$^1$H-NMR (CD$_3$COCD$_3$) δ: 0.70 (3H, t, J=7.1 Hz), 0.76 (3H, t, J=7.1 Hz), 0.98-1.11 (1H, m), 1.16-1.34 (16H, m), 1.39-1.47 (2H, m), 1.53-1.66 (3H, m), 1.70 (3H, t, J=2.2 Hz), 1.82-1.89 (2H, m), 2.81-2.98 (6H, m), 3.21 (1H, d, J=8.2 Hz), 3.55 (3H, s), 4.52-4.57 (3H, m), 5.37-5.52 (2H, m), 6.05 (1H, br.s), 6.74 (2H, d, J=8.2 Hz), 7.03 (2H, d, J=8.2 Hz), 7.66 (1H, br.s).

ESI (LC/MS positive mode) m/z 679 (M+H); Rt 2.18 min.

88. No. 5504586

(E)-(2S,3S)-3-[(S)-2-(4-But-2-ynyloxy-phenyl)-1-carboxy-ethylcarbamoyl]-11-hexylsulfamoyl-2-hydroxy-2-propyl-undec-4-enoic acid

[Chem. 186]

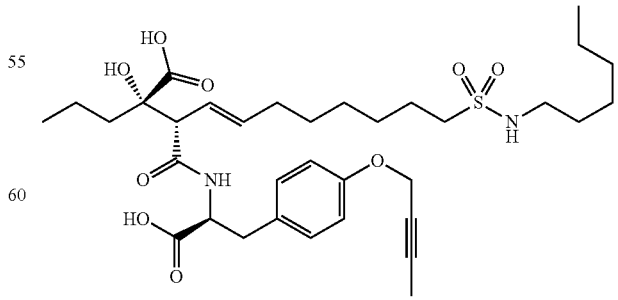

(E)-(2S,3S)-3-[(S)-2-(4-But-2-ynyloxy-phenyl)-1-carboxy-ethylcarbamoyl]-11-hexylsulfamoyl-2-hydroxy-2- propyl-undec-4-enoic acid (No. 5504586) was synthesized by the synthetic method of (E)-(2S,3S)-3-[(S)-2-(4-but-2-ynyloxy-phenyl)-1-carboxy-ethylcarbamoyl]-12,12-difluoro-2-hydroxy-2-propyl-nonadec-4-enoic acid (No. 5501825) using (E)-(2S,3S)-3-[(S)-2-(4-but-2-ynyloxy-phenyl)-1-methoxycarbonyl-ethylcarbamoyl]-11-hexylsulfamoyl-2-hydroxy-2-propyl-undec-4-enoic acid (No. 5502842) as a starting material.

$^1$H-NMR (CD$_3$COCD$_3$) δ: 0.71 (3H, t, J=7.1 Hz), 0.76 (3H, t, J=7.1 Hz), 0.98-1.08 (1H, m), 1.16-1.32 (16H, m), 1.39-1.46 (2H, m), 1.57-1.64 (3H, m), 1.70 (3H, t, J=2.2 Hz), 1.81-1.90 (2H, m), 2.80-3.04 (6H, m), 3.24 (1H, d, J=8.2 Hz), 4.49-4.55 (3H, m), 5.41-5.53 (2H, m), 5.83 (1H, br.s), 6.73 (2H, d, J=8.2 Hz), 7.06 (2H, d, J=8.2 Hz), 7.72 (1H, br.s).

ESI (LC/MS positive mode) m/z 665 (M+H); Rt 1.72 min.

Synthesis of No. 4935048 and salt-free form

[Chem. 187]

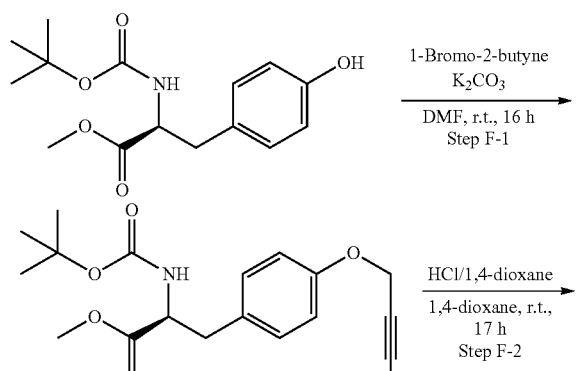

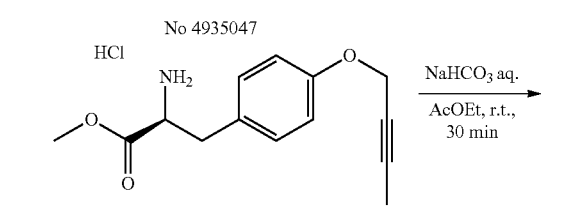

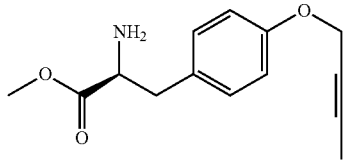

Step F-1

Under a nitrogen atmosphere, at room temperature, a commercially available reagent of methyl (S)-2-tert-butoxycarbonylamino-3-(4-hydroxy-phenyl)-propionate (199 g, 673 mmol) was dissolved in DMF (795 mL), and a commercially available reagent of 1-bromo-2-butyne (100 g, 752 mmol) and potassium carbonate (112 g, 807 mmol) were added. The mixture was stirred at room temperature for 19 hours. To the reaction solution were added a saturated aqueous solution of ammonium chloride and ethyl acetate and the mixture was extracted. The organic layer was washed with water and a saturated brine in order, dried over anhydrous magnesium sulfate, and filtered. The solvent was distilled off. The residue was then dried under reduced pressure to obtain methyl (S)-2-tert-butoxycarbonylamino-3-(4-but-2-ynyloxy-phenyl)-propionate (ESI (LC/MS positive mode) m/z 348 (M+H); Rt 2.50 min.; No. 4935047; 233 g, quant.).

Step F-2

Under a nitrogen atmosphere, methyl (S)-2-tert-butoxycarbonylamino-3-(4-but-2-ynyloxy-phenyl)-propionate (233 g, 673 mmol) obtained in Step F-1 was dissolved in 1,4-dioxane (1,525 mL), and a solution of 4 M hydrogen chloride-dioxane (942 mL, 3.77 mol) was added at room temperature.
The mixture was stirred at room temperature for 17 hours. The reaction solution was filtered. The precipitate was washed with 1,4-dioxane, and dried under reduced pressure to obtain methyl (S)-2-amino-3-(4-but-2-ynyloxy-phenyl)-propionate hydrochloride (ESI (LC/MS positive mode) m/z 248 (M+H); Rt 1.09 min.; No. 4935048; 186 g, 98% yield).

Step F-3

Methyl (S)-2-amino-3-(4-but-2-ynyloxy-phenyl)-propionate hydrochloride (2.51 g, 8.85 mmol) obtained in Step F-2 was dissolved in ethyl acetate (38 mL), and N,N-diisopropylethylamine (1.85 mL, 10.6 mmol) was added at room temperature.
The mixture was stirred at room temperature for 30 minutes. Water was added to the reaction solution to stop the reaction, and the solution was extracted with ethyl acetate. The organic layer was washed with water and a saturated brine in order, dried over anhydrous sodium sulfate, and filtered. The solvent was distilled off. The residue was then dried under reduced pressure to obtain 1.98 g of methyl (S)-2-amino-3-(4-but-2-ynyloxy-phenyl)-propionate (ESI (LC/MS positive mode) m/z 248 (M+H); Rt 1.09 min.).

No. 5510137

(E)-(2S,3S)-3-[(S)-2-(4-But-2-ynyloxy-phenyl)-1-carboxy-ethylcarbamoyl]-2-hydroxy-12-oxo-2-propyl-nonadec-4-enoic acid

[Chem. 188]

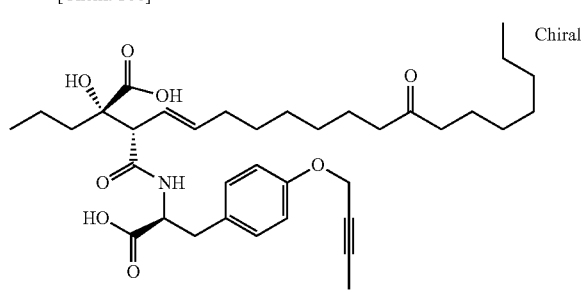

(E)-(2S,3S)-3-[(S)-2-(4-But-2-ynyloxy-phenyl)-1-methoxycarbonyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(4-butynylxy-phenyl) -propionate hydrochloride was used instead of methyl (S)-2-aimno-3-(4-butoxy-phenyl)-propionate. Finally, methyl ester was hydrolyzed by the synthetic method of No. 5501825 to obtain the target compound.

¹H-NMR (CDCl₃) δ: 0.86 (6H, m), 1.07-1.37 (14H, m), 1.38-1.62 (6H, m), 1.70 (1H, m), 1.86 (3H, s), 2.02 (2H, m), 2.40-2.48 (4H, m), 3.07 (2H, m), 3.07-3.37 (2H, m), 3.50 (2H, br.s) 4.61 (2H, s), 4.75 (1H, br.s), 5.56 (2H, m), 6.87 (2H, d, J=6.6 Hz), 7.09 (2H, d, J=7.7 Hz)

ESI (LC/MS positive mode) m/z 629 (M+H); Rt 0.76 min.

No. 5512990

(E)-(2S,3S)-3-[(S)-2-(4-But-2-ynyloxy-phenyl)-1-methoxycarbamoyl-ethylcarbamoyl]-2-hydroxy-12-oxo-2-propyl-nonadec-4-enoic acid

[Chem. 189]

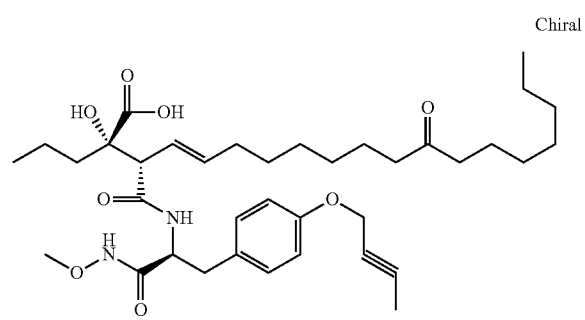

The target compound was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-but-2-ynyloxy-phenyl)-N-methoxy-propionamide was used instead of methyl (S)-2-amino-3-(4-butoxy-phenyl)-propionate.

¹H-NMR (CDCl₃) δ: 0.76-0.93 (6H, m), 0.76-0.93 (14H, m), 1.47-1.62 (4H, m), 1.85 (3H, s), 1.86 (3H, s), 2.02 (4H, m), 2.40-2.49 (4H, m), 3.01 (2H, m), 3.17 (1H, d=J=7.7 Hz), 3.62 (2H, m), 4.12 (3H, q, J=7.1 Hz), 4.41 (1H, m), 4.60 (2H, s), 5.30 (1H, s), 5.55 (2H, m), 6.87 (2H, m), 7.04 (1H, m), 7.12 (1H, m)

ESI (LC/MS positive mode) m/z 658 (M+H); Rt 1.02 min.

No. 5512991

(E)-(2S,3S)-3-[(S)-2-(4-But-2-ynyloxy-phenyl)-1-hydroxycarbamoyl-ethylcarbamoyl]-2-hydroxy-12-oxo-2-propyl-nonadec-4-enoic acid

[Chem. 190]

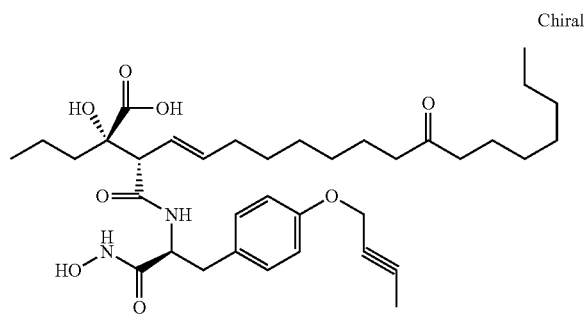

The target compound was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-but-2-ynyloxy-phenyl)-N-hydroxy-propionamide was used instead of methyl (S)-2-amino-3-(4-butoxy-phenyl)-propionate.

¹H-NMR (CD₃OD) δ: 0.82 (3H, m), 0.90 (3H, t, J=6.6 Hz), 1.20-1.39 (14H, m), 1.47-1.58 (4H, m), 1.81 (3H, t, J=2.2 Hz), 1.97 (2H, m), 2.43 (4H, m), 2.85 (1H, m), 3.00 (1H, m), 3.13 (1H, m), 3.48 (1H, m), 4.50 (1H, m), 4.60 (2H, s), 5.53 (2H, m), 6.85 (2H, d, J=8.2 Hz), 7.15 (2H, d, J=8.8 Hz)

ESI (LC/MS positive mode) m/z 644 (M+H); Rt 0.98 min.

No. 5512992

(E)-(2S,3S)-3-[(S)-2-(4-Butoxy-phenyl)-1-methoxycarbonyl-ethylcarbamoyl]-2-hydroxy-12-oxo-2-propyl-nonadec-4-enoic acid

[Chem. 191]

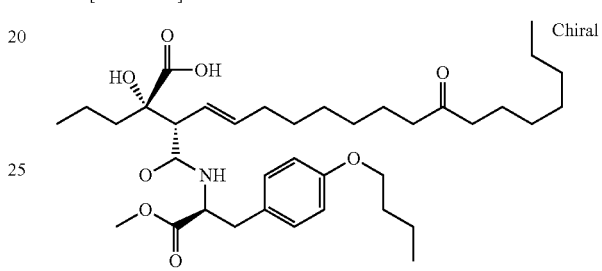

The target compound was obtained by the synthesis similar to Step A, except that, in A-1 step, tert-butyl 2-oxo-pentanoate was used instead of tert-butyl 4-methoxy-2-oxo-butyrate.

¹H-NMR (CDCl₃) δ: 0.86 (6H, m), 0.98 (3H, td, J=7.4, 3.3 Hz), 1.12-1.40, (14H, m), 1.43-1.66 (8H, m), 1.76 (4H, m), 2.02 (2H, m), 2.41 (4H, m), 3.07 (2H, m), 3.16 (1H, d, J=5.5 Hz), 3.75 (3H, s), 3.93 (2H, m), 4.81 (1H, m), 5.10 (1H, m), 5.58 (2H, m), 6.53 (1H, d, J=6.6 Hz), 6.79 (2H, d, J=4.9 Hz), 6.97 (2H, d, J=5.5 Hz)

ESI (LC/MS positive mode) m/z 647 (M+H); Rt 1.20 min.

No. 5513199

(E)-(2S,3S)-3-[(S)-2-(4-But-2-ynyloxy-phenyl)-1-ethoxycarbamoyl-ethylcarbamoyl]-2-hydroxy-12-oxo-2-propyl-nonadec-4-enoic acid

[Chem. 192]

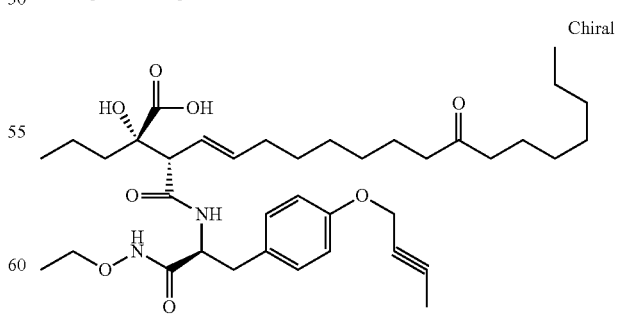

The target compound was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-but-2-ynyloxy-phenyl)-

N-ethoxy-propionamide was used instead of methyl (S)-2-amino-3-(4-butoxy-phenyl)-propionate.

¹H-NMR (CD₃OD) δ: 0.84 (3H, t, J=7.1 Hz), 0.89 (3H, t, J=6.9 Hz), 1.13 (3H, t, J=6.9 Hz), 1.21-1.37 (14H, m), 1.36-1.48 (2H, m), 1.59-1.75 (8H, m), 1.81 (3H, t, J=2.2 Hz), 1.97 (2H, m), 2.43 (3H, t, J=7.4 Hz), 2.87 (1H, dd, J=13.7, 8.2 Hz), 2.97 (1H, dd, J=13.7, 7.7 Hz), 3.70-3.80 (2H, m), 4.41 (1H, t, J=7.4 Hz), 4.61 (2H, m), 5.55 (2H, m), 6.86 (2H, d, J=8.2 Hz), 7.15 (2H, d, J=8.8 Hz) ESI (LC/MS positive mode) m/z 672 (M+H); Rt 1.05 min.

No. 5514975

(E)-(2S,3S)-3-[(S)-2-(4-But-2-ynyloxy-phenyl)-1-propoxycarbamoyl-ethylcarbamoyl]-2-hydroxy-12-oxo-2-propyl-nonadec-4-enoic acid

[Chem. 193]

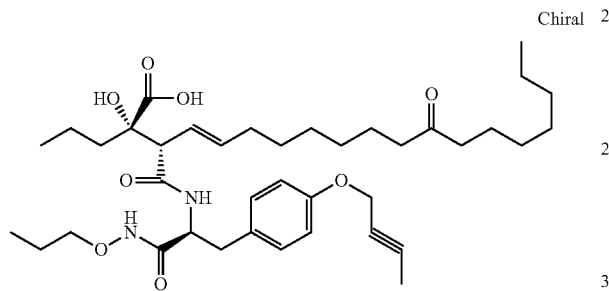

The target compound was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-but-2-ynyloxy-phenyl)-N-propoxy-propionamide was used instead of methyl (S)-2-amino-3-(4-butoxy-phenyl)-propionate.

¹H-NMR (CD₃OD) δ: 0.92 (9H, m), 1.31 (16H, m), 1.57 (7H, m), 1.71 (1H, m), 1.83 (3H, m), 1.99 (2H, m), 2.45 (4H, t, 7.2 Hz), 2.94 (2H, m), 3.23 (1H, m), 3.66 (2H, m), 4.42 (1H, m), 4.63 (2H, m), 5.57 (2H, m), 6.88 (2H, d, J=8.7 Hz), 7.17 (2H, d, J=8.4 Hz)
ESI (LC/MS positive mode) m/z 686 (M+H); Rt 1.07 min.

No. 5514978

(E)-(2S,3S)-3-[(S)-2-(4-But-2-ynyloxy-phenyl)-1-isopropoxycarbamoyl-ethylcarbamoyl]-2-hydroxy-12-oxo-2-propyl-nonadec-4-enoic acid

[Chem. 194]

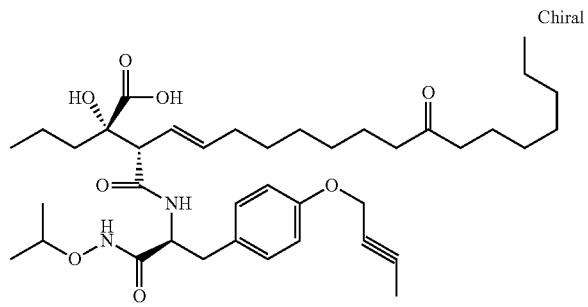

The target compound was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-but-2-ynyloxy-phenyl)-N-isopropoxy-propionamide was used instead of methyl (S)-2-amino-3-(4-butoxy-phenyl)-propionate.

¹H-NMR (CD₃OD) δ: 0.89 (6H, m), 1.07 (3H, d, J=1.8 Hz), 1.08 (3H, d, J=1.8 Hz), 1.16-1.57 (22H, m), 1.82 (3H, m), 2.00 (2H, m), 2.45 (4H, t, J=7.5 Hz), 2.94 (2H, m), 3.26 (1H, m), 3.94 (1H, m), 4.46 (1H, m), 4.63 (2H, m), 5.57 (2H, m), 6.89 (2H, d, J=8.7 Hz), 7.17 (2H, d, J=8.7 Hz)
ESI (LC/MS positive mode) ink 686 (M+H); Rt 1.06 min.

No. 5514980

(E)-(2S,3S)-3-[(S)-2-(4-Butoxy-phenyl)-1-carboxyethylcarbamoyl]-2-hydroxy-12-oxo-2-propyl-nonadec-4-enoic acid

[Chem. 195]

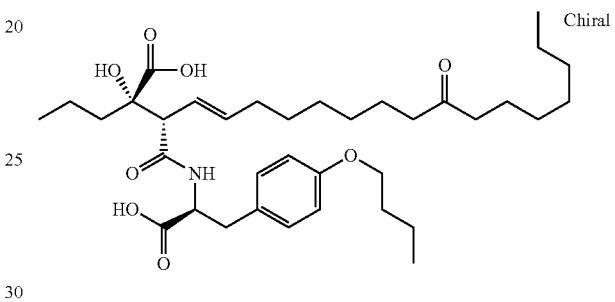

By the synthetic method of No. 5501825, the methyl ester in No. 5512992 (E)-(2S,3S)-3-[(S)-2-(4-butoxy-phenyl)-1-methoxycarbonyl-ethylcarbamoyl]-2-hydroxy-12-oxo-2-propyl-nonadec-4-enoic acid was hydrolyzed to obtain the target compound.

¹H-NMR (DMSO-d₆) δ: 0.78 (3H, t, J=7.1 Hz), 0.85 (3H, t, J=6.9 Hz), 0.92 (3H, t, J=7.1 Hz), 1.01 (1H, m), 1.13-1.29 (8H, m), 1.32-1.48 (4H, m), 1.57 (1H, dd, J=15.1, 11.8 Hz), 1.66 (2H, m), 1.87 (2H, m), 2.37 (4H, m), 2.78 (2H, dd, J=13.7, 9.3 Hz), 2.98 (2H, dd, J=13.7, 4.4 Hz), 3.17 (1H, m), 3.89 (2H, t, J=6.6 Hz), 4.36 (1H, td, J=8.5, 4.6 Hz), 5.0 (1H, br.s), 5.40 (2H, m), 6.77 (2H, d, J=8.8 Hz), 7.09 (2H, d, J=8.8 Hz), 8.17 (1H, d, J=7.7 Hz)
ESI (LC/MS positive mode) m/z 633 (M+H); Rt 1.12 min.

No. 5515116

(E)-(2S,3S)-3-[(S)-2-(4-But-2-ynyloxy-phenyl)-1-carboxymethyl-ethylcarbamoyl]-2-hydroxy-12-oxo-2-propyl-nonadec-4-enoic acid

[Chem. 196]

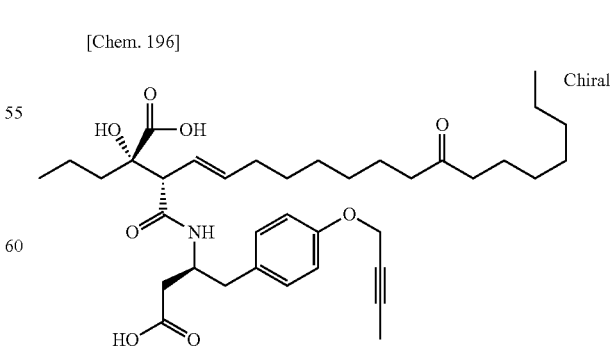

(E)-(2S,3S)-3-[(S)-2-(4-But-2-ynyloxy-phenyl)-1-methoxycarbonylmethyl-ethylcarbamoyl]-2-hydroxy-12-oxo-2- propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-3-amino-4-(4-but-2-ynyloxy-phenyl)-butyrate hydrochloride was used instead of methyl (S)-2-amino-3-(4-butoxy-phenyl)-propionate. Finally, by the synthetic method of No. 5501825, the methyl ester was hydrolyzed to obtain the target compound.

$^1$H-NMR (DMSO-d$_6$) δ: 0.79 (3H, t, J=7.1 Hz), 0.85 (3H, t, J=6.9 Hz), 1.01 (1H, m), 1.10-1.30 (14H, m), 1.43 (6H, m), 1.54 (1H, m), 1.82 (3H, t, J=5.5 Hz), 1.90 (2H, m), 2.36 (6H, m), 2.64 (2H, m), 3.07 (1H, d, J=7.7 Hz), 4.17 (1H, m), 4.66 (2H, d, J=2.2 Hz), 5.05 (1H, s), 5.42 (2H, m), 6.82 (2H, d, J=8.2 Hz), 7.06 (2H, d, J=8.2 Hz), 7.99 (1H, d, J=8.2 Hz)

ESI (LC/MS positive mode) m/z 643 (M+H); Rt 1.03 min.

No. 5515117

(E)-(2S,3S)-3-[(S)-2-(4-Butoxy-phenyl)-1-carbamoyl-ethylcarbamoyl]-2-hydroxy-12-oxo-2-propyl-nonadec-4-enoic acid

[Chem. 197]

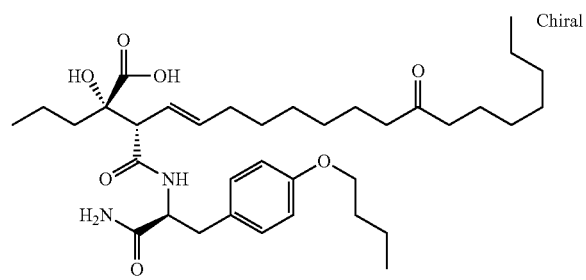

(E)-(2S,3S)-3-[(S)-2-(4-Butoxy-phenyl)-1-carbamoyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, ((S)-2-amino-3-(4-butoxy-phenyl)-propionamide hydrochloride was used instead of methyl (S)-2-amino-3-(4-butoxy-phenyl)-propionate.

$^1$H-NMR (DMSO-d$_6$) δ: 0.75 (3H, t, J=7.0 Hz), 0.85 (3H, t, J=6.9 Hz), 0.92 (3H, t, J=7.1 Hz), 1.02 (1H, m), 1.14-1.31 (14H, m), 1.42 (4H, m), 1.55 (1H, m), 1.66 (2H, m), 1.88 (2H, m), 2.37 (4H, m), 2.70 (2H, m), 2.92 (1H, dd, J=14.0, 4.7 Hz), 3.11 (1H, dd, J=21.4, 8.2 Hz), 3.88 (2H, t, J=6.3 Hz), 4.35 (1H, td, J=8.8, 4.4 Hz), 5.13 (1H, s), 5.41 (2H, m), 6.76 (2H, d, J=8.8 Hz), 7.09 (2H, d, J=8.2 Hz), 7.36 (1H, d, J=15.9 Hz), 8.00 (1H, d, J=8.2 Hz)

ESI (LC/MS positive mode) m/z 632 (M+H); Rt 1.09 min.

No. 5515118

(E)-(2S,3S)-3-[(S)-2-(4-Butoxy-phenyl)-1-methylcarbamoyl-ethylcarbamoyl]-2-hydroxy-12-oxo-2-propyl-nonadec-4-enoic acid

[Chem. 198]

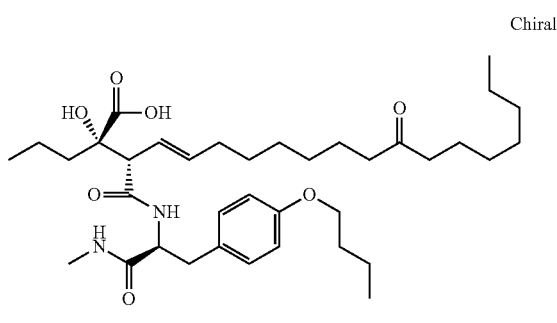

(E)-(2S,3S)-3-[(S)-2-(4-Butoxy-phenyl)-1-methylcarbamoyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-butoxy-phenyl)-N-methyl-propionamide hydrochloride was used instead of methyl (S)-2-amino-3-(4-butoxy-phenyl)-propionate.

$^1$H-NMR (DMSO-d$_6$) δ: 0.76 (3H, t, J=7.1 Hz), 0.85 (3H, t, J=6.9 Hz), 0.92 (3H, t, J=7.4 Hz), 1.00 (1H, m), 1.14-1.28 (12H, m), 1.42 (8H, m), 1.51-1.72 (3H, m), 1.86 (2H, m), 2.36 (4H, m), 2.56 (3H, d, J=4.4 Hz), 2.65 (1H, m), 2.79 (1H, m), 2.92 (1H, dd, J=14.0, 4.2 Hz), 3.05 (1H, d, J=7.7 Hz), 3.88 (2H, m), 4.32 (1H, m), 5.36 (2H, m), 6.75 (2H, d, J=8.8 Hz), 7.06 (2H, d, J=8.2 Hz), 7.97 (1H, m),

ESI (LC/MS positive mode) adz 646 (M+H); Rt 1.12 min.

No. 5515119

(E)-(2S,3S)-3-[(S)-2-(4-Butoxy-phenyl)-1-dimethylcarbamoyl-ethylcarbamoyl]-2-hydroxy-12-oxo-2-propyl-nonadec-4-enoic acid

[Chem. 199]

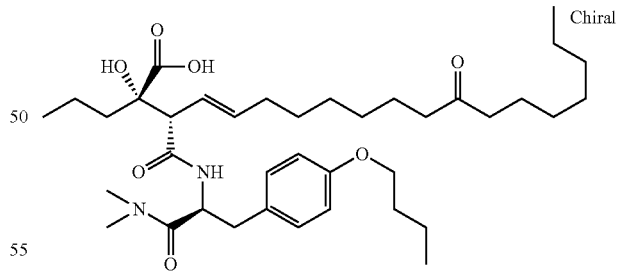

(E)-(2S,3S)-3-[(S)-2-(4-Butoxy-phenyl)-1-dimethylcarbamoyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(4-butoxy-phenyl)-N,N-dimethyl-propionamide hydrochloride was used instead of methyl (S)-2-amino-3-(4-butoxy-phenyl)-propionate.

$^1$H-NMR (DMSO-d$_6$) δ: 0.78 (3H, t, J=7.4 Hz), 0.85 (3H, t, J=6.9 Hz), 0.92 (3H, t, J=7.4 Hz), 1.02 (1H, m), 1.12-1.29

(12H, m), 1.42 (8H, m), 1.54 (1H, m), 1.66 (2H, m), 1.89 (2H, m), 2.36 (4H, t, J=7.4 Hz), 2.68 (1H, dd, J=13.7, 7.7 Hz), 2.78 (3H, s), 2.82 (1H, dd, J=14.8, 7.1 Hz), 2.87 (3H, s), 3.16 (1H, m), 3.89 (2H, t, J=6.3 Hz), 4.81 (1H, q, J=7.5 Hz), 5.42 (2H, m), 6.77 (2H, d, J=8.8 Hz), 7.08 (2H, d, J=8.2 Hz), 7.18 (1H, d, J=8.2 Hz),

ESI (LC/MS positive mode) m/z 660 (M+H); Rt 1.16 min.

No. 5521486

(E)-(2S,3S)-2-Hydroxy-3-[(S)-1-methoxycarbonyl-2-(4'-methyl-biphenyl-4-yl)-ethylcarbamoyl]-12-oxo-2-propyl-nonadec-4-enoic acid

[Chem. 200]

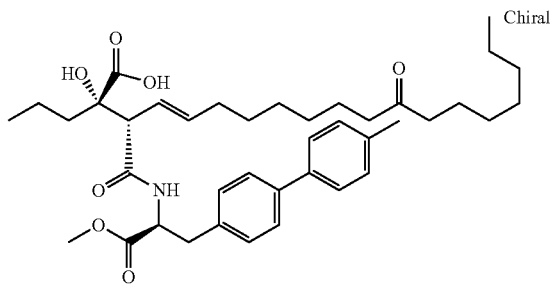

(E)-(2S,3S)-2-Hydroxy-3-[(S)-1-methoxycarbonyl-2-(4'-methyl-biphenyl-4-yl)-ethylcarbamoyl]-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(4'-methyl-biphenyl-4-yl)-propionate hydrochloride was used instead of methyl (S)-2-amino-3-(4-butoxy-phenyl)-propionate.

$^1$H-NMR (DMSO-$d_6$) δ: 0.77 (3H, t, J=7.1 Hz), 0.85 (3H, t, J=6.9 Hz), 1.09 (3H, m), 1.16-1.29 (9H, m), 1.32-1.42 (6H, m), 1.58 (1H, m), 1.81 (2H, m), 2.33 (4H, m), 2.92 (1H, dd, J=13.7, 9.9 Hz), 3.09 (1H, dd, J=14.3, 4.9 Hz), 3.19 (1H, d, J=8.2 Hz), 3.64 (3H, s), 4.52 (1H, m), 4.91 (1H, br.s), 5.40 (2H, m), 7.26 (4H, t, J=7.7 Hz), 7.52 (2H, d, J=7.7 Hz), 8.38 (1H, d, J=8.2 Hz)

ESI (LC/MS positive mode) m/z 664 (M+H); Rt 1.21 min.

No. 5522439

(E)-(2S,3S)-2-Hydroxy-3-{(S)-1-methoxycarbonyl-2-[4-(3-methyl-butoxy)-phenyl]-ethylcarbamoyl}-12-oxo-2-propyl-nonadec-4-enoic acid

[Chem. 201]

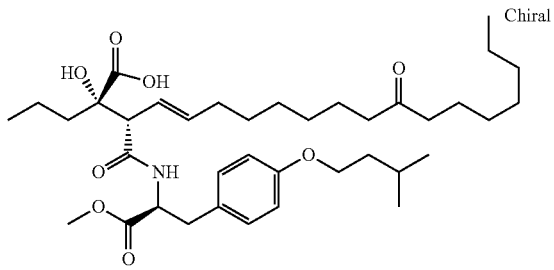

(E)-(2S,3S)-2-Hydroxy-3-{(S)-1-methoxycarbonyl-2-[4-(3-methyl-butoxy)-phenyl]-ethylcarbamoyl}-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-[4-(3-methyl-butoxy)-phenyl]-propionate hydrochloride was used instead of methyl (S)-2-amino-3-(4-butoxy-phenyl)-propionate.

$^1$H-NMR (DMSO-$d_6$) δ: 0.78 (3H, t, J=7.1 Hz), 0.85 (3H, t, J=6.9 Hz), 0.91 (6H, d, J=6.6 Hz), 1.00 (1H, m), 1.20-1.45 (20H, m), 1.58 (2H, q, J=6.6 Hz), 1.76 (1H, m), 1.87 (2H, m), 2.37 (4H, m), 2.67 (1H, m), 2.81 (1H, dd, J=13.7, 9.3 Hz), 2.97 (1H, dd, J=13.7, 4.4 Hz), 3.16 (1H, m), 3.61 (3H, s), 3.92 (2H, t, J=6.6 Hz), 4.42 (1H, m), 4.90 (1H, br.s), 5.39 (2H, m), 6.79 (2H, d, J=8.8 Hz), 7.08 (2H, d, J=8.8 Hz), 7.52 (2H, d, J=7.7 Hz), 8.24 (1H, br.s)

ESI (LC/MS positive mode) m/z 661 (M+H); Rt 1.23 min.

No. 5523856

(E)-(2S,3S)-3-[(S)-2-(4-Benzyloxy-phenyl)-1-methoxycarbonyl-ethylcarbamoyl]-2-hydroxy-12-oxo-2-propyl-nonadec-4-enoic acid

[Chem. 202]

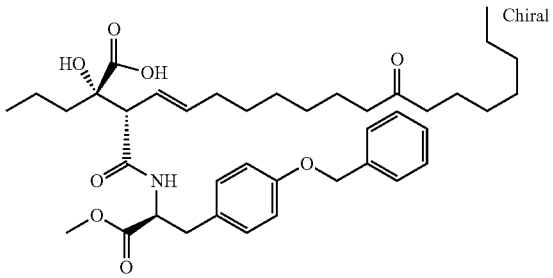

(E)-(2S,3S)-3-[(S)-2-(4-Benzyloxy-phenyl)-1-methoxycarbonyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(4-benzyloxy-phenyl)-propionate hydrochloride was used instead of methyl (S)-2-amino-3-(4-butoxy-phenyl)-propionate.

$^1$H-NMR (CD$_3$OD) δ: 0.86 (3H, t, J=7.4 Hz), 0.89 (3H, t, J=6.9 Hz), 1.11 (1H, m), 1.24-1.32 (14H, m), 1.49 (6H, m), 1.68 (1H, m), 1.96 (2H, m), 2.39 (4H, q, J=7.0 Hz), 2.90 (1H, dd, J=13.7, 9.3 Hz), 3.12 (1H, dd, J=14.3, 4.9 Hz), 3.22 (1H, d, J=8.2 Hz), 3.70 (3H, s), 4.64 (1H, m), 5.03 (3H, s), 5.49 (1H, dd, J=15.4, 8.2 Hz), 5.56 (1H, dd, J=15.1, 6.3 Hz), 6.89 (2H, d, J=8.8 Hz), 7.11 (2H, d, J=8.2 Hz), 7.29 (1H, t, J=7.1 Hz), 7.36 (2H, t, J=7.1 Hz), 7.41 (2H, t, J=7.1 Hz), 8.25 (1H, d, J=7.7 Hz)

ESI (LC/MS positive mode) m/z 680 (M+H); Rt 1.16 min.

No. 5523857

(E)-(2S,3S)-2-Hydroxy-3-[(S)-1-methoxycarbonyl-2-(4-phenoxy-phenyl)-ethylcarbamoyl]-12-oxo-2-propyl-nonadec-4-enoic acid

[Chem. 203]

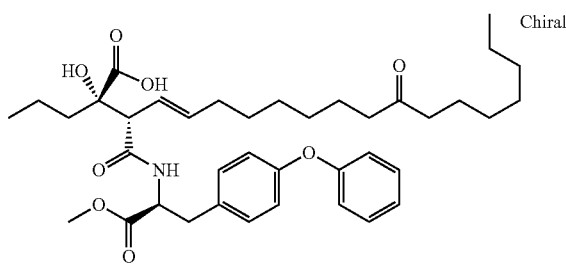

(E)-(2S,3S)-2-Hydroxy-3-[(S)-1-methoxycarbonyl-2-(4-phenoxy-phenyl)-ethylcarbamoyl]-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(4-phenoxy-phenyl)-propionate hydrochloride was used instead of methyl (S)-2-amino-3-(4-butoxy-phenyl)-propionate.

$^1$H-NMR (CD$_3$OD) δ: 0.86 (3H, t, J=7.4 Hz), 0.89 (3H, t, J=6.9 Hz), 1.30 (1H, m), 1.20-1.38 (14H, m), 1.52 (6H, m), 1.70 (1H, m), 1.95 (2H, m), 2.41 (4H, m), 2.95 (1H, dd, J=14.3, 9.3 Hz), 3.17 (1H, dd, J=13.7, 4.9 Hz), 3.24 (1H, d, J=8.8 Hz), 3.72 (3H, s), 4.67 (1H, dd, J=9.3, 4.9 Hz), 5.54 (2H, m), 6.88 (2H, d, J=8.8 Hz), 6.94 (2H, d, J=8.8 Hz), 7.09 (1H, t, J=7.4 Hz), 7.18 (2H, t, J=8.2 Hz), 7.33 (2H, t, J=8.0 Hz), 8.31 (1H, d, J=8.2 Hz)

ESI (LC/MS positive mode) m/z 666 (M+H); Rt 1.17 min.

No. 5523858

(E)-(2S,3S)-3-((S)-2-Biphenyl-4-yl-1-methoxycarbonyl-ethylcarbamoyl)-2-hydroxy-12-oxo-2-propyl-nonadec-4-enoic acid

[Chem. 204]

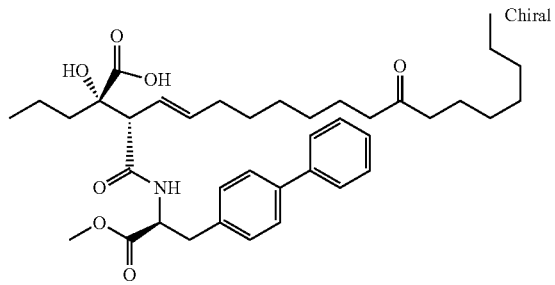

(E)-(2S,3S)-3-((S)-2-Biphenyl-4-yl-1-methoxycarbonyl-ethylcarbamoyl)-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-biphenyl-4-yl-propionate hydrochloride was used instead of methyl (S)-2-amino-3-(4-butoxy-phenyl)-propionate.

$^1$H-NMR (CD$_3$OD) δ: 0.82 (3H, t, J=6.6 Hz), 0.89 (3H, t, J=6.0 Hz), 1.11 (1H, m), 1.12-1.35 (14H, m), 1.49 (6H, m), 1.68 (1H, m), 1.91 (2H, m), 2.37 (2H, t, J=7.1 Hz), 2.40 (2H, t, J=8.2 Hz), 3.00 (1H, dd, J=14.0, 9.6 Hz), 3.24 (1H, m), 3.73 (3H, s), 4.73 (1H, m), 5.51 (2H, m), 7.29 (3H, m), 7.41 (2H, t, J=7.4 Hz), 7.53 (2H, d, J=6.6 Hz), 7.58 (2H, d, J=7.7 Hz), 8.34 (1H, d, J=7.1 Hz)

ESI (LC/MS positive mode) m/z 651 (M+H); Rt 1.22 min.

No. 5523859

(E)-(2S,3S)-2-Hydroxy-3-[(S)-2-(3'-methoxy-biphenyl-4-yl)-1-methoxycarbonyl-ethylcarbamoyl]-12-oxo-2-propyl-nonadec-4-enoic acid

[Chem. 205]

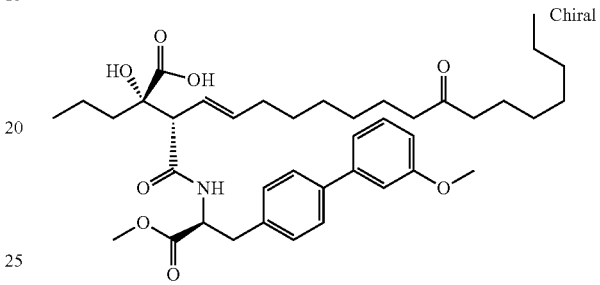

(E)-(2S,3S)-2-Hydroxy-3-[(S)-2-(3'-methoxy-biphenyl-4-yl)-1-methoxycarbonyl-ethylcarbamoyl]-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(3'-methoxy-biphenyl-4-yl)-propionate hydrochloride was used instead of methyl (S)-2-amino-3-(4-butoxy-phenyl)-propionate.

$^1$H-NMR (CD$_3$OD) δ: 0.82 (3H, t, J=7.1 Hz), 0.89 (3H, t, J=6.9 Hz), 1.10 (1H, m), 1.15-1.32 (14H, m), 1.49 (6H, m), 1.69 (1H, m), 1.90 (2H, q, J=6.6 Hz), 2.36 (2H, t, J=7.4 Hz), 2.40 (2H, t, J=8.2 Hz), 2.99 (1H, dd, J=14.0, 9.6 Hz), 3.24 (1H, m), 3.35 (1H, m), 3.74 (3H, s), 3.83 (3H, s), 4.73 (1H, dd, J=9.6, 4.7 Hz), 5.46 (1H, dd, J=15.4, 7.7 Hz), 5.53 (1H, dd, J=15.4, 6.0 Hz), 6.88 (1H, dd, J=8.0, 2.5 Hz), 7.10 (1H, t, J=1.9 Hz), 7.15 (1H, d, J=7.7 Hz), 7.27 (2H, d, J=8.2 Hz), 7.32 (2H, t, J=8.0 Hz), 7.53 (2H, d, J=8.8 Hz)

ESI (LC/MS positive mode) m/z 680 (M+H); Rt 1.16 min.

No. 5523860

(E)-(2S,3S)-3-[(S)-2-(2'-Fluoro-biphenyl-4-yl)-1-methoxycarbonyl-ethylcarbamoyl]-2-hydroxy-12-oxo-2-propyl-nonadec-4-enoic acid

[Chem. 206]

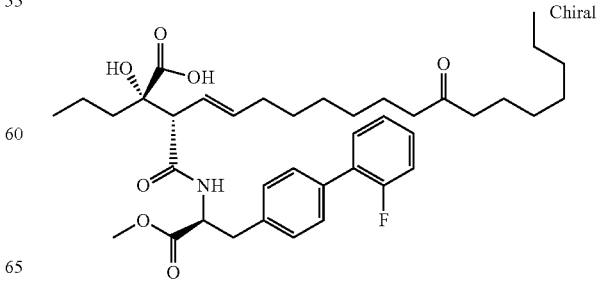

(E)-(2S,3S)-3-[(S)-2-(2'-Fluoro-biphenyl-4-yl)-1-methoxycarbonyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(2'-fluoro-biphenyl-4-yl)-propionate hydrochloride was used instead of methyl (S)-2-amino-3-(4-butoxy-phenyl)-propionate.

¹H-NMR (CD₃OD) δ: 0.83 (3H, t, J=7.1 Hz), 0.89 (3H, t, J=6.6 Hz), 1.11 (1H, m), 1.15-1.37 (14H, m), 1.50 (6H, m), 1.69 (1H, m), 1.92 (2H, q, J=6.6 Hz), 2.37 (2H, t, J=7.1 Hz), 2.41 (2H, t, J=7.4 Hz), 3.02 (1H, dd, J=14.0, 9.6 Hz), 3.24 (1H, m), 3.74 (3H, s), 4.74 (1H, dd, J=9.3, 4.4 Hz), 5.49 (1H, dd, J=15.4, 8.2 Hz), 5.56 (1H, dd, J=15.4, 6.0 Hz), 7.14-7.37 (5H, m), 7.45 (2H, m), 8.37 (1H, d, J=8.8 Hz)

ESI (LC/MS positive mode) m/z 668 (M+H); Rt 1.16 min.

No. 5523861

(E)-(2S,3S)-3-{(S)-2-[4-(3-Fluoro-propoxy)-phenyl]-1-methoxycarbonyl-ethylcarbamoyl}-2-hydroxy-12-oxo-2-propyl-nonadec-4-enoic acid

[Chem. 207]

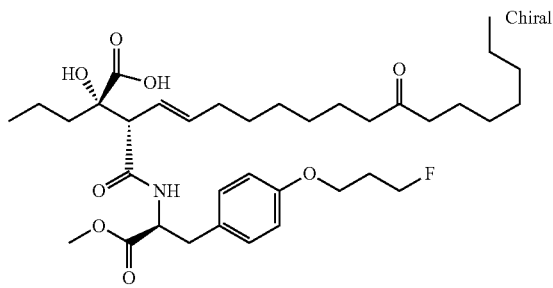

(E)-(2S,3S)-3-{(S)-2-[4-(3-Fluoro-propoxy)-phenyl]-1-methoxycarbonyl-ethylcarbamoyl}-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-[4-(3-fluoro-propoxy)-phenyl]-propionate hydrochloride was used instead of methyl (S)-2-amino-3-(4-butoxy-phenyl)-propionate.

¹H-NMR (CD₃OD) δ: 0.85 (3H, t, J=7.1 Hz), 0.89 (3H, t, J=6.9 Hz), 1.11 (1H, m), 1.22-1.37 (14H, m), 1.39-1.58 (6H, m), 1.66 (1H, m), 1.97 (1H, m), 2.09 (1H, m), 2.15 (1H, m), 2.43 (4H, m), 2.90 (1H, td, J=10.6, 6.6 Hz), 3.11 (1H, dd, J=14.0, 5.2 Hz), 3.22 (1H, d, J=8.2 Hz), 3.71 (3H, s), 4.05 (2H, t, J=6.3 Hz), 4.54 (1H, t, J=5.8 Hz), 4.63 (1H, dd, 11.5, 5.5 Hz), 4.65 (1H, q, J=5.9 Hz), 5.49 (1H, dd, J=15.4, 8.2 Hz), 5.57 (1H, dd, J=15.4, 6.0 Hz), 6.83 (2H, d, J=8.2 Hz), 7.11 (2H, d, J=8.2 Hz), 8.24 (1H, d, J=7.7 Hz)

ESI (LC/MS positive mode) m/z 651 (M+H); Rt 1.10 min.

No. 5524810

(E)-(2S,3S)-3-[(S)-2-(4'-Dimethylamino-biphenyl-4-yl)-1-methoxycarbonyl-ethylcarbamoyl]-2-hydroxy-12-oxo-2-propyl-nonadec-4-enoic acid

[Chem. 208]

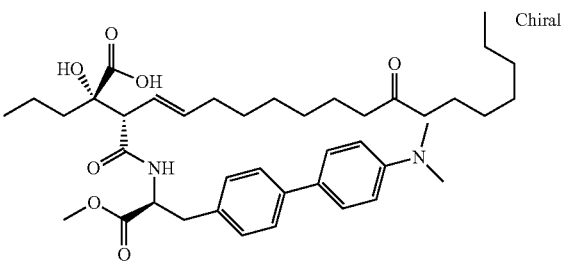

(E)-(2S,3S)-3-[(S)-2-(4'-Dimethylamino-biphenyl-4-yl)-1-methoxycarbonyl-ethylcarbamoyl]-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, methyl (S)-2-amino-3-(4'-dimethylamino-biphenyl-4-yl)-propionate hydrochloride was used instead of methyl (S)-2-amino-3-(4-butoxy-phenyl)-propionate.

¹H-NMR (CD₃OD) δ: 0.83 (3H, t, J=7.1 Hz), 0.89 (3H, t, J=6.9 Hz), 1.10-1.35 (15H, m), 1.39-1.57 (6H, m), 1.69 (1H, m), 1.90 (1H, q, J=6.4 Hz), 2.01 (1H, m), 2.35 (2H, t, J=7.1), 2.40 (2H, t, J=7.1 Hz), 2.97 (3H, s), 2.99 (1H, m), 3.22 (1H, dd, J=17.0, 6.0 Hz), 3.74 (3H, s), 4.72 (1H, dd, 9.3, 4.4 Hz), 5.47 (1H, dd, J=15.1, 7.4 Hz), 5.51 (1H, dd, J=16.2, 10.0 Hz), 6.86 (2H, d, J=8.8 Hz), 7.21 (2H, d, J=8.2 Hz), 7.48 (4H, dd, J=8.5, 2.5 Hz), 8.34 (1H, d, J=7.7 Hz)

ESI (LC/MS positive mode) m/z 693 (M+H); Rt 1.18 min.

No. 5541189

(E)-(2S,3S)-3-{(S)-2-[4-(3-Fluoro-propoxy)-phenyl]-1-methoxycarbonyl-ethylcarbamoyl}-2-hydroxy-12-oxo-2-propyl-nonadec-4-enoic acid

[Chem. 209]

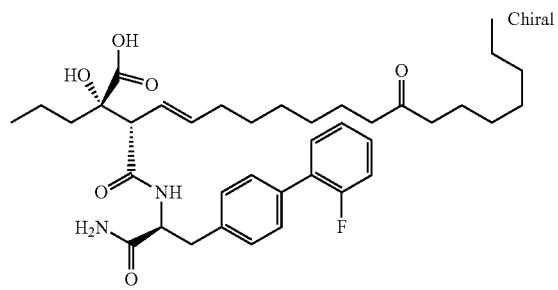

(E)-(2S,3S)-3-{(S)-2-[4-(3-Fluoro-propoxy)-phenyl]-1-methoxycarbonyl-ethylcarbamoyl}-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-(2'-fluoro-biphenyl-4-yl)-propionamide hydrochloride was used instead of methyl (S)-2-amino-3-(4-butoxy-phenyl)-propionate.

¹H-NMR (CD₃OD) δ: 0.82 (3H, t, J=7.2 Hz), 0.91 (3H, t, J=6.3 Hz), 1.10-1.31 (15H, m), 1.39-1.57 (6H, m), 1.69 (1H, m), 1.96 (2H, m), 2.41 (4H, m), 3.05 (1H, m), 3.22 (2H, m), 4.69 (1H, m), 5.55 (2H, m), 7.21 (2H, m), 7.32 (3H, m), 7.47 (3H, m)

ESI (LC/MS positive mode) m/z 653 (M+H); Rt 1.07 min.

No. 5541190

(E)-(2S,3S)-3-[(S)-2-(4'-Dimethylamino-biphenyl-4-yl)-1-methoxycarbonyl-ethylcarbamoyl]-2-hydroxy-12-oxo-2-propyl-nonadec-4-enoic acid

[Chem. 210]

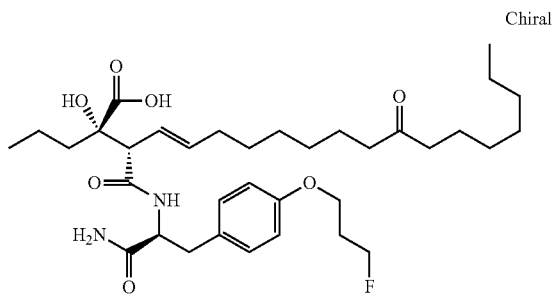

(E)-(2S,3S)-3-{(S)-2-[4-(3-Fluoro-propoxy)-phenyl]-1-methoxycarbonyl-ethylcarbamoyl}-2-hydroxy-12-oxo-2-propyl-nonadec-4-enoic acid was obtained by the synthesis similar to Step A, except that, in A-1 step, tert-butyl 2-oxo-pentanoate was used instead of tert-butyl 4-methoxy-2-oxo-butyrate, and, in Step A-2a, (S)-2-amino-3-[4-(3-fluoro-propoxy)-phenyl]-propionamide hydrochloride was used instead of methyl (S)-2-amino-3-(4-butoxy-phenyl)-propionate.

¹H-NMR (DMSO-d₆) δ: 0.77 (3H, t, J=7.4 Hz), 0.85 (3H, t, J=6.9 Hz), 1.00 (1H, m), 1.13-1.35 (15H, m), 1.39-1.47 (6H, m), 1.54 (1H, m), 1.87 (2H, m), 2.04 (1H, m), 2.10 (1H, m), 2.37 (4H, m), 2.69 (1H, m), 2.92 (1H, dd, J=13.7, 4.4 Hz), 3.14 (1H, d, J=8.2 Hz), 3.99 (2H, t, J=6.3 Hz), 4.35, 1H, td, J=8.8, 4.4 Hz), 4.52 (1H, t, J=6.0 Hz), 4.64 (1H, t, J=6.0 Hz), 5.12 (1H, s), 5.41 (2H, m), 6.78 (2H, d, J=8.8 Hz), 7.11 (3H, m), 7.35 (1H, d, J=14.3 Hz), 7.98 (1H, d, J=8.2 Hz)

ESI (LC/MS positive mode) m/z 635 (M+H); Rt 1.00 min.

No. 5541191

(E)-(2S,3S)-3-[(S)-1-Carbamoyl-2-(2'-fluoro-biphenyl-4-yl)-ethylcarbamoyl]-2-hydroxy-12-oxo-2-propyl-nonadec-4-enoic acid

[Chem. 211]

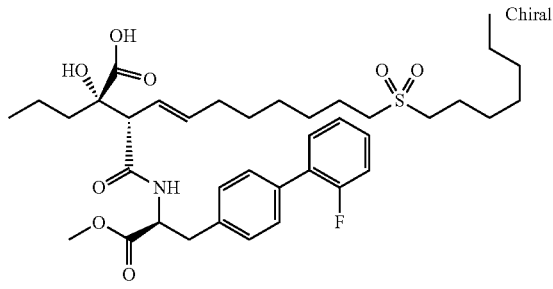

(E)-(2S,3S)-3-[(S)-1-Carbamoyl-2-(T-fluoro-biphenyl-4-yl)-ethylcarbamoyl]-2-hydroxy-12-oxo-2-propyl-nonadec-4-enoic acid was obtained by the synthesis similar to Step C, except that, in C-5 step, tert-butyl 2-oxo-pentanoate was used instead of tert-butyl 4-methoxy-2-oxo-butyrate, and, in Step C-6, methyl (S)-2-amino-3-(2'-fluoro-biphenyl-4-yl)-propionate hydrochloride was used instead of methyl (S)-2-amino-3-(4-butoxy-phenyl)-propionate.

¹H-NMR (DMSO-d₆) δ: 0.78 (3H, t, J=7.1 Hz), 0.86 (3H, t, J=6.6 Hz), 1.02 (1H, m), 1.13-1.47 (15H, m), 1.63 (6H, m), 1.86 (2H, m), 1.98 (1H, m), 3.00 (4H, m), 3.12 (1H, dd, J=14.0, 4.7 Hz), 3.19 (1H, d, J=7.1 Hz), 3.55 (1H, d, J=9.3 Hz), 3.65 (3H, s), 3.99 (2H, t, J=6.3 Hz), 4.54 (1H, m), 4.92 (1H, br.s), 5.42 (2H, m), 7.30 (3H, m), 7.39 (1H, m), 7.48 (1H, m), 8.39 (1H, d, J=7.7 Hz)

ESI (LC/MS positive mode) m/z 704 (M+H); Rt 1.05 min.

No. 5541193

(E)-(2S,3S)-3-{(S)-1-Carbamoyl-2-[4-(3-fluoro-propoxy)-phenyl]-ethylcarbamoyl}-2-hydroxy-12-oxo-2-propyl-nonadec-4-enoic acid

[Chem. 212]

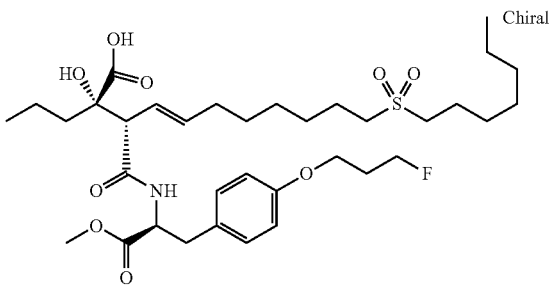

(E)-(2S,3S)-3-{(S)-1-Carbamoyl-2-[4-(3-fluoro-propoxy)-phenyl]-ethylcarbamoyl}-2-hydroxy-12-oxo-2-propyl-nonadec-4-enoic acid was obtained by the synthesis similar to Step C, except that, in C-5 step, tert-butyl 2-oxo-pentanoate was used instead of tert-butyl 4-methoxy-2-oxo-butyrate, and, in Step C-6, methyl (S)-2-amino-3-[4-(3-fluoro-propoxy)-phenyl]-propionate hydrochloride was used instead of methyl (S)-2-amino-3-(4-butoxy-phenyl)-propionate.

¹H-NMR (DMSO-d₆) δ: 0.79 (3H, t, J=7.1 Hz), 0.86 (3H, t, J=6.6 Hz), 1.00 (1H, m), 1.19-1.45 (16H, m), 1.64 (6H, m), 1.89 (2H, m), 2.04 (1H, m), 2.11 (1H, m), 2.821H, (dd, J=13.7.9.3 Hz), 2.97 (1H, dd, J=14.0, 5.2 Hz), 3.03 (4H, m), 3.17 (1H, d, J=7.7 Hz), 3.61 (3H, s), 4.01 (2H, t, J=6.0 Hz), 4.43 (1H, m), 4.53 (1H, t, J=6.0 Hz), 4.65 (1H, t, J=6.0 Hz) 4.94 (1H, br.s), 5.38 (1H, dd, J=14.8, 5.5 Hz), 5.44 (1H, dd, J=15.4, 7.1 Hz), 6.82 (2H, d, J=8.8 Hz), 7.10 (2H, d, J=8.8 Hz), 8.27 (1H, d, J=8.2 Hz)

ESI (LC/MS positive mode) m/z 686 (M+H); Rt 0.98 min.

No. 5542552

(E)-(2S,3S)-3-[(S)-2-(2'-Fluoro-biphenyl-4-yl)-1-methoxycarbonyl-ethylcarbamoyl]-11-(heptane-1-sulfonyl)-2-hydroxy-2-propyl-undec-4-enoic acid

[Chem. 213]

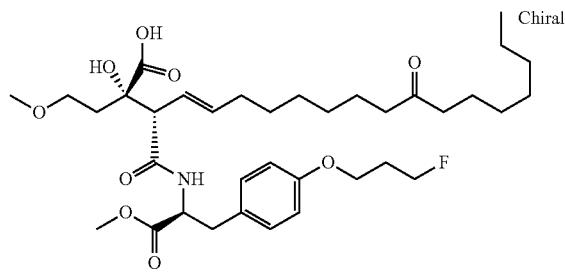

(E)-(2S,3S)-3-[(S)-2-(2'-Fluoro-biphenyl-4-yl)-1-methoxycarbonyl-ethylcarbamoyl]-11-(heptane-1-sulfonyl)-2-hydroxy-2-propyl-undec-4-enoic acid was obtained by the synthesis similar to Step A, except that, in A-2a, methyl (S)-2-amino-3-[4-(3-fluoro-propoxy)-phenyl]-propionate hydrochloride was used instead of methyl (S)-2-amino-3-(4-butoxy-phenyl)-propionate.

$^1$H-NMR (DMSO-$d_6$) δ: 0.85 (3H, t, J=6.9 Hz), 1.13-1.30 (14H, m), 1.42 (4H, m), 1.65 (1H, m), 1.88 (1H, m), 1.94 (1H, dd, J=15.4, 6.6 Hz), 2.04 (1H, m), 2.11 (1H, m), 2.36 (4H, m), 2.82 (1H, dd, J=13.7, 9.3 Hz), 2.96 (1H, dd, J=13.7, 5.5 Hz), 3.19 (1H, m), 3.25 (1H, dd, J=15.4, 8.8 Hz), 3.61 (3H, s), 4.01 (2H, t, J=6.3 Hz), 4.42 (1H, m), 4.53 (1H, t, J=5.8 Hz), 4.65 (1H, t, J=5.8 Hz) 4.99 (1H, br.s), 5.40 (1H, d, J=4.4 Hz), 5.44 (1H, dd, J=15.4, 7.1 Hz), 6.81 (2H, d, J=8.8 Hz), 7.09 (2H, d, J=8.2 Hz), 8.32 (1H, d, J=7.7 Hz)

ESI (LC/MS positive mode) m/z 666 (M+H); Rt 1.07 min.

No. 5543387

(E)-(2S,3S)-3-{(S)-2-[4-(3-Fluoro-propoxy)-phenyl]-1-methoxycarbonyl-ethylcarbamoyl}-11-(heptane-1-sulfonyl)-2-hydroxy-2-propyl-undec-4-enoic acid

[Chem. 214]

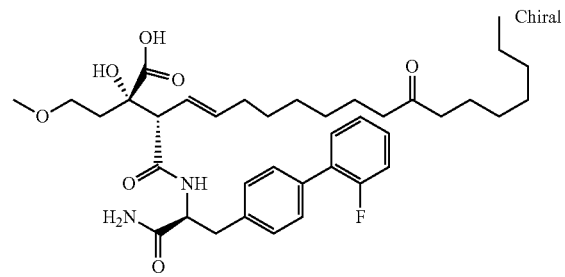

(E)-(2S,3S)-3-{(S)-2-[4-(3-Fluoro-propoxy)-phenyl]-1-methoxycarbonyl-ethylcarbamoyl}-11-(heptane-1-sulfonyl)-2-hydroxy-2-propyl-undec-4-enoic acid was obtained by the synthesis similar to Step A, except that, in Step A-2a, (S)-2-amino-3-(2'-fluoro-biphenyl-4-yl)-propionamide hydrochloride was used instead of methyl (S)-2-amino-3-(4-butoxy-phenyl)-propionate.

$^1$H-NMR (DMSO-$d_6$) δ: 0.85 (3H, t, J=6.9 Hz), 1.04-1.29 (14H, m), 1.31-1.47 (4H, m), 1.63 (1H, m), 1.83 (2H, m), 1.93 (1H, m), 2.30 (2H, t, J=7.4 Hz), 2.35 (2H, t, J=7.4 Hz), 2.82 (1H, dd, J=13.7, 9.9 Hz), 3.05 (1H, s), 3.07 (1H, dd, J=13.7, 4.4 Hz), 3.12 (3H, s), 3.18 (1H, d, J=7.7 Hz), 3.25 (1H, m), 4.46 (1H, m), 5.20 (1H, br.s), 5.41 (2H, m), 7.16 (1H, br.s), 7.24-7.33 (4H, m), 7.36-7.53 (4H, m), 8.17 (1H, d, J=8.2 Hz)

ESI (LC/MS positive mode) m/z 669 (M+H); Rt 1.02 min.

No. 5543388

(E)-(2S,3S)-3-{(S)-2-[4-(3-Fluoro-propoxy)-phenyl]-1-methoxycarbonyl-ethylcarbamoyl}-2-hydroxy-2-(2-methoxy-ethyl)-12-oxo-nonadec-4-enoic acid

[Chem. 215]

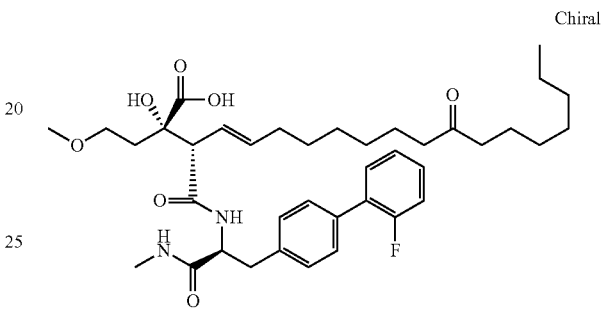

(E)-(2S,3S)-3-{(S)-2-[4-(3-Fluoro-prop oxy)-phenyl]-1-methoxycarbonyl-ethylcarbamoyl}-2-hydroxy-2-(2-methoxy-ethyl)-12-oxo-nonadec-4-enoic acid was obtained by the synthesis similar to Step A, except that, in A-2a, (S)-2-amino-3-(2'-fluoro-biphenyl-4-yl)-N-methyl-propionamide hydrochloride was used instead of methyl (S)-2-amino-3-(4-butoxy-phenyl)-propionate.

$^1$H-NMR (DMSO-$d_6$) δ: 0.85 (3H, t, J=6.9 Hz), 1.05-1.29 (14H, m), 1.32-1.46 (4H, m), 1.61 (1H, m), 1.83 (2H, m), 1.93 (1H, m), 2.30 (2H, t, J=7.4 Hz), 2.35 (2H, t, J=7.4 Hz), 2.61 (3H, d, J=4.4 Hz), 2.80 (1H, dd, J=13.7, 9.3 Hz), 3.03 (1H, dd, J=13.7, 4.1 Hz), 3.18 (1H, d, J=7.7 Hz), 3.25 (1H, m), 4.45 (1H, td, J=8.9, 4.4 Hz), 5.22 (1H, br.s), 5.41 (2H, m), 7.25-7.31 (4H, m), 7.35-7.43 (3H, m), 7.48 (1H, td, J=8.0, 1.6 Hz), 7.90 (1H, d, J=4.4 Hz), 8.21 (1H, d, J=8.2 Hz)

ESI (LC/MS positive mode) m/z 683 (M+H); Rt 1.05 min.

No. 5543389

(E)-(2S,3S)-3-[(S)-1-Carbamoyl-2-(2'-fluoro-biphenyl-4-yl)-ethylcarbamoyl]-2-hydroxy-2-(2-methoxy-ethyl)-12-oxo-nonadec-4-enoic acid

[Chem. 216]

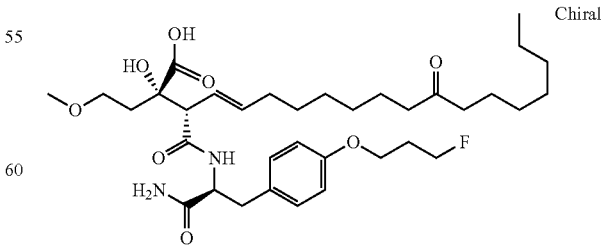

(E)-(2S,3S)-3-[(S)-1-Carbamoyl-2-(T-fluoro-biphenyl-4-yl)-ethylcarbamoyl]-2-hydroxy-2-(2-methoxy-ethyl)-12-oxo-nonadec-4-enoic acid was obtained by the synthesis similar to Step A, except that, in Step A-2a, (S)-2-amino-3-[4-(3-fluoro-propoxy)-phenyl]-propionamide hydrochloride was used instead of methyl (S)-2-amino-3-(4-butoxy-phenyl)-propionate.

$^1$H-NMR (DMSO-d$_6$) δ: 0.85 (3H, t, J=6.9 Hz), 1.15-1.29 (14H, m), 1.42 (4H, m), 1.61 (1H, m), 1.83-1.96 (3H, m), 2.04 (1H, m), 2.10 (1H, m), 2.36 (4H, m), 2.68 (1H, dd, J=14.3, 9.3 Hz), 2.92 (1H, dd, J=14.0, 4.7 Hz), 3.14 (3H, s), 3.15 (1H, m), 4.00 (2H, t, J=6.3 Hz), 4.35 (1H, td, J=8.9, 4.4 Hz), 4.52 (1H, t, J=6.0 Hz), 4.64 (1H, t, J=6.0 Hz), 5.20 (1H, br.s), 5.40 (2H, m), 6.78 (2H, d, J=8.8 Hz), 7.10 (1H, d, J=8.8 Hz), 7.36 (1H, s), 8.04 (1H, d, J=8.2 Hz)

ESI (LC/MS positive mode) m/z 651 (M+H); Rt 0.95 min.

No. 5543390

(E)-(2S,3S)-3-[(S)-2-(2'-Fluoro-biphenyl-4-yl)-1-methylcarbamoyl-ethylcarbamoyl]-2-hydroxy-2-(2-methoxy-ethyl)-12-oxo-nonadec-4-enoic acid

[Chem. 217]

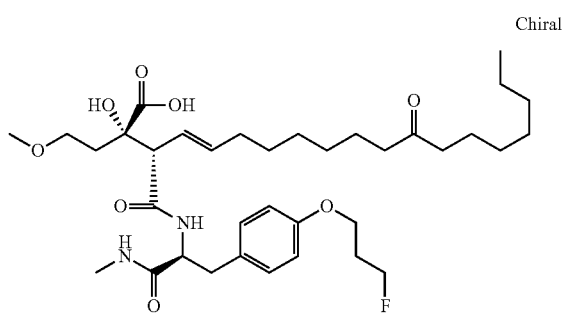

(E)-(2S,3S)-3-[(S)-2-(T-Fluoro-biphenyl-4-yl)-1-methylcarbamoyl-ethylcarbamoyl]-2-hydroxy-2-(2-methoxy-ethyl)-12-oxo-nonadec-4-enoic acid was obtained by the synthesis similar to Step A, except that, in A-2a, (S)-2-amino-3-[4-(3-fluoro-propoxy)-phenyl]-N-methyl-propionamide hydrochloride was used instead of methyl (S)-2-amino-3-(4-butoxy-phenyl)-propionate.

$^1$H-NMR (DMSO-d$_6$) δ: 0.85 (3H, t, J=6.9 Hz), 1.14-1.29 (14H, m), 1.42 (4H, m), 1.59 (1H, m), 1.83-1.95 (3H, m), 2.04 (1H, m), 2.10 (1H, m), 2.36 (4H, m), 2.57 (3H, d, J=4.4 Hz), 2.67 (1H, dd, J=13.7, 9.9 Hz), 2.88 (1H, dd, J=13.7, 4.4 Hz), 3.14 (3H, s), 3.25 (1H, dd, J=16.5, 7.7 Hz), 3.35 (1H, dd, J=9.3, 4.9 Hz), 4.00 (2H, t, J=6.3 Hz), 4.34 (1H, td, J=8.9, 4.6 Hz), 4.52 (1H, t, J=6.0 Hz), 4.64 (1H, t, J=6.0 Hz), 5.22 (1H, br.s), 5.39 (2H, m), 6.78 (2H, d, J=8.8 Hz), 7.08 (1H, d, J=8.2 Hz), 7.83 (1H, d, J=4.9 Hz), 8.09 (1H, d, J=8.2 Hz)

ESI (LC/MS positive mode) m/z 665 (M+H); Rt 0.97 min.

No. 5546909

(E)-(2S,3S)-3-{(S)-1-Carbamoyl-2-[4-(3-fluoro-propoxy)-phenyl]-ethylcarbamoyl}-2-hydroxy-2-(2-methoxy-ethyl)-12-oxo-nonadec-4-enoic acid

[Chem. 218]

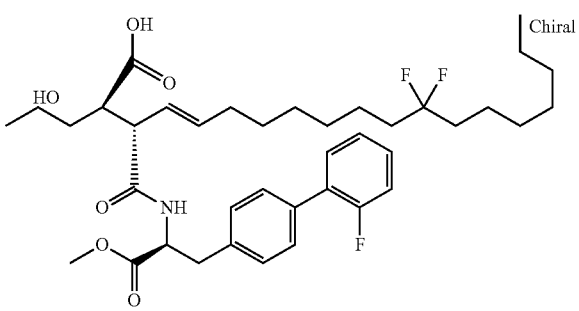

(E)-(2S,3S)-3-{(S)-1-Carbamoyl-2-[4-(3-fluoro-propoxy)-phenyl]-ethylcarbamoyl}-2-hydroxy-2-(2-methoxy-ethyl)-12-oxo-nonadec-4-enoic acid was obtained by the synthesis similar to Step B, except that, in B-6 step, tert-butyl 2-oxo-pentanoate was used instead of tert-butyl 4-methoxy-2-oxo-butyrate, and, in Step B-7, methyl (S)-2-amino-3-(2'-fluoro-biphenyl-4-yl)-propionate hydrochloride was used instead of methyl (S)-2-amino-3-(4-but-2-ynyloxy-phenyl)-propionate.

$^1$H-NMR (DMSO-d$_6$) δ: 0.78 (3H, t, J=7.1 Hz), 0.85 (3H, t, J=6.9 Hz), 1.03 (1H, m), 1.16-1.43 (20H, m), 1.59 (1H, m), 1.67-1.89 (6H, m), 2.95 (1H, dd, J=13.7, 9.9 Hz), 3.12 (1H, dd, J=14.0, 4.7 Hz), 3.20 (1H, d, J=7.7 Hz), 3.65 (3H, s), 4.53 (1H, m), 4.90 (1H, br.s), 5.42 (2H, m), 7.25-7.33 (4H, m), 7.35-7.42 (1H, m), 7.42-7.55 (3H, m), 8.39 (1H, d, J=7.7 Hz)

ESI (LC/MS positive mode) m/z 690 (M+H); Rt 1.22 min.

No. 5546911

(E)-(2S,3S)-3-{(S)-2-[4-(3-Fluoro-propoxy)-phenyl]-1-methylcarbamoyl-ethylcarbamoyl}-2-hydroxy-2-(2-methoxy-ethyl)-12-oxo-nonadec-4-enoic acid

[Chem. 219]

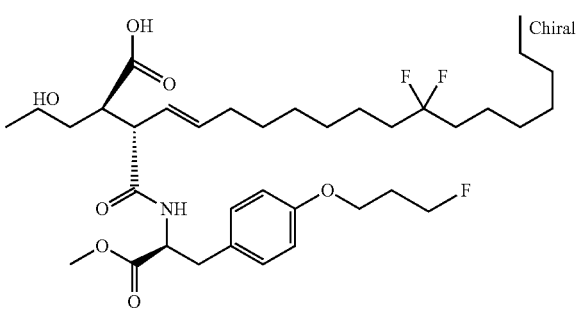

(E)-(2S,3S)-3-{(S)-2-[4-(3-Fluoro-propoxy)-phenyl]-1-methylcarbamoyl-ethylcarbamoyl}-2-hydroxy-2-(2-methoxy-ethyl)-12-oxo-nonadec-4-enoic acid was obtained by the synthesis similar to Step B, except that, in B-6 step, tert-butyl 2-oxo-pentanoate was used instead of tert-butyl 4-methoxy-2-oxo-butyrate, and, in Step B-7, methyl (S)-2-amino-3-[4-

(3-fluoro-propoxy)-phenyl]-propionate hydrochloride was used instead of methyl (S)-2-amino-3-(4-but-2-ynyloxy-phenyl)-propionate.

$^1$H-NMR (DMSO-d$_6$) δ: 0.79 (3H, t, J=7.1 Hz), 0.86 (3H, t, J=6.9 Hz), 1.19-1.45 (20H, m), 1.57 (1H, m), 1.73-1.93 (5H, m), 2.04 (1H, m), 2.11 (1H, m), 2.82 (1H, dd, J=13.7, 9.3 Hz), 2.97 (1H, dd, J=14.0, 5.2 Hz), 3.18 (1H, d, J=8.2 Hz), 3.61 (3H, s), 4.01 (2H, t, J=6.3 Hz), 4.42 (1H, m), 4.53 (1H, t, J=5.8 Hz), 4.64 (1H, t, J=5.8 Hz), 4.91 (1H, br.s), 5.42 (2H, m), 6.81 (2H, d, J=8.2 Hz), 7.10 (2H, d, J=8.2 Hz), 8.27 (1H, d, J=7.7 Hz)

ESI (LC/MS positive mode) m/z 672 (M+H); Rt 1.16 min.

No. 5550736

(E)-(2S,3S)-12,12-Difluoro-3-[(S)-2-(2'-fluoro-biphenyl-4-yl)-1-methoxycarbonyl-ethylcarbamoyl]-2-hydroxy-2-propyl-nonadec-4-enoic acid

[Chem. 220]

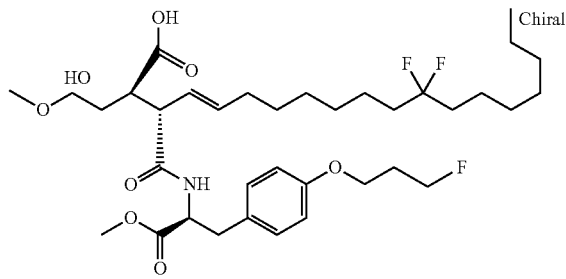

(E)-(2S,3S)-3-{(S)-2-[4-(3-Fluoro-propoxy)-phenyl]-1-methylcarbamoyl-ethylcarbamoyl}-2-hydroxy-2-(2-methoxy-ethyl)-12-oxo-nonadec-4-enoic acid was obtained by the synthesis similar to Step B, except that, in Step B-7, methyl (S)-2-amino-3-[4-(3-fluoro-propoxy)-phenyl]-propionate hydrochloride was used instead of methyl (S)-2-amino-3-(4-but-2-ynyloxy-phenyl)-propionate.

$^1$H-NMR (DMSO-d$_6$) δ: 0.86 (3H, t, J=6.9 Hz), 1.17-1.42 (20H, m), 1.65 (1H, m), 1.72-1.97 (6H, m), 2.04 (1H, m), 2.11 (1H, m), 2.81 (1H, dd, J=13.7, 9.3 Hz), 2.96 (1H, dd, J=13.7, 4.9 Hz), 3.19 (1H, m), 3.25 (1H, m), 3.34 (1H, m), 3.60 (3H, s), 4.01 (2H, t, J=6.3 Hz), 4.41 (1H, m), 4.52 (1H, t, J=5.8 Hz), 4.64 (1H, t, J=5.8 Hz), 4.97 (1H, br.s), 5.41 (2H, m), 6.80 (2H, d, J=8.8 Hz), 7.09 (2H, d, J=8.8 Hz), 8.31 (1H, d, J=7.7 Hz)

ESI (LC/MS positive mode) m/z 688 (M+H); Rt 0.87 min.

Synthesis of ethyl (S)-2-tert-butoxycarbonylamino-3-(4-but-2-ynyloxy-phenyl)-propionate

[Chem. 221]

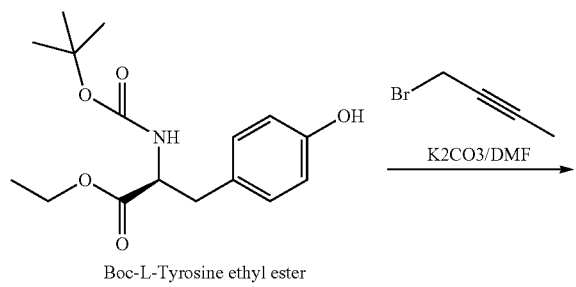

Boc-L-Tyrosine ethyl ester

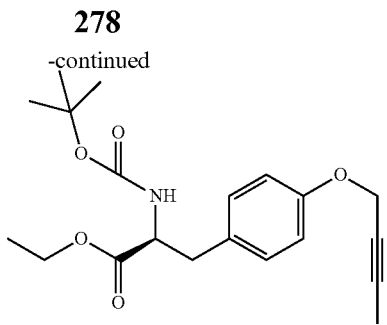

C20H27NO5 = 361.44

In dehydrated DMF (5.0 mL) was dissolved 1.35 g (4.23 mmol) of Boc-L-tyrosine ethyl ester (AK Scientific, Inc catalogue No 71054), and anhydrous potassium carbonate (0.7 g, 5.08 mmol) and 1-bromo-2-butyne (0.619 g, 4.65 mmol) were added at room temperature. The mixture was stirred under argon atmosphere for 21 hours. Subsequently, a saturated aqueous solution of ammonium chloride was added to the reaction solution until generation of carbon dioxide gas stopped. This reaction solution was extracted with ethyl acetate, and washed with water and a saturated brine in this order. The extracted organic layer was dried over anhydrous sodium sulfate. The solvent was then distilled off under reduced pressure. The obtained oily residue was purified by silica gel chromatography (20 g cartridge was used) using 10% ethyl acetate/n-hexane as an elution solvent to obtain 1.47 g (92% yield) of the title compound as clear and colorless oil.

ESI (LC/MS positive mode) m/z 362 (M+H); Rt 0.90 min.

Synthesis of (S)-2-tert-butoxycarbonylamino-3-(4-but-2-ynyloxy-phenyl)-propionic acid

[Chem. 222]

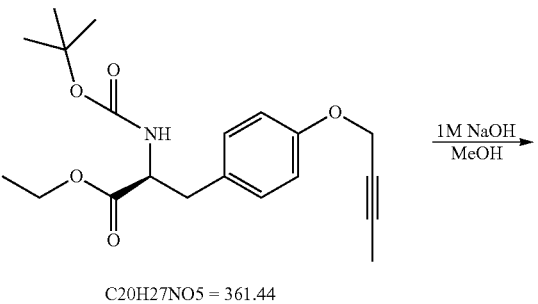

C20H27NO5 = 361.44

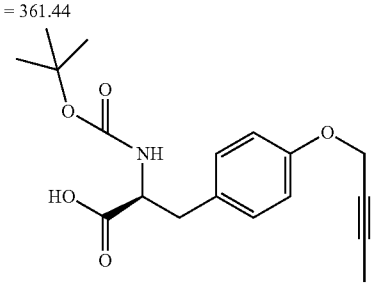

C18H23NO5 = 333.38

Ethyl (S)-2-tert-butoxycarbonylamino-3-(4-but-2-ynyloxy-phenyl)-propionate (1.407 g, 3.89 mmol) was dissolved in methanol (20 mL), and an aqueous solution (4.0 mL) of 1

M sodium hydroxide was added. The mixture was stirred at room temperature for 2 hours. Although remaining starting materials were found in small amounts by TLC, the progress of the reaction was stopped by adding 1 M hydrochloric acid until neutral pH was reached. The solvent was then concentrated under reduced pressure and the residue was extracted with ethyl acetate.

The extract was washed with a saturated brine, and then dried over anhydrous sodium sulfate. The solvent was distilled off under reduced pressure. The crude product was purified by silica gel chromatography (the purification was performed using a 5 g silica gel cartridge and an elution solvent while generating an elution solvent concentration gradient by using 20% ethyl acetate/n-hexane first, 40% ethyl acetate/n-hexane next, and 100% ethyl acetate last) to obtain the title compound (1.139 g, 88% yield).

ESI (LC/MS positive mode) m/z 334 (M+H); Rt 0.73 min.
ESI (LC/MS negative mode) m/z 332 (M−H); Rt 0.73 min.

Synthesis of methyl [(S)-2-tert-butoxycarbonylamino-3-(4-but-2-ynyloxy-phenyl)-propionylamino]-acetate

[Chem. 223]

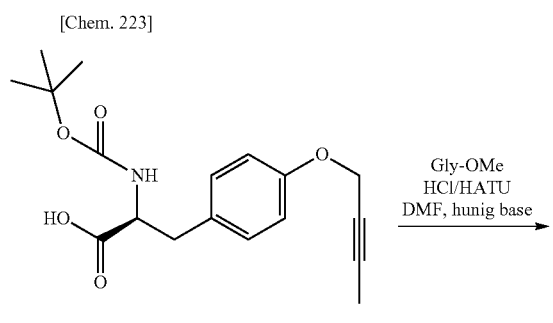

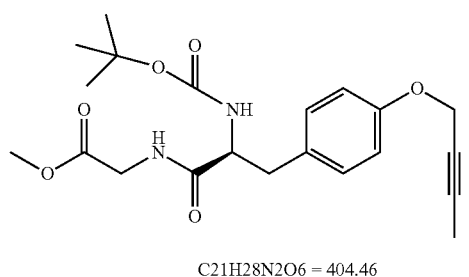

(S)-2-tert-Butoxycarbonylamino-3-(4-but-2-ynyloxy-phenyl)-propionic acid (169 mg, 0.507 mmol) was dissolved in dehydrated DMF (2.0 mL), and a commercially available glycine methyl ester (76 mg, 0.608 mmol), HATU (231.2 mg, 0.608 mmol), and N,N-diisopropylethylamine (177 µL, 1.014 mmol) were added in this order. The mixture was stirred at room temperature for 30 minutes. After completing the reaction, ethyl acetate was added and the mixture was extracted. The organic layer was washed with 1 M hydrochloric acid and a saturated brine in this order, and dried over anhydrous sodium sulfate. The solvent was distilled off under reduced pressure.

The crude product was purified by silica gel chromatography (using 2 g silica gel cartridge and an elution solvent of 40% ethyl acetate/n-hexane) to obtain the title compound as white solid (141 mg, 69% yield).

ESI (LC/MS positive mode) m/z 405 (M+H); Rt 0.74 min.

Synthesis of methyl [(S)-2-amino-3-(4-but-2-ynyloxy-phenyl)-propionylamino]-acetate hydrochloride

[Chem. 224]

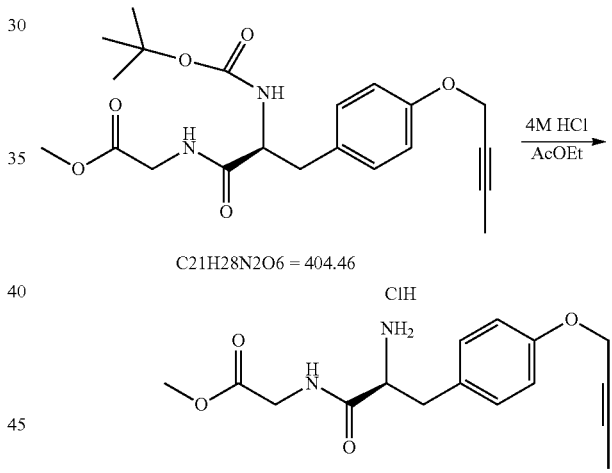

Methyl [(S)-2-tert-butoxycarbonylamino-3-(4-but-2-ynyloxy-phenyl)-propionylamino]-acetate (141 mg, 0.349 mmol) was dissolved in ethyl acetate (2.0 mL), and 4 M hydrogen chloride/ethyl acetate (0.2 mL) was added. The mixture was stirred at room temperature for 18 hours.

The reaction solution was diluted in ethyl acetate and then extracted. The organic layer was washed with 1 M hydrochloric acid and a saturated brine in this order, and dried over anhydrous sodium sulfate. The solvent was distilled off under reduced pressure.

The obtained white waxy product (109 mg, 91% yield) was used in the reaction of the next step without purification.

ESI (LC/MS positive mode) m/z 305 (M+H); Rt 0.74 min.

Synthesis of tert-butyl (E)-(2S,3S)-2-[2-(tert-butyl-dimethyl-silanyloxy)-ethyl]-3-[(S)-2-(4-but-2-yny-loxy-phenyl)-

1-(methoxycarbonylmethyl-carbamoyl)-ethylcar-bamoyl]-11-(2-heptyl-[1,3]dioxolan-2-yl)-2-hy-droxy-undec-4-enoate

[Chem. 225]

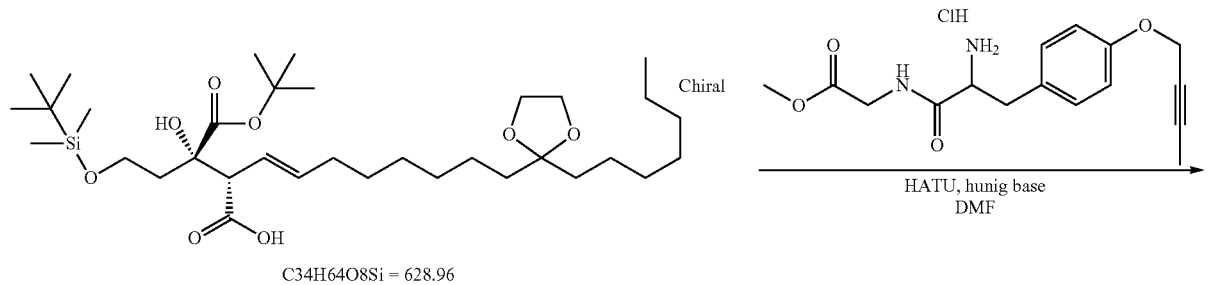

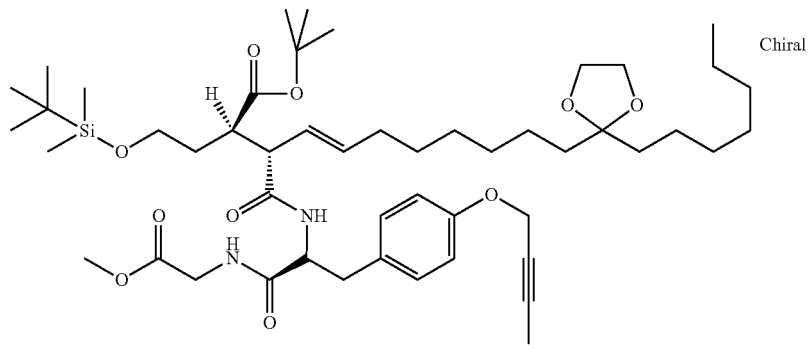

1-tert-Butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (180.3 mg, 0.287 mmol) and methyl [(S)-2-amino-3-(4-but-2-ynyloxy-phenyl)-propionylamino]-acetate hydrochloride (109 mg, 0.319 mmol) were dissolved in dehydrated DMF (2 mL), and 1-[bis(dimethylamino)methyliumyl]-1H-1,2,3-triazolo[4,5-B]pyridine-3-oxide hexafluorophosphate (120.0 mg, 0.3157 mmol) and N,N-diisopropylethylamine (177 µL, 1.014 mmol) were added in this order. The mixture was stirred at room temperature for 4 hours. After completing the reaction, ethyl acetate was added and the mixture was extracted. The organic layer was washed with an aqueous solution of 0.5 M $KHSO_4$ and a saturated brine in this order, and dried over anhydrous sodium sulfate. The solvent was distilled off under reduced pressure.

The crude product was purified by silica gel chromatography (using 2 g silica gel cartridge and performing elution with an elution solvent while generating a concentration gradient by using 20% ethyl acetate/n-hexane first and 40% ethyl acetate/n-hexane next) to obtain the title compound (171 mg, 61% yield) as an oily product.

ESI (LC/MS positive mode) m/z 916 (M+H); Rt 3.15 min.

Synthesis of tert-butyl (E)-(2S,3S)-3-[(S)-2-(4-but-2-ynyloxy-phenyl)-1-(methoxycarbonylmethyl-carbamoyl)-ethylcarbamoyl]-2-hydroxy-2-(2-hydroxyethyl)-12-oxo-nonadec-4-enoate

[Chem. 226]

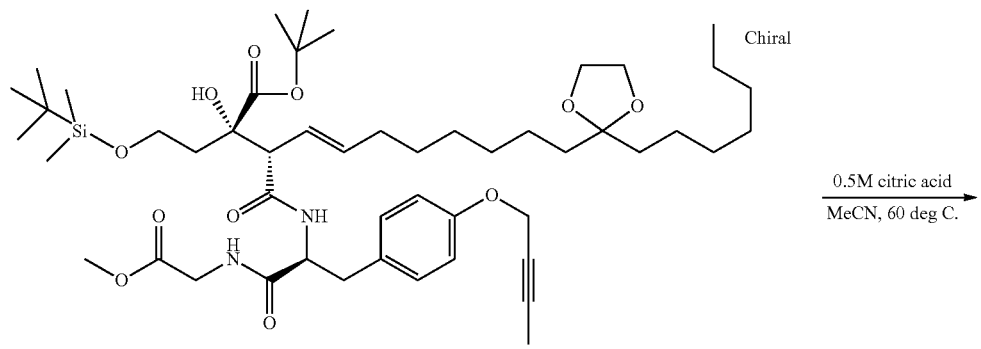

tert-Butyl (E)-(2S,3S)-2-[2-(tert-butyl-dimethyl-silanyloxy)-ethyl]-3-[(S)-2-(4-but-2-ynyloxy-phenyl)-1-(methoxycarbonylmethyl-carbamoyl)-ethylcarbamoyl]-11-(2-heptyl-[1,3]dioxolan-2-yl)-2-hydroxy-undec-4-enoate (167.6 mg, 0.183 mmol) was dissolved in acetonitrile (2.0 mL), and an aqueous solution (0.8 mL) of 0.5 M citric acid was added. The mixture was warmed to 60° C. and stirred for 2 hours. After completing the reaction, the mixture was extracted with 20% ethyl acetate/n-hexane solution/brine. The organic layer was washed with a saturated brine in this order, and dried over anhydrous sodium sulfate. The solvent was distilled off under reduced pressure.

The crude product was purified by silica gel chromatography (using 5 g silica gel cartridge and performing elution with an elution solvent of 30% acetone/n-hexane) to obtain the title compound (119 mg, 86% yield) as an oily product.

ESI (LC/MS positive mode) m/z 758 (M+H); Rt 0.81 min.

Synthesis of 1-tert-butyl (S)-2-{(E)-(S)-1-[(S)-2-(4-but-2-ynyloxy-phenyl)-1-(methoxycarbonylmethyl-carbamoyl)-ethylcarbamoyl]-10-oxo-heptadec-2-enyl}-2-hydroxy-succinate

[Chem. 227]

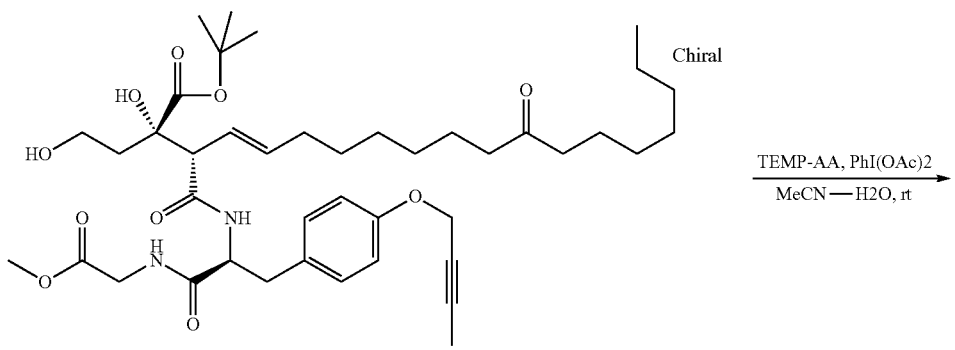

-continued

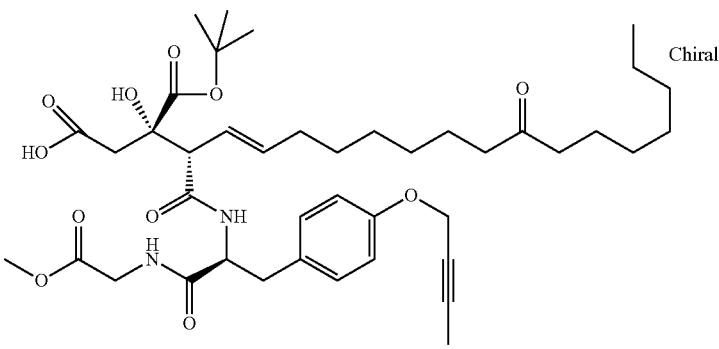

tert-Butyl (E)-(2S,3S)-3-[(S)-2-(4-but-2-ynyloxy-phenyl)-1-(methoxycarbonylmethyl-carbamoyl)-ethylcarbamoyl]-2-hydroxy-2-(2-hydroxy-ethyl)-12-oxo-nonadec-4-enoate (107.6 mg, 0.142 mmol) was dissolved in a mixed solvent of acetonitrile-water (1 mL-0.2 mL), and TEMPO-AA (6.1 mg, 0.0284 mmol) and diacetoxyiodobenzene (96.1 mg, 0.298 mmol) were added. The mixture was stirred at room temperature for 4.5 hours. After completing the reaction, the reaction solution was concentrated under reduced pressure. The crude product was purified by silica gel chromatography (using 5 g silica gel cartridge and performing elution with an elution solvent of 2% methanol/methylene chloride) to obtain the title compound (99.5 mg, 91% yield) as an oily product.

ESI (LC/MS positive mode) m/z 772 (M+H); Rt 0.79 min.
ESI (LC/MS negative mode) m/z 770 (M−H); Rt 0.79 min.

Synthesis of No. 5509910

(E)-(2S,3S)-12,12-difluoro-3-{(S)-2-[4-(3-fluoropropoxy)-phenyl]-1-methoxy carbonyl-ethylcarbamoyl}-2-hydroxy-2-propyl-nonadec-4-enoic acid

[Chem. 228]

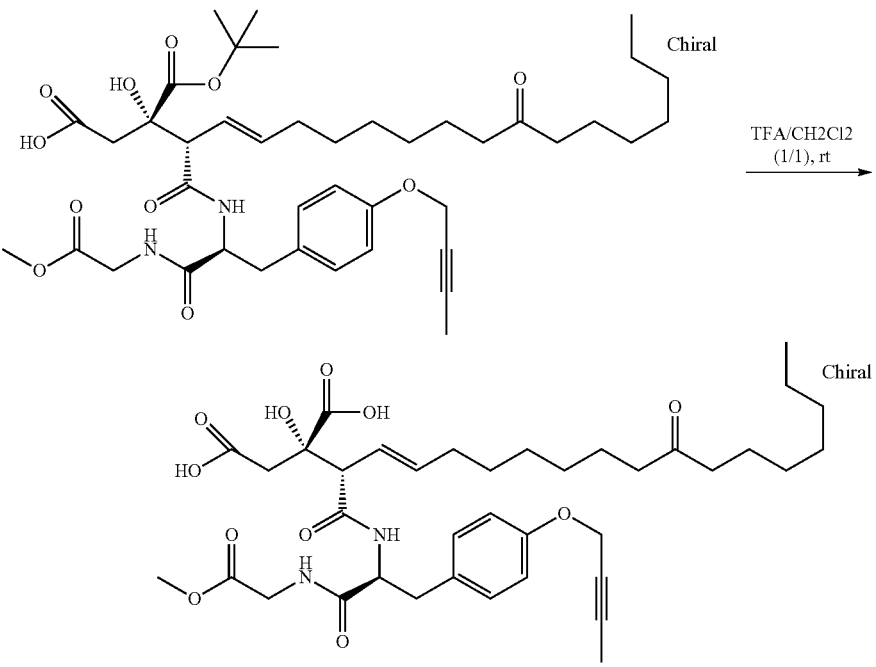

1-tert-Butyl (S)-2-{(E)-(S)-1-[(S)-2-(4-but-2-ynyloxyphenyl)-1-(methoxycarbonylmethyl-carbamoyl)-ethylcarbamoyl]-10-oxo-heptadec-2-enyl}-2-hydroxy-succinate (99.5 mg, 0.116 mmol) was dissolved in methylene chloride (1.0 mL), and trifluoroacetic acid (1.0 mL) was added at room temperature. The mixture was stirred for 2 hours. After completing the reaction, the solvent was distilled off under reduced pressure.

The crude product was purified by diol column chromatography (using 2 g diol column and performing elution with an elution solvent of 40% acetone/n-hexane) to obtain the title compound (63.8 mg, 77% yield) as an oily product.

¹H-NMR (CDCl₃) δ: 0.87 (3H, t, J=6.6 Hz), 1.18-1.36 (14H, m), 1.54 (4H, m), 1.85 (3H, d, J=2.2 Hz), 1.99 (2H, m), 2.39 (4H, m), 2.60 (1H, d, J=16.5 Hz), 1.96 (1H, d, J=17.0 Hz), 3.07 (1H, dd, J=14.3, 6.6 Hz), 3.26 (1H, d, J=9.3 Hz), 3.72 (3H, s), 3.98 (2H, m) 4.58 (2H, s), 4.69 (1H, m), 5.49 (1H, dd, J=14.6, 9.6 Hz), 5.64 (1H, m), 6.84 (2H, d, J=7.1 Hz), 6.96 (1H, br.s), 7.09 (2H, d, J=7.7 Hz), 7.31 (1H, br.s)

ESI (LC/MS positive mode) m/z 716 (M+H); Rt 0.69 min.

Synthesis of No. 5510284

(E)-(2S,3S)-12,12-Difluoro-3-{(S)-2-[4-(3-fluoropropoxy)-phenyl]-1-methoxy carbonyl-ethylcarbamoyl}-2-hydroxy-2-(2-methoxy-ethyl)-nonadec-4-enoic acid

[Chem. 229]

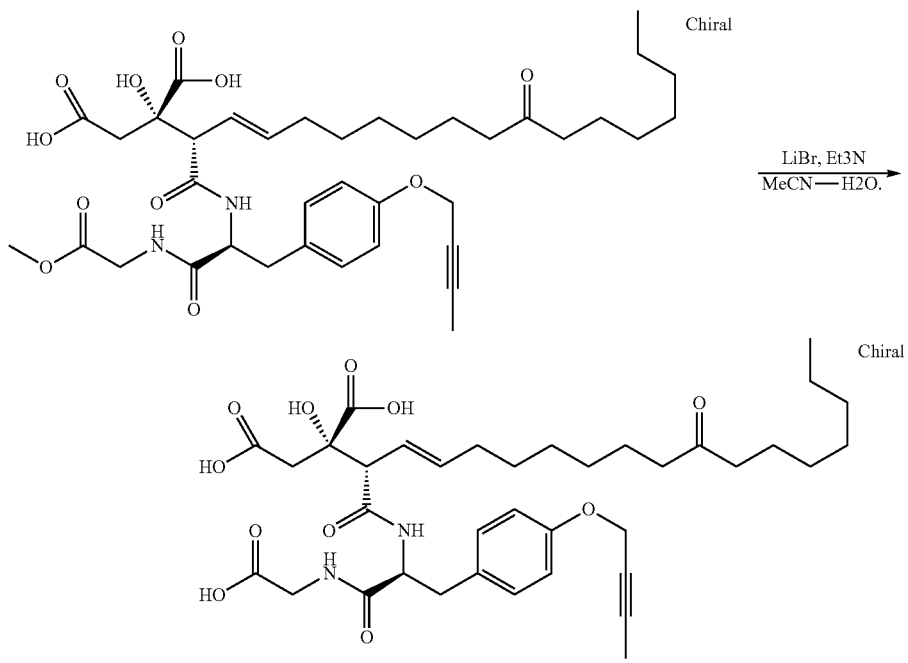

(E)-(2S,3S)-12,12-Difluoro-3-{(S)-2-[4-(3-fluoropoxy)-phenyl]-1-methoxycarbonyl-ethylcarbamoyl}-2-hydroxy-2-propyl-nonadec-4-enoic acid (10.63 mg, 0.0149 mmol) was dissolved in acetonitrile (1.0 mL), and water (1.0 mL) was added. Then, lithium bromide (25 mg, 0.298 mmol) and triethylamine (12.5 μL, 0.089 mmol) were added and the mixture was reacted at room temperature. The reaction was completed 2 hours later. The reaction mixture was extracted with ethyl acetate, washed with dilute hydrochloric acid and a saturated brine in this order, and dried over anhydrous sodium sulfate. The solvent was then distilled off under reduced pressure.

The crude product was purified by diol column chromatography (using 2 g diol column and performing elution with an elution solvent of 60% acetone/n-hexane) to obtain the title compound (2.0 mg, 19% yield) as an oily product.

¹H-NMR (DMSO-d₆) δ: 0.85 (3H, t, J=6.9 Hz), 1.15-1.28 (15H, m), 1.44 (4H, m), 1.82 (3H, t, J=2.2 Hz), 1.86 (2H, m), 2.37 (4H, t, J=7.4 Hz), 2.72 (2H, m), 2.98 (1H, dd, J=13.7, 3.8 Hz), 3.17 (1H, m), 3.80 (2H, m) 4.45 (1H, td, J=9.1, 3.8 Hz), 4.64 (2H, d, J=2.2 Hz), 5.26 (1H, br.s), 5.37 (2H, m), 6.79 (2H, d, J=8.8 Hz), 7.14 (2H, d, J=8.8 Hz), 8.21 (1H, d, J=8.2 Hz), 8.26 (1H, t, J=5.8 Hz)

ESI (LC/MS positive mode) m/z 702 (M+H); Rt 0.65 min.

ESI (LC/MS negative mode) m/z 700 (M–H); Rt 0.65 min.

tert-Butyl 2-oxo-pentanoate

[Chem. 230]

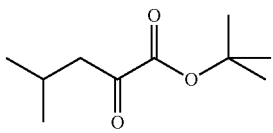

The title compound was obtained by the synthesis similar to that of tert-butyl 4-methoxy-2-oxo-butyrate, except that 1-iodopropane was used instead of 2-bromomethyl methyl ether.

¹H-NMR (CDCl₃) δ: 0.96 (3H, t, J=7.5 Hz), 1.55 (9H, s), 1.65 (2H, q, J=7.4 Hz), 2.75 (2H, t, J=7.3 Hz).

tert-Butyl 4-methyl-2-oxo-pentanoate

[Chem. 231]

The title compound was obtained by the synthesis similar to that of tert-butyl 4-methoxy-2-oxo-butyrate, except that 1-iodo-2-methylpropane was used instead of 2-bromomethyl methyl ether.

¹H-NMR (CDCl₃) δ: 0.95 (3H, s), 0.97 (3H, s), 1.54 (9H, s), 2.12-2.22 (1H, m), 2.65 (2H, d, J=6.6 Hz).

tert-Butyl 4,4-difluoro-2-oxo-butyrate

[Chem. 232]

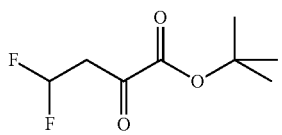

The title compound was obtained by the synthesis similar to that of tert-butyl 4-methoxy-2-oxo-butyrate, except that 1,1-difluoro-2-iodoethane was used instead of 2-bromomethyl methyl ether.

¹H-NMR (CDCl₃) δ: 1.55 (7H, s), 3.39 (2H, td, J=15.0, 4.9 Hz), 6.26 (1H, t, J=55.6 Hz).

tert-Butyl 5-methoxy-2-oxo-pentanoate

[Chem. 233]

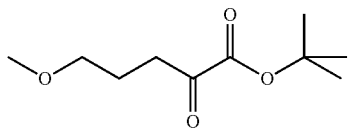

The title compound was obtained by the synthesis similar to that of tert-butyl 4-methoxy-2-oxo-butyrate, except that 1-bromo-3-methoxypropane was used instead of 2-bromomethyl methyl ether.

¹H-NMR (CDCl₃) δ: 1.54 (9H, s), 1.91 (2H, dt, J=14.8, 5.1 Hz), 2.85 (2H, t, J=7.1 Hz), 3.30 (3H, s), 3.40 (2H, t, J=6.0 Hz).

tert-Butyl 3-methoxy-2-oxo-propionate

[Chem. 234]

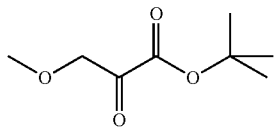

The title compound was obtained by the synthesis similar to that of tert-butyl 4-methoxy-2-oxo-butyrate, except that chloromethyl methyl ether was used instead of 2-bromomethyl methyl ether.

¹H-NMR (CDCl₃) δ: 1.54 (9H, s), 3.45 (3H, s), 4.51 (2H, s).

5-Methyl 1-tert-butyl 2-oxo-pentanedioate

[Chem. 235]

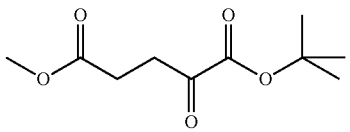

The title compound was obtained by the synthesis similar to that of tert-butyl 4-methoxy-2-oxo-butyrate, except that methyl 3-bromo-propionate was used instead of 2-bromomethyl methyl ether.

¹H-NMR (CDCl₃) δ: 1.55 (9H, s), 2.65 (2H, t, J=6.8 Hz), 3.12 (2H, t, J=7.1 Hz), 3.69 (3H, s).

6-Methyl 1-tert-butyl 2-oxo-hexanedioate

[Chem. 236]

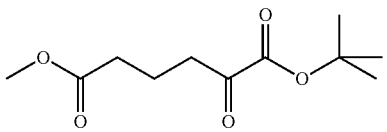

The title compound was obtained by the synthesis similar to that of tert-butyl 4-methoxy-2-oxo-butyrate, except that methyl 4-bromo-butyrate was used instead of 2-bromomethyl methyl ether.

¹H-NMR (CDCl₃) δ: 1.54 (9H, s), 1.91-1.98 (2H, m), 2.38 (2H, t, J=7.1 Hz), 2.86 (2H, td, J=7.1, 0.9 Hz), 3.68 (3H, s).

No. 5519556 (E)-(2S,3S)-3-[(S)-2-(4-Butoxy-phenyl)-1-methylcarbamoyl-ethylcarbamoyl]-2-hydroxy-2-(2-methoxy-ethyl)-12-oxo-nonadec-4-enoic acid was produced according to the following synthetic scheme.

[Chem. 237]

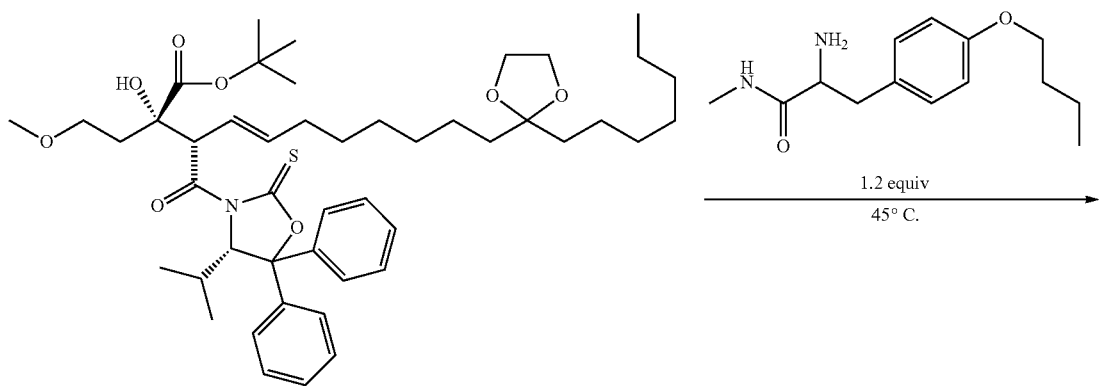

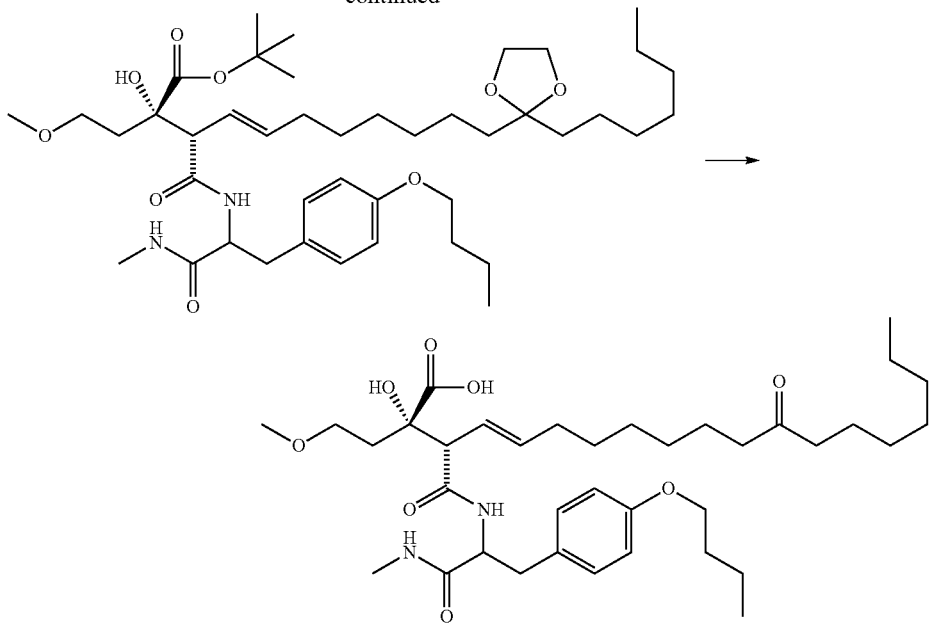

No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate (62 mg, 0.0824 mmol) and (S)-2-amino-3-(4-butoxy-phenyl)-N-methyl-propionamide (23 mg, 0.0989 mmol) were dissolved in dichloromethane. The solvent was distilled off under reduced pressure. The resulting residue was reacted at 45° C. for 4 days. After confirming the consumption of the starting materials by LCMS, the reaction mixture was purified with SP1 to obtain No. 6801292, tert-butyl (E)-(2S,3S)-3-[(S)-2-(4-butoxy-phenyl)-1-methylcarbamoyl-ethylcarbamoyl]-11-(2-hept yl-[1,3]dioxolan-2-yl)-2-hydroxy-2-(2-methoxy-ethyl)-undec-4-enoate (33 mg, 54% yield, ESI (LC/MS positive mode) m/z 762 (M+H); Rt 3.02 min.). To the obtained No. 6801292 (40 mg, 0.0526 mmol) were added dichloromethane (3.0 mL) and trifluoroacetic acid (1.0 mL), and the mixture was stirred at room temperature. After confirming the consumption of the starting materials by LCMS, the solvent was distilled off under reduced pressure. The residue was purified by preparative HPLC. The purified fraction was freeze-dried to obtain the title compound (27 mg, 78% yield, white powder).

$^1$H-NMR (CD$_3$OD) δ: 0.90 (3H, t, J=7.1 Hz), 0.98 (3H, t, J=7.3 Hz), 1.20-1.40 (14H, m), 1.45-1.57 (6H, m), 1.60-1.66 (1H, m), 1.70-1.77 (2H, m), 1.93-2.09 (3H, m), 2.43 (4H, t, J=7.3 Hz), 2.70 (3H, d, J=4.4 Hz), 2.80 (1H, dd, J=14.1, 9.3 Hz), 3.04 (1H, dd, J=14.1, 5.7 Hz), 3.19 (1H, t, J=4.2 Hz), 3.24 (3H, s), 3.41 (2H, q, J=6.5 Hz), 3.93 (2H, t, J=6.4 Hz), 4.51 (1H, dd, J=9.0, 5.5 Hz), 5.51-5.55 (2H, m), 6.79 (2H, d, J=8.4 Hz), 7.10 (2H, d, J=8.4 Hz), 7.83 (1H, d, J=4.9 Hz), 8.04 (OH, d, J=8.4 Hz).

ESI (LC/MS positive mode) m/z 661 (M+H); Rt 2.73 min.

No. 5535539 (E)-(2S,3S)-3-[(S)-2-(2'-fluoro-biphenyl-4-yl)-1-methoxycarbonyl-ethylcarbamoyl]-2-hydroxy-2-(2-methoxy-ethyl)-12-oxo-nonadec-4-enoic acid. The compound was produced according to the following synthetic scheme.

[Chem. 238]

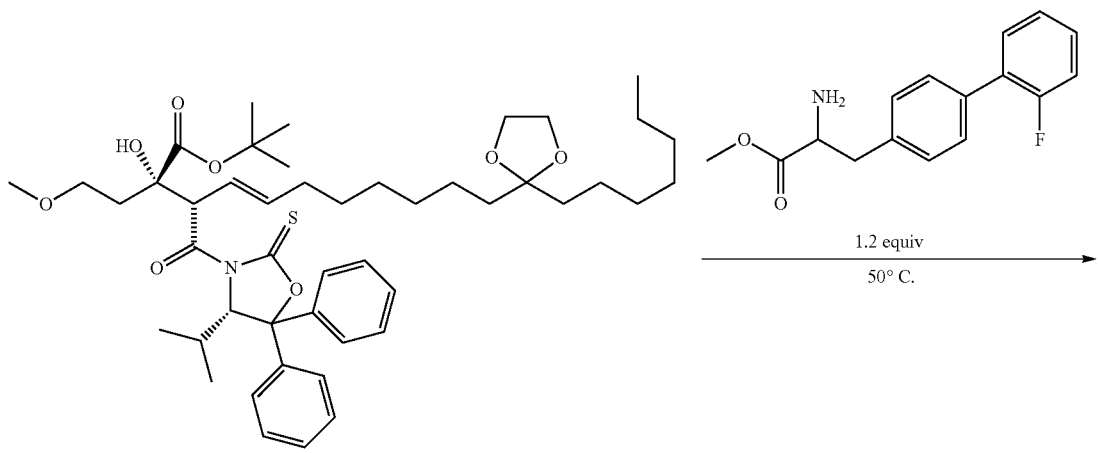

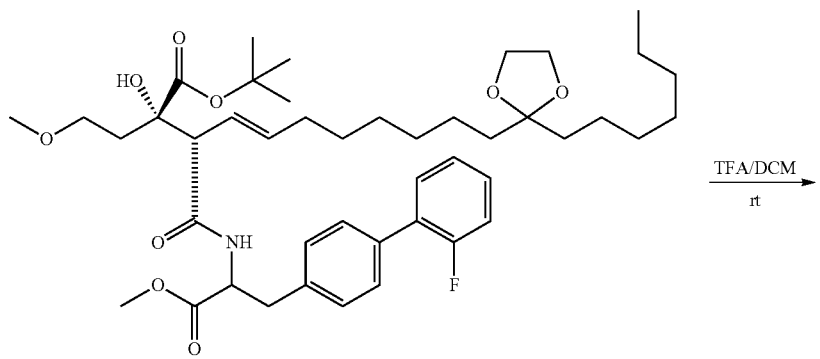

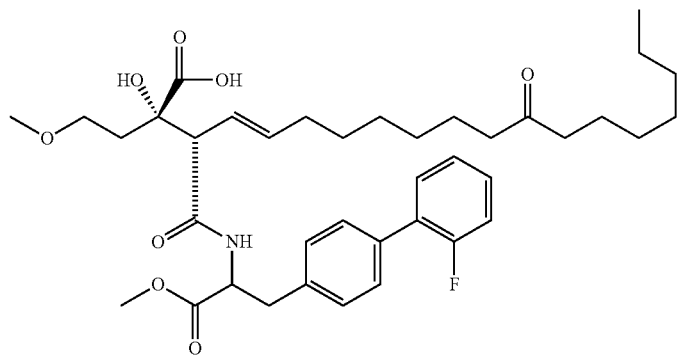

An intermediate, tert-butyl (E)-(2S,3S)-3-[(S)-2-(2'-fluoro-biphenyl-4-yl)-1-methoxycarbonyl-ethylcarbamoyl]-11-(2-heptyl-[1,3]dioxolan-2-yl)-2-hydroxy-2-(2-methoxy-ethyl)-undec-4-enoate (ESI (LC/MS positive mode) m/z 784 (M+H); Rt 2.30 min.) was synthesized by a method similar to that of Step A-2a, except that methyl (S)-2-amino-3-(2'-fluoro-biphenyl-4-yl)-propionate was used instead of methyl (S)-2-amino-3-(4-butoxy-phenyl)-propionate. The title compound was obtained by the synthesis under conditions similar to those in Step A-3 using the obtained compound as a starting material.

$^1$H-NMR (CD$_3$OD) δ: 0.89 (3H, t, J=7.1 Hz), 1.15-1.34 (14H, m), 1.50 (4H, dq, J=28.7, 7.2 Hz), 1.73 (1H, dt, J=13.8, 5.8 Hz), 1.93 (2H, q, J=6.8 Hz), 2.03-2.10 (1H, m), 2.36-2.43 (4H, m), 3.02 (1H, dd, J=14.1, 9.3 Hz), 3.21 (3H, s), 3.22-3.28 (2H, m), 3.39-3.43 (2H, m), 3.74 (3H, s), 4.76 (1H, dq, J=13.8, 3.7 Hz), 5.46-5.60 (2H, m), 7.14-7.25 (2H, m), 7.29 (2H, d, J=8.4 Hz), 7.31-7.37 (1H, m), 7.42-7.50 (3H, m), 8.32 (1H, d, J=7.9 Hz).

ESI (LC/MS positive mode) m/z 684 (M+H); Rt 2.95 min.

No. 5206735

[(3S,4S)-4-[(S)-2-(4-But-2-ynyloxy-phenyl)-1-methylcarbamoyl-ethylcarbamoyl]-3-hydroxy-1-methyl-2-oxo-5-(8-oxo-pentadecyl)-pyrrolidin-3-yl]-acetic acid

[Chem. 239]

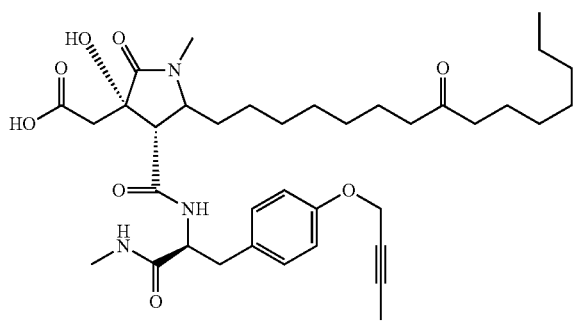

To No. 5153510, (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinic acid (20 mg, 0.0303 mmol) was added 2 M methylamine-methanol solution (2.0 mL) and the mixture was stirred at 60° C. After confirming the completion of the reaction by LCMS, the organic solvent was distilled off under reduced pressure. The resulting residue was purified by preparative HPLC and then freeze-dried to obtain the title compound (2.0 mg, 10%, white powder).

$^1$H-NMR (CD$_3$OD) δ: 0.90 (3H, t, J=7.1 Hz), 1.20-1.40 (18H, m), 1.45-1.60 (4H, m), 1.81 (3H, t, J=2.3 Hz), 2.20 (2H, dd, J=30.2, 16.5 Hz), 2.42-2.46 (4H, m), 2.67 (3H, s), 2.80 (3H, s), 2.83-2.90 (2H, m), 3.02 (1H, dd, J=13.7, 6.4 Hz), 3.61-3.64 (1H, m), 4.52 (1H, dd, J=8.9, 6.2 Hz), 4.60 (2H, q, J=2.3 Hz), 6.87 (2H, d, J=8.7 Hz), 7.17 (2H, d, J=8.2 Hz).

ESI (LC/MS positive mode) m/z 670 (M+H); Rt 2.60 min.

No. 5207921

(S)-2-{(E)-(S)-1-[(S)-2-(4-But-2-ynyloxy-phenyl)-1-methylcarbamoyl-ethylcarbamoyl]-10-oxo-heptadec-2-enyl}-2-hydroxy-succinic acid

[Chem. 240]

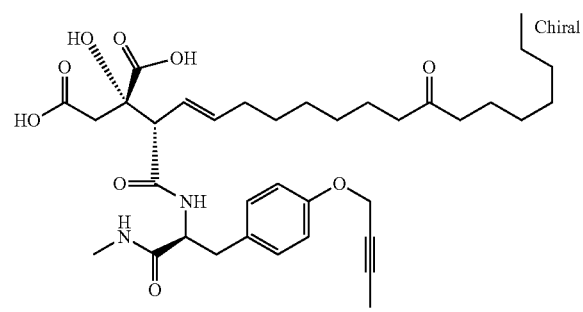

The title compound was obtained by the synthesis similar to that of No. 5206735, (3S,4S)-4-[(S)-2-(4-but-2-ynyloxy-phenyl)-1-methylcarbamoyl-ethylcarbamoyl]-3-hydroxy-1-methyl-2-oxo-5-(8-oxo-pentadecyl)-pyrrolidin-3-yl]-acetic acid.

$^1$H-NMR (CD$_3$OD) δ: 0.89 (3H, t, J=6.9 Hz), 1.20-1.35 (14H, m), 1.48-1.60 (4H, m), 1.81 (3H, t, J=2.3 Hz), 1.93-2.03 (2H, m), 2.44 (4H, t, J=7.3 Hz), 2.71 (3H, s), 2.77-2.95 (2H, m), 3.00-3.10 (3H, m), 4.52 (1H, dd, J=8.9, 5.3 Hz), 4.57-4.63 (2H, m), 5.50-5.55 (2H, m), 6.84 (2H, d, J=8.7 Hz), 7.12 (2H, d, J=8.7 Hz).

ESI (LC/MS positive mode) m/z 657 (M+H); Rt 2.66 min.

No. 5208387

(E)-(2S,3S)-3-[(S)-2-(4-But-2-ynyloxy-phenyl)-1-carboxy-ethylcarbamoyl]-2-hydroxy-2-(2-hydroxy-ethyl)-12-oxo-nonadec-4-enoic acid

[Chem. 241]

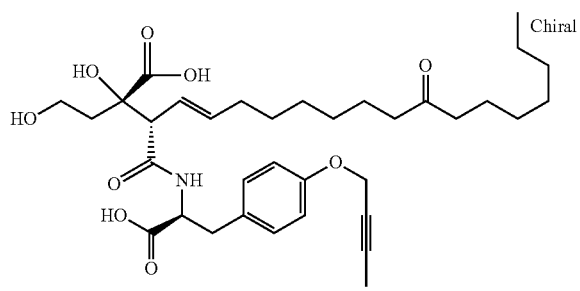

No. 5214354, (E)-(2S,3S)-2-(2-acetoxy-ethyl)-3-[(S)-2-(4-but-2-ynyloxy-phenyl)-1-methoxycarbonyl-ethylcarbamoyl]-2-hydroxy-12-oxo-nonadec-4-enoic acid (120 mg, 0.175 mmol) was dissolved in methanol (10 mL), and an aqueous solution (1 mL) of 2 M LiOH was added, and the mixture was stirred at room temperature. After confirming the consumption of the starting materials by LCMS, methanol was distilled off under reduced pressure. To the residue was added 1 M hydrochloric acid, and the mixture was extracted with ethyl acetate. The organic layer was washed with a saturated brine and then dried over anhydrous sodium sulfate. The filtrate was concentrated under reduced pressure. The resulting residue was purified by preparative HPLC and freeze-dried to obtain the title compound (20 mg, 18% yield, white powder).

$^1$H-NMR (CD$_3$OD) δ: 0.89 (3H, t, J=6.9 Hz), 1.23-1.35 (14H, m), 1.48-1.60 (4H, m), 1.81 (3H, t, J=2.3 Hz), 1.93-2.10 (4H, m), 2.43 (4H, t, J=7.3 Hz), 2.92 (1H, dd, J=14.0, 8.9 Hz), 3.10-3.25 (2H, m), 3.53-3.68 (2H, m), 4.59-4.66 (3H, m), 5.45-5.63 (2H, m), 6.84 (2H, d, J=8.7 Hz), 7.12 (2H, d, J=8.7 Hz).

ESI (LC/MS positive mode) m/z 630 (M+H); Rt 3.45 min.

No. 5208845

(S)-2-{(E)-(S)-1-[(S)-2-(4-But-2-ynyloxy-phenyl)-1-carbamoyl-ethylcarbamoyl]-10-oxo-heptadec-2-enyl}-2-hydroxy-succinic acid

[Chem. 242]

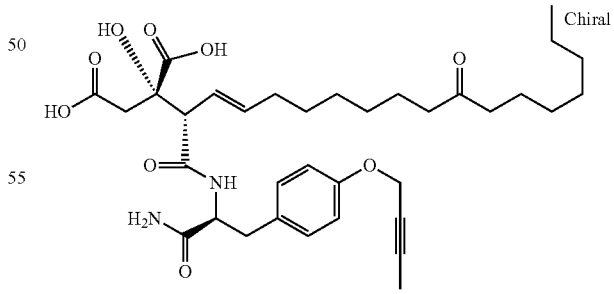

The title compound was obtained by the synthesis similar to that of No. 5206735, [(3S,4S)-4-[(S)-2-(4-but-2-ynyloxy-phenyl)-1-methylcarbamoyl-ethylcarbamoyl]-3-hydroxy-1-methyl-2-oxo-5-(8-oxo-pentadecyl)-pyrrolidin-3-yl]-acetic acid, except that a 2 M ammonia-methanol solution was used instead of the 2 M methylamine-methanol solution and a reaction temperature of 40° C. was used.

¹H-NMR (CD₃OD) δ: 0.90 (3H, t, J=6.9 Hz), 1.26-1.37 (14H, m), 1.49-1.57 (4H, m), 1.82 (3H, t, J=2.3 Hz), 1.93-2.00 (2H, m), 2.44 (4H, t, J=7.3 Hz), 2.77-2.90 (2H, m), 3.12 (2H, dd, J=14.9, 6.2 Hz), 3.21 (1H, d, J=7.3 Hz), 4.55-4.63 (3H, m), 5.49-5.54 (2H, m), 6.84 (2H, d, J=8.7 Hz), 7.15 (2H, d, J=8.7 Hz).

ESI (LC/MS positive mode) m/z 643 (M+H); Rt 1.84 min.

No. 5211162

(E)-(2S,3S)-3-[(S)-2-(4-But-2-ynyloxy-phenyl)-1-carboxy-ethylcarbamoyl]-2-cyanomethyl-2-hydroxy-12-oxo-nonadec-4-enoic acid

[Chem. 243]

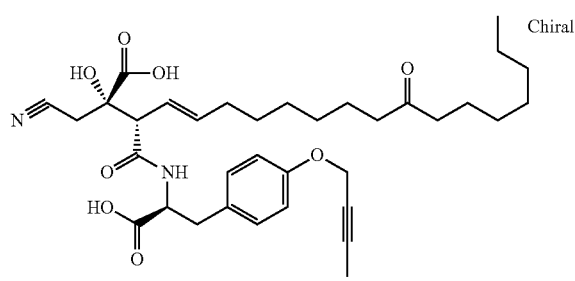

No. 5250270, (E)-(2S,3S)-3-[(S)-2-(4-but-2-ynyloxy-phenyl)-1-methoxycarbonyl-ethylcarbamoyl]-2-cyanomethyl-2-hydroxy-12-oxo-nonadec-4-enoic acid (81 mg, 0.127 mmol) was dissolved in methanol (4.0 mL), and 2 M LiOH (0.40 mL) was added. The mixture was stirred at room temperature. After confirming the consumption of the starting materials by LCMS, 1 M hydrochloric acid was added, and the mixture was extracted with ethyl acetate. The resulting organic layer was washed with a saturated brine and then dried over anhydrous sodium sulfate. The filtrate was concentrated under reduced pressure. The resulting residue was purified by preparative HPLC and freeze-dried to obtain the title compound (11 mg, 14% yield, yellow oil).

¹H-NMR (CD₃OD) δ: 0.89 (3H, t, J=6.9 Hz), 1.20-1.40 (14H, m), 1.48-1.58 (4H, m), 1.82 (3H, t, J=2.3 Hz), 1.99 (2H, q, J=6.4 Hz), 2.44 (4H, t, J=7.3 Hz), 2.61 (1H, d, J=16.5 Hz), 2.80-2.95 (2H, m), 3.19 (1H, dd, J=14.9, 6.2 Hz), 3.27 (1H, d, J=9.2 Hz), 4.57-4.68 (3H, m), 5.45-5.68 (2H, m), 6.86 (2H, d, J=8.7 Hz), 7.13 (2H, d, J=8.7 Hz).

ESI (LC/MS positive mode) m/z 625 (M+H); Rt 2.11 min.

Synthesis of No. 5214357 (Compound T)

[Chem. 244]

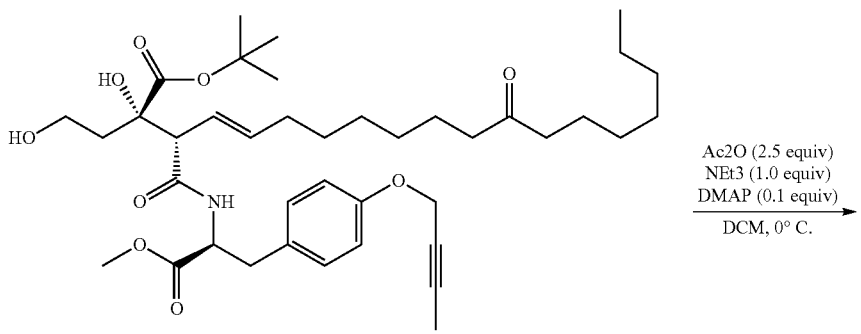

No 5217614-000
Compound D

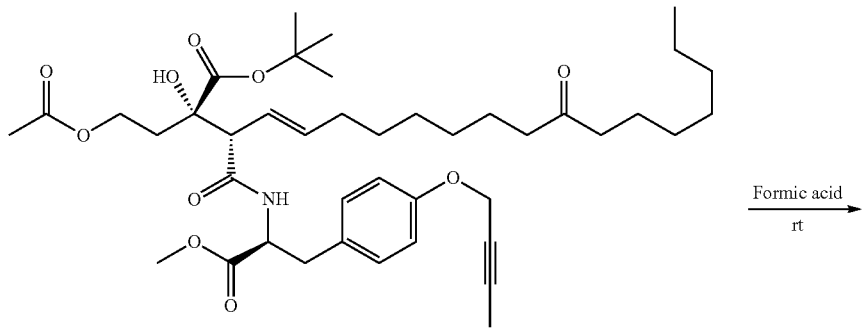

No 5318799-000
Compound R

-continued

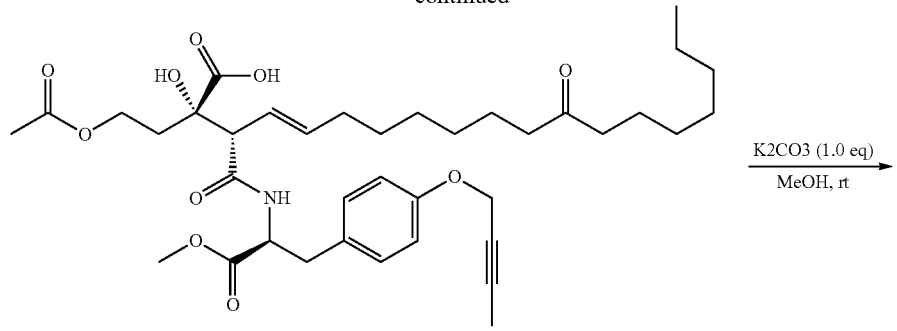

No 5214364-000
Compound S

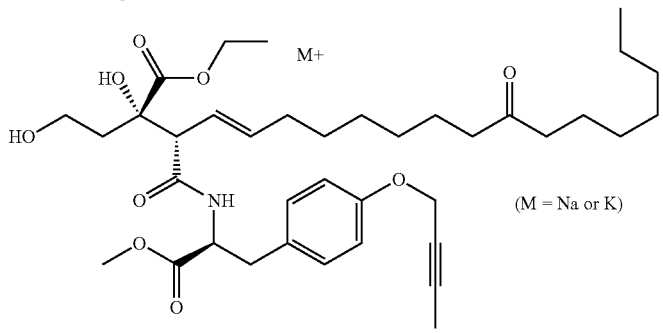

No 5214357-001
Compound T

No. 5318799 (Compound R)

tert-Butyl (E)-(2S,3S)-2-(2-acetoxy-ethyl)-3-[(S)-2-(4-but-2-ynyloxy-phenyl)-1-methoxycarbonyl-ethyl-carbamoyl]-2-hydroxy-12-oxo-nonadec-4-enoate

[Chem. 245]

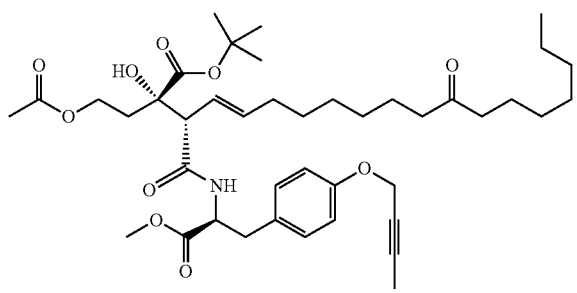

No. 5217614, tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate, Compound D (13.7 g, 19.6 mmol) was dissolved in dichloromethane (274 mL), and then acetic anhydride (4.64 mL, 49.1=mop, triethylamine (2.74 mL, 19.7 mmol), and dimethylaminopyridine (240 mg, 1.96 mmol) were added at 0° C. After stirring for 1.5 hours, the mixture was quenched with water (195 mL) and then separated. The aqueous layer was extracted with dichloromethane (195 mL). The dichloromethane layers were combined, then washed with a saturated aqueous solution (140 mL) of sodium chloride, then dried over anhydrous sodium sulfate, and filtered. The organic layer was concentrated under reduced pressure. The residue was purified on Biotage (silica gel, n-hexane/ethyl acetate) to obtain 11.0 g (14.8 mmol, yield 76%) of No. 5318799 (Compound R).

$^1$H-NMR (CD$_3$OD) δ: 0.88 (3H, t, J=7.0 Hz), 1.20-1.38 (14H, m), 1.45 (9H, s), 1.46-1.58 (4H, m), 1.68-1.78 (1H, m), 1.80 (3H, t, J=2.3 Hz), 1.92-2.08 (3H, m), 1.98 (3H, s), 2.42 (4H, t, J=7.4 Hz), 2.88 (1H, dd, J=14.1, 9.4 Hz), 3.12 (1H, dd, J=14.1, 4.9 Hz), 3.19 (1H, d, J=9.2 Hz), 3.70 (3H, s), 3.92-4.12 (2H, m), 4.60 (2H, q, J=2.3 Hz), 4.64 (1H, dd, J=9.4, 4.9 Hz), 5.45-5.52 (1H, m), 5.59 (1H, dt, J=15.3, 6.4 Hz), 6.84 (2H, d, J=8.5 Hz), 7.09 (2H, d, J=8.5 Hz)

ESI (LC/MS positive mode) m/z 742 (M+H); Rt 3.33 min.

No. 5214354 (Compound S) (E)-(2S,3S)-2-(2-Acetoxy-ethyl)-3-[(S)-2-(4-but-2-ynyloxy-phenyl)-1-methoxy carbonyl-ethylcarbamoyl]-2-hydroxy-12-oxo-nonadec-4-enoic acid

[Chem. 246]

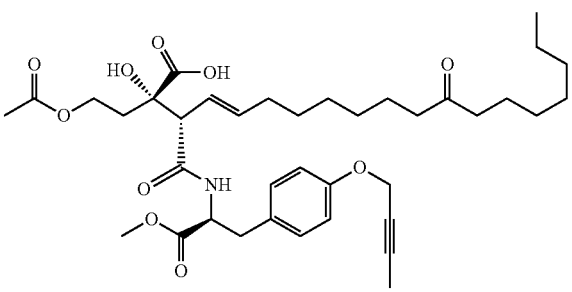

No. 5318799, tert-butyl (E)-(2S,3S)-2-(2-acetoxy-ethyl)-3-[(S)-2-(4-but-2-ynyloxy-phenyl)-1-methoxycarbonyl-ethylcarbamoyl]-2-hydroxy-12-oxo-nonadec-4-enoate (Compound R; 11.4 g, 15.4 mmol) was dissolved in formic acid (229 mL), and the solution was then stirred at room temperature for 3 hours. The reaction mixture was concentrated under reduced pressure, then dissolved in ethyl acetate (250 mL), washed twice with a 6:1 mixture (250 mL) of an aqueous solution of 1% sodium bicarbonate and a saturated aqueous solution of sodium chloride, then with a 6:1 mixture (220 mL) of an aqueous solution of 10% ammonium chloride and a saturated aqueous solution of sodium chloride, and finally with a saturated aqueous solution (100 mL) of sodium chloride, then dried over anhydrous sodium sulfate, and filtered. The organic layer was concentrated under reduced pressure. The residue was purified on Biotage (silica gel, dichloromethane/methanol) to obtain 10.5 g (15.3 mmol, yield 99%) of No. 5214354 (Compound S).

$^1$H-NMR (CD$_3$OD) δ: 0.88 (3H, t, J=7.0 Hz), 1.19-1.38 (14H, m), 1.40-1.58 (4H, m), 1.60-1.71 (1H, m), 1.76-1.84 (3H, m), 1.90-2.03 (2H, m), 1.95 (3H, s), 2.07-2.20 (1H, m), 2.42 (4H, t, J=7.2 Hz), 2.88 (1H, dd, J=14.1, 9.2 Hz), 3.12 (1H, dd, J=14.1, 4.9 Hz), 3.19 (1H, d, J=8.8 Hz), 3.70 (3H, s), 4.00-4.10 (2H, m), 4.60 (2H, brq, J=2.2 Hz), 4.65 (1H, dd, J=9.2, 4.9 Hz), 5.47 (1H, dd, J=15.3, 8.8 Hz), 5.56 (1H, dt, J=15.3, 6.5 Hz), 6.84 (2H, d, J=8.6 Hz), 7.09 (2H, d, J=8.6 Hz)

ESI (LC/MS positive mode) m/z 686 (M+H); Rt 4.68 min.

No. 5214357 (E)-(2S,3S)-3-[(S)-2-(4-But-2-ynyloxy-phenyl)-1-methoxycarbonyl-ethylcarbamoyl]-2-hydroxy-2-(2-hydroxy-ethyl)-12-oxo-nonadec-4-enoic acid was produced according to the following synthetic scheme.

To a mixture of No. 5217614, tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate (150 mg, 0.214 mmol) and dichloromethane (15 mL) were added trifluoroacetic acid anhydride (TFAA, 36 µL, 0.258 mmol), triethylamine (89 µL, 0.642 mmol), and DMAP (1.3 mg, 0.0107 mmol), and the mixture was stirred at room temperature. After being stirred for 3 hours, trifluoroacetic acid anhydride (72 µL, 0.516 mmol) was added again. After confirming the consumption of No. 5217614 tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate by LCMS, formic acid (5 mL) was added and the mixture was stirred overnight. The solvent was distilled off under reduced pressure. THF (5 mL) and a saturated aqueous solution (0.5 mL) of NaHCO$_3$ were then added and the mixture was stirred at room temperature for 10 minutes. The solvent was distilled off under reduced pressure. The residue was then purified by preparative HPLC. The purified fraction was freeze-dried to obtain the title compound (67 mg, 48% yield, yellow oil).

$^1$H-NMR (CD$_3$OD) δ: 0.85-0.95 (3H, m), 1.23-1.40 (14H, m), 1.48-1.58 (4H, m), 1.75-1.84 (4H, m), 1.96-2.04 (3H, m), 2.44 (4H, t, J=7.3 Hz), 2.92 (1H, dd, J=14.2, 8.7 Hz), 3.11 (1H, dd, J=14.2, 5.0 Hz), 3.24 (1H, d, J=8.7 Hz), 3.55-3.65 (2H, m), 3.71 (3H, s), 4.58-4.68 (3H, m), 5.45-5.63 (2H, m), 6.85 (2H, d, J=8.2 Hz), 7.10 (2H, d, J=8.7 Hz).

ESI (LC/MS positive mode) m/z 644 (M+H); Rt 2.19 min.

[Chem. 247]

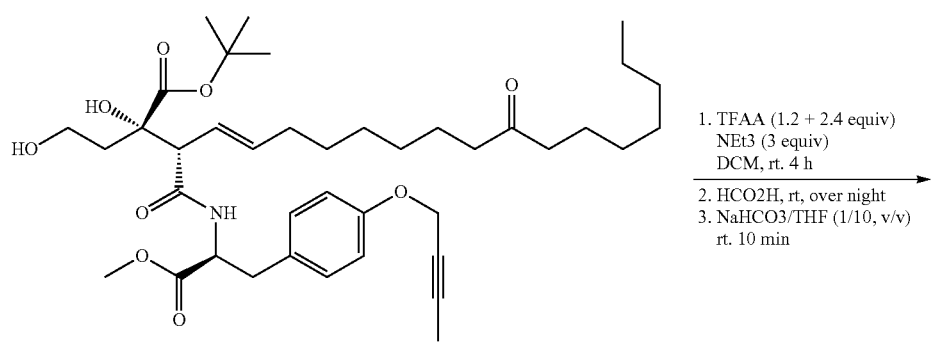

1. TFAA (1.2 + 2.4 equiv)
   NEt3 (3 equiv)
   DCM, rt. 4 h
2. HCO2H, rt, over night
3. NaHCO3/THF (1/10, v/v)
   rt. 10 min

No. 5214805

Methyl (S)-3-(4-but-2-ynyloxy-phenyl)-2-[(E)-(S)-2-((S)-3-hydroxy-2-oxo-tetrahydrofuran-3-yl)-11-oxo-octadec-3-enoylamino]-propionate

[Chem. 248]

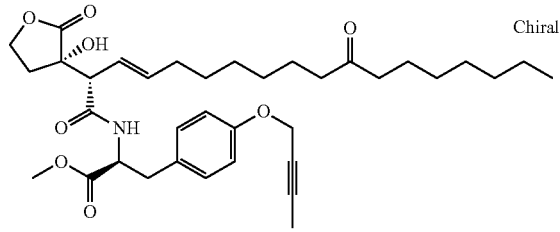

To No. 5214357, (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoic acid (20 mg, 0.0310 mmol) was added a mixture of dichloromethane/trifluoroacetic acid (9/1, v/v, 2 mL) and the mixture was stirred at room temperature for 1 hour. After confirming the consumption of the starting materials by LCMS, the organic solvent was distilled off under reduced pressure. The resulting residue was purified by preparative HPLC and then freeze-dried to obtain No. 5214805 (11 mg, 56% yield, white powder).

$^1$H-NMR (CD$_3$OD) δ: 0.89 (3H, t, J=6.9 Hz), 1.22-1.40 (14H, m), 1.50-1.60 (4H, m), 1.82 (3H, t, J=2.3 Hz), 1.97-2.07 (3H, m), 2.42-2.47 (4H, m), 2.49-2.55 (1H, m), 2.89 (1H, dd, J=14.2, 9.1 Hz), 3.12 (1H, dd, =13.7, 5.0 Hz), 3.42 (1H, d, J=8.2 Hz), 3.71 (3H, s), 4.22-4.36 (2H, m), 4.61-4.66 (3H, m), 5.38 (1H, dd, J=15.6, 8.2 Hz), 5.53-5.60 (1H, m), 6.86 (2H, d, J=8.7 Hz), 7.09 (2H, d, J=8.7 Hz), 7.86 (1H, d, 8.2 Hz).

ESI (LC/MS positive mode) m/z 626 (M+H); Rt 2.54 min.

No. 5217613

(S)-3-(4-But-2-ynyloxy-phenyl)-2-[(E)-(S)-2-((S)-3-hydroxy-2-oxo-tetrahydrofuran-3-yl)-11-oxo-octadec-3-enoylamino]-propionic acid

[Chem. 249]

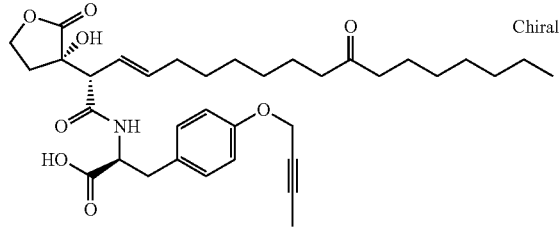

To a mixture of No. 5214357, (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoic acid (20 mg, 0.0292 mmol) and methanol (2.0 mL) was added an aqueous solution (0.2 mL) of 2 M LiOH and the mixture was stirred at room temperature. After confirming the consumption of No. 5214357, (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoic acid by LCMS, methanol was distilled off under reduced pressure. Water was then added, and the mixture was extracted with ethyl acetate. To the aqueous layer was added 1 M hydrochloric acid until pH 7 was reached. The organic layer was washed with a saturated brine and dried over anhydrous sodium sulfate. The filtrate was then concentrated under reduced pressure to obtain No. 5208387, (E)-(2S,3S)-3-[(S)-2-(4-but-2-ynyloxy-phenyl)-1-carboxy-ethylcarbamoyl]-2-hydroxy-2-(2-hydroxy-ethyl)-12-oxo-nonadec-4-enoic acid (20 mg, 99% yield, ESI (LC/MS positive mode) m/z 630 (M+H); Rt 1.62 min.). To the obtained No. 5208387, (E)-(2S,3S)-3-[(S)-2-(4-but-2-ynyloxy-phenyl)-1-carboxy-ethylcarbamoyl]-2-hydroxy-2-(2-hydroxy-ethyl)-12-oxo-nonadec-4-enoic acid (10 mg, 0.0159 mmol) was added a mixture of dichloromethane/trifluoroacetic acid (9/1, v/v, 2 mL), and the mixture was stirred at room temperature for 1 hour. After confirming the consumption of the starting materials by LCMS, the organic solvent was distilled off under reduced pressure. The resulting residue was purified by preparative HPLC and then freeze-dried to obtain No. 5217613 (9.6 mg, 99% yield, yellow oil).

$^1$H-NMR (CD$_3$OD) δ: 0.89 (3H, t, J=6.9 Hz), 1.23-1.40 (14H, m), 1.49-1.58 (4H, m), 1.82 (3H, t, J=2.3 Hz), 1.97-2.08 (3H, m), 2.40-2.49 (5H, m), 2.90 (1H, dd, J=14.2, 8.7 Hz), 3.15 (1H, dd, J=14.0, 4.8 Hz), 3.42 (1H, d, J=8.7 Hz), 4.23 (1H, td, J=8.7, 4.6 Hz), 4.32 (1H, q, J=7.9 Hz), 4.58-4.62 (3H, m), 5.36 (1H, dd, J=15.3, 8.9 Hz), 5.60 (1H, dt, J=15.2, 6.6 Hz), 6.85 (2H, d, J=8.7 Hz), 7.11 (2H, d, J=8.2 Hz).

ESI (LC/MS positive mode) m/z 612 (M+H); Rt 2.24 min.

No. 5217615

Methyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate

[Chem. 250]

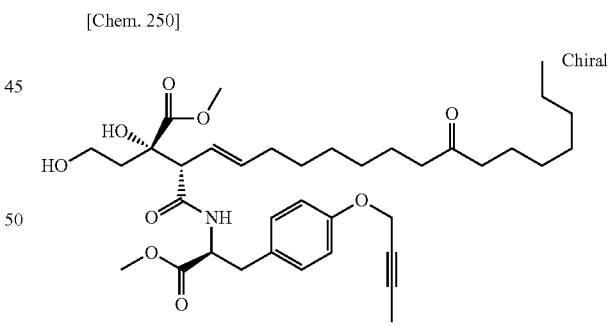

To a mixture of No. 5217614, tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate (150 mg, 0.214 mmol) and dichloromethane (15 mL) were added trifluoroacetic acid anhydride (36 μL, 0.258 mmol), triethylamine (89 μL, 0.642 mmol), and DMAP (1.3 mg, 0.0107 mmol), and the mixture was stirred at room temperature. After being stirred for 3 hours, trifluoroacetic acid anhydride (72 μL, 0.516 mmol) was added again. After confirming the consumption of No. 5217614 by LCMS, formic acid (5.0 mL) was added and the mixture was stirred overnight. The solvent was distilled off under reduced pressure to obtain (E)-(2S,3S)-3-[(S)-2-(4-but-2-ynyloxy-phenyl)-1-methoxycarbonyl-ethylcarbamoyl]-2-hydroxy-12-oxo-2-[2-(2,2,2-trifluoro-acetoxy)-ethyl]-nonadec-4-enoic acid (ESI (LC/MS positive mode) m/z 740 (M+H); Rt 2.64 min.). To the obtained (E)-(2S,3S)-3-[(S)-2-(4-but-2-ynyloxy-phenyl)-1-methoxycarbonyl-ethylcarbamoyl]-2-hydroxy-12-oxo-2-[2-(2,2,2-trifluoro-acetoxy)-ethyl]-nonadec-4-enoic acid (16 mg, 0.0216 mmol) were added toluene (3.0 mL), methanol (1.0 mL), and trimethylsilyldiazomethane (0.6 M in n-hexane, 54 µL, 0.0324 mmol), and the mixture was stirred at room temperature. After being stirred for 1.5 hours, trimethylsilyldiazomethane (0.6 M in n-hexane, 54 µL, 0.0324 mmol) was added. After stirring for 1 hour, the organic solvent was distilled off under reduced pressure. The resulting residue was purified by preparative HPLC and then freeze-dried to obtain the title compound (17 mg, 99% yield, white solid).

$^1$H-NMR (CD$_3$OD) δ: 0.89 (3H, t, J=6.9 Hz), 1.25-1.40 (14H, m), 1.48-1.58 (4H, m), 1.72 (1H, dt, J=13.7, 5.5 Hz), 1.82 (3H, t, J=2.3 Hz), 1.93-2.10 (3H, m), 2.44 (4H, t, J=7.3 Hz), 2.90 (1H, dd, J=14.2, 9.1 Hz), 3.11 (1H, dd, J=14.2, 5.0 Hz), 3.23 (1H, d, J=8.7 Hz), 3.58 (2H, t, J=6.4 Hz), 3.68 (3H, s), 3.71 (3H, s), 4.57-4.68 (3H, m), 5.51 (2H, tt, J=20.6, 6.8 Hz), 6.84 (2H, d, J=8.7 Hz), 7.08 (2H, d, J=8.7 Hz), 8.27 (1H, d, J=7.3 Hz).

ESI (LC/MS positive mode) m/z 658 (M+H); Rt 2.41 min.

No. 5218666 (E)-(2S,3S)-2-(2-Acetoxy-ethyl)-3-[(S)-2-(4-but-2-ynyloxy-phenyl)-1-carboxy-ethylcarbamoyl]-2-hydroxy-12-oxo-nonadec-4-enoic acid was produced according to the following synthetic scheme.

A mixture of No. 4984967, tert-butyl (E)-(2S,3S)-3-[(S)-1-tert-butoxycarbonyl-2-(4-but-2-ynyloxy-phenyl)-ethylcarbamoyl]-2-hydroxy-2-(2-hydroxy-ethyl)-12-oxo-nonadec-4-enoate (112 mg, 0.152 mmol) and dichloromethane (1.3 mL) was cooled to 4° C., and acetic anhydride (35.8 µL, 0.379 mmol), triethylamine (23.3 µL, 0.167 mmol), and DMAP (1.9 mg, 0.02 mmol) were added. After stirring for 2 hours, the consumption of the starting materials was confirmed by LCMS. The solvent was distilled off under reduced pressure. Formic acid (10 mL) was added and the mixture was stirred at room temperature for 15 hours. Formic acid was distilled off under reduced pressure. The resulting residue was purified by preparative HPLC and then freeze-dried to obtain the title compound (46 mg, 45% yield, colorless oil).

$^1$H-NMR (CD$_3$OD) δ: 0.89 (3H, t, J=5.0 Hz), 1.28 (14H, s), 1.48-1.57 (4H, m), 1.64-1.71 (1H, m), 1.81 (3H, t, J=2.3 Hz), 1.92-2.01 (5H, m), 2.11-2.18 (1H, m), 2.43 (4H, t, J=7.3 Hz), 2.90 (1H, dd, J=13.7, 9.1 Hz), 3.15-3.20 (2H, m), 4.01-4.10 (2H, m), 4.58-4.68 (3H, m), 5.52 (2H, tt, J=24.0, 8.0 Hz), 6.84 (2H, d, J=8.7 Hz), 7.12 (2H, d, J=8.7 Hz).

ESI (LC/MS positive mode) m/z 672 (M+H); Rt 2.10 min.

No. 5233427 (E)-(2S,3S)-3-[(S)-2-(4-But-2-ynyloxy-phenyl)-1-methoxycarbonyl-ethylcarbamoyl]-2-hydroxy-2-(2-methoxy-ethyl)-12-oxo-nonadec-4-enoic acid was produced according to the following synthetic scheme.

[Chem. 251]

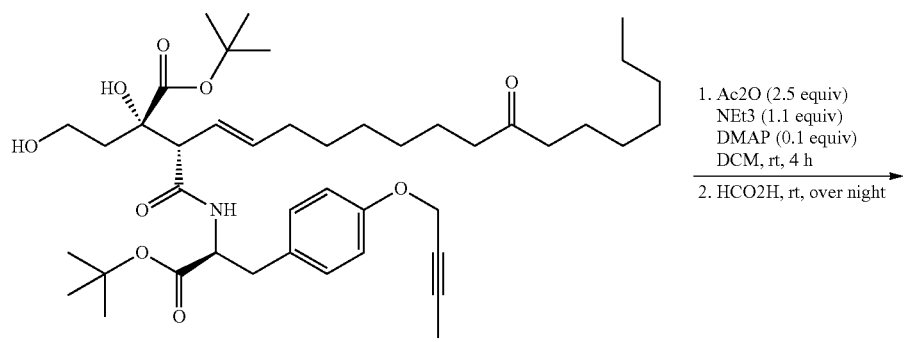

No 4984967

1. Ac2O (2.5 equiv)
   NEt3 (1.1 equiv)
   DMAP (0.1 equiv)
   DCM, rt, 4 h
2. HCO2H, rt, over night

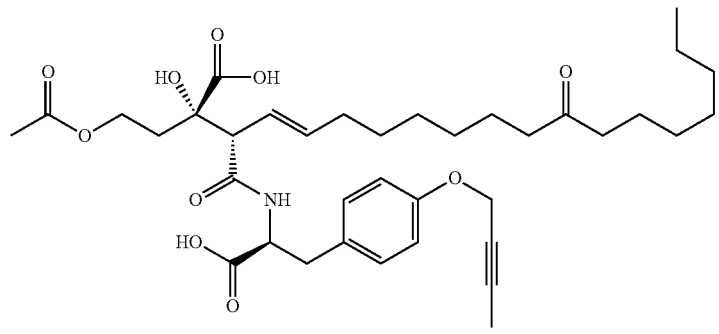

No 5218666

[Chem. 252]

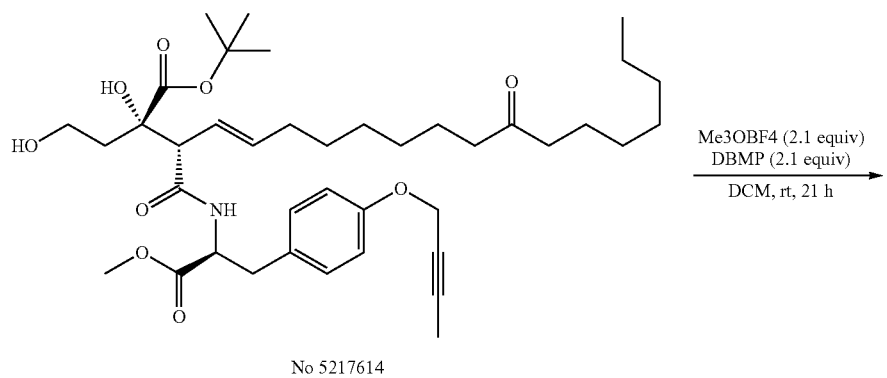

No 5217614

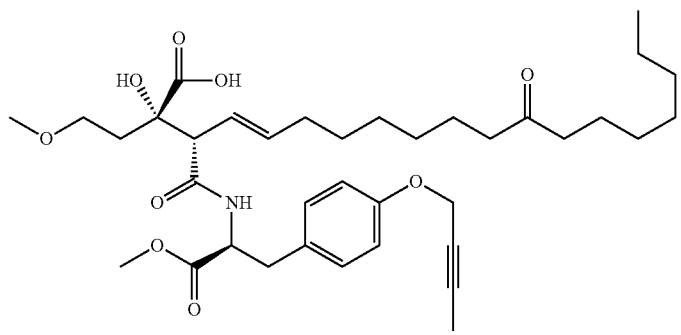

No 5233427

To a mixture of No. 5217614, tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate (25 mg, 0.0357 mmol), 2,6-di-tert-butyl-4-methyl pyridine (15.4 mg, 0.075 mmol), and dichloromethane (2 mL) was added trimethyloxonium tetrafluoroborate (11 mg, 0.075 mmol) and the mixture was stirred at room temperature for 21 hours. After confirming the consumption of the starting materials by LCMS, methanol and water were added. The organic solvent was distilled off under reduced pressure. The resulting residue was purified by preparative HPLC and then freeze-dried to obtain the title compound (7 mg, 30% yield, white solid).

$^1$H-NMR (CD$_3$CN) δ: 0.87 (3H, t, J=6.9 Hz), 1.21-1.28 (14H, m), 1.43-1.52 (4H, m), 1.72 (1H, td, J=13.4, 6.3 Hz), 1.81 (3H, t, J=2.3 Hz), 1.91-1.95 (11H, m), 1.99-2.06 (1H, m), 2.36 (4H, t, J=7.3 Hz), 2.85-2.95 (1H, m), 3.06 (4H, ddd, J=21.6, 9.7, 5.4 Hz), 3.14-3.20 (4H, m), 3.34-3.43 (2H, m), 3.66 (3H, s), 4.57-4.63 (3H, m), 5.35-5.60 (2H, m), 6.83 (2H, d, J=8.7 Hz), 7.06 (2H, d, J=8.7 Hz).

ESI (LC/MS positive mode) m/z 658 (M+H); Rt 1.55 min.

No. 5236115 (E)-(2S,3S)-3-[(S)-2-(4-But-2-ynyloxy-phenyl)-1-carboxy-ethylcarbamoyl]-2-hydroxy-2-(2-methoxy-ethyl)-12-oxo-nonadec-4-enoic acid

[Chem. 253]

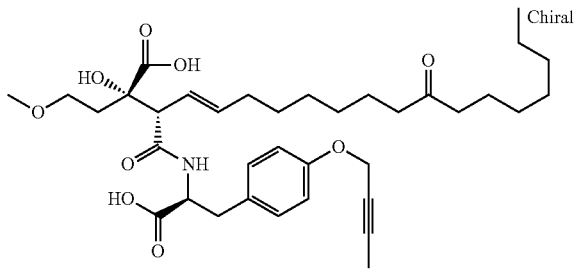

To a mixture of No. 5233427, (E)-(2S,3S)-3-[(S)-2-(4-but-2-ynyloxy-phenyl)-1-methoxycarbonyl-ethylcarbamoyl]-2-hydroxy-2-(2-methoxy-ethyl)-12-oxo-nonadec-4-enoic acid (30 mg, 0.042 mmol) and methanol (4.0 mL) was added an aqueous solution (400 μL) of 2 M LiOH, and the mixture was stirred at room temperature. After confirming the consumption of the starting materials by LCMS, 1 M hydrochloric acid was added and the mixture was extracted with ethyl acetate. The organic layer was washed with a saturated brine and dried over anhydrous sodium sulfate. The filtrate was then concentrated under reduced pressure. The resulting residue was purified by preparative HPLC and then freeze-dried to obtain the title compound (13.2 mg, 49%, white solid).

$^1$H-NMR (CDCl$_3$) δ: 0.88 (3H, t, J=6.8 Hz), 1.22-1.31 (14H, m), 1.55 (4H, td, J=14.2, 7.0 Hz), 1.74 (1H, dt, J=14.3, 5.8 Hz), 1.86 (3H, t, J=2.2 Hz), 1.97-2.03 (2H, m), 2.07-2.13 (1H, m), 2.35-2.47 (4H, m), 3.02 (1H, dd, J=14.1, 7.8 Hz), 3.15-3.26 (2H, m), 3.29 (3H, s), 3.42-3.55 (2H, m), 4.61 (2H, q, J=2.2 Hz), 4.77 (1H, dd, J=12.7, 7.6 Hz), 5.51 (1H, dd, J=15.3, 9.0 Hz), 5.59-5.66 (1H, m), 6.87 (2H, d, J=8.6 Hz), 6.97 (1H, d, J=6.7 Hz), 7.10 (2H, d, J=8.6 Hz).

ESI (LC/MS positive mode) m/z 644 (M+H); Rt 2.30 min.

No. 5250270 (E)-(2S,3S)-3-[(S)-2-(4-But-2-ynyloxy-phenyl)-1-methoxycarbonyl-ethylcarbamoyl]-2-cyanomethyl-2-hydroxy-12-oxo-nonadec-4-enoic acid was produced according to the following synthetic scheme.

[Chem. 254]

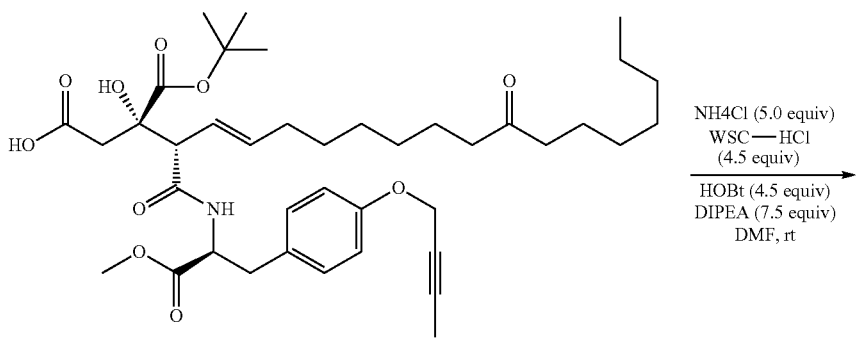

No 5317776

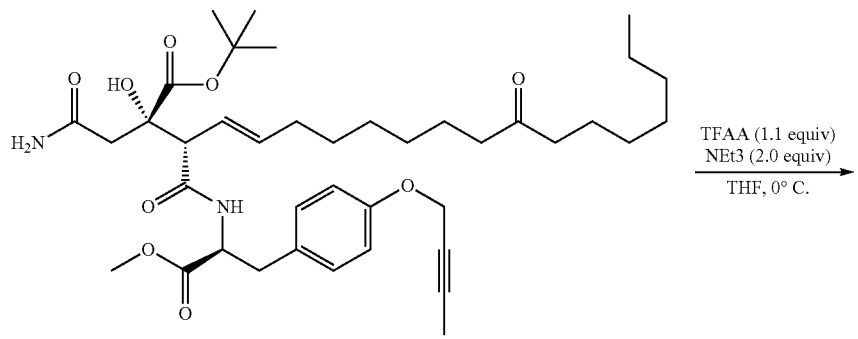

No 5463635

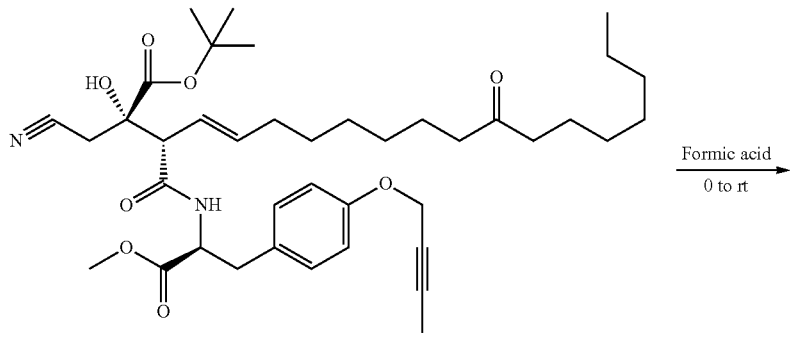

No 6801972

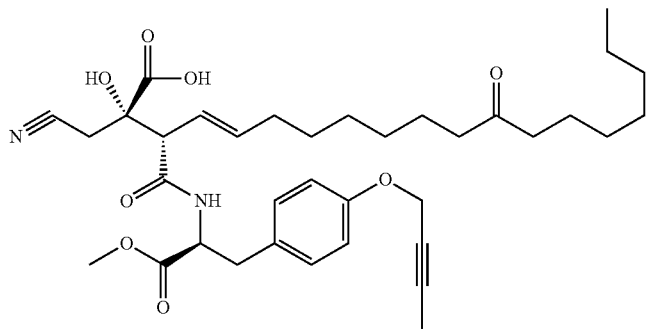

No 5250270

To a mixture of No. 5317776, 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate (863 mg, 1.21 mmol), ammonium chloride (324 mg, 6.06 mmol), and DMF (40 mL) were added HOBt (735 mg, 5.44 mmol), 1-ethyl-3-(3-dimethylaminopropyl)carbodiimide hydrochloride (1,043 mg, 5.44 mmol), and N,N-diisopropylethylamine (1.57 mL, 9.11 mmol), and the mixture was stirred at room temperature for 1 day. After confirming the consumption of the starting materials by LCMS, ethyl acetate was added. The mixture was washed with water and a saturated brine, and dried over anhydrous sodium sulfate. The filtrate was then concentrated under reduced pressure. The resulting residue was purified with SP1 (SiO$_2$ cartridge, 5% methanol/dichloromethane, Rf=0.3) to obtain No. 5463635, tert-butyl (E)-(2S,3S)-3-[(S)-2-(4-but-2-ynyloxy-phenyl)-1-methoxycarbonyl-ethylcarbamoyl]-2-carbamoylmethyl-2-hydroxy-12-oxo-nonadec-4-enoate (672 mg, 78%, ESI (LC/MS positive mode) m/z 713 (M+H); Rt 2.97 min.). A mixture of No. 5463635 and THF (30 mL) was cooled to 0° C., and trifluoroacetic acid anhydride (145 µL, 1.04 mmol) and triethylamine (263 µL, 1.89 mmol) were added. After stirring for 3 hours, the consumption of the starting materials was confirmed by LCMS. Ethyl acetate and water were added, and the mixture was extracted with ethyl acetate. The organic layer was washed with water and a saturated brine, and then dried over anhydrous sodium sulfate. The filtrate was concentrated under reduced pressure to obtain No. 6801972, tert-butyl (E)-(2S,3S)-3-[(S)-2-(4-but-2-ynyloxy-phenyl)-1-methoxycarbonyl-ethylcarbamoyl]-2-carbamoylmethyl-2-hydroxy-12-oxo-nonadec-4-enoate (600 mg, 91%, ESI (LC/MS positive mode) m/z 695 (M+H); Rt 3.28 min.). To No. 6801972 (520 mg, 0.748 mmol) was added formic acid (15 mL) and the mixture was stirred at room temperature. After confirming the consumption of the starting materials by LCMS, formic acid was distilled off under reduced pressure. The resulting residue was purified by preparative HPLC. The obtained fraction was freeze-dried to obtain the title compound (160 mg, 33% yield, white solid).

$^1$H-NMR (CDCl$_3$) δ: 0.88 (3H, t, J=6.8 Hz), 1.21-1.37 (14H, m), 1.50-1.65 (4H, m), 1.86 (3H, t, J=2.3 Hz), 1.98 (1H, td, J=14.4, 7.6 Hz), 2.06-2.12 (1H, m), 2.38-2.54 (4H, m), 2.68 (1H, d, J=16.8 Hz), 2.81 (1H, d, J=16.8 Hz), 2.99 (1H, dd, J=14.1, 7.0 Hz), 3.12 (1H, dd, J=14.1, 5.1 Hz), 3.32 (1H, d, J=9.8 Hz), 3.75 (3H, s), 4.63 (2H, q, J=2.2 Hz), 4.81 (1H, dd, J=13.3, 7.0 Hz), 5.50 (1H, dd, J=15.1, 9.6 Hz), 5.72-5.79 (1H, m), 6.69 (1H, d, J=7.8 Hz), 6.89 (2H, d, J=8.6 Hz), 7.03 (2H, d, J=8.6 Hz).

ESI (LC/MS positive mode) m/z 639 (M+H); Rt 2.67 min.

No. 5257015 (E)-(2S,3S)-2-(2-Acetoxy-ethyl)-3-[(S)-1-acetoxymethyl-2-(4-but-2-ynyloxy-phenyl)-ethylcarbamoyl]-2-hydroxy-12-oxo-nonadec-4-enoic acid was produced according to the following synthetic scheme.

[Chem. 255]

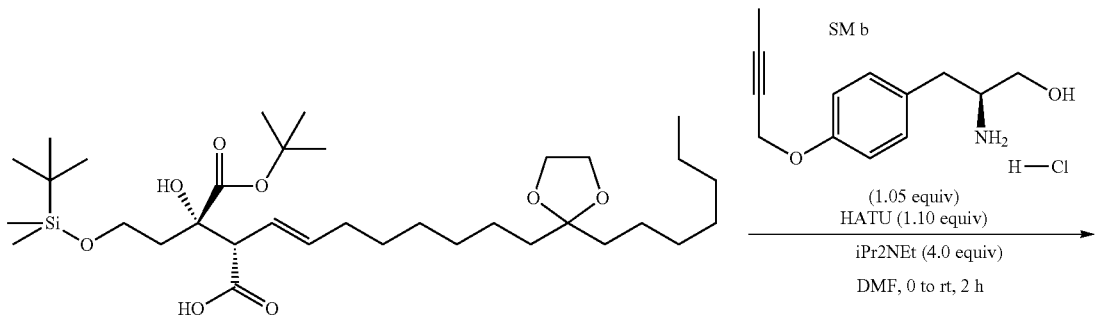

No 4976198

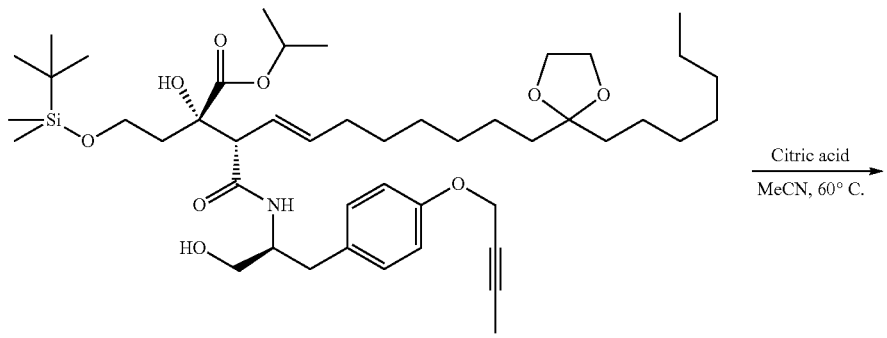
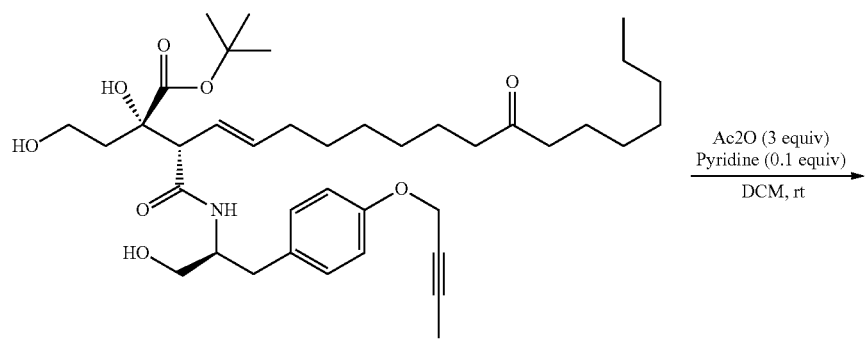
No 6801976
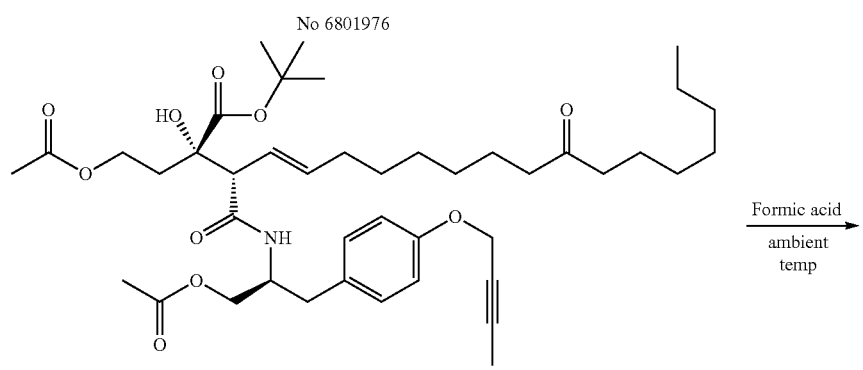
No 6801977
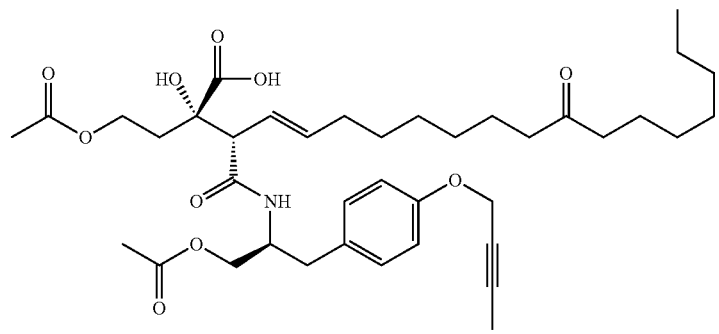
No 5257015
An intermediate, tert-butyl (E)-(2S,3S)-2-[2-(tert-butyl-dimethyl-silanyloxy)-ethyl]-3-[(S)-2-(4-but-2-ynyloxy-phenyl)-1-hydroxymethyl-ethylcarbamoyl]-11-(2-heptyl-[1,3]dioxolan-2-yl)-2-hydroxy-undec-4-enoate (ESI (LC/MS positive mode) m/z 831 (M+H); Rt 3.98 min.) was synthesized by the synthetic method similar to that of No. 5327507, tert-butyl (E)-(2S,3S)-2-[2-(tert-butyl-dimethyl-silanyloxy)-ethyl]-3-[(S)-2-(4-but-2-ynyloxy-phenyl)-1-methoxycarbonyl-ethylcarbamoyl]-11-(2-heptyl-[1,3]dioxolan-2-yl)-2-hydroxy-undec-4-enoate, except that (S)-2-amino-3-(4-but-2-ynyloxy-phenyl)-propan-1-ol hydrochloride was used instead of methyl (S)-2-amino-3-(4-but-2-ynyloxy-phenyl)-propionate hydrochloride. From the obtained intermediate, No. 6801976 (ESI (LC/MS positive mode) m/z 672 (M+H); Rt 2.70 min.) was synthesized by a synthetic method similar to that of No. 5217614, tert-butyl (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate.

To a mixture of No. 6801976, tert-butyl (E)-(2S,3S)-3-[(S)-2-(4-but-2-ynyloxy-phenyl)-1-hydroxymethyl-ethyl-carbamoyl]-2-hydroxy-2-(2-hydroxy-ethyl)-12-oxo-nonadec-4-enoate (304 mg, 0.45 mmol) and dichloromethane (15 mL) were added acetic anhydride (129 µL, 1.36 mmol) and pyridine (10 µL, 0.12 mmol), and the mixture was stirred at room temperature for 6 hours. Water was added and the mixture was extracted with dichloromethane, and dried over anhydrous sodium sulfate. The filtrate was then concentrated under reduced pressure. The resulting residue was left in a refrigerator overnight to obtain No. 6801977, tert-butyl (E)-(2S,3S)-2-(2-acetoxy-ethyl)-3-[(S)-1-acetoxymethyl-2-(4-but-2-ynyloxy-phenyl)-ethylcarbamoyl]-2-hydroxy-12-oxo-nonadec-4-enoate (328 mg, 96% yield, ESI (LC/MS positive mode) m/z 757 (M+H); Rt 3.37 min.). Formic acid (15 mL) was added to No. 6801977 (328 mg, 0.43 mmol) and the mixture was stirred at room temperature for 4 hours. After confirming the consumption of the starting materials by LCMS, formic acid was distilled off under reduced pressure. The residue was purified by preparative HPLC to obtain the title compound (35 mg, 11% yield, yellow oil).

$^1$H-NMR (CDCl$_3$) δ: 0.87 (3H, t, J=6.8 Hz), 1.18-1.40 (14H, m), 1.50-1.62 (4H, m), 1.70 (1H, d, J=12.5 Hz), 1.86 (3H, t, J=2.3 Hz), 1.90-2.07 (8H, m), 2.19-2.26 (1H, m), 2.36-2.52 (4H, m), 2.77 (2H, dq, J=26.7, 7.0 Hz), 3.12 (1H, d, J=8.6 Hz), 4.00-4.20 (4H, m), 4.35-4.45 (1H, m), 4.55-4.65 (2H, m), 5.44 (1H, dd, J=14.7, 10.0 Hz), 5.57-5.64 (1H, m), 6.46 (1H, br.s), 6.88 (2H, d, J=8.6 Hz), 7.08 (2H, d, J=8.2 Hz).

ESI (LC/MS positive mode) m/z 700 (M+H); Rt 2.63 min.

No. 5257016

(E)-(2S,3S)-3-[(S)-2-(4-But-2-ynyloxy-phenyl)-1-hydroxymethyl-ethylcarbamoyl]-2-hydroxy-2-(2-hydroxy-ethyl)-12-oxo-nonadec-4-enoic acid

[Chem. 256]

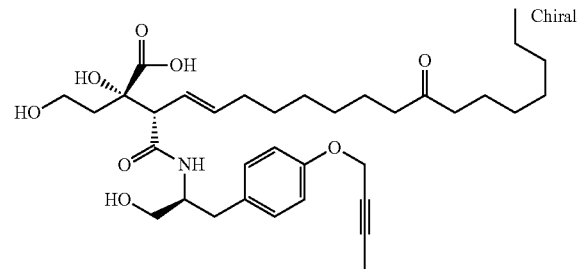

To a mixture of No. 5257015 , (E)-(2S,3S)-2-(2-acetoxy-ethyl)-3-[(S)-1-acetoxymethyl-2-(4-but-2-ynyloxy-phenyl)-ethylcarbamoyl]-2-hydroxy-12-oxo-nonadec-4-enoic acid (17 mg, 0.0244 mmol) and methanol (1.7 mL) were added water (49 µL) and LiOH (2.4 mg, 0.0983 mmol), and the mixture was stirred at room temperature. After confirming the consumption of the starting materials by LCMS, the reaction solution was purified directly by preparative HPLC, and freeze-dried to obtain the title compound (9 mg, 60% yield, yellow oil).

$^1$H-NMR (CD$_3$OD) δ: 0.90 (3H, t, J=7.0 Hz), 1.22-1.37 (14H, m), 1.49-1.57 (4H, m), 1.75-1.85 (4H, m), 1.95-2.05 (3H, m), 2.43 (4H, t, J=7.2 Hz), 2.64 (1H, dd, J=13.7, 8.6 Hz), 2.87 (1H, dd, J=14.1, 5.5 Hz), 3.21 (1H, d, J=7.4 Hz), 3.52 (2H, d, =5.1 Hz), 3.57-3.71 (2H, m), 4.06-4.16 (1H, m), 4.59-4.62 (2H, m), 5.49-5.55 (2H, m), 6.84 (2H, d, J=8.6 Hz), 7.12 (2H, d, J=8.2 Hz), 7.99 (1H, d, J=9.0 Hz).

ESI (LC/MS positive mode) m/z 616 (M+H); Rt 2.05 min.

No. 5257018 (S)-3-(4-But-2-ynyloxy-phenyl)-2-[(E)-(S)-2-((S)-1-carbamoyl-1,3-dihydroxy-propyl)-11-oxo-octadec-3-enoylamino]-propionic acid was produced according to the following synthetic scheme.

[Chem. 257]

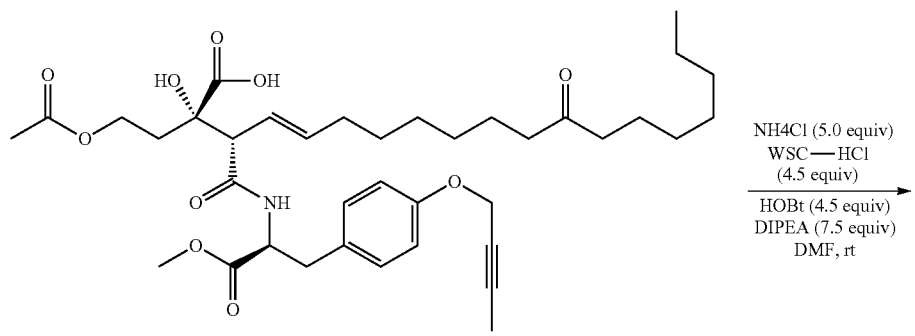

No 5214354

-continued

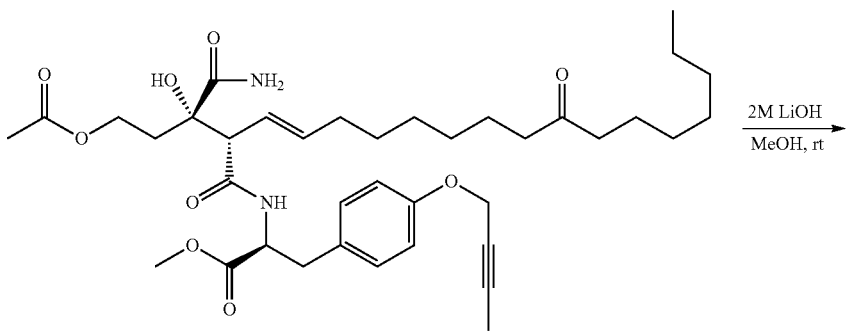

No 6801995

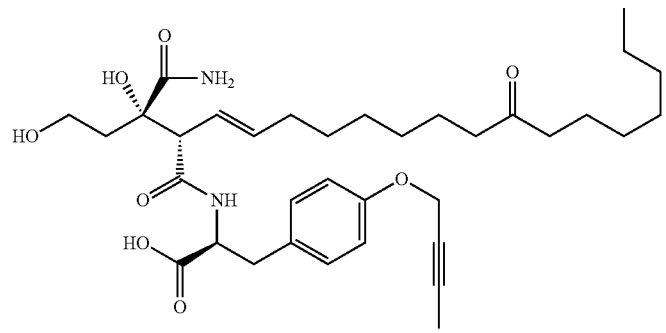

No 5257018

No. 6801995, methyl (S)-2-[(E)-(S)-2-((S)-3-acetoxy-1-carbamoyl-1-hydroxy-propyl)-11-oxo-octadec-3-enoylamino]-3-(4-but-2-ynyloxy-phenyl)-propionate (ESI (LC/MS positive mode) m/z 685 (M+H); Rt 3.40 min.) was synthesized by the synthesis similar to that of No. 5453635, 2-cyclohexyl-5H-pyrrolo[2,3-b]pyrazine-7-carboxylic acid ((S)-2-hydroxy-1,2-dimethyl-propyl)-amide, except that No. 5214354, (E)-(2S,3S)-2-(2-acetoxy-ethyl)-3-[(S)-2-(4-but-2-ynyloxy-phenyl)-1-methoxycarbonyl-ethylcarbamoyl]-2-hydroxy-12-oxo-nonadec-4-enoic acid was used instead of No. 5317776, 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate. From methyl (S)-2-[(E)-(S)-2-((S)-3-acetoxy-1-carbamoyl-1-hydroxy-propyl)-11-oxo-octadec-3-enoylamino]-3-(4-but-2-ynyloxy-phenyl)-propionate, the title compound was obtained by the synthesis by a synthetic method similar to that of No. 5257016, (E)-(2S,3S)-3-[(S)-2-(4-but-2-ynyloxy-phenyl)-1-hydroxymethyl-ethylcarbamoyl]-2-hydroxy-2-(2-hydroxy-ethyl)-12-oxo-nonadec-4-enoic acid.

$^1$H-NMR (CD$_3$OD) δ: 0.90 (3H, t, J=7.0 Hz), 1.20-1.40 (14H, m), 1.50-1.60 (4H, m), 1.81-1.84 (4H, m), 1.90-1.98 (2H, m), 2.05 (1H, ddd, J=17.5, 8.1, 4.2 Hz), 2.44 (4H, dd, J=8.6, 5.9 Hz), 2.89 (1H, dd, J=14.3, 9.2 Hz), 3.16 (1H, dd, J=13.9, 4.5 Hz), 3.23 (1H, d, J=7.8 Hz), 3.56 (1H, ddd, J=12.0, 6.6, 3.6 Hz), 3.68 (1H, dt, J=9.3, 3.6 Hz), 4.60-4.68 (3H, m), 5.44 (2H, t, J=5.7 Hz), 6.84 (2H, d, J=8.6 Hz), 7.12 (2H, d, J=8.6 Hz), 8.47 (1H, d, J=8.2 Hz).

ESI (LC/MS positive mode) m/z 629 (M+H); Rt 2.10 min.

No. 5286993

Potassium (E)-(2S,3S)-3-[(S)-2-(4-but-2-ynyloxy-phenyl)-1-methoxycarbonyl-ethylcarbamoyl]-2,12-dihydroxy-2-(2-hydroxy-ethyl)-nonadec-4-enoate

[Chem. 258]

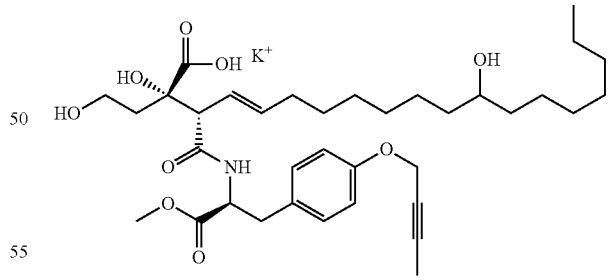

To a mixture of No. 5214357, a mixture of sodium and potassium (E)-(2S,3S)-3-[(S)-2-(4-but-2-ynyloxy-phenyl)-1-methoxycarbonyl-ethylcarbamoyl]-2-hydroxy-2-(2-hydroxy-ethyl)-12-oxo-nonadec-4-enoate (100 mg, 0.147 mmol) and methanol (5 mL) was added NaBH$_4$ (5.5 mg, 0.146 mmol) at room temperature. After stirring for 1.5 hours, NaBH$_4$ (5.5 mg, 0.146 mmol) was added again. After stirring for 30 minutes, the consumption of the starting materials was confirmed by LCMS. Water was added and the mixture was extracted with ethyl acetate. The organic layer was washed with a saturated brine, and dried over anhydrous sodium sulfate. The filtrate was then concentrated under reduced pressure to obtain the title compound (100 mg, yield 99% or more, white solid).

$^1$H-NMR (CD$_3$OD) δ: 0.90 (3H, t, J=6.9 Hz), 1.20-1.50 (22H, m), 1.74-1.82 (4H, m), 1.91-2.00 (3H, m), 2.98 (1H, dd, J=14.0, 8.3 Hz), 3.08 (1H, dd, J=14.0, 5.4 Hz), 3.22 (1H, d, J=8.2 Hz), 3.45-3.55 (2H, m), 3.60-3.70 (4H, m), 4.60-4.68 (3H, m), 5.45 (1H, dd, J=15.5, 8.2 Hz), 5.52-5.59 (1H, m), 6.87 (2H, d, J=9.4 Hz), 7.13 (2H, d, J=8.8 Hz).

ESI (LC/MS positive mode) m/z 646 (M+H); Rt 2.52 min.

No. 5287782

(E)-(2S,3S)-3-[(S)-2-(4-But-2-ynyloxy-phenyl)-1-carboxy-ethylcarbamoyl]-2,12-dihydroxy-2-(2-hydroxy-ethyl)-nonadec-4-enoic acid

[Chem. 259]

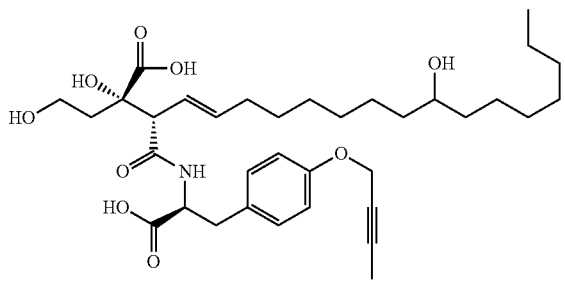

To a mixture of No. 5286993, potassium (E)-(2S,3S)-3-[(S)-2-(4-but-2-ynyloxy-phenyl)-1-methoxycarbonyl-ethylcarbamoyl]-2,12-dihydroxy-2-(2-hydroxy-ethyl)-nonadec-4-enoate (40 mg, 0.0584 mmol) and methanol (2.0 mL) were added water (2.0 mL) and potassium carbonate (40 mg, 0.146 mmol), and the mixture was stirred at room temperature for 4 hours. After confirming the consumption of the starting materials by LCMS, water was added and the mixture was extracted with ethyl acetate. To the aqueous layer was then added 1 M hydrochloric acid until pH 7 was reached. The organic layer was washed with a saturated brine, and dried over anhydrous sodium sulfate. The filtrate was then concentrated under reduced pressure to obtain the title compound (15 mg, 41% yield, white solid).

$^1$H-NMR (CD$_3$OD) δ: 0.90 (3H, t, J=6.8 Hz), 1.25-1.50 (22H, m), 1.75-1.85 (4H, m), 1.93-2.07 (3H, m), 2.93 (1H, dd, J=14.0, 8.7 Hz), 3.15 (1H, dd, J=14.0, 5.0 Hz), 3.23 (1H, d, J=8.6 Hz), 3.45-3.70 (3H, m), 4.60-4.68 (3H, m), 5.45-5.65 (2H, m), 6.85 (2H, d, J=8.8 Hz), 7.12 (2H, d, J=8.6 Hz), 8.13 (1H, d, J=8.2 Hz).

ESI (LC/MS positive mode) m/z 632 (M+H); Rt 2.22 min.

No. 5321601

(S)-2-{(E)-(S)-1-[(S)-2-(4-But-2-ynyloxy-phenyl)-1-methoxycarbonyl-ethylcarbamoyl]-10-hydroxy-heptadec-2-enyl}-2-hydroxy-succinic acid

[Chem. 260]

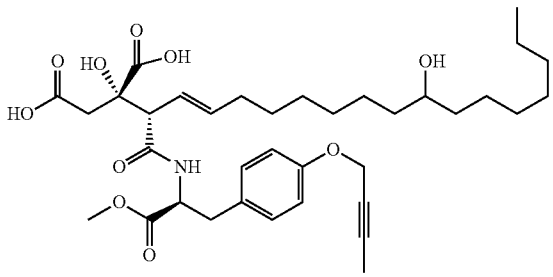

To a mixture of No. 5153510, (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinic acid (20 mg, 0.0304 mmol) and methanol was added NaBH$_4$ (7.4 mg, 0.196 mmol), and the mixture was stirred at room temperature. After confirming the consumption of the starting materials by LCMS, a saturated aqueous solution of ammonium chloride was added, and the mixture was extracted with ethyl acetate. The organic layer was washed with a saturated brine, and dried over anhydrous sodium sulfate. The filtrate was then concentrated under reduced pressure. The resulting residue was purified by preparative HPLC, and then extracted with ethyl acetate. The organic layer was washed with a saturated brine, and then dried over anhydrous sodium sulfate. The organic solvent was distilled off under reduced pressure to obtain the title compound (8 mg, 40%, colorless oil).

$^1$H-NMR (CD$_3$OD) δ: 0.90 (3H, t, J=6.9 Hz), 1.29-1.42 (22H, m), 1.82 (3H, t, J=2.3 Hz), 1.96-2.01 (2H, m), 2.58 (1H, d, J=16.2 Hz), 2.88-2.95 (2H, m), 3.10-3.15 (1H, m), 3.21 (1H, d, J=8.6 Hz), 3.45-3.53 (1H, m), 3.72 (3H, s), 4.60-4.68 (3H, m), 5.45-5.62 (2H, m), 6.85 (2H, d, J=8.4 Hz), 7.10 (2H, d, J=8.6 Hz), 8.29 (1H, d, J=7.8 Hz).

ESI (LC/MS positive mode) m/z 660 (M+H); Rt 2.50 min.

No. 5434281

(E)-(2S,3S)-3-[(S)-2-(4-But-2-ynyloxy-phenyl)-1-methoxycarbonyl-ethylcarbamoyl]-2-hydroxy-12-oxo-2-propyl-nonadec-4-enoic acid

[Chem. 261]

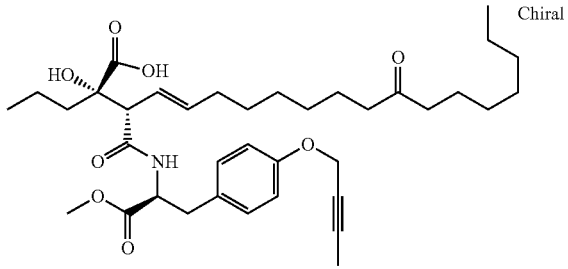

An intermediate, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-propyl-undec-4-enoate (ESI (LC/MS positive mode) m/z 793 (M+H); Rt 4.33 min.) was synthesized by the synthesis similar to Step A-1, except that tert-butyl 2-oxo-pentanoate was used instead of tert-butyl 4-methoxy-2-oxo-butyrate. From the obtained intermediate, an intermediate, tert-butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-propyl-undec-4-enoate (ESI (LC/MS positive mode) m/z 743 (M+H); Rt 2.27 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CD$_3$OD) δ: 0.83-0.93 (6H, m), 1.23-1.35 (22H, m), 1.41-1.53 (5H, m), 1.65-1.67 (1H, m), 1.81 (3H, t, J=2.3 Hz), 1.95-1.98 (2H, m), 2.43 (4H, t, J=7.3 Hz), 2.91 (1H, dd, J=14.1, 9.2 Hz), 3.11 (1H, dd, J=14.0, 5.0 Hz), 3.22 (1H, d, J=8.2 Hz), 3.70 (3H, s), 4.60-4.65 (3H, m), 5.45-5.60 (2H, m), 6.85 (2H, d, J=8.8 Hz), 7.11 (2H, d, J=8.8 Hz).

ESI (LC/MS positive mode) m/z 642 (M+H); Rt 2.92 min.

No. 5435877 (E)-(2S,3S)-3-[(S)-2-(4-But-2-ynyloxy-phenyl)-1-methoxycarbamoyl-ethylcarbamoyl]-2-hydroxy-2-(2-methoxy-ethyl)-12-oxo-nonadec-4-enoic acid was produced according to the following synthetic scheme.

[Chem 262]

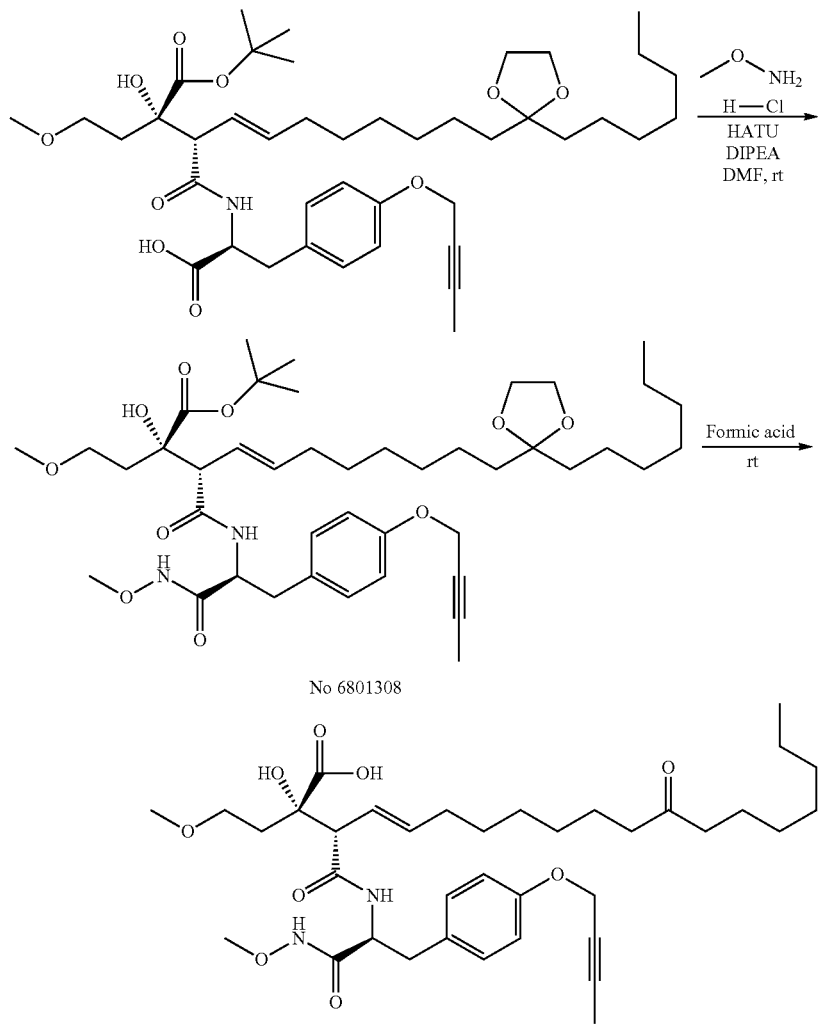

(S)-3-(4-(But-2-ynyloxy)phenyl)-2-((S,E)-2-((S)-1-tert-butoxy-2-hydroxy-4-methoxy-1-oxobutan-2-yl)-10-(2-heptyl-1,3-dioxolan-2-yl)dec-3-ene amide)propanoic acid (25 mg, 0.0357 mmol), O-methylhydroxylamine hydrochloride (4.5 mg, 0.0536 mmol) and HATU (20.4 mg, 0.0536 mmol) were dissolved in DMF (1.0 m), and N,N-diisopropylethylamine (25 μL, 0.1429 mmol) was added. The mixture was stirred at room temperature. After confirming the consumption of the starting materials by LCMS, water was added and the mixture was extracted with ethyl acetate. The organic layer was washed with a saturated brine, and dried over anhydrous sodium sulfate. The filtrate was then concentrated under reduced pressure to obtain No. 6801308, tert-butyl (E)-(2S,3S)-3-[(S)-2-(4-but-2-ynyloxy-phenyl)-1-methoxycarbamoyl-ethylcarbamoyl]-11-(2-heptyl-[1,3]dioxolan-2-yl)-2-hydroxy-2-(2-methoxy-ethyl)-undec-4-enoate (25 mg, yield 99% or more, ESI (LC/MS positive mode) m/z 774

(M+H); Rt 3.37 min.). The resulting residue was dissolved in formic acid (3.0 mL) and the mixture was stirred at room temperature. After confirming the consumption of the starting materials by LCMS, the formic acid was distilled off under reduced pressure. The resulting residue was purified by preparative HPLC. Water was added to the purified fraction, and the mixture was extracted with ethyl acetate. The organic layer was washed with a saturated brine, and then dried over anhydrous sodium sulfate. The organic solvent was distilled out of the filtrate under reduced pressure to obtain the title compound (15 mg, 63% yield over 2 steps).

$^1$H-NMR (CD$_3$OD) δ: 0.90 (3H, t, J=6.9 Hz), 1.24-1.40 (14H, m), 1.47-1.57 (4H, m), 1.63-1.69 (1H, m), 1.81 (3H, t, J=2.3 Hz), 1.98 (2H, dd, J=14.7, 7.8 Hz), 2.03-2.10 (1H, m), 2.43 (4H, t, J=7.4 Hz), 2.86 (1H, dd, J=13.6, 8.3 Hz), 2.99 (1H, dd, J=13.7, 7.0 Hz), 3.22 (1H, d, J=8.0 Hz), 3.24 (3H, s), 3.42 (2H, t, J=6.7 Hz), 3.56 (3H, s), 4.41 (1H, dd, J=8.4, 7.0 Hz), 4.61 (2H, q, J=2.3 Hz), 5.55 (2H, ddd, J=26.6, 15.3, 6.9 Hz), 6.86 (2H, d, J=10.2 Hz), 7.14 (2H, d, J=9.6 Hz).

ESI (LC/MS positive mode) m/z 673 (M+H); Rt 2.28 min.

No. 5451136 (E)-(2S,3S)-3-[(S)-2-(4-But-2-ynyloxy-phenyl)-1-methoxycarbonyl-ethylcarbamoyl]-2-hydroxy-2-(2-methoxycarbamoyl-methyl)-12-oxo-nonadec-4-enoic acid was produced according to the following synthetic scheme.

[Chem. 263]

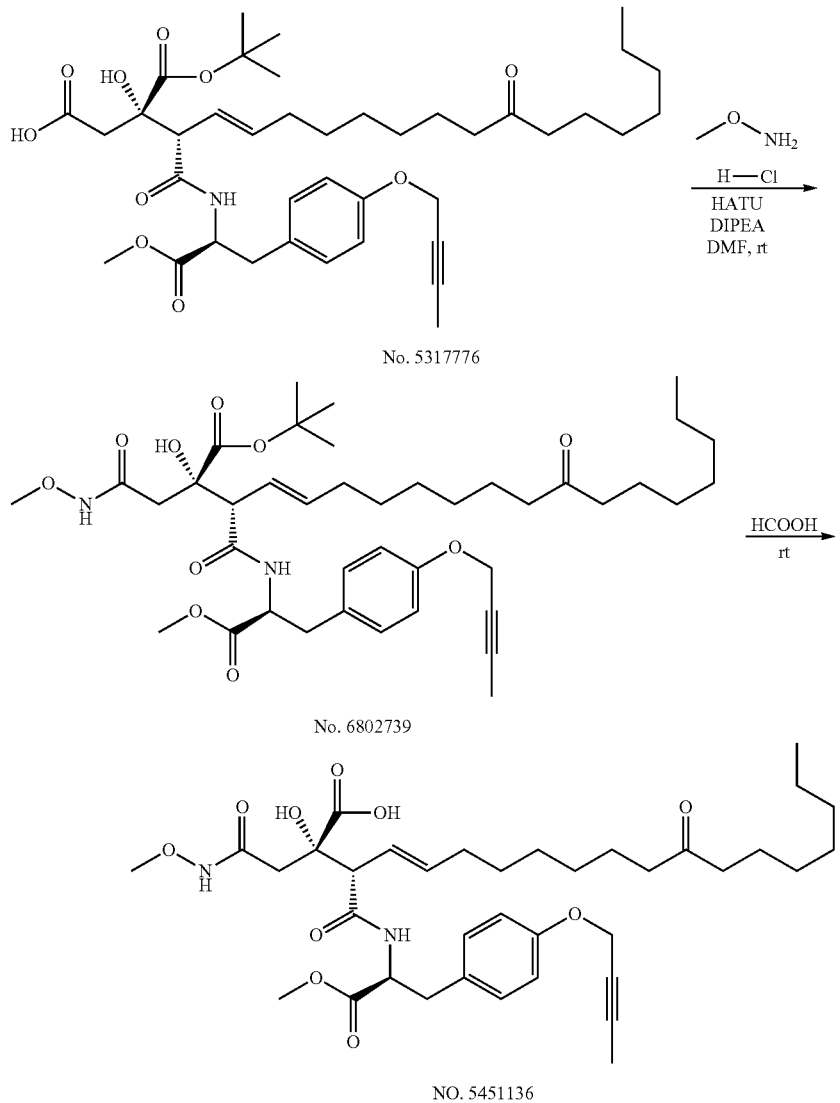

No. 6802739, tert-butyl (E)-(2S,3S)-3-[(S)-2-(4-but-2-ynyloxy-phenyl)-1-methoxycarbonyl-ethylcarbamoyl]-2-hydroxy-2-(methoxycarbamoyl-methyl)-12-oxo-nonadec-4-enoate (ESI (LC/MS positive mode) m/z 743 (M+H); Rt 2.96 min.) was synthesized by a synthetic method similar to that of No. 5463635, tert-butyl (E)-(2S,3S)-3-[(S)-2-(4-but-2-ynyloxy-phenyl)-1-methoxycarbonyl-ethyl carbamoyl]-2-carbamoylmethyl-2-hydroxy-12-oxo-nonadec-4-enoate, except that O-methylhydroxylamine hydrochloride was used instead of ammonium chloride. The obtained No. 6802739, tert-butyl (E)-(2S,3S)-3-[(S)-2-(4-but-2-ynyloxy-phenyl)-1-methoxycarbonyl-ethyl carbamoyl]-2-hydroxy-2-(2-methoxycarbamoyl-methyl)-12-oxo-nonadec-4-enoate was used in a synthetic method similar to that of No. 5250270, (E)-(2S,3S)-3-[(S)-2-(4-but-2-ynyloxy-phenyl)-1-methoxycarbonyl-ethylcarbamoyl]-2-cyanomethyl-2-hydroxy-12-oxo-nonadec- 4-enoic acid, and subjected to purification by preparative HPLC. To the obtained fraction was added an aqueous solution of 1% NaHCO$_3$ and the mixture was extracted with ethyl acetate, washed with a saturated aqueous solution of ammonium chloride, and dried over anhydrous sodium sulfate. The filtrate was concentrated under reduced pressure to obtain the title compound.

$^1$H-NMR (CD$_3$OD) δ: 0.90 (3H, t, J=6.8 Hz), 1.21-1.38 (14H, m), 1.47-1.57 (4H, m), 1.82 (3H, t, J=2.2 Hz), 1.92-2.02 (2H, m), 2.27 (1H, d, J=14.5 Hz), 2.43 (4H, td, J=7.3, 1.5 Hz), 2.59 (1H, d, J=14.5 Hz), 2.94 (1H, dd, J=14.0, 8.9 Hz), 3.12 (1H, dd, J=14.1, 5.1 Hz), 3.26 (1H, d, J=7.4 Hz), 3.66 (3H, s), 3.70 (3H, s), 4.60 (2H, q, J=2.3 Hz), 4.66 (1H, dd, J=8.8, 5.1 Hz), 5.52 (2H, ddd, J=25.3, 15.3, 6.7 Hz), 6.85 (2H, d, J=8.6 Hz), 7.12 (2H, d, J=8.6 Hz).

ESI (LC/MS positive mode) m/z 687 (M+H); Rt 2.35 min.

No. 5452084

(E)-(2S,3S)-3-[(S)-2-(4-But-2-ynyloxy-phenyl)-1-carboxy-ethylcarbamoyl]-2-hydroxy-2-(2-methoxy-carbamoyl-methyl)-12-oxo-nonadec-4-enoic acid

[Chem. 264]

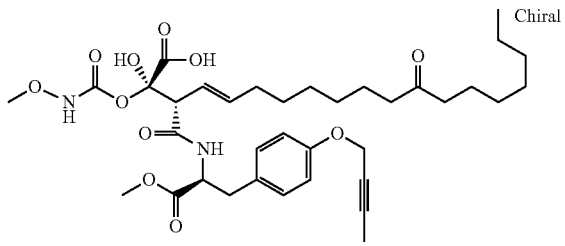

The title compound was obtained by the synthesis by a method similar to that of No. 5451136, (E)-(2S,3S)-3-[(S)-2-(4-but-2-ynyloxy-phenyl)-1-methoxycarbonyl-ethylcarbamoyl]-2-hydroxy-2-(2-methoxycarbamoyl-methyl)-12-oxo-nonadec-4-enoic acid, except that No. 4986981, 1-tert-butyl (R)-2-[(E)-(R)-1-[(R)-1-tert-butoxycarbonyl-2-(4-but-2-ynyloxy-phenyl)-ethylcarbamoyl]-9-(2-heptyl-[1,3]dioxolan-2-yl)-non-2-enyl]-2-hydroxy-succinate was used instead of No. 5317776, 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate.

$^1$H-NMR (CD$_3$OD) δ: 0.89 (3H, t, J=6.8 Hz), 1.22-1.37 (14H, m), 1.47-1.59 (4H, m), 1.81 (3H, d, J=1.8 Hz), 1.97 (2H, q, J=6.0 Hz), 2.31 (1H, d, J=14.6 Hz), 2.44 (4H, t, J=7.3 Hz), 2.64 (1H, d, J=14.6 Hz), 2.93 (1H, dd, J=14.3, 9.0 Hz), 3.17 (1H, dd, J=14.3, 4.6 Hz), 3.26 (1H, d, J=8.4 Hz), 3.66 (3H, s), 4.57-4.67 (3H, m), 5.46-5.62 (2H, m), 6.84 (2H, d, J=8.8 Hz), 7.13 (2H, d, J=8.4 Hz).

ESI (LC/MS positive mode) m/z 673 (M+H); Rt 2.07 min.

No. 5502322 (E)-(2S,3S)-3-[(S)-2-(4-But-2-yny-loxy-phenyl)-1-methoxycarbonyl-ethylcarbamoyl]-2-hydroxy-2-isobutyl-12-oxo-nonadec-4-enoic acid

[Chem. 265]

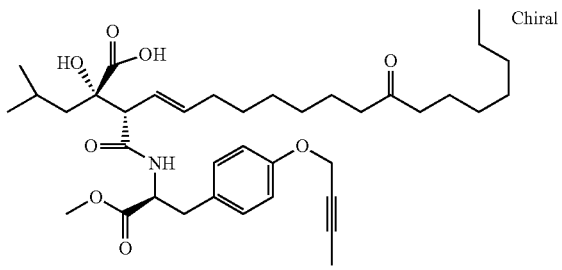

An intermediate, 5-methyl 1-tert-butyl (S)-2-[(E)-(S)-9-(2-heptyl-[1,3]dioxolan-2-yl)-1-((S)-4-isopropyl-5,5-diphenyl-2-thioxo-oxazolidine-3-carbonyl)-non-2-enyl]-2-hydroxy-pentanedioate was synthesized by the synthesis similar to Step A-1, except that 5-methyl 1-tert-butyl 2-oxo-pentanedioate was used instead of tert-butyl 4-methoxy-2-oxo-butyrate. From the obtained intermediate, an intermediate, tert-butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-isobutyl-undec-4-enoate (ESI (LC/MS positive mode) m/z 757 (M+H); Rt 2.57 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.83-0.90 (6H, m), 0.92 (3H, d, J=6.2 Hz), 1.16-1.38 (14H, m), 1.49-1.63 (5H, m), 1.72-1.83 (2H, m), 1.86 (3H, t, J=2.4 Hz), 1.93-2.11 (2H, m), 2.34-2.49 (4H, m), 3.00-3.08 (2H, m), 3.12 (1H, d, J=8.8 Hz), 3.73 (3H, s), 4.61 (2H, q, J=2.2 Hz), 4.81 (1H, dd, J=13.2, 5.7 Hz), 5.50-5.67 (2H, m), 6.63 (1H, br.s), 6.85 (2H, d, J=8.8 Hz), 7.00 (2H, d, J=8.8 Hz).

ESI (LC/MS positive mode) m/z 657 (M+H); Rt 2.23 min.

No. 5507802

5-Methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-pentanedioate

[Chem. 266]

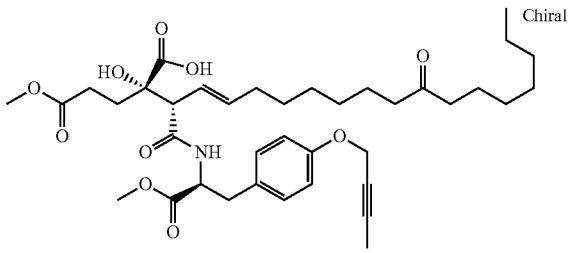

An intermediate, 5-methyl 1-tert-butyl (S)-2-[(E)-(S)-9-(2-heptyl-[1,3]dioxolan-2-yl)-1-((S)-4-isopropyl-5,5-diphenyl-2-thioxo-oxazolidine-3-carbonyl)-non-2-enyl]-2-hydroxy-pentanedioate (ESI (LC/MS positive mode) m/z 837 (M+H); Rt 3.78 min.) was synthesized by the synthesis similar to Step A-1, except that tert-butyl 4-methyl-2-oxo-pentanoate was used instead of tert-butyl 4-methoxy-2-oxo-butyrate. From the obtained intermediate, an intermediate, 5-methyl 1-tert-butyl (S)-2-[(E)-(S)-1-[(S)-2-(4-but-2-ynyloxy-phenyl)-1-methoxycarbonyl-ethylcarbamoyl]-9-(2-heptyl-[1,3]dioxolan-2-yl)-non-2-enyl]-2-hydroxy-pentanedioate (ESI (LC/MS positive mode) m/z 787 (M+H); Rt 1.68 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.87 (3H, t, J=6.2 Hz), 1.16-1.34 (14H, m), 1.46-1.61 (4H, m), 1.76-1.88 (4H, m), 1.93-2.02 (2H, m), 2.03-2.15 (1H, m), 2.18-2.28 (1H, m), 2.31-2.43 (5H, m), 2.94-3.07 (2H, m), 3.16 (1H, d, J=8.8 Hz), 3.58 (3H, s), 3.68 (3H, s), 4.53-4.60 (2H, m), 4.68-4.78 (1H, m), 5.67-5.80 (1H, m), 6.82 (2H, d, J=8.8 Hz), 6.98 (2H, d, J=7.9 Hz).

ESI (LC/MS positive mode) m/z 686 (M+H); Rt 2.70 min.

No. 5507803

(S)-2-{(E)-(S)-1-[(S)-2-(4-But-2-ynyloxy-phenyl)-1-carboxy-ethylcarbamoyl]10-oxo-heptadec-2-enyl}-2-hydroxy-pentanedioic acid

[Chem. 267]

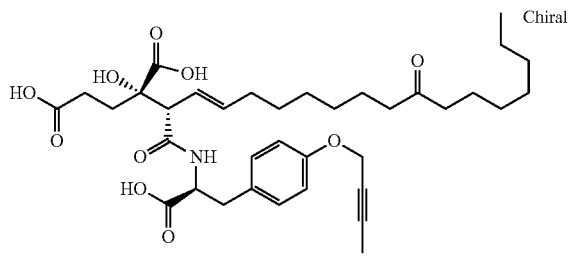

To a mixture of No. 5507802, 5-methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-pentanedioate (18 mg, 0.0262 mmol), acetonitrile (450 μL), and water (9 μL) were added triethylamine (21.9 μL, 0.157 mmol) and lithium bromide (45.6 mg, 0.525 mmol), and the mixture was stirred at 50° C. After confirming the consumption of No. 5507802 by LCMS, 0.1 M hydrochloric acid was added and the mixture was extracted with ethyl acetate. The organic layer was washed with a saturated brine, and dried over anhydrous sodium sulfate. The filtrate was then concentrated under reduced pressure. The resulting residue was purified by SP1 (Diol cartridge, 80% ethyl acetate/n-hexane Rf=0.6) to obtain the title compound (9.6 mg, 56% yield, white solid).

$^1$H-NMR (CDCl$_3$) δ: 0.87 (3H, t, J=7.1 Hz), 1.14-1.36 (14H, m), 1.47-1.61 (4H, m), 1.85 (3H, t, J=2.2 Hz), 1.93-2.02 (2H, m), 2.06-2.15 (2H, m), 2.19-2.29 (1H, m), 2.33-2.46 (4H, m), 2.52-2.64 (1H, m), 3.02 (1H, dd, J=14.1, 8.4 Hz), 3.16 (1H, dd, J=14.3, 4.6 Hz), 3.27 (1H, d, J=8.8 Hz), 4.55-4.63 (2H, m), 4.68 (1H, dd, J=13.0, 7.7 Hz), 5.47 (1H, dd, J=15.0, 8.8 Hz), 5.55-5.62 (1H, m), 6.87 (2H, d, J=8.8 Hz), 7.00 (1H, s), 7.09 (2H, d, J=8.4 Hz).

ESI (LC/MS positive mode) m/z 658 (M+H); Rt 2.12 min.

No. 5508500

(E)-(2S,3S)-3-[(S)-2-(4-But-2-ynyloxy-phenyl)-1-methoxycarbonyl-ethylcarbamoyl]-2-hydroxy-2-(3-methoxy-propyl)-12-oxo-nonadec-4-enoic acid

[Chem. 268]

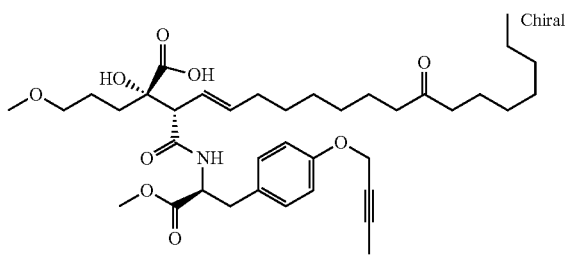

An intermediate, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(3-methoxy-propyl)-undec-4-enoate (ESI (LC/MS positive mode) m/z 823 (M+H); Rt 3.58) was synthesized by the synthesis similar to Step A-1, except that tert-butyl 5-methoxy-2-oxo-pentanoate was used instead of tert-butyl 4-methoxy-2-oxo-butyrate. From the obtained intermediate, an intermediate, tert-butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-(3-methoxy-propyl)-undec-4-enoate (ESI (LC/MS positive mode) m/z 773 (M+H); Rt 1.83 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.88 (3H, t, J=6.8 Hz), 1.21-1.38 (14H, m), 1.46-1.67 (6H, m), 1.69-1.78 (1H, m), 1.86 (3H, t, J=2.2 Hz), 1.88-1.94 (1H, m), 1.97-2.11 (2H, m), 2.36-2.50 (4H, m), 3.06 (2H, dq, J=26.9, 6.5 Hz), 3.17 (1H, d, J=9.3 Hz), 3.27-3.37 (5H, m), 3.74 (3H, s), 4.61 (2H, q, J=2.2 Hz), 4.81 (1H, dt, J=10.4, 3.9 Hz), 5.53-5.70 (2H, m), 6.61 (1H, d, J=7.5 Hz), 6.86 (2H, d, J=7.9 Hz), 7.00 (2H, d, J=8.8 Hz).

ESI (LC/MS positive mode) m/z 672 (M+H); Rt 2.70 min.

No. 5508503

(E)-(2R,3S)-3-[(S)-2-(4-But-2-ynyloxy-phenyl)-1-methoxycarbonyl-ethylcarbamoyl]-2-hydroxy-2-methoxymethyl-12-oxo-nonadec-4-enoic acid

[Chem. 269]

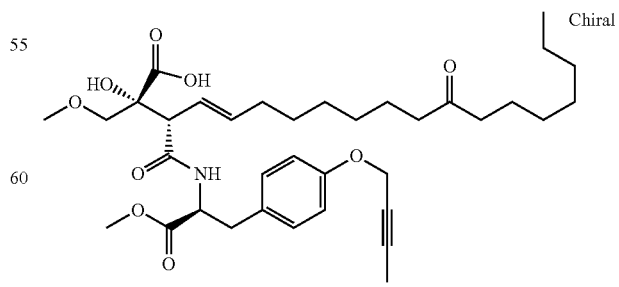

An intermediate, tert-butyl (E)-(2R,3S)-11-(2-heptyl-[1,3] dioxolan-2-yl)-2-hydroxy-3-((S)-4-isopropyl-5,5-diphenyl- 2-thioxo-oxazolidine-3-carbonyl)-2-methoxymethyl-undec-4-enoate (ESI (LC/MS positive mode) m/z 795 (M+H); Rt 3.88 min.) was synthesized by the synthesis similar to Step A-1, except that tert-butyl 3-methoxy-2-oxo-propionate was used instead of tert-butyl 4-methoxy-2-oxo-butyrate. From the obtained intermediate, an intermediate, tert-butyl (E)-(2R,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-methoxymethyl-undec-4-enoate (ESI (LC/MS positive mode) m/z 747 (M+H); Rt 1.67 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.88 (3H, t, J=6.8 Hz), 1.18-1.36 (14H, m), 1.50-1.62 (4H, m), 1.86 (3H, t, J=2.4 Hz), 1.93-2.05 (2H, m), 2.34-2.47 (4H, m), 2.96-3.10 (2H, m), 3.23-3.34 (4H, m), 3.40 (1H, d, J=9.7 Hz), 3.55 (1H, d, J=9.7 Hz), 3.69 (3H, s), 4.56-4.63 (2H, m), 4.71-4.82 (1H, m), 5.56-5.71 (2H, m), 6.85 (2H, d, J=8.4 Hz), 7.02 (2H, d, J=8.8 Hz).

ESI (LC/MS positive mode) m/z 644 (M+H); Rt 2.60 min.

No. 5509211

(E)-(2R,3S)-3-[(S)-2-(4-But-2-ynyloxy-phenyl)-1-methoxycarbonyl-ethylcarbamoyl]-2-hydroxy-2-methoxymethyl-12-oxo-nonadec-4-enoic acid

[Chem. 270]

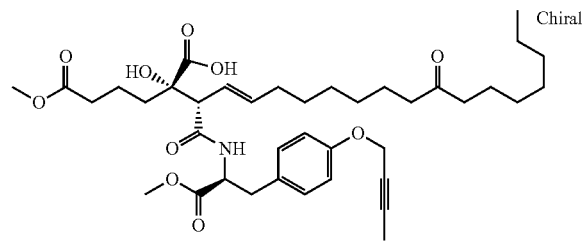

An intermediate, 6-methyl 1-tert-butyl (S)-2-[(E)-(S)-9-(2-heptyl-[1,3]dioxolan-2-yl)-1-((S)-4-isopropyl-5,5-diphenyl-2-thioxo-oxazolidine-3-carbonyl)-non-2-enyl]-2-hydroxy-hexanedioate (ESI (LC/MS positive mode) m/z 851 (M+H); Rt 3.82 min.) was synthesized by the synthesis similar to Step A-1, except that 5-methyl 1-tert-butyl 2-oxo-hexanedioate was used instead of tert-butyl 4-methoxy-2-oxo-butyrate. From the obtained intermediate, an intermediate, 6-methyl 1-tert-butyl (S)-2-[(E)-(S)-1-[(S)-2-(4-but-2-ynyloxy-phenyl)-1-methoxycarbonyl-ethylcarbamoyl]-9-(2-heptyl-[1,3]dioxolan-2-yl)-non-2-enyl]-2-hydroxy-hexanedioate (ESI (LC/MS positive mode) m/z 801 (M+H); Rt 1.75 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.88 (3H, t, J=7.1 Hz), 1.26 (14H, ddd, J=28.0, 19.2, 6.4 Hz), 1.47-1.62 (6H, m), 1.77-1.83 (2H, m), 1.87 (3H, dd, J=6.8, 4.2 Hz), 1.93-2.10 (2H, m), 2.27 (2H, t, J=7.1 Hz), 2.36-2.51 (4H, m), 3.05 (2H, ddd, J=23.2, 14.1, 6.0 Hz), 3.17 (1H, d, J=9.3 Hz), 3.65 (3H, s), 3.74 (3H, s), 4.61 (2H, q, J=2.2 Hz), 4.80 (1H, q, J=6.5 Hz), 5.36 (1H, s), 5.54 (1H, dd, J=15.2, 9.0 Hz), 5.65 (1H, dt, J=16.3, 5.6 Hz), 6.64 (1H, d, J=7.5 Hz), 6.86 (2H, d, J=8.4 Hz), 7.01 (2H, d, J=8.8 Hz).

ESI (LC/MS positive mode) m/z 700 (M+H); Rt 2.75 min.

No. 5509213

(S)-2-{(E)-(S)-1-[(S)-2-(4-But-2-ynyloxy-phenyl)-1-carboxy-ethylcarbamoyl]-10-oxo-heptadec-2-enyl}-2-hydroxy-hexanedioic acid

[Chem. 271]

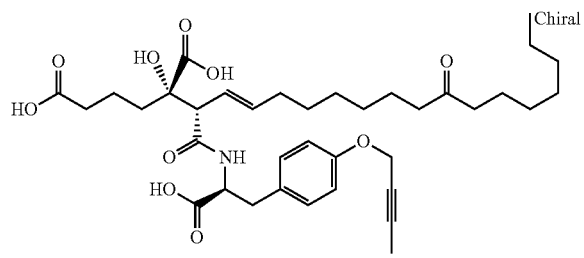

The title compound was obtained by the synthesis by a method similar to that of No. 5507803, (S)-2-{(E)-(S)-1-[(S)-2-(4-but-2-ynyloxy-phenyl)-1-carboxy-ethylcarbamoyl]-10-oxo-heptadec-2-enyl}-2-hydroxy-pentanedioic acid, except that No. 5509211, 6-methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-hexanedioate was used instead of No. 5507802, 5-methyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-pentanedioate.

$^1$H-NMR (CD$_3$OD) δ: 0.90 (3H, t, J=7.1 Hz), 1.22-1.38 (14H, m), 1.41-1.60 (6H, m), 1.68-1.80 (2H, m), 1.81 (3H, t, J=2.4 Hz), 1.92-2.03 (2H, m), 2.15-2.26 (2H, m), 2.42-2.46 (4H, m), 2.92 (1H, dd, J=14.1, 8.8 Hz), 3.12-3.18 (1H, m), 3.21 (1H, d, J=7.1 Hz), 4.54-4.65 (3H, m), 5.47-5.63 (2H, m), 6.85 (2H, d, J=8.8 Hz), 7.13 (2H, d, J=8.4 Hz).

ESI (LC/MS positive mode) m/z 672 (M+H); Rt 2.15 min.

No. 5509214

(E)-(2S,3S)-3-[(S)-2-(4-But-2-ynyloxy-phenyl)-1-methoxycarbonyl-ethylcarbamoyl]-2-(2,2-difluoro-ethyl)-2-hydroxy-12-oxo-nonadec-4-enoic acid

[Chem. 272]

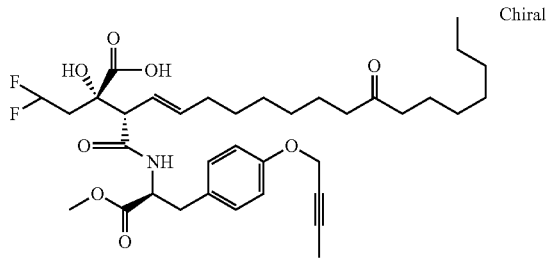

An intermediate, tert-butyl (E)-(2S,3S)-2-(2,2-difluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate (ESI (LC/MS positive mode) m/z 815 (M+H); Rt 3.93 min.) was synthesized by the synthesis similar to Step A-1, except that tert-butyl 4,4-difluoro-2-oxo-butyrate was used instead of tert-butyl 4-methoxy-2-oxo-butyrate. From the obtained intermediate, an intermediate, tert-butyl (E)-(2S,3S)-3-[(S)-2-(4-but-2-ynyloxy-phenyl)-1-methoxycarbonyl-ethylcarbamoyl]-2-(2,2-difluoro-ethyl)-11-(2-heptyl-[1,3]dioxolan-2-yl)-2-hydroxy-undec-4-enoate (ESI (LC/MS positive mode) m/z 764 (M+H); Rt 1.85 min.) was obtained by the synthesis similar to Step A-2a, except that methyl (S)-2-amino-3-(4-but-2-ynyloxy-phenyl)-propionate was used instead of methyl (S)-2-amino-3-(4-butoxy-phenyl)-propionate. From the obtained intermediate, the title compound was obtained by the synthesis similar to Step A-3.

$^1$H-NMR (CDCl$_3$) δ: 0.87 (3H, t, J=7.1 Hz), 1.15-1.36 (14H, m), 1.49-1.61 (4H, m), 1.85 (3H, t, J=2.4 Hz), 1.98-2.13 (3H, m), 2.28-2.46 (5H, m), 3.01 (2H, ddd, J=31.9, 14.0, 5.8 Hz), 3.21 (1H, d, J=8.4 Hz), 3.69 (3H, s), 4.58 (2H, q, J=2.2 Hz), 4.68-4.79 (1H, m), 5.52-5.72 (2H, m), 5.94 (1H, t, J=55.8 Hz), 6.83 (2H, d, J=8.8 Hz), 6.98 (2H, d, J=8.4 Hz).

ESI (LC/MS positive mode) m/z 664 (M+H); Rt 2.78 min.

No. 5515488 (E)-(2S,3S)-3-[(S)-2-(4-Butoxy-phenyl)-1-methoxycarbonyl-ethylcarbamoyl]-12,12-difluoro-2-hydroxy-2-propyl-nonadec-4-enoic acid was produced according to the following synthetic scheme.

[Chem. 273]

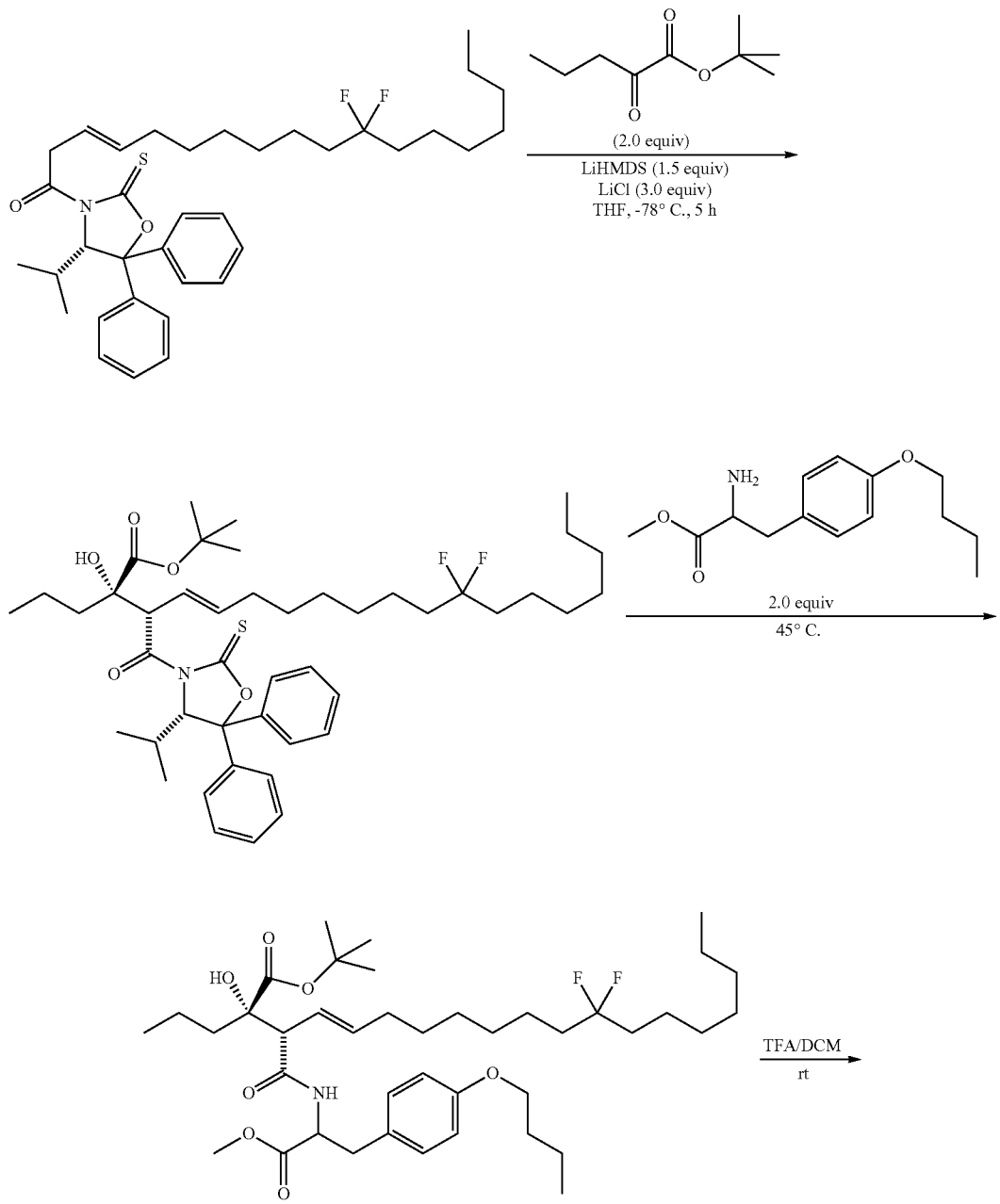

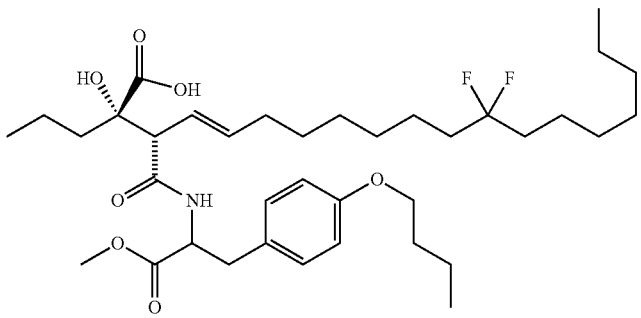

An intermediate, tert-butyl (E)-(2S,3S)-12,12-difluoro-2-hydroxy-3-((S)-4-isopropyl-5,5-diphenyl-2-thioxo-oxazolidine-3-carbonyl)-2-propyl-nonadec-4-enoate (ESI (LC/MS positive mode) m/z 771 (M+H); Rt 3.83 min.) was synthesized by the synthesis similar to Step B-6, except that tert-butyl 2-oxo-pentanoate was used instead of tert-butyl 4-methoxy-2-oxo-butyrate. From the obtained intermediate, an intermediate, tert-butyl (E)-(2S,3S)-3-[(S)-2-(4-butoxy-phenyl)-1-methoxycarbonyl-ethylcarbamoyl]-12,12-difluoro-2-hydroxy-2-propyl-nonadec-4-enoate (ESI (LC/MS positive mode) m/z 724 (M+H); Rt 2.18 min.) was obtained by the synthesis similar to Step B-7. From the obtained intermediate, the title compound was obtained by the synthesis similar to Step B-8.

$^1$H-NMR (CDCl$_3$) δ: 0.82 (3H, t, J=7.1 Hz), 0.88 (3H, t, J=6.8 Hz), 0.98 (3H, dd, J=17.4, 9.9 Hz), 1.13-1.54 (22H, m), 1.66-1.88 (8H, m), 1.93-2.09 (2H, m), 2.94-3.09 (2H, m), 3.11-3.23 (1H, m), 3.70 (3H, s), 3.90 (2H, t, J=6.4 Hz), 4.69-4.83 (1H, m), 5.54-5.65 (1H, m), 5.67-5.80 (1H, m), 6.76 (2H, d, J=8.4 Hz), 6.94 (2H, d, J=8.4 Hz).

ESI (LC/MS positive mode) m/z 669 (M+H); Rt 0.92 min.

No. 5515490

(E)-(2S,3S)-3-[(S)-2-(4-Butoxy-phenyl)-1-methylcarbamoyl-ethylcarbamoyl]-12,12-difluoro-2-hydroxy-2-propyl-nonadec-4-ene

[Chem. 274]

Chiral

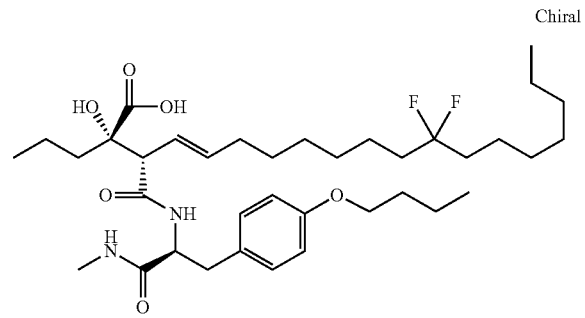

From tert-butyl (E)-(2S,3S)-12,12-difluoro-2-hydroxy-3-((S)-4-isopropyl-5,5-diphenyl-2-thioxo-oxazolidine-3-carbonyl)-2-propyl-nonadec-4-enoate (ESI (LC/MS positive mode) m/z 771 (M+H); Rt 3.83 min.), which is a synthetic intermediate of No. 5515488, (E)-(2S,3S)-3-[(S)-2-(4-butoxy-phenyl)-1-methoxycarbonyl-ethylcarbamoyl]-12,12-difluoro-2-hydroxy-2-propyl-nonadec-4-enoic acid, an intermediate, tert-butyl (E)-(2S,3S)-3-[(S)-2-(4-butoxy-phenyl)-1-methylcarbamoyl-ethylcarbamoyl]-11-heptylsulfanyl-2-hydroxy-2-propyl-undec-4-enoate (ESI (LC/MS positive mode) m/z 706 (M+H); Rt 1.70 min.) was obtained by the synthesis similar to Step B-7, except that (S)-2-amino-3-(4-butoxy-phenyl)-N-methyl-propionamide was used instead of methyl (S)-2-amino-3-(4-but-2-ynyloxy-phenyl)-propionate. From the obtained intermediate, the title compound was obtained by the synthesis similar to Step B-8.

$^1$H-NMR (CDCl$_3$) δ: 0.82 (3H, t, J=7.1 Hz), 0.88 (3H, t, J=6.8 Hz), 0.98 (3H, dd, J=17.4, 9.9 Hz), 1.13-1.54 (22H, m), 1.66-1.88 (8H, m), 1.93-2.09 (2H, m), 2.94-3.09 (2H, m), 3.11-3.23 (1H, m), 3.70 (3H, s), 3.90 (2H, t, J=6.4 Hz), 4.69-4.83 (1H, m), 5.54-5.65 (1H, m), 5.67-5.80 (1H, m), 6.76 (2H, d, J=8.4 Hz), 6.94 (2H, d, J=8.4 Hz).

ESI (LC/MS positive mode) m/z 669 (M+H); Rt 0.92 min.

No. 5515491

(E)-(2S,3S)-3-[(S)-2-(4-Butoxy-phenyl)-1-methoxycarbonyl-ethylcarbamoyl]-11-(heptane-1-sulfonyl)-2-hydroxy-2-propyl-undec-4-enoic acid was produced according to the following synthetic scheme.

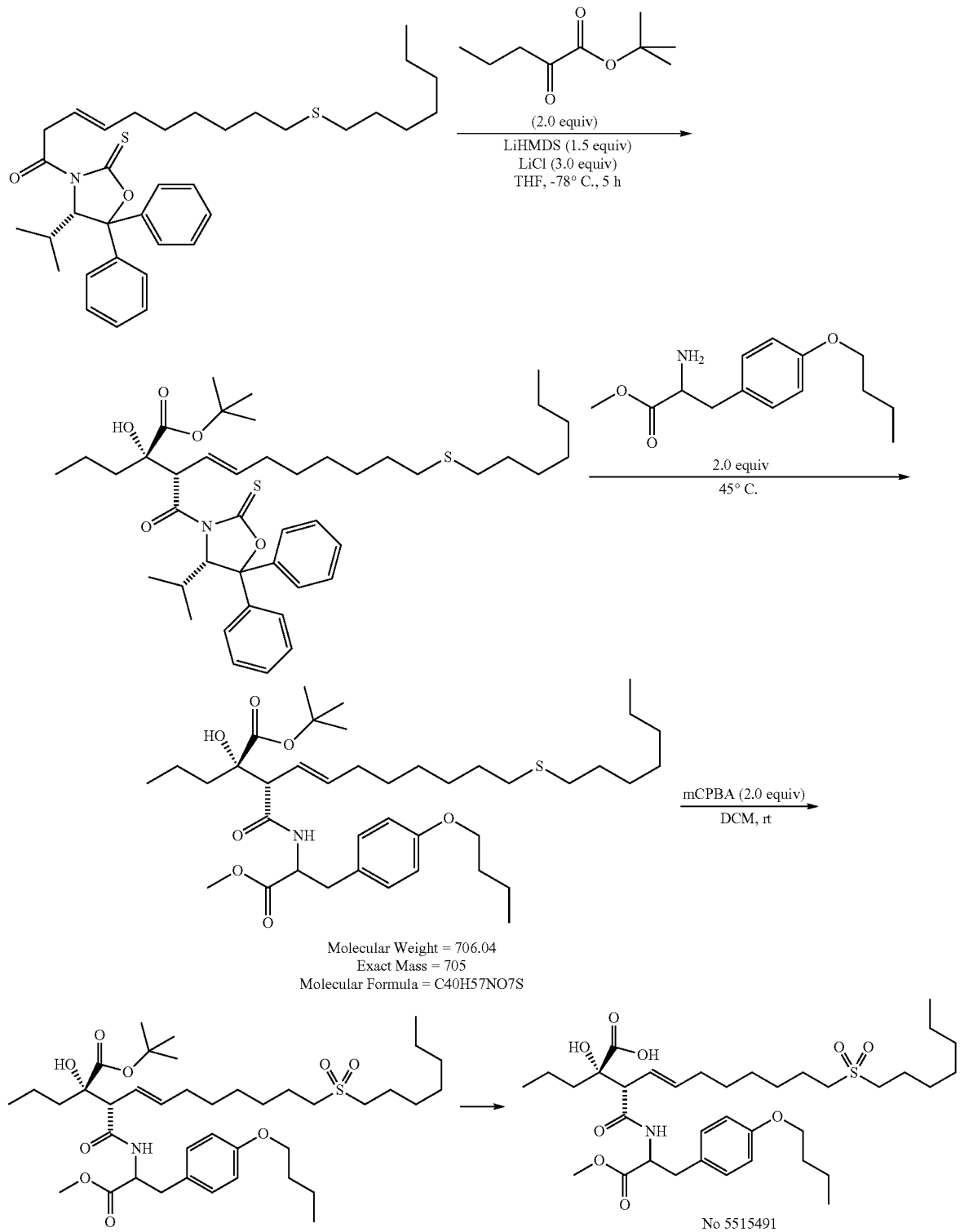

An intermediate, tert-butyl (E)-(2S,3S)-11-heptylsulfanyl-2-hydroxy-3-((S)-4-isopropyl-5,5-diphenyl-2-thioxo-oxazolidine-3-carbonyl)-2-propyl-undec-4-enoate (ESI (LC/MS positive mode) m/z 753 (M+H); Rt 2.07 min.) was synthesized by the synthesis similar to Step C-5, except that tert-butyl 2-oxo-pentanoate was used instead of tert-butyl 4-methoxy-2-oxo-butyrate.

From the obtained intermediate, an intermediate, tert-butyl (E)-(2S,3S)-3-[(S)-2-(4-butoxy-phenyl)-1-methoxycarbonyl-ethylcarbamoyl]-11-heptylsulfanyl-2-hydroxy-2-propyl-undec-4-enoate (ESI (LC/MS positive mode) m/z 707 (M+H); Rt 2.32 min.) was obtained by the synthesis similar to Step C-6, except that methyl (S)-2-amino-3-(4-butoxy-phenyl)-propionate was used instead of methyl (S)-2-amino-3-(4-but-2-ynyloxy-phenyl)-propionate.

From the obtained intermediate, an intermediate, tert-butyl (E)-(2S,3S)-3-[(S)-2-(4-butoxy-phenyl)-1-methoxycarbonyl-ethylcarbamoyl]-11-(heptane-1-sulfonyl)-2-hydroxy-2-propyl-undec-4-enoate (ESI (LC/MS positive mode) m/z 739 (M+H); Rt 3.48 min.) was obtained by a reaction similar to Step C-7.

From the obtained intermediate, the title compound was obtained by the synthesis similar to Step C-8.

$^1$H-NMR (CDCl$_3$) δ: 0.83 (3H, t, J=7.1 Hz), 0.89 (3H, q, J=7.2 Hz), 0.96 (3H, dd, J=13.9, 6.4 Hz), 1.15-1.52 (20H, m), 1.66-1.89 (6H, m), 1.91-2.10 (2H, m), 2.90-3.07 (6H, m), 3.19 (1H, d, J=8.8 Hz), 3.70 (3H, s), 3.90 (2H, t, J=6.6 Hz), 4.74 (1H, dd, J=6.3, 3.2 Hz), 5.50-5.74 (2H, m), 6.77 (2H, d, J=8.4 Hz), 6.98 (2H, d, J=8.4 Hz).

ESI (LC/MS positive mode) m/z 682 (M+H); Rt 2.77 min.

No. 5515492

(E)-(2S,3S)-3-[(S)-2-(4-Butoxy-phenyl)-1-methylcarbamoyl-ethylcarbamoyl]-11-(heptane-1-sulfonyl)-2-hydroxy-2-propyl-undec-4-enoic acid

[Chem. 276]

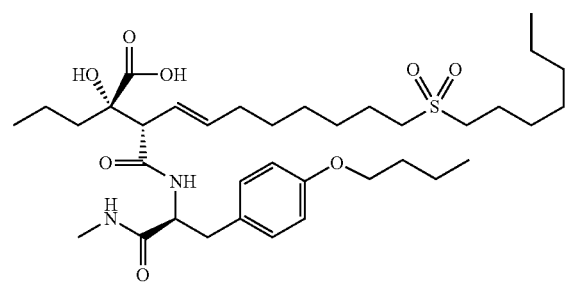

From tert-butyl (E)-(2S,3S)-11-heptylsulfanyl-2-hydroxy-3-((S)-4-isopropyl-5,5-diphenyl-2-thioxo-oxazolidine-3-carbonyl)-2-propyl-undec-4-enoate (ESI (LC/MS positive mode) m/z 753 (M+H); Rt 2.07 min.), which is a synthesis intermediate of No. 5515491, (E)-(2S,3S)-3-[(S)-2-(4-butoxy-phenyl)-1-methoxycarbonyl-ethylcarbamoyl]-11-(heptane-1-sulfonyl)-2-hydroxy-2-propyl-undec-4-enoic acid, tert-butyl (E)-(2S,3S)-3-[(S)-2-(4-butoxy-phenyl)-1-methylcarbamoyl-ethylcarbamoyl]-11-heptylsulfanyl-2-hydroxy-2-propyl-undec-4-enoate (ESI (LC/MS positive mode) m/z 707 (M+H); Rt 2.32 min.) was obtained by the synthesis similar to Step C-6, except that (S)-2-amino-3-(4-butoxy-phenyl)-N-methyl-propionamide was used instead of methyl (S)-2-amino-3-(4-but-2-ynyloxy-phenyl)-propionate.

From the obtained intermediate, the title compound was obtained by the synthesis similar to Steps C-7 and C-8.

$^1$H-NMR (CDCl$_3$) δ: 0.77-0.92 (6H, m), 0.96 (3H, t, J=7.3 Hz), 1.11-1.54 (22H, m), 1.71-1.85 (8H, m), 1.92-2.09 (2H, m), 2.67 (3H, s), 2.85-3.04 (6H, m), 3.08-3.29 (1H, m), 3.82-3.96 (2H, m), 4.37-4.56 (1H, m), 5.46-5.82 (2H, m), 6.70-6.83 (2H, m), 7.04 (2H, d, J=7.9 Hz).

ESI (LC/MS positive mode) m/z 682 (M+H); Rt 2.32 min.

No. 5519559

(E)-(2S,3S)-3-[(S)-2-(4-Butoxy-phenyl)-1-carbamoyl-ethylcarbamoyl]-2-hydroxy-2-(2-methoxy-ethyl)-12-oxo-nonadec-4-enoic acid

[Chem. 277]

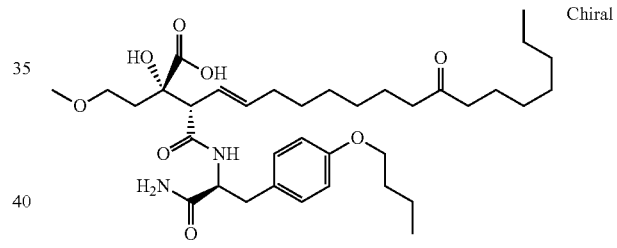

An intermediate was synthesized by a method similar to that of No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate, except that (S)-2-amino-3-(4-butoxy-phenyl)-propionamide was used instead of (S)-2-amino-3-(4-butoxy-phenyl)-N-methyl-propionamide, and the title compound was obtained by a synthetic method similar to that of No. 5444958, (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoic acid.

$^1$H-NMR (CD$_3$OD) δ: 0.89 (3H, t, J=6.8 Hz), 0.98 (3H, t, J=7.3 Hz), 1.21-1.37 (14H, m), 1.44-1.65 (7H, m), 1.70-1.77 (2H, m), 1.91-2.07 (3H, m), 2.43 (4H, t, J=7.5 Hz), 2.81 (1H, dd, J=14.3, 9.5 Hz), 3.09 (1H, dd, J=13.9, 5.1 Hz), 3.19 (1H, d, J=8.4 Hz), 3.23 (3H, s), 3.37-3.44 (2H, m), 3.93 (2H, t, J=6.4 Hz), 4.56-4.61 (1H, m), 5.52 (2H, dt, J=22.8, 9.2 Hz), 6.79 (2H, d, J=7.5 Hz), 7.13 (2H, d, J=8.4 Hz), 8.03 (1H, d, J=8.4 Hz).

ESI (LC/MS positive mode) m/z 647 (M+H); Rt 2.63 min.

5527776

(E)-(2S,3S)-3-[(S)-2-(4-Butoxy-phenyl)-1-carboxy-ethylcarbamoyl]-2-(2,2-difluoro-ethyl)-2-hydroxy-12-oxo-nonadec-4-enoic acid

[Chem. 278]

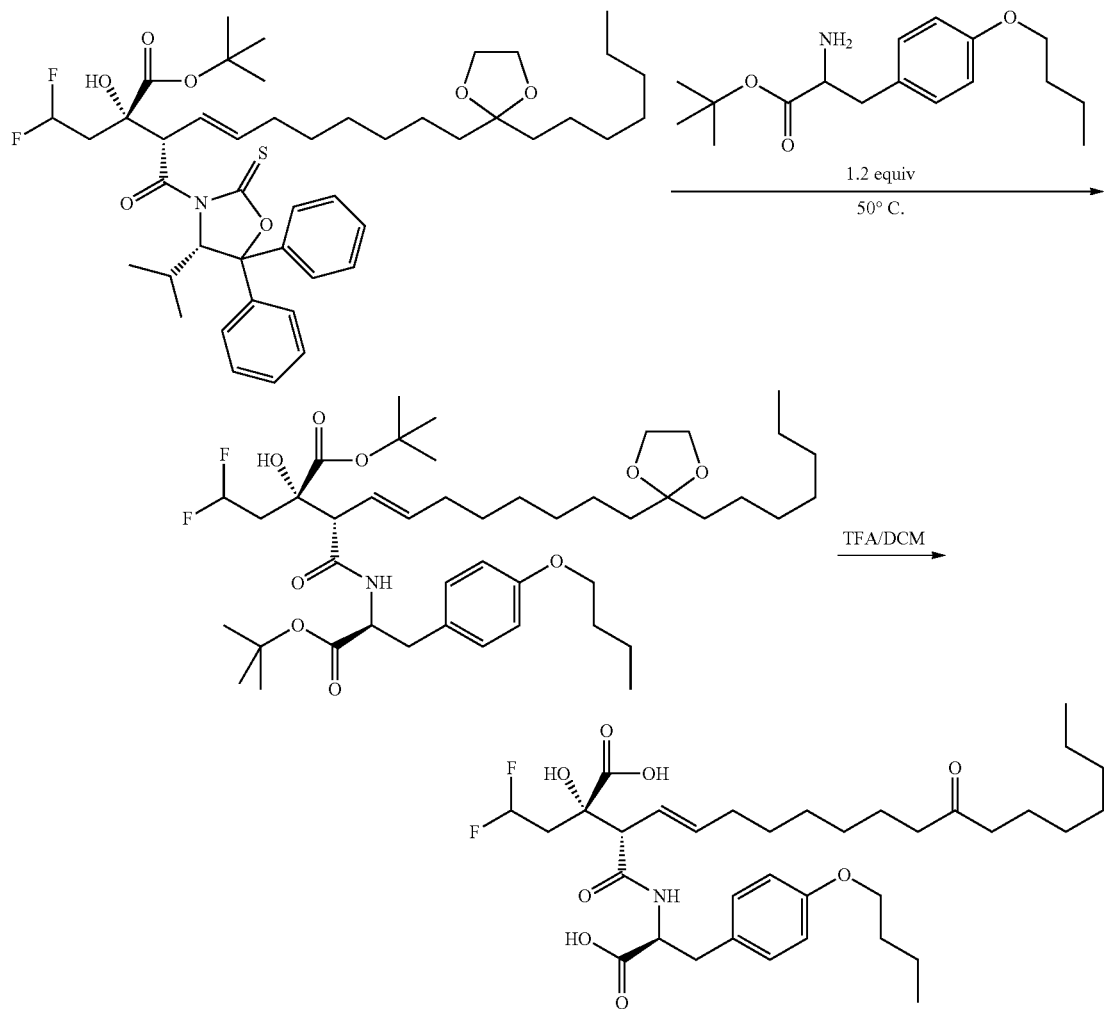

The title compound was synthesized by a method similar to that of No. 5509214, (E)-(2S,3S)-3-[(S)-2-(4-but-2-ynyloxy-phenyl)-1-methoxycarbonyl-ethylcarbamoyl]-2-(2,2-difluoro-ethyl)-2-hydroxy-12-oxo-nonadec-4-enoic acid, except that tert-butyl (S)-2-amino-3-(4-butoxy-phenyl)-propionate was used instead of No. 5509214, methyl (S)-2-amino-3-(4-butoxy-phenyl)-propionate.

$^1$H-NMR (CD$_3$OD) δ: 0.89 (3H, t, J=6.8 Hz), 0.98 (3H, t, J=7.3 Hz), 1.21-1.37 (14H, m), 1.44-1.58 (6H, m), 1.68-1.77 (2H, m), 1.92-2.16 (4H, m), 2.43 (4H, td, J=7.3, 2.1 Hz), 2.90 (1H, t, J=11.2 Hz), 3.16 (1H, dd, J=17.4, 7.7 Hz), 3.19-3.25 (1H, m), 3.92 (2H, t, J=6.4 Hz), 4.54-4.62 (1H, m), 5.46-5.61 (2H, m), 5.94 (1H, t, J=54.9 Hz), 6.78 (2H, d, J=8.8 Hz), 7.10 (2H, d, J=8.8 Hz).

ESI (LC/MS positive mode) m/z 654 (M+H); Rt 2.90 min.

No. 5328362

Ethyl (S)-2-amino-3-(4-but-2-ynyloxy-phenyl)-propionate hydrochloride

The synthetic scheme of the above compound is as follows.

[Chem. 279]

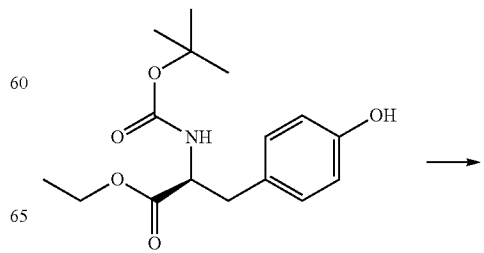

-continued

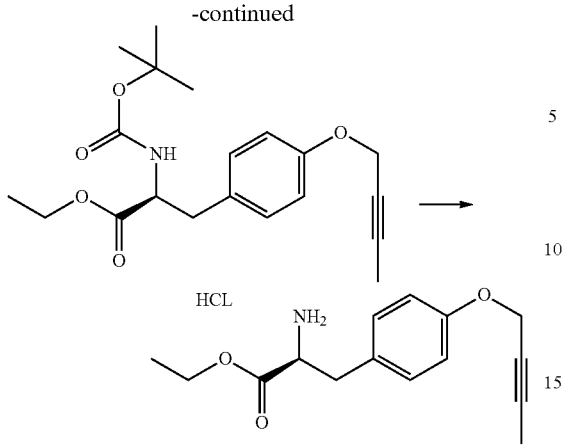

No 5328632

A commercially available reagent of ethyl (S)-2-tert-butoxycarbonylamino-3-(4-hydroxy-phenyl)-propionate (4.84 g, 15.6 mmol) was dissolved in N,N-dimethylformamide (39 mL), and 1-bromo-2-butyne (1.65 mL, 18.8 mmol) and potassium carbonate (3.25 g, 23.5 mmol) were then added at room temperature. After stirring at 60° C. for 6 hours, and the reaction solution was cooled to room temperature. 1-Bromo-2-butyne (0.55 mL, 6.28 mmol) was added at room temperature, and the mixture was then stirred at 60° C. for 5 hours. The reaction solution was cooled to room temperature, and potassium carbonate (0.433 g, 3.13 mmol) was then added. After stirring at 60° C. for 4.5 hours, the reaction solution was cooled to room temperature. Water (70 mL) was added, and the mixture was then extracted twice with ethyl acetate (70 mL). The organic layer was washed with saturated aqueous solution (30 mL) of sodium chloride, dried over anhydrous sodium sulfate, and filtered. The solvent was distilled off under reduced pressure. The residue was purified on Biotage (silica gel, n-hexane/ethyl acetate) to obtain 5.02 g (13.9 mmol, yield 89%) of ethyl (S)-2-tert-butoxycarbonylamino-3-(4-but-2-ynyloxy-phenyl)-propionate.

$^1$H-NMR (CDCl$_3$) δ: 1.22 (3H, t, J=7.2 Hz), 1.41 (9H, s), 1.85 (3H, t, J=2.3 Hz), 2.87-3.08 (2H, m), 4.14 (2H, q, J=7.2 Hz), 4.50 (1H, m), 4.60 (2H, q, J=2.3 Hz), 4.96 (1H, br.d, J=8.0 Hz), 6.87 (2H, d, J=8.7 Hz), 7.03 (2H, d, J=8.7 Hz)

ESI (LC/MS positive mode) m/z 362 (M+H); Rt 2.57 min.

No. 5328632

After dissolving 4.97 g of ethyl (S)-2-tert-butoxycarbonylamino-3-(4-but-2-ynyloxy-phenyl)-propionic acid (13.8 mmol) in ethyl acetate (50 mL), 4 M hydrogen cloride/ethyl acetate (10.3 mL, 41.2 mmol) was added. The mixture was stirred at room temperature for 3 hours and 4 M hydrogen chloride/ethyl acetate (10.3 mL, 41.2 mmol) was then added. The mixture was stirred at room temperature for 3 hours. Precipitated solid was then filtered. The solid obtained was washed twice with ethyl acetate (50 mL) to obtain 3.74 g (12.6 mmol, 91% yield) of the title compound, No. 5328632.

$^1$H-NMR (DMSO-d$_6$) δ: 1.10 (3H, t, J=7.3 Hz), 1.81 (3H, t, J=2.3 Hz), 3.00 (1H, dd, J=14.1, 7.6 Hz), 3.13 (1H, dd, J=14.1, 5.6 Hz), 4.02-4.19 (3H, m), 4.70 (2H, q, J=2.3 Hz), 6.90 (2H, d, J=8.6 Hz), 7.16 (2H, d, J=8.6 Hz)

ESI (LC/MS positive mode) m/z 262 (M+H); Rt 1.13 min.

Synthesis of No. 5321161

[Chem. 280]

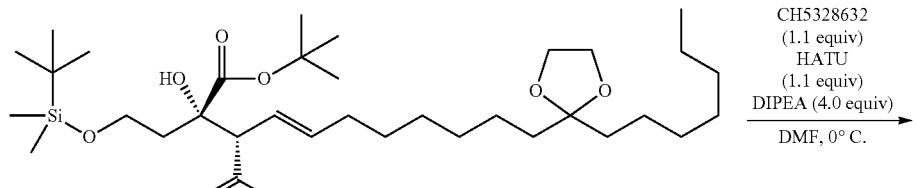

No 4976198

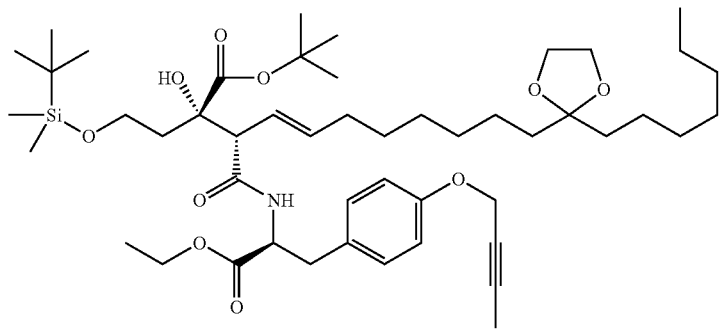

-continued

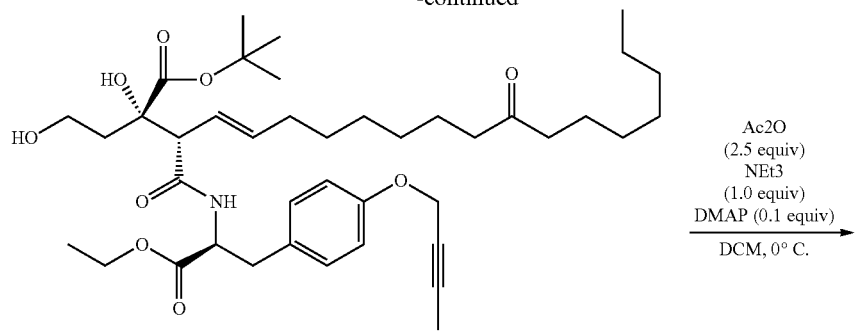

No 5328627

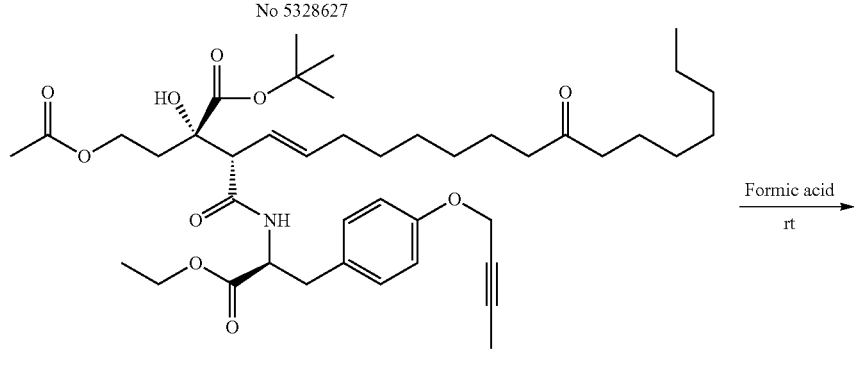

No 5328456

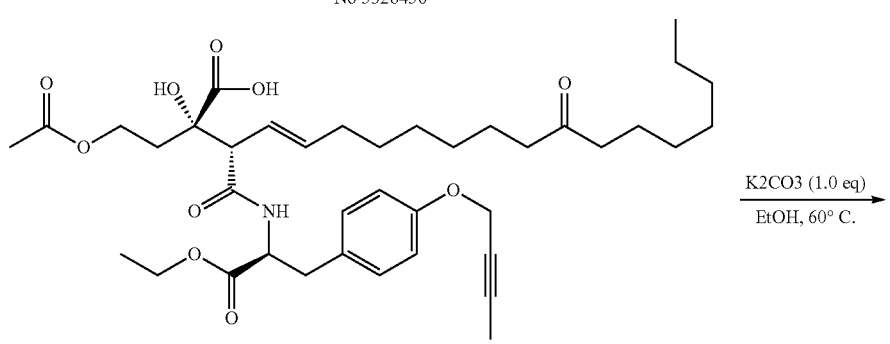

No5328412-000

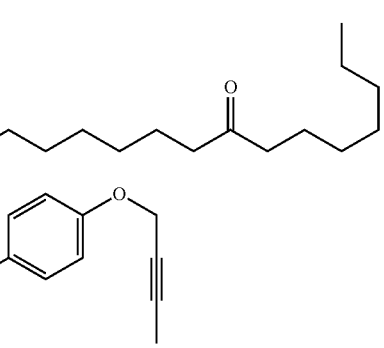

No 5321166

No. 5328627, 1-tert-butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (2.81 g, 4.47 mmol) was dissolved in N,N-dimethylformamide (70 mL) and the mixture was then cooled to 0° C. in an ice bath. No. 5328632 (ethyl (S)-2-amino-3-(4-but-2-yloxy-phenyl)-propionate hydrochloride; 1.46 g, 4.90 mmol), N,N-diisopropylethylamine (3.1 mL, 17.80 mmol), and O-(7-azabenzotriazol-1-yl)-N,N,N',N'-tetramethyluronium hexafluorophosphate (1.87 g, 4.92 mmol) were added in this order, and the mixture was then stirred at 0° C. for 1.5 hours. After quenching with a mixture of a cooled solution (14 mL) of 0.5 M potassium hydrogen sulfate and water (84 mL), the mixture was extracted with 20% ethyl acetate/n-hexane (54 mL). The aqueous layer was further extracted three times with 20% ethyl acetate/n-hexane (27 mL). The organic layers were combined, and then washed with a mixture of a saturated aqueous solution (2.8 mL) of sodium chloride and water (14 mL), and with a saturated aqueous solution (14 mL) of sodium chloride in this order. The organic layers were combined, and then dried over anhydrous sodium sulfate. After filtration, the solvent was distilled off under reduced pressure to obtain 3.95 g (4.53 mmol, quant.) of tert-butyl (E)-(2S,3S)-2-[2-(tert-butyl-dimethyl-silanyloxy)-ethyl]-3-[(S)-2-(4-but-2-ynyloxy-phenyl)-1-ethoxycarbonyl-ethylcarbamoyl]-11-(2-heptyl-[1,3]dioxolan-2-yl)-2-hydroxy-undec-4-enoate.

$^1$H-NMR (CDCl$_3$) δ: 0.05 (3H, s), 0.06 (3H, s), 0.87 (3H, t, J=7.0 Hz), 0.89 (9H, s), 1.20 (3H, t, J=7.0 Hz), 1.20-1.65 (22H, m), 1.43 (9H, s), 1.85 (3H, t, J=2.4 Hz), 1.78-2.01 (4H, m), 2.99-3.10 (2H, m), 3.16 (1H, d, J=9.4 Hz), 3.56-3.72 (2H, m), 3.91 (4H, s), 4.12 (2H, q, J=7.0 Hz), 4.36 (1H, s), 4.60 (2H, q, J=2.4 Hz), 4.76-4.83 (1H, m), 5.49 (1H, dd, J=15.2, 9.4 Hz), 5.65 (1H, dt, J=15.2, 6.7 Hz), 6.85 (2H, d, J=8.6 Hz), 7.06-7.10 (3H, m)

ESI (LC/MS positive mode) m/z 872 (M+H); Rt 4.95 min.

No. 5328627, tert-butyl (E)-(2S,3S)-3-[(S)-2-(4-but-2-ynyloxy-phenyl)-1-ethoxycarbonyl-ethylcarbamoyl]-2-hydroxy-2-(2-hydroxy-ethyl)-12-oxo-nonadec-4-enoate

[Chem. 281]

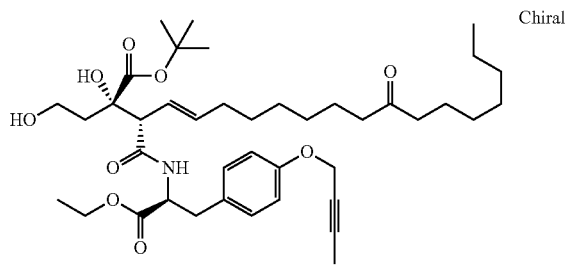

tert-Butyl (E)-(2S,3S)-2-[2-(tert-butyl-dimethyl-silanyloxy)-ethyl]-3-[(S)-2-(4-but-2-ynyloxy-phenyl)-1-ethoxycarbonyl-ethylcarbamoyl]-11-(2-heptyl-[1,3]dioxolan-2-yl)-2-hydroxy-undec-4-enoate (3.92 g, 4.49 mmol) was dissolved in acetonitrile (43 mL), and an aqueous solution of 0.5 M citric acid (19 mL, 9.50 mmol) was then added. The mixture was then stirred at 60° C. for 2.5 hours. The reaction solution was cooled to room temperature, and a mixture of a saturated aqueous solution (3.0 mL) of sodium chloride and water (60 mL) was then added. The solution was extracted three times with 20% ethyl acetate/n-hexane (32 mL). The organic layers were combined, then washed twice with a saturated aqueous solution (32 mL) of sodium chloride, dried over anhydrous sodium sulfate, and filtered. The solvent was then distilled off under reduced pressure to obtain 3.24 g (4.54 mmol, quant) of No. 5328627.

$^1$H-NMR (CD$_3$OD) δ: 0.88 (3H, t, J=7.0 Hz), 1.21 (3H, t, J=7.2 Hz), 1.20-1.40 (14H, m), 1.43 (9H, s), 1.45-1.57 (4H, m), 1.72 (1H, ddd, J=13.7, 7.3, 5.3 Hz), 1.80 (3H, t, J=2.3 Hz), 1.89-2.03 (3H, m), 2.42 (4H, t, J=7.4 Hz), 2.92 (1H, dd, J=14.1, 9.0 Hz), 3.08 (1H, dd, J=14.1, 5.1 Hz), 3.19 (1H, d, J=9.0 Hz), 3.45-3.63 (2H, m), 4.13 (2H, q, J=7.2 Hz), 4.55-4.63 (3H, m), 5.42-5.65 (2H, m), 6.86 (2H, d, J=8.8 Hz), 7.11 (2H, d, J=8.8 Hz)

ESI (LC/MS positive mode) m/z 714 (M+H); Rt 3.05 min.

No. 5328456, tert-butyl (E)-(2S,3S)-2-(2-acetoxy-ethyl)-3-[(S)-2-(4-but-2-ynyloxy-phenyl)-1-ethoxycarbonyl-ethylcarbamoyl]-2-hydroxy-12-oxo-nonadec-4-enoate

[Chem. 282]

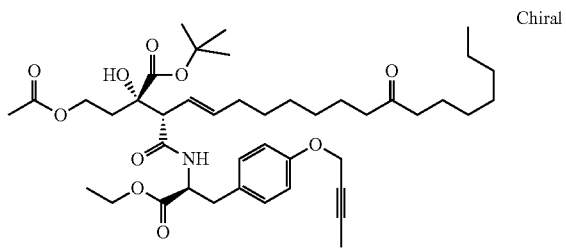

tert-Butyl (E)-(2S,3S)-3-[(S)-2-(4-but-2-ynyloxy-phenyl)-1-ethoxycarbonyl-ethylcarbamoyl]-2-hydroxy-2-(2-hydroxy-ethyl)-12-oxo-nonadec-4-enoate (3.22 g, 4.51 mmol) was dissolved in dichloromethane (64 mL), and the mixture was then cooled to 0° C. in an ice bath. Acetic anhydride (1.07 mL, 11.3 mmol), triethylamine (0.63 mL, 4.52 mmol), and dimethylaminopyridine (55.1 mg, 0.451 mmol) were added in this order, and the mixture was then stirred at 0° C. for 1.5 hours. The mixture was quenched with water (46 mL), and then extracted with dichloromethane (46 mL). The organic layer was washed with a saturated aqueous solution (33 mL) of sodium chloride, then dried over anhydrous sodium sulfate, and filtered. The solvent was distilled off under reduced pressure. The residue was purified on Biotage (silica gel, n-hexane/ethyl acetate) to obtain 2.65 g (3.51 mmol, 78% yield) of No. 5328456.

$^1$H-NMR (CD$_3$OD) δ: 0.90 (3H, t, J=7.0 Hz), 1.24 (3H, t, J=7.2 Hz), 1.20-1.39 (14H, m), 1.46 (9H, s), 1.47-1.60 (4H, m), 1.74 (1H, ddd, J=13.1, 8.0, 4.9 Hz), 1.81 (3H, t, J=2.4 Hz), 1.90-2.10 (3H, m), 1.97 (3H, s), 2.42 (4H, t, J=7.4 Hz), 2.88 (1H, dd, J=14.1, 9.0 Hz), 3.11 (1H, dd, J=14.1, 5.1 Hz), 3.19 (1H, d, J=9.2 Hz), 3.92-4.12 (2H, m), 4.14 (2H, q, J=7.0 Hz), 4.60 (2H, q, J=2.4 Hz), 4.58-4.63 (1H, m), 5.42-5.64 (2H, m), 6.84 (2H, d, J=8.8 Hz), 7.10 (2H, d, J=8.8 Hz)

ESI (LC/MS positive mode) m/z 756 (M+H); Rt 3.44 min.

No. 5328412, (E)-(2S,3S)-2-(2-acetoxy-ethyl)-3-[(S)-2-(4-but-2-ynyloxy-phenyl)-1-ethoxycarbonyl-ethylcarbamoyl]-2-hydroxy-12-oxo-nonadec-4-enoic acid

[Chem. 283]

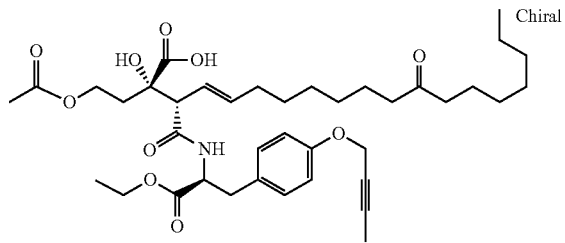

tert-Butyl (E)-(2S,3S)-2-(2-acetoxy-ethyl)-3-[(S)-2-(4-but-2-ynyloxy-phenyl)-1-ethoxycarbonyl-ethylcarbamoyl]-2-hydroxy-12-oxo-nonadec-4-enoate (2.63 g, 3.48 mmol) was dissolved in formic acid (52 mL), and the solution was then stirred at room temperature for 3.5 hours. Formic acid was distilled off under reduced pressure. The residue was then dissolved in ethyl acetate (57 mL), and then washed with a mixture of an aqueous solution (48.9 mL) of 1% sodium bicarbonate and a saturated aqueous solution (8.1 mL) of sodium chloride, further twice with an aqueous solution (50 mL) of 10% ammonium chloride, and then with a saturated aqueous solution (23 mL) of sodium chloride. The organic layer was dried over anhydrous sodium sulfate. After filtration, the solvent was distilled off under reduced pressure to obtain 2.35 g (3.36 mmol, 97% yield) of No. 5328412, (E)-(2S,3S)-2-(2-acetoxy-ethyl)-3-[(S)-2-(4-but-2-ynyloxy-phenyl)-1-ethoxycarbonyl-ethylcarbamoyl]-2-hydroxy-12-oxo-nonadec-4-enoic acid.

$^1$H-NMR (CD$_3$OD) δ: 0.89 (3H, t, J=7.0 Hz), 1.23 (3H, t, J=7.0 Hz), 1.20-1.37 (14H, m), 1.44-1.60 (4H, m), 1.66 (1H, dt, J=13.9, 5.1 Hz), 1.81 (3H, t, J=2.3 Hz), 1.89-2.07 (3H, m), 1.95 (3H, s), 2.12 (1H, dt, J=13.9, 7.8 Hz), 2.42 (4H, t, J=7.2 Hz), 2.89 (1H, dd, J=14.1, 9.0 Hz), 3.11 (1H, dd, J=14.1, 5.1 Hz), 3.19 (1H, d, J=8.6 Hz), 4.00-4.08 (2H, m), 4.14 (2H, q, J=7.0 Hz), 4.57-4.65 (3H, m), 5.42-5.62 (2H, m), 6.84 (2H, d, J=8.6 Hz), 7.10 (2H, d, J=8.6 Hz)

ESI (LC/MS positive mode) m/z 700 (M+H); Rt 2.55 m.

No. 5321166, sodium (E)-(2S,3S)-3-[(S)-2-(4-but-2-ynyloxy-phenyl)-1-ethoxycarbonyl-ethylcarbamoyl]-2-hydroxy-2-(2-hydroxy-ethyl)-12-oxo-nonadec-4-enoate

[Chem. 284]

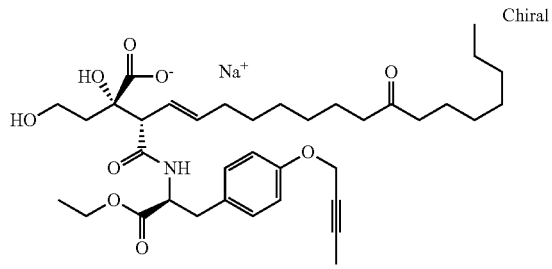

(E)-(2S,3S)-2-(2-Acetoxy-ethyl)-3-[(S)-2-(4-but-2-ynyloxy-phenyl)-1-ethoxycarbonyl-ethylcarbamoyl]-2-hydroxy-12-oxo-nonadec-4-enoic acid (182.7 mg, 0.261 mmol) was dissolved in ethanol (9.7 mL), and potassium carbonate (36.1 mg, 0.261 mmol) was then added at room temperature. The mixture was stirred at an outer temperature of 60° C. for 23 hours, then cooled to room temperature, quenched with a mixture of a saturated aqueous solution (4.0 mL) of sodium chloride and water (8.0 mL), and then extracted with ethyl acetate (16 mL). The aqueous layer was extracted twice with ethyl acetate (8.0 mL). The organic layers were combined, then washed twice with a saturated aqueous solution (5.0 mL) of sodium chloride, then dried over anhydrous sodium sulfate, and filtered. The solvent was distilled off under reduced pressure. After repeating the operation of adding methanol (2.0 mL) to the residue and concentrating the mixture three times, 10% methanol/ethyl acetate (100 mL) was added. Insoluble material was removed by filtration. The filtrate was concentrated, and n-hexane (50 mL) was then added. Precipitated white solid was filtered, and then washed twice with n-hexane (20 mL) to obtain 57.2 mg of the title compound (0.0822 mmol, 31% yield).

$^1$H-NMR (CD$_3$OD) δ: 0.88 (3H, t, J=6.8 Hz), 1.20 (3H, t, J=7.0 Hz), 1.20-1.34 (14H, m), 1.45-1.57 (4H, m), 1.80 (3H, t, J=2.4 Hz), 1.70-2.05 (4H, m), 2.40 (4H, t, J=7.4 Hz), 2.88-3.00 (1H, m), 3.01-3.13 (1H, m), 3.20 (1H, dd, J=10.7, 8.4 Hz), 3.44-3.53 (1H, m), 3.58-3.69 (1H, m), 4.07-4.19 (2H, m), 4.55-4.65 (3H, m), 5.30-5.58 (2H, m), 6.80-6.88 (2H, m), 7.07-7.15 (2H, m)

ESI (LC/MS positive mode) m/z 658 (M+H); Rt 4.44 min.

No. 5456815

(E)-(2S,3S)-3-[(S)-2-(4-But-2-ynyloxy-phenyl)-1-methoxycarbonyl-ethylcarbamoyl]-2-(2-fluoro-ethyl)-2-hydroxy-12-oxo-nonadec-4-enoic acid was produced according to the following synthetic scheme.

[Chem. 285]

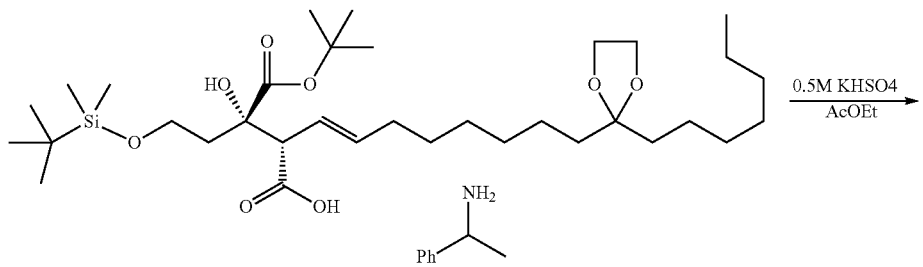

349 350
-continued
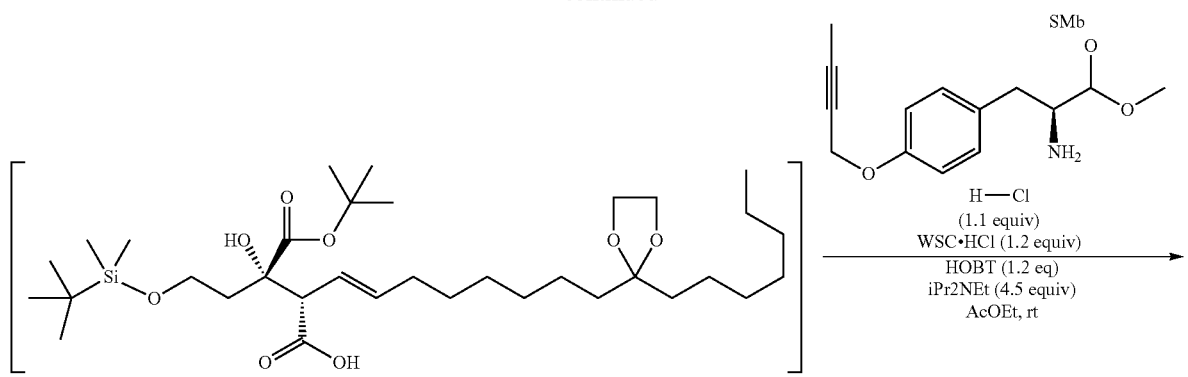
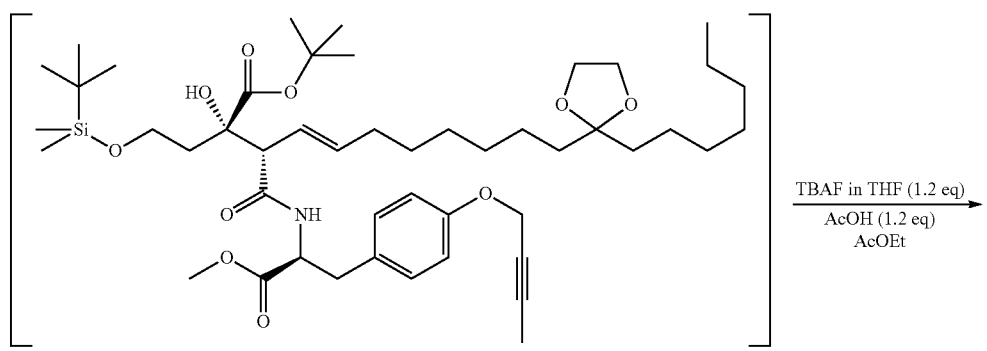
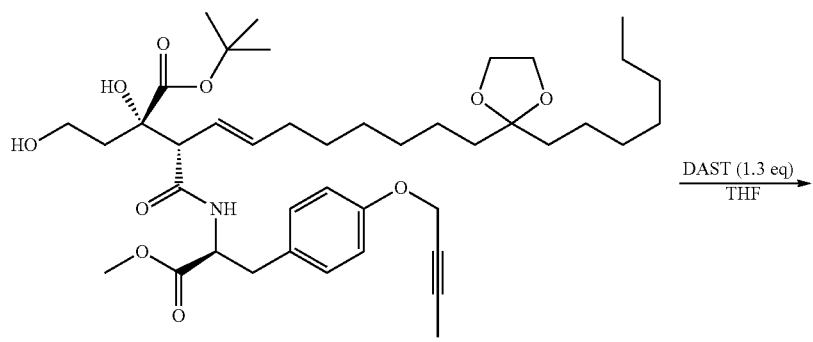
No 5452997
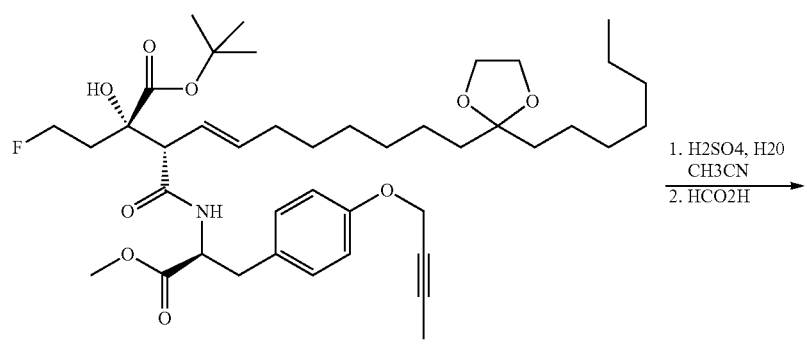

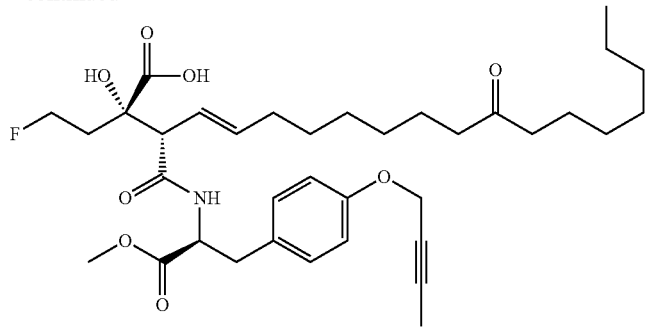

No 5456815

No. 5452997, tert-butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-(2-hydroxy-ethyl)-undec-4-enoate (S)-1-Phenyl-ethylamine salt of 1-tert-butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (1:1; 3.01 g, 4.01 mmol) was dissolved in ethyl acetate (15 mL), and an aqueous solution (15 mL) of 5% potassium hydrogen sulfate was then added. The mixture was stirred vigorously for 30 minutes and then transferred into a separatory funnel. After removing the aqueous layer from the funnel, the ethyl acetate layer was washed with an aqueous solution (15 mL) of 5% sodium chloride, and transferred into a flask. N,N-Diisopropylethylamine (3.15 mL, 18.1 mmol), methyl (S)-2-amino-3-(4-but-2-ynyloxy-phenyl)-propionate hydrochloride (1.25 g, 4.41 mmol), 1-hydroxy-1H-benzotriazole (651 mg, 4.82 mmol), and 1-ethyl-3-(3-dimethylaminopropyl)carbodiimide hydrochloride (923 mg, 4.82 mmol) were then added in order at room temperature. The mixture was stirred at room temperature for 3.5 hours and then quenched with an aqueous solution (30 mL) of 10% citric acid. After separating the mixture and removing the aqueous layer, the ethyl acetate layer was washed with an aqueous solution (30 mL) of 5% sodium chloride, and transferred into a flask. Acetic acid (0.275 mL, 4.80 mmol) was then added. A solution (4.8 mL, 4.80 mmol) of 1 M tetrabutylammonium fluoride in tetrahydrofuran was further added over 3 minutes. The mixture was stirred at room temperature for 25 hours, and then quenched with an aqueous solution (30 mL) of 5% sodium bicarbonate. After separating the mixture and removing the aqueous layer, the ethyl acetate layer was washed with a saturated aqueous solution (30 mL) of sodium chloride, dried over anhydrous sodium sulfate, and filtered. The solvent was distilled off under reduced pressure. The residue was purified on Biotage (silica gel, n-hexane/acetone) to obtain 1.40 g (18.8 mmol, 47% yield) of tert-butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-(2-hydroxy-ethyl)-undec-4-enoate.

¹H-NMR (CD₃OD) δ: 0.88 (3H, t, J=7.0 Hz), 1.18-1.35 (14H, m), 1.43 (9H, s), 1.50-1.60 (4H, m), 1.72 (1H, ddd, J=13.0, 7.4, 5.4 Hz), 1.80 (3H, t, J=2.4 Hz), 1.90-2.03 (3H, m), 2.90 (1H, dd, J=14.1, 9.0 Hz), 3.09 (1H, dd, J=14.1, 5.1 Hz), 3.19 (1H, d, J=9.2 Hz), 3.47-3.64 (2H, m), 3.69 (3H, s), 3.88 (4H, s), 4.60 (2H, q, J=2.4 Hz), 4.63 (1H, dd, J=9.0, 5.1 Hz), 5.46 (1H, dd, J=15.3, 9.2 Hz), 5.58 (1H, dd, J=15.3, 6.4 Hz), 6.84 (2H, d, J=8.8 Hz), 7.08 (2H, d, J=8.8 Hz) ESI (LC/MS positive mode) m/z 744 (M+H); Rt 3.38 min.

tert-Butyl (E)-(2S,3S)-3-[(S)-2-(4-but-2-ynyloxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate

[Chem. 286]

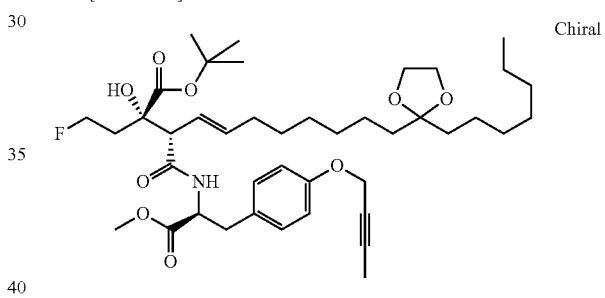

tert-Butyl (E)-(2S,3S)-3-[(S)-2-(4-but-2-ynyloxy-phenyl)-1-methoxycarbonyl-ethylcarbamoyl]-11-(2-heptyl-[1,3]dioxolan-2-yl)-2-hydroxy-2-(2-hydroxy-ethyl)-undec-4-enoate (157 mg, 0.211 mmol) was dissolved in tetrahydrofuran (5.0 mL), and (diethylamino)sulfur trifluoride (0.0360 mL, 0.273 mmol) was then added at room temperature. The mixture was stirred for 4 hours, then quenched with a saturated aqueous solution (15 mL) of sodium bicarbonate, and extracted with dichloromethane (15 mL). The organic layer was then dried over anhydrous sodium sulfate and filtered. The solvent was distilled off under reduced pressure. The residue was purified on Biotage (silica gel, n-hexane/ethyl acetate) to obtain 71.1 mg (0.0953 mmol, 45% yield) of tert-butyl (E)-(2S,3S)-3-[(S)-2-(4-but-2-ynyloxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate.

¹H-NMR (CD₃OD) δ: 0.88 (3H, t, J=7.1 Hz), 1.20-1.68 (23H, m), 1.41 (9H, s), 1.80 (3H, t, J=2.2 Hz), 1.90-2.24 (3H, m), 2.87 (1H, dd, J=14.1, 9.7 Hz), 3.12 (1H, dd, J=14.1, 4.8 Hz), 3.18 (1H, d, J=8.8 Hz), 3.70 (3H, s), 3.88 (4H, s), 4.20-4.58 (2H, m), 4.60 (2H, q, J=2.2 Hz), 4.65 (1H, dd, J=9.7, 4.8 Hz), 5.47 (1H, dd, J=15.0, 9.3 Hz), 5.60 (1H, dt, J=15.0, 6.6 Hz), 6.84 (2H, d, J=8.8 Hz), 7.08 (2H, d, J=8.8 Hz)

ESI (LC/MS positive mode) m/z 746 (M+H); Rt 2.55 min.

No. 5456815

(E)-(2S,3S)-3-[(S)-2-(4-But-2-ynyloxy-phenyl)-1-methoxycarbonyl-ethylcarbamoyl]-2-(2-fluoro-ethyl)-2-hydroxy-12-oxo-nonadec-4-enoic acid tert-Butyl (E)-(2S,3S)-3-[(S)-2-(4-but-2-ynyloxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate (64.0 mg, 0.0855 mmol) was dissolved in acetonitrile (0.96 mL), and water (0.03 mL, 1.67 mmol) and sulfuric acid (0.016 mL, 0.300 mmol) were then added at room temperature. After stirring for 18.5 hours, ethyl acetate (10 mL) and water (10 mL) were added, and the mixture was separated. The ethyl acetate layer was washed with a saturated aqueous solution (10 mL) of sodium chloride. The organic layer was dried over anhydrous sodium sulfate and filtered. The solvent was distilled off under reduced pressure. Formic acid (0.016 mL, 0.424 mmol) was added to the obtained residue (41.0 mg) at room temperature, and the mixture was then stirred for 21 hours. Formic acid was distilled off under reduced pressure. The residue was then purified by preparative HPLC and preparative TLC (diol, n-hexane/acetone=2/1) to obtain 15.9 mg of the title compound (0.0246 mmol, yield 29%).

$^1$H-NMR (CD$_3$OD) δ: 0.88 (3H, t, J=7.1 Hz), 1.15-1.39 (14H, m), 1.46-1.57 (4H, m), 1.69 (1H, ddt, J=32.6, 14.6, 4.4 Hz), 1.80 (3H, t, J=2.2 Hz), 1.90-2.05 (2H, m), 2.13-2.27 (1H, m), 2.42 (4H, t, J=7.1 Hz), 2.88 (1H, dd, J=14.1, 9.3 Hz), 3.12 (1H, dd, J=14.1, 4.8 Hz), 3.21 (1H, d, J=8.8 Hz), 3.70 (3H, s), 4.25-4.59 (2H, m), 4.60 (2H, q, J=2.2 Hz), 4.65 (1H, dd, J=9.3, 4.8 Hz), 5.47 (1H, dd, J=15.4, 8.8 Hz), 5.52-5.63 (1H, m), 6.83 (2H, d, J=8.8 Hz), 7.08 (2H, d, J=8.8 Hz)

ESI (LC/MS positive mode) m/z 646 (M+H); Rt 2.12 min.

No. 5456819 (E)-(2S,3S)-3-[(S)-2-(4-But-2-ynyloxy-phenyl)-1-carboxy-ethylcarbamoyl]-2-(2-fluoro-ethyl)-2-hydroxy-12-oxo-nonadec-4-enoic acid was produced according to the following synthetic scheme.

[Chem. 287]

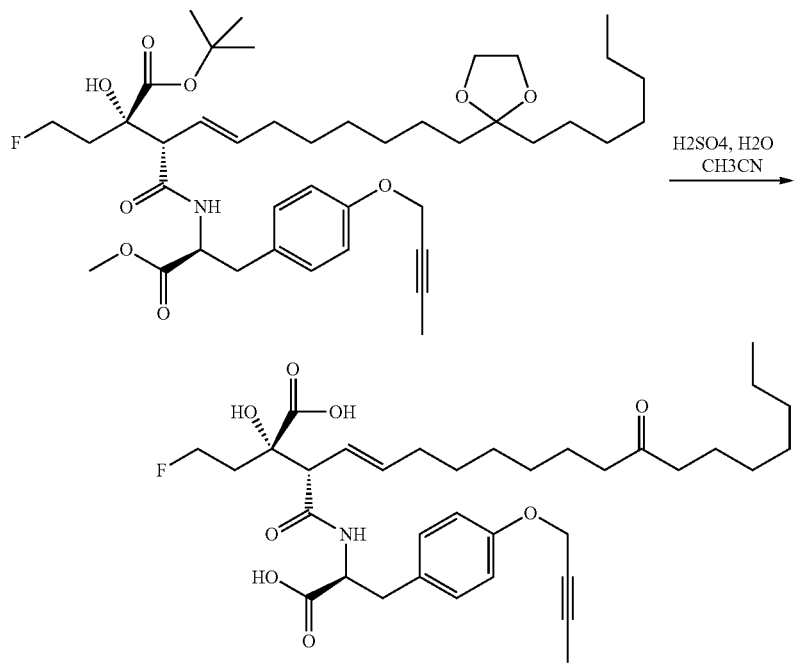

No 5456819 tert-Butyl (E)-(2S,3S)-3-[(S)-2-(4-but-2-ynyloxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate (21.0 mg, 0.0282 mmol) was dissolved in acetonitrile (1.0 mL), and water (0.01 mL, 0.556 mmol) and sulfuric acid (0.005 mL, 0.0938 mmol) were then added at room temperature. After stirring for 26 hours, ethyl acetate (10 mL) and water (10 mL) were added and the mixture was separated. The ethyl acetate layer was washed with a saturated aqueous solution (10 mL) of sodium chloride. The organic layer was dried over anhydrous sodium sulfate and filtered. The solvent was distilled off under reduced pressure. The obtained residue was purified by preparative TLC (diol, n-hexane/acetone=4/1) to obtain 2.3 mg of the title compound (0.00356 mmol, yield 13%) as a minor component.

$^1$H-NMR (CD$_3$OD) δ: 0.88 (3H, t, J=7.1 Hz), 1.20-1.35 (14H, m), 1.46-1.53 (4H, m), 1.69 (1H, ddt, J=32.6, 14.5, 4.4 Hz), 1.80 (3H, t, J=2.2 Hz), 1.90-2.03 (2H, m), 2.11-2.27 (1H, m), 2.42 (4H, t, J=7.4 Hz), 2.88 (1H, dd, J=14.1, 9.3 Hz), 3.17 (1H, dd, J=14.1, 4.8 Hz), 3.21 (1H, d, J=8.8 Hz), 4.27-4.59 (2H, m), 4.60 (2H, q, J=2.2 Hz), 4.63 (1H, dd, J=9.3, 4.8 Hz), 5.47 (1H, dd, J=15.4, 8.8 Hz), 5.56 (1H, dt, J=15.4, 6.6 Hz), 6.83 (2H, d, J=8.8 Hz), 7.10 (2H, d, J=8.8 Hz) ESI (LC/MS positive mode) m/z 632 (M+H); Rt 1.97 min.

No. 5486732 (2S,3S)-3-[(S)-2-(4-Butoxy-phenyl)-1-methoxycarbonyl-ethylcarbamoyl]-2-carbamoylmethyl-2- hydroxy-12-oxo-nonadecanoic acid was produced according to the following synthetic scheme.

[Chem. 288]

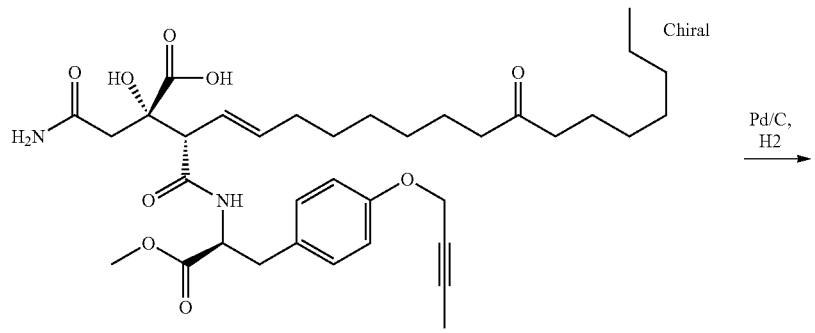

No 5283374

No 5486732

No. 5283374 ((E)-(2S,3S)-3-[(S)-2-(4-but-2-ynyloxy-phenyl)-1-methoxycarbonyl-ethylcarbamoyl]-2-carbamoyl-methyl-2-hydroxy-12-oxo-nonadec-4-enoic acid) was dissolved in methanol (3.0 mL), and Pd—C (4.4 mg) was then added at room temperature. After stirring for 5 hours under hydrogen atmosphere, insoluble material was filtered off, and washed with methanol (3.0 mL). The filtrate was concentrated under reduced pressure. The residue was then purified by preparative HPLC to obtain 16.1 mg (0.0243 mmol, yield 36%) of the title compound.

$^1$H-NMR (CD$_3$OD) δ: 0.88 (3H, t, J=7.1 Hz), 0.96 (3H, t, J=7.5 Hz), 1.07-1.77 (28H, m), 2.36-2.45 (5H, m), 2.55 (1H, dd, J=11.9, 3.5 Hz), 2.74 (1H, d, J=15.4 Hz), 2.84 (1H, dd, J=14.1, 10.6 Hz), 3.17 (1H, dd, J=14.1, 4.4 Hz), 3.72 (3H, s), 3.90 (2H, t, J=6.2 Hz), 4.72 (1H, dd, J=10.6, 4.4 Hz), 6.79 (2H, d, J=8.4 Hz), 7.11 (2H, d, J=8.4 Hz)

ESI (LC/MS positive mode) m/z 663 (M+H); Rt 2.22 min.

No. 5488895 (2S,3S)-3-[(S)-2-(4-Butoxy-phenyl)-1-carboxy-ethylcarbamoyl]-2-carbamoylmethyl-2-hydroxy-12-oxo-nonadecanoic acid was produced according to the following synthetic scheme.

[Chem. 289]

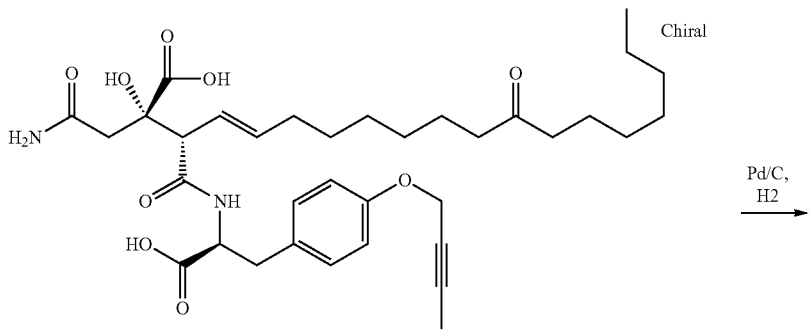

No 5322163

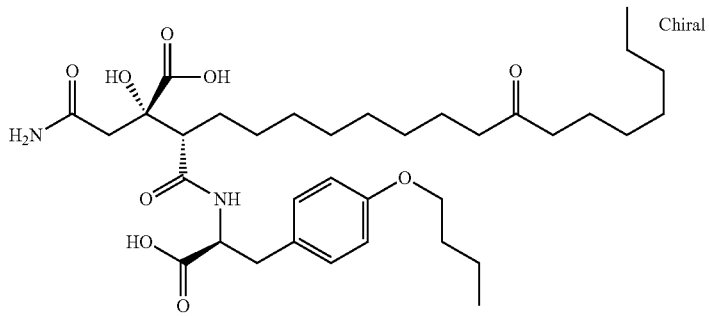

No 5488895

The title compound was obtained by a synthetic method similar to that of No. 5486732, except that No. 5322163 ((E)-(2S,3S)-3-[(S)-2-(4-but-2-ynyloxy-phenyl)-1-carboxy-ethylcarbamoyl]-2-carbamoylmethyl-2-hydroxy-12-oxo-nonadec-4-enoic acid) was used instead of No. 5283374, (E)-(2S,3S)-3-[(S)-2-(4-but-2-ynyloxy-phenyl)-1-methoxy-carbonyl-ethylcarbamoyl]-2-carbamoylmethyl-2-hydroxy-12-oxo-nonadec-4-enoic acid.

$^1$H-NMR (CD$_3$OD) δ: 0.90 (3H, t, J=6.9 Hz), 0.98 (3H, t, J=7.2 Hz), 1.07-1.80 (28H, m), 2.42-2.51 (5H, m), 2.56 (1H, dd, J=10.9, 2.3 Hz), 2.74 (1H, d, J=15.2 Hz), 2.85 (1H, dd, J=14.1, 10.5 Hz), 3.23 (1H, dd, J=14.1, 4.4 Hz), 3.92 (2H, t, J=6.6 Hz), 4.71 (1H, dd, J=10.5, 4.1 Hz), 6.80 (2H, d, J=8.6 Hz), 7.16 (2H, d, J=8.6 Hz)

ESI (LC/MS positive mode) m/z 649 (M+H); Rt 2.08 min.

No. 5501025 (E)-(2S,3S)-3-[(S)-2-(4-But-2-ynyloxy-phenyl)-1-methoxycarbonyl-ethylcarbamoyl]-2-hydroxy-10-(octane-1-sulfonylamino)-2-propyl-dec-4-enoic acid The synthetic scheme of the above compound is as follows.

[Chem. 290]

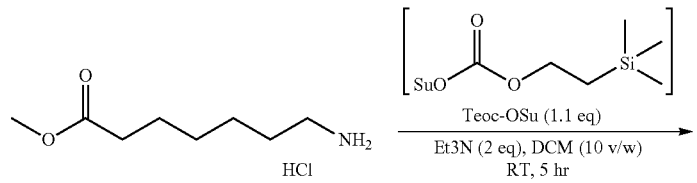

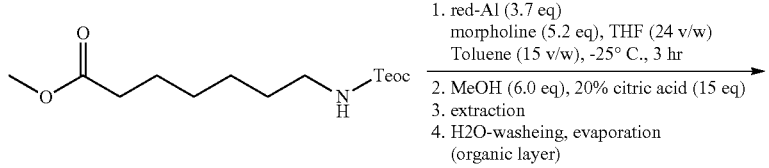

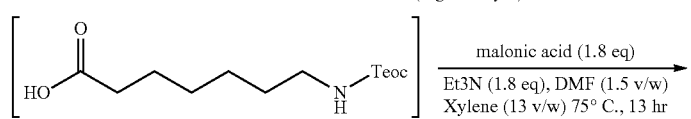

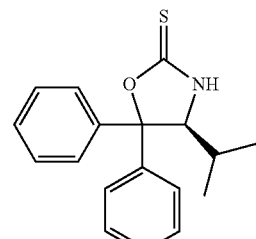

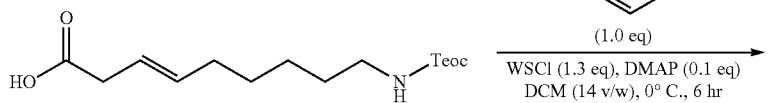

-continued
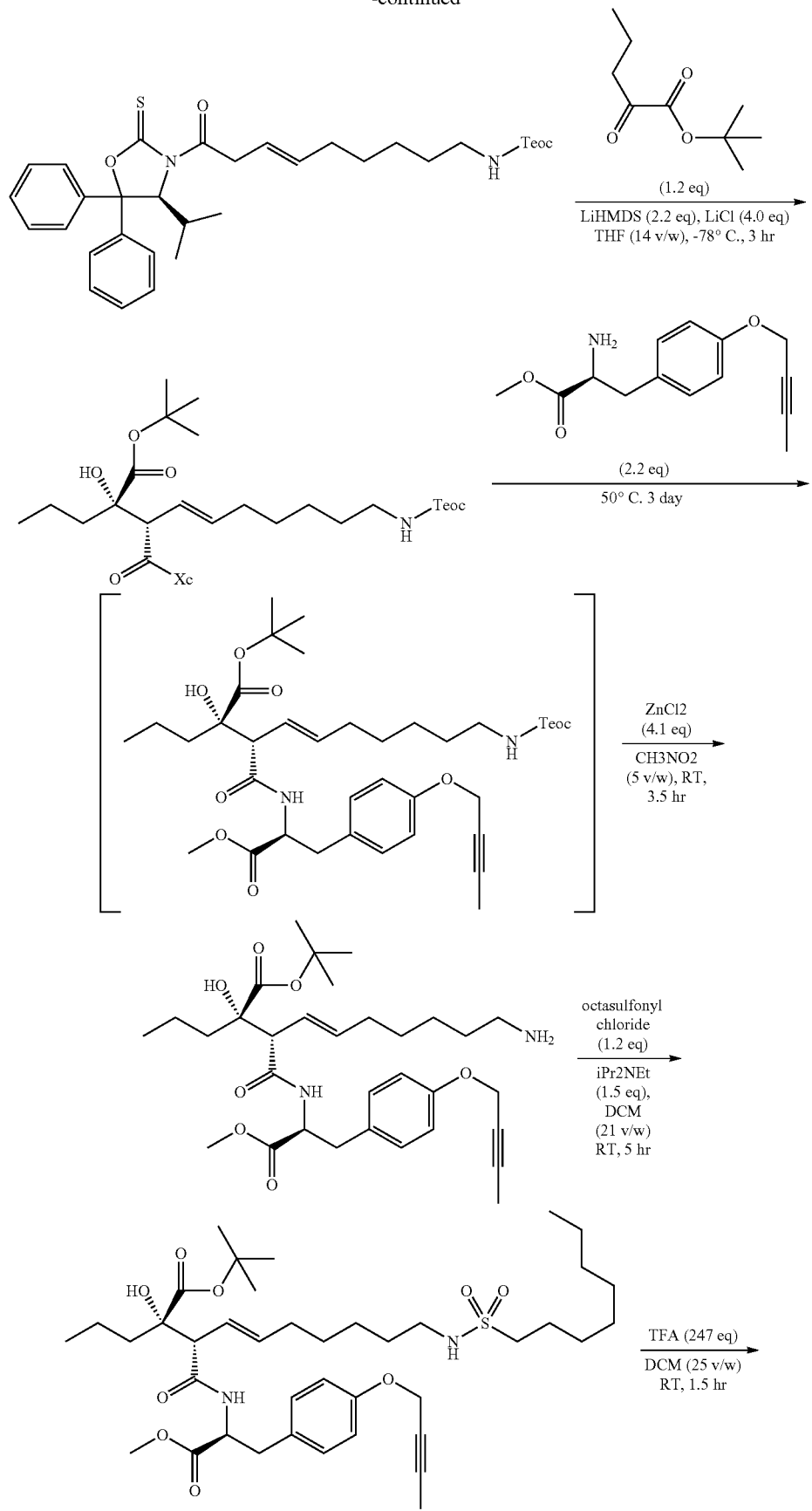

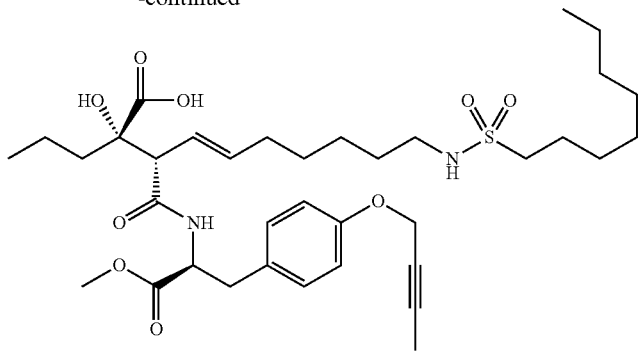

No 5501025

The starting material of the formula below (methyl 7-amino-heptanoate hydrochloride) is a known compound and was synthesized by a method described in J. Med. Chem. 2006, 49, 6094-6103.

[Chem. 291]

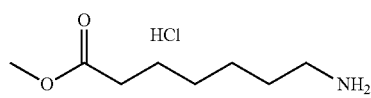

Methyl 7-(2-trimethylsilanyl-ethoxycarbonylamino)-heptanoate

[Chem. 292]

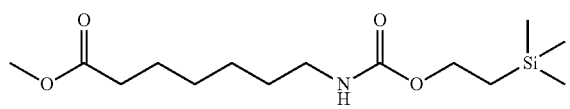

Methyl 7-amino-heptanoate hydrochloride (7.0 g, 35.9 mmol) was dissolved in dichloromethane (75.4 mL), and N-[2-(trimethylsilyl)ethoxycarbonyloxy]succinimide (10.0 g, 38.6 mmol) and triethylamine (10 mL, 71.7 mmol) were then added at room temperature. The mixture was stirred for 5 hours, and then quenched with water (100 mL), and separated. The aqueous layer was extracted with dichloromethane (50 mL). The organic layers were combined, then dried over anhydrous sodium sulfate, and filtered. The solvent was distilled off under reduced pressure to obtain 8.89 g (29.3 mmol, 82% yield) of methyl 7-(2-trimethylsilanyl-ethoxycarbonylamino)-heptanoate.

$^1$H-NMR (CDCl$_3$) δ: 0.04 (9H, s), 0.97 (2H, br.t, J=8.4 Hz), 1.20-1.76 (8H, m), 2.31 (2H, t, J=7.4 Hz), 3.07-3.23 (2H, m), 3.67 (3H, s), 4.14 (2H, br.t, J=8.4 Hz), 4.50-4.70 (1H, m)

ESI (LC/MS positive mode) m/z 304 (M+H); Rt 2.72 min.

(E)-9-(2-Trimethylsilanyl-ethoxycarbonylamino)-non-3-enoic acid

[Chem. 293]

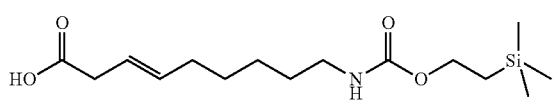

Tetrahydrofuran (120 mL) was cooled to −25° C., and sodium bis(2-methoxyethoxy)aluminum hydride (17.0 mL, 61.2 mmol) and morpholine (7.5 mL, 85.6 mmol) were added. A solution of methyl 7-(2-trimethylsilanyl-ethoxycarbonylamino)-heptanoate (5.00 g, 16.5 mmol) in anhydrous toluene (75.0 mL) was then added. The mixture was stirred for 3 hours. Methanol (4.0 mL, 98.8 mmol) and an aqueous solution (238 mL) of 20% citric acid were then added in order and the mixture was separated. The organic layer was then washed with water (10 mL), and then concentrated under reduced pressure. The resulting residue (5.73 g) was dissolved in xylene (65 mL), and triethylamine (4.2 mL, 30.1 mmol) was then added at room temperature. Subsequently, a solution of malonic acid (3.11 g, 29.9 mmol) in N,N-dimethylformamide (7.5 mL, 97.1 mmol) was added. The mixture was stirred at an outer temperature of 75° C. for 13 hours. The outer temperature was changed to room temperature. After confirming that inner temperature had returned to room temperature, an aqueous solution (59 mL) of 15% potassium dihydrogen phosphate was added and the mixture was separated. To the organic layer were then added acetonitrile (16.2 mL) and an aqueous solution (30 mL) of 5% sodium hydroxide. After separating the mixture and removing the organic layer, toluene (75 mL), an aqueous solution (75 mL) of 15% potassium dihydrogen phosphate, 1 M hydrochloric acid (130 mL), and ethyl acetate (50 mL) were added to the aqueous layer in order. After separating the mixture and removing the aqueous layer, the organic layer was washed with water (50 mL). The solvent was then distilled off under reduced pressure. The residue was purified on Biotage (silica gel, n-hexane/ethyl acetate) to obtain 3.59 g (11.4 mmol, 69% yield) of (E)-9-(2-trimethylsilanyl-ethoxycarbonylamino)-non-3-enoic acid.

$^1$H-NMR (CDCl$_3$) δ: 0.04 (9H, s), 0.97 (2H, br.t, J=8.4 Hz), 1.19-1.62 (6H, m), 1.95-2.15 (2H, m), 3.06 (2H, d, J=5.8 Hz), 3.03-3.25 (2H, m), 4.05-4.30 (2H, m), 4.54-4.74 (1H, m), 5.42-5.66 (2H, m) ESI (LC/MS positive mode) m/z 316 (M+H); Rt 2.48 min.

2-Trimethylsilanyl-ethyl [(E)-9-((S)-4-isopropyl-5,5-diphenyl-2-thioxo-oxazolidin-3-yl)-9-oxo-non-6-enyl]-carbamate

[Chem. 294]

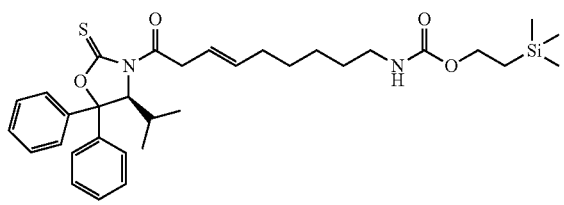

(S)-4-Isopropyl-5,5-diphenyl-oxazolidine-2-thione (2.3 g, 8.28 mmol) was suspended in dichloromethane (17.5 mL), and the mixture was then cooled to 0° C. in an ice bath. Dimethylaminopyridine (97 mg, 0.794 mmol) and 1-(3-dimethylaminopropyl)-3-ethylcarbodiimide hydrochloride (2.00 g, 10.4 mmol) were added and the mixture was then stirred for 25 minutes. To this suspension was added a solution of (E)-9-(2-trimethylsilanyl-ethoxycarbonylamino)-non-3-enoic acid (2.50 g, 7.92 mmol) in dichloromethane (17.5 mL). After stirring at 0° C. for 7.5 hours, an aqueous solution (50 mL) of 10% potassium dihydrogen phosphate and dichloromethane (40 mL) were added and the mixture was separated. The organic layer was washed with a saturated aqueous solution (40 mL) of sodium chloride, then dried over anhydrous sodium sulfate, and filtered. The solvent was distilled off under reduced pressure. The residue was purified on Biotage (silica gel, n-hexane/ethyl acetate) to obtain 3.01 g (5.06 mmol, yield 64%) of 2-trimethylsilanyl-ethyl [(E)-9-((S)-4-isopropyl-5,5-diphenyl-2-thioxo-oxazolidin-3-yl)-9-oxo-non-6-enyl]-carbamate.

$^1$H-NMR (CDCl$_3$) δ: 0.03 (9H, s), 0.78 (3H, d, J=6.9 Hz), 0.85 (3H, d, J=6.9 Hz), 0.97 (2H, br.t, J=8.4 Hz), 1.17-1.55 (6H, m), 1.85-2.15 (3H, m), 3.14 (2H, dd, J=12.6, 6.4 Hz), 3.79-4.06 (2H, m), 4.08-4.22 (2H, m), 4.50-4.75 (1H, m), 5.42-5.53 (2H, m), 5.60 (1H, d, J=3.8 Hz), 7.23-7.50 (10H, m)

ESI (LC/MS positive mode) m/z 595 (M+H); Rt 3.92 min.

tert-Butyl (E)-(2S,3S)-2-hydroxy-3-((S)-4-isopropyl-5,5-diphenyl-2-thioxo-oxazolidine-3-carbonyl)-2-propyl-10-(2-trimethylsilanyl-ethoxycarbonylamino)-dec-4-enoate

[Chem. 295]

2-Trimethylsilanyl-ethyl [(E)-9-((S)-4-isopropyl-5,5-diphenyl-2-thioxo-oxazolidin-3-yl)-9-oxo-non-6-enyl]-carbamate (400 mg, 0.672 mmol) and dried lithium chloride (114 mg, 2.69 mmol) were dissolved in tetrahydrofuran (3.2 mL), and the mixture was then cooled to −78° C. in a dry ice-acetone bath. Lithium hexamethyldisilazide (a solution of 1 M tetrahydrofuran, 1.51 mL, 1.51 mmol) was added in order, and the mixture was then stirred for 1 hour. A solution of tert-butyl 2-oxo-pentanoate (130 mg, 0.755 mmol) in tetrahydrofuran (2.4 mL) was added, and the mixture was then stirred at −78° C. for further 6 hours, and quenched with acetic acid (0.160 mL, 2.80 mmol). The dry ice-acetone bath was then removed. Ethyl acetate (30 mL) and water (10 mL) were added and the mixture was then separated. The organic layer was washed with a saturated aqueous solution (20 mL) of sodium chloride, then dried over anhydrous sodium sulfate, and filtered. The solvent was then distilled off under reduced pressure. The residue was purified on Biotage (silica gel, n-hexane/ethyl acetate) to obtain 270 mg (0.352 mmol, 52% yield) of tert-butyl (E)-(2S,3S)-2-hydroxy-3-((S)-4-isopropyl-5,5-diphenyl-2-thioxo-oxazolidine-3-carbonyl)-2-propyl-10-(2-trimethylsilanyl-ethoxycarbonylamino)-dec-4-enoate.

$^1$H-NMR (CDCl$_3$) δ: 0.03 (9H, s), 0.64 (3H, t, J=6.8 Hz), 0.73 (3H, d, J=6.9 Hz), 0.79 (3H, d, J=6.9 Hz), 0.75-1.50 (12H, m), 1.48 (9H, s), 1.89-2.10 (3H, m), 3.12 (2H, dd, J=13.0, 6.7 Hz), 3.37 (1H, s), 4.00-4.22 (2H, m), 4.50-4.73 (1H, m), 5.57 (1H, dd, J=15.3, 9.2 Hz), 5.71 (1H, d, J=3.9 Hz), 5.91 (1H, dt, J=15.3, 7.0 Hz), 6.17 (1H, d, J=9.2 Hz), 7.18-7.55 (10H, m)

ESI (LC/MS positive mode) m/z 768 (M+H); Rt 2.77 min.

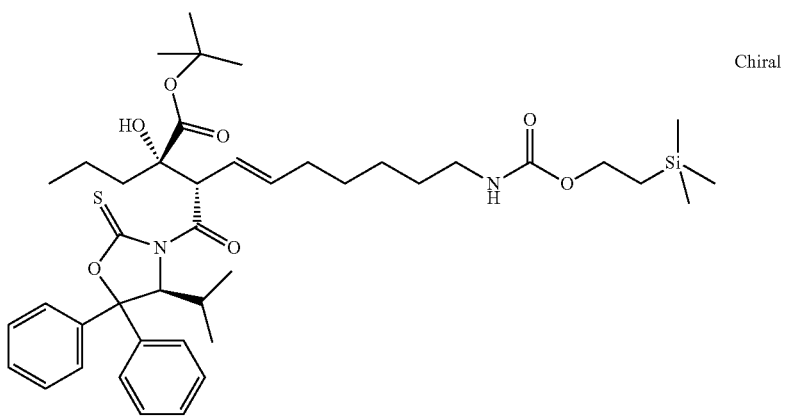

Chiral

365 tert-Butyl (E)-(2S,3S)-3-[(S)-2-(4-but-2-ynyloxy-phenyl)-1-methoxycarbonyl-ethyl carbamoyl]-2-hydroxy-2-propyl-10-(2-trimethylsilanyl-ethoxycarbonylamino)-dec-4-enoate

[Chem. 296]

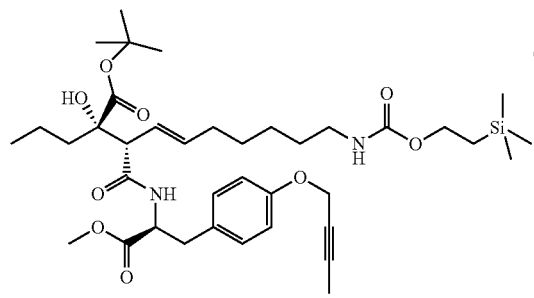

tert-Butyl (E)-(2S,3S)-2-hydroxy-3-((S)-4-isopropyl-5,5-diphenyl-2-thioxo-oxazolidine-3-carbonyl)-2-propyl-10-(2-trimethylsilanyl-ethoxycarbonylamino)-dec-4-enoate (582 mg, 0.759 mmol) and methyl (S)-2-amino-3-(4-but-2-ynyloxy-phenyl)-propionate (376 mg, 1.52 mmol) were dissolved in dichloromethane (10 mL), and dichloromethane was then distilled off under reduced pressure. The obtained mixture was warmed at 40° C. for 41 hours. The reaction mixture was purified on Biotage (silica gel, n-hexane/ethyl acetate) to obtain 443 mg (0.0618 mmol, 81% yield) of tert-butyl (E)-(2S,3S)-3-[(S)-2-(4-but-2-ynyloxy-phenyl)-1-methoxycarbonyl-ethylcarbamoyl]-2-hydroxy-2-propyl-10-(2-trimethylsilanyl-ethoxycarbonylamino)-dec-4-enoate.

$^1$H-NMR (CDCl$_3$) δ: 0.04 (9H, s), 0.82 (3H, t, J=7.1 Hz), 0.84-1.75 (12H, m), 1.44 (9H, s), 1.86 (3H, t, J=2.3 Hz), 1.99 (2H, dd, J=13.7, 6.9 Hz), 2.99 (1H, dd, J=14.1, 7.6 Hz), 3.05-3.24 (3H, m), 3.15 (1H, d, J=9.2 Hz), 3.70 (3H, s), 3.90 (1H, s), 4.06-4.24 (2H, m), 4.61 (2H, q, J=2.3 Hz), 4.72-4.86 (2H, m), 5.45 (1H, dd, J=15.2, 9.2 Hz), 5.64 (1H, dt, J=15.2, 6.6 Hz), 6.87 (2H, d, J=8.7 Hz), 7.00-7.15 (3H, m)

ESI (LC/MS positive mode) m/z 718 (M+H); Rt 2.26 min.

366 tert-Butyl (E)-(2S,3S)-10-amino-3-[(S)-2-(4-but-2-ynyloxy-phenyl)-1-methoxycarbonyl-ethylcarbamoyl]-2-hydroxy-2-propyl-dec-4-enoate

[Chem. 297]

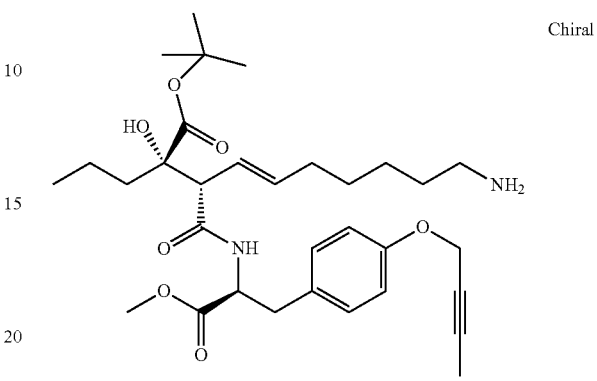

tert-Butyl (E)-(2S,3S)-3-[(S)-2-(4-but-2-ynyloxy-phenyl)-1-methoxycarbonyl-ethylcarbamoyl]-2-hydroxy-2-propyl-10-(2-trimethylsilanyl-ethoxycarbonylamino)-dec-4-enoate (298 mg, 0.415 mmol) was dissolved in nitromethane (1.5 mL), and zinc chloride (235 mg, 1.72 mmol) was then added at room temperature. The mixture was stirred for 4 hours, and then purified by preparative HPLC to obtain 192 mg (0.335 mmol, 81% yield) of tert-butyl (E)-(2S,3S)-10-amino-3-[(S)-2-(4-but-2-ynyloxy-phenyl)-1-methoxycarbonyl-ethylcarbamoyl]-2-hydroxy-2-propyl-dec-4-enoate.

$^1$H-NMR (CDCl$_3$) δ: 0.04 (9H, s), 0.80 (3H, t, J=6.8 Hz), 0.85-1.75 (12H, m), 1.43 (9H, s), 1.86 (3H, t, J=2.3 Hz), 1.92-2.13 (2H, m), 2.88-3.04 (3H, m), 3.06-3.19 (2H, m), 3.49 (1H, s), 3.72 (3H, s), 4.60 (2H, q, J=2.3 Hz), 4.70-4.81 (2H, m), 5.40-5.70 (2H, m), 6.87 (2H, d, J=8.6 Hz), 7.08 (2H, d, J=8.6 Hz), 7.14 (1H, d, J=7.6 Hz)

ESI (LC/MS positive mode) m/z 573 (M+H); Rt 1.30 min.

tert-Butyl (E)-(2S,3S)-3-[(S)-2-(4-but-2-ynyloxy-phenyl)-1-methoxycarbonyl-ethylcarbamoyl]-2-hydroxy-10-(octane-1-sulfonylamino)-2-propyl-dec-4-enoate

[Chem. 298]

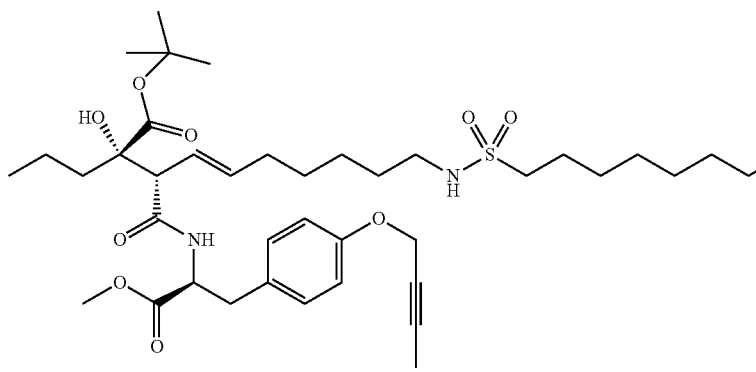

tert-Butyl (E)-(2S,3S)-10-amino-3-[(S)-2-(4-but-2-yny-loxy-phenyl)-1-methoxycarbonyl-ethylcarbamoyl]-2-hydroxy-2-propyl-dec-4-enoate (48.0 mg, 0.0838 mmol) was dissolved in dichloromethane (1.0 mL), and octasulfonyl chloride (0.02 mL, 0.102 mmol) and N,N-diisopropylethylamine (0.023 mL, 0.129 mmol) were then added at room temperature. The reaction mixture was stirred for 5 hours, and then concentrated under reduced pressure. The residue was purified on Biotage (silica gel, dichloromethane/methanol) to obtain 48.4 mg (0.0646 mmol, 77% yield) of tert-butyl (E)-(2S,3S)-3-[(S)-2-(4-but-2-ynyloxy-phenyl)-1-methoxycarbonyl-ethylcarbamoyl]-2-hydroxy-10-(octane-1-sulfonylamino)-2-propyl-dec-4-enoate.

$^1$H-NMR (CDCl$_3$) δ: 0.81 (3H, t, J=7.1 Hz), 0.88 (3H, t, J=7.1 Hz), 0.90-1.84 (22H, m), 1.44 (9H, s), 1.86 (3H, t, J=2.3 Hz), 1.93-2.12 (2H, m), 2.89-3.26 (7H, m), 3.72 (3H, s), 3.94 (1H, s), 4.61 (2H, q, J=2.3 Hz), 4.66 (1H, t, J=6.1 Hz), 4.73-4.86 (1H, m), 5.47 (1H, dd, J=15.3, 9.2 Hz), 5.62 (1H, dt, J=15.3, 6.4 Hz), 6.87 (2H, d, J=8.6 Hz), 7.01-7.20 (3H, m)

ESI (LC/MS positive mode) m/z 749 (M+H); Rt 2.42 min.

No. 5501025, (E)-(2S,3S)-3-[(S)-2-(4-but-2-ynyloxy-phenyl)-1-methoxycarbonyl-ethylcarbamoyl]-2-hydroxy-10-(octane-1-sulfonylamino)-2-propyl-dec-4-enoic acid tert-Butyl (E)-(2S,3S)-3-[(S)-2-(4-but-2-ynyloxy-phenyl)-1-methoxycarbonyl-ethylcarbamoyl]-2-hydroxy-10-(octane-1-sulfonylamino)-2-propyl-dec-4-enoate (35.0 mg, 0.0467 mmol) was dissolved in dichloromethane (1.0 mL), and trifluoroacetic acid (1.0 mL, 13.6 mmol) was then added at room temperature. The mixture was stirred for 75 minutes, and then concentrated under reduced pressure. The resulting crude product was purified by preparative HPLC to obtain 29.1 mg (0.0420 mmol, 90% yield) of the title compound.

$^1$H-NMR (CD$_3$OD) δ: 0.85 (3H, t, J=7.3 Hz), 0.90 (3H, t, J=6.6 Hz), 1.00-1.80 (22H, m), 1.82 (3H, t, J=2.3 Hz), 1.95-2.08 (2H, m), 2.90 (1H, dd, J=14.0, 9.2 Hz), 2.96-3.06 (4H, m), 3.12 (1H, dd, J=14.0, 4.9 Hz), 3.23 (1H, d, J=8.2 Hz), 3.71 (3H, s), 4.61 (2H, q, J=2.3 Hz), 4.64 (1H, dd, J=9.2, 4.9 Hz), 5.44-5.63 (2H, m), 6.86 (2H, d, J=8.7 Hz), 7.11 (2H, d, J=8.7 Hz)

ESI (LC/MS positive mode) m/z 693 (M+H); Rt 2.52 min.

No. 5502780, (E)-(2S,3S)-3-[(S)-2-(4-but-2-ynyloxy-phenyl)-1-carboxy-ethylcarbamoyl]-2-hydroxy-10-(octane-1-sulfonylamino)-2-propyl-dec-4-enoic acid No. 5501025 (9.8 mg, 0.0141 mmol) was dissolved in acetonitrile (0.197 mL), and water (0.0005 mL, 0.0278 mmol), triethylamine (0.0012 mL, 0.0861 mmol), and anhydrous lithium bromide (25 mg, 0.288 mmol) were then added at room temperature. The reaction solution was stirred at 50° C. for 20 hours, cooled to room temperature, and then purified by preparative HPLC to obtain 8.0 mg of the title compounds (0.0118 mmol, 84% yield).

$^1$H-NMR (CD$_3$OD) δ: 0.85 (3H, t, J=7.3 Hz), 0.90 (3H, t, J=6.6 Hz), 1.00-1.80 (22H, m), 1.82 (3H, t, J=2.3 Hz), 1.92-2.13 (2H, m), 2.90 (1H, dd, J=14.1, 9.2 Hz), 2.96-3.08 (4H, m), 3.16 (1H, dd, J=14.1, 4.8 Hz), 3.22 (1H, d, J=8.4 Hz), 4.61 (2H, q, J=2.3 Hz), 4.63 (1H, dd, J=9.2, 4.8 Hz), 5.44-5.63 (2H, m), 6.85 (2H, d, J=8.7 Hz), 7.14 (2H, d, J=8.7 Hz)

ESI (LC/MS positive mode) m/z 679 (M+H); Rt 1.83 min.

No. 5509955 (E)-(2S,3S)-3-[(S)-2-(4-But-2-ynyloxy-phenyl)-1-methoxycarbonyl-ethylcarbamoyl]-2-hydroxy-12-oxo-16-phenyl-2-propyl-hexadec-4-enoic acid The synthetic scheme of the above compound is as follows.

[Chem. 299]

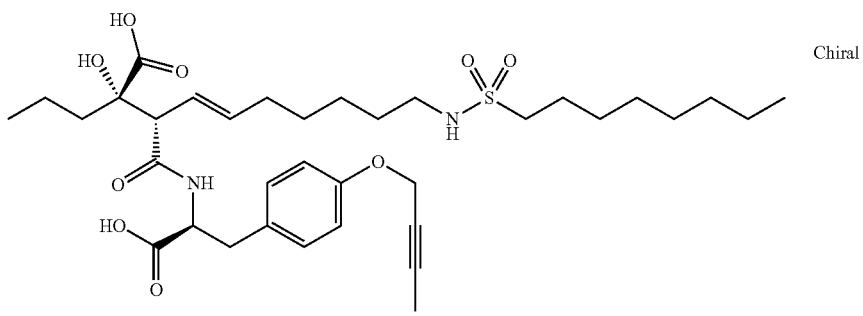

[Chem. 300]
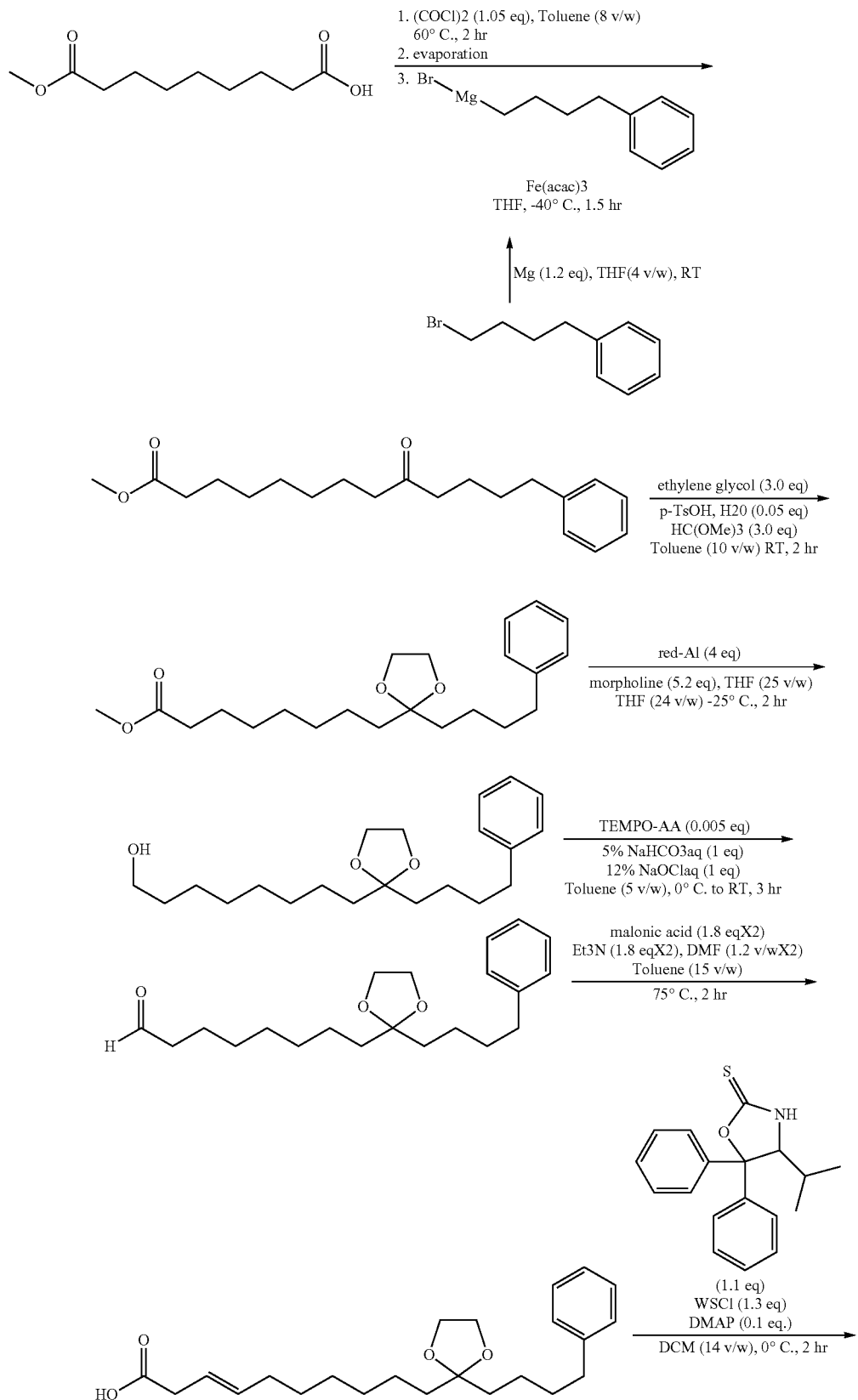

371
372
-continued
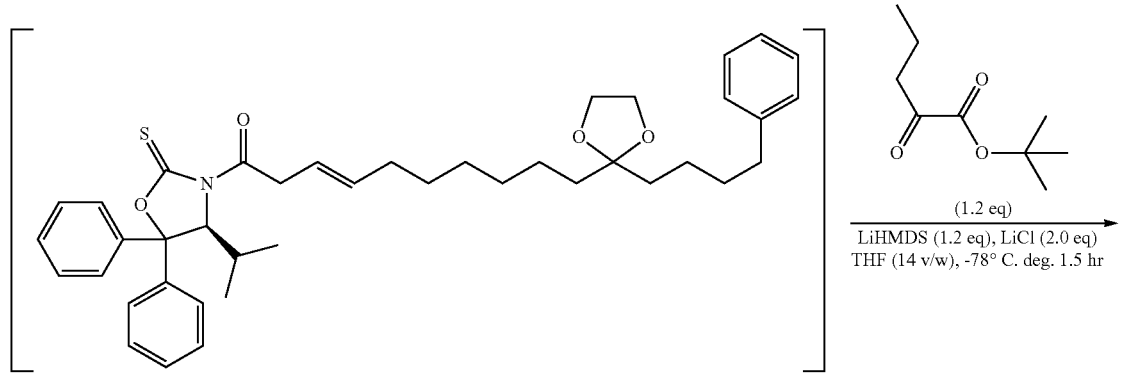
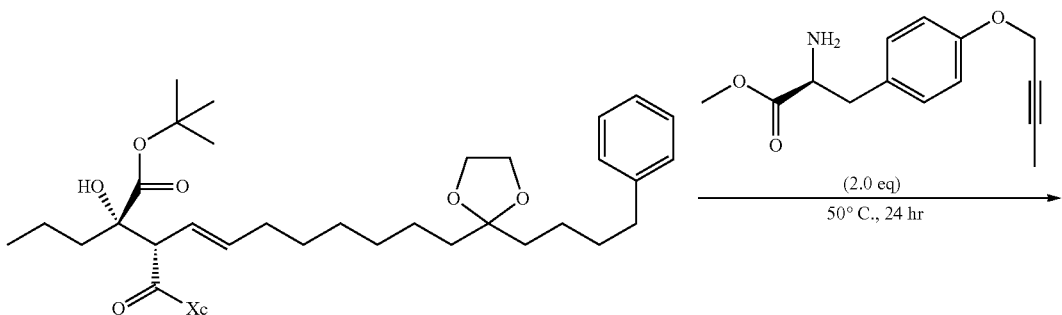
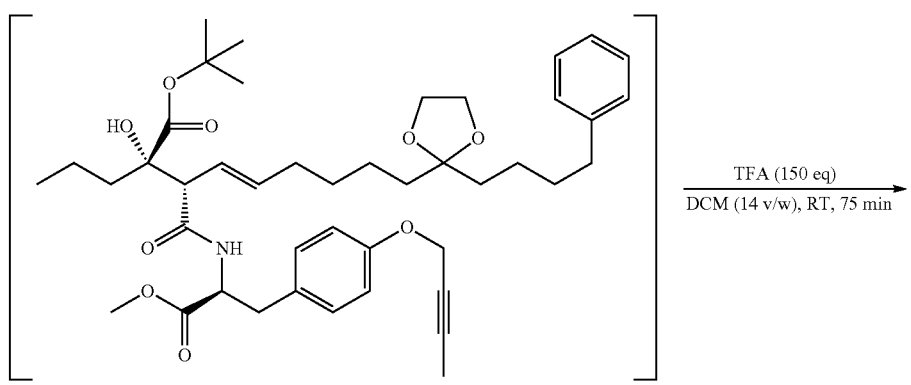
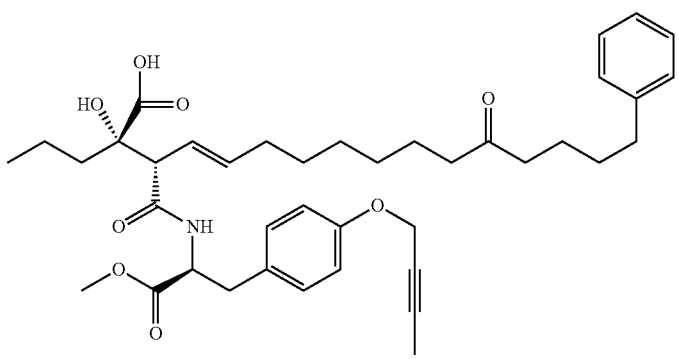
No 5509955

Methyl 9-oxo-13-phenyl-tridecanoate

[Chem. 301]

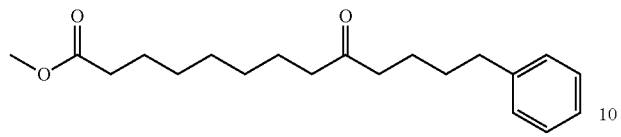

A commercially available reagent of monomethyl azelate (2.73 g, 13.5 mmol) was dissolved in toluene (21 mL), and N,N-dimethylformamide (0.00085 mL, 0.110 mmol) and oxalyl chloride (1.5 mL, 11.8 mmol) were then added. The reaction mixture was stirred at 60° C. for 2 hours, and then concentrated under reduced pressure. The residue was dissolved in tetrahydrofuran (27 mL), and the solution was then cooled to −40° C. Iron (III) tris(acetylacetonate) (200 mg, 0.566 mmol) was added. Magnesium 4-phenylbutyl bromide, prepared beforehand, was then added dropwise over 10 minutes [Magnesium 4-phenylbutyl bromide was prepared as follows: 4-phenylbutyl bromide (2.96 g, 13.9 mmol) was dissolved in tetrahydrofuran (11 mL), and magnesium (337 mg, 13.9 mmol) was then added, and subsequently dissolved by stirring the mixture for 30 minutes with occasional warming by a dryer]. After 1.5 hours, ethyl acetate (100 mL) and a saturated aqueous solution (100 mL) of ammonium chloride were added. The outer temperature was then cooled to room temperature. After separation, the organic layer was washed with a saturated aqueous solution (100 mL) of sodium chloride. The solvent was then distilled off under reduced pressure. The residue was purified on Biotage (silica gel, n-hexane/ethyl acetate) to obtain 1.81 g (5.68 mmol, 42% yield) of methyl 9-oxo-13-phenyl-tridecanoate.

$^1$H-NMR (CDCl$_3$) δ: 1.15-1.75 (14H, m), 2.24-2.48 (6H, m), 2.56-2.70 (2H, m), 3.67 (3H, s), 7.13-7.34 (5H, m)

ESI (LC/MS positive mode) m/z 319 (M+H); Rt 1.05 min.

Methyl 8-[2-(4-phenyl-butyl)-[1,3]dioxolan-2-yl]-octanoate

[Chem. 302]

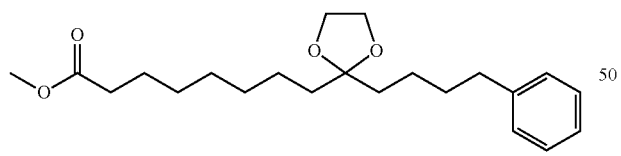

Methyl 9-oxo-13-phenyl-tridecanoate (1.8 g, 5.65 mmol) was dissolved in toluene (5.0 mL), and ethylene glycol (0.935 mL, 16.8 mmol), methyl orthoformate (1.85 mL, 16.8 mmol), and p-toluenesulfonic acid monohydrate (53.0 mg, 0.279 mmol) were then added in order at room temperature. The mixture was stirred for 40 minutes, and then quenched with a saturated aqueous solution (30 mL) of sodium bicarbonate, and 10% methanol/ethyl acetate (100 mL) was then added. The mixture was separated. The organic layer was washed with a mixture of water (10 mL) and a saturated aqueous solution (30 mL) of sodium chloride, dried over anhydrous sodium sulfate, and filtered. The solvent was then distilled off under reduced pressure. The residue was purified on Biotage (silica gel, n-hexane/ethyl acetate) to obtain 1.88 g (5.19 mmol, yield 92%) of methyl 8-[2-(4-phenyl-butyl)-[1,3]dioxolan-2-yl]-octanoate.

$^1$H-NMR (CDCl$_3$) δ: 1.20-1.75 (18H, m), 2.30 (2H, t, J=7.7 Hz), 2.61 (2H, t, J=7.9 Hz), 3.67 (3H, s), 3.92 (4H, s), 7.10-7.38 (5H, m)

ESI (LC/MS positive mode) m/z 363 (M+H); Rt 1.13 min.

8-[2-(4-Phenyl-butyl)-[1,3]dioxolan-2-yl]-octan-1-ol

[Chem. 303]

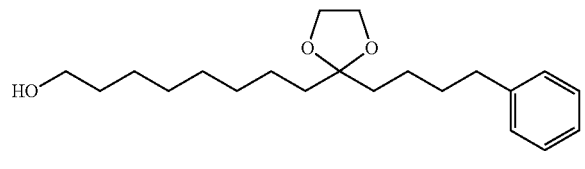

Tetrahydrofuran (45 mL) was cooled to −25° C. and sodium bis(2-methoxyethoxy)aluminum hydride (3.6 M solution in toluene, 6.5 mL, 23.4 mmol) and morpholine (2.7 mL, 30.5 mmol) were then added. Subsequently, a solution of methyl 8-[2-(4-phenyl-butyl)-[1,3]dioxolan-2-yl]-octanoate (1.87 g, 5.87 mmol) in anhydrous toluene (28 mL) was added. After stirring for 2 hours, methanol (1.2 mL, 66.6 mmol), an aqueous solution (75 mL) of 20% citric acid, and water (30 mL) were added in order. Ethyl acetate (100 mL) was added at room temperature and the mixture was then separated. The organic layer was washed with water (10 mL), and then concentrated under reduced pressure. The resulting residue was dissolved in toluene (24 mL). Triethylamine (1.47 mL, 10.5 mmol) and a solution of malonic acid (1.1 g, 10.6 mmol) in DMF (2.2 mL) were then added at room temperature. The mixture was stirred at 75° C. for 18 hours, and then quenched with an aqueous solution (22 mL) of 20% sodium dihydrogen phosphate at room temperature. Ethyl acetate (50 mL) was added, and the mixture was then separated. The organic layer was washed with water (50 mL), and then concentrated under reduced pressure. The residue was purified on Biotage (silica gel, n-hexane/ethyl acetate) to obtain 836 mg (2.51 mmol, 43% yield) of 8-[2-(4-phenyl-butyl)-[1,3]dioxolan-2-yl]-octan-1-ol.

$^1$H-NMR (CDCl$_3$) δ: 1.10-1.90 (20H, m), 2.61 (2H, t, J=7.6 Hz), 3.64 (2H, t, J=6.6 Hz), 3.92 (4H, s), 7.12-7.38 (5H, m)

ESI (LC/MS positive mode) m/z 335 (M+H); Rt 1.01 min.

8-[2-(4-Phenyl-butyl)-[1,3]dioxolan-2-yl]-octanal

[Chem. 304]

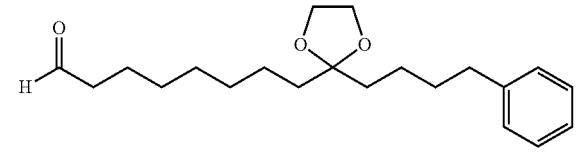

8-[2-(4-Phenyl-butyl)-[1,3]dioxolan-2-yl]-octan-1-ol (830 mg, 2.48 mmol) was dissolved in toluene (4.2 mL), and 4-acetamide-2,2,6,6-tetramethylpiperidine 1-oxyl (2.6 mg, 0.0122 mmol) and an aqueous solution of 5% sodium bicarbonate (4.2 mL, 2.50 mmol) were then added. The mixture was then cooled to 0° C. An aqueous solution of 12% sodium hypochlorite (1.55 mL, 2.50 mmol) was added over 15 minutes. The mixture was then stirred at room temperature for 3 hours, and extracted twice with ethyl acetate (50 mL). The organic layer was then concentrated under reduced pressure. The residue was purified on Biotage (diol, n-hexane/ethyl acetate) to obtain 528 mg of the title compound (1.59 mmol, 64% yield).

$^1$H-NMR (CDCl$_3$) δ: 1.20-1.76 (18H, m), 2.42 (2H, td, J=7.4, 1.8 Hz), 2.61 (2H, t, J=7.9 Hz), 3.92 (4H, s), 7.12-7.36 (5H, m), 9.76 (1H, t, J=1.8 Hz)

ESI (LC/MS positive mode) m/z 333 (M+H); Rt 1.09 min.

$^1$H-NMR (CDCl$_3$) δ: 1.18-1.68 (16H, m), 1.96-2.06 (2H, m), 2.59 (2H, t, J=7.9 Hz), 3.05 (2H, d, J=7.1 Hz), 3.90 (4H, s), 5.43-5.63 (2H, m), 7.12-7.18 (3H, m), 7.21-7.30 (2H, m)

ESI (LC/MS positive mode) m/z 375 (M+H); Rt 1.03 min.

tert-Butyl (E)-(2S,3S)-2-hydroxy-3-((S)-4-isopropyl-5,5-diphenyl-2-thioxo-oxazolidine-3-carbonyl)-11-[2-(4-phenyl-butyl)-[1,3]dioxolan-2-yl]-2-propyl-undec-4-enoate

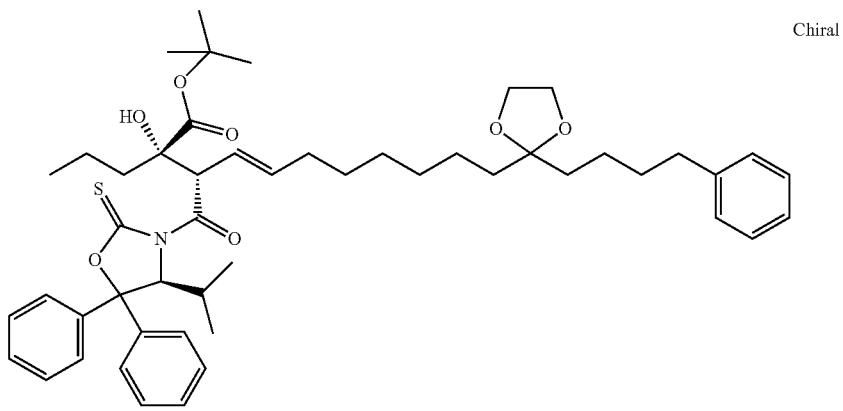

(E)-10-[2-(4-Phenyl-butyl)-[1,3]dioxolan-2-yl]-dec-3-enoic acid

[Chem. 305]

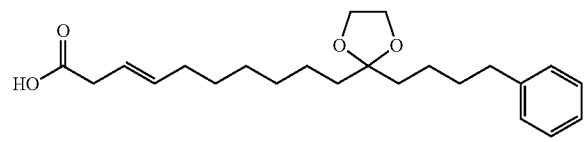

8-[2-(4-Phenyl-butyl)-[1,3]dioxolan-2-yl]-octanal (520 mg, 1.56 mmol) was dissolved in toluene (6.4 mL). A solution of malonic acid (293 mg, 2.82 mmol) in N,N-dimethylformamide (0.587 mL, 7.61 mmol) and triethylamine (0.392 mL, 3.77 mmol) were then added at room temperature. The mixture was stirred at an outer temperature of 75° C., for 15 hours. A solution of malonic acid (293 mg, 2.82 mmol) in N,N-dimethylformamide (0.587 mL, 7.61 mmol) and triethylamine (0.392 mL, 3.77 mmol) were added at room temperature. The mixture was then stirred again at an outer temperature of 75° C. for 8 hours.

The outer temperature was changed to room temperature. After confirming that the inner temperature had returned to room temperature, an aqueous solution (20 mL) of 30% sodium dihydrogen phosphate and ethyl acetate (50 mL) were added. After separating the mixture and removing the aqueous layer, the organic layer was washed with water (50 mL). The solvent was distilled off under reduced pressure. The residue was purified on Biotage (silica gel, n-hexane/ethyl acetate) to obtain 482 mg of (E)-10-[2-(4-phenyl-butyl)-[1,3]dioxolan-2-yl]-dec-3-enoic acid (1.29 mmol, 82% yield).

(S)-4-Isopropyl-5,5-diphenyl-oxazolidine-2-thione (412 mg, 1.39 mmol) was suspended in dichloromethane (3.3 mL), and then cooled to 0° C. in an ice bath. Dimethylaminopyridine (16 mg, 0.131 mmol) and 1-(3-dimethylaminopropyl)-3-ethylcarbodiimide hydrochloride (315 mg, 1.64 mmol) were added in this order. A solution of a commercially available reagent of (E)-10-[2-(4-phenyl-butyl)-[1,3]dioxolan-2-yl]-dec-3-enoic acid (476 mg, 1.27 mmol) in dichloromethane (3.4 mL) was then added. After stirring at 0° C. for 2 hours, an aqueous solution (50 mL) of 10% sodium dihydrogen phosphate and ethyl acetate (50 mL) were added and the mixture was separated. The organic layer was washed with a saturated aqueous solution (40 mL) of sodium chloride, then dried over anhydrous sodium sulfate, and filtered. The solvent was distilled off under reduced pressure. The residue was purified on Biotage (silica gel, n-hexane/ethyl acetate) to obtain 445 mg (0.681 mmol, 54% yield) of (E)-1-((S)-4-isopropyl-5,5-diphenyl-2-thioxo-oxazolidin-3-yl)-10-[2-(4-phenyl-butyl)-[1,3]dioxolan-2-yl]-dec-3-en-1-one (ESI (LC/MS positive mode) m/z 654 (M+H); Rt 3.07 min.).

The obtained compound (240 mg, 0.367 mmol) was dissolved in tetrahydrofuran (2.9 mL), and then cooled to −78° C. in a dry ice-acetone bath. Dried lithium chloride (31.2 mg, 0.736 mmol) and lithium hexamethyldisilazide (1 M solution in tetrahydrofuran, 0.442 mL, 0.442 mmol) were added in order and then stirred for 15 minutes. A solution of tert-butyl 2-oxo-pentanoate (76.0 mg, 0.441 mmol) in tetrahydrofuran (2.2 mL) was added and the mixture was then stirred at −78° C. for further 1.5 hours. After quenching with acetic acid (0.042 mL, 0.734 mmol), a dry ice-acetone bath was removed. Water (10 mL) was added, and the mixture was then extracted with ethyl acetate (20 mL). The organic layer was washed with a saturated aqueous solution (20 mL) of sodium chloride, then dried over anhydrous sodium sulfate, and filtered. The solvent was then distilled off under reduced pressure. The residue was purified on Biotage (silica gel, n-hexane/ethyl acetate) to obtain 146 mg (0.177 mmol, 48% yield) of tert-butyl (E)-(2S,3S)-2-hydroxy-3-((S)-4-isopropyl-5,5-diphenyl-2-thioxo-oxazolidine-3-carbonyl)-11-[2-(4-phenyl-butyl)-[1,3]dioxolan-2-yl]-2-propyl-undec-4-enoate.

$^1$H-NMR (CDCl$_3$) δ: 0.64 (3H, t, J=7.1 Hz), 0.72 (3H, d, J=7.0 Hz), 0.77 (3H, d, J=7.0 Hz), 0.79-1.68 (20H, m), 1.47 (9H, s), 1.90-2.07 (3H, m), 2.53-2.63 (2H, m), 3.34 (1H, s), 3.89 (4H, s), 5.56 (1H, dd, J=15.4, 9.3 Hz), 5.70 (1H, d, J=4.0 Hz), 5.92 (1H, dd, J=15.4, 6.6 Hz), 6.15 (1H, d, J=9.3 Hz), 7.10-7.50 (15H, m)

ESI (LC/MS positive mode) m/z 826 (M+H); Rt 3.58 min.

No. 5509955 (E)-(2S,3S)-3-[(S)-2-(4-But-2-ynyloxy-phenyl)-1-methoxycarbonyl-ethylcarbamoyl]-2-hydroxy-12-oxo-16-phenyl-2-propyl-hexadec-4-enoic acid tert-Butyl (E)-(2S,3S)-2-hydroxy-3-((S)-4-isopropyl-5,5-diphenyl-2-thioxo-oxazolidine-3-carbonyl)-11-[2-(4-phenyl-butyl)-[1,3]dioxolan-2-yl]-2-propyl-undec-4-enoate (124 mg, 0.150 mmol) and methyl (S)-2-amino-3-(4-but-2-ynyloxy-phenyl)-propionate (70.0 mg, 0.283 mmol) were dissolved in dichloromethane (3.0 mL). Dichloromethane was distilled off under reduced pressure. The residue was then stirred at an outer temperature of 50° C. for 24 hours. The reaction mixture was purified on Biotage (silica gel, n-hexane/ethyl acetate) to obtain 72.0 mg (0.0928 mmol, 62% yield, purity 78%) of tert-butyl (E)-(2S,3S)-3-[(S)-2-(4-but-2-ynyloxy-phenyl)-1-methoxycarbonyl-ethylcarbamoyl]-2-hydroxy-11-[2-(4-phenyl-butyl)-[1,3]dioxolan-2-yl]-2-propyl-undec-4-enoate (ESI (LC/MS positive mode) m/z 776 (M+H); Rt 2.47 min.).

The obtained compound (70.0 mg, 0.0902 mmol) was dissolved in dichloromethane (1.0 mL), and then trifluoroacetic acid (1.0 mL, 13.6 mmol) was added at room temperature. After stirring for 1 hour, trifluoroacetic acid was distilled off under reduced pressure. The resulting residue was purified by preparative HPLC to obtain 47.2 mg (0.0698 mmol, 77% yield) of the title compound.

$^1$H-NMR (CD$_3$OD) δ: 0.84 (3H, t, J=7.1 Hz), 1.00-1.72 (16H, m), 1.79 (3H, t, J=2.2 Hz), 1.89-2.02 (2H, m), 2.40 (2H, t, J=7.1 Hz), 2.45 (2H, t, J=6.6 Hz), 2.54-2.67 (2H, m), 2.88 (1H, dd, J=14.1, 9.2 Hz), 3.10 (1H, dd, J=14.1, 4.9 Hz), 3.21 (1H, d, J=7.9 Hz), 3.68 (3H, s), 4.58 (2H, q, J=2.2 Hz), 4.62 (1H, dd, J=9.2, 4.9 Hz), 5.42-5.60 (2H, m), 6.83 (2H, d, J=8.8 Hz), 7.08 (2H, d, J=8.8 Hz), 7.10-7.17 (3H, m), 7.19-7.26 (2H, m)

ESI (LC/MS positive mode) m/z 676 (M+H); Rt 2.08 min.

Synthesis of No. 6804452, (S)-2-amino-3-(4-butoxy-phenyl)-N-methyl-propionamide

[Chem. 307]

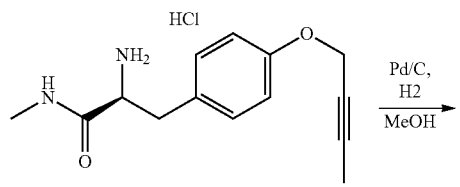

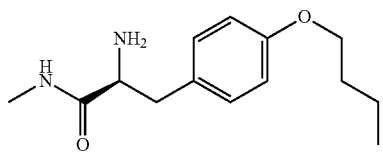

(S)-2-Amino-3-(4-but-2-ynyloxy-phenyl)-N-methyl-propionamide hydrochloride (2.00 g, 7.07 mmol) was dissolved in methanol (100 mL), and Pd/C (230 mg) was then added at room temperature. After stirring for 17 hours under a hydrogen atmosphere, insoluble material was filtered off, and washed with methanol (3.0 mL). The filtrate was concentrated under reduced pressure, and then dissolved in ethyl acetate (150 mL). The solution was washed with sodium bicarbonate (100 mL) and a saturated aqueous solution (50 mL) of sodium chloride in this order, then dried over anhydrous sodium sulfate, and filtered. The solvent was distilled off under reduced pressure to obtain 1.77 g of the title compound (7.07 mmol, quant.).

$^1$H-NMR (CDCl$_3$) δ: 0.97 (3H, t, J=7.4 Hz), 1.30-1.60 (4H, m), 1.69-1.87 (2H, m), 2.63 (1H, dd, J=13.8, 9.4 Hz), 2.82 (3H, d, J=5.1 Hz), 3.19 (1H, dd, J=13.8, 4.1 Hz), 3.56 (1H, dd, J=9.4, 4.1 Hz), 3.94 (2H, t, J=6.6 Hz), 6.85 (2H, d, J=8.7 Hz), 7.11 (2H, d, J=8.7 Hz), 7.13-7.35 (1H, m)

ESI (LC/MS positive mode) m/z 251 (M+H); Rt 0.44 min.

Synthesis of No. 6804455, (S)-2-amino-3-(4-butoxy-phenyl)-propionamide

[Chem. 308]

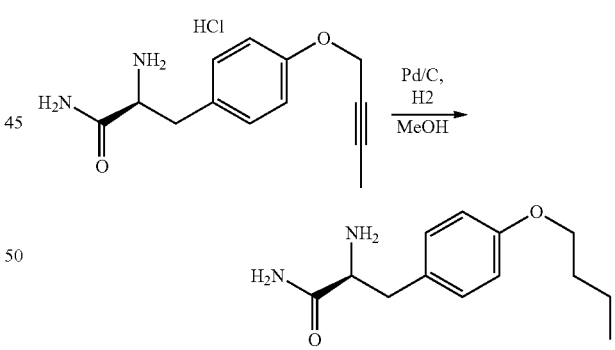

No. 6804455 was obtained by a synthetic method similar to that of No. 6804452, except that (S)-2-amino-3-(4-but-2-ynyloxy-phenyl)-propionamide hydrochloride was used instead of (S)-2-amino-3-(4-but-2-ynyloxy-phenyl)-N-methyl-propionamide hydrochloride.

$^1$H-NMR (CDCl$_3$) δ: 0.97 (3H, t, J=7.4 Hz), 1.30-1.64 (4H, m), 1.68-1.90 (2H, m), 2.68 (1H, dd, J=13.7, 9.4 Hz), 3.18 (1H, dd, J=13.7, 4.1 Hz), 3.57 (1H, dd, J=9.4, 4.1 Hz), 3.94 (2H, t, J=6.6 Hz), 5.40-5.75 (1H, m), 6.86 (2H, d, J=8.7 Hz), 7.00-7.20 (1H, m), 7.14 (2H, d, J=8.7 Hz)

ESI (LC/MS positive mode) m/z 237 (M+H); Rt 0.38 min.

Synthesis of tert-butyl 2-(2-fluoro-ethyl)-[1,3]dithiane-2-carboxylate

[Chem. 309]

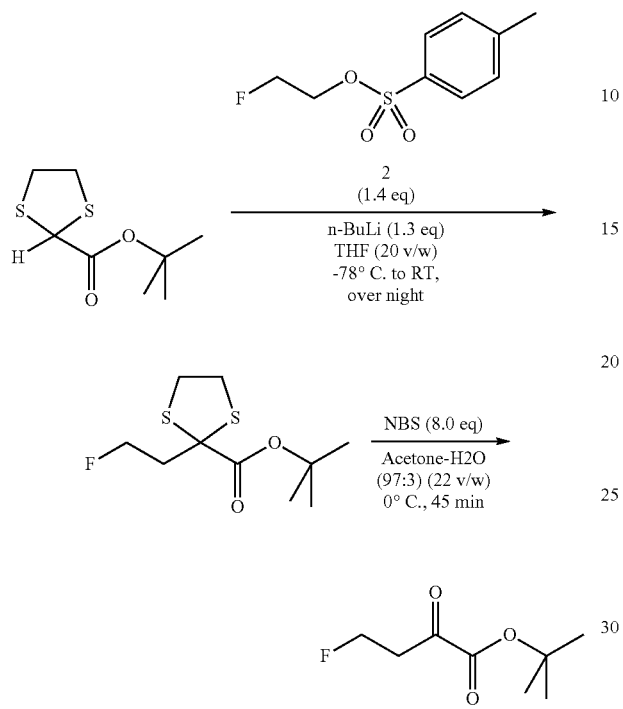

A solution of commercially available reagent of tert-butyl [1,3]dithiane-2-carboxylate (2.0 g, 9.69 mmol) in THF (20 mL) was cooled to −78° C., and n-butyl lithium (1.67 M solution in n-hexane, 8.62 mL, 13.6 mmol) was then added over 10 minutes. The mixture was stirred for 80 minutes, and 2-fluoro-ethyl toluene-4-sulfonate (2.95 g, 13.5 mmol, known compound, ref. Tetrahedron (2005), 61 (35), 8410-8418) was then added. The mixture was stirred at −78° C. for 30 minutes, and the cooling bath was then removed. The mixture was stirred while allowing the temperature to gradually return to room temperature, and stirred at room temperature for 20 hours. After confirming the consumption of the starting materials by LCMS, the mixture was quenched with water (100 mL), and then extracted with dichloromethane (100 mL). The aqueous layer was further extracted with dichloromethane (50 mL). The combined dichloromethane layer was washed with a saturated aqueous solution (100 mL) of ammonium chloride and a saturated aqueous solution (100 mL) of sodium chloride in this order, then dried over anhydrous sodium sulfate, and filtered. The organic layer was concentrated under reduced pressure. The resulting residue was purified on Biotage (silica gel, n-hexane/ethyl acetate) to obtain tert-butyl 2-(2-fluoro-ethyl)-[1,3]dithiane-2-carboxylate (2.79 g, quant.).

$^1$H-NMR (CDCl$_3$) δ: 1.52 (9H, s), 1.77-1.97 (1H, m), 2.07-2.21 (1H, m), 2.42 (2H, dt, J=20.6, 6.6 Hz), 2.60-2.73 (2H, m), 3.23-3.40 (2H, m), 4.68 (2H, dt, J=47.0, 6.6 Hz),

ESI (LC/MS positive mode) m/z 267 (M+H); Rt 0.91 min.

tert-Butyl 4-fluoro-2-oxo-butyrate

[Chem. 310]

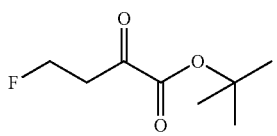

N-Bromosuccinimide (4.20 g, 23.6 mmol) was suspended in acetone (13.5 mL) and water (0.5 mL), and the suspension was cooled to 0° C. in an ice bath. A solution of tert-butyl 2-(2-fluoro-ethyl)-[1,3]dithiane-2-carboxylic acid (786 mg, 2.95 mmol) in acetone (3.0 mL) was then added. The mixture was stirred for 75 minutes, then quenched with a saturated aqueous solution (25 mL) of sodium bicarbonate, and extracted with dichloromethane (100 mL). The dichloromethane layer was then washed with an aqueous solution (65 mL) of 5% sodium thiosulfate and a saturated aqueous solution (30 mL) of sodium chloride in this order, then dried over anhydrous sodium sulfate, and filtered. The organic layer was concentrated under reduced pressure. The resulting residue was dissolved in n-hexane (50 mL). Water (50 mL) was then added and the mixture was separated. The hexane layer was dried over anhydrous sodium sulfate, then filtered, and concentrated under reduced pressure to obtain tert-butyl 4-fluoro-2-oxo-butyrate (361 mg, 54% yield).

$^1$H-NMR (CDCl$_3$) δ: 1.56 (9H, s), 3.20 (2H, dt, J=24.0, 5.8 Hz), 4.77 (2H, dt, J=46.5, 5.8 Hz).

tert-Butyl 2-oxo-hexanoate

[Chem. 311]

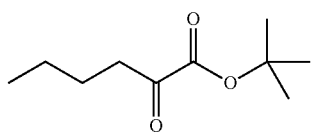

The title compound was obtained as a minor component by the synthesis similar to that of tert-butyl 4-methoxy-2-oxo-butyrate, except that 1,1-difluoro-2-iodoethane was used instead of 2-bromomethyl methyl ether.

$^1$H-NMR (CDCl$_3$) δ: 0.92 (3H, t, J=7.3 Hz), 1.20-1.47 (4H, m), 1.55 (9H, s), 2.77 (2H, t, J=7.2 Hz).

Synthetic Schemes of No. 5513181 and Others
[Chem. 312]
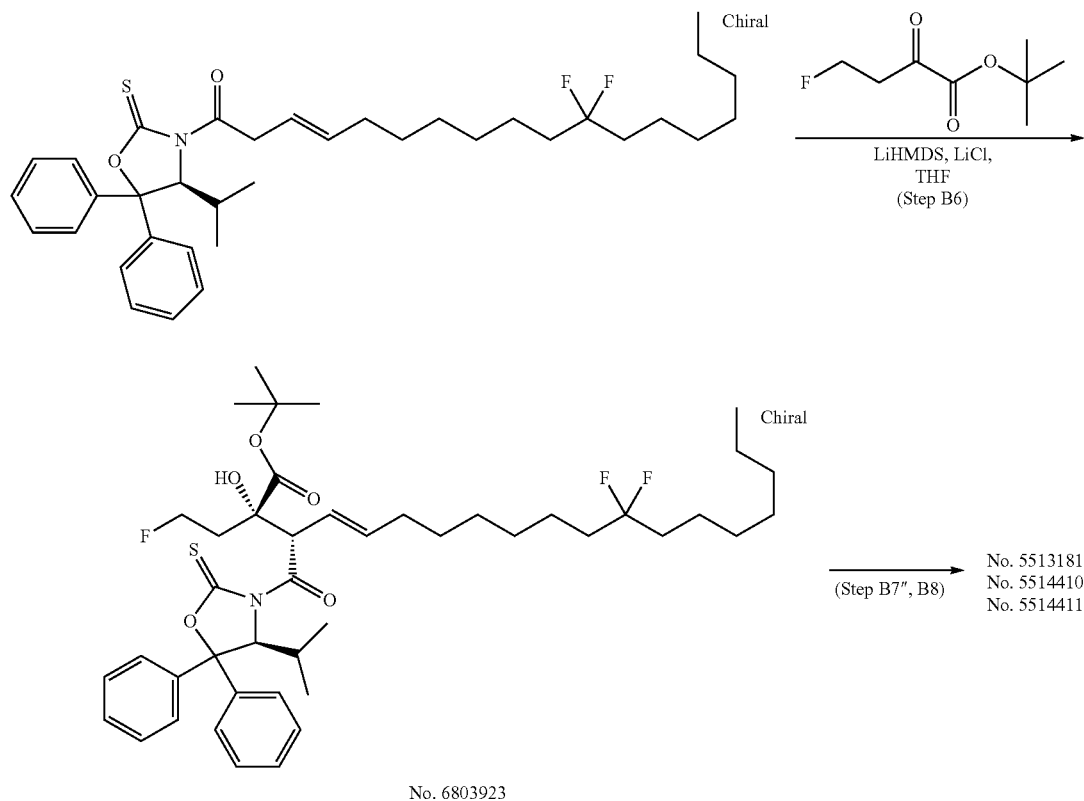
No. 6803923 → (Step B7″, B8) → No. 5513181, No. 5514410, No. 5514411
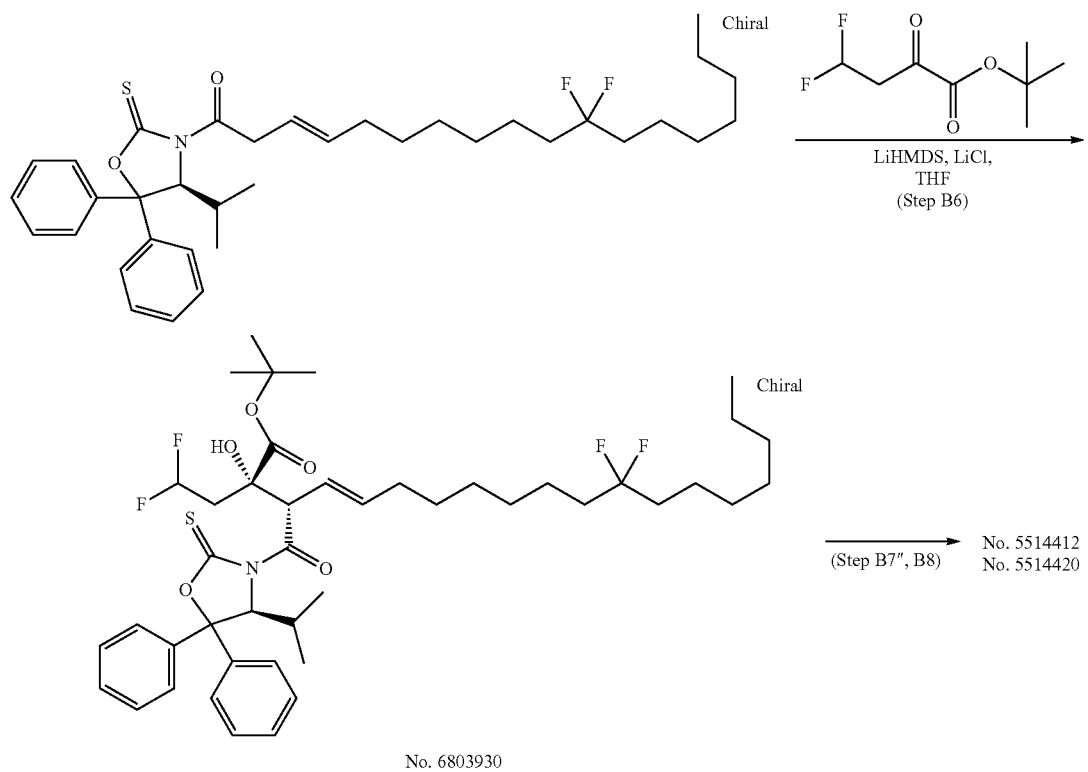
No. 6803930 → (Step B7″, B8) → No. 5514412, No. 5514420

-continued
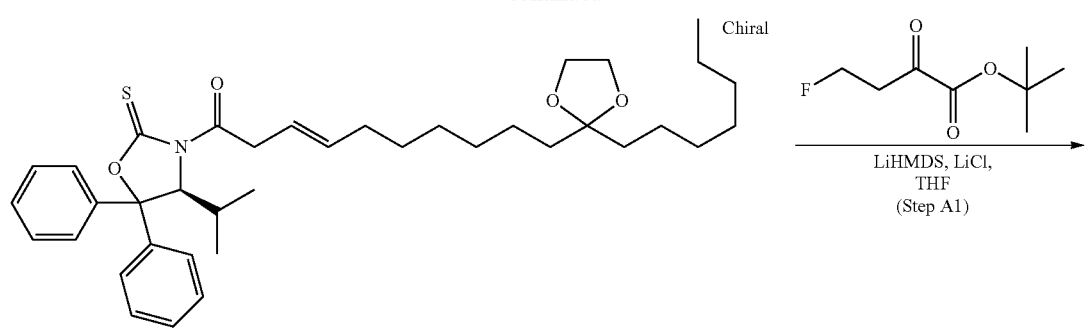
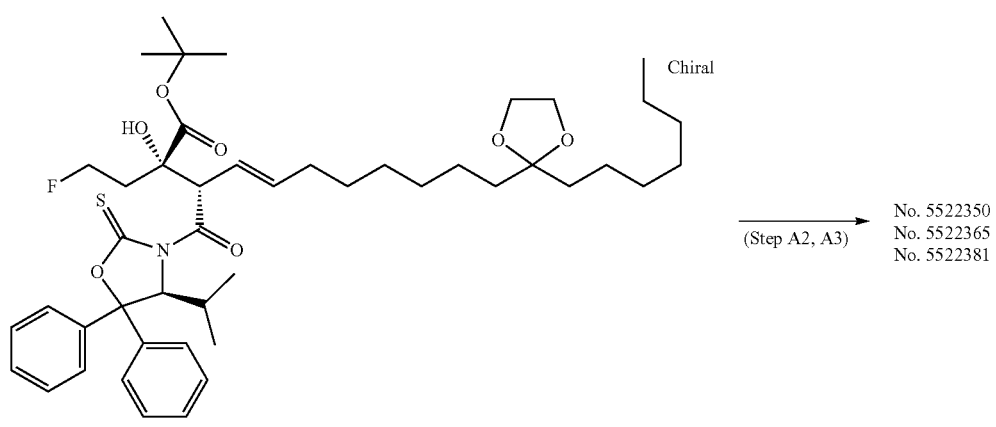
No. 6804093
(Step A2, A3) → No. 5522350
No. 5522365
No. 5522381
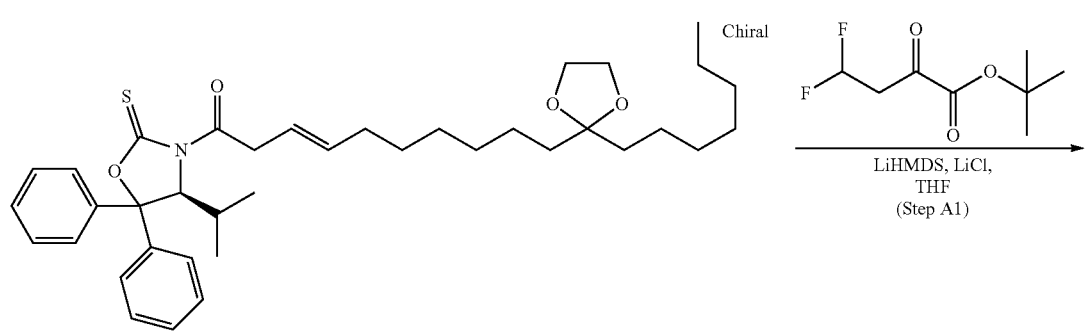
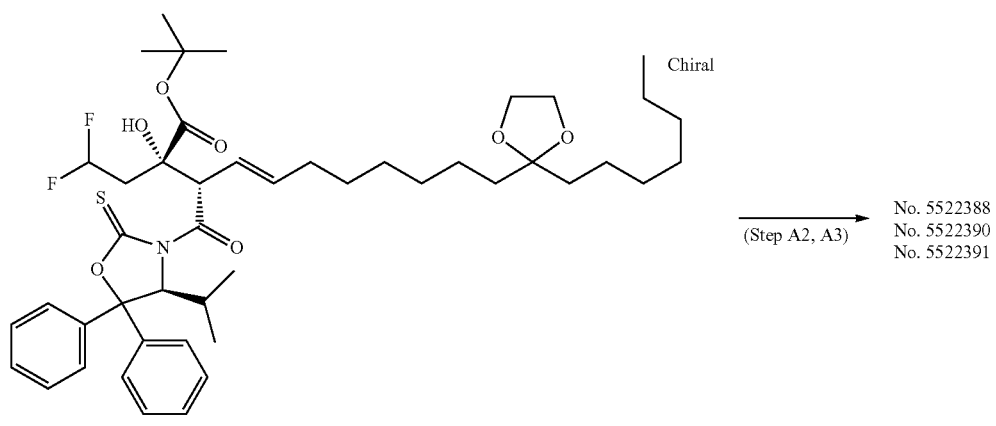
No. 6804095
(Step A2, A3) → No. 5522388
No. 5522390
No. 5522391

385
-continued
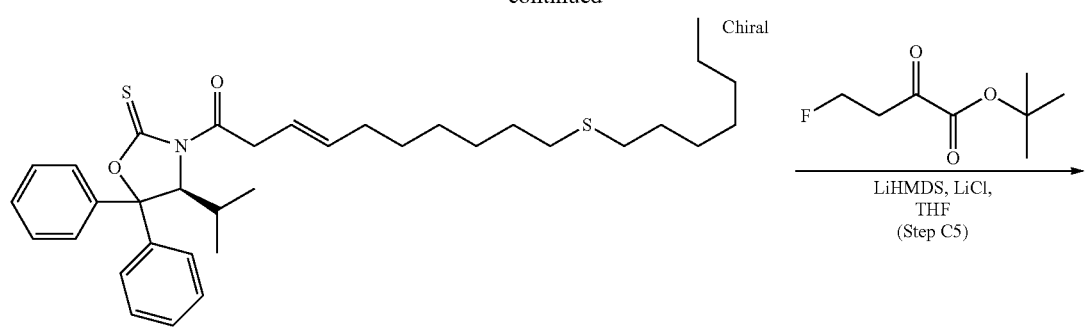
(Step C5)
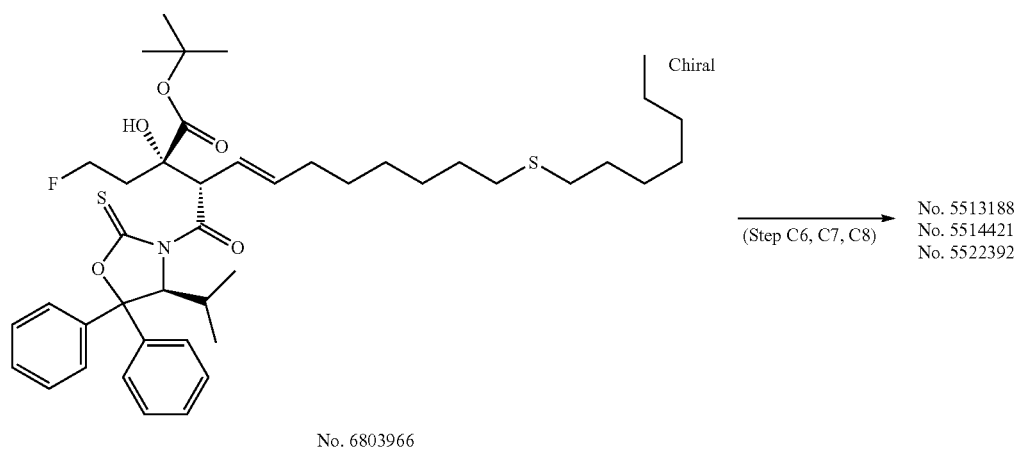
No. 6803966
(Step C6, C7, C8) → No. 5513188
No. 5514421
No. 5522392
386
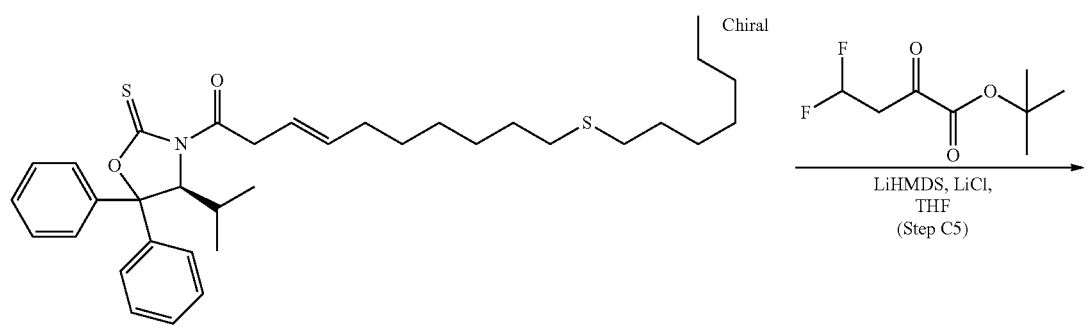
(Step C5)
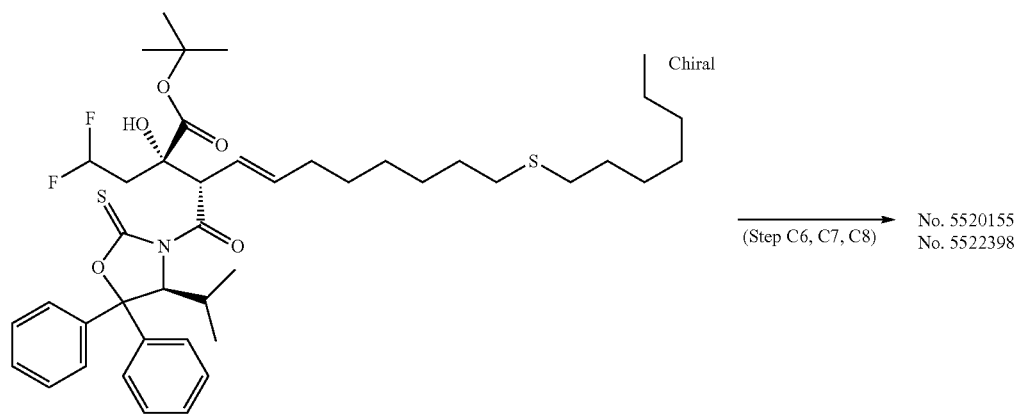
No. 6803864
(Step C6, C7, C8) → No. 5520155
No. 5522398

Synthesis of No. 5513181, No. 5514410, and No. 5514411

Synthesis of No. 6803923, tert-butyl (E)-(2S,3S)-12, 12-difluoro-2-(2-fluoro-ethyl)-2-hydroxy-3-((S)-4-isopropyl-5,5-diphenyl-2-thioxo-oxazolidine-3-carbonyl)-nonadec-4-enoate No. 6803923 was obtained by the method of Step B-6, except that tert-butyl 4-fluoro-2-oxo-butyrate was used instead of tert-butyl 4-methoxy-2-oxo-butyrate.

$^1$H-NMR (CDCl$_3$) δ: 0.74 (3H, d, J=7.0 Hz), 0.80 (3H, d, J=7.0 Hz), 0.87 (3H, t, J=7.1 Hz), 0.97-2.13 (27H, m), 1.47 (9H, s), 3.52 (1H, s), 4.00-4.19 (1H, m), 4.37 (1H, ddd, J=46.3, 9.2, 3.8 Hz), 5.57 (1H, dd, J=15.5, 9.3 Hz), 5.67 (1H, d, J=4.0 Hz), 5.92 (1H, dt, J=15.5, 6.6 Hz), 6.14 (1H, d, J=9.3 Hz), 7.24-7.55 (10H, m)

ESI (LC/MS positive mode) m/z 774 (M+H); Rt 3.78 min.

No. 5513181 (E)-(2S,3S)-3-[(S)-2-(4-But-2-ynyloxy-phenyl)-1-methoxycarbonyl-ethylcarbamoyl]-12,12-difluoro-2-(2-fluoro-ethyl)-2-hydroxy-nonadec-4-enoic acid 5552816 (tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate)-octadec-3-en-1-one).

The title compound was then obtained by the method of Step B-8, except that tert-butyl (E)-(2S,3S)-3-[(S)-2-(4-but-2-ynyloxy-phenyl)-1-methoxycarbonyl-ethylcarbamoyl]-12,12-difluoro-2-(2-fluoro-ethyl)-2-hydroxy-nonadec-4-enoate was used instead of No. 6804236, tert-butyl (E)-(2S, 3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate.

$^1$H-NMR (CD$_3$OD) δ: 0.90 (3H, t, J=6.9 Hz), 1.15-1.52 (18H, m), 1.57-1.91 (5H, m), 1.81 (3H, t, J=2.3 Hz), 1.92-2.07 (2H, m), 2.10-2.35 (1H, m), 2.90 (1H, dd, J=14.0, 9.4 Hz), 3.14 (1H, dd, J=14.0, 5.2 Hz), 3.24 (1H, d, J=7.9 Hz), 3.71 (3H, s), 4.30-4.63 (4H, m), 4.67 (1H, dd, J=9.4, 5.2 Hz), 5.43-5.65 (2H, m), 6.85 (2H, d, J=8.7 Hz), 7.10 (2H, d, J=8.7 Hz)

ESI (LC/MS positive mode) m/z 668 (M+H); Rt 2.25 min.

No. 5514410 (E)-(2S,3S)-3-[(S)-2-(4-Butoxy-phenyl)-1-methoxycarbonyl-ethylcarbamoyl]-12,12-difluoro-2-(2-fluoro-ethyl)-2-hydroxy-nonadec-4-enoic acid

[Chem. 313]

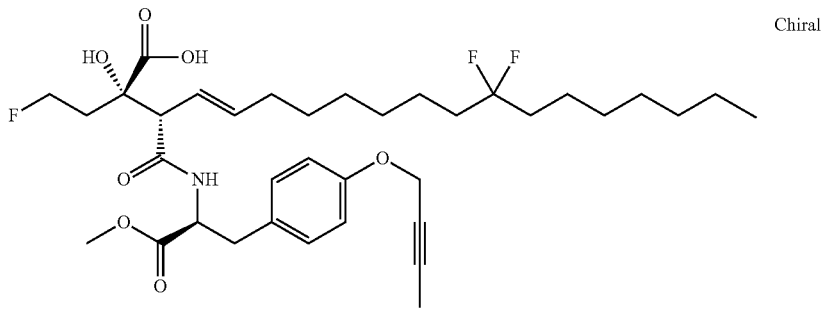

Chiral tert-Butyl (E)-(2S,3S)-3-[(S)-2-(4-but-2-ynyloxy-phenyl)-1-methoxycarbonyl-ethylcarbamoyl]-12,12-difluoro-2-(2-fluoro-ethyl)-2-hydroxy-nonadec-4-enoate was obtained (ESI (LC/MS positive mode) m/z 724 (M+H); Rt 2.52 min.) by the method of Step B-7, except that No. 6803923 (tert-butyl (E)-(2S,3S)-12,12-difluoro-2-(2-fluoro-ethyl)-2-hydroxy-3-((S)-4-isopropyl-5,5-diphenyl-2-thioxo-oxazolidine-3-carbonyl)-nonadec-4-enoate) was used instead of No.

[Chem. 314]

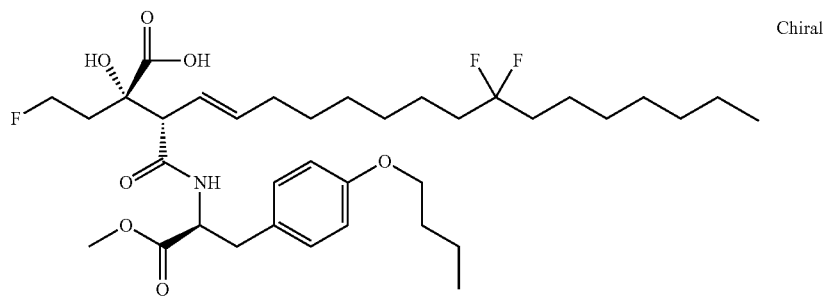

Chiral tert-Butyl (E)-(2S,3S)-3-[(S)-2-(4-butoxy-phenyl)-1-methoxycarbonyl-ethylcarbamoyl]-12,12-difluoro-2-(2-fluoro-ethyl)-2-hydroxy-nonadec-4-enoate was obtained (ESI (LC/MS positive mode) m/z 728 (M+H); Rt 2.87 min.) by the method of Step B-7, except that No. 6803923, tert-butyl (E)-(2S,3S)-12,12-difluoro-2-(2-fluoro-ethyl)-2-hydroxy-3-((S)-4-isopropyl-5,5-diphenyl-2-thioxo-oxazolidine-3-carbonyl)-nonadec-4-enoate was used instead of No. 5552816, tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate)-octadec-3-en-1-one, and methyl (S)-2-amino-3-(4-butoxy-phenyl)-propionate was used instead of methyl (S)-2-amino-3-(4-but-2-ynyloxy-phenyl)-propionate.

The title compound, No. 5514410, (E)-(2S,3S)-3-[(S)-2-(4-butoxy-phenyl)-1-methoxycarbonyl-ethylcarbamoyl]-12,12-difluoro-2-(2-fluoro-ethyl)-2-hydroxy-nonadec-4-enoic acid was obtained by the method of Step B-8, except that tert-butyl (E)-(2S,3S)-3-[(S)-2-(4-butoxy-phenyl)-1-methoxycarbonyl-ethylcarbamoyl]-12,12-difluoro-2-(2-fluoro-ethyl)-2-hydroxy-nonadec-4-enoate was used instead of No. 6804236, tert-butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate.

$^1$H-NMR (CD$_3$OD) δ: 0.90 (3H, t, J=6.9 Hz), 0.98 (3H, t, J=7.4 Hz), 1.18-1.91 (27H, m), 1.92-2.05 (2H, m), 2.14-2.34 (1H, m), 2.88 (1H, dd, J=14.0, 9.2 Hz), 3.13 (1H, dd, J=14.0, 5.1 Hz), 3.24 (1H, d, J=8.2 Hz), 3.71 (3H, s), 4.25-4.72 (3H, m), 5.41-5.66 (2H, m), 6.79 (2H, d, J=8.7 Hz), 7.08 (2H, d, J=8.7 Hz)

ESI (LC/MS positive mode) m/z 672 (M+H); Rt 2.47 min.

No. 5514411 (E)-(2S,3S)-3-[(S)-2-(4-Butoxy-phenyl)-1-methylcarbamoyl-ethylcarbamoyl]-12,12-difluoro-2-(2-fluoro-ethyl)-2-hydroxy-nonadec-4-enoic acid tert-Butyl (E)-(2S,3S)-3-[(S)-2-(4-butoxy-phenyl)-1-methylcarbamoyl-ethylcarbamoyl]-12,12-difluoro-2-(2-fluoro-ethyl)-2-hydroxy-nonadec-4-enoate was obtained (ESI (LC/MS positive mode) m/z 727 (M+H); Rt 2.67 min.) by the method of Step B-7, except that No. 6803923, tert-butyl (E)-(2S,3S)-12,12-difluoro-2-(2-fluoro-ethyl)-2-hydroxy-3-((S)-4-isopropyl-5,5-diphenyl-2-thioxo-oxazolidine-3-carbonyl)-nonadec-4-enoate was used instead of No. 5552816, tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate)-octadec-3-en-1-one, and (S)-2-amino-3-(4-butoxy-phenyl)-N-methyl-propionamide was used instead of methyl (S)-2-amino-3-(4-but-2-ynyloxy-phenyl)-propionate.

The title compound was obtained by the method of Step B-8, except that tert-butyl (E)-(2S,3S)-3-[(S)-2-(4-butoxy-phenyl)-1-methylcarbamoyl-ethylcarbamoyl]-12,12-difluoro-2-(2-fluoro-ethyl)-2-hydroxy-nonadec-4-enoate was used instead of No. 6804236, tert-butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate.

$^1$H-NMR (CD$_3$OD) δ: 0.90 (3H, t, J=6.9 Hz), 0.97 (3H, t, J=7.4 Hz), 1.19-1.90 (27H, m), 1.92-2.05 (2H, m), 2.10-2.31 (1H, m), 2.67-2.73 (3H, m), 2.79 (1H, dd, J=14.1, 9.3 Hz), 3.04 (1H, dd, J=14.0, 5.6 Hz), 3.21 (1H, d, J=8.4 Hz), 3.92 (2H, t, J=6.4 Hz), 4.18-4.67 (3H, m), 5.45-5.64 (2H, m), 6.79 (2H, d, J=8.7 Hz), 7.10 (2H, d, J=8.7 Hz)

ESI (LC/MS positive mode) m/z 671 (M+H); Rt 2.33 min.

Synthesis of No. 5514412 and No. 5514420

Synthesis of No. 6803930, tert-butyl (E)-(2S,3S)-2-(2,2-difluoro-ethyl)-12,12-difluoro-2-hydroxy-3-((S)-4-isopropyl-5,5-diphenyl-2-thioxo-oxazolidine-3-carbonyl)-nonadec-4-enoate No. 6803930 was obtained by the method of Step B-6, except that tert-butyl 4,4-difluoro-2-oxo-butyrate was used instead of tert-butyl 4-methoxy-2-oxo-butyrate.

$^1$H-NMR (CDCl$_3$) δ: 0.74 (3H, d, J=6.8 Hz), 0.78 (3H, d, J=6.8 Hz), 0.88 (3H, t, J=6.6 Hz), 1.18-2.15 (27H, m), 1.49 (9H, s), 3.52 (1H, s), 5.45-6.06 (3H, m), 5.68 (1H, d, J=3.9 Hz), 6.13 (1H, d, J=9.4 Hz), 7.23-7.56 (10H, m)

ESI (LC/MS positive mode) m/z 792 (M+H); Rt 3.83 min.

[Chem. 315]

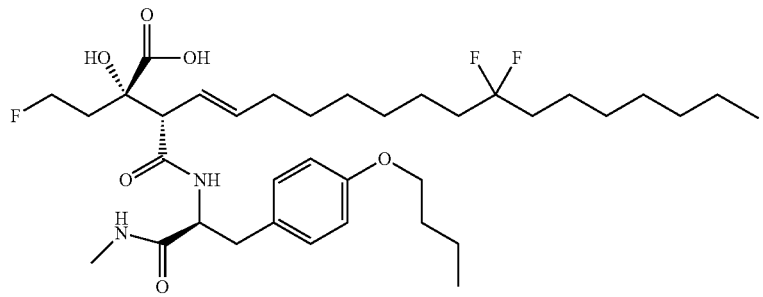

Chiral

No. 5514412 (E)-(2S,3S)-3-[(S)-2-(4-Butoxy-phenyl)-1-methoxycarbonyl-ethylcarbamoyl]-2-(2,2-difluoro-ethyl)-12,12-difluoro-2-hydroxy-nonadec-4-enoic acid

[Chem. 316]

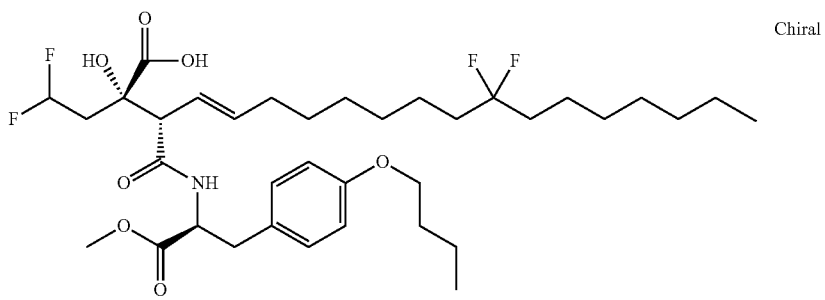

tert-Butyl (E)-(2S,3S)-3-[(S)-2-(4-butoxy-phenyl)-1-methoxycarbonyl-ethylcarbamoyl]-2-(2,2-difluoro-ethyl)-12,12-difluoro-2-hydroxy-nonadec-4-enoate was obtained (ESI (LC/MS positive mode) m/z 746 (M+H); Rt 2.85 min.) by the method of Step B-7, except that No. 6803930, tert-butyl (E)-(2S,3S)-2-(2,2-difluoro-ethyl)-12,12-difluoro-2-hydroxy-3-((S)-4-isopropyl-5,5-diphenyl-2-thioxo-oxazolidine-3-carbonyl)-nonadec-4-enoate was used instead of No. 5552816, tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate)-octadec-3-en-1-one, and methyl (S)-2-amino-3-(4-butoxy-phenyl)-propionate was used instead of methyl (S)-2-amino-3-(4-but-2-ynyloxy-phenyl)-propionate.

The title compound was obtained by the method of Step B-8, except that tert-butyl (E)-(2S,3S)-3-[(S)-2-(4-butoxy-phenyl)-1-methoxycarbonyl-ethylcarbamoyl]-2-(2,2-difluoro-ethyl)-12,12-difluoro-2-hydroxy-nonadec-4-enoate was used instead of No. 6804236, tert-butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate.

$^1$H-NMR (CD$_3$OD) δ: 0.90 (3H, t, J=6.9 Hz), 0.97 (3H, t, J=7.4 Hz), 1.20-1.90 (26H, m), 1.91-2.43 (4H, m), 2.88 (1H, dd, J=14.0, 9.5 Hz), 3.13 (1H, dd, J=14.0, 4.9 Hz), 3.24 (1H, d, J=7.6 Hz), 3.71 (3H, s), 3.92 (2H, t, J=6.4 Hz), 4.64 (1H, dd, J=9.5, 4.9 Hz), 5.38-5.65 (2H, m), 5.92 (1H, tdd, J=56.4, 7.3, 2.5 Hz), 6.79 (2H, d, J=8.7 Hz), 7.08 (2H, d, J=8.7 Hz)
ESI (LC/MS positive mode) m/z 690 (M+H); Rt 2.45 min.

No. 5514420 (E)-(2S,3S)-3-[(S)-2-(4-Butoxy-phenyl)-1-methylcarbamoyl-ethylcarbamoyl]-2-(2,2-difluoro-ethyl)-12,12-difluoro-2-hydroxy-nonadec-4-enoic acid

[Chem. 317]

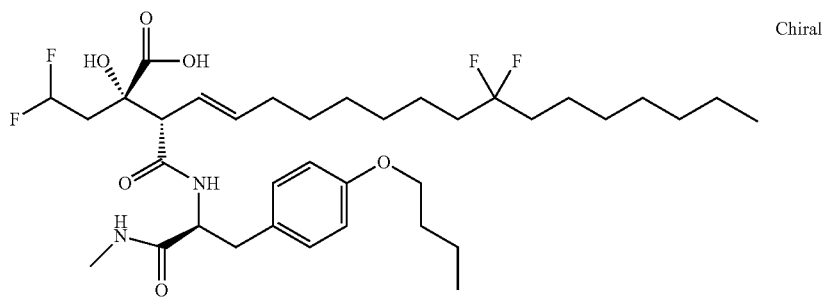

tert-Butyl (E)-(2S,3S)-3-[(S)-2-(4-butoxy-phenyl)-1-methylcarbamoyl-ethylcarbamoyl]-2-(2,2-difluoro-ethyl)-12,12-difluoro-2-hydroxy-nonadec-4-enoate was obtained (ESI (LC/MS positive mode) m/z 745 (M+H); Rt 2.70 min.) by the method of Step B-7, except that No. 6803930, tert-butyl (E)-(2S,3S)-2-(2,2-difluoro-ethyl)-12,12-difluoro-2-hydroxy-3-((S)-4-isopropyl-5,5-diphenyl-2-thioxo-oxazolidine-3-carbonyl)-nonadec-4-enoate was used instead of No. 5552816, tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate)-octadec-3-en-1-one, and (S)-2-amino-3-(4-butoxy-phenyl)-N-methyl-propionamide was used instead of methyl (S)-2-amino-3-(4-but-2-ynyloxy-phenyl)-propionate.

The title compound was obtained by the method of Step B-8, except that tert-butyl (E)-(2S,3S)-3-[(S)-2-(4-butoxy-phenyl)-1-methylcarbamoyl-ethylcarbamoyl]-2-(2,2-difluoro-ethyl)-12,12-difluoro-2-hydroxy-nonadec-4-enoate was used instead of No. 6804236, tert-butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate.

¹H-NMR (CD₃OD) δ: 0.90 (3H, t, J=6.9 Hz), 0.97 (3H, t, J=7.4 Hz), 1.15-1.90 (26H, m), 1.90-2.42 (4H, m), 2.71 (3H, s), 2.79 (1H, dd, J=14.0, 9.4 Hz), 3.03 (1H, dd, J=14.0, 5.4 Hz), 3.20 (1H, d, J=8.4 Hz), 3.92 (2H, t, J=6.4 Hz), 4.52 (1H, dd, J=9.4, 5.4 Hz), 5.40-5.68 (2H, m), 5.92 (1H, tdd, J=56.6, 7.1, 2.5 Hz), 6.79 (2H, d, J=8.7 Hz), 7.10 (2H, d, J=8.7 Hz) ESI (LC/MS positive mode) m/z 689 (M+H); Rt 2.35 min.

Synthesis of No. 5522350, No. 5522365, and No. 5522381

Synthesis of No. 6804093, tert-butyl (E)-(2S,3S)-2-(2-fluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate No. 6804093 was obtained by the method of Step A-1, except that tert-butyl 4-fluoro-2-oxo-butyrate was used instead of tert-butyl 4-methoxy-2-oxo-butyrate.

¹H-NMR (CDCl₃) δ: 0.75 (3H, d, J=6.8 Hz), 0.80 (3H, d, J=6.9 Hz), 0.87 (3H, t, J=6.9 Hz), 0.92-1.75 (22H, m), 1.47 (9H, s), 1.80-2.17 (5H, m), 3.52 (1H, s), 3.91 (4H, s), 3.93-4.24 (1H, m), 4.38 (1H, dtd, J=47.8, 9.5, 3.9 Hz), 5.57 (1H, dd, J=15.3, 9.4 Hz), 5.67 (1H, d, J=3.9 Hz), 5.93 (1H, dt, J=15.3, 6.7 Hz), 6.16 (1H, d, J=9.4 Hz), 7.23-7.60 (10H, m) ESI (LC/MS positive mode) m/z 796 (M+H); Rt 4.13 min.

No. 5522350 (E)-(2S,3S)-3-[(S)-2-(4-Butoxy-phenyl)-1-methoxycarbonyl-ethylcarbamoyl]-2-(2-fluoro-ethyl)-2-hydroxy-12-oxo-nonadec-4-enoic acid Rt 2.90 min.) by the method of Step A-2, except that No. 6804093, tert-butyl (E)-(2S,3S)-2-(2-fluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S, 3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and methyl (S)-2-amino-3-(4-butoxy-phenyl)-propionate was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate was used instead of No. 5534988, tert-butyl (E)-(2S, 3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

¹H-NMR (CD₃OD) δ: 0.90 (3H, t, J=6.9 Hz), 0.98 (3H, t, J=7.4 Hz), 1.18-1.85 (23H, m), 1.89-2.10 (2H, m), 2.12-2.33 (1H, m), 2.43 (4H, t, J=7.3 Hz), 2.88 (1H, dd, J=14.0, 9.4 Hz), 3.12 (1H, dd, J=14.0, 5.1 Hz), 3.23 (1H, d, J=8.2 Hz), 3.71 (3H, s), 3.93 (2H, t, J=6.4 Hz), 4.25-4.62 (1H, m), 4.65 (1H, dd, J=9.4, 5.1 Hz), 5.42-5.65 (2H, m), 6.79 (2H, d, J=8.7 Hz), 7.08 (2H, d, J=8.7 Hz) ESI (LC/MS positive mode) m/z 650 (M+H); Rt 2.30 min.

No. 5522365 (E)-(2S,3S)-3-[(S)-2-(4-Butoxy-phenyl)-1-methylcarbamoyl-ethylcarbamoyl]-2-(2-fluoro-ethyl)-2-hydroxy-12-oxo-nonadec-4-enoic acid

[Chem. 318]

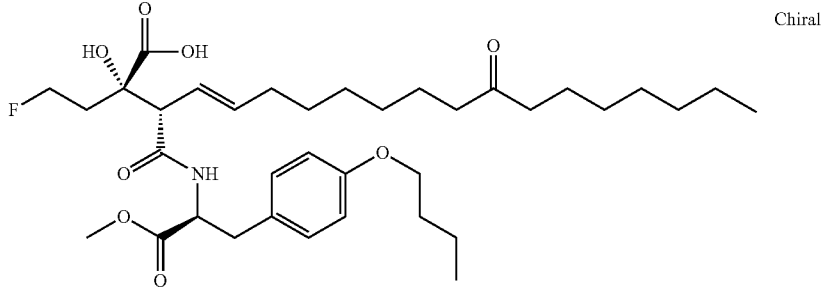

tert-Butyl (E)-(2S,3S)-3-[(S)-2-(4-butoxy-phenyl)-1-methoxycarbonyl-ethylcarbamoyl]-2-(2-fluoro-ethyl)-11-(2-heptyl-[1,3]dioxolan-2-yl)-2-hydroxy-undec-4-enoate was obtained (ESI (LC/MS positive mode) m/z 750 (M+H);

[Chem. 319]

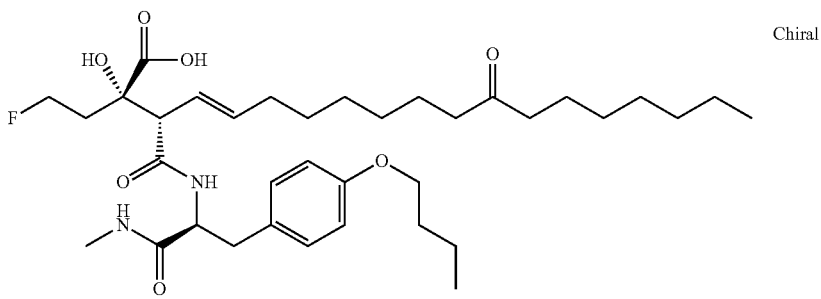

tert-Butyl (E)-(2S,3S)-3-[(S)-2-(4-butoxy-phenyl)-1-methylcarbamoyl-ethylcarbamoyl]-2-(2-fluoro-ethyl)-11-(2-heptyl-[1,3]dioxolan-2-yl)-2-hydroxy-undec-4-enoate was obtained (ESI (LC/MS positive mode) m/z 749 (M+H); Rt 2.67 min.) by the method of Step A-2, except that No. 6804093, tert-butyl (E)-(2S,3S)-2-(2-fluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S, 3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and (S)-2-amino-3-(4-butoxy-phenyl)-N-methyl-propionamide was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-methylcarbamoyl-ethylcarbamoyl]-2-(2-fluoro-ethyl)-11-(2-heptyl-[1,3]dioxolan-2-yl)-2-hydroxy-undec-4-enoate was used instead of No. 5534988, tert-butyl (E)-(2S, 3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

$^1$H-NMR (CD$_3$OD) δ: 0.90 (3H, t, J=6.9 Hz), 0.97 (3H, t, J=7.4 Hz), 1.16-1.81 (23H, m), 1.90-2.10 (2H, m), 2.10-2.35 (1H, m), 2.43 (4H, t, J=7.4 Hz), 2.70 (3H, s), 2.79 (1H, dd, J=14.0, 9.4 Hz), 3.03 (1H, dd, J=14.0, 5.4 Hz), 3.20 (1H, d, J=8.4 Hz), 3.92 (2H, t, J=6.4 Hz), 4.24-4.65 (3H, m), 5.45-5.63 (2H, m), 6.79 (2H, d, J=8.6 Hz), 7.10 (2H, d, J=8.6 Hz)

ESI (LC/MS positive mode) m/z 649 (M+H); Rt 2.15 min.

No. 5522381 (E)-(2S,3S)-3-[(S)-2-(4-Butoxy-phenyl)-1-carbamoyl-ethylcarbamoyl]-2-(2-fluoro-ethyl)-2-hydroxy-12-oxo-nonadec-4-enoic acid tert-Butyl (E)-(2S,3S)-3-[(S)-2-(4-butoxy-phenyl)-1-carbamoyl-ethylcarbamoyl]-2-(2-fluoro-ethyl)-11-(2-heptyl-[1,3]dioxolan-2-yl)-2-hydroxy-undec-4-enoate was obtained (ESI (LC/MS positive mode) m/z 735 (M+H); Rt 2.62 min.) by the method of Step A-2, except that No. 6804093, tert-butyl (E)-(2S,3S)-2-(2-fluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and (S)-2-amino-3-(4-butoxy-phenyl)-propionamide was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-carbamoyl-ethylcarbamoyl]-2-(2-fluoro-ethyl)-11-(2-heptyl-[1,3]dioxolan-2-yl)-2-hydroxy-undec-4-enoate was used instead of No. 5534988, tert-butyl (E)-(2S, 3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

$^1$H-NMR (CD$_3$OD) δ: 0.90 (3H, t, J=6.9 Hz), 0.98 (3H, t, J=7.4 Hz), 1.18-1.80 (23H, m), 1.90-2.05 (2H, m), 2.09-2.29 (1H, m), 2.43 (4H, t, J=7.4 Hz), 2.80 (1H, dd, J=14.0, 9.7 Hz), 3.10 (1H, dd, J=14.0, 5.1 Hz), 3.20 (1H, d, J=8.9 Hz), 3.92 (2H, t, J=6.2 Hz), 4.20-4.67 (3H, m), 5.43-5.63 (2H, m), 6.79 (2H, d, J=8.7 Hz), 7.13 (2H, d, J=8.7 Hz)

ESI (LC/MS positive mode) m/z 635 (M+H); Rt 2.10 min.

Synthesis of No. 5522388, No. 5522390, and No. 5522391

Synthesis of No. 6804095, tert-butyl (E)-(2S,3S)-2-(2,2-difluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate No. 6804095 was obtained by the method of Step A-1, except that tert-butyl 4,4-difluoro-2-oxo-butyrate was used instead of tert-butyl 4-methoxy-2-oxo-butyrate.

[Chem. 320]

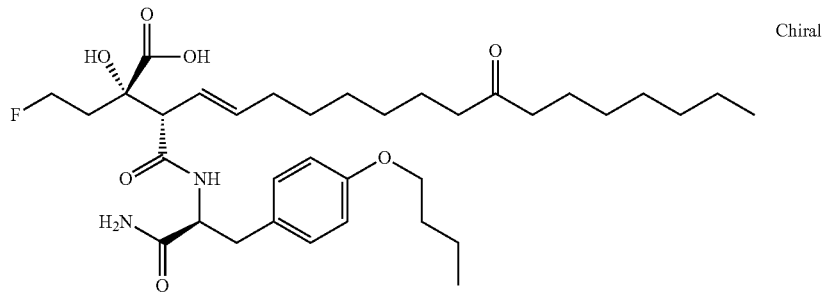

Chiral $^1$H-NMR (CDCl$_3$) δ: 0.74 (3H, d, J=6.8 Hz), 0.78 (3H, d, J=6.8 Hz), 0.87 (3H, t, J=6.5 Hz), 0.93-1.68 (24H, m), 1.49 (9H, s), 1.90-2.12 (3H, m), 3.53 (1H, s), 3.91 (4H, s), 5.43-6.07 (3H, m), 5.67 (1H, d, J=4.1 Hz), 6.14 (1H, d, J=9.4 Hz), 7.20-7.55 (10H, m)

ESI (LC/MS positive mode) m/z 814 (M+H); Rt 4.12 min.

397

No. 5522388 (E)-(2S,3S)-3-[(S)-2-(4-Butoxy-phenyl)-1-methoxycarbonyl-ethylcarbamoyl]-2-(2,2-difluoro-ethyl)-2-hydroxy-12-oxo-nonadec-4-enoic acid

[Chem. 321]

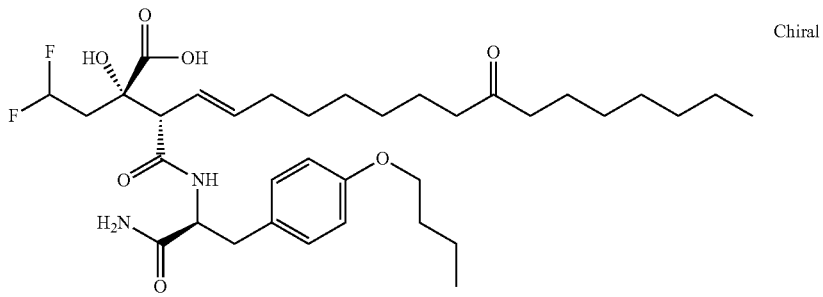

tert-Butyl (E)-(2S,3S)-3-[(S)-2-(4-butoxy-phenyl)-1-carbamoyl-ethylcarbamoyl]-2-(2,2-difluoro-ethyl)-11-(2-heptyl-[1,3]dioxolan-2-yl)-2-hydroxy-undec-4-enoate was obtained (ESI (LC/MS positive mode) m/z 753 (M+H); Rt 2.62 min.) by the method of Step A-2, except that No. 6804095, tert-butyl (E)-(2S,3S)-2-(2,2-difluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and (S)-2-amino-3-(4-butoxy-phenyl)-propionamide was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-carbamoyl-ethylcarbamoyl]-2-(2,2-difluoro-ethyl)-11-(2-heptyl-[1,3]dioxolan-2-yl)-2-hydroxy-undec-4-enoate was used instead of No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

$^{1}$H-NMR (CD$_{3}$OD) δ: 0.90 (3H, t, J=6.9 Hz), 0.97 (3H, t, J=7.4 Hz), 1.16-1.80 (23H, m), 1.85-2.40 (3H, m), 2.43 (4H, t, J=7.3 Hz), 2.80 (1H, dd, J=14.2, 9.9 Hz), 3.10 (1H, dd, J=14.2, 5.1 Hz), 3.19 (1H, d, J=8.4 Hz), 3.92 (2H, t, J=6.4 Hz), 4.58 (1H, dd, J=9.9, 5.1 Hz), 5.42-5.64 (2H, m), 5.90 (1H, tdd, J=56.6, 7.1, 2.5 Hz), 6.79 (2H, d, J=8.7 Hz), 7.13 (2H, d, J=8.7 Hz) ESI (LC/MS positive mode) m/z 653 (M+H); Rt 2.13 min.

398

No. 5522390 (E)-(2S,3S)-3-[(S)-2-(4-Butoxy-phenyl)-1-methoxycarbonyl-ethylcarbamoyl]-2-(2,2-difluoro-ethyl)-2-hydroxy-12-oxo-nonadec-4-enoic acid

[Chem. 322]

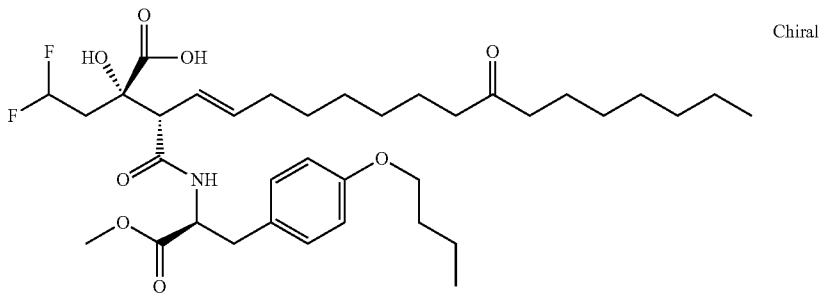

tert-Butyl (E)-(2S,3S)-3-[(S)-2-(4-butoxy-phenyl)-1-methoxycarbonyl-ethylcarbamoyl]-2-(2,2-difluoro-ethyl)-11-(2-heptyl-[1,3]dioxolan-2-yl)-2-hydroxy-undec-4-enoate was obtained (ESI (LC/MS positive mode) m/z 768 (M+H); Rt 2.90 min.) by the method of Step A-2, except that No. 6804095, tert-butyl (E)-(2S,3S)-2-(2,2-difluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and methyl (S)-2-amino-3-(4-butoxy-phenyl)-propionate was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-methoxycarbonyl-ethylcarbamoyl]-2-(2,2-difluoro-ethyl)-11-(2-heptyl-[1,3]dioxolan-2-yl)-2-hydroxy-undec-4-enoate was used instead of No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

$^{1}$H-NMR (CD$_{3}$OD) δ: 0.90 (3H, t, J=7.1 Hz), 0.97 (3H, t, J=7.4 Hz), 1.15-1.84 (23H, m), 1.87-2.40 (3H, m), 2.43 (4H, t, J=6.4 Hz), 2.88 (1H, dd, J=14.0, 9.4 Hz), 3.06-3.20 (1H, m), 3.26 (1H, d, J=8.6 Hz), 3.71 (3H, s), 3.92 (2H, t, J=6.4 Hz), 4.55-4.73 (1H, m), 5.35-5.67 (2H, m), 5.92 (1H, tdd, J=54.4, 7.2, 2.3 Hz), 6.79 (2H, d, J=8.7 Hz), 7.08 (2H, d, J=8.7 Hz)

ESI (LC/MS positive mode) m/z 668 (M+H); Rt 2.32 min.

No. 5522391 (E)-(2S,3S)-3-[(S)-2-(4-Butoxy-phenyl)-1-methylcarbamoyl-ethylcarbamoyl]-2-(2,2-difluoro-ethyl)-2-hydroxy-12-oxo-nonadec-4-enoic acid

[Chem. 323]

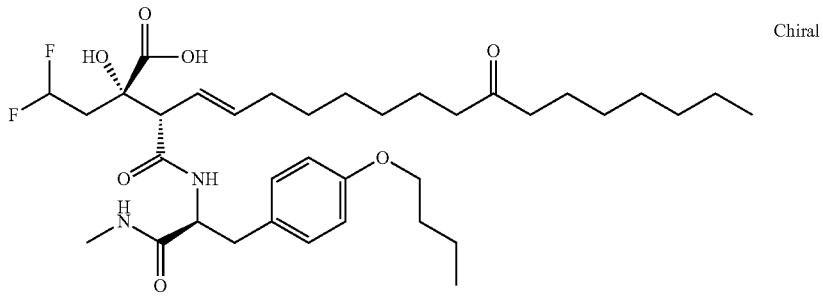

tert-Butyl (E)-(2S,3S)-3-[(S)-2-(4-butoxy-phenyl)-1-methylcarbamoyl-ethylcarbamoyl]-2-(2,2-difluoro-ethyl)-11-(2-heptyl-[1,3]dioxolan-2-yl)-2-hydroxy-undec-4-enoate was obtained (ESI (LC/MS positive mode) m/z 767 (M+H); Rt 2.70 min.) by the method of Step A-2, except that No. 6804095, tert-butyl (E)-(2S,3S)-2-(2,2-difluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate was used instead of No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and (S)-2-amino-3-(4-butoxy-phenyl)-N-methyl-propionamide was used instead of methyl (S)-2-amino-3-(4-but-2-ynyloxy-phenyl)-propionate.

The title compound was obtained by the method of Step A-3, except that tert-butyl (E)-(2S,3S)-3-[(S)-2-(4-butoxy-phenyl)-1-methylcarbamoyl-ethylcarbamoyl]-2-(2,2-difluoro-ethyl)-11-(2-heptyl-[1,3]dioxolan-2-yl)-2-hydroxy-undec-4-enoate was used instead of No. 5534988, tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate.

$^{1}$H-NMR (CD$_3$OD) δ: 0.90 (3H, t, J=6.9 Hz), 0.97 (3H, t, J=7.4 Hz), 1.15-1.83 (23H, m), 1.85-2.40 (3H, m), 2.43 (4H, t, J=7.4 Hz), 2.70 (3H, s), 2.78 (1H, dd, J=14.0, 9.2 Hz), 3.04 (1H, dd, J=14.0, 5.4 Hz), 3.20 (1H, d, J=8.3 Hz), 4.51 (1H, dd, J=9.2, 5.4 Hz), 5.40-5.67 (2H, m), 5.91 (1H, tdd, J=56.5, 7.1, 2.3 Hz), 6.79 (2H, d, J=8.7 Hz), 7.10 (2H, d, J=8.7 Hz)

ESI (LC/MS positive mode) m/z 667 (M+H); Rt 2.18 min.

Synthesis of No. 5513188, No. 5514421, and No. 5522392

Synthesis of No. 6803966, tert-butyl (E)-(2S,3S)-2-(2-fluoro-ethyl)-11-heptylsulfanyl-2-hydroxy-3-((S)-4-isopropyl-5,5-diphenyl-2-thioxo-oxazolidine-3-carbonyl)-undec-4-enoate No. 6803966 was obtained by the method of Step C-5, except that tert-butyl 4-fluoro-2-oxo-butyrate was used instead of tert-butyl 4-methoxy-2-oxo-butyrate.

$^{1}$H-NMR (CDCl$_3$) δ: 0.73 (3H, d, J=6.6 Hz), 0.78 (3H, d, J=7.0 Hz), 0.86 (3H, t, J=7.0 Hz), 0.95-1.67 (18H, m), 1.46 (9H, s), 1.80-2.10 (5H, m), 2.46 (4H, td, J=7.5, 2.2 Hz), 3.50 (1H, s), 3.98-4.17 (1H, m), 4.36 (1H, dtd, J=47.6, 9.2, 3.6 Hz), 5.55 (1H, dd, J=15.4, 9.2 Hz), 5.65 (1H, d, J=4.0 Hz), 5.91 (1H, dt, J=15.4, 7.1 Hz), 6.14 (1H, d, J=9.2 Hz), 7.20-7.53 (10H, m)

ESI (LC/MS positive mode) m/z 756 (M+H); Rt 4.32 min.

No. 5513188 (E)-(2S,3S)-3-[(S)-2-(4-but-2-ynyloxy-phenyl)-1-methoxycarbonyl-ethylcarbamoyl]-2-(2-fluoro-ethyl)-11-(heptane-1-sulfonyl)-2-hydroxy-2-undec-4-enoic acid

[Chem. 324]

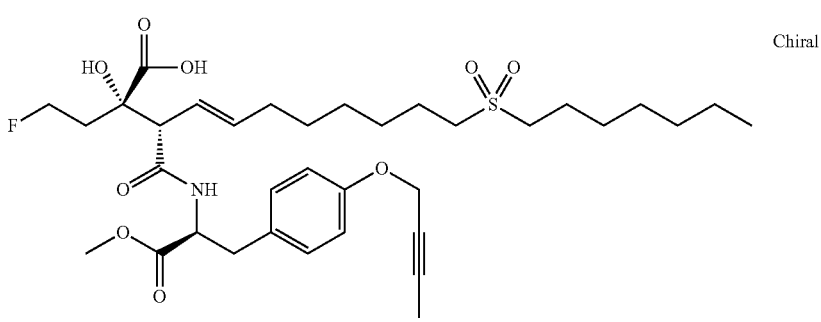

tert-Butyl (E)-(2S,3S)-3-[(S)-2-(4-but-2-ynyloxy-phenyl)-1-methoxycarbonyl-ethylcarbamoyl]-2-(2-fluoro-ethyl)-11-heptylsulfanyl-2-hydroxy-undec-4-enoate was obtained (ESI (LC/MS positive mode) m/z 706 (M+H); Rt 2.58 min.) by the method of Step C-6, except that No. 6803966, tert-butyl (E)-(2S,3S)-2-(2-fluoro-ethyl)-11-heptylsulfanyl-2-hydroxy-3-((S)-4-isopropyl-5,5-diphenyl-2-thioxo-oxazolidine-3-carbonyl)-undec-4-enoate was used instead of No. 6804239, tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate.

tert-Butyl (E)-(2S,3S)-3-[(S)-2-(4-but-2-ynyloxy-phenyl)-1-methoxycarbonyl-ethylcarbamoyl]-2-(2-fluoro-ethyl)-11-(heptane-1-sulfonyl)-2-hydroxy-2-undec-4-enoate was obtained (ESI (LC/MS positive mode) m/z 738 (M+H); Rt 0.81 min.) by the method of Step C-7, except that tert-butyl (E)-(2S,3S)-3-[(S)-2-(4-but-2-ynyloxy-phenyl)-1-methoxycarbonyl-ethylcarbamoyl]-2-(2-fluoro-ethyl)-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-but-2-ynyloxy-phenyl)-1-methoxycarbonyl-ethylcarbamoyl]-2-(2-fluoro-ethyl)-11-(heptane-1-sulfonyl)-2-hydroxy-2-undec-4-enoate was used instead of No. 6804464, tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate.

$^1$H-NMR (CD$_3$OD) δ: 0.91 (3H, t, J=6.9 Hz), 1.19-1.85 (19H, m), 1.82 (3H, t, J=2.3 Hz), 1.92-2.10 (2H, m), 2.12-2.34 (1H, m), 2.89 (1H, dd, J=14.0, 9.4 Hz), 2.98-3.10 (4H, m), 3.15 (1H, dd, J=14.0, 4.9 Hz), 3.24 (1H, d, J=8.2 Hz), 3.72 (3H, s), 4.26-4.65 (4H, m), 4.67 (1H, dd, J=9.4, 4.9 Hz), 5.43-5.65 (2H, m), 6.86 (2H, d, J=8.6 Hz), 7.11 (2H, d, J=8.6 Hz)

ESI (LC/MS positive mode) m/z 682 (M+H); Rt 1.85 min.

No. 5514421 (E)-(2S,3S)-3-[(S)-2-(4-Butoxy-phenyl)-1-methoxycarbonyl-ethylcarbamoyl]-2-(2-fluoro-ethyl)-11-(heptane-1-sulfonyl)-2-hydroxy-2-undec-4-enoic acid tert-Butyl (E)-(2S,3S)-3-[(S)-2-(4-butoxy-phenyl)-1-methoxycarbonyl-ethylcarbamoyl]-2-(2-fluoro-ethyl)-11-heptylsulfanyl-2-hydroxy-undec-4-enoate was obtained (ESI (LC/MS positive mode) m/z 710 (M+H); Rt 3.02 min.) by the method of Step C-6, except that No. 6803966, tert-butyl (E)-(2S,3S)-2-(2-fluoro-ethyl)-11-heptylsulfanyl-2-hydroxy-3-((S)-4-isopropyl-5,5-diphenyl-2-thioxo-oxazolidine-3-carbonyl)-undec-4-enoate was used instead of No. 6804239, tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate, and methyl (S)-2-amino-3-(4-butoxy-phenyl)-propionate was used instead of methyl (S)-2-amino-3-(4-but-2-ynyloxy-phenyl)-propionate.

tert-Butyl (E)-(2S,3S)-3-[(S)-2-(4-butoxy-phenyl)-1-methoxycarbonyl-ethylcarbamoyl]-2-(2-fluoro-ethyl)-11-(heptane-1-sulfonyl)-2-hydroxy-2-undec-4-enoate was obtained (ESI (LC/MS positive mode) m/z 742 (M+H); Rt 2.32 min.) by the method of Step C-7, except that tert-butyl (E)-(2S,3S)-3-[(S)-2-(4-butoxy-phenyl)-1-methoxycarbonyl-ethylcarbamoyl]-2-(2-fluoro-ethyl)-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-butoxy-phenyl)-1-methoxycarbonyl-ethylcarbamoyl]-2-(2-fluoro-ethyl)-11-(heptane-1-sulfonyl)-2-hydroxy-2-undec-4-enoate was used instead of No. 6804464, tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate.

$^1$H-NMR (CD$_3$OD) δ: 0.91 (3H, t, J=6.7 Hz), 0.98 (3H, t, J=7.4 Hz), 1.20-1.88 (23H, m), 1.91-2.12 (2H, m), 2.13-2.38 (1H, m), 2.88 (1H, dd, J=14.2, 9.4 Hz), 2.98-3.10 (4H, m), 3.13 (1H, dd, J=14.2, 5.1 Hz), 3.24 (1H, d, J=8.1 Hz), 3.71 (3H, s), 4.25-4.71 (3H, m), 5.43-5.64 (2H, m), 6.80 (2H, d, J=8.6 Hz), 7.09 (2H, d, J=8.6 Hz)

ESI (LC/MS positive mode) m/z 686 (M+H); Rt 2.07 min.

[Chem. 325]

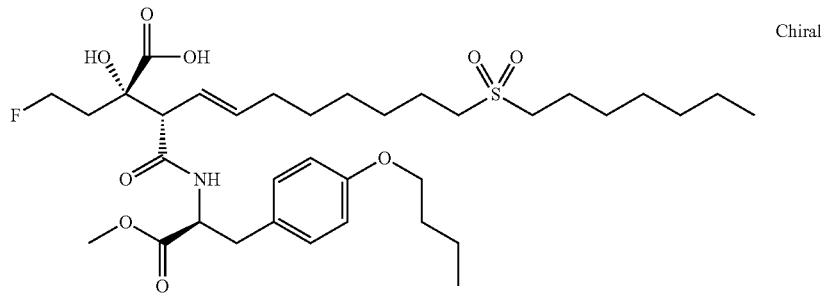

No. 5522392 (E)-(2S,3S)-3-[(S)-2-(4-Butoxy-phenyl)-1-carbamoyl-ethylcarbamoyl]-2-(2-fluoro-ethyl)-11-(heptane-1-sulfonyl)-2-hydroxy-2-undec-4-enoic acid

[Chem. 326]

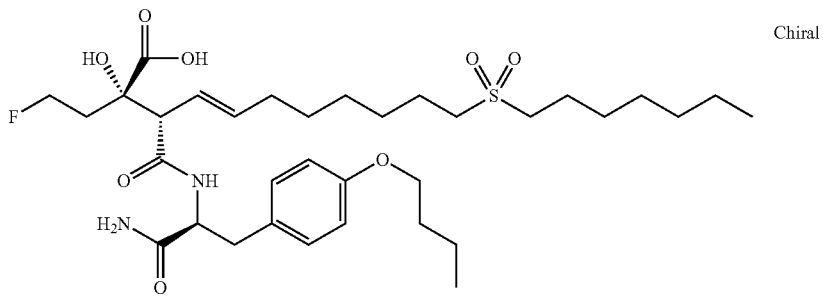

tert-Butyl (E)-(2S,3S)-3-[(S)-2-(4-butoxy-phenyl)-1-carbamoyl-ethylcarbamoyl]-2-(2-fluoro-ethyl)-11-heptylsulfanyl-2-hydroxy-undec-4-enoate was obtained (ESI (LC/MS positive mode) m/z 695 (M+H); Rt 2.70 min.) by the method of Step C-6, except that No. 6803966, tert-butyl (E)-(2S,3S)-2-(2-fluoro-ethyl)-11-heptylsulfanyl-2-hydroxy-3-((S)-4-isopropyl-5,5-diphenyl-2-thioxo-oxazolidine-3-carbonyl)-undec-4-enoate was used instead of No. 6804239, tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate.

tert-Butyl (E)-(2S,3S)-3-[(S)-2-(4-butoxy-phenyl)-1-carbamoyl-ethylcarbamoyl]-2-(2-fluoro-ethyl)-11-(heptane-1-sulfonyl)-2-hydroxy-undec-4-enoate was obtained (ESI (LC/MS positive mode) m/z 727 (M+H); Rt 2.12 min.) by the method of Step C-7, except that tert-butyl (E)-(2S,3S)-3-[(S)-2-(4-butoxy-phenyl)-1-carbamoyl-ethylcarbamoyl]-2-(2-fluoro-ethyl)-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-butoxy-phenyl)-1-carbamoyl-ethylcarbamoyl]-2-(2-fluoro-ethyl)-11-(heptane-1-sulfonyl)-2-hydroxy-2-undec-4-enoate was used instead of No. 6804464, tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate.

$^1$H-NMR (CD$_3$OD) δ: 0.91 (3H, t, J=6.9 Hz), 0.98 (3H, t, J=7.4 Hz), 1.20-1.87 (23H, m), 1.90-2.07 (2H, m), 2.08-2.30 (1H, m), 2.80 (1H, dd, J=14.0, 9.9 Hz), 2.96-3.16 (5H, m), 3.20 (1H, d, J=8.6 Hz), 3.93 (2H, t, J=6.4 Hz), 4.20-4.66 (2H, m), 5.45-5.64 (2H, m), 6.80 (2H, d, J=8.7 Hz), 7.14 (2H, d, J=8.7 Hz)

ESI (LC/MS positive mode) m/z 671 (M+H); Rt 1.80 min.

Synthesis of No. 5520155 and No. 5522398

Synthesis of No. 6803864, tert-butyl (E)-(2S,3S)-2-(2,2-difluoro-ethyl)-11-heptylsulfanyl-2-hydroxy-3-((S)-4-isopropyl-5,5-diphenyl-2-thioxo-oxazolidine-3-carbonyl)-undec-4-enoate No. 6803864 was obtained by the method of Step C-5, except that tert-butyl 4,4-difluoro-2-oxo-butyrate was used instead of tert-butyl 4-methoxy-2-oxo-butyrate.

$^1$H-NMR (CDCl$_3$) δ: 0.74 (3H, d, J=6.7 Hz), 0.79 (3H, d, J=6.9 Hz), 0.88 (3H, t, J=7.3 Hz), 1.20-1.73 (20H, m), 1.49 (9H, s), 1.90-2.18 (3H, m), 2.48 (4H, td, J=7.1, 1.8 Hz), 3.53 (1H, s), 5.52-6.07 (3H, m), 5.67 (1H, d, J=4.1 Hz), 6.13 (1H, d, J=9.4 Hz), 7.23-7.60 (10H, m)

ESI (LC/MS positive mode) m/z 774 (M+H); Rt 4.27 min.)

No. 5521055 (E)-(2S,3S)-3-[(S)-2-(4-Butoxy-phenyl)-1-methoxycarbonyl-ethylcarbamoyl]-2-(2,2-difluoro-ethyl)-11-(heptane-1-sulfonyl)-2-hydroxy-2-undec-4-enoic acid

[Chem. 327]

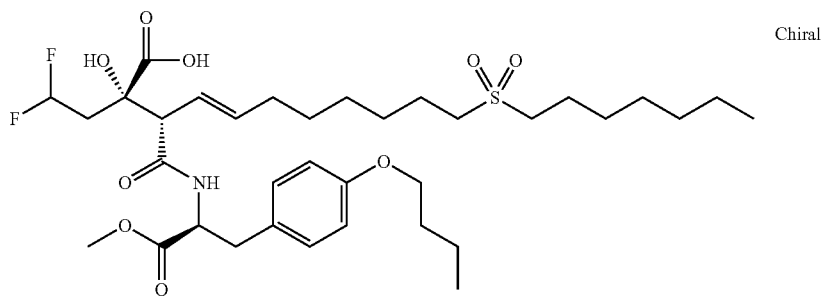

tert-Butyl (E)-(2S,3S)-3-[(S)-2-(4-butoxy-phenyl)-1-methoxycarbonyl-ethylcarbamoyl]-2-(2,2-difluoro-ethyl)-11-heptylsulfanyl-2-hydroxy-undec-4-enoate was obtained (ESI (LC/MS positive mode) m/z 728 (M+H); Rt 3.02 min.) by the method of Step C-6, except that No. 6803864, tert-butyl (E)-(2S,3S)-2-(2,2-difluoro-ethyl)-11-heptylsulfanyl-2-hydroxy-34S)-4-isopropyl-5,5-diphenyl-2-thioxo-oxazolidine-3-carbonyl)-undec-4-enoate was used instead of No. 6804239, tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate, and methyl (S)-2-amino-3-(4-butoxy-phenyl)-propionate was used instead of methyl (S)-2-amino-3-(4-but-2-ynyloxy-phenyl)-propionate.

tert-Butyl (E)-(2S,3S)-3-[(S)-2-(4-butoxy-phenyl)-1-methoxycarbonyl-ethylcarbamoyl]-2-(2,2-difluoro-ethyl)-11-(heptane-1-sulfonyl)-2-hydroxy-2-undec-4-enoate was obtained (EST (LC/MS positive mode) m/z 760 (M+H); Rt 2.32 min.) by the method of Step C-7, except that tert-butyl (E)-(2S,3S)-3-[(S)-2-(4-butoxy-phenyl)-1-methoxycarbonyl-ethylcarbamoyl]-2-(2,2-difluoro-ethyl)-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-butoxy-phenyl)-1-methoxycarbonyl-ethylcarbamoyl]-2-(2,2-difluoro-ethyl)-11-(heptane-1-sulfonyl)-2-hydroxy-undec-4-enoate was used instead of No. 6804464, tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate.

$^1$H-NMR (CD$_3$OD) δ: 0.91 (3H, t, J=7.1 Hz), 0.98 (3H, t, J=7.4 Hz), 1.20-1.88 (23H, m), 1.90-2.42 (3H, m), 2.88 (1H, dd, J=14.0, 9.6 Hz), 2.96-3.21 (5H, m), 3.24 (1H, d, J=8.2 Hz), 3.72 (3H, s), 3.93 (2H, t, J=6.4 Hz), 4.59-4.72 (1H, m), 5.38-5.67 (2H, m), 5.92 (1H, tdd, J=56.7, 7.5, 2.5 Hz), 6.80 (2H, d, J=8.6 Hz), 7.09 (2H, d, J=8.6 Hz)

ESI (LC/MS positive mode) m/z 704 (M+H); Rt 2.07 min.

No. 5522398 (E)-(2S,3S)-3-[(S)-2-(4-Butoxy-phenyl)-1-carbamoyl-ethylcarbamoyl]-2-(2,2-difluoro-ethyl)-11-(heptane-1-sulfonyl)-2-hydroxy-undec-4-enoic acid tert-Butyl (E)-(2S,3S)-3-[(S)-2-(4-butoxy-phenyl)-1-carbamoyl-ethylcarbamoyl]-2-(2,2-difluoro-ethyl)-11-heptylsulfanyl-2-hydroxy-undec-4-enoate was obtained (ESI (LC/MS positive mode) m/z 713 (M+H); Rt 2.72 min.) by the method of Step C-6, except that No. 6803864, tert-butyl (E)-(2S,3S)-2-(2,2-difluoro-ethyl)-11-heptylsulfanyl-2-hydroxy-3-((S)-4-isopropyl-5,5-diphenyl-2-thioxo-oxazolidine-3-carbonyl)-undec-4-enoate was used instead of No. 6804239, tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate.

tert-Butyl (E)-(2S,3S)-3-[(S)-2-(4-butoxy-phenyl)-1-carbamoyl-ethylcarbamoyl]-2-(2,2-difluoro-ethyl)-11-(heptane-1-sulfonyl)-2-hydroxy-2-undec-4-enoate was obtained (ESI (LC/MS positive mode) m/z 745 (M+H); Rt 2.13 min.) by the method of Step C-7, except that tert-butyl (E)-(2S,3S)-3-[(S)-2-(4-butoxy-phenyl)-1-carbamoyl-ethylcarbamoyl]-2-(2,2-difluoro-ethyl)-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-butoxy-phenyl)-1-carbamoyl-ethylcarbamoyl]-2-(2,2-difluoro-ethyl)-11-(heptane-1-sulfonyl)-2-hydroxy-2-undec-4-enoate was used instead of No. 6804464, tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate.

$^1$H-NMR (CD$_3$OD) δ: 0.91 (3H, t, J=6.9 Hz), 0.98 (3H, t, J=7.4 Hz), 1.17-1.87 (23H, m), 1.85-2.11 (2H, m), 2.11-2.40 (1H, m), 2.80 (1H, dd, J=14.2, 9.9 Hz), 2.95-3.17 (5H, m), 3.20 (1H, d, J=8.2 Hz), 3.92 (2H, t, J=6.4 Hz), 4.51-4.67 (1H, m), 5.35-5.64 (2H, m), 5.89 (1H, tdd, J=56.5, 7.1, 2.3 Hz), 6.80 (2H, d, J=8.7 Hz), 7.14 (2H, d, J=8.7 Hz)

ESI (LC/MS positive mode) m/z 689 (M+H); Rt 1.83 min.

[Chem. 328]

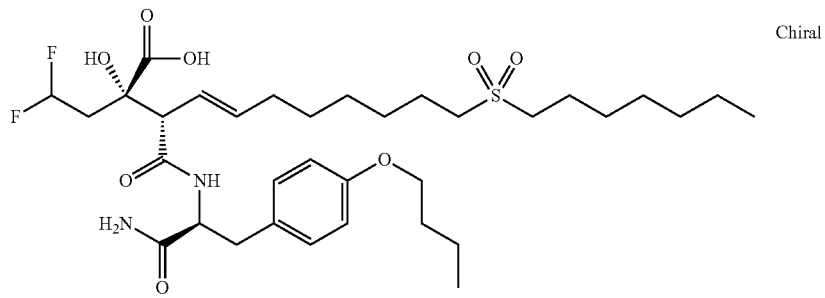

No. 5523885 (E)-(2S,3S)-3-[(S)-2-(4-Butoxy-phenyl)-1-carbamoyl-ethylcarbamoyl]-2-butyl-11-(heptane-1-sulfonyl)-2-hydroxy-undec-4-enoic acid

[Chem. 329]

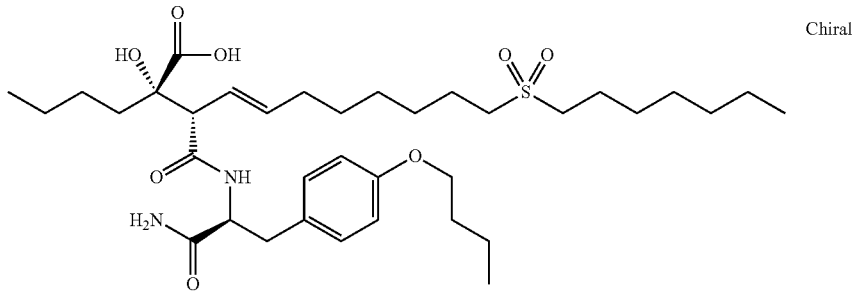

tert-Butyl (E)-(2S,3S)-2-butyl-11-heptylsulfanyl-2-hydroxy-3-((S)-4-isopropyl-5,5-diphenyl-2-thioxo-oxazolidine-3-carbonyl)-undec-4-enoate was obtained (ESI (LC/MS positive mode) m/z 766 (M+H); Rt 6.30 min.) by the method of Step C-5, except that tert-butyl 2-oxo-hexanoate was used instead of tert-butyl 4-methoxy-2-oxo-butyrate.

tert-Butyl (E)-(2S,3S)-3-[(S)-2-(4-butoxy-phenyl)-1-carbamoyl-ethylcarbamoyl]-2-butyl-11-heptylsulfanyl-2-hydroxy-undec-4-enoate was obtained (ESI (LC/MS positive mode) m/z 705 (M+H); Rt 3.16 min.) by the method of Step C-6, except that tert-butyl (E)-(2S,3S)-2-butyl-11-heptylsulfanyl-2-hydroxy-3-((S)-4-isopropyl-5,5-diphenyl-2-thioxo-oxazolidine-3-carbonyl)-undec-4-enoate was used instead of No. 6804239 (tert-butyl (E)-(2S,3S)-11-heptylsulfanyl-2-hydroxy-3-((S)-4-isopropyl-5,5-diphenyl-2-thioxo-oxazolidine-3-carbonyl)-2-(2-methoxy-ethyl)-undec-4-enoate).

tert-Butyl (E)-(2S,3S)-3-[(S)-2-(4-butoxy-phenyl)-1-carbamoyl-ethylcarbamoyl]-2-butyl-11-(heptane-1-sulfonyl)-2-hydroxy-undec-4-enoate (ESI (LC/MS positive mode) m/z 737 (M+H); Rt 2.28 min) was obtained by the method of Step C-7, except that tert-butyl (E)-(2S,3S)-3-[(S)-2-(4-butoxy-phenyl)-1-carbamoyl-ethylcarbamoyl]-2-butyl-11-heptylsulfanyl-2-hydroxy-undec-4-enoate was used instead of No. 6804240, tert-butyl (E)-(2S,3S)-3-[(S)-2-(4-but-2-ynyloxy-phenyl)-1-methoxycarbonyl-ethylcarbamoyl]-11-heptylsulfanyl-2-hydroxy-2-(2-methoxy-ethyl)-undec-4-enoate.

The title compound was obtained by the method of Step C-8, except that tert-butyl (E)-(2S,3S)-3-[(S)-2-(4-butoxy-phenyl)-1-carbamoyl-ethylcarbamoyl]-2-butyl-11-(heptane-1-sulfonyl)-2-hydroxy-undec-4-enoate was used instead of No. 6804464 (tert-butyl (E)-(2S,3S)-3-[(S)-2-(4-but-2-ynyloxy-phenyl)-1-methoxycarbonyl-ethylcarbamoyl]-11-(heptane-1-sulfonyl)-2-hydroxy-2-(2-methoxy-ethyl)-undec-4-enoate).

$^1$H-NMR (CD$_3$OD) δ: 0.86 (3H, t, J=7.4 Hz), 0.91 (3H, t, J=6.6 Hz), 0.98 (3H, t, J=7.3 Hz), 1.11-1.87 (28H, m), 1.90-2.12 (2H, m), 2.81 (1H, dd, J=14.1, 9.6 Hz), 2.96-3.14 (5H, m), 3.14-3.22 (2H, m), 3.92 (2H, t, J=6.3 Hz), 4.56 (1H, dd, J=9.6, 5.0 Hz), 5.45-5.62 (2H, m), 6.80 (2H, d, J=8.6 Hz), 7.14 (2H, d, J=8.6 Hz)

ESI (LC/MS positive mode) m/z 681 (M+H); Rt 1.93 min.

163. No. 5532885 (E)-(2S,3S)-3-[(S)-2-(4-Butoxy-phenyl)-1-carboxy-ethylcarbamoyl]-2-(2-fluoro-ethyl)-2-hydroxy-12-oxo-nonadec-4-enoic acid

[Chem. 330]

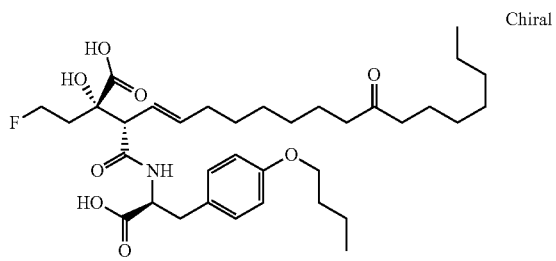

tert-Butyl (E)-(2S,3S)-3-[(S)-1-tert-butoxycarbonyl-2-(4-butoxy-phenyl)-ethylcarbamoyl]-2-(2-fluoro-ethyl)-11-(2-heptyl-[1,3]dioxolan-2-yl)-2-hydroxy-undec-4-enoate was obtained (ESI (LC/MS positive mode) m/z 793 (M+H); Rt 1.68 min.) by the method of Step A-2, except that No. 6804093 (tert-butyl (E)-(2S,3S)-2-(2-fluoro-ethyl)-11-(2-heptyl-[1,3]dioxolan-2-yl)-2-hydroxy-3-((S)-4-isopropyl-5,5-diphenyl-2-thioxo-oxazolidine-3-carbonyl)-undec-4-enoate) was used instead of No. 6801291, tert-butyl (E)-(2S,3S)-11-(2-heptyl-[1,3]dioxolan-2-yl)-2-hydroxy-3-((S)-4-isopropyl-5,5-diphenyl-2-thioxo-oxazolidine-3-carbonyl)-2-(2-methoxy-ethyl)-undec-4-enoate, and tert-butyl (S)-2-amino-3-(4-butoxy-phenyl)-propionate was used instead of methyl (S)-2-amino-3-(4-but-2-ynyloxy-phenyl)-propionate.

The title compound was obtained by the method of Step A-3, except that tert-butyl (E)-(2S,3S)-3-[(S)-1-tert-butoxycarbonyl-2-(4-butoxy-phenyl)-ethylcarbamoyl]-2-(2-fluoro-ethyl)-11-(2-heptyl-[1,3]dioxolan-2-yl)-2-hydroxy-undec-4-enoate was used instead of No. 5534988 (tert-butyl (E)-(2S,3S)-3-[(S)-2-(4-butoxy-phenyl)-1-methoxycarbonyl-ethylcarbamoyl]-11-(2-heptyl-[1,3]dioxolan-2-yl)-2-hydroxy-2-(2-methoxy-ethyl)-undec-4-enoate).

$^1$H-NMR (CD$_3$OD) δ: 0.91 (3H, t, J=7.1 Hz), 0.98 (3H, t, J=7.4 Hz), 1.20-1.88 (23H, m), 1.90-2.42 (3H, m), 2.88 (1H, dd, J=14.0, 9.6 Hz), 2.96-3.21 (5H, m), 3.24 (1H, d, J=8.2 Hz), 3.72 (3H, s), 3.93 (2H, t, J=6.4 Hz), 4.59-4.72 (1H, m), 5.38-5.67 (2H, m), 6.80 (2H, d, J=8.6 Hz), 7.09 (2H, d, J=8.6 Hz)

ESI (LC/MS positive mode) m/z 636 (M+H); Rt 2.17 min.

No. 5538573 (E)-(2S,3S)-12,12-Difluoro-3-[(S)-2-(2'-fluoro-biphenyl-4-yl)-1-methoxycarbonyl-ethyl-carbamoyl]-2-hydroxy-2-(2-methoxy-ethyl)-nonadec-4-enoic acid

[Chem. 331]

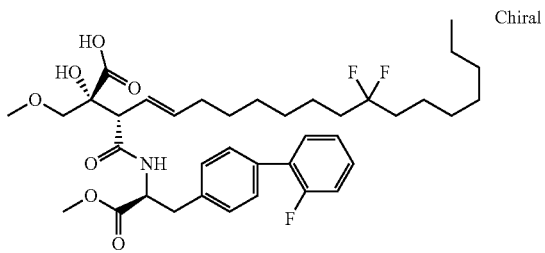

tert-Butyl (E)-(2S,3S)-12,12-difluoro-3-[(S)-2-(2'-fluoro-biphenyl-4-yl)-1-methoxycarbonyl-ethylcarbamoyl]-2-hydroxy-2-(2-methoxy-ethyl)-nonadec-4-enoate was obtained by the method of Step B-7, except that methyl (S)-2-amino-3-(2'-fluoro-biphenyl-4-yl)-propionate was used instead of methyl (S)-2-amino-3-(4-but-2-ynyloxy-phenyl)-propionate.

$^1$H-NMR (CDCl$_3$) δ: 0.88 (3H, t, J=6.9 Hz), 1.19-1.89 (22H, m), 1.42 (9H, s), 1.89-2.09 (3H, m), 3.07 (1H, dd, J=14.0, 8.0 Hz), 3.15 (3H, s), 3.16 (1H, d, J=9.2 Hz), 3.19-3.40 (3H, m), 3.74 (3H, s), 4.17 (1H, s), 4.90 (1H, td, J=8.0, 5.3 Hz), 5.46 (1H, dd, J=15.1, 9.2 Hz), 5.68 (1H, dt, J=15.1, 6.6 Hz), 7.08-7.56 (8H, m)

The title compound was obtained by the method of Step B-8, except that tert-butyl (E)-(2S,3S)-12,12-difluoro-3-[(S)-2-(2'-fluoro-biphenyl-4-yl)-1-methoxycarbonyl-ethylcarbamoyl]-2-hydroxy-2-(2-methoxy-ethyl)-nonadec-4-enoate was used instead of No. 6804236, tert-butyl (E)-(2S,3S)-3-[(S)-2-(4-but-2-ynyloxy-phenyl)-1-methoxycarbonyl-ethyl-carbamoyl]-12,12-difluoro-2-hydroxy-2-(2-methoxy-ethyl)-nonadec-4-enoate.

$^1$H-NMR (CD$_3$OD) δ: 0.90 (3H, t, J=6.9 Hz), 1.12-1.51 (18H, m), 1.60-2.16 (7H, m), 3.02 (1H, dd, J=14.0, 9.4 Hz), 3.20 (3H, s), 3.23-3.50 (4H, m), 3.74 (3H, s), 4.76 (1H, dd, J=9.4, 4.9 Hz), 5.42-5.66 (2H, m), 7.11-7.56 (8H, m)

ESI (LC/MS positive mode) m/z 706 (M+H); Rt 2.43 min.

No. 5538574 (E)-(2S,3S)-3-[(S)-1-Carboxy-2-(2'-fluoro-biphenyl-4-yl)-ethylcarbamoyl]-12,12-difluoro-2-hydroxy-2-(2-methoxy-ethyl)-nonadec-4-enoic acid

[Chem. 332]

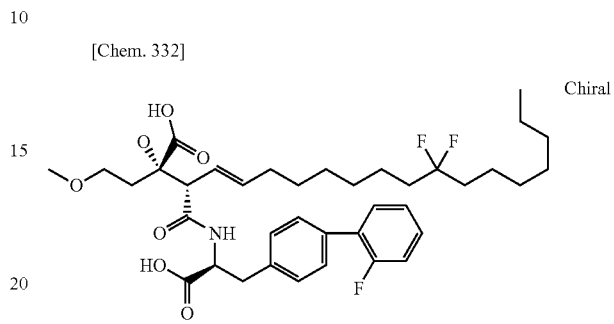

No. 5538573, (E)-(2S,3S)-12,12-difluoro-3-[(S)-2-(2'-fluoro-biphenyl-4-yl)-1-methoxycarbonyl-ethylcarbamoyl]-2-hydroxy-2-(2-methoxy-ethyl)-nonadec-4-enoic acid (8.2 mg, 0.0116 mmol) was dissolved in acetonitrile (0.328 mL), and water (0.0011 mL, 0.0611 mmol), triethylamine (0.0097 mL, 0.0696 mmol), and anhydrous lithium bromide (20.1 mg, 0.231 mmol) were then added at room temperature. The reaction mixture was stirred at 50° C. for 3.5 hours, cooled to room temperature, and then purified by preparative HPLC to obtain 6.7 mg of the title compound (0.00969 mmol, 83% yield).

$^1$H-NMR (CD$_3$OD) δ: 0.90 (3H, t, J=7.2 Hz), 1.00-1.50 (18H, m), 1.55-2.18 (8H, m), 3.02 (1H, dd, J=13.7, 9.2 Hz), 3.15-3.50 (4H, m), 3.20 (3H, s), 4.74 (1H, dd, J=9.2, 4.6 Hz), 5.42-5.67 (2H, m), 7.11-7.56 (8H, m)

ESI (LC/MS positive mode) m/z 679 (M+H); Rt 1.83 min.

Alternative synthetic method of No. 6804236, an intermediate of No. 5513213 Alternative method: Step B-9 B-"

[Chem. 333]

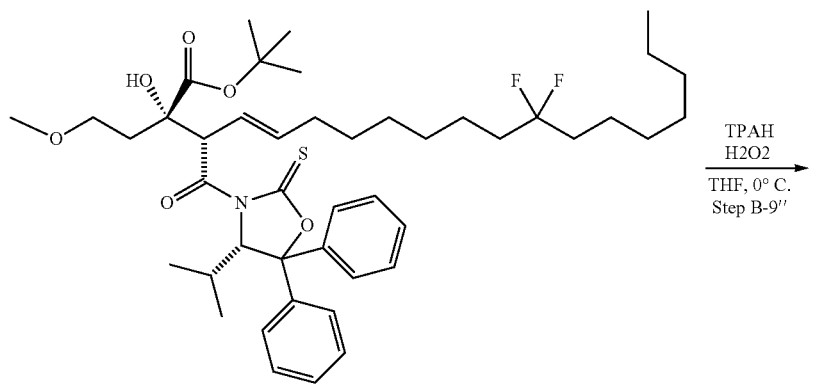

No 5552816

-continued

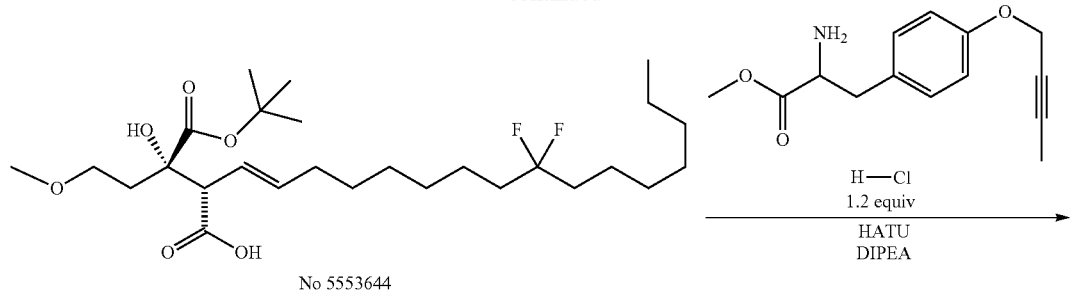

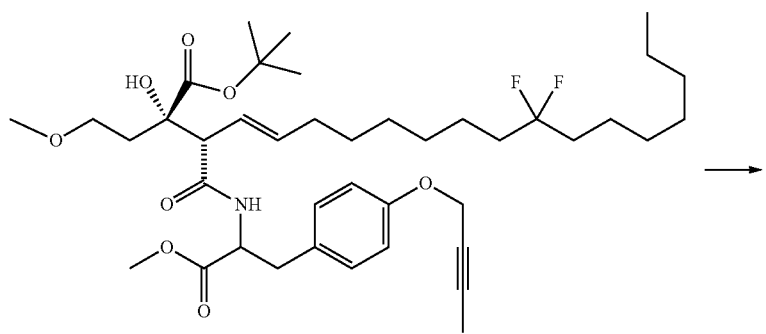

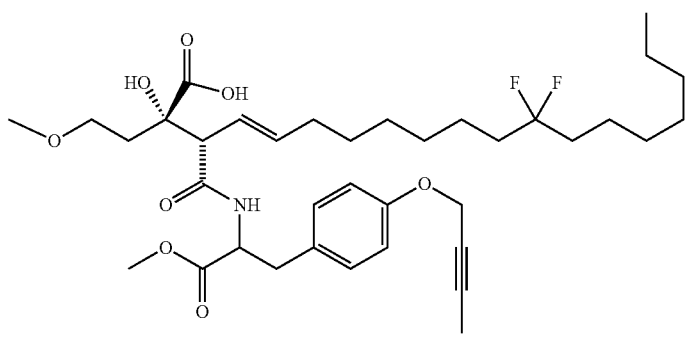

No. 5553644 Synthesis of 1-tert-butyl (2S,3S)-3-((E)-9,9-difluoro-hexadec-1-enyl)-2-hydroxy-2-(2-methoxy-ethyl)-succinate No. 5552816, tert-butyl (E)-(2S,3S)-12,12-difluoro-2-hydroxy-3-((S)-4-isopropyl-5,5-diphenyl-2-thioxo-oxazolidine-3-carbonyl)-2-(2-methoxy-ethyl)-nonadec-4-enoate (90.4 mg, 0.115 mmol) was dissolved in THF (0.9 mL), and the mixture was cooled to 0° C. An aqueous solution of 35% hydrogen peroxide (0.021 mL, 0.238 mmol) and tetrapropylammonium hydroxide (40% aqueous solution, 0.119 mL, 0.237 mmol) were added. After stirring for 1.5 hours, an aqueous solution of 20% sodium thiosulfate was added and the mixture was stirred for 5 minutes. An aqueous solution (8.0 mL) of 8% citric acid was added, and the mixture was then extracted with ethyl acetate (100 mL). The aqueous layer was extracted with ethyl acetate (100 mL) again. The organic layers were combined, dried over anhydrous sodium sulfate, and filtered. The solvent was then distilled off under reduced pressure. The residue was purified by preparative HPLC to obtain 36.5 mg (0.07204 mmol, 63% yield) of No. 5553644.

$^1$H-NMR (CD$_3$OD) δ: 0.94 (3H, t, J=6.6 Hz), 1.26-1.55 (18H, m), 1.52 (9H, s), 1.75-1.94 (5H, m), 2.04-2.13 (2H, m), 2.16 (1H, dt, J=14.1, 6.6 Hz), 3.24-3.30 (4H, m), 3.50 (2H, t, J=6.6 Hz), 5.62-5.76 (2H, m),

ESI (LCMS positive mode) m/z 529 (M+Na); Rt 0.69 min.

No. 6804236 tert-Butyl (E)-(2S,3S)-3-[(S)-2-(4-but-2-ynyloxy-phenyl)-1-methoxycarbonyl-ethylcarbamoyl]-12,12-difluoro-2-hydroxy-2-(2-methoxy-ethyl)-nonadec-4-enoate No. 6804236 was obtained by the synthetic method in Step A-4 (dehydration condensation with 1-[bis(dimethylamino)methyliumyl]-1H-1,2,3-triazolo[4,5-B]pyridine-3-oxide hexafluorophosphate), except that No. 5553644, 1-tert-butyl (2S,3S)-3-((E)-9,9-difluoro-hexadec-1-enyl)-2-hydroxy-2-(2-methoxy-ethyl)-succinate was used instead of No. 6801710, 1-tert-butyl (2S,3S)-3-[(E)-8-(2-heptyl-[1,3]dioxolan-2-yl)-oct-1-enyl]-2-hydroxy-2-(2-methoxy-ethyl)-succinate, and methyl (S)-2-amino-3-(4-butoxy-phenyl)-propionate was used instead of methyl (S)-2-amino-3-(4-but-2-ynyloxy-phenyl)-propionate.

No. 5322163 Synthesis of (E)-(2S,3S)-3-[(S)-2-(4-but-2-ynyloxy-phenyl)-1-carboxy-ethylcarbamoyl]-2-carbamoylmethyl-2-hydroxy-12-oxo-nonadec-4-enoic acid $^1$H-NMR (DMSO-d$_6$) δ: 0.85 (3H, t, J=6.7 Hz), 1.12-1.31 (14H, m), 1.36-1.48 (4H, m), 1.82 (3H, t, J=2.1 Hz), 1.85-1.94 (2H, m), 2.29 (1H, d, J=15.2 Hz), 2.35 (4H, t, J=7.3 Hz), 2.55 (1H, d, J=15.2 Hz), 2.83 (1H, dd, J=14.0, 8.5 Hz), 2.97 (1H, dd, J=14.0, 4.9 Hz), 3.13-3.24 (1H, m), 4.34-4.42 (1H, m), 4.63-4.68 (2H, m), 5.35-5.46 (2H, m), 6.80 (2H, d, J=8.5 Hz), 6.97 (1H, s), 7.10 (2H, d, J=8.5 Hz), 7.31 (1H, s), 8.05 (1H, d, J=7.9 Hz).

[Chem. 334]

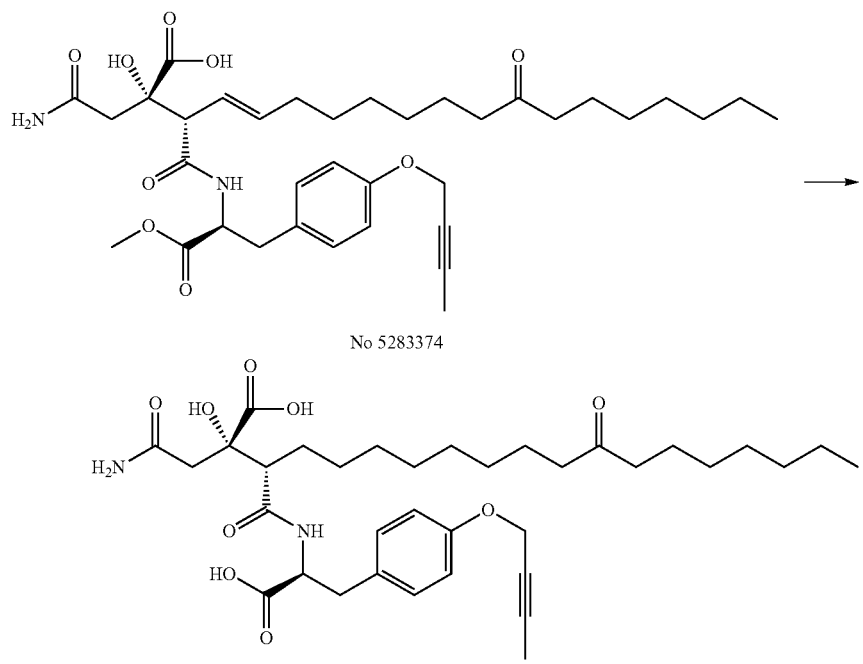

No. 5283374 (20 mg, 0.030 mmol) was dissolved in methanol (1.7 mL), and an aqueous solution (230 μL) of 0.1 M sodium hydroxide was added. The mixture was stirred at room temperature overnight. The reaction solution was diluted in an aqueous solution of 0.5 M citric acid, and extracted with ethyl acetate. The separated organic layer was washed with water and a saturated brine in order, then dried over anhydrous sodium sulfate, and filtered. The filtrate was concentrated. The residue was purified by diol thin layer chromatography (dichloromethane:methanol=9 9) to obtain the target compound as white solid at a yield of 90%.

ESI (LC/MS positive mode) m/z 643 (M+H); Rt 1.00 min.

No. 5322164 Synthesis of (E)-(2S,3S)-3-[(S)-2-(4-but-2-ynyloxy-phenyl)-1-methoxycarbonyl-ethylcarbamoyl]-2-carbamoylmethyl-2,12-dihydroxy-nonadec-4-enoic acid

[Chem. 335]

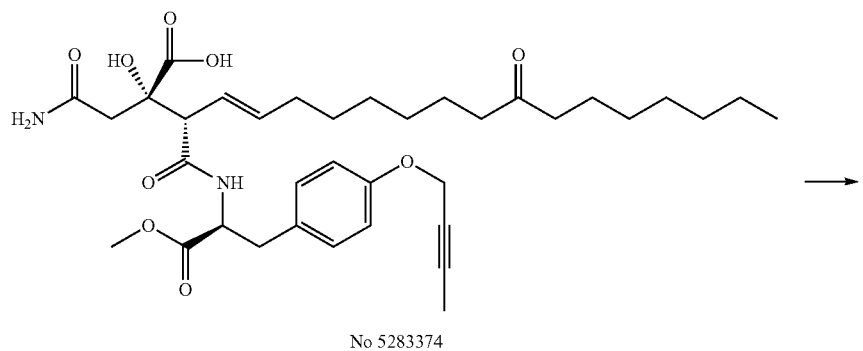

-continued

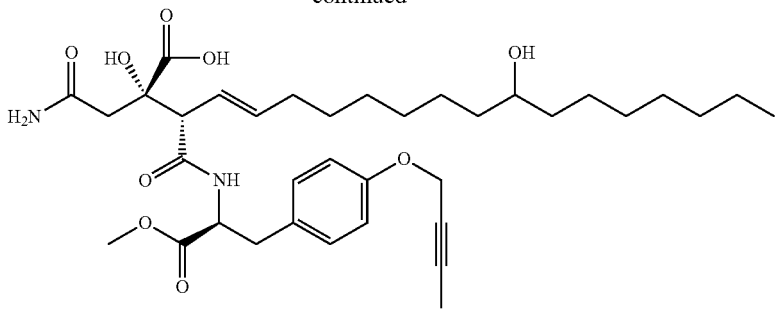

No 5322164

No. 5283374 (12.5 mg, 0.019 mmol) was dissolved in methanol (1.0 mL), and the solution was cooled in an ice bath. Sodium tetrahydroboron (4.3 mg, 0.11 mmol) was added, and the mixture was stirred overnight at the same temperature. The progress of the reaction was stopped by adding water (3.0 mL), and ethyl acetate was then added. An aqueous solution of 0.5 M citric acid was further added to adjust pH of the aqueous layer to 5-6. The separated organic layer was washed with water and a saturated brine in order, then dried over anhydrous sodium sulfate, and filtered. The filtrate was concentrated. The residue was purified by diol thin layer chromatography (dichloromethane:methanol=20 20) to obtain the target compound as white solid at a yield of 89%.

$^1$H-NMR (CDCl$_3$) δ: 0.88 (3H, t, J=6.7 Hz), 1.16-1.51 (22H, m), 1.86 (3H, t, J=2.1 Hz), 1.86-2.11 (2H, m), 2.40 (1H, d, J=15.2 Hz), 2.73 (1H, d, J=15.2 Hz), 2.99 (1H, dd, J=14.6, 7.9 Hz), 3.12 (2H, m), 3.55-3.70 (1H, m), 3.74 (3H, s), 4.58-4.64 (2H, m), 4.79 (1H, dd, J=6.9, 6.9 Hz), 5.49 (1H, dd, J=15.2, 9.1 Hz), 5.62-5.80 (2H, m), 6.10 (1H, br.s), 6.84-6.90 (3H, m), 7.07 (2H, d, J=8.5 Hz).

ESI (LC/MS positive mode) m/z 659 (M+H); Rt 1.30 min.

No. 5322165 Synthesis of (E)-(2S,3S)-3-[(S)-2-(4-but-2-ynyloxy-phenyl)-1-carboxy-ethylcarbamoyl]-2-carbamoylmethyl-2,12-dihydroxy-nonadec-4-enoic acid

[Chem. 336]

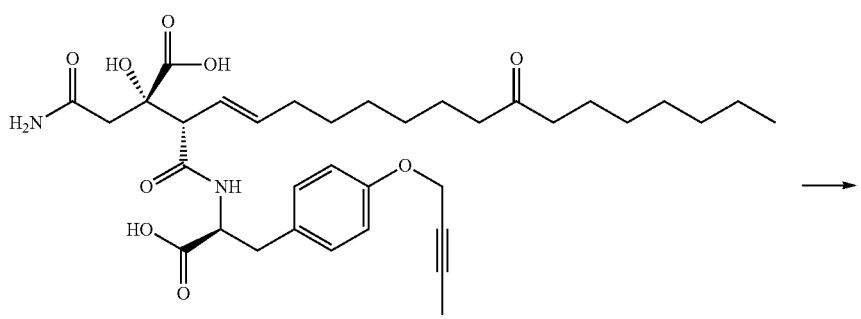

No 5322163

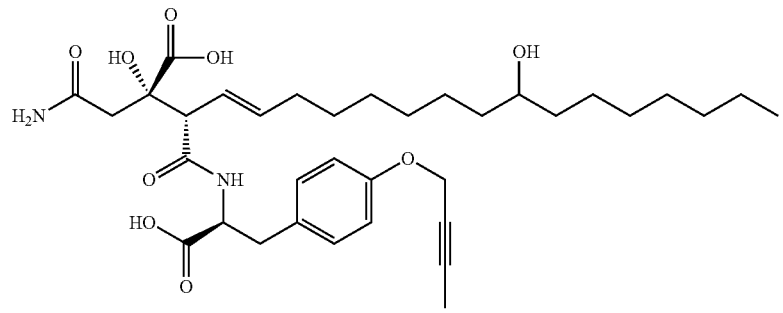

No 5322165

No. 5322163 (6.7 mg, 0.01 mmol) was dissolved in methanol (1.0 mL), and the solution was cooled in an ice bath. Sodium tetrahydroborate (5.4 mg, 0.14 mmol) was added, and the mixture was stirred at the same temperature for 2 hours. Water (3.0 mL) was added. An aqueous solution of 0.5 M citric acid (5.0 mL) was further added, and the mixture was then extracted with ethyl acetate. The separated organic layer was washed with an aqueous solution of 0.5 M citric acid, water, and a saturated brine in order, then dried over anhydrous sodium sulfate, and then filtered. The filtrate was concentrated. The residue was purified by diol thin layer chromatography (dichloromethane:methanol=9 9) to obtain the target compound as white solid at a yield of 87%.

$^1$H-NMR (CD$_3$OD) δ: 0.90 (3H, t, J=6.7 Hz), 1.22-1.49 (22H, m), 1.82 (3H, t, J=2.1 Hz), 1.94-2.03 (2H, m), 2.45 (1H, d, J=15.3 Hz), 2.73 (1H, d, J=15.3 Hz), 2.93 (1H, dd, J=14.0, 9.2 Hz), 3.14-3.24 (2H, m), 3.46-3.53 (1H, m), 4.58-4.62 (2H, m), 4.65 (1H, dd, J=9.2, 4.9 Hz), 5.47-5.62 (2H, m), 6.85 (2H, d, J=8.5 Hz), 7.13 (2H, d, J=8.5 Hz).

ESI (LC/MS positive mode) m/z 645 (M+H); Rt 0.89 min.

Synthesis of No. 5323410 (E)-(2S,3S)-3-[(S)-2-(4-But-2-ynyloxy-phenyl)-1-methoxycarbonyl-ethylcarbamoyl]-2,12-dihydroxy-2-(2-methoxy-ethyl)-nonadec-4-enoic acid Synthesis of tert-butyl 2-(2-methoxyethyl)-1,3-dithiane-2-carboxylate

[Chem. 337]

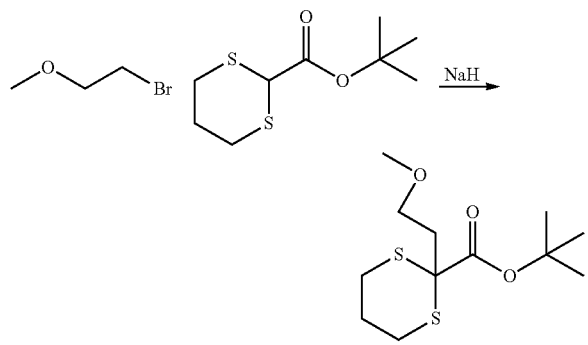

Under a nitrogen atmosphere, 60% sodium hydride (705 mg, 16.2 mmol) was suspended in anhydrous toluene (21 mL), and the suspension was cooled to 0° C. in an ice bath. In a different flask, tert-butyl 1,3-dithiane-2-carboxylate (3.235 g, 14.7 mmol) and 1-bromo-2-methoxyethane (1.52 mL, 16.15 mmol) were dissolved in N,N-dimethylformamide (7.0 mL), and the solution was added dropwise to the first flask over 15 minutes. After completion of the dropwise addition, the mixture was stirred at the same temperature for 5 minutes, and successively at room temperature for further 2 hours. The progress of the reaction was stopped by adding a saturated aqueous solution of ammonium chloride. The mixture was extracted with a mixture (1:1 v/v) of n-hexane and ethyl acetate. The separated organic layer was washed twice with water, dried over anhydrous sodium sulfate, and filtered. The filtrate was concentrated. The residue was purified by silica gel column chromatography (n-hexane/ethyl acetate) to obtain the target compound at a yield of 90% (GC m/z 278 (M+); Rt 5.3 min.).

Synthesis of tert-butyl 4-methoxy-2-oxobutanoate

[Chem. 338]

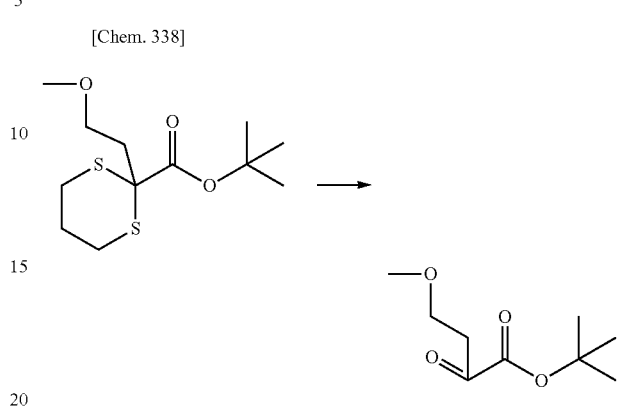

tert-Butyl 2-(2-methoxyethyl)-1,3-dithiane-2-carboxylate (1.68 g, 6.03 mmol) was dissolved in acetone (57 mL), and water (3.0 mL) was added. The flask was cooled in a cold bath at −30° C. Small aliquots of N-bromosuccinimide (10.68 g, 60 mmol) were added over 20 minutes. The reaction mixture was stirred at the same temperature for 10 minutes, and then quenched by adding an aqueous solution of sodium bicarbonate (5.05 g in 50 mL of water). Insoluble material was removed by filtration, and the solid was washed with n-hexane. To the filtrate was then added an aqueous solution of 5% sodium sulfite until the filtrate became colorless from yellow. The filtrate was diluted in water to a total volume of 250 mL, and extracted twice with n-hexane. The organic layer was washed with a saturated brine, then dried over anhydrous sodium sulfate, and filtered. The filtrate was concentrated. The residue was purified by silica gel column chromatography (n-hexane/ethyl acetate) to obtain the target compound as oil at a yield of 67%.

$^1$H-NMR (CDCl$_3$) δ: 1.54 (9H, s), 3.04 (2H, t, J=6.1 Hz), 3.34 (3H, s), 3.70 (2H, t, J=6.1 Hz).

Synthesis of (2S,3S,E)-tert-butyl 11-(2-heptyl-1,3-dioxolan-2-yl)-2-hydroxy-3-((S)-4-isopropyl-5,5-diphenyl-2-thioxoooxazolidine-3-carbonyl)-2-(2-methoxyethyl)undec-4-enoate

[Chem. 339]

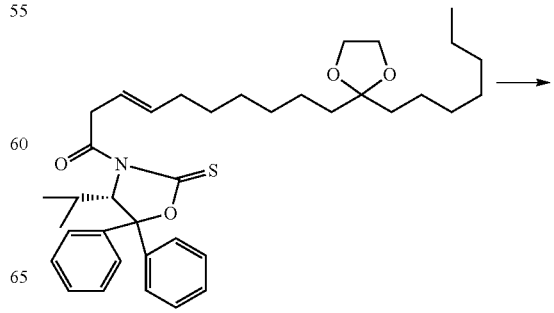

-continued

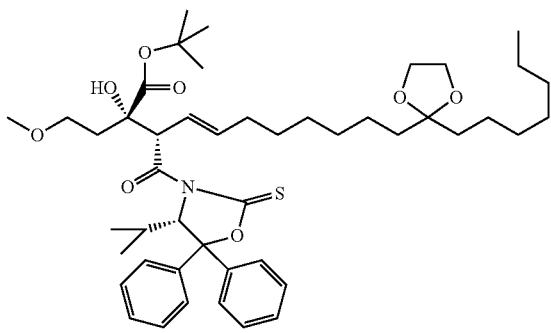

Under a nitrogen atmosphere, (S,E)-10-(2-heptyl-1,3-dioxolan-2-yl)-1-(4-isopropyl-5,5-diphenyl-2-thioxooxazolidin-3-yl)dec-3-en-1-one (2.337 g, 3.77 mmol) and lithium chloride (480 mg, 11.31 mmol) were dissolved in anhydrous tetrahydrofuran (30 mL), and cooled to −78° C. in a cold bath of dry ice-methanol. Lithium hexamethyldisilazide (1 M, tetrahydrofuran solution, 3.958 mL) was added. The mixture was stirred at the same temperature for 1 hour, and then in a cold bath at −25° C. for 10 minutes. The reaction flask was again cooled in a cold bath at −78° C. tert-Butyl 4-methoxy-2-oxobutanoate (745 mg, 3.96 mol) was dissolved in tetrahydrofuran (3.0 mL), and the solution was added dropwise to the solution in the flask above. The mixture was stirred at the same temperature for 10 minutes, and the progress of the reaction was then stopped by adding a solution of acetic acid (432 μL, 7.54 mmol) in tetrahydrofuran (1.0 mL). The reaction mixture was warmed to room temperature, diluted in water, and then extracted with ethyl acetate. The separated organic layer was washed with a saturated brine, then dried over anhydrous sodium sulfate, and filtered. The filtrate was concentrated. The residue was purified by silica gel column chromatography (n-hexane/ethyl acetate) to obtain the target compound as colorless oil at a yield of 79% (FAB(mNBA) m/z 814 (M+Li$^+$)).

Synthesis of (2S,3S,E)-tert-butyl 3-((S)-3-(4-(but-2-ynyloxy)phenyl)-1-methoxy-1-oxopropan-2-ylcarbamoyl)-11-(2-heptyl-1,3-dioxolan-2-yl)-2-hydroxy-2-(2-methoxy-ethyl)-undec-4-enoate

[Chem. 340]

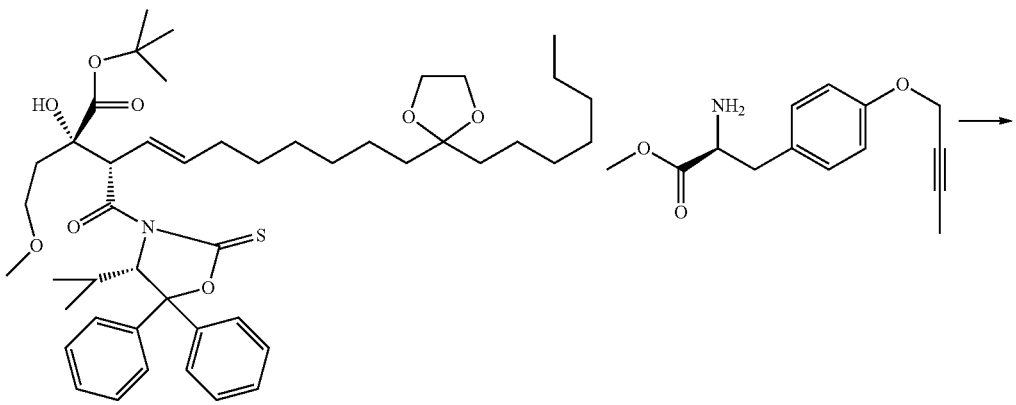

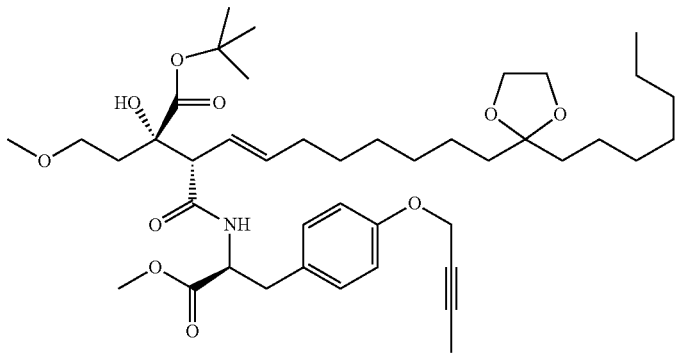

421

(2S,3S,E)-tert-Butyl 11-(2-heptyl-1,3-dioxolan-2-yl)-2-hydroxy-3-((S)-4-isopropyl-5,5-diphenyl-2-thioxooxazolidine-3-carbonyl)-2-(2-methoxyethyl)undec-4-enoate (2.416 g, 2.99 mmol) and (S)-methyl 2-amino-3-(4-(but-2-ynyloxy)phenyl)propanoate (1.60 g, 6.45 mmol) were transferred into a flask, and dissolved in acetonitrile (5.0 mL). The solution was concentrated, and then stirred at 40° C. under a nitrogen atmosphere for 12 hours. The reaction mixture was purified by silica gel column chromatography (n-hexane/ethyl acetate), and again by silica gel column chromatography (dichloromethane/methanol) to obtain the target compound as yellow oil at a yield of 85%.

ESI (LC/MS positive mode) m/z 758 (M+H); Rt 3.76 min.

Synthesis of (2S,3S,E)-3-((S)-3-(4-(but-2-ynyloxy)phenyl)-1-methoxy-1-oxopropan-2-ylcarbamoyl)-2-hydroxy-2-(2-methoxyethyl)-12-oxononadec-4-enoic acid, No. 5233427

[Chem. 341]

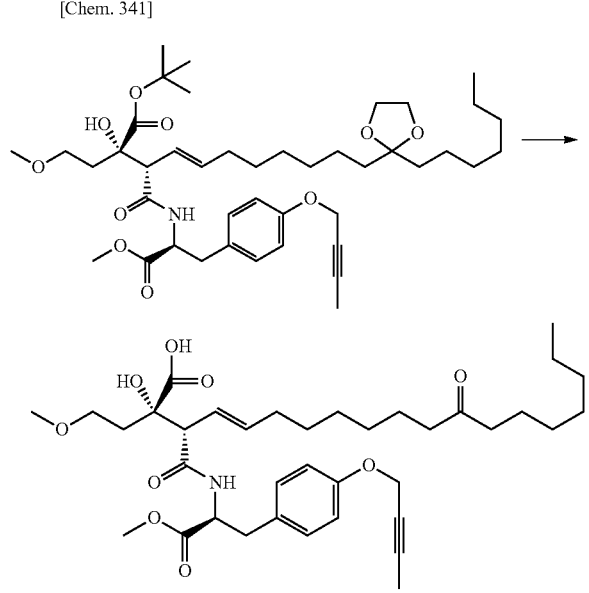

(2S,3S,E)-tert-Butyl 3-((S)-3-(4-(but-2-ynyloxy)phenyl)-1-methoxy-1-oxopropan-2-ylcarbamoyl)-11-(2-heptyl-1,3-dioxolan-2-yl)-2-hydroxy-2-(2-methoxyethyl)-undec-4-enoate (1.619 g, 2.136 mmol) was dissolved in formic acid (8.0 mL), and water (420 µL) was added. The reaction mixture was stirred at room temperature for 24 hours, and concentrated. After subsequently repeating twice the operation of dissolution in ethyl acetate and concentration, the residue was purified by diol column chromatography (dichloromethane/ethyl acetate) to obtain the target compound at a yield of 80%.

ESI (LC/MS positive mode) m/z 658 (M+H); Rt 2.31 min.

422

Synthesis of (E)-(2S,3S)-3-[(S)-2-(4-but-2-ynyloxy-phenyl)-1-methoxycarbonyl-ethylcarbamoyl]-2,12-dihydroxy-2-(2-methoxy-ethyl)-nonadec-4-enoic acid, No. 5323410

[Chem. 342]

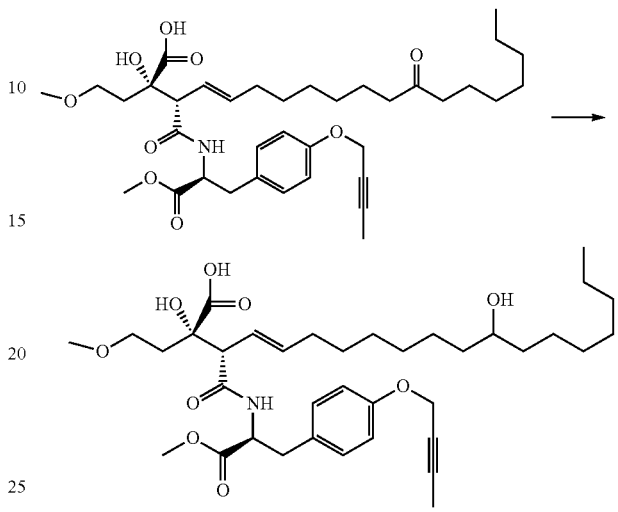

No. 5233427 (14.4 mg, 0.022 mmol) was dissolved in methanol (1.0 mL), and the solution was cooled to 0° C. in an ice bath. Sodium tetrahydroborate (5 mg, 0.13 mmol) was added, and the mixture was stirred for 3 hours. The progress of the reaction was stopped by adding water, and the mixture was diluted in ethyl acetate. An aqueous solution of 0.5 M citric acid was added and the mixture was separated. The separated organic layer was washed with water and a saturated brine in order, dried over anhydrous sodium sulfate, and then filtered. The filtrate was concentrated. The residue was purified by diol thin layer chromatography (dichloromethane:methanol=50 50) to obtain the target compound at a yield of 57%.

$^1$H-NMR (CDCl$_3$) δ: 0.88 (3H, t, J=6.7 Hz), 1.20-1.50 (22H, m), 1.78 (1H, dt, J=14.6, 5.8 Hz), 1.86 (3H, t, J=2.1 Hz), 1.94-2.14 (2H, m), 3.01 (1H, dd, J=14.3, 6.4 Hz), 3.07-3.13 (1H, m), 3.20 (1H, d, J=9.8 Hz), 3.28 (3H, s), 3.40-3.56 (2H, m), 3.59-3.68 (1H, m), 3.73 (3H, s), 4.61 (2H, q, J=2.2 Hz), 4.82 (1H, dd, J=13.7, 5.8 Hz), 5.53 (1H, dd, J=15.3, 9.8 Hz), 5.61-5.72 (1H, m), 6.75 (1H, d, J=7.9 Hz), 6.84-6.88 (2H, m), 6.99-7.05 (2H, m).

ESI (LC/MS positive mode) m/z 660 (M+H); Rt 2.86 min.

No. 5323411 (E)-(2S,3S)-3-[(S)-2-(4-But-2-ynyloxy-phenyl)-1-carboxy-ethylcarbamoyl]-2,12-dihydroxy-2-(2-methoxy-ethyl)-nonadec-4-enoic acid

[Chem. 343]

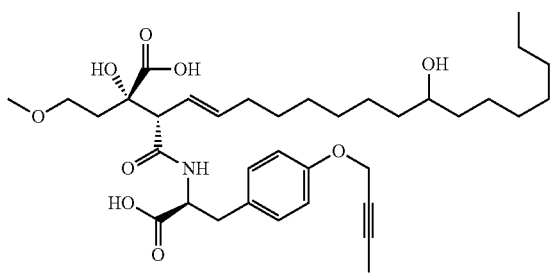

No. 5236115 (9.5 mg, 0.0148 mmol) was dissolved in methanol (2.0 mL), and an aqueous solution of 1 M sodium hydroxide (98 µL) was added. The mixture was stirred for a whole day and night at room temperature. The progress of the reaction was stopped by adding an aqueous solution of 0.5 M citric acid, and the mixture was then extracted with ethyl acetate. The separated organic layer was washed with water, dried over anhydrous sodium sulfate, and filtered. The filtrate was concentrated. The residue was purified by diol thin layer chromatography (dichloromethane:methanol=30 30) to obtain the target compound at a yield of 86%.

$^1$H-NMR (DMSO-$d_6$) δ: 0.85 (3H, t, J=6.7 Hz), 1.14-1.39 (22H, m), 1.63-1.72 (1H, m), 1.82 (3H, t, J=2.1 Hz), 1.85-1.96 (2H, m), 2.80 (1H, dd, J=14.0, 9.2 Hz), 2.98 (1H, dd, J=14.0, 4.9 Hz), 3.14 (3H, s), 3.12-3.37 (4H, m), 4.19 (1H, br.s), 4.37 (1H, td, J=8.5, 4.9 Hz), 4.64-4.68 (2H, m), 5.34-5.48 (2H, m), 6.82 (2H, d, J=8.5 Hz), 7.11 (2H, d, J=8.5 Hz), 8.21 (1H, d, J=7.9 Hz).

ESI (LC/MS positive mode) m/z 646 (M+H); Rt 1.43 min.

No. 5398770 (E)-(2S,3S)-3-[(S)-2-(4-But-2-ynyloxy-phenyl)-1-methoxycarbonyl-ethylcarbamoyl]-2-hydroxy-2-methyl-12-oxo-nonadec-4-enoic acid

[Chem. 344]

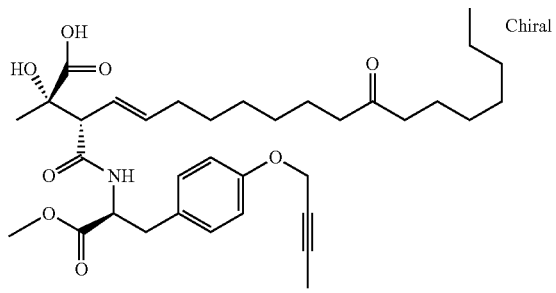

Synthesis of tert-butyl 2-methyl-1,3-dithiane-2-carboxylate

[Chem. 345]

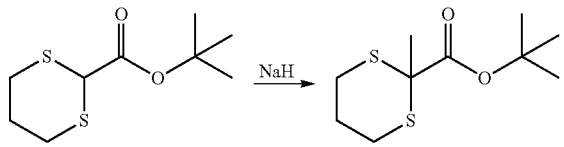

Under a nitrogen atmosphere, 60% sodium hydride (2.08 g, 52 mmol) was suspended in anhydrous toluene (75 mL). In a different flask, tert-butyl 1,3-dithiane-2-carboxylate (10 g, 45.4 mmol) and iodomethane (3.0 mL, 47.7 mmol) were dissolved in N,N-dimethylformamide (35 mL), and the solution was added dropwise to the first flask at room temperature. After the dropwise addition, the mixture was stirred at room temperature for further 2 hours. The progress of the reaction was then stopped by adding a saturated aqueous solution of ammonium chloride. The mixture was extracted with a mixture (1:1 v/v, 200 mL) of n-hexane and ethyl acetate. The separated organic layer was washed twice with water, dried over anhydrous sodium sulfate, and then filtered. The filtrate was concentrated. The residue was purified by silica gel column chromatography (n-hexane/ethyl acetate) to obtain quantitatively the target compound as white solid.

ESI (LC/MS positive mode) m/z 235 (M+H); Rt 3.92 min.

Synthesis of tert-butyl 2-oxopropanate

[Chem. 346]

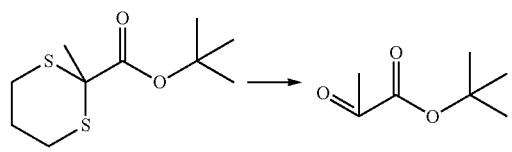

tert-Butyl 2-methyl-1,3-dithiane-2-carboxylate (2 g, 8.547 mmol) was dissolved in acetone (85.5 mL), and water (0.5 mL) was added. The flask was then cooled in a cold bath at −20° C. Small aliquots of N-bromosuceinimide (15.4 g, 85.47 mmol) were added over 20 minutes. The reaction mixture was stirred at the same temperature for further 30 minutes, and then quenched by adding an aqueous solution of sodium bicarbonate (7.18 g, 85.47 mmol in 90 mL of water). Insoluble material was removed by filtration. The filtrate was diluted in water (200 mL) and extracted with tert-butyl methyl ether (150 mL). The separated organic layer was washed with water and a saturated brine in order, then dried over anhydrous sodium sulfate, and then filtered. The filtrate was concentrated. The residue was purified by silica gel column chromatography (n-hexane/ethyl acetate) to obtain the target compound as pale yellow oil at a yield of 40%.

$^1$H-NMR (CDCl$_3$) δ: 1.54 (9H, s), 2.42 (3H, s).

Synthesis of (2S,3S,E)-tert-butyl (11-(2-heptyl-1,3-dioxolan-2-yl)-2-hydroxy-3-((S)-4-isopropyl-5,5-diphenyl-2-thioxo-oxazolidine-3-carbonyl)-2-methylundec-4-enoate

[Chem. 347]

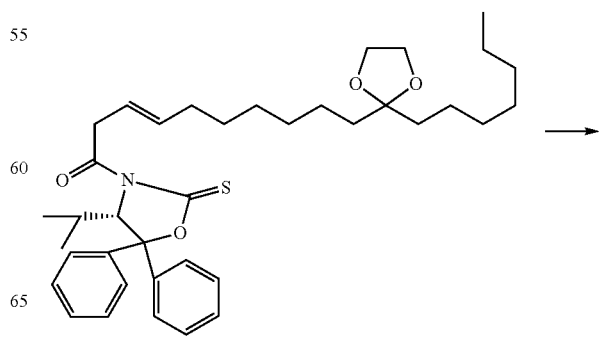

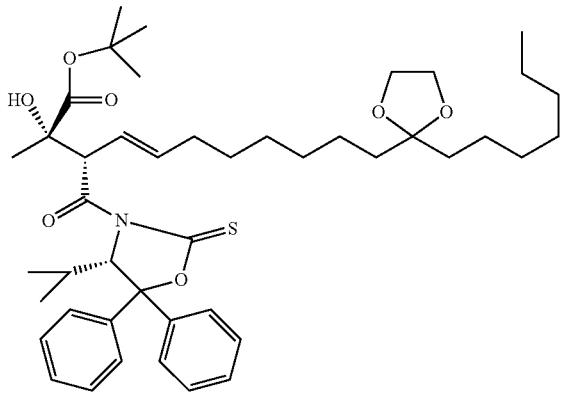

Under a nitrogen atmosphere, (S,E)-10-(2-heptyl-1,3-dioxolan-2-yl)-1-(4-isopropyl-5,5-diphenyl-2-thioxooxazolidin-3-yl)dec-3-en-1-one (2.0 g, 3.23 mmol) and lithium chloride (410 mg, 9.68 mmol) were dissolved in anhydrous tetrahydrofuran (30 mL), and cooled to −78° C. in a cold bath of dry ice-methanol. Lithium hexamethyldisilazide (1 M, tetrahydrofuran solution, 3.39 mL) was added. The mixture was stirred at the same temperature for 1 hour, and then in a cold bath at −25° C. for 10 minutes. The reaction flask was again cooled in a cold bath at −78° C. tert-Butyl 2-oxopropanoate (500 mg, 3.47 mol) was dissolved in tetrahydrofuran (3.0 mL) and the solution was added dropwise to the solution in the flask above. The mixture was stirred at the same temperature for 30 minutes, and the progress of the reaction was then stopped by adding a solution of acetic acid (370 μL, 6.45 mmol) in tetrahydrofuran (1.0 mL). The reaction mixture was warmed to room temperature, diluted in water, and then extracted with ethyl acetate. The separated organic layer was washed with a saturated brine, then dried over anhydrous sodium sulfate, and filtered. The filtrate was concentrated. The residue was purified by silica gel column chromatography (n-hexane/ethyl acetate) to obtain the target compound as colorless oil at a yield of 62% (FAB (mNBA) m/z 764 (M+H), 786 (MNa$^+$)).

Synthesis of (2S,3S,E)-tert-butyl 3-((S)-3-(4-(but-2-ynyloxy)phenyl)-1-methoxy-1-oxopropan-2-ylcarbamoyl)-11-(2-heptyl-1,3-dioxolan-2-yl)-2-hydroxy-2-methylundec-4-enoate

[Chem. 348]

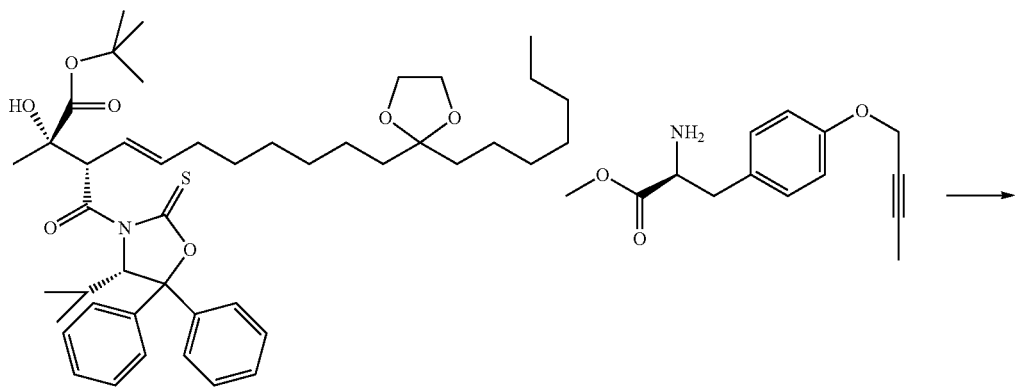

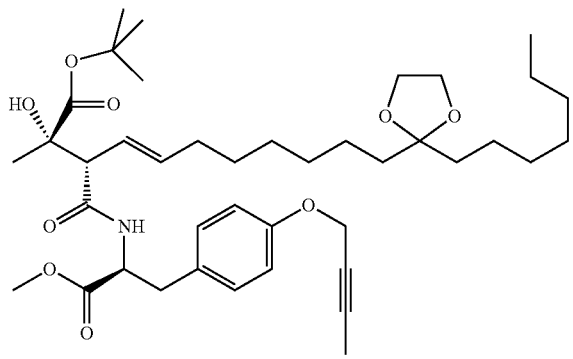

(2S,3S,E)-tert-Butyl 11-(2-heptyl-1,3-dioxolan-2-yl)-2-hydroxy-3-((S)-4-isopropyl-5,5-diphenyl-2-thioxo-oxazolidine-3-carbonyl)-2-methylundec-4-enoate (760 mg, 0.99 mmol) and (S)-methyl 2-amino-3-(4-(but-2-ynyloxy)phenyl)propanoate (500 mg, 2 mmol) were stirred at 40° C. under a nitrogen atmosphere for 3 days. The reaction mixture was purified by silica gel column chromatography (dichloromethane/methanol), and again by silica gel column chromatography (n-hexane/ethyl acetate) to obtain the target compound as yellow oil at a yield of 79%.

ESI (LC/MS positive mode) m/z 714 (M+H); Rt 3.95 min.

Synthesis of (E)-(2S,3S)-3-[(S)-2-(4-but-2-ynyloxyphenyl)-1-methoxycarbonyl-ethylcarbamoyl]-2-hydroxy-2-methyl-12-oxo-nonadec-4-enoic acid, No. 5398770

[Chem. 349]

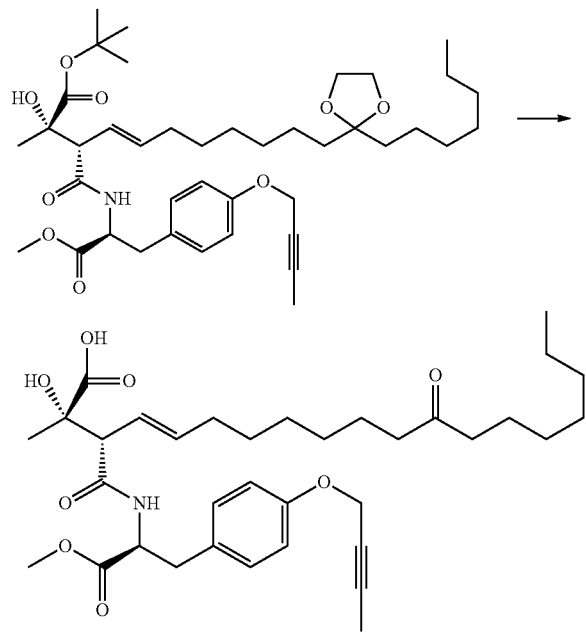

(2S,3S,E)-tert-Butyl 3-((S)-3-(4-(but-2-ynyloxy)phenyl)-1-methoxy-1-oxopropan-2-ylcarbamoyl)-11-(2-heptyl-1,3-dioxolan-2-yl)-2-hydroxy-2-methylundec-4-enoate (540 mg, 0.756 mmol) was dissolved in dichloromethane (3.5 mL), and water (0.35 mL) was added. Trifluoroacetic acid (10 mL) was added and the mixture was stirred at room temperature for 2 hours. The reaction solution was concentrated. The residue was then purified by diol column chromatography (n-hexane/acetone) to obtain the target compound as pale yellow oil at a yield of 91%.

$^1$H-NMR (CDCl$_3$) δ: 0.87 (3H, t, J=6.7 Hz), 1.16-1.37 (14H, m), 1.41 (3H, s), 1.51-1.62 (4H, m), 1.86 (3H, t, J=2.4 Hz), 1.92-2.11 (2H, m), 2.35-2.50 (4H, m), 3.01-3.11 (2H, m), 3.17 (1H, d, J=9.1 Hz), 3.74 (3H, s), 4.61 (2H, q, J=2.4 Hz), 4.81 (1H, dd, J=13.7, 5.8 Hz), 5.56 (1H, dd, J=15.5, 8.8 Hz), 5.60-5.70 (1H, m), 6.57 (1H, d, J=7.9 Hz), 6.86 (2H, d, J=8.5 Hz), 7.00 (2H, d, J=8.5 Hz).

ESI (LC/MS positive mode) m/z 614 (M+H); Rt 2.31 min.

Synthesis of No. 5398772

Synthesis of (E)-(2S,3S)-3-[(S)-2-(4-but-2-ynyloxyphenyl)-1-carboxy-ethylcarbamoyl]-2-hydroxy-2-methyl-12-oxo-nonadec-4-enoic acid

[Chem. 350]

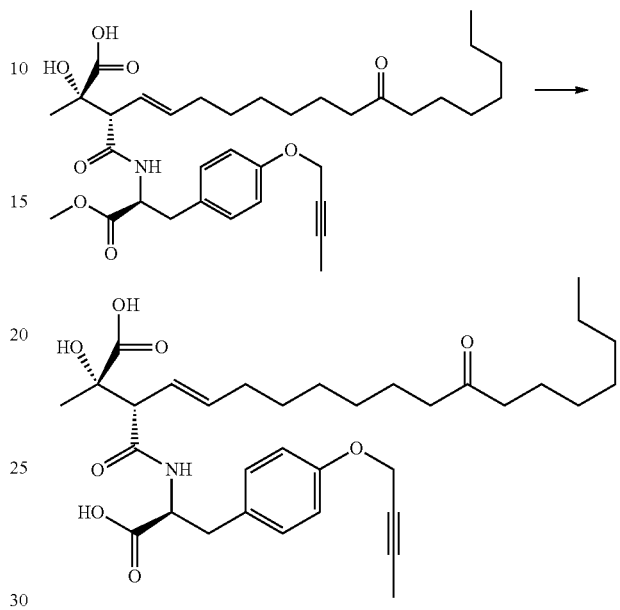

No. 5398770 (20 mg, 0.0326 mmol) was dissolved in methanol (0.4 mL), and an aqueous solution of 1 M sodium hydroxide (65 μL, 0.065 mmol) was added. The mixture was stirred at room temperature for 2 hours. To the resulting white suspension was added an aqueous solution of 0.5 M citric acid, and the mixture was extracted with ethyl acetate. The separated organic layer was washed twice with water, dried over anhydrous sodium sulfate, and then filtered. The filtrate was concentrated. The residue was purified by diol thin layer chromatography (dichloromethane/methanol) to obtain the target compound as clear and colorless solid at a yield of 70%.

$^1$H-NMR (CD$_3$OD) δ: 0.89 (3H, t, J=6.7 Hz), 1.20-1.36 (14H, m), 1.33 (3H, s), 1.47-1.58 (4H, m), 1.79-1.83 (3H, m), 1.93-2.00 (2H, m), 2.43 (4H, t, J=7.3 Hz), 2.93 (1H, dd, J=13.7, 8.9 Hz), 3.15 (1H, dd, J=13.7, 4.9 Hz), 3.25 (1H, d, J=8.5 Hz), 4.58-4.68 (3H, m), 5.44-5.61 (2H, m), 6.85 (2H, d, J=8.5 Hz), 7.13 (2H, d, J=8.5 Hz).

ESI (LC/MS positive mode) m/z 600 (M+H); Rt 1.68 min.

Synthesis of No. 5427561 (E)-(2S,3S)-3-[(S)-2-(4-But-2-ynyloxy-phenyl)-1-(2-hydroxy-ethylcarbamoyl)-ethylcarbamoyl]-2-hydroxy-2-(2-methoxy-ethyl)-12-oxo-nonadec-4-enoic acid

[Chem. 351]

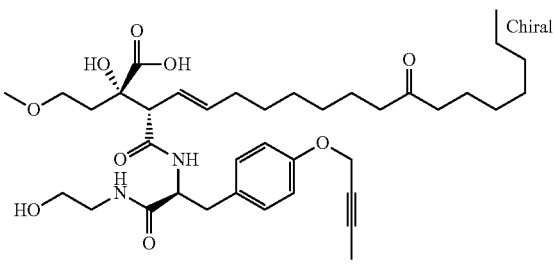

429

Synthesis of (S)-3-(4-(but-2-ynyloxy)phenyl)-2-((S,E)-2-((S)-1-tert-butoxy-2-hydroxy-4-methoxy-1-oxobutan-2-yl)-10-(2-heptyl-1,3-dioxolan-2-yl)dec-3-eneamide)propanoic acid

[Chem. 352]

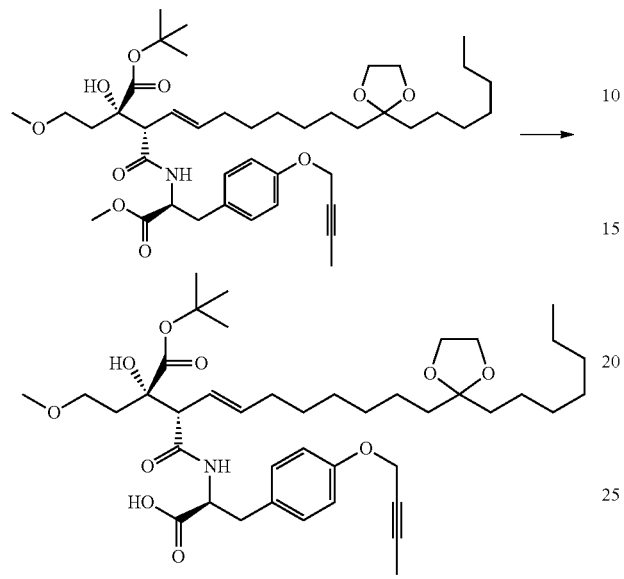

430

(2S,3S,E)-tert-Butyl 3-((S)-3-(4-(but-2-ynyloxy)phenyl)-1-methoxy-1-oxopropan-2-ylcarbamoyl)-11-(2-heptyl-1,3-dioxolan-2-yl)-2-hydroxy-2-(2-methoxyethyl)-undec-4-enoate (300 mg, 0.396 mol) was dissolved in methanol (2.0 mL), and lithium hydroxide monohydrate (17.4 mg, 0.42 mmol) was added. The mixture was stirred at room temperature for 5 hours. The progress of the reaction was stopped by adding an aqueous solution of 0.5 M citric acid, and the mixture was extracted with ethyl acetate. The separated organic layer was washed twice with water, dried over anhydrous sodium hydroxide, and filtered. The filtrate was concentrated. The resulting residue was purified by diol column chromatography (dichloromethane/methanol) to obtain the target compound as pale yellow oil at a yield of 77%.

ESI (LC/MS positive mode) m/z 744 (M+H), Rt 3.57

Synthesis of (2S,3S,E)-tert-butyl 3-((S)-3-(4-(but-2-ynyloxy)phenyl)-1-(2-hydroxyethylamino)-1-oxopropan-2-ylcarbamoyl)-11-(2-heptyl-1,3-dioxolan-2-yl)-2-hydroxy-2-(2-methoxyethyl)undec-4-enoate

[Chem. 353]

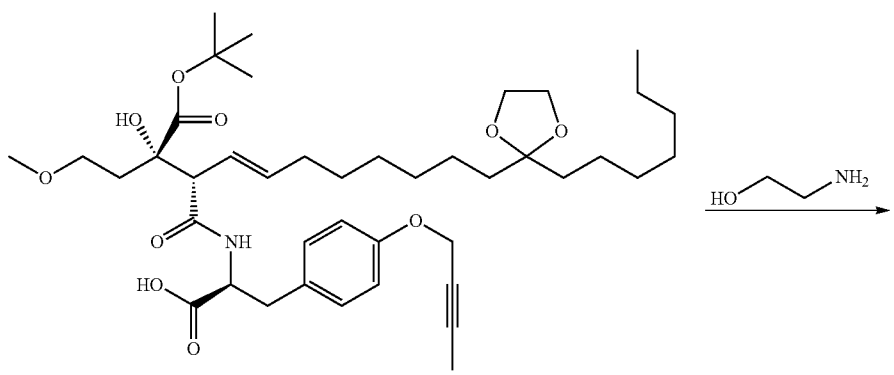

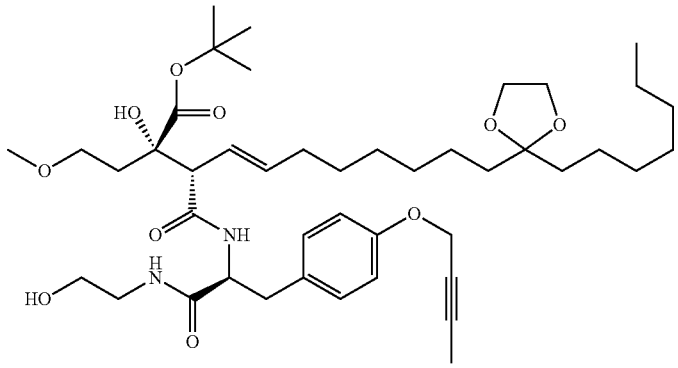

(S)-3-(4-(But-2-ynyloxy)phenyl)-2-((S,E)-2-((S)-1-tert-butoxy-2-hydroxy-4-methoxy-1-oxobutan-2-yl)-10-(2-heptyl-1,3-dioxolan-2-yl)dec-3-ene amide)propanoic acid (38 mg, 0.051 mmol) was dissolved in N,N-dimethylformamide (1 mL), and 1H-benzo[d][1,2,3]triazol-1-ol hydrate (58 mg, 0.30 mmol), 2-aminoethanol (20 μL), N1-((ethylimino)methylene)-N3,N3-dimethylpropane-1,3-diamine hydrochloride (52.4 mg, 0.273 mmol), and N-ethyl-N-isopropylpropane-2-amine (26 μL) were added in order. The reaction mixture was stirred at room temperature overnight, diluted in water, and extracted with ethyl acetate. The separated organic layer was further washed twice with water, and with a saturated aqueous solution of ammonium chloride, then dried over anhydrous sodium sulfate, filtered, and then concentrated. The resulting residue was purified by amino silica gel thin layer chromatography (dichloromethane/methanol=30 30) to obtain the target compound as pale yellow oil at a yield of 28%.

ESI (LC/MS positive mode) m/z 787 (M+H); Rt 3.16 min.

Synthesis of No. 5427561, (E)-(2S,3S)-3-[(S)-2-(4-but-2-ynyloxy-phenyl)-1-(2-hydroxy-ethylcarbamoyl)-ethylcarbamoyl]-2-hydroxy-2-(2-methoxy-ethyl)-12-oxo-nonadec-4-enoic acid

[Chem. 354]

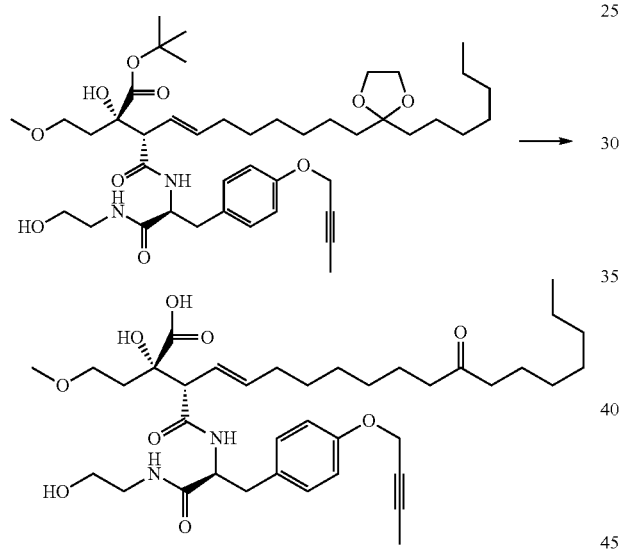

(2S,3S,E)-tert-Butyl 3-((S)-3-(4-(but-2-ynyloxy)phenyl)-1-(2-hydroxyethylamino)-1-oxopropan-2-ylcarbamoyl)-11-(2-heptyl-1,3-dioxolan-2-yl)-2-hydroxy-2-(2-methoxyethyl)undec-4-enoate (11.3 mg, 0.014 mmol) was dissolved in dichloromethane (0.5 mL), and water (50 μL) was added. Trifluoroacetic acid (1.5 mL) was further added. The reaction mixture was stirred at room temperature for 5 hours, and then concentrated. The resulting residue was dissolved in methanol (1.0 mL). To the solution was added an aqueous solution (50 μL) of 28% ammonia and the mixture was stirred at room temperature for 1 hour. The reaction mixture was concentrated, and the resulting residue was then diluted in ethyl acetate, and washed with an aqueous solution of 0.5 M citric acid. The separated organic layer was washed with a saturated brine, dried over anhydrous sodium sulfate, then filtered, and concentrated. The resulting residue was purified by diol silica gel thin layer chromatography (dichloromethane/methanol) to obtain the target compound as colorless oil at a yield of 80%.

$^1$H-NMR (CD$_3$OD) δ: 0.90 (3H, t, J=7.0 Hz), 1.19-1.39 (18H, m), 1.47-1.58 (2H, m), 1.64 (1H, dt, J=14.0, 5.0 Hz), 1.82 (3H, t, J=2.1 Hz), 1.92-2.09 (3H, m), 2.44 (4H, t, J=7.3 Hz), 2.82 (1H, dd, J=13.4, 9.8 Hz), 3.09 (1H, dd, J=14.0, 5.5 Hz), 3.15-3.61 (8H, m), 4.52-4.63 (3H, m), 5.45-5.62 (2H, m), 6.85 (2H, d, J=8.5 Hz), 7.14 (2H, d, J=8.5 Hz).

ESI (LC/MS positive mode) m/z 687 (M+H); Rt 1.18 min.

No. 5427562

Synthesis of (E)-(2S,3S)-3-[(S)-2-(4-but-2-ynyloxy-phenyl)-1-(2-methoxy-ethylcarbamoyl)-ethylcarbamoyl]-2-hydroxy-2-(2-methoxy-ethyl)-12-oxo-nonadec-4-enoic acid

[Chem. 355]

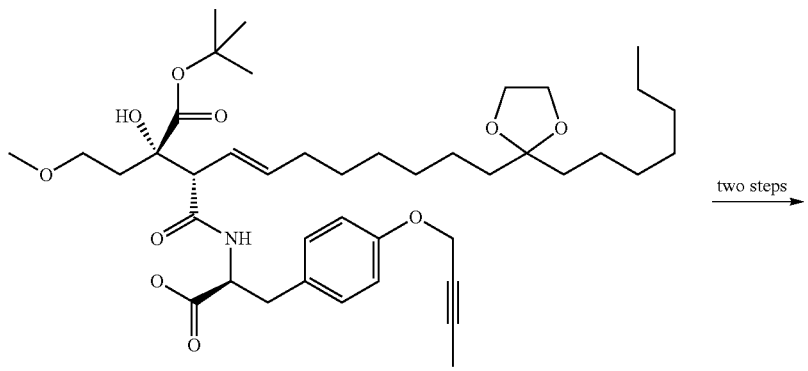

product of step 1
for synthesis of #30 two steps →

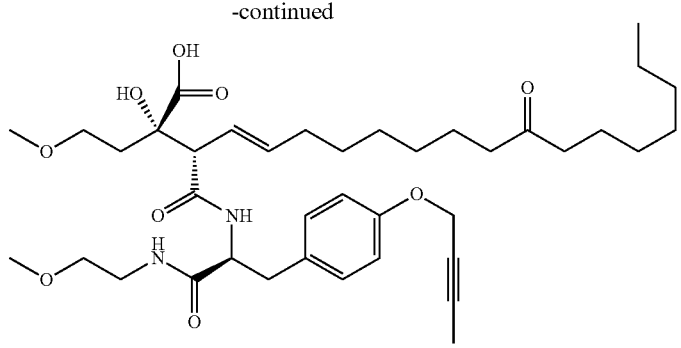

(2S,3S,E)-tert-Butyl 3-((S)-3-(4-(but-2-ynyloxy)phenyl)-1-(2-methoxyethylamino)-1-oxopropan-2-ylcarbamoyl)-11-(2-heptyl-1,3-dioxolan-2-yl)-2-hydroxy-2-(2-methoxyethyl)undec-4-enoate was obtained as colorless oil at a yield of 80% by the amidation under reaction conditions similar to those of the synthesis of No. 5427561, except that 2-methoxyethaneamine was used instead of 2-aminoethanol.

ESI (LC/MS positive mode) m/z 801 (M+H); Rt 3.64 min.

This was treated with an acid similar to that used in the synthesis of No. 5427561 to obtain the target compound as colorless oil at a yield of 61%.

$^1$H-NMR (CD$_3$OD) δ: 0.89 (3H, t, J=7.0 Hz), 1.20-1.37 (18H, m), 1.47-1.67 (m, 5H), 1.81 (3H, t, J=2.1 Hz), 1.93-2.09 (3H, m), 2.43 (4H, t, J=7.6 Hz), 2.82 (1H, dd, J=14.0, 9.1 Hz), 3.05 (1H, dd, J=14.0, 5.5 Hz), 3.16-3.23 (1H, m), 3.24 (3H, s), 3.31 (3H, s), 3.32-3.48 (6H, m), 4.52-4.63 (3H, m), 5.45-5.61 (2H, m), 6.84 (2H, d, J=8.5 Hz), 7.13 (2H, d, J=8.5 Hz).

ESI (LC/MS positive mode) m/z 701 (M+H); Rt 1.76 min.

No. 5427563

(E)-(2S,3S)-3-[(S)-2-(4-But-2-ynyloxy-phenyl)-1-(3-methoxy-propylcarbamoyl)-ethylcarbamoyl]-2-hydroxy-2-(2-methoxy-ethyl)-12-oxo-nonadec-4-enoic acid

[Chem. 356]

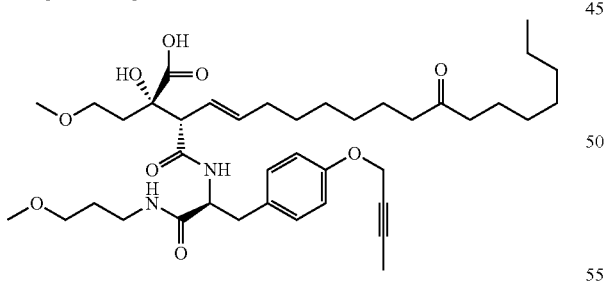

(2S,3S,E)-tert-Butyl 3-((S)-3-(4-(but-2-ynyloxy)phenyl)-1-(3-methoxypropylamino)-1-oxopropan-2-ylcarbamoyl)-11-(2-heptyl-1,3-dioxolan-2-yl)-2-hydroxy-2-(2-methoxyethyl)undec-4-enoate was obtained as colorless oil at a yield of 72% by the amidation, under reaction conditions similar to those of the synthesis of No. 5427561, except that 3-methoxypropan-1-amine was used instead of 2-aminoethanol.

ESI (LC/MS positive mode) m/z 815 (M+H); Rt 3.68 min.

This was treated under acidic conditions similar to those used in the synthesis of No. 5427561 to obtain the target compound as colorless oil at a yield of 58%.

¹H-NMR (CD₃OD) δ: 0.90 (3H, t, J=6.7 Hz), 1.19-1.37 (18H, m), 1.47-1.58 (m, 4H), 1.58-1.71 (3H, m), 1.81 (3H, t, J=2.4 Hz), 1.94-2.09 (3H, m), 2.43 (4H, t, J=7.3 Hz), 2.83 (1H, dd, J=13.7, 8.8 Hz), 3.02 (1H, dd, J=14.0, 6.1 Hz), 3.10-3.47 (13H, m), 4.48-4.63 (3H, m), 5.47-5.62 (2H, m), 6.84 (2H, d, J=8.5 Hz), 7.13 (2H, d, J=8.5 Hz).
ESI (LC/MS positive mode) m/z 715 (M+H); Rt 1.80 min.
Synthetic Schemes of No. 5321942 and Others
[Chem. 357]
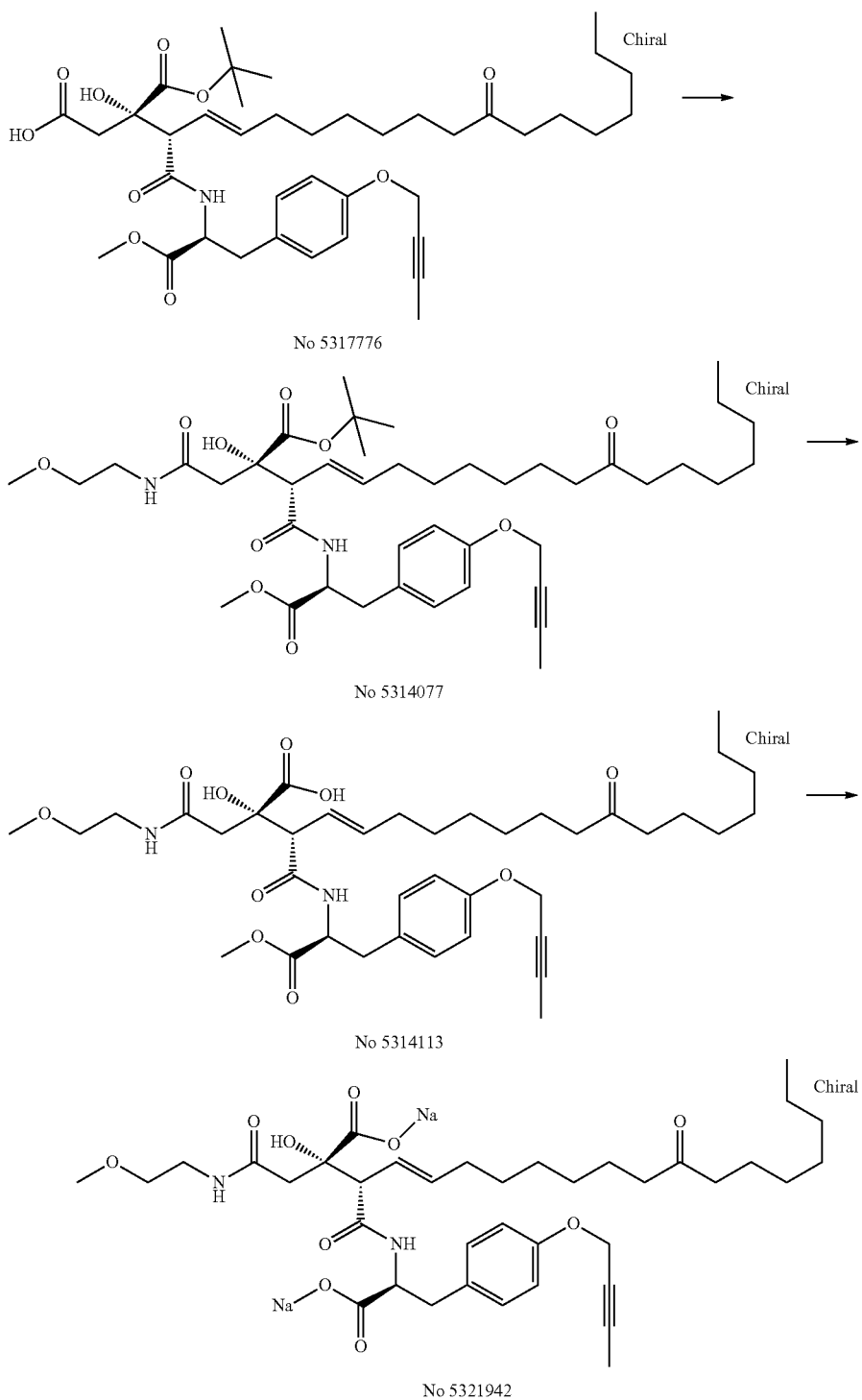

To a mixture of No. 5317776 (1,494 mg, 2.09 mmol) and DMF (20.9 mL) were added commercially available 2-methoxyethylamine (271 μL, 3.14 mmol), WSC/HCl (521 mg, 2.72 mmol), HOBt (367 mg, 2.72 mmol), and N,N-diisopropylethylamine (1,097 μL), and the mixture was stirred at room temperature. After being stirred for 16 hours, 2-methoxyethylamine (271 μL, 3.14 mmol), 1-ethyl-3-(3-dimethylaminopropyl)carbodiimide hydrochloride (521 mg, 2.72 mmol), HOBt (367 mg, 2.72 mmol), and N,N-diisopropylethylamine (1,097 μL) were added again, and the mixture was further stirred at room temperature. After being stirred for 4 hours, ethyl acetate (40 mL) was added to the reaction solution. The resulting organic layer was washed with water (20 mL×3), 0.1 N hydrochloric acid (20 mL×3), a saturated aqueous solution of NaHCO₃ (20 mL×3), an aqueous solution (10 mL) of 5% sodium sulfite, and a saturated brine (10 mL) in order. The resulting organic layer was dried over anhydrous sodium sulfate, then filtered, and concentrated under reduced pressure. The collected residue was purified by silica gel chromatography (n-hexane/ethyl acetate, amino column 40+M) to obtain 1,212 mg of No. 5314077.

ESI (LC/MS positive mode) m/z 772 (M+H), Rt ESI (LC/MS positive mode) m/z 772 (M+H), Rt; 3. min To No. 5314077 (902 mg, 1.17 mmol) was added formic acid (5.8 mL). The mixture was stirred at room temperature for 9 hours, and then freeze-dried. The resulting residue was purified by silica gel chromatography (dichloromethane/methanol, diol column) to obtain 624 mg of No. 5314113.

ESI (LC/MS positive mode) m/z 715 (M+H), Rt ESI (LC/MS positive mode) m/z 715 (M+H), Rt; 2. min.

To a mixture of No. 5314113 (14 mg, 0.020 mmol) and methanol (0.2 mL) was added an aqueous solution of 0.1 M sodium hydroxide (196 μL, 0.020 mmol) and the mixture was stirred at room temperature. After being stirred for 2 hours, an aqueous solution of 0.1 N sodium hydroxide was added and the mixture was stirred at room temperature for further 1 hour. Water (30 mL) was then added. The reaction solution was then freeze-dried to obtain No. 5321942 (14.7 mg, 100%, white powder).

No. 5321942

Disodium (E)-(2S,3S)-3-[(S)-2-(4-but-2-ynyloxy-phenyl)-1-carboxy-ethylcarbamoyl]-2-hydroxy-2-[(2-methoxy-ethylcarbamoyl)-methyl]-12-oxo-nonadec-4-enoate ¹H-NMR (CD₃OD) δ(PPM) 0.88 (3H, t, J=8 Hz), 1.22-1.32 (14H, m), 1.50-1.56 (4H, m), 1.79-1.81 (3H, m), 1.92-1.97 (2H, m), 2.38-2.43 (5H, m), 2.64 (1H, d, J=16 Hz), 2.95-2.93 (2H, m), 3.00-3.17 (2H, m), 3.27-3.32 (4H, m), 3.39-4.41 (2H, m), 4.42-4.45 (1H, m), 4.55-4.57 (2H, m), 5.48-5.54 (2H, m), 6.79 (2H, d, J=8 Hz), 7.13 (2H, d, J=8 Hz), 8.53 (1H, S)

ESI (LC/MS positive mode) m/z 702 (M+1-1), Rt ESI (LC/MS positive mode) m/z 702 (M+1-1), Rt; 2. min.

No. 6810892

Synthesis of carboxymethyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate

[Chem. 358]

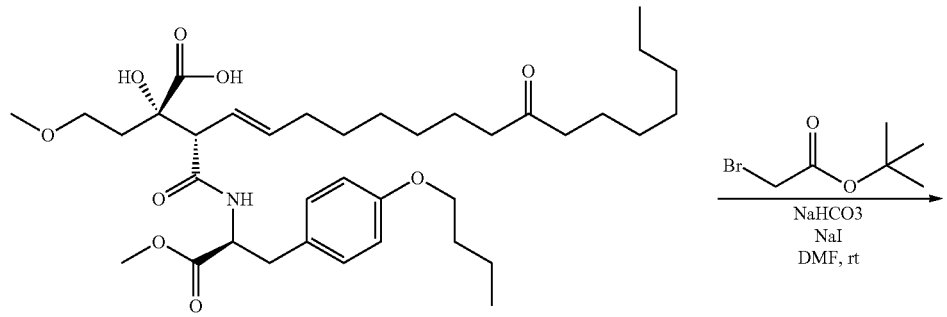

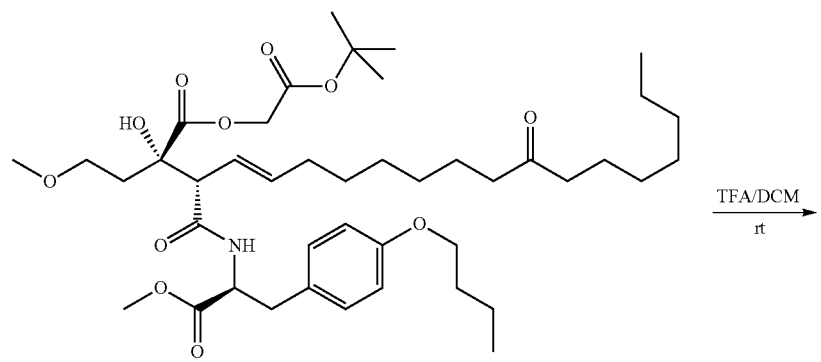

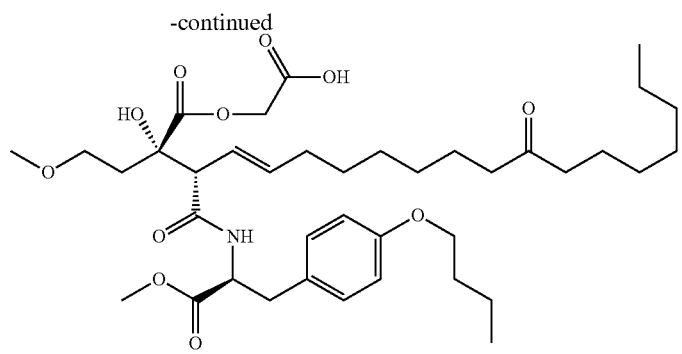

No 6810892

An intermediate, tert-butoxycarbonylmethyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate (ESI (LC/MS positive mode) m/z 777 (M+H); Rt 1.25 min.) was obtained by the synthesis by a method similar to that of No. 6808754, except that a commercially available product of tert-butyl bromoacetate was used instead of 4-chloromethyl-5-methyl-1,3-dioxol-2-one. The obtained intermediate was used in the next synthesis without purification.

To this intermediate (48 mg, 0.0618 mmol) were added dichloromethane (1.0 mL) and trifluoroacetic acid (1 mL), and the mixture was stirred at room temperature. After confirming the consumption of the starting materials by LCMS, the solvent was distilled off under reduced pressure. The residue was purified by preparative HPLC. The obtained fraction was freeze-dried to obtain the title compound (44 mg, 98% yield, white powder).

$^1$H-NMR (CD$_3$OD) δ: 0.89 (3H, t, J=7.1 Hz), 0.98 (3H, t, J=7.3 Hz), 1.22-1.36 (14H, m), 1.45-1.57 (6H, m), 1.68-1.79 (3H, m), 1.93-2.01 (2H, m), 2.09-2.16 (2H, m), 2.43 (4H, t, J=7.5 Hz), 2.89 (2H, dd, J=14.1, 9.3 Hz), 3.10 (2H, dd, J=13.9, 5.1 Hz), 3.24 (3H, s), 3.30-3.31 (1H, m), 3.42-3.56 (3H, m), 3.71 (3H, s), 3.93 (2H, t, J=6.4 Hz), 4.53-4.57 (2H, m), 4.63-4.68 (1H, m), 5.47-5.62 (2H, m), 6.79 (2H, d, J=8.4 Hz), 7.07 (2H, d, J=8.8 Hz).

ESI (LC/MS positive mode) m/z 720 (M+H) Rt; 1.05 min.

No. 6809530

Synthesis of methyl (E)-(2S,3S)-3-[(S)-2-(4-butoxy-phenyl)-1-methoxycarbonyl-ethylcarbamoyl]-2-hydroxy-2-(2-methoxy-ethyl)-12-oxo-nonadec-4-enoate

[Chem. 359]

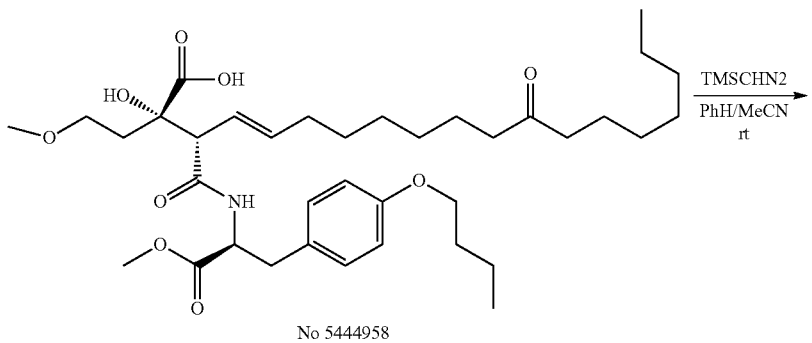

No 5444958

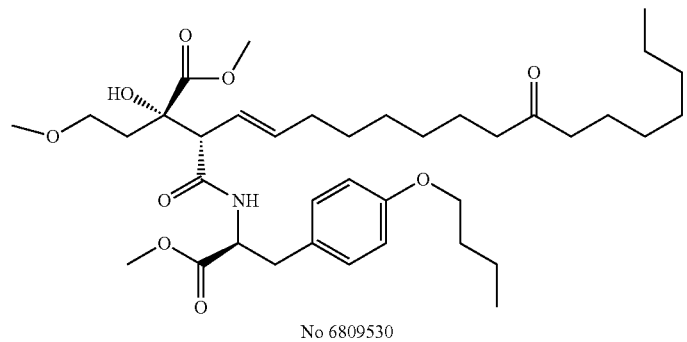

No 6809530

No. 5444958 (50 mg, 0.0733 mmol) was dissolved in methanol (0.4 mL) and benzene (1.2 mL), and trimethylsilyl diazomethane (244 μL, 0.146 mmol) was added at room temperature. After confirming the consumption of the starting materials by LCMS, the solvent was distilled off under reduced pressure. The residue was purified by preparative HPLC. The obtained fraction was freeze-dried to obtain the title compound (48 mg, 97% yield, white powder).

$^1$H-NMR (CD$_3$OD) δ: 0.89 (3H, t, J=6.8 Hz), 0.98 (3H, t, J=7.3 Hz), 1.23-1.37 (14H, m), 1.44-1.65 (7H, m), 1.69-1.78 (2H, m), 1.92-2.00 (2H, m), 2.01-2.10 (1H, m), 2.43 (4H, t, J=7.3 Hz), 2.87 (1H, dd, J=13.9, 9.5 Hz), 3.11 (1H, dd, J=13.9, 5.1 Hz), 3.18-3.22 (3H, m), 3.32-3.36 (1H, m), 3.39-3.43 (1H, m), 3.65 (3H, s), 3.70 (3H, s), 3.93 (2H, t, J=6.4 Hz), 4.63 (1H, dd, J=9.5, 5.1 Hz), 5.42-5.58 (2H, m), 6.79 (2H, d, J=8.8 Hz), 7.07 (2H, d, J=8.4 Hz).

ESI (LC/MS positive mode) m/z 676 (M+H); Rt 1.16 min.

No. 6810070

Synthesis of methoxycarbonylmethyl (E)-(2S,3S)-3-[(S)-2-(4-butoxy-phenyl)-1-methoxycarbonyl-ethyl-carbamoyl]-2-hydroxy-2-(2-methoxy-ethyl)-12-oxo-nonadec-4-enoate

[Chem. 360]

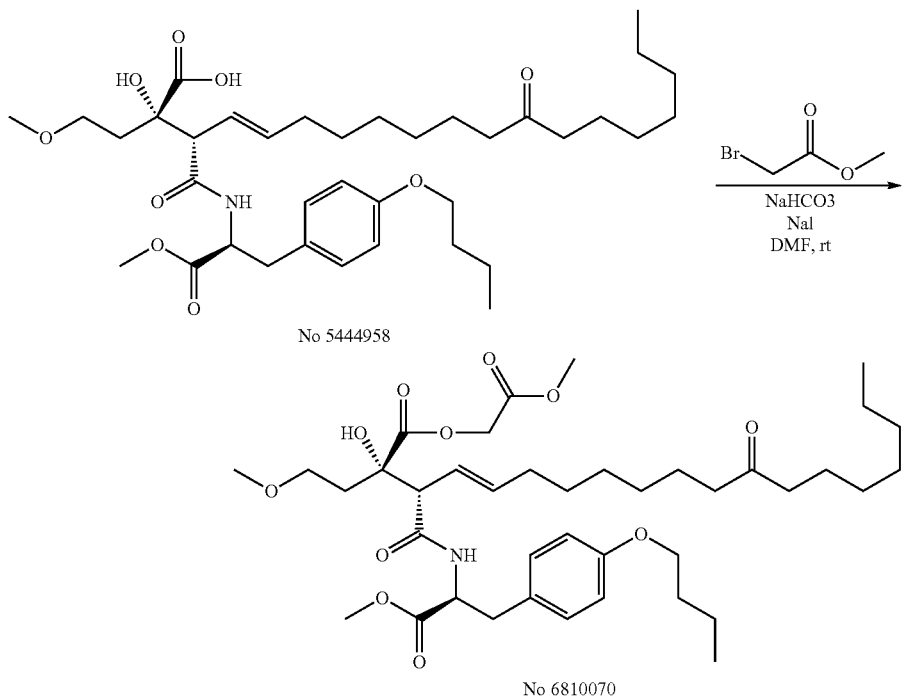

The title compound was obtained by the synthesis by a method similar to that of No. 6808754, except that a commercially available reagent of methyl bromoacetate was used instead of 4-chloromethyl-5-methyl-1,3-dioxol-2-one.

$^1$H-NMR (CD$_3$OD) δ: 0.89 (3H, t, J=6.8 Hz), 0.98 (3H, t, J=7.5 Hz), 1.22-1.37 (14H, m), 1.45-1.59 (6H, m), 1.74 (3H, dt, J=20.9, 6.6 Hz), 1.93-2.01 (2H, m), 2.06-2.13 (1H, m), 2.43 (4H, t, J=7.5 Hz), 2.88 (2H, dd, J=13.7, 9.3 Hz), 3.11 (2H, dd, J=14.3, 5.1 Hz), 3.24 (3H, s), 3.28 (1H, d, J=10.0 Hz), 3.48 (2H, ddd, J=24.7, 10.8, 6.8 Hz), 3.71 (3H, s), 3.75

(3H, s), 3.93 (2H, t, J=6.4 Hz), 4.58-4.69 (4H, m), 5.47-5.62 (2H, m), 6.79 (2H, d, J=8.8 Hz), 7.07 (2H, d, J=8.8 Hz).

ESI (LC/MS positive mode) m/z 734 (M+H); Rt 1.15

No. 6808754

Synthesis of 5-methyl-2-oxo-[1,3]dioxol-4-ylmethyl (E)-(2S,3S)-3-[(S)-2-(4-butoxy-phenyl)-1-methoxy-carbonyl-ethylcarbamoyl]-2-hydroxy-2-(2-methoxy-ethyl)-12-oxo-nonadec-4-enoate

[Chem. 361]

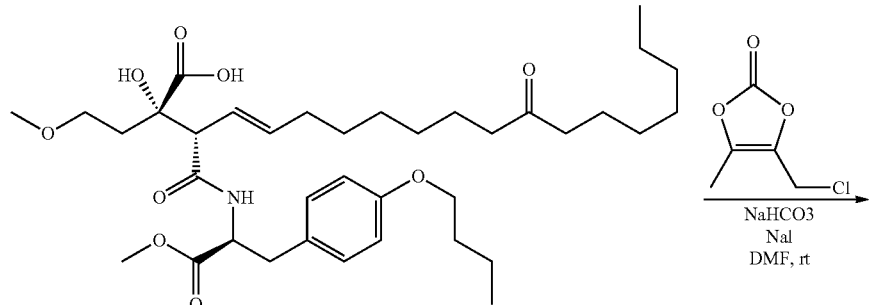

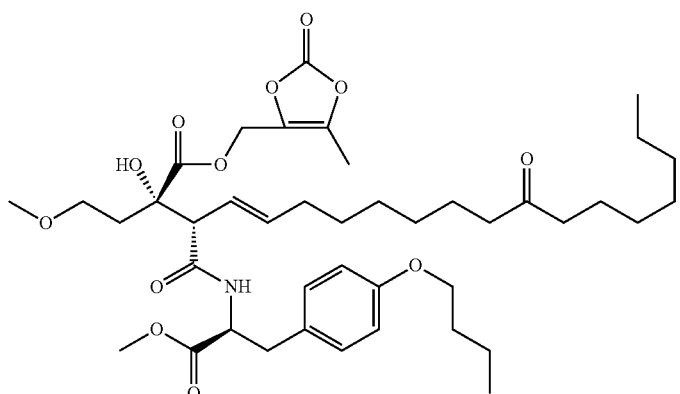

To a mixture of No. 5444958 (50 mg, 0.0733 mmol), sodium iodide (16.5 mg, 0.110 mmol), sodium bicarbonate (7.4 mg, 0.0880 mmol), and DMF (1.0 mL) was added a commercially available reagent of 4-chloromethyl-5-methyl-1,3-dioxol-2-one (15.9 μL, 0.146 mmol) at room temperature, and the mixture was stirred as it was for 5 hours. After confirming the consumption of the starting materials by LCMS, the reaction solution was filtered through a syringe filter, and purified as it was by preparative HPLC. The purified fraction was freeze-dried to obtain the title compound (47 mg, 83% yield, colorless oil).

$^1$H-NMR (CD$_3$OD) δ: 0.89 (3H, t, J=6.8 Hz), 0.98 (3H, t, J=7.5 Hz), 1.20-1.40 (14H, m), 1.43-1.57 (6H, m), 1.62 (1H, td, J=9.4, 4.6 Hz), 1.70-1.77 (2H, m), 1.86-2.01 (2H, m), 2.05-2.12 (1H, m), 2.43 (3H, t, J=7.3 Hz), 2.86 (1H, dd, J=14.1, 9.3 Hz), 3.10 (1H, dd, J=14.3, 5.1 Hz), 3.18 (3H, s), 3.22 (1H, d, J=8.4 Hz), 3.32-3.37 (1H, m), 3.44 (1H, td, J=9.7, 4.4 Hz), 3.70 (3H, s), 3.92 (2H, t, J=6.4 Hz), 4.63 (1H, td, J=8.6, 4.9 Hz), 4.83 (1H, d, J=14.1 Hz), 4.95 (1H, d, J=14.1 Hz), 5.42-5.57 (2H, m), 6.79 (2H, d, J=8.8 Hz), 7.06 (2H, d, J=8.8 Hz), 8.23 (1H, d, J=7.9 Hz).

ESI (LC/MS positive mode) m/z 774 (M+H); Rt 1.14 min.

No. 5247609, (E)-(2S,3S)-3-[(S)-2-(4-but-2-ynyloxy-phenyl)-1-methylcarbamoyl-ethylcarbamoyl]-2-hydroxy-2-(2-hydroxyethyl)-12-oxo-nonadec-4-enoic acid

[Chem. 362]

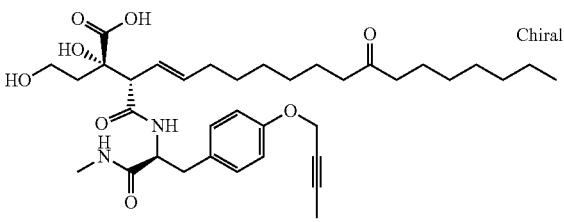

The title compound was obtained by the method similar to Step A2-b by carrying out the condensation using (S)-2-amino-3-(4-but-2-ynyloxy-phenyl)-N-methyl-propionamide instead of methyl (S)-2-amino-3-(4-butoxy-phenyl)-propionate, and an acid treatment similar to Step A3.

¹H-NMR (DMSO-d₆) δ(PPM) 8.07 (1H, d, J=8.1 Hz), 7.86 (1H, br.s), 7.08 (2H, d, J=8.4 Hz), 6.80 (2H, d, J=8.4 Hz), 5.40-5.30 (2H, m), 5.23 (1H, br.s), 4.65 (2H, m), 4.40-4.30 (1H, m), 3.40-3.20 (1H, m), 3.00-2.50 (9H, m), 2.40-2.30 (4H, m), 1.82 (3H, s), 2.10-1.10 (20H, m), 0.85 (3H, t, J=6.6 Hz),
ESI (LC/MS positive mode) m/z 643 (M+H)

¹H-NMR (CDCl₃) δ(PPM) 7.10 (2H, d, J=8.4 Hz), 6.88 (2H, d, J=8.4 Hz), 6.80 (1H, br.s), 5.75-5.60 (1H, m), 5.60-5.40 (2H, m), 4.90-4.70 (1H, m), 4.61 (2H, br.s), 3.78 (3H, s), 3.22-3.15 (2H, m), 3.05-2.95 (1H, m), 2.80-2.65 (2H, m), 2.50-2.30 (5H, m), 2.20-1.10 (18H, m), 1.85 (3H, br.s), 0.87 (3H, t, J=6.6 Hz),
ESI (LC/MS positive mode) m/z 657 (M+H)

No. 5283374, (E)-(2S,3S)-3-[(S)-2-(4-but-2-ynyloxy-phenyl)-1-methoxycarbonyl-ethylcarbarnoyl]-2-carbamoylmethyl-2-hydroxy-12-oxo-nonadec-4-enoic acid No. 5300967, (E)-(2S,3S)-3-[(S)-2-(4-but-2-ynyloxy-phenyl)-1-methoxycarbonyl-ethylcarbamoyl]-2-hydroxy-2-[(2-methylsulfanyl-ethylcarbamoyl)-methyl]-12-oxo-nonadec-4-enoic acid

[Chem. 363]

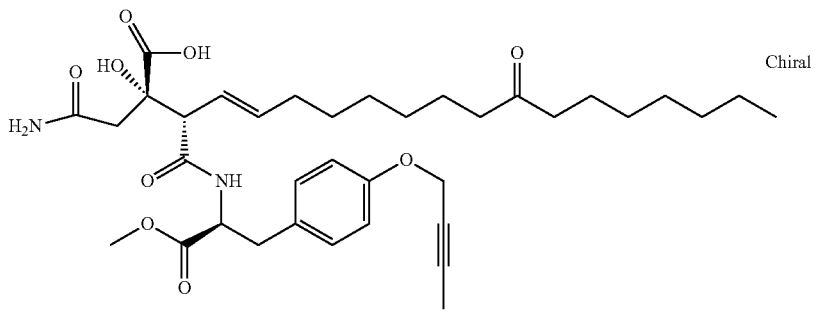

No. 5317776, 1-tert-butyl (S)-2-{(E)-(S)-1-[(S)-2-(4-but-2-ynyloxy-phenyl)-1-methoxycarbonyl-ethylcarbamoyl]-10-oxo-heptadec-2-enyl}-2-hydroxy-succinate (40.6 mg, 56.9 nmol) was dissolved in DMF (1.0 mL), and ammonium chloride (9.13 mg, 170.6 nmol), WSC (16.4 mg, 85.3 nmol), HOBt (11.5 mg, 85.3 nmol), N,N-diisopropylethylamine (59.4 mL, 341.2 nmol) were added. The mixture was stirred at room temperature for 20 hours. To the reaction solution was added water. The mixture was extracted with ethyl acetate,

[Chem. 364]

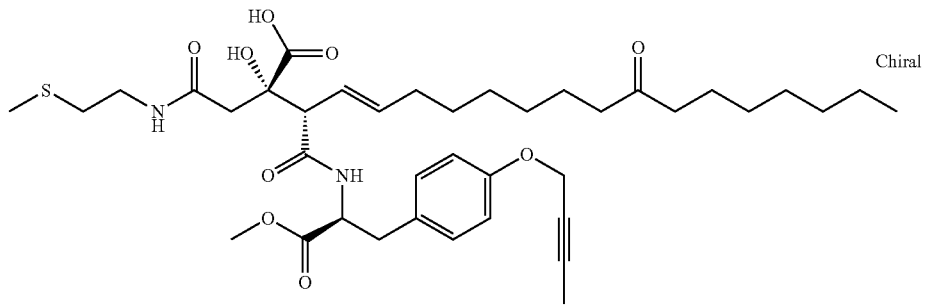

washed with 1 M hydrochloric acid, an aqueous solution of sodium bicarbonate, and a saturated brine. The organic layer was dried over anhydrous magnesium sulfate. The solvent was then distilled off under reduced pressure.

The resulting mixture was dissolved in formic acid (1.0 mL), and the solution was stirred at room temperature for 3 hours. The solvent was distilled out of the reaction solution under reduced pressure. The resulting residue was purified by silica gel column chromatography to obtain the target compound (12.5 mg, 33% yield) as white solid.

The title compound was obtained by a method similar to that of No. 5283374, except that 2-methyl-sulfanylmethylamine was used instead of ammonium chloride.
¹H-NMR (CDCl₃) δ(PPM) 7.10 (2H, d, J=8.4 Hz), 6.88 (2H, d, J=8.4 Hz), 6.84 (1H, br.s), 6.50-6.30 (1H, m), 5.60-5.40 (2H, m), 4.90-4.70 (1H, m), 4.61 (2H, br.s), 3.75 (3H, s), 3.55-3.35 (2H, m), 3.25-3.10 (2H, m), 3.05-2.90 (1H, m), 2.45-2.25 (8H, m), 2.12 (3H, s), 2.05-1.95 (2H, m), 1.85 (3H, br.s), 1.30-1.10 (18H, m), 0.87 (3H, t, J=6.6 Hz),
ESI (LC/MS positive mode) m/z 731 (M+H)

No. 5300966, (E)-(2S,3S)-3-[(S)-2-(4-but-2-yny-loxy-phenyl)-1-methoxycarbonyl-ethylcarbamoyl]-2-hydroxy-12-oxo-2-[(2,2,2-trifluoro-ethylcarbamoyl)-methyl-nonadec-4-enoic acid

[Chem. 365]

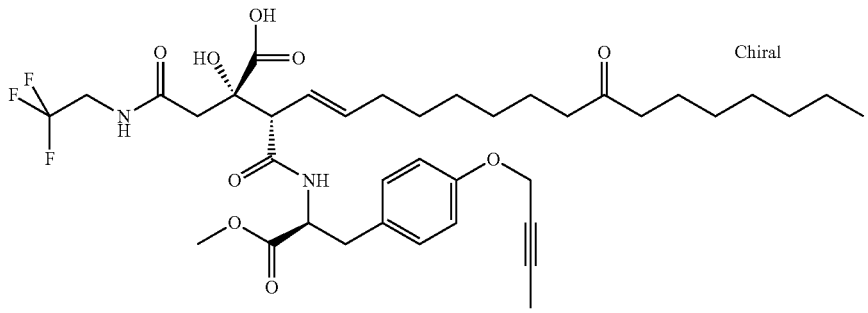

The title compound was obtained by a method similar to that of No. 5283374, except that 2-trifluoroethyl amine was used instead of ammonium chloride.

$^1$H-NMR (CDCl$_3$) δ(PPM) 7.10 (2H, d, J=8.4 Hz), 6.88 (2H, d, J=8.4 Hz), 6.84 (1H, br.s), 5.70-5.50 (2H, m), 4.90-4.70 (1H, m), 4.61 (2H, br.s), 4.00-3.80 (2H, m), 3.75 (3H, s), 3.35-3.15 (2H, m), 3.10-2.80 (2H, m), 2.55-2.25 (5H, m), 2.05-1.95 (2H, m), 1.85 (3H, br.s), 1.30-1.10 (18H, m), 0.87 (3H, t, J=6.6 Hz),
ESI (LC/MS positive mode) m/z 739 (M+H)

No. 5300964, (E)-(2S,3S)-3-[(S)-2-(4-but-2-yny-loxy-phenyl)-1-methoxycarbonyl-ethylcarbamoyl]-2-[(carbamoylmethyl-carbamoyl)-methyl]-2-hydroxy-12-oxo-nonadec-4-enoic acid

[Chem. 366]

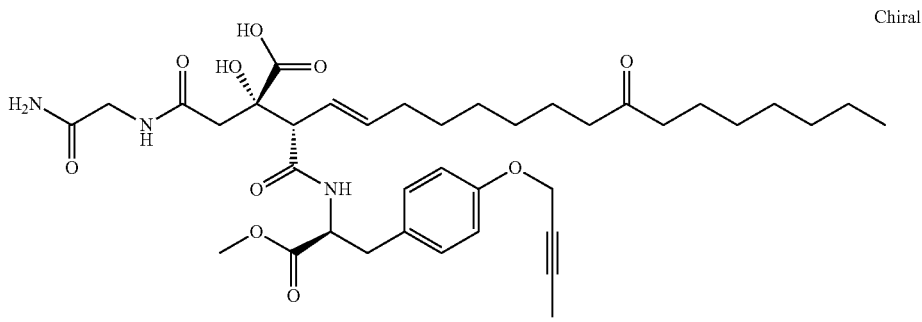

The title compound was obtained by a method similar to that of No. 5283374, except that 2-amino acetamide was used instead of ammonium chloride.

$^1$H-NMR (CDCl$_3$) δ(PPM) 7.30-7.00 (5H, m, J=8.4 Hz), 6.88 (2H, d, J=8.4 Hz), 6.50-6.30 (1H, m), 5.60-5.40 (2H, m), 4.90-4.70 (1H, m), 4.61 (2H, br.s), 4.10-3.90 (2H, m), 3.75 (3H, s), 3.55-2.85 (3H, m), 2.75-2.50 (2H, m), 2.45-2.30 (4H, m), 2.05-1.95 (2H, m), 1.85 (3H, br.s), 1.30-1.10 (18H, m), 0.87 (3H, t, J=6.6 Hz),
ESI (LC/MS positive mode) m/z 714 (M+H)

No. 5308315, (E)-(2S,3S)-3-[(S)-2-(4-but-2-yny-loxy-phenyl)-1-methoxycarbonyl-ethylcarbamoyl]-2-hydroxy-2-[(3-methoxypropylcarbamoyl)-methyl]-12-oxo-nonadec-4-enoic acid

[Chem. 367]

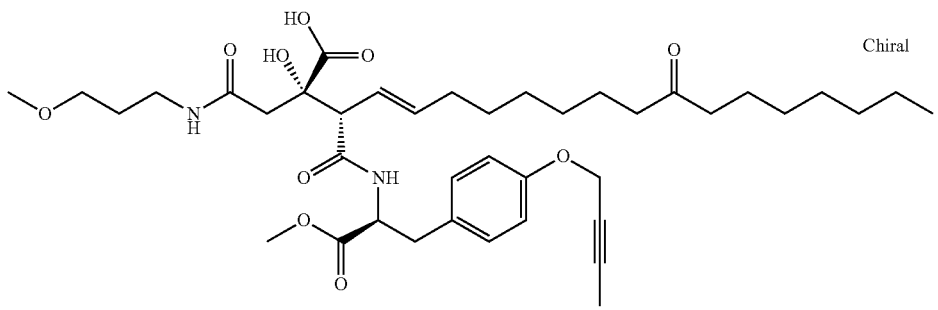

The title compound was obtained by a method similar to that of No. 5283374, except that 3-methoxypropylamine was used instead of ammonium chloride.

$^1$H-NMR (CDCl$_3$) δ(PPM) 7.10 (2H, d, J=8.4 Hz), 7.00-6.75 (3H, m), 6.60-6.50 (1H, m), 5.80-5.40 (2H, m), 4.80-4.70 (1H, m), 4.62 (2H, m), 3.75 (3H, s), 3.55-3.35 (2H, m), 3.35-3.25 (3H, m), 3.25-3.10 (2H, m), 3.05-2.90 (1H, m), 2.45-2.25 (4H, m), 2.05-1.95 (2H, m), 1.85 (3H, br.s), 1.80-1.70 (2H, m), 1.60-1.10 (18H, m), 0.87 (3H, t, J=6.6 Hz),
ESI (LC/MS positive mode) m/z 729 (M+H)

No. 5289502, (E)-(2S,3S)-3-[(S)-2-(4-but-2-yny-loxy-phenyl)-1-methoxycarbonyl-ethylcarbamoyl]-2-{[(furan-2-ylmethyl)-carbamoyl]-methyl}-2-hydroxy-12-oxo-nonadec-4-enoic acid

[Chem. 368]

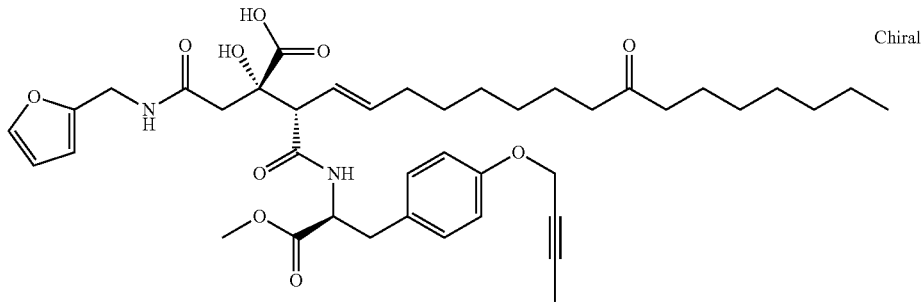

The title compound was obtained by a method similar to that of No. 5283374, except that furanylmethylamine was used instead of ammonium chloride.

$^1$H-NMR (CDCl$_3$) δ(PPM) 7.40-7.30 (1H, m), 7.10 (2H, d, J=8.4 Hz), 7.00-6.75 (3H, m), 6.60-6.50 (1H, m), 6.45-6.25 (2H, m), 5.80-5.40 (2H, m), 4.80-4.70 (1H, m), 4.60 (2H, m), 4.50-4.25 (2H, m), 3.73 (3H, s), 3.25-3.10 (2H, m), 3.05-2.95 (1H, m), 2.70 (1H, d, J=15.4 Hz), 2.55-2.25 (5H, m), 2.05-1.95 (2H, m), 1.85 (3H, br.s), 1.60-1.10 (18H, m), 0.87 (3H, t, J=6.6 Hz),
ESI (LC/MS positive mode) m/z 737 (M+H)

No. 5290168, (E)-(2S,3S)-3-[(S)-2-(4-but-2-yny-loxy-phenyl)-1-methoxycarbonyl-ethylcarbamoyl]-2-[(carbamoylmethyl-carbamoyl)-methyl]-2-hydroxy-12-oxo-nonadec-4-enoic acid

[Chem. 369]

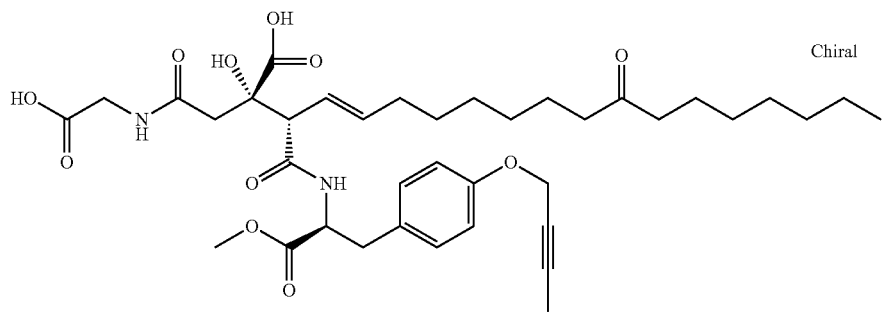

The title compound was obtained by a method similar to that of No. 5283374, except that glycine hydrochloride was used instead of ammonium chloride.

$^1$H-NMR (CDCl$_3$ δ(PPM) 7.30-7.00 (5H, m, J=8.4 Hz), 5.70-5.45 (2H, m), 4.80-4.60 (1H, m), 4.61 (2H, br.s), 4.10-3.90 (2H, m), 3.73 (3H, s), 3.40-2.65 (4H, m), 2.30-2.25 (5H, m), 2.05-1.95 (2H, m), 1.85 (3H, br.s), 1.30-1.10 (18H, m), 0.87 (3H, t, J=6.6 Hz),

ESI (LC/MS positive mode) m/z 715 (M+H)

No. 5289511, (E)-(2S,3S)-3-[(S)-2-(4-but-2-yny-loxy-phenyl)-1-methoxycarbonyl-ethylcarbamoyl]-2-cyclohexylcarbamoylmethyl-2-hydroxy-12-oxo-nonadec-4-enoic acid

[Chem. 370]

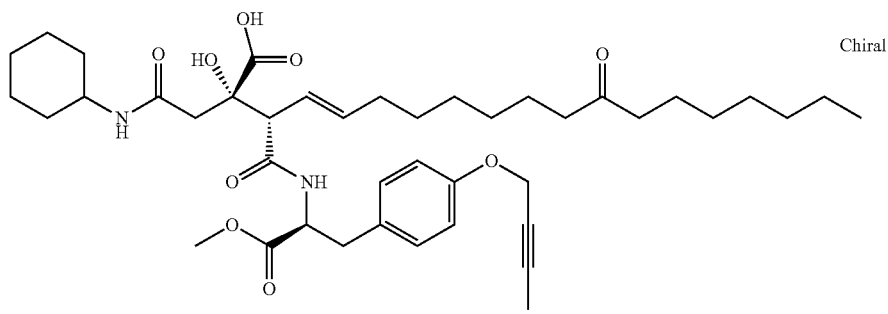

The title compound was obtained by a method similar to that of No. 5283374, except that cyclohexylamine was used instead of ammonium chloride.

$^1$H-NMR (CDCl$_3$) δ(PPM) 7.15 (2H, d, J=8.4 Hz), 7.00-6.80 (3H, m), 6.60-6.50 (1H, m), 5.80-5.40 (2H, m), 5.20 (1H, br.s), 4.80-4.65 (3H, m), 3.75 (3H, s), 3.75-3.60 (4H, m), 3.25-2.95 (3H, m), 2.65-2.30 (6H, m), 2.05-1.00 (33H, m), 0.87 (3H, t, J=6.6 Hz),

ESI (LC/MS positive mode) m/z 739 (M+H)

No. 5289512, (E)-(2S,3S)-3-[(S)-2-(4-but-2-yny-loxy-phenyl)-1-methoxycarbonyl-ethylcarbamoyl]-2-hydroxy-2-{[(2-methoxy-ethyl)-methyl-carbamoyl]-methyl}-12-oxo-nonadec-4-enoic acid

[Chem. 371]

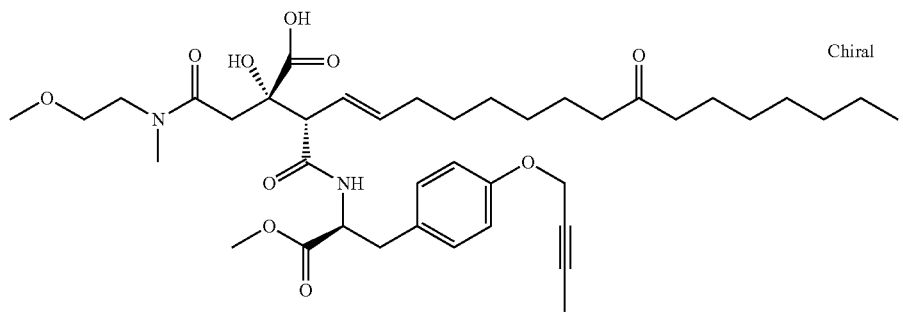

The title compound was obtained by a method similar to that of No. 5283374, except that (2-methoxyethyl)methylamine was used instead of ammonium chloride.

$^1$H-NMR (CDCl$_3$) δ(PPM) 7.10 (2H, d, J=8.4 Hz), 6.95-6.75 (3H, m), 5.75-5.40 (2H, m), 4.80-4.70 (1H, m), 4.61 (2H, br.s), 3.75 (3H, s), 3.70-2.80 (15H, m), 2.45-2.25 (4H, m), 2.05-1.95 (2H, m), 1.85 (3H, br.s), 1.30-1.10 (18H, m), 0.87 (3H, t, J=6.6 Hz),

ESI (LC/MS positive mode) m/z 729 (M+H)

No. 5287225, (E)-(2S,3S)-2-butylcarbamoylmethyl-3-[(S)-2-(4-but-2-ynyloxy-phenyl)-1-methoxycarbonyl-ethylcarbamoyl]-2-hydroxy-12-oxo-nonadec-4-enoic acid

[Chem. 372]

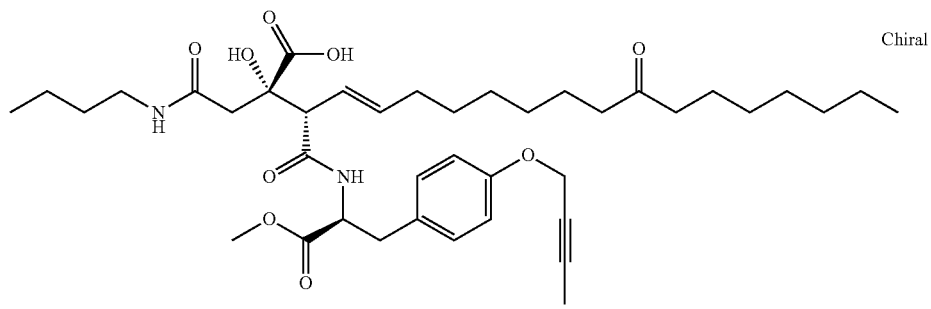

The title compound was obtained by a method similar to that of No. 5283374, except that hexylamine was used instead of ammonium chloride.

$^1$H-NMR (CDCl$_3$) δ(PPM) 7.15 (2H, d, J=8.4 Hz), 7.00-6.80 (3H, m), 6.60-6.50 (1H, m), 5.80-5.40 (2H, m), 5.35 (1H, br.s), 4.80-4.65 (1H, m), 4.62 (2H, m), 3.75 (3H, s), 3.25-2.90 (5H, m), 2.64 (1H, d, J=14.6 Hz), 2.50-2.35 (5H, m), 2.05-1.95 (2H, m), 1.85 (3H, s), 1.80-1.10 (22H, m), 1.00-0.85 (6H, m),

ESI (LC/MS positive mode) m/z 713 (M+H)

No. 5285053, (E)-(2S,3S)-3-[(S)-2-(4-but-2-yny-loxy-phenyl)-1-methoxycarbonyl-ethylcarbamoyl]-2-hydroxy-2-methylcarbamoylmethyl-12-oxo-nona-dec-4-enoic acid

[Chem. 373]

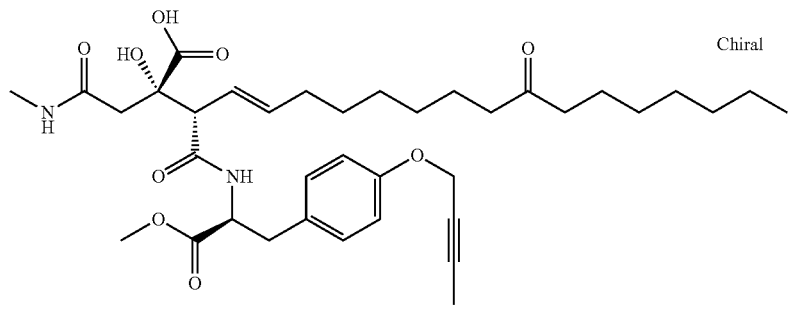

The title compound was obtained by a method similar to that of No. 5283374, except that methylamine was used instead of ammonium chloride.

$^1$H-NMR (CDCl$_3$) δ(PPM) 7.15 (2H, d, J=8.4 Hz), 7.00-6.80 (3H, m), 6.00-5.90 (1H, m), 5.80-5.40 (2H, m), 5.36 (1H, br.s), 4.80-4.65 (1H, m), 4.62 (2H, m), 3.75 (3H, s), 3.25-2.90 (3H, m), 2.85-2.75 (3H, m), 2.64 (1H, d, J=14.6 Hz), 2.50-2.35 (5H, m), 2.05-1.95 (2H, m), 1.85 (3H, s), 1.80-1.10 (18H, m), 0.87 (3H, t, J=6.6 Hz)

ESI (LC/MS positive mode) m/z 671 (M+H)

No. 5285054, (E)-(2S,3S)-3-[(S)-2-(4-but-2-yny-loxy-phenyl)-1-methoxycarbonyl-ethylcarbamoyl]-2-hydroxy-2-dimethylcarbamoylmethyl-12-oxo-nona-dec-4-enoic acid

[Chem. 374]

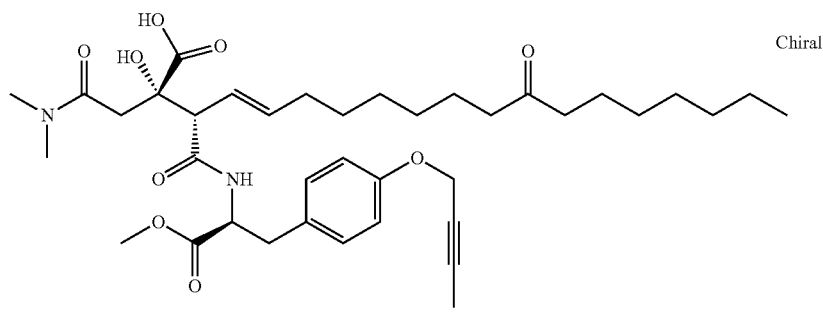

The title compound was obtained by a method similar to that of No. 5283374, except that dimethylamine was used instead of ammonium chloride.

$^1$H-NMR (CDCl$_3$) δ(PPM) 7.15 (2H, d, J=8.4 Hz), 7.00-6.80 (3H, m), 5.80-5.40 (2H, m), 4.80-4.65 (1H, m), 4.62 (2H, m), 3.75 (3H, s), 3.25-2.75 (9H, m), 2.50-2.25 (6H, m), 2.05-1.95 (2H, m), 1.85 (3H, m), 1.80-1.10 (18H, m), 0.87 (3H, t, J=6.6 Hz)

ESI (LC/MS positive mode) m/z 685 (M+H)

No. 5285055, (E)-(2S,3S)-3-[(S)-2-(4-but-2-yny-loxy-phenyl)-1-methoxycarbonyl-ethylcarbamoyl]-2-hydroxy-12-oxo-2-phenylcarbamoylmethyl-nona-dec-4-enoic acid

[Chem. 375]

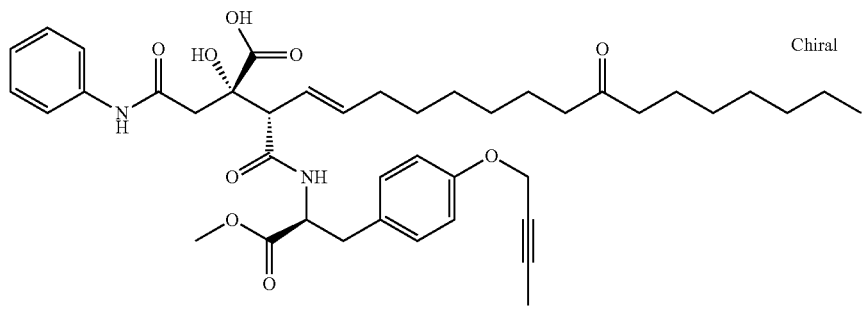

The title compound was obtained by a method similar to that of No. 5283374, except that phenylamine was used instead of ammonium chloride.

$^1$H-NMR (CDCl$_3$) δ(PPM) 8.22 (1H, br.s), 7.55 (9H m), 5.80-5.40 (2H, m), 4.80-4.65 (1H, m), 4.62 (2H, m), 3.75 (3H, s), 3.50-2.75 (3H, m), 2.60-2.25 (5H, m), 2.05-1.95 (2H, m), 1.85 (3H, s), 1.80-1.10 (18H, m), 0.87 (3H, t, J=6.6 Hz)

ESI (LC/MS positive mode) m/z 733 (M+H)

No. 5287221, (E)-(2S,3S)-3-[(S)-2-(4-but-2-yny-loxy-phenyl)-1-methoxycarbonyl-ethylcarbamoyl]-2-hydroxy-12-oxo-2-(2-oxo-2-pyrrolidin-1-yl-ethyl)-nonadec-4-enoic acid

[Chem. 376]

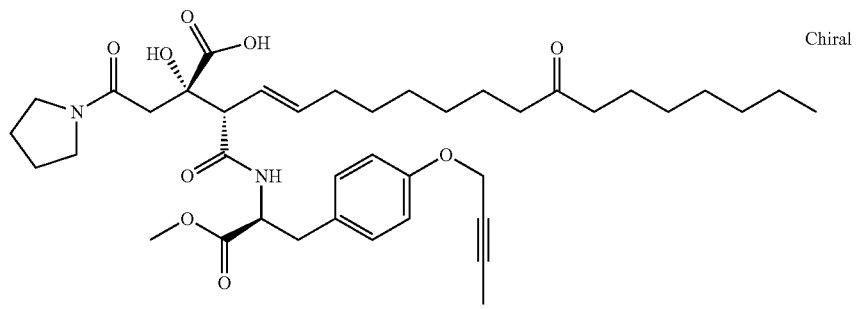

The title compound was obtained by a method similar to that of No. 5283374, except that pyrrolidine was used instead of ammonium chloride.

$^1$H-NMR (CDCl$_3$) δ(PPM) 7.15 (2H, d, J=8.4 Hz), 7.00-6.80 (3H, m), 5.90-5.80 (1H, m), 5.80-5.40 (2H, m), 4.80-4.65 (1H, m), 4.62 (2H, m), 3.72 (3H, s), 3.60-3.45 (2H, m), 3.30-2.75 (6H, m), 2.50-2.35 (5H, m), 2.05-1.95 (2H, m), 1.85 (3H, m), 1.80-1.10 (18H, m), 0.87 (3H, t, J=6.6 Hz)

ESI (LC/MS positive mode) m/z 711 (M+H)

No. 5287223, (E)-(2S,3S)-3-[(S)-2-(4-but-2-yny-loxy-phenyl)-1-methoxycarbonyl-ethylcarbamoyl]-2-cyclopropylcarbamoylmethyl-2-hydroxy-12-oxo-nonadec-4-enoic acid

[Chem. 377]

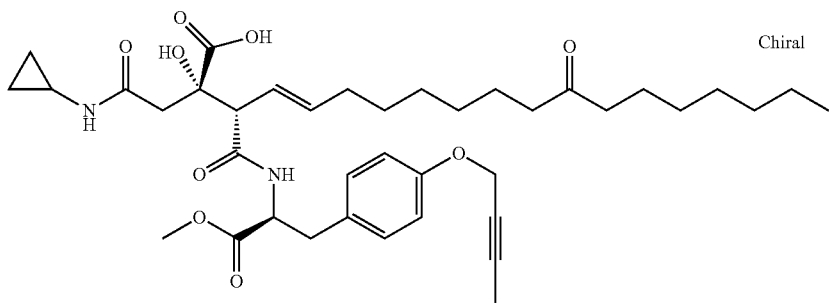

The title compound was obtained by a method similar to that of No. 5283374, except that cyclopropylamine was used instead of ammonium chloride.

$^1$H-NMR (CDCl$_3$) δ(PPM) 7.15 (2H, d, J=8.4 Hz), 7.00-6.80 (3H, m), 6.20-6.10 (1H, m), 5.70-5.60 (1H, m), 5.45-5.35 (1H, m), 4.15 (1H, br.s), 4.70-4.60 (3H, m), 3.72 (3H, s), 3.60-3.45 (2H, m), 3.25-2.95 (3H, m), 2.75-2.55 (2H, m), 2.50-2.40 (5H, m), 2.05-1.95 (2H, m), 1.85 (3H, m), 1.80-1.10 (18H, m), 0.87 (3H, t, J=6.6 Hz), 0.85-0.50 (4H, m)

ESI (LC/MS positive mode) m/z 697 (M+H)

No. 5289502 (E)-(2S,3S)-3-[(S)-2-(4-But-2-yny-loxy-phenyl)-1-methoxycarbonyl-ethylcarbamoyl]-2-{[(furan-2-ylmethyl)-carbamoyl]-methyl}-2-hydroxy-12-oxo-nonadec-4-enoic acid

[Chem. 378]

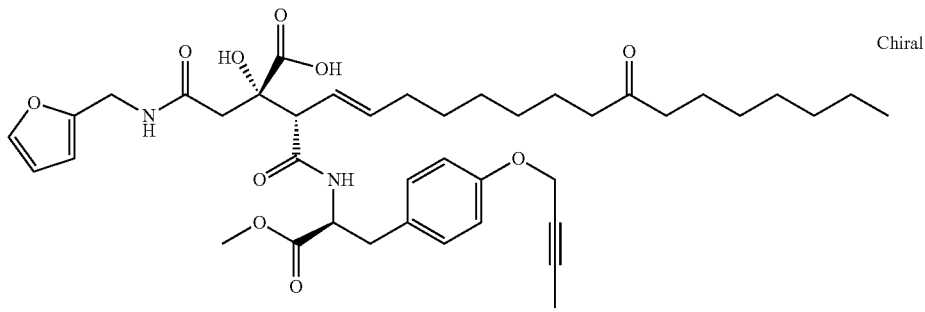

The title compound was obtained by a synthetic method similar to that of No. 5283374, except that furfurylamine was used instead of ammonium chloride.

$^1$H-NMR (CDCl$_3$) δ: 0.88 (3H, t, J=6.8 Hz), 1.20-1.30 (14H, m), 1.50-1.60 (4H, m), 1.85 (3H, t, J=1.6 Hz), 1.90-2.10 (2H, m), 2.30-2.50 (5H, m), 2.71 (1H, d, J=15.4 Hz), 2.95-3.05 (1H, m), 3.08-3.20 (1H, m), 3.19 (1H, d, J=9.2 Hz), 3.73 (3H, s), 4.35-4.50 (2H, m), 4.55-4.60 (2H, m), 4.73-4.80 (1H, m), 5.40 (1H, dd, J=15.5, 9.6 Hz), 5.65 (1H, dt, J=15.5, 6.8 Hz), 6.27 (1H, d, J=3.3 Hz), 6.30-6.34 (1H, m), 6.42-6.50 (1H, m), 6.84 (2H, d, J=8.6 Hz), 6.84-6.88 (1H, m), 7.06 (2H, d, J=8.6 Hz), 7.34-7.38 (1H, m).

ESI (LC/MS positive mode) m/z 737 (M+H); Rt 3.12 min.

No. 5304109 (E)-(2S,3S)-3-[(S)-2-(4-But-2-yny-loxy-phenyl)-1-methoxycarbonyl-ethylcarbamoyl]-2-hydroxy-12-oxo-2-(thiazol-2-ylcarbamoylmethyl)-nonadec-4-enoic acid

[Chem. 379]

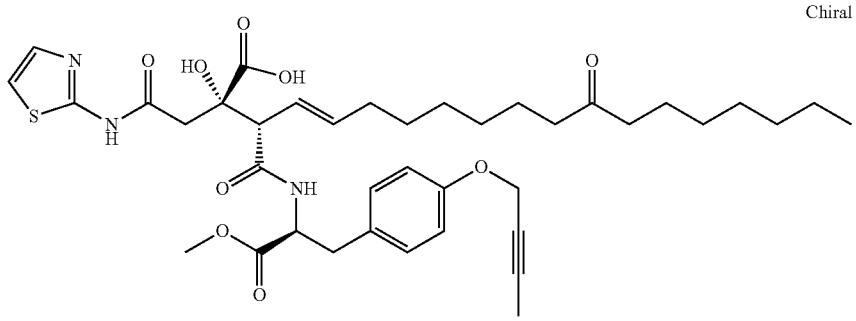

The title compound was obtained by a synthetic method similar to that of No. 5283374, except that thiazolamine was used instead of ammonium chloride.

$^1$H-NMR (CDCl$_3$) δ: 0.88 (3H, t, J=6.3 Hz), 1.20-1.30 (14H, m), 1.50-1.60 (4H, m), 1.85 (3H, t, J=1.8 Hz), 1.90-2.10 (2H, m), 2.30-2.50 (5H, m), 2.65-2.80 (1H, m), 2.95-3.15 (2H, m), 3.25-3.35 (1H, m), 4.35-4.50 (2H, m), 4.55-4.60 (2H, m), 5.50-5.75 (2H, m), 6.80-7.40 (6H, m).

ESI (LC/MS positive mode) m/z 740 (M+H); Rt 3.08 min.

No. 5282144 (E)-(2S,3S)-3-[(S)-2-(4-But-2-yny-loxy-phenyl)-1-methoxycarbonyl-ethylcarbamoyl]-2-hydroxy-12-methoxyimino-2-(2-methoxyimino-ethyl)-nonadec-4-enoic acid

[Chem. 380]

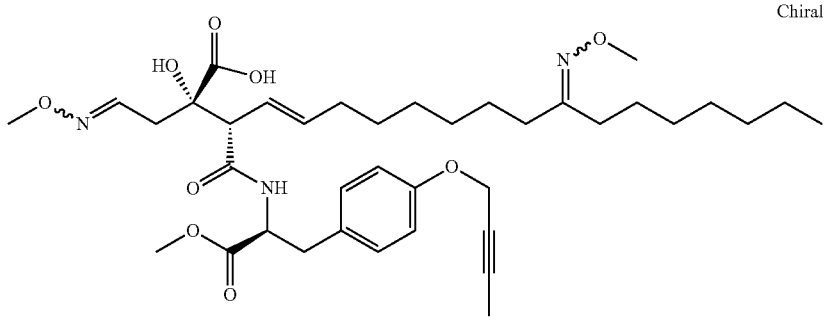

The title compound was obtained by a synthetic method similar to that of No. 5283374, except that furfurylamine was used instead of ammonium chloride.

$^1$H-NMR (CDCl$_3$) δ: 0.88 (3H, t, J=6.8 Hz), 1.20-1.35 (14H, m), 1.40-1.55 (4H, m), 1.86 (3H, m), 2.00-2.20 (4H, m), 2.22-2.30 (2H, m), 2.35-2.85 (2H, m), 2.93-3.30 (3H, m), 3.70-3.88 (9H, m), 4.57-4.60 (2H, m), 4.75-4.85 (1H, m), 5.50-5.75 (2H, m), 6.70-7.08 (5H, m).

ESI (LC/MS positive mode) m/z 700 (M+H); Rt 3.09 min.

t-Butyl [(S)-2-(4-but-2-ynyloxy-phenyl)-1-hydroxym-ethyl-ethyl]-carbamate

[Chem. 381]

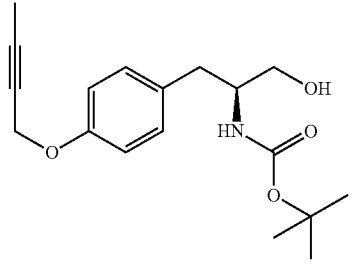

4-((S)-2-Amino-3-hydroxy-propyl)-phenol hydrochloride (500 mg, 2.45 mmol) was dissolved in methanol (8.2 mL), and di-tert-butyl dicarbonate (1.24 mL, 5.39 mmol) and tri-ethylamine (343 µL, 2.45 mmol) were added at room temperature. The reaction mixture was stirred for 3 hours, then poured into an aqueous solution of sodium bicarbonate, and extracted with ethyl acetate. The organic extract was washed with a saturated brine, dried over anhydrous magnesium sulfate, and concentrated under reduced pressure. The resulting residue was dissolved in DMF (7.5 mL). To the solution were added 1-bromo-but-2-yne (0.217 mL, 2.48 mmol) and potassium carbonate (389 mg, 2.82 mmol) at room temperature. The reaction mixture was stirred at room temperature for 3 hours. A saturated brine was added, and the mixture was extracted with ethyl acetate. The organic extract was dried over magnesium sulfate, and concentrated under reduced pressure to obtain the title compound (719 mg, 94% yield).

ESI (LC/MS positive mode) m/z 320 (M+H); Rt 2.10 min.

(S)-2-t-Butoxycarbonylamino-3-(4-but-2-ynyloxy-phenyl)-propyl acetate

[Chem. 382]

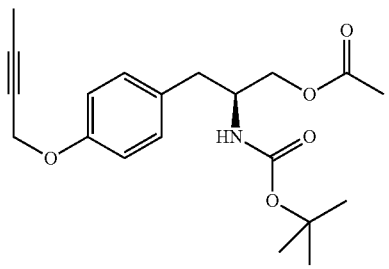

tert-Butyl [(S)-2-(4-but-2-ynyloxy-phenyl)-1-hydroxymethyl-ethyl]-carbamate (402 mg, 1.26 mmol) was dissolved in dichloromethane (6.3 mL), and acetic anhydride (0.179 mL, 1.89 mmol) and pyridine (204 μL, 2.52 mmol) were added at room temperature. The reaction mixture was stirred for 7 hours, then poured into a saturated brine, and extracted with ethyl acetate. The organic extract was dried over magnesium sulfate, and concentrated under reduced pressure to obtain the title compound (468 mg).

ESI (LC/MS positive mode) m/z 362 (M+H); Rt 2.53 min.

(S)-2-Amino-3-(4-but-2-ynyloxy-phenyl)-propyl acetate hydrochloride

[Chem. 383]

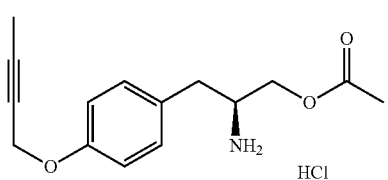

(S)-2-tert-Butoxycarbonylamino-3-(4-but-2-ynyloxy-phenyl)-propyl acetate was dissolved in a solution (3.0 mL) of 1 M hydrogen chloride/ethyl acetate, and the mixture was stirred at room temperature for 3 hours. The reaction mixture was then concentrated under reduced pressure to obtain the title compound.

ESI (LC/MS positive mode) m/z 262 (M-Cl); Rt 1.13 min.

No. 5208502 (S)-2-{(E)-(S)-1-[(S)-1-Acetoxymethyl-2-(4-but-2-ynyloxy-phenyl)-ethylcarbamoyl]-10-oxo-heptadec-2-enyl}-2-hydroxy-succinic acid

[Chem. 384]

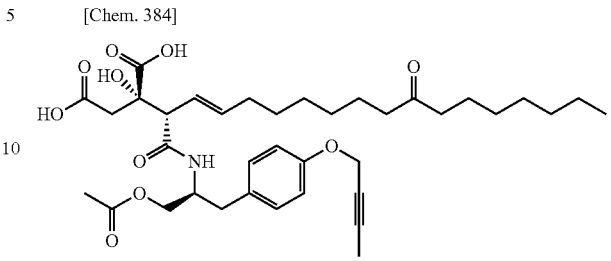

1-tert-Butyl (2S,3S)-2-[2-(tert-butyl-dimethyl-silanyloxy)-ethyl]-3-[(E)-8-(2-heptyl-[1,3]dioxolan-2-yl)-oct-1-enyl]-2-hydroxy-succinate (787 mg, 1.05 mmol) and (S)-2-amino-3-(4-but-2-ynyloxy-phenyl)-propyl acetate hydrochloride (375 mg, 1.26 mmol) were dissolved in DMF (18 mL), and O-(7-azabenzotriazol-1-yl)-N,N,N',N'-tetramethyluronium hexafluorophosphate (439 mg, 1.16 mmol) and N,N-diisopropylethylamine (814 μL, 4.73 mmol) were added. The mixture was stirred at room temperature for 2 hours. To the reaction mixture was then added an aqueous solution of 0.5 M potassium hydrogen sulfate. The mixture was extracted with ethyl acetate. The organic extract was washed with a saturated brine, dried over anhydrous magnesium sulfate, and concentrated under reduced pressure. The resulting residue was dissolved in acetonitrile (5.0 mL), and an aqueous solution (2.0 mL) of 0.5 M citric acid was added. The mixture was stirred at 60° C. for 2 hours. Water was added to the reaction mixture, which was followed by extraction with ethyl acetate. The organic extract was dried over magnesium sulfate, and concentrated under reduced pressure. The resulting residue was dissolved in acetonitrile (4.5 mL) and water (1.0 mL), and 4-acetamide-2,2,6,6-tetramethylpiperidine-1-oxyl (16.8 mg, 78.8 μmol) and diacetoxyiodobenzene (372 mg, 1.16 mmol) were added. The mixture was stirred at room temperature for 2 hours. An aqueous solution of citric acid was added to the reaction mixture, which was followed by extraction with ethyl acetate. The organic extract was washed with an aqueous solution of 10% sodium thiosulfate and a saturated brine, dried over anhydrous magnesium sulfate, and concentrated under reduced pressure. The resulting residue was dissolved in formic acid (3.0 mL) and the solution was stirred at room temperature for 5 hours. The reaction mixture was concentrated and the resulting residue was purified by preparative HPLC to obtain the title compound (12.3 mg).

No. 5208516, (S)-2-{(E)-(S)-1-[(S)-2-(4-but-2-ynyloxy-phenyl)-1-hydroxymethyl-ethylcarbamoyl]-10-oxo-heptadec-2-enyl}-2-hydroxy-succinic acid

[Chem. 385]

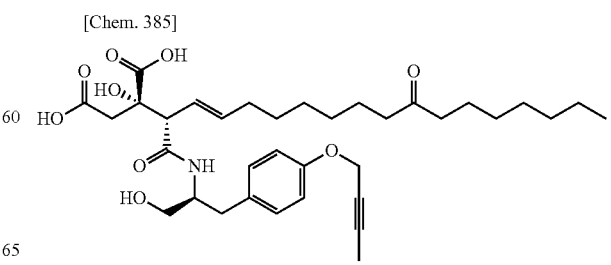

No. 5208502 (66.2 mg, 0.986 mmol) was dissolved in methanol (3.0 mL), and potassium carbonate (68.2 mg, 0.493 mmol) was added. The reaction mixture was stirred at room temperature for 2 hours, and purified by preparative HPLC to obtain the title compound (15 mg, 24% yield).

$^1$H-NMR (CDCl$_3$) δ: 0.88 (3H, t, J=6.3 Hz), 1.20-1.30 (14H, m), 1.50-1.60 (4H, m), 1.80-1.90 (3H, m), 1.90-2.10 (2H, m), 2.30-2.45 (4H, m), 2.50-2.80 (3H, m), 2.95-3.30 (2H, m), 3.45-3.75 (2H, m), 4.05-4.15 (2H, m), 4.55-4.60 (2H, m), 5.50-5.75 (2H, m), 6.80-6.85 (2H, m), 6.90-7.20 (2H, m).

ESI (LC/MS positive mode) m/z 630 (M+H); Rt 2.88 min.

tert-Butyl [(S)-2-(4-but-2-ynyloxy-phenyl)-1-dimethylcarbamoyl-ethyl]-carbamate

[Chem. 386]

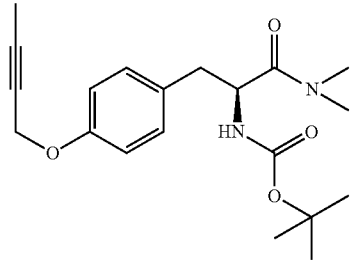

(S)-2-tert-Butoxycarbonylamino-3-(4-but-2-ynyloxy-phenyl)-propionic acid (432 mg, 1.29 mmol) was dissolved in DMF (5.0 mL), and a solution of dimethylamine in tetrahydrofuran (2.92 mL, 5.84 mmol), 1-ethyl-3-(3-dimethylaminopropyl)carbodiimide hydrochloride (370 mg, 1.94 mmol), and 1-hydroxybenzotriazole (262 mg, 1.94 mmol) were added. The reaction mixture was stirred at room temperature for 72 hours, and then poured into an aqueous solution of sodium bicarbonate and the mixture was extracted with ethyl acetate. The organic layer was washed with a saturated brine, dried over anhydrous magnesium sulfate, and concentrated under reduced pressure. The resulting residue was purified by silica gel column chromatography to obtain the title compound (103 mg, 22% yield).

ESI (LC/MS positive mode) m/z 361 (M+H); Rt 2.22 min.

(S)-2-Amino-3-(4-but-2-ynyloxy-phenyl)-N,N-dimethyl-propionamide

[Chem. 387]

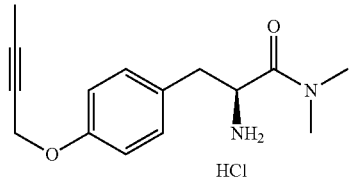

tert-Butyl [(S)-2-(4-but-2-ynyloxy-phenyl)-1-dimethylcarbamoyl-ethyl]-carbamate (227 mg, 0.630 mmol) was dissolved in a solution (10 mL) of 1 M hydrogen chloride/ethyl acetate, and the mixture was stirred at room temperature for 7 hours. The reaction mixture was concentrated under reduced pressure to obtain the title compound (184 mg, 94%).

ESI (LC/MS positive mode) m/z 261 (M-Cl); Rt 0.92 min.

tert-Butyl (E)-(2S,3S)-2-[2-(tert-butyl-dimethyl-silanyloxy)-ethyl]-3-[(S)-2-(4-but-2-ynyloxy-phenyl)-1-dimethylcarbamoyl-ethylcarbamoyl]-11-(2-heptyl-[1,3]dioxolan-2-yl)-2-hydroxy-undec-4-enoate

[Chem. 388]

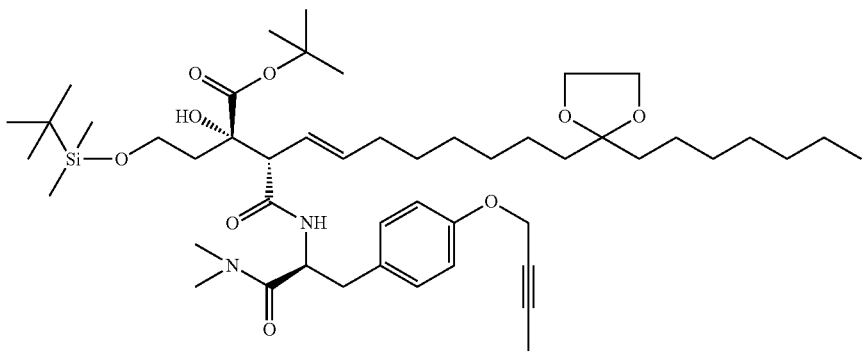

The title compound was obtained by a method similar to that of No. 5327507, except that (S)-2-amino-3-(4-but-2-ynyloxy-phenyl)-N,N-dimethyl-propionamide was used instead of No. 4935048.

ESI (LC/MS positive mode) m/z 871 (M+H); Rt 7.78 min.

tert-Butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate tert-Butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate (96.8 mg, 0.133 mmol) was dissolved in acetonitrile (2.0 mL) and water (0.6 mL), and 4-acetamide-2,2,6,6-tetramethylpiperidine-1-oxyl (4.3 mg, 19.9 μmol) and diacetoxyiodobenzene (85.7 mg, 0.266 mmol) were added. The mixture was stirred at room temperature for 4 hours. An aqueous solution of citric acid was added to the reaction mixture, which was followed by extraction with ethyl acetate. The organic extract was washed with sodium thiosulfate and a saturated brine, dried over anhydrous magnesium sulfate, and concentrated under reduced pressure. The resulting residue was dissolved in for-

[Chem. 389]

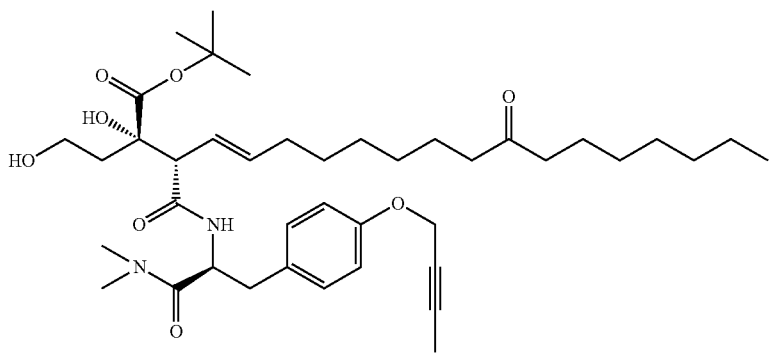

The title compound was obtained by a method similar to that of No. 5217614, except that tert-butyl (E)-(2S,3S)-2-[2-(tert-butyl-dimethyl-silanyloxy)-ethyl]-3-[(S)-2-(4-but-2-ynyloxy-phenyl)-1-dimethylcarbamoyl-ethylcarbamoyl]-11-(2-heptyl-[1,3]dioxolan-2-yl)-2-hydroxy-undec-4-enoate was used instead of No. 5327507.

ESI (LC/MS positive mode) m/z 713 (M+H); Rt 4.90 min.

No. 5209429, (S)-2-{(E)-(S)-1-[(S)-2-(4-but-2-ynyloxy-phenyl)-1-dimethylcarbamoyl-ethylcarbamoyl]-10-oxo-heptadec-2-enyl}-2-hydroxy-succinic acid mic acid (4.0 mL) and the mixture was stirred at room temperature for 5 hours. The reaction mixture was concentrated under reduced pressure. The resulting residue was purified with preparative HPLC to obtain the title compound (43.2 mg).

¹H-NMR (CDCl₃) δ(PPM) 7.87 (1H, d, J=7.8 Hz), 6.90 (2H, d, J=8.4 Hz), 6.85 (2H, d, J=8.4 Hz), 5.69 (1H, ddd, J=16.7 Hz, 15.1 Hz, 6.5 Hz), 5.50 (1H, dd, J=15.1 Hz, 9.2 Hz), 4.60 (2H, m), 3.18 (1H, d, J=9.2 Hz), 2.85-3.15 (3H, m), 2.87 (3H, s), 2.71 (3 h, s), 2.64 (1H, d, J=16.7 Hz), 2.50-2.30 (4H, m), 2.10-1.90 (2H, m), 1.85 (3H, br.s), 1.60-1.40 (3H, m), 1.60-1.10 (18H, m), 0.87 (3H, t, J=6.6 Hz), ESI (LC/MS positive mode) m/z 671 (M+H)

[Chem. 390]

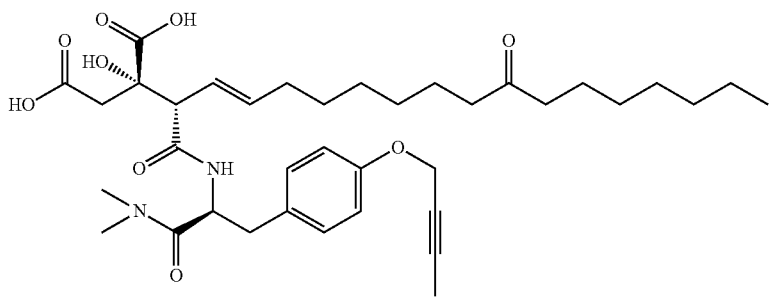

tert-Butyl (E)-(2S,3S)-2-(2-acetoxy-ethyl)-3-[(S)-2-(4-but-2-ynyloxy-phenyl)-1-dimethylcarbamoyl-ethylcarbamoyl]-2-hydroxy-12-oxo-nonadec-4-enoate

[Chem. 391]

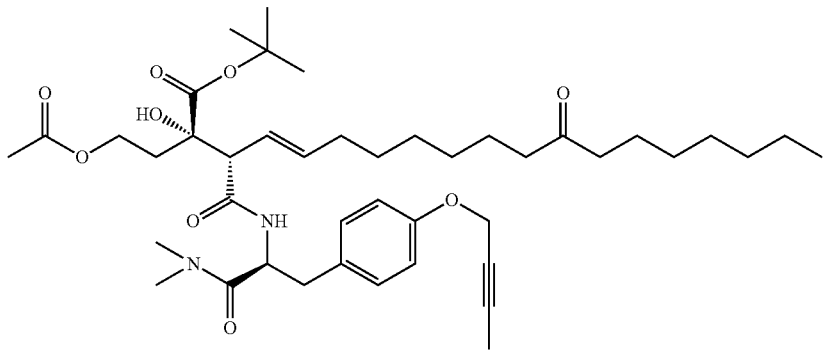

The title compound was obtained by a method similar to that of No. 5318799, except that tert-butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate was used instead of No. 5217614.

ESI (LC/MS positive mode) m/z 755 (M+H); Rt 3.53 min.

No. 5247676, (E)-2-(2S,3S)-3-[(S)-2-(4-but-2-ynyloxy-phenyl)-1-dimethylcarbamoyl-ethylcarbamoyl]-2-hydroxy-2-(2-methoxyethyl)-12-oxo-nonadec-4-enoic acid

[Chem. 392]

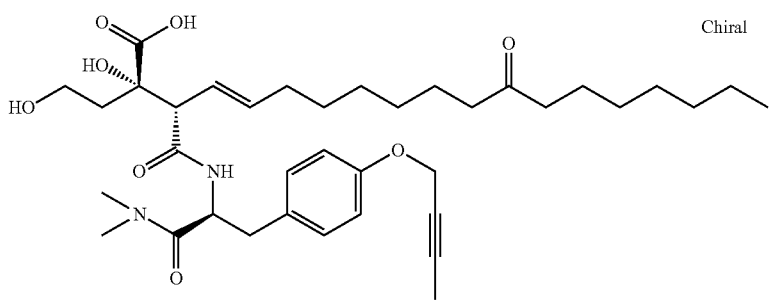

tert-Butyl (E)-(2S,3S)-2-(2-acetoxy-ethyl)-3-[(S)-2-(4-but-2-ynyloxy-phenyl)-1-dimethylcarbamoyl-ethylcarbamoyl]-2-hydroxy-12-oxo-nonadec-4-enoate (22 mg, 29.1 μmol) was dissolved in formic acid (1.0 mL) and the mixture was stirred at room temperature for 7 hours. The reaction mixture was then concentrated under reduced pressure. The resulting residue was dissolved in methanol (0.5 mL). An aqueous solution (50 μL) of 2 M LiOH was added at 0° C., and the mixture was stirred for 2 hours. The reaction mixture was purified by preparative HPLC to obtain the title compound (4.0 mg).

$^1$H-NMR (CDCl$_3$) δ(PPM) 7.35-7.20 (1H, m), 7.09 (2H, d, J=8.4 Hz), 6.80 (2H, d, J=8.4 Hz), 5.70-5.55 (2H, m), 5.10-5.00 (1H, m), 4.61 (2H, br.s), 3.79 (2H, m), 3.30-3.25 (1H, m), 2.92 (3H, s), 2.71 (3H, s), 3.00-2.50 (6H, m), 2.40-2.30 (4H, m), 1.82 (3H, s), 2.10-1.10 (20H, m), 0.87 (3H, t, J=6.6 Hz)

ESI (LC/MS positive mode) m/z 657 (M+H)

No. 5253251 (E)-(S)-2-((S)-3-hydroxy-2-oxo-tetrahydro-furan-3-yl)-11-oxo-N—[(S)-2-(4-but-2-ynyloxy-phenyl)-1-dimethylcarbamoyl-ethyl]-octadec-3-enoamide

[Chem. 393]

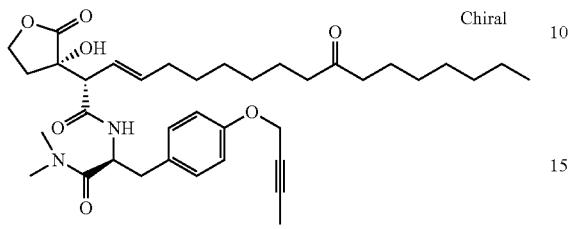

No. 5247676 (60 mg, 0.858 mmol) was dissolved in ethyl acetate, and the mixture was left to stand at room temperature for 24 hours. The reaction mixture was then washed with water, dried over anhydrous magnesium sulfate, and concentrated under reduced pressure. The resulting residue was purified by preparative HPLC to obtain the title compound (19.9 mg, 33% yield).

$^1$H-NMR (CDCl$_3$) δ: 0.88 (3H, t, J=6.8 Hz), 1.20-1.30 (14H, m), 1.50-1.60 (4H, m), 1.85 (3H, t, J=1.4 Hz), 1.90-2.50 (8H, m), 2.65 (3H, s), 2.86 (3H, s), 2.86-3.10 (2H, m), 3.24 (1H, d, J=9.2 Hz), 4.15-4.25 (2H, m), 4.40-4.50 (1H, m), 4.57-4.63 (2H, m), 5.00-5.10 (1H, m), 5.32 (1H, dd, J=15.5, 9.6 Hz), 5.83 (1H, dt, J=15.5, 6.8 Hz), 6.86 (2H, d, J=8.6 Hz), 6.88-6.96 (1H, m), 7.09 (2H, d, J=8.6 Hz).

ESI (LC/MS positive mode) m/z 639 (M+H); Rt 3.15 min.

tert-Butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate

[Chem. 394]

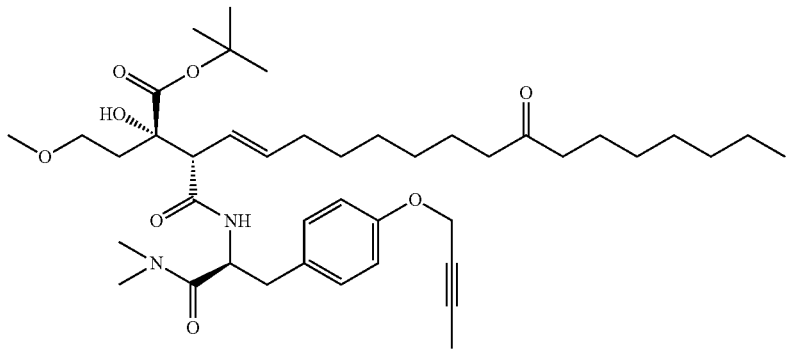

tert-Butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate (15.0 mg, 21.5 μmol) was dissolved in dichloromethane (0.5 mL), and trimethyloxonium tetrafluoroborate (6.7 mg, 45.1 μmol) and 2,6-di-tert-butyl-4-methylpyridine (9.3 mg, 45.1 μmol) were added at 0° C. The mixture was stirred at room temperature for 5 hours. The reaction mixture was purified by preparative HPLC to obtain the title compound (3.5 mg, 22% yield).

ESI (LC/MS positive mode) m/z 727 (M+H); Rt 3.61 min.

No. 5250397, (E)-2-(2S,3S)-3-[(S)-2-(4-but-2-yny-loxy-phenyl)-1-dimethylcarbamoyl-ethylcarbamoyl]-2-hydroxy-2-(2-methoxyethyl)-12-oxo-nonadec-4-enoic acid

[Chem. 395]

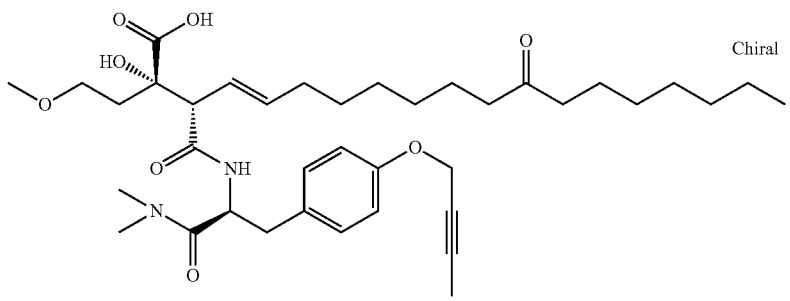

tert-Butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate (4.5 mg, 6.19 µmol) was dissolved in formic acid (1.0 mL), and the mixture was stirred at room temperature for 2 hours. The reaction mixture was concentrated under reduced pressure. The resulting residue was purified by preparative HPLC to obtain the title compound (3.5 mg, 85%).

$^1$H-NMR (DMSO-$d_6$) δ(PPM) 8.24 (1H, d, J=8.9 Hz), 7.09 (2H, d, J=8.4 Hz), 6.80 (2H, d, J=8.4 Hz), 5.45-5.30 (2H, m), 4.90-4.70 (1H, m), 4.65 (2H, m), 3.40-3.20 (1H, m), 3.14 (3H, s), 2.85 (3H, s), 2.78 (3H, s), 3.00-2.50 (6H, m), 2.40-2.30 (4H, m), 1.82 (3H, s), 2.10-1.10 (20H, m), 0.85 (3H, t, J=6.6 Hz)

ESI (LC/MS positive mode) m/z 671 (M+H)

tert-Butyl [(S)-2-(4-but-2-ynyloxy-phenyl)-1-carbamoyl-ethyl]-carbamate

[Chem. 396]

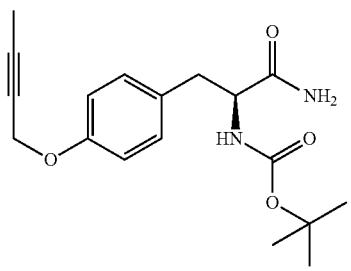

The title compound was obtained by a method similar to that of tert-butyl [(S)-2-(4-but-2-ynyloxy-phenyl)-1-dimethylcarbamoyl-ethyl]-carbamate, except that ammonium chloride was used instead of a solution of dimethylamine in tetrahydrofuran.

ESI (LC/MS positive mode) m/z 333 (M+H); Rt 2.03 min.

(S)-2-Amino-3-(4-but-2-ynyloxy-phenyl)-propionamide

[Chem. 397]

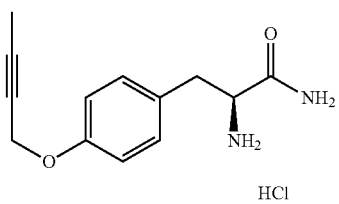

The title compound was obtained by a method similar to that of (S)-2-amino-3-(4-but-2-ynyloxy-phenyl)-N,N-dimethyl-propionamide, except that tert-butyl [(S)-2-(4-but-2-ynyloxy-phenyl)-1-carbamoyl-ethyl]-carbamate was used instead of tert-butyl [(S)-2-(4-but-2-ynyloxy-phenyl)-1-dimethylcarbamoyl-ethyl]-carbamate.

ESI (LC/MS positive mode) m/z 233 (M-Cl); Rt 0.82 min.

tert-Butyl (E)-(2S,3S)-2-[2-(tert-butyl-dimethyl-silanyloxy)-ethyl]-3-[(S)-2-(4-but-2-ynyloxy-phenyl)-1-carbamoyl-ethylcarbamoyl]-11-(2-heptyl-[1,3]dioxolan-2-yl)-2-hydroxy-undec-4-enoate

[Chem. 398]

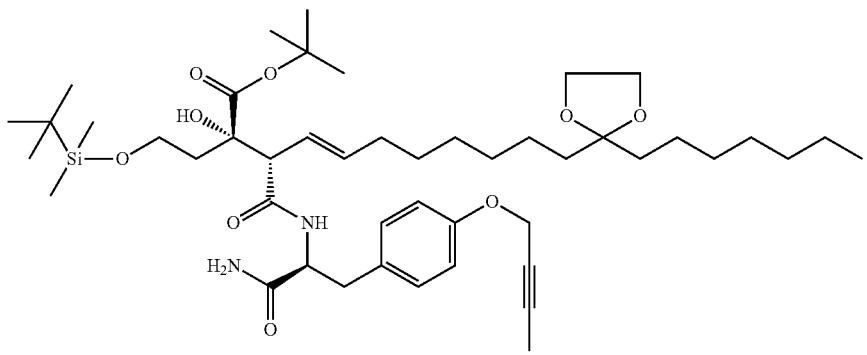

The title compound was obtained by a method similar to that of No. 5327507, except that (S)-2-amino-3-(4-but-2-ynyloxy-phenyl)-propionamide was used instead of No. 4935048.

ESI (LC/MS positive mode) m/z 844 (M+H); Rt 4.61 min.

tert-Butyl (E)-(2S,3S)-3-[(S)-2-(4-but-2-ynyloxy-phenyl)-1-carbamoyl-ethylcarbamoyl]-2-hydroxy-2-(2-hydroxy-ethyl)-12-oxo-nonadec-4-enoate

[Chem. 399]

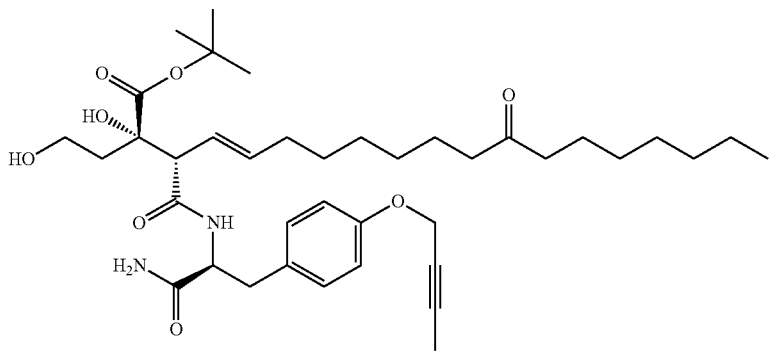

The title compound was obtained by a method similar to that of No. 5217614, except that tert-butyl (E)-(2S,3S)-2-[2-(tert-butyl-dimethyl-silanyloxy)-ethyl]-3-[(S)-2-(4-but-2-ynyloxy-phenyl)-1-carbamoyl-ethylcarbamoyl]-11-(2-heptyl-[1,3]dioxolan-2-yl)-2-hydroxy-undec-4-enoate was used instead of No. 5327507.

ESI (LC/MS positive mode) m/z 685 (M+H); Rt 4.41 min.

tert-Butyl (E)-(2S,3S)-2-(2-acetoxy-ethyl)-3-[(S)-2-(4-but-2-ynyloxy-phenyl)-1-carbamoyl-ethylcarbamoyl]-2-hydroxy-12-oxo-nonadec-4-enoate

[Chem. 400]

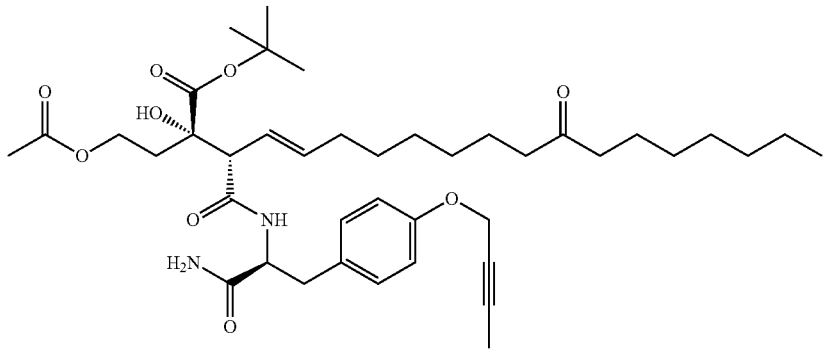

The title compound was obtained by a method similar to that of No. 5318799, except that tert-butyl (E)-(2S,3S)-3-[(S)-2-(4-but-2-ynyloxy-phenyl)-1-carbamoyl-ethylcarbamoyl]-2-hydroxy-2-(2-hydroxy-ethyl)-12-oxo-nonadec-4-enoate was used instead of No. 5217614.

ESI (LC/MS positive mode) m/z 727 (M+H) Rt; 5.09 min.

tert-Butyl (E)-(2S,3S)-3-[(S)-2-(4-but-2-ynyloxy-phenyl)-1-carbamoyl-ethylcarbamoyl]-2-hydroxy-2-(2-methoxy-ethyl)-12-oxo-nonadec-4-enoate

[Chem. 401]

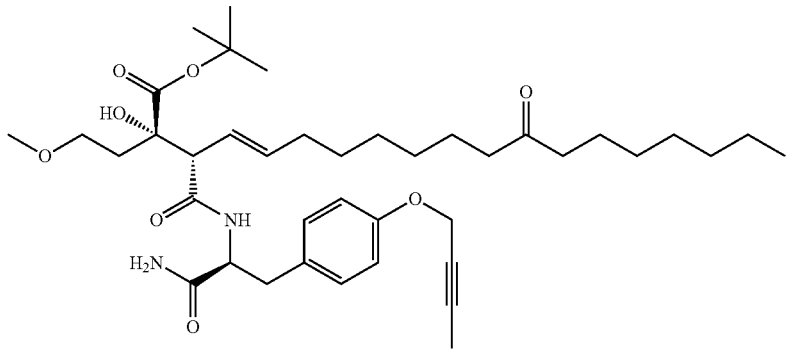

The title compound was obtained by a method similar to that of tert-butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate, except that tert-butyl (E)-(2S,3S)-3-[(S)-2-(4-but-2-ynyloxy-phenyl)-1-carbamoyl-ethylcarbamoyl]-2-hydroxy-2-(2-hydroxy-ethyl)-12-oxo-nonadec-4-enoate was used instead of tert-butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate.

ESI (LC/MS positive mode) m/z 699 (M+H); Rt 5.23 min.

No. 5248113: (E)-2-(2S,3S)-3-[(S)-2-(4-but-2-yny-loxy-phenyl)-1-carbamoyl-ethylcarbamoyl]-2-hydroxy-2-(2-methoxyethyl)-12-oxo-nonadec-4-enoic acid

[Chem. 402]

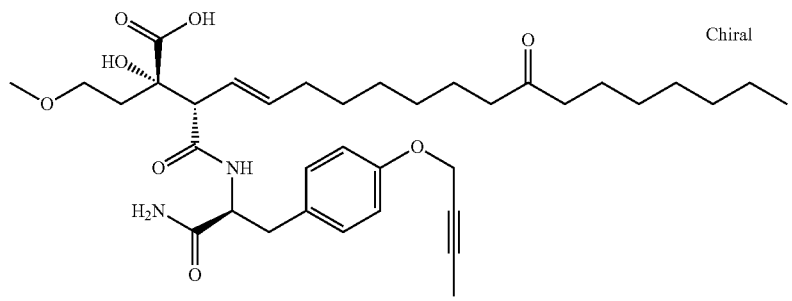

The title compound was obtained by a method similar to that of No. 5247676, except that tert-butyl (E)-(2S,3S)-3-[(S)-2-(4-but-2-ynyloxy-phenyl)-1-carbamoyl-ethylcarbamoyl]-2-hydroxy-2-(2-methoxy-ethyl)-12-oxo-nonadec-4-enoate was used instead of tert-butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate.

$^1$H-NMR (DMSO-$d_6$ δ(PPM) 8.05 (1H, d, J=8.6 Hz), 7.11 (2H, d, J=8.4 Hz), 6.80 (2H, d, J=8.4 Hz), 5.50-5.30 (2H, m), 4.66 (2H, m), 4.40-4.30 (1H, m), 3.40-3.20 (1H, m), 3.14 (3H, s), 3.00-2.46 (6H, m), 2.45-2.35 (4H, m), 1.82 (3H, s), 2.10-1.10 (20H, m), 0.85 (3H, t, J=6.6 Hz),

ESI (LC/MS positive mode) m/z 643 (M+H)

tert-Butyl [(S)-2-(4-but-2-ynyloxy-phenyl)-1-methylcarbamoyl-ethyl]-carbamate

{Chem. 403]

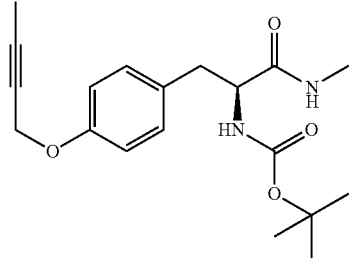

The title compound was obtained by a method similar to that of tert-butyl [(S)-2-(4-but-2-ynyloxy-phenyl)-1-dimethylcarbamoyl-ethyl]-carbamate, except that methylamine hydrochloride was used instead of a solution of dimethylamine in tetrahydrofuran.

ESI (LC/MS positive mode) m/z 347 (M+H); Rt 1.94 min.

(S)-2-Amino-3-(4-but-2-ynyloxy-phenyl)-N-methyl-propionamide

[Chem. 404]

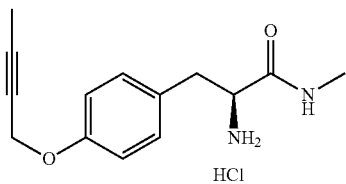

The title compound was obtained by a method similar to that of (S)-2-amino-3-(4-but-2-ynyloxy-phenyl)-N,N-dimethyl-propionamide, except that tert-butyl [(S)-2-(4-but-2-ynyloxy-phenyl)-1-methylcarbamoyl-ethyl]-earbamate was used instead of tert-butyl [(S)-2-(4-but-2-ynyloxy-phenyl)-1-dimethylcarbamoyl-ethyl]-carbamate.

ESI (LC/MS positive mode) m/z 247 (M-Cl); Rt 0.91 min.

tert-Butyl (E)-(2S,3S)-2-[2-(tert-butyl-dimethyl-silanyloxy)-ethyl]-3-[(S)-2-(4-but-2-ynyloxy-phenyl)-1-methylcarbamoyl-ethylcarbamoyl]-11-(2-heptyl-[1,3]dioxolan-2-yl)-2-hydroxy-undec-4-enoate

[Chem. 405]

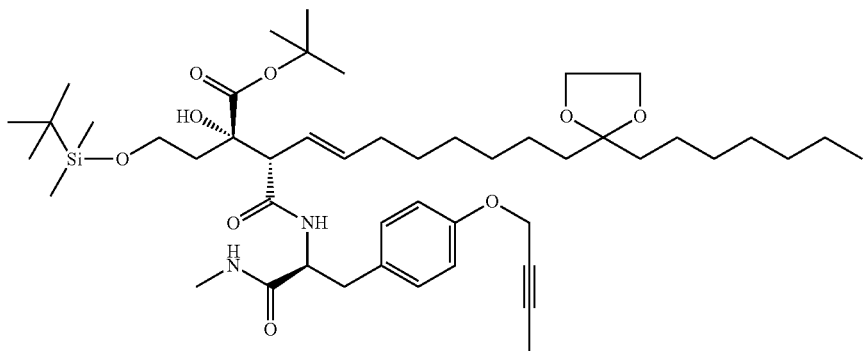

The title compound was obtained by a method similar to that of No. 5327507, except that (S)-2-amino-3-(4-but-2-ynyloxy-phenyl)-N-methyl-propionamide was used instead of No. 4935048.

ESI (LC/MS positive mode) m/z 858 (M+H); Rt 7.52 min.

tert-Butyl (E)-(2S,3S)-3-[(S)-2-(4-but-2-ynyloxy-phenyl)-1-methylcarbamoyl-ethylcarbamoyl]-2-hydroxy-2-(2-hydroxy-ethyl)-12-oxo-nonadec-4-enoate

[Chem. 406]

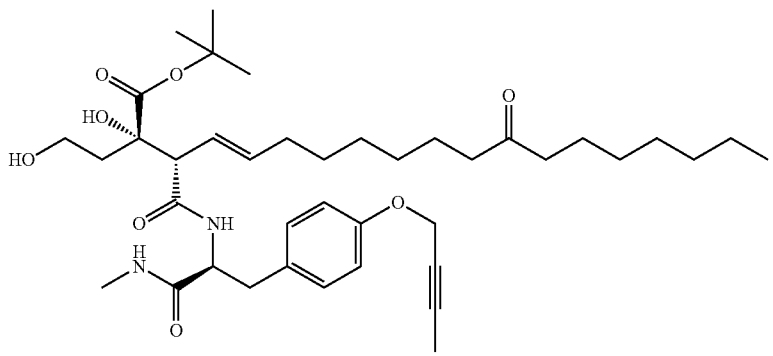

The title compound was obtained by a method similar to that of No. 5217614, except that tert-butyl (E)-(2S,3S)-2-[2-(tert-butyl-dimethyl-silanyloxy)-ethyl]-3-[(S)-2-(4-but-2-ynyloxy-phenyl)-1-methylcarbamoyl-ethylcarbamoyl]-11-(2-heptyl-[1,3]dioxolan-2-yl)-2-hydroxy-undec-4-enoate was used instead of No. 5327507.

ESI (LC/MS positive mode) m/z 699 (M+H); Rt 4.59 min.

tert-Butyl (E)-(2S,3S)-2-(2-acetoxy-ethyl)-3-[(S)-2-(4-but-2-ynyloxy-phenyl)-1-methylcarbamoyl-ethyl-carbamoyl]-2-hydroxy-12-oxo-nonadec-4-enoate

[Chem. 407]

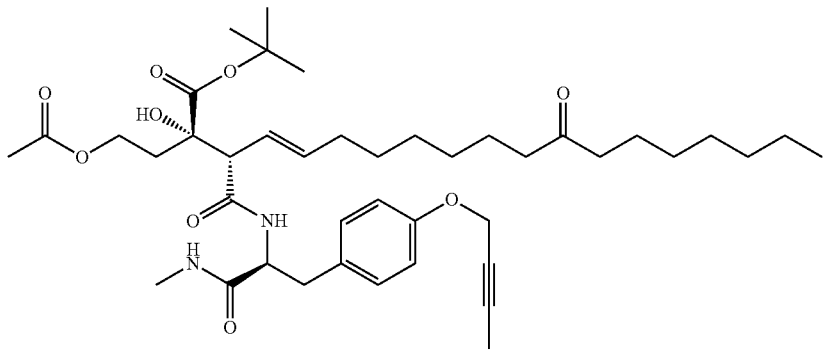

The title compound was obtained by a method similar to that of No. 5318799, except that tert-butyl (E)-(2S,3S)-3-[(S)-2-(4-but-2-ynyloxy-phenyl)-1-methylcarbamoyl-ethyl-carbamoyl]-2-hydroxy-2-(2-hydroxy-ethyl)-12-oxo-nonadec-4-enoate was used instead of No. 5217614.

ESI (LC/MS positive mode) m/z 741 (M+H); Rt 5.23 min.

No. 5247264: (E)-2-(2S,3S)-3-[(S)-2-(4-but-2-yny-loxy-phenyl)-1-carbamoyl-ethylcarbamoyl]-2-hydroxy-2-(2-hydroxyethyl)-12-oxo-nonadec-4-enoic acid

[Chem. 408]

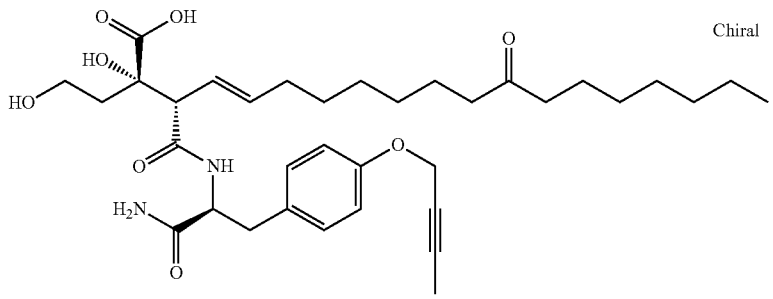

The title compound was obtained by a method similar to that of No. 5247676, except that tert-butyl (E)-(2S,3S)-2-(2-acetoxy-ethyl)-3-[(S)-2-(4-but-2-ynyloxy-phenyl)-1-carbamoyl-ethylcarbamoyl]-2-hydroxy-12-oxo-nonadec-4-enoate was used instead of tert-butyl (E)-(2S,3S)-2-(2-acetoxy-ethyl)-3-[(S)-2-(4-but-2-ynyloxy-phenyl)-1-dimethylcarbamoyl-ethylcarbamoyl]-2-hydroxy-12-oxo-nonadec-4-enoate.

$^1$H-NMR (DMSO-$d_6$ δ(PPM) 8.05 (1H, d, J=8.6 Hz), 7.38 (1H, br.s), 7.11 (2H, d, J=8.4 Hz), 6.80 (2H, d, J=8.4 Hz), 5.50-5.30 (2H, m), 4.66 (2H, m), 4.40-4.30 (1H, m), 3.50-3.20 (1H, m), 3.00-2.46 (6H, m), 2.45-2.35 (4H, m), 1.82 (3H, s), 2.10-1.10 (20H, m), 0.85 (3H, t, J=6.6 Hz),

ESI (LC/MS positive mode) m/z 629 (M+H)

tert-Butyl (E)-(2S,3S)-3-[(S)-2-(4-but-2-ynyloxy-phenyl)-1-methylcarbamoyl-ethylcarbamoyl]-2-hydroxy-2-(2-methoxy-ethyl)-12-oxo-nonadec-4-enoate

[Chem. 409]

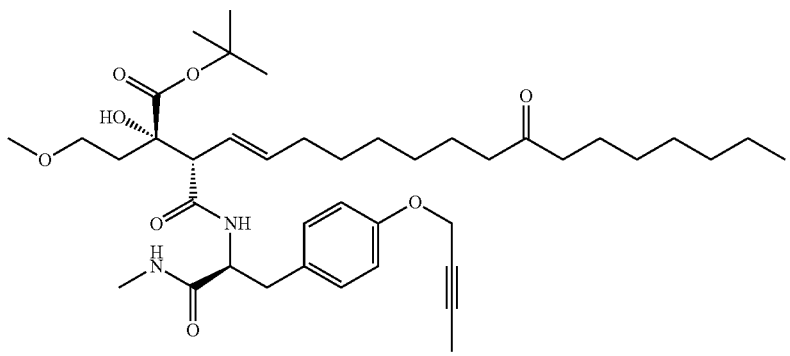

The title compound was obtained by a method similar to that of tert-butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate, except that tert-butyl (E)-(2S,3S)-3-[(S)-2-(4-but-2-ynyloxy-phenyl)-1-methylcarbamoyl-ethylcarbamoyl]-2-hydroxy-2-(2-hydroxy-ethyl)-12-oxo-nonadec-4-enoate was used instead of tert-butyl (E)-(2S,3S)-3-[(S)-2-(4-but-2-ynyloxy-phenyl)-1-dimethylcarbamoyl-ethylcarbamoyl]-2-hydroxy-2-(2-hydroxy-ethyl)-12-oxo-nonadec-4-enoate.

ESI (LC/MS positive mode) ink 713 (M+H); Rt 5.32 min.

No. 5247862: (E)-(2S,3S)-3-[(S)-2-(4-but-2-ynyloxy-phenyl)-1-methylcarbamoyl-ethylcarbamoyl]-2-hydroxy-2-(2-methoxyethyl)-12-oxo-nonadec-4-enoic acid

[Chem. 410]

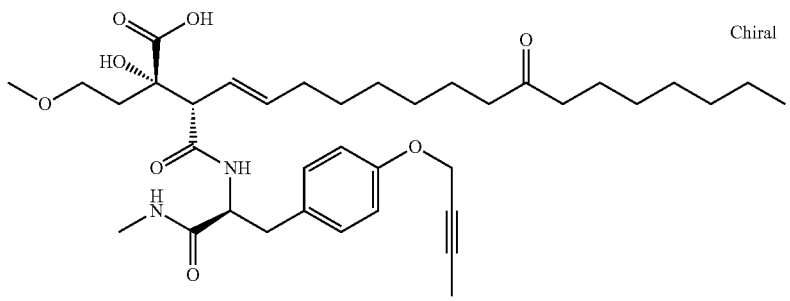

The title compound was obtained by a method similar to that of No. 5247676, except that tert-butyl (E)-(2S,3S)-3-[(S)-2-(4-but-2-ynyloxy-phenyl)-1-methylcarbamoyl-ethyl-carbamoyl]-2-hydroxy-2-(2-methoxy-ethyl)-12-oxo-nonadec-4-enoate was used instead of tert-butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate.

$^1$H-NMR (DMSO-$d_6$ δ(PPM) 8.12 (1H, d, J=8.1 Hz), 7.86 (1H, br.s), 7.08 (2H, d, J=8.4 Hz), 6.80 (2H, d, J=8.4 Hz), 5.40-5.30 (2H, m), 5.23 (1H, br.s), 4.65 (2H, br), 4.40-4.30 (1H, m), 3.40-3.20 (1H, m), 3.15 (3H, s), 3.00-2.50 (9H, m), 2.40-2.30 (4H, m), 1.82 (3H, s), 2.10-1.10 (20H, m), 0.85 (3H, t, J=6.6 Hz),

ESI (LC/MS positive mode) m/z 657 (M+H)

tert-Butyl (E)-(2S,3S)-2-hydroxy-2-(2-hydroxy-ethyl)-3-[(S)-2-(4-hydroxy-phenyl)-1-(5-methyl-oxazol-2-yl)-ethylcarbamoyl]-12-oxo-nonadec-4-enoate

[Chem. 411]

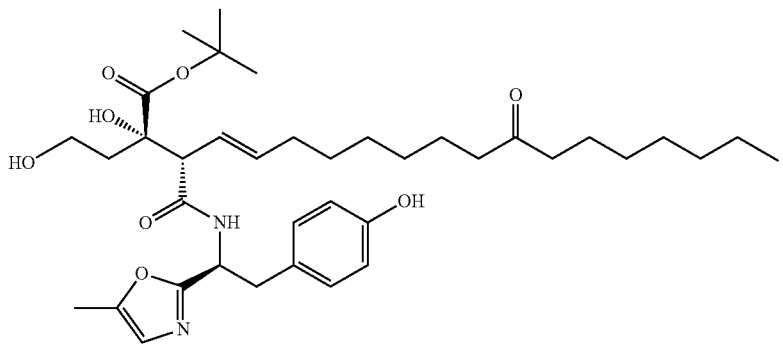

No. 4976198 (168 mg, 0.267 mmol) and 4-[(S)-2-amino-2-(5-methyl-oxazol-2-yl)-ethyl]-phenol (58.3 mg, 0.267 mmol; a compound described in WO2007/022241) were dissolved in DMF (3 mL), and O-(7-azabenzotriazol-1-yl)-N,N,N',N'-tetramethyluronium hexafluorophosphate (122 mg, 0.320 mmol) and N,N-diisopropylethylamine (207 μL, 1.20 mmol) were added. The mixture was stirred at room temperature for 4 hours. To the reaction mixture was then added an aqueous solution of 0.5 M potassium hydrogen sulfate. The mixture was extracted with ethyl acetate. The organic layer was washed with a saturated brine, dried over anhydrous magnesium sulfate, and concentrated under reduced pressure. The resulting residue was dissolved in acetonitrile (2.4 mL), and an aqueous solution of 0.5 M citric acid (0.6 mL) was added. The mixture was stirred at 60° C. for 2 hours. An aqueous solution of sodium bicarbonate was added to the reaction mixture, which was followed by extraction with ethyl acetate. The organic layer was washed with a saturated brine, dried over anhydrous magnesium sulfate, and concentrated under reduced pressure. The resulting residue was purified by preparative HPLC to obtain the title compound (5.0 mg, 3% yield).

ESI (LC/MS positive mode) m/z 671 (M+H); Rt 5.09 min.

tert-Butyl (E)-(2S,3S)-2-(2-acetoxy-ethyl)-3-[(S)-2-(4-but-2-ynyloxy-phenyl)-1-(5-methyl-oxazol-2-yl)-ethylcarbamoyl]-2-hydroxy-12-oxo-nonadec-4-enoate

[Chem. 412]

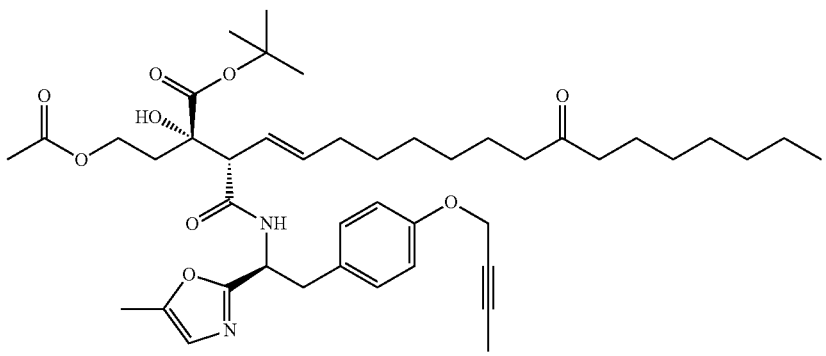

tert-Butyl (E)-(2S,3S)-2-hydroxy-2-(2-hydroxy-ethyl)-3-[(S)-2-(4-hydroxy-phenyl)-1-(5-methyl-oxazol-2-yl)-ethylcarbamoyl]-12-oxo-nonadec-4-enoate (3.5 mg, 5.22 μmol) was dissolved in DMF (0.3 mL), and potassium carbonate (1.4 mg, 10.4 μmol) and 1-bromo-but-2-yne (0.7 μL, 7.83 μmol) were added. The mixture was stirred at room temperature for 24 hours. A saturated brine was then added to the reaction mixture, which was followed by extraction with ethyl acetate. The organic extract was dried over magnesium sulfate, and concentrated under reduced pressure. The resulting residue was dissolved in dichloromethane (0.5 mL), and acetic anhydride (1.0 μL, 10.4 μmol), DMAP (0.06 mg, 0.52 μmol), and triethylamine (2.9 μL, 20.9 μmol) were added. The mixture was stirred at room temperature for 9 hours. A saturated brine was then added to the reaction mixture, which was followed by extraction with ethyl acetate. The organic extract was dried over magnesium sulfate, and concentrated under reduced pressure to obtain the title compound (4 mg).

ESI (LC/MS positive mode) m/z 765 (M+H); Rt 5.90 min.

No. 5217032, (E)-(2S,3S)-3-[(S)-2-(4-but-2-ynyloxy-phenyl)-1-(5-methyl-oxazol-2-yl)-ethylcarbamoyl]-2-hydroxy-2-(2-hydroxy-ethyl)-12-oxo-nonadec-4-enoic acid

[Chem. 413]

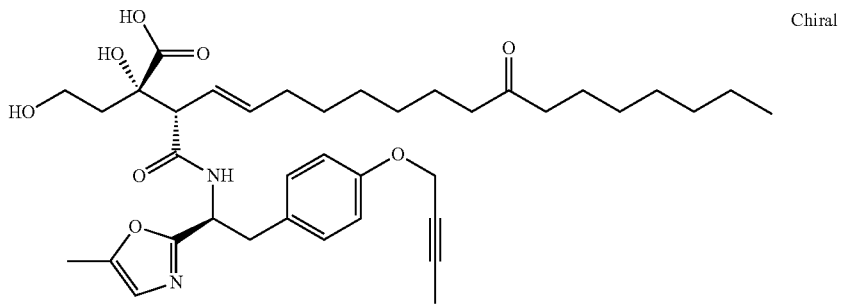

tert-Butyl (E)-(2S,3S)-2-(2-acetoxy-ethyl)-3-[(S)-2-(4-but-2-ynyloxy-phenyl)-1-(5-methyl-oxazol-2-yl)-ethylcarbamoyl]-2-hydroxy-12-oxo-nonadec-4-enoate (4.0 mg) was dissolved in formic acid (0.5 mL), and the mixture was stirred at room temperature for 24 hours.

The reaction mixture was then concentrated under reduced pressure. The resulting residue was dissolved in methanol (0.5 mL), and an aqueous solution (10.4 µL) of 2 M lithium hydroxide was added at 0° C. The reaction mixture was stirred for 3 hours, and purified by preparative HPLC to obtain the title compound (1.7 mg).

$^1$H-NMR (CDCl$_3$) δ(PPM) 6.92 (2H, d, J=8.4 Hz), 6.83 (2H, d, J=8.4 Hz), 6.64 (1H, s), 570-5.57 (1H, m), 5.55-5.45 (1H, m), 5.45-5.30 (1H, m), 4.60 (2H, m), 3.90-3.60 (2H, m), 3.40-2.90 (5H, m), 2.50-2.35 (4H, m), 2.30 (3H, s), 1.85 (3H, s), 2.10-1.10 (20H, m), 0.87 (3H, t, J=6.6 Hz),

ESI (LC/MS positive mode) m/z 667 (M+H)

tert-Butyl (E)-(2S,3S)-2-[2-(tert-butyl-dimethyl-silanyloxy)-ethyl]-3-[(S)-1-ethoxycarbonyl-2-(4-hydroxy-phenyl)-ethylcarbamoyl]-11-(2-heptyl-[1,3]dioxolan-2-yl)-2-hydroxy-undec-4-enoate

[Chem. 414]

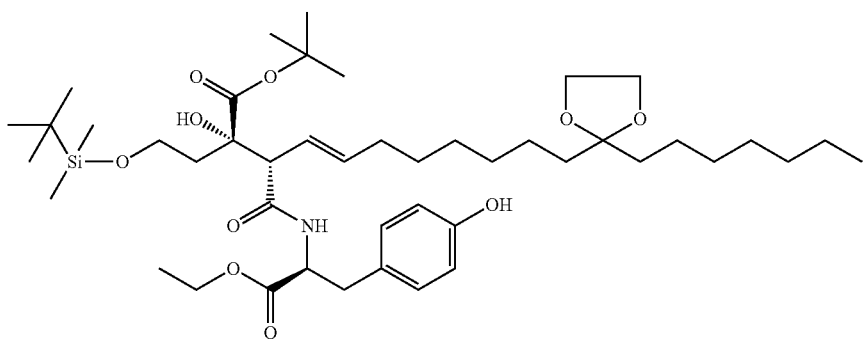

The title compound was obtained by a method similar to that of No. 5327507, except that ethyl (S)-2-amino-3-(4-hydroxy-phenyl)-propionate hydrochloride was used instead of No. 4935048.

ESI (LC/MS positive mode) m/z 821 (M+H); Rt 7.71 min.

tert-Butyl (E)-(2S,3S)-3-[(S)-2-(4-but-2-ynyloxy-phenyl)-1-ethoxycarbonyl-ethylcarbamoyl]-2-hydroxy-2-(2-hydroxy-ethyl)-12-oxo-nonadec-4-enoate

[Chem. 415]

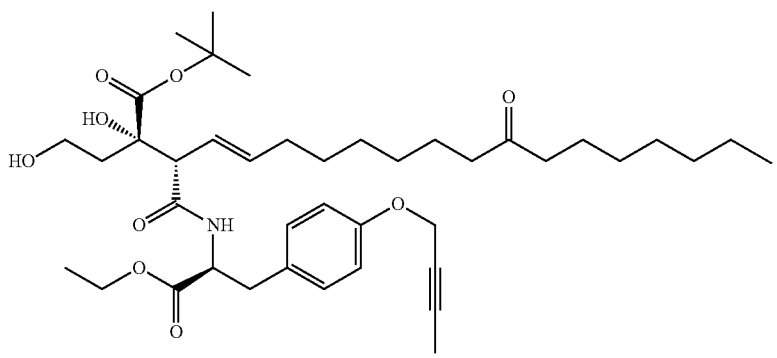

tert-Butyl (E)-(2S,3S)-2-[2-(tert-butyl-dimethyl-silanyloxy)-ethyl]-3-[(S)-1-ethoxycarbonyl-2-(4-hydroxy-phenyl)-ethylcarbamoyl]-11-(2-heptyl-[1,3]dioxolan-2-yl)-2-hydroxy-undec-4-enoate (909 mg) was dissolved in acetonitrile (9.0 mL), and an aqueous solution (3.6 mL) of 0.5 M citric acid was added. The mixture was stirred at 60° C. for 3 hours. Water was then added to the reaction mixture, which was followed by extraction with a mixed solvent of ethyl acetate/n-hexane. The organic extract was dried over magnesium sulfate, and concentrated under reduced pressure to obtain a crude product (660 mg). The obtained crude product (182 mg) was dissolved in DMF, and potassium carbonate (49.4 mg) and 1-bromo-but-2-yne (28.9 μL) were added. The mixture was stirred at room temperature for 20 hours. Water was then added to the reaction mixture, which was followed by extraction with a mixed solvent of ethyl acetate/n-hexane. The organic layer was washed with a saturated brine, dried over anhydrous magnesium sulfate, and concentrated under reduced pressure. The resulting residue was purified by silica gel column chromatography to obtain the title compound (74 mg).

ESI (LC/MS positive mode) m/z 714 (M+H); Rt 2.13 min.

1-tert-Butyl (S)-2-{(E)-(S)-1-[(S)-2-(4-but-2-ynyloxy-phenyl)-1-ethoxycarbonyl-ethylcarbamoyl]-10-oxo-heptadec-2-enyl}-2-hydroxy-succinate

[Chem. 416]

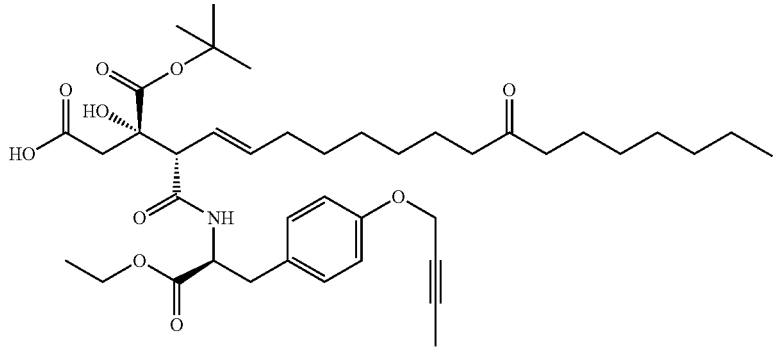

The title compound was obtained by a method similar to that of No. 5317776, except that tert-butyl (E)-(2S,3S)-3-[(S)-2-(4-but-2-ynyloxy-phenyl)-1-ethoxycarbonyl-ethylcarbamoyl]-2-hydroxy-2-(2-hydroxy-ethyl)-12-oxo-nonadec-4-enoate was used instead of No. 5217614.

ESI (LC/MS positive mode) m/z 728 (M+H); Rt 2.18 min.

No. 5204226: (S)-2-{(E)-(S)-1-[(S)-2-(4-but-2-ynyloxy-phenyl)-1-ethoxycarbonyl-ethylcarbamoyl]-10-oxo-heptadec-2-enyl}-2-hydroxy-succinic acid

[Chem. 417]

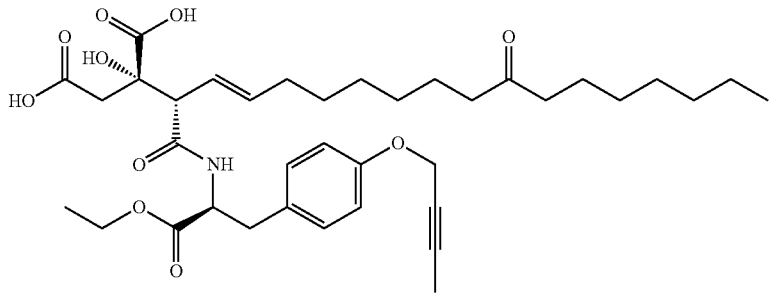

The title compound was obtained by a method similar to that of No. 5250397, except that 1-tert-butyl (S)-2-{(E)-(S)-1-[(S)-2-(4-but-2-ynyloxy-phenyl)-1-ethoxycarbonyl-ethyl-carbamoyl]-10-oxo-heptadec-2-enyl}-2-hydroxy-succinate was used instead of tert-butyl (E)-(2S,3S)-3-[(S)-2-(4-but-2-ynyloxy-phenyl)-1-dimethylcarbamoyl-ethylcarbamoyl]-2-hydroxy-2-(2-methoxy-ethyl)-12-oxo-nonadec-4-enoate.

$^1$H-NMR (CDCl$_3$) δ(PPM) 6.90 (2H, d, J=8.4 Hz), 6.85 (2H, d, J=8.4 Hz), 5.69 (1H, ddd, J=16.7 Hz, 15.1 Hz, 6.5 Hz), 5.50 (1H, dd, J=15.1 Hz, 9.2 Hz), 4.60 (2H, m), 4.18 (2H, q, J=6.6 Hz), 3.18 (1H, d, J=9.2 Hz), 3.15-2.90 (3H, m), 2.64 (1H, d, J=16.7 Hz), 2.50-2.30 (4H, m), 2.10-1.90 (2H, m), 1.60-1.10 (21H, m), 1.85 (3H, s), 0.87 (3H, t, J=6.6 Hz)

ESI (LC/MS positive mode) m/z 672 (M+H)

Industrial Applicability

A pharmaceutical composition including a compound of the present invention is extremely useful as an anti-HCV prophylactic/therapeutic agent for oral administration, since compounds of the present invention have good anti-HCV activities and bioavailabilities sufficient to maintain adequate efficacy concentrations in the liver, a target organ of the anti-HCV agent, when administered orally.

The invention claimed is:

1. A compound represented by formula (1) below or a pharmaceutically acceptable salt thereof:

[Chem. 418]

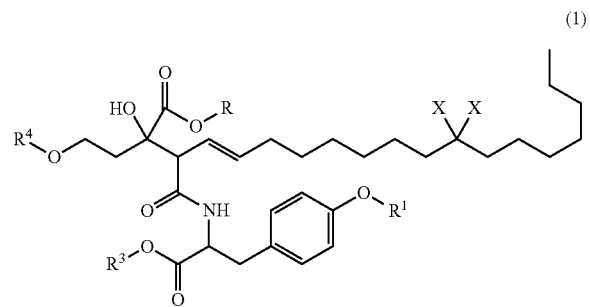

(1)

wherein R is selected from a hydrogen atom and a group represented by formula (2) below:

[Chem. 419]

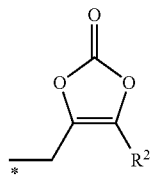

(2)

wherein
R$^1$ is C$_{1-10}$ alkyl;
R$^2$ is selected from a hydrogen atom, C$_{1-6}$ alkyl, and aryl;
R$^3$ is selected from a hydrogen atom and C$_{1-6}$ alkyl;
R$^4$ is C$_{1-6}$ alkyl; and
two Xs are the same or different, and each represent a halogen atom.

2. The compound according to claim 1 or a pharmaceutically acceptable salt thereof, wherein the compound is represented by formula (1') below:

[Chem. 420]

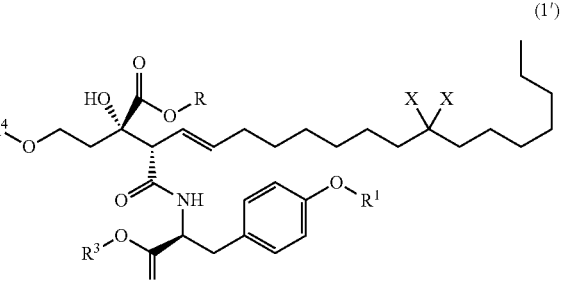

(1')

wherein R, R$^1$, R$^3$, R$^4$, and X are as defined in claim 1.

3. The compound according to claim 1 or a pharmaceutically acceptable salt thereof, wherein the two Xs are the same and each represent a fluorine atom.

4. The compound according to claim 1 or a pharmaceutically acceptable salt thereof, wherein R$^1$ is n-butyl.

5. The compound according to claim 1 or a pharmaceutically acceptable salt thereof, wherein $R^4$ is methyl.

6. The compound according to claim 1 or a pharmaceutically acceptable salt thereof, wherein R is a group represented by formula (2) below:

[Chem. 421]

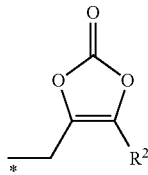

(2)

wherein $R^2$ is as defined in claim 1.

7. The compound according to claim 6 or a pharmaceutically acceptable salt thereof, wherein $R^2$ is methyl.

8. The compound according to claim 6 or a pharmaceutically acceptable salt thereof, wherein the compound is (5-methyl-2-oxo-[1,3]dioxol-4-yl)methyl (E)-(2S, 3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4-enoate, represented by formula (1a) below:

[Chem. 422]

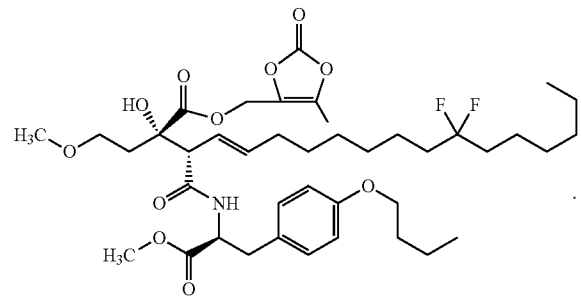

(1a)

9. The compound according to claim 1 or a pharmaceutically acceptable salt thereof, wherein R is a hydrogen atom.

10. The compound according to claim 9 or a pharmaceutically acceptable salt thereof, wherein $R^3$ is a hydrogen atom or methyl.

11. The compound according to claim 9 or a pharmaceutically acceptable salt thereof, wherein the compound is selected from (E)-(2S, 3S)-3-[(S)-2-(4-butoxy-phenyl)-1-methoxycarbonyl-ethylcarbamoyl]-12,12-difluoro-2-hydroxy-2-(2-methoxy-ethyl)-nonadec-4enoic acid and (E)-(2S, 3S)-3-[(S)-2-(4-butoxy-phenyl)-1-carboxy-ethylcarbamoyl]-12,12-difluoro-2-hydroxy-2-(2-methoxy-ethyl)-nonadec-4-enoic acid, respectively represented by formulae (1b) and (1c) below:

[Chem. 423]

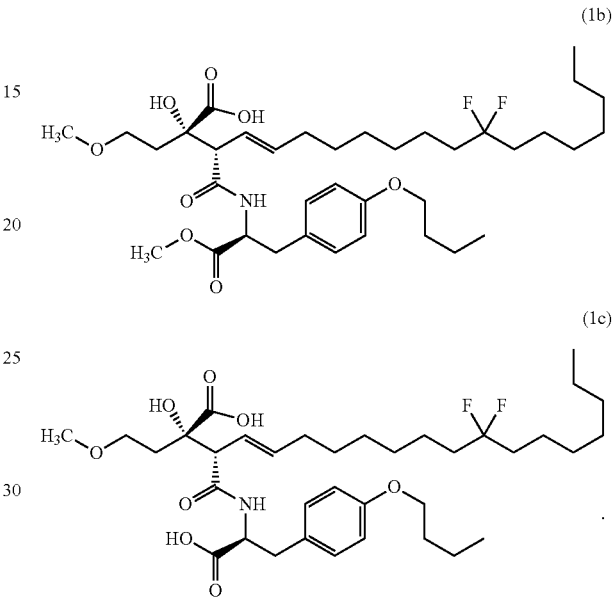

12. A pharmaceutical composition comprising the compound according to claim 1 or a pharmaceutically acceptable salt thereof as an active ingredient.

13. A prophylactic and/or therapeutic agent for hepatitis C virus infection, comprising the compound according to claim 1 or a pharmaceutically acceptable salt thereof as an active ingredient.

14. The prophylactic and/or therapeutic agent according to claim 13, wherein the hepatitis C virus infection is hepatitis C.

15. The compound according to claim 2 or a pharmaceutically acceptable salt thereof, wherein the two Xs are the same and each represent a fluorine atom.

* * * * *